US012534519B2

(12) United States Patent
Tsika et al.

(10) Patent No.: US 12,534,519 B2
(45) Date of Patent: Jan. 27, 2026

(54) MOLECULES FOR THERAPY AND DIAGNOSIS

(71) Applicant: AC Immune SA, Lausanne (CH)

(72) Inventors: Elpida Tsika, Lausanne (CH); John Warner, Lausanne (CH); Jan Peter Henning Stöhr, Lausanne (CH)

(73) Assignee: AC Immune SA, Lausanne (CH)

( * ) Notice: Subject to any disclaimer, the term of this patent is extended or adjusted under 35 U.S.C. 154(b) by 1063 days.

(21) Appl. No.: 17/603,513

(22) PCT Filed: Apr. 17, 2020

(86) PCT No.: PCT/EP2020/060898
§ 371 (c)(1),
(2) Date: Oct. 13, 2021

(87) PCT Pub. No.: WO2020/212593
PCT Pub. Date: Oct. 22, 2020

(65) Prior Publication Data

US 2022/0298231 A1 Sep. 22, 2022

(30) Foreign Application Priority Data

Apr. 18, 2019 (EP) .................................... 19170207
Nov. 5, 2019 (EP) .................................... 19207105
Mar. 23, 2020 (EP) .................................... 20165055

(51) Int. Cl.
*C07K 16/18* (2006.01)
*A61K 39/00* (2006.01)
*A61P 25/00* (2006.01)
*A61P 25/28* (2006.01)
*G01N 33/58* (2006.01)
*G01N 33/68* (2006.01)

(52) U.S. Cl.
CPC .............. *C07K 16/18* (2013.01); *A61P 25/00* (2018.01); *A61P 25/28* (2018.01); *G01N 33/6896* (2013.01); *A61K 2039/505* (2013.01); *C07K 2317/24* (2013.01); *C07K 2317/34* (2013.01); *C07K 2317/92* (2013.01); *G01N 33/582* (2013.01)

(58) Field of Classification Search
CPC ................ C07K 16/18; C07K 2317/24; C07K 2317/34; C07K 2317/92; A61P 25/00; A61P 25/28; G01N 33/6896; G01N 33/582; A61K 2039/505
See application file for complete search history.

(56) References Cited

U.S. PATENT DOCUMENTS

2005/0147989 A1 7/2005 Bertsch et al.
2018/0194833 A1 7/2018 Kallunki et al.

FOREIGN PATENT DOCUMENTS

WO 2017009312 1/2017
WO WO-2017009312 A1 * 1/2017 ........... A61K 39/395
WO 2018109058 6/2018
WO 2019040617 2/2019
WO WO-2019040617 A1 * 2/2019 ......... G01N 33/6896

OTHER PUBLICATIONS

Harding (2010) MAbs 2(3): 256-265 (Year: 2010).*
Landeck (Molecular Neurodegeneration (2020) 15: 49) (Year: 2020).*
Tsika et al. U.S. Appl. No. 17/782,536. Unpublished. Novel Molecules for Therapy and Diagnosis. (Year: 2022).*
Emadi et al. (2007) “Isolation of a Human Single Chain Antibody Fragment Against Oligomeric α-Synuclein that Inhibits Aggregation and Prevents α-Synuclein-induced Toxicity” Journal of Molecular Biology, 368(4):1132-1144.
Li et al. (2019) “Naturally occurring antibodies isolated from PD patients inhibit synuclein seeding in vitro and recognize Lewy pathology” Acta Neuropathologica, 137(5):825-836.
Mirecka et al. (2014) “Sequestration of a [beta]-Hairpin for Control of [alpha]-Synuclein Aggregation” Angewandte Chemie, 53(16):4227-4230.

* cited by examiner

*Primary Examiner* — Julie Wu
*Assistant Examiner* — Elizabeth A Shupe
(74) *Attorney, Agent, or Firm* — Brian E. Davy; Bozicevic, Field & Francis LLP

(57) ABSTRACT

The present invention relates to novel molecules that can be employed for the prevention, alleviation, treatment and/or diagnosis of diseases, disorders and abnormalities associated with alpha-synuclein (a-synuclein, A-synuclein, aSynuclein, A-syn, α-syn, aSyn, a-syn) aggregates, including, but not limited to, Lewy bodies and/or Lewy neurites, such as Parkinson's disease, Multiple System Atrophy, Lewy Body dementia (LBD; dementia with Lewy bodies (DLB) (“pure” Lewy body dementia), Parkinson's disease dementia (FDD)) or Diffuse Lewy Body Disease. The invention relates to alpha-synuclein binding molecules, in particular to alpha-synuclein antibodies or an antigen-binding fragment or a derivative thereof and uses thereof. The present molecules can also be used for determining a predisposition to such a disorder, disease or abnormality, monitoring residual disorder, disease or abnormality, or predicting the responsiveness of a patient who is suffering from such a disorder, disease or abnormality to treatment with a certain medicament.

21 Claims, 26 Drawing Sheets

Figure 1:
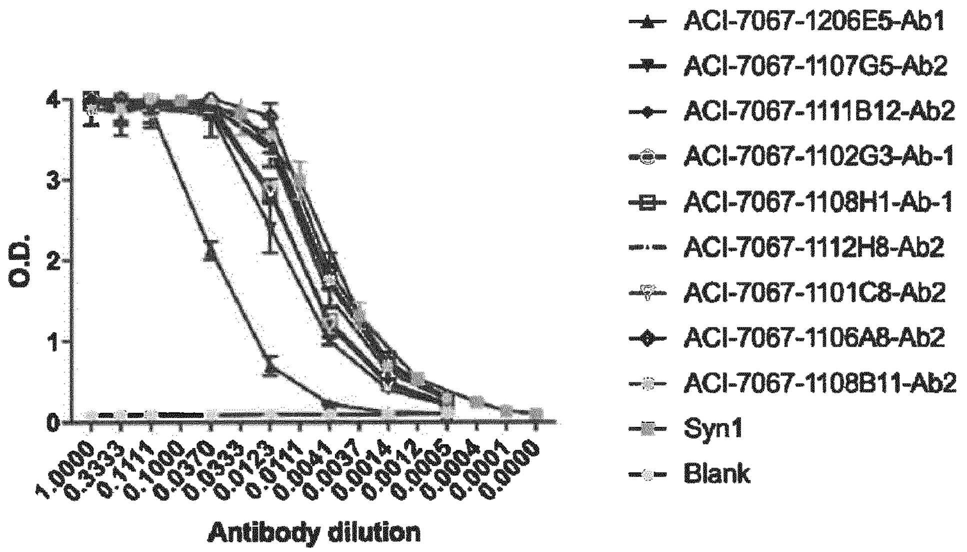

Specification includes a Sequence Listing.

A

B

A

A cont.

B

B cont.

A

B

A

B

A

B

A

B

SEQUENCE LISTING

```
<160> NUMBER OF SEQ ID NOS: 728

<210> SEQ ID NO 1
<211> LENGTH: 140
<212> TYPE: PRT
<213> ORGANISM: Unknown
<220> FEATURE:
<223> OTHER INFORMATION: Organism of the class Mammalia

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140


<210> SEQ ID NO 2
<211> LENGTH: 5
<212> TYPE: PRT
<213> ORGANISM: Unknown
<220> FEATURE:
<223> OTHER INFORMATION: Organsim of the class Mammalia

<400> SEQUENCE: 2
```

Gly Val Leu Tyr Val
1 5

<210> SEQ ID NO 3
<211> LENGTH: 7
<212> TYPE: PRT
<213> ORGANISM: Unknown
<220> FEATURE:
<223> OTHER INFORMATION: Organism of the class Mammalia

<400> SEQUENCE: 3

Gly Val Ala Thr Val Ala Glu
1 5

<210> SEQ ID NO 4
<211> LENGTH: 10
<212> TYPE: PRT
<213> ORGANISM: Unknown
<220> FEATURE:
<223> OTHER INFORMATION: Organism of the class Mammalia

<400> SEQUENCE: 4

Asn Val Gly Gly Ala Val Val Thr Gly Val
1 5 10

<210> SEQ ID NO 5
<211> LENGTH: 17
<212> TYPE: PRT
<213> ORGANISM: Unknown
<220> FEATURE:
<223> OTHER INFORMATION: Organism of the class Mammalia

<400> SEQUENCE: 5

Asn Val Gly Gly Ala Val Val Thr Gly Val Thr Ala Val Ala Gln Lys
1 5 10 15

Thr

<210> SEQ ID NO 6

<400> SEQUENCE: 6

000

<210> SEQ ID NO 7
<211> LENGTH: 8
<212> TYPE: PRT
<213> ORGANISM: Unknown
<220> FEATURE:
<223> OTHER INFORMATION: Organism of the class Mammalia

<400> SEQUENCE: 7

Ala Tyr Glu Met Pro Ser Glu Glu
1 5

<210> SEQ ID NO 8
<211> LENGTH: 8
<212> TYPE: PRT
<213> ORGANISM: Unknown
<220> FEATURE:
<223> OTHER INFORMATION: Organism of the class Mammalia

<400> SEQUENCE: 8

Pro Ser Glu Glu Gly Tyr Gln Asp
1 5

<210> SEQ ID NO 9
<211> LENGTH: 10
<212> TYPE: PRT
<213> ORGANISM: Unknown
<220> FEATURE:
<223> OTHER INFORMATION: Organism of the class Mammalia

<400> SEQUENCE: 9

```
Glu Gly Tyr Gln Asp Tyr Glu Pro Glu Ala
1               5                   10
```

<210> SEQ ID NO 10
<211> LENGTH: 121
<212> TYPE: PRT
<213> ORGANISM: Artificial Sequence
<220> FEATURE:
<223> OTHER INFORMATION: ACI-7067-1101C8-Ab2 1101C8F7 VH

<400> SEQUENCE: 10

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Ala Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg Val Gly Leu Arg Phe Tyr Ala Met Asp Tyr Trp Gly
            100                 105                 110

Gln Gly Thr Ser Val Thr Val Ser Ser
        115                 120
```

<210> SEQ ID NO 11
<211> LENGTH: 5
<212> TYPE: PRT
<213> ORGANISM: Artificial Sequence
<220> FEATURE:
<223> OTHER INFORMATION: ACI-7067-1101C8-Ab2 1101C8F7 VH CDR1

<400> SEQUENCE: 11

```
Ile Tyr Ala Met Asn
1               5
```

<210> SEQ ID NO 12
<211> LENGTH: 19
<212> TYPE: PRT
<213> ORGANISM: Artificial Sequence
<220> FEATURE:
<223> OTHER INFORMATION: ACI-7067-1101C8-Ab2 1101C8F7 VH CDR2

<400> SEQUENCE: 12

```
Arg Ile Arg Ser Lys Ser Asn Asn Tyr Ala Thr Tyr Tyr Ala Asp Ser
1               5                   10                  15

Val Lys Asp
```

<210> SEQ ID NO 13
<211> LENGTH: 10
<212> TYPE: PRT
<213> ORGANISM: Artificial Sequence
<220> FEATURE:
<223> OTHER INFORMATION: ACI-7067-1101C8-Ab2 1101C8F7 VH CDR3

<400> SEQUENCE: 13

Val Gly Leu Arg Phe Tyr Ala Met Asp Tyr
1 5 10

<210> SEQ ID NO 14
<211> LENGTH: 112
<212> TYPE: PRT
<213> ORGANISM: Artificial Sequence
<220> FEATURE:
<223> OTHER INFORMATION: ACI-7067-1101C8-Ab2 1101C8F7 VL

<400> SEQUENCE: 14

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser Gln Gly Pro Leu Thr Phe Gly Ala Gly Thr Lys Leu Glu Leu Lys
100 105 110

<210> SEQ ID NO 15
<211> LENGTH: 16
<212> TYPE: PRT
<213> ORGANISM: Artificial Sequence
<220> FEATURE:
<223> OTHER INFORMATION: ACI-7067-1101C8-Ab2 1101C8F7 VL CDR1

<400> SEQUENCE: 15

Arg Ser Ser Gln Ser Ile Val His Ser Asn Gly Asn Thr Tyr Leu Glu
1 5 10 15

<210> SEQ ID NO 16
<211> LENGTH: 7
<212> TYPE: PRT
<213> ORGANISM: Artificial Sequence
<220> FEATURE:
<223> OTHER INFORMATION: ACI-7067-1101C8-Ab2 1101C8F7 VL CDR2

<400> SEQUENCE: 16

Lys Val Ser Asn Arg Phe Ser
1 5

<210> SEQ ID NO 17
<211> LENGTH: 9
<212> TYPE: PRT
<213> ORGANISM: Artificial Sequence
<220> FEATURE:
<223> OTHER INFORMATION: ACI-7067-1101C8-Ab2 1101C8F7 VL CDR3

<400> SEQUENCE: 17

Phe Gln Gly Ser Gln Gly Pro Leu Thr
1 5

<210> SEQ ID NO 18
<211> LENGTH: 363
<212> TYPE: DNA
<213> ORGANISM: Artificial Sequence
<220> FEATURE:
<223> OTHER INFORMATION: ACI-7067-1101C8-Ab2 1101C8F7 VH

<400> SEQUENCE: 18
gaggtgcagc ttgttgagtc tggtggagga ttggtgcagc ctaaagggtc attgaaactc 60
tcatgtgcag cctctggatt cagcttcaat atctacgcca tgaactgggt ccgccaggct 120
ccaggaaagg gtttggaatg ggttgctcgc ataagaagta aaagtaataa ttatgcaaca 180
tattatgccg attcagtgaa agacagattc accatctcca gagctgattc agaaagcatg 240
ctctatctgc aaatgaacaa cttgaaaact gaggacacag ccatgtatta ctgtgtaagg 300
gtgggcctac ggttctatgc tatggactac tggggtcaag gcacctcagt caccgtctcc 360
tca 363

<210> SEQ ID NO 19
<211> LENGTH: 336
<212> TYPE: DNA
<213> ORGANISM: Artificial Sequence
<220> FEATURE:
<223> OTHER INFORMATION: ACI-7067-1101C8-Ab2 1101C8F7 VL

<400> SEQUENCE: 19
gatgttttga tgacccaaac tccactctcc ctgcctgtca gtcttggaga tcaagcctcc 60
atctcttgca gatctagtca gagcattgta catagtaatg gaaacaccta tttagaatgg 120
tacttgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acaaggtccg 300
ctcacgttcg gtgctgggac caagctggag ctgaaa 336

<210> SEQ ID NO 20
<211> LENGTH: 114
<212> TYPE: PRT
<213> ORGANISM: Artificial Sequence
<220> FEATURE:
<223> OTHER INFORMATION: ACI-7067-1102G3-Ab1 1102G3F2 VH

<400> SEQUENCE: 20

Glu Val Lys Leu Glu Glu Ser Gly Gly Gly Leu Val Gln Pro Gly Gly
1 5 10 15

Ser Met Lys Leu Ser Cys Ala Ala Ser Gly Phe Thr Phe Ser Asp Ala
20 25 30

Trp Met Asn Trp Val Arg Gln Ser Pro Glu Lys Gly Leu Glu Trp Val
35 40 45

Ala Glu Ile Arg Asn Lys Ala His Asn His Ala Thr Tyr Tyr Ala Glu
50 55 60

Ser Val Lys Gly Arg Phe Thr Ile Ser Gly Asp Asp Ser Lys Ser Ser
65 70 75 80

Val Tyr Leu Gln Met Asn Asn Leu Arg Ala Glu Asp Thr Gly Ile Tyr
85 90 95

Tyr Cys Thr Ile Tyr Ser Tyr Trp Gly Gln Gly Thr Leu Val Thr Val
100 105 110

Ser Ala

```
<210> SEQ ID NO 21
<211> LENGTH: 4
<212> TYPE: PRT
<213> ORGANISM: Artificial Sequence
<220> FEATURE:
<223> OTHER INFORMATION: ACI-7067-1102G3-Ab1 1102G3F2 VH CDR1

<400> SEQUENCE: 21

Asp Ala Trp Met
1


<210> SEQ ID NO 22
<211> LENGTH: 19
<212> TYPE: PRT
<213> ORGANISM: Artificial Sequence
<220> FEATURE:
<223> OTHER INFORMATION: ACI-7067-1102G3-Ab1 1102G3F2 VH CDR2

<400> SEQUENCE: 22

Glu Ile Arg Asn Lys Ala His Asn His Ala Thr Tyr Tyr Ala Glu Ser
1               5                   10                  15

Val Lys Gly


<210> SEQ ID NO 23

<400> SEQUENCE: 23

000


<210> SEQ ID NO 24
<211> LENGTH: 107
<212> TYPE: PRT
<213> ORGANISM: Artificial Sequence
<220> FEATURE:
<223> OTHER INFORMATION: ACI-7067-1102G3-Ab1 1102G3F2 VL

<400> SEQUENCE: 24

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Lys Asp
            20                  25                  30

Val Ala Trp Tyr Gln Gln Lys Pro Gly Gln Ser Pro Lys Leu Leu Ile
        35                  40                  45

Tyr Ser Thr Ser Asn Arg Tyr Ser Gly Val Pro Asp Arg Phe Thr Gly
    50                  55                  60

Ser Gly Tyr Gly Thr Asp Phe Thr Phe Thr Ile Asn Thr Val Gln Thr
65                  70                  75                  80

Glu Asp Leu Ala Val Tyr Phe Cys Gln Gln Asp Tyr Arg Ile Pro Tyr
                85                  90                  95

Thr Phe Gly Gly Gly Thr Lys Leu Glu Ile Lys
            100                 105


<210> SEQ ID NO 25
<211> LENGTH: 11
<212> TYPE: PRT
<213> ORGANISM: Artificial Sequence
<220> FEATURE:
<223> OTHER INFORMATION: ACI-7067-1102G3-Ab1 1102G3F2 VL CDR1

<400> SEQUENCE: 25

Lys Ala Ser Gln Ser Val Thr Lys Asp Val Ala
1               5                   10
```

<210> SEQ ID NO 26
<211> LENGTH: 7
<212> TYPE: PRT
<213> ORGANISM: Artificial Sequence
<220> FEATURE:
<223> OTHER INFORMATION: ACI-7067-1102G3-Ab1 1102G3F2 VL CDR2

<400> SEQUENCE: 26

Ser Thr Ser Asn Arg Tyr Ser
1 5

<210> SEQ ID NO 27
<211> LENGTH: 9
<212> TYPE: PRT
<213> ORGANISM: Artificial Sequence
<220> FEATURE:
<223> OTHER INFORMATION: ACI-7067-1102G3-Ab1 1102G3F2 VL CDR3

<400> SEQUENCE: 27

Gln Gln Asp Tyr Arg Ile Pro Tyr Thr
1 5

<210> SEQ ID NO 28
<211> LENGTH: 342
<212> TYPE: DNA
<213> ORGANISM: Artificial Sequence
<220> FEATURE:
<223> OTHER INFORMATION: ACI-7067-1102G3-Ab1 1102G3F2 VH

<400> SEQUENCE: 28
gaagtgaagc ttgaggagtc tggaggaggc ttggtgcaac ctggaggatc catgaaactc 60
tcttgtgctg cctctggatt cacttttagt gacgcctgga tgaactgggt ccgccagtct 120
ccagagaagg ggcttgagtg ggttgctgaa attagaaaca aagctcataa tcatgcaaca 180
tactatgctg agtctgtgaa agggaggttc accatctcag gagatgattc caaaagtagt 240
gtctacctgc aaatgaacaa cttaagagct gaagacactg gcatttatta ctgtaccatt 300
tactcttatt ggggccaagg gactctggtc actgtctctg ca 342

<210> SEQ ID NO 29
<211> LENGTH: 321
<212> TYPE: DNA
<213> ORGANISM: Artificial Sequence
<220> FEATURE:
<223> OTHER INFORMATION: ACI-7067-1102G3-Ab1 1102G3F2 VL

<400> SEQUENCE: 29
agtattgtga tgacccagac tcccaaattc ctgcttgtat cagcaggaga cagggttacc 60
ataacctgca aggccagtca gagtgtgact aaagatgtag cttggtacca acagaagcca 120
gggcagtctc ctaaactgct gatatactct acatccaatc gctacagtgg agtccctgat 180
cgcttcactg gcagtggata tgggacggat ttcactttca ccatcaatac tgtgcagact 240
gaagacctgg cagtttattt ctgtcagcag gattacagga ttccgtacac gttcggaggg 300
gggaccaagc tggaaataaa a 321

<210> SEQ ID NO 30
<211> LENGTH: 120
<212> TYPE: PRT
<213> ORGANISM: Artificial Sequence
<220> FEATURE:
<223> OTHER INFORMATION: ACI-7067-1106A8-Ab2 1106A8H3 VH

<400> SEQUENCE: 30

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Gly Ser Asn Tyr Ala Thr Asn Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly His Gly Ser Ser Tyr Phe Ser Tyr Trp Gly Gln
            100                 105                 110

Gly Thr Leu Val Thr Val Ser Ala
        115                 120
```

<210> SEQ ID NO 31
<211> LENGTH: 5
<212> TYPE: PRT
<213> ORGANISM: Artificial Sequence
<220> FEATURE:
<223> OTHER INFORMATION: ACI-7067-1106A8-Ab2 1106A8H3 VH CDR1

<400> SEQUENCE: 31

```
Thr Tyr Ala Met His
1               5
```

<210> SEQ ID NO 32
<211> LENGTH: 19
<212> TYPE: PRT
<213> ORGANISM: Artificial Sequence
<220> FEATURE:
<223> OTHER INFORMATION: ACI-7067-1106A8-Ab2 1106A8H3 VH CDR2

<400> SEQUENCE: 32

```
Arg Ile Arg Ser Lys Gly Ser Asn Tyr Ala Thr Asn Tyr Ala Asp Ser
1               5                   10                  15

Val Lys Asp
```

<210> SEQ ID NO 33
<211> LENGTH: 9
<212> TYPE: PRT
<213> ORGANISM: Artificial Sequence
<220> FEATURE:
<223> OTHER INFORMATION: ACI-7067-1106A8-Ab2 1106A8H3 VH CDR3

<400> SEQUENCE: 33

```
Gly His Gly Ser Ser Tyr Phe Ser Tyr
1               5
```

<210> SEQ ID NO 34
<211> LENGTH: 106
<212> TYPE: PRT
<213> ORGANISM: Artificial Sequence
<220> FEATURE:
<223> OTHER INFORMATION: ACI-7067-1106A8-Ab2 1106A8H3 VL

<400> SEQUENCE: 34

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
```

```
            20                  25                  30

His Trp Tyr Gln Gln Lys Ser Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser His Pro Pro Thr
                85                  90                  95

Phe Gly Ala Gly Thr Lys Leu Glu Leu Lys
            100                 105
```

<210> SEQ ID NO 35
<211> LENGTH: 8
<212> TYPE: PRT
<213> ORGANISM: Artificial Sequence
<220> FEATURE:
<223> OTHER INFORMATION: ACI-7067-1106A8-Ab2 1106A8H3 VL CDR1

<400> SEQUENCE: 35

```
Ser Ala Ser Ser Ser Val Ser Tyr
1               5
```

<210> SEQ ID NO 36
<211> LENGTH: 7
<212> TYPE: PRT
<213> ORGANISM: Artificial Sequence
<220> FEATURE:
<223> OTHER INFORMATION: ACI-7067-1106A8-Ab2 1106A8H3 VL CDR2

<400> SEQUENCE: 36

```
Asp Thr Ser Asn Leu Ala Ser
1               5
```

<210> SEQ ID NO 37
<211> LENGTH: 9
<212> TYPE: PRT
<213> ORGANISM: Artificial Sequence
<220> FEATURE:
<223> OTHER INFORMATION: ACI-7067-1106A8-Ab2 1106A8H3 VL CDR3

<400> SEQUENCE: 37

```
Gln Gln Trp Asn Ser His Pro Pro Thr
1               5
```

<210> SEQ ID NO 38
<211> LENGTH: 360
<212> TYPE: DNA
<213> ORGANISM: Artificial Sequence
<220> FEATURE:
<223> OTHER INFORMATION: ACI-7067-1106A8-Ab2 1106A8H3 VH

<400> SEQUENCE: 38

```
gaggtgcagc ttgttgagtc tggtggagga ttggtgcagc ctaaaggatc attgaaactc     60

tcatgtgccg cctctggttt caccttcaat acctatgcca tgcactgggt ccgccaggct    120

ccaggaaagg gtttggaatg ggttgctcgc ataagaagta aaggtagtaa ttatgcaaca    180

aattatgccg attcagtgaa agacagattc accatctcca gagatgattc gcaaagcatg    240

ctctatctgc aaatgaacaa cctgaaaact gaggacacag ccatgtatta ctgtgtgaga    300

ggacacggta gtagctactt ttcttactgg ggccaaggga ctctggtcac tgtctctgca    360
```

<210> SEQ ID NO 39
<211> LENGTH: 318
<212> TYPE: DNA
<213> ORGANISM: Artificial Sequence
<220> FEATURE:
<223> OTHER INFORMATION: ACI-7067-1106A8-Ab2 1106A8H3 VL

<400> SEQUENCE: 39

```
caaattgttc tcacccagtc tccagcaatc atgtctgcat ctccagggga gaaggtcacc     60

atgacctgca gtgccagctc aagtgtaagt tacatgcact ggtaccagca gaagtcaggc    120

acctccccca aaagatggat ttatgacaca tccaatctgg cttctggagt ccctgctcgc    180

ttcagtggca gtgggtctgg gacctcttac tctctcacaa tcagcagcat ggaggctgaa    240

gatgctgcca cttattactg ccagcagtgg aatagtcacc cacccacgtt cggtgctggg    300

accaagctgg aactgaaa                                                  318
```

<210> SEQ ID NO 40
<211> LENGTH: 113
<212> TYPE: PRT
<213> ORGANISM: Artificial Sequence
<220> FEATURE:
<223> OTHER INFORMATION: ACI-7067-1107G5-Ab2 1107G5B6 VH

<400> SEQUENCE: 40

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Lys Tyr
            20                  25                  30

Trp Met His Trp Val Lys Gln Arg Pro Gly Gln Gly Leu Glu Trp Ile
        35                  40                  45

Gly Asn Ile Asn Pro Asn Asn Gly Asp Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Ala Met Asp Tyr Trp Gly Gln Gly Thr Ser Val Thr Val Ser
            100                 105                 110

Ser
```

<210> SEQ ID NO 41
<211> LENGTH: 5
<212> TYPE: PRT
<213> ORGANISM: Artificial Sequence
<220> FEATURE:
<223> OTHER INFORMATION: ACI-7067-1107G5-Ab2 1107G5B6 VH CDR1

<400> SEQUENCE: 41

```
Lys Tyr Trp Met His
1               5
```

<210> SEQ ID NO 42
<211> LENGTH: 17
<212> TYPE: PRT
<213> ORGANISM: Artificial Sequence
<220> FEATURE:
<223> OTHER INFORMATION: ACI-7067-1107G5-Ab2 1107G5B6 VH CDR2

<400> SEQUENCE: 42

```
Asn Ile Asn Pro Asn Asn Gly Asp Thr Asn Tyr Asn Glu Lys Phe Lys
1               5                   10                  15
```

Ser

<210> SEQ ID NO 43
<211> LENGTH: 4
<212> TYPE: PRT
<213> ORGANISM: Artificial Sequence
<220> FEATURE:
<223> OTHER INFORMATION: ACI-7067-1107G5-Ab2 1107G5B6 VH CDR3

<400> SEQUENCE: 43

Ala Met Asp Tyr
1

<210> SEQ ID NO 44
<211> LENGTH: 107
<212> TYPE: PRT
<213> ORGANISM: Artificial Sequence
<220> FEATURE:
<223> OTHER INFORMATION: ACI-7067-1107G5-Ab2 1107G5B6 VL

<400> SEQUENCE: 44

```
Asp Ile Gln Met Thr Gln Ser Pro Ser Ser Leu Ser Ala Phe Leu Gly
1               5                   10                  15

Glu Arg Val Ser Leu Thr Cys Arg Ala Ser Gln Asp Ile Gly Asn Asn
            20                  25                  30

Leu Asn Trp Phe Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Glu Tyr Ser Leu Thr Ile Ser Ser Leu Glu Ser
65                  70                  75                  80

Glu Asp Phe Val Asp Tyr Tyr Cys Leu Gln Phe Gly Ser Ser Pro Leu
                85                  90                  95

Thr Phe Gly Ala Gly Thr Lys Leu Glu Leu Lys
            100                 105
```

<210> SEQ ID NO 45
<211> LENGTH: 11
<212> TYPE: PRT
<213> ORGANISM: Artificial Sequence
<220> FEATURE:
<223> OTHER INFORMATION: ACI-7067-1107G5-Ab2 1107G5B6 VL CDR1

<400> SEQUENCE: 45

```
Arg Ala Ser Gln Asp Ile Gly Asn Asn Leu Asn
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: ACI-7067-1107G5-Ab2 1107G5B6 VL CDR2

<400> SEQUENCE: 46

```
Ala Thr Ser Ser Leu Asp Ser
1               5
```

<210> SEQ ID NO 47
<211> LENGTH: 9
<212> TYPE: PRT
<213> ORGANISM: Artificial Sequence
<220> FEATURE:

<223> OTHER INFORMATION: ACI-7067-1107G5-Ab2 1107G5B6 VL CDR3

<400> SEQUENCE: 47

Leu Gln Phe Gly Ser Ser Pro Leu Thr
1 5

<210> SEQ ID NO 48
<211> LENGTH: 339
<212> TYPE: DNA
<213> ORGANISM: Artificial Sequence
<220> FEATURE:
<223> OTHER INFORMATION: ACI-7067-1107G5-Ab2 1107G5B6 VH

<400> SEQUENCE: 48
caggtccaac tgcagcagcc tgggactgaa ctggtgaagc ctggggcttc agtgaagctg 60
tcctgcaagg cttctggcta caccttcacc aaatactgga tgcactgggt gaagcagagg 120
cctggacaag gccttgagtg gattggaaat attaatccta acaatggtga tactaactac 180
aatgagaagt tcaagagcaa ggccacactg actgtagaca aatcctccag cacagcctac 240
atgcagctca gcagtctgac atctgaggac tctgcggtct attattgtgc aattgctatg 300
gactactggg gtcaaggaac ctcagtcacc gtctcctca 339

<210> SEQ ID NO 49
<211> LENGTH: 321
<212> TYPE: DNA
<213> ORGANISM: Artificial Sequence
<220> FEATURE:
<223> OTHER INFORMATION: ACI-7067-1107G5-Ab2 1107G5B6 VL

<400> SEQUENCE: 49
gacatccaga tgacccagtc tccatcctcc ttatctgcct ttctgggaga aagagtcagt 60
ctcacttgtc gggcaagtca ggacattggt aataacttaa actggtttca gcaggaacca 120
gatggaacta ttaaacgtct gatctacgcc acatccagtt tagattctgg tgtccccaaa 180
aggttcagtg gcagtaggtc tgggtcagaa tattctctca ccatcagcag ccttgagtct 240
gaagattttg tagactatta ctgtctacaa tttggtagtt ctccgctcac gttcggtgct 300
gggaccaagc tggagctgaa a 321

<210> SEQ ID NO 50
<211> LENGTH: 114
<212> TYPE: PRT
<213> ORGANISM: Artificial Sequence
<220> FEATURE:
<223> OTHER INFORMATION: ACI-7067-1108H1-Ab1 1108H1E1 VH

<400> SEQUENCE: 50

Glu Val Lys Leu Val Glu Ser Gly Gly Gly Leu Val Gln Pro Gly Gly
1 5 10 15

Ser Met Lys Leu Ser Cys Thr Ala Ser Gly Phe Thr Phe Ser Asp Ala
20 25 30

Trp Met Asn Trp Val Arg Gln Ser Pro Glu Lys Gly Leu Glu Trp Val
35 40 45

Ala Glu Ile Arg Asn Lys Ala His Asn His Ala Thr Asn Tyr Ala Glu
50 55 60

Ser Val Lys Gly Arg Phe Thr Ile Ser Gly Asp Asp Ser Lys Ser Ser
65 70 75 80

Val Tyr Leu Gln Met Asn Asn Leu Arg Ala Glu Asp Thr Gly Ile Tyr
85 90 95

```
Tyr Cys Thr Ile Tyr Ser Phe Trp Gly Gln Gly Thr Leu Val Thr Val
            100                 105                 110

Ser Ala


<210> SEQ ID NO 51
<211> LENGTH: 4
<212> TYPE: PRT
<213> ORGANISM: Artificial Sequence
<220> FEATURE:
<223> OTHER INFORMATION: ACI-7067-1108H1-Ab1 1108H1E1 VH CDR1

<400> SEQUENCE: 51

Asp Ala Trp Met
1


<210> SEQ ID NO 52
<211> LENGTH: 19
<212> TYPE: PRT
<213> ORGANISM: Artificial Sequence
<220> FEATURE:
<223> OTHER INFORMATION: ACI-7067-1108H1-Ab1 1108H1E1 VH CDR2

<400> SEQUENCE: 52

Glu Ile Arg Asn Lys Ala His Asn His Ala Thr Asn Tyr Ala Glu Ser
1               5                   10                  15

Val Lys Gly


<210> SEQ ID NO 53
<211> LENGTH: 4
<212> TYPE: PRT
<213> ORGANISM: Artificial Sequence
<220> FEATURE:
<223> OTHER INFORMATION: ACI-7067-1108H1-Ab1 1108H1E1 VH CDR3
<220> FEATURE:
<221> NAME/KEY: VARIANT
<222> LOCATION: (1)..(1)
<223> OTHER INFORMATION: Xaa is any amino acid

<400> SEQUENCE: 53

Xaa Tyr Ser Phe
1


<210> SEQ ID NO 54
<211> LENGTH: 107
<212> TYPE: PRT
<213> ORGANISM: Artificial Sequence
<220> FEATURE:
<223> OTHER INFORMATION: ACI-7067-1108H1-Ab1 1108H1E1 VL

<400> SEQUENCE: 54

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Asn Tyr
            20                  25                  30

Val Ala Trp Tyr His Gln Lys Pro Gly Gln Ser Pro Lys Leu Leu Ile
        35                  40                  45

Tyr Ser Ala Ser Asn Arg Tyr Ser Gly Val Pro Asp Arg Phe Thr Gly
    50                  55                  60

Ser Gly Tyr Gly Thr Asp Phe Thr Phe Thr Ile Asn Thr Val Gln Thr
65                  70                  75                  80

Glu Asp Leu Ala Val Tyr Phe Cys Gln Gln Asp Tyr Arg Ile Pro Tyr
                85                  90                  95

Thr Phe Gly Gly Gly Thr Lys Leu Glu Ile Lys
```

100 105

<210> SEQ ID NO 55
<211> LENGTH: 11
<212> TYPE: PRT
<213> ORGANISM: Artificial Sequence
<220> FEATURE:
<223> OTHER INFORMATION: ACI-7067-1108H1-Ab1 1108H1E1 VL CDR1

<400> SEQUENCE: 55

Lys Ala Ser Gln Ser Val Thr Asn Tyr Val Ala
1 5 10

<210> SEQ ID NO 56
<211> LENGTH: 7
<212> TYPE: PRT
<213> ORGANISM: Artificial Sequence
<220> FEATURE:
<223> OTHER INFORMATION: ACI-7067-1108H1-Ab1 1108H1E1 VL CDR2

<400> SEQUENCE: 56

Ser Ala Ser Asn Arg Tyr Ser
1 5

<210> SEQ ID NO 57
<211> LENGTH: 9
<212> TYPE: PRT
<213> ORGANISM: Artificial Sequence
<220> FEATURE:
<223> OTHER INFORMATION: ACI-7067-1108H1-Ab1 1108H1E1 VL CDR3

<400> SEQUENCE: 57

Gln Gln Asp Tyr Arg Ile Pro Tyr Thr
1 5

<210> SEQ ID NO 58
<211> LENGTH: 342
<212> TYPE: DNA
<213> ORGANISM: Artificial Sequence
<220> FEATURE:
<223> OTHER INFORMATION: ACI-7067-1108H1-Ab1 1108H1E1 VH

<400> SEQUENCE: 58
gaggtgaagc tggtggagtc tggaggaggc ttggtgcaac ctggaggatc catgaaactc 60
tcttgtactg cctctggatt cacttttagt gacgcctgga tgaactgggt ccgccagtct 120
ccagagaagg ggcttgagtg ggttgctgaa attagaaaca aagctcataa tcatgcaaca 180
aactatgctg agtctgtgaa ggggaggttc accatctcag gagatgattc caaaagtagt 240
gtctacctgc aaatgaacaa cttaagagct gaagacactg gcatttatta ctgtaccatt 300
tactcttttt ggggccaagg gactctggtc actgtctctg ca 342

<210> SEQ ID NO 59
<211> LENGTH: 321
<212> TYPE: DNA
<213> ORGANISM: Artificial Sequence
<220> FEATURE:
<223> OTHER INFORMATION: ACI-7067-1108H1-Ab1 1108H1E1 VL

<400> SEQUENCE: 59
agtattgtga tgacccagac tcccaaattc ctgcttgtat cagcaggaga cagggttacc 60
ataacctgca aggccagtca gagtgtgact aattatgtag cttggtacca tcagaagcca 120
gggcagtctc ctaaactgct gatatactct gcatccaatc gctacagtgg agtccctgat 180
cgcttcactg gcagtggata tgggacggat ttcactttca ccatcaatac tgtgcagact 240
gaagacctgg cagtttattt ctgtcagcag gattacagga ttccgtacac gttcggaggg 300
gggactaagc tggaaataaa a 321

<210> SEQ ID NO 60
<211> LENGTH: 113
<212> TYPE: PRT
<213> ORGANISM: Artificial Sequence
<220> FEATURE:
<223> OTHER INFORMATION: ACI-7067-1111B12-Ab2 1111B12H10 VH

<400> SEQUENCE: 60

Gln Val Gln Leu Leu Gln Pro Gly Thr Ala Leu Val Met Pro Gly Ala
1 5 10 15

Ser Val Lys Leu Ser Cys Lys Ala Ser Gly Tyr Thr Phe Thr Thr Tyr
20 25 30

Trp Met His Trp Val Lys Gln Arg Pro Gly Gln Gly Leu Glu Trp Ile
35 40 45

Gly Asn Ile Asn Pro Ile Asn Gly Gly Ser Asn Tyr Asn Glu Lys Phe
50 55 60

Lys Ser Lys Ala Ser Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Val Ile Ala Met Asp Tyr Trp Gly Gln Gly Thr Ser Val Thr Val Ser
100 105 110

Ser

<210> SEQ ID NO 61
<211> LENGTH: 5
<212> TYPE: PRT
<213> ORGANISM: Artificial Sequence
<220> FEATURE:
<223> OTHER INFORMATION: ACI-7067-1111B12-Ab2 1111B12H10 VH CDR1

<400> SEQUENCE: 61

Thr Tyr Trp Met His
1 5

<210> SEQ ID NO 62
<211> LENGTH: 17
<212> TYPE: PRT
<213> ORGANISM: Artificial Sequence
<220> FEATURE:
<223> OTHER INFORMATION: ACI-7067-1111B12-Ab2 1111B12H10 VH CDR2

<400> SEQUENCE: 62

Asn Ile Asn Pro Ile Asn Gly Gly Ser Asn Tyr Asn Glu Lys Phe Lys
1 5 10 15

Ser

<210> SEQ ID NO 63
<211> LENGTH: 4
<212> TYPE: PRT
<213> ORGANISM: Artificial Sequence
<220> FEATURE:
<223> OTHER INFORMATION: ACI-7067-1111B12-Ab2 1111B12H10 VH CDR3

<400> SEQUENCE: 63

Ala Met Asp Tyr
1

<210> SEQ ID NO 64
<211> LENGTH: 107
<212> TYPE: PRT
<213> ORGANISM: Artificial Sequence
<220> FEATURE:
<223> OTHER INFORMATION: ACI-7067-1111B12-Ab2 1111B12H10 VL

<400> SEQUENCE: 64

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ile Ser
            20                  25                  30

Leu Asn Trp Phe Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Asn Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Phe Ala Ser Ser Pro Leu
                85                  90                  95

Thr Phe Gly Ala Gly Thr Lys Leu Glu Leu Lys
            100                 105

<210> SEQ ID NO 65
<211> LENGTH: 11
<212> TYPE: PRT
<213> ORGANISM: Artificial Sequence
<220> FEATURE:
<223> OTHER INFORMATION: ACI-7067-1111B12-Ab2 1111B12H10 VL CDR1

<400> SEQUENCE: 65

Arg Ala Ser Gln Asp Ile Gly Ile Ser Leu Asn
1               5                   10

<210> SEQ ID NO 66
<211> LENGTH: 7
<212> TYPE: PRT
<213> ORGANISM: Artificial Sequence
<220> FEATURE:
<223> OTHER INFORMATION: ACI-7067-1111B12-Ab2 1111B12H10 VL CDR2

<400> SEQUENCE: 66

Ala Thr Ser Ser Leu Asp Ser
1               5

<210> SEQ ID NO 67
<211> LENGTH: 9
<212> TYPE: PRT
<213> ORGANISM: Artificial Sequence
<220> FEATURE:
<223> OTHER INFORMATION: ACI-7067-1111B12-Ab2 1111B12H10 VL CDR3

<400> SEQUENCE: 67

Leu Gln Phe Ala Ser Ser Pro Leu Thr
1               5

<210> SEQ ID NO 68
<211> LENGTH: 339
<212> TYPE: DNA
<213> ORGANISM: Artificial Sequence
<220> FEATURE:
<223> OTHER INFORMATION: ACI-7067-1111B12-Ab2 1111B12H10 VH

<400> SEQUENCE: 68
caggtccaac tgctgcagcc tgggactgca ctggtgatgc ctggggcttc agtgaagctg 60
tcctgcaagg cttctggcta caccttcacc acctactgga tgcactgggt gaagcagagg 120
cctggacaag gccttgagtg gattggaaat attaatccta tcaatggtgg tagtaactac 180
aatgagaagt tcaagagcaa ggcctcactg actgtagaca agtcctccag cacagcctac 240
atgcagctca gcagcctgac atctgaggac tctgcggtct attattgtgt cattgctatg 300
gactactggg gtcaaggaac ctcagtcacc gtctcctca 339

<210> SEQ ID NO 69
<211> LENGTH: 321
<212> TYPE: DNA
<213> ORGANISM: Artificial Sequence
<220> FEATURE:
<223> OTHER INFORMATION: ACI-7067-1111B12-Ab2 1111B12H10 VL

<400> SEQUENCE: 69
gacatccaga tgacccagtc tccatcctcc ttatctgcct ctctgggaga aagagtcagt 60
ctcacatgtc gggcaagtca ggacattggt attagcttaa actggtttca gcaggaacca 120
gatggaacta ttaaacgcct gatctacgcc acatccagtt tagattctgg tgtccccaaa 180
aggttcagtg gcaataggtc tgggtcagat tattctctca ccatcagtag ccttgagtct 240
gaagattttg cagactatta ctgtctacaa tttgctagtt ctccgctcac gttcggtgct 300
gggaccaagc tggagctgaa a 321

<210> SEQ ID NO 70
<211> LENGTH: 114
<212> TYPE: PRT
<213> ORGANISM: Artificial Sequence
<220> FEATURE:
<223> OTHER INFORMATION: ACI-7067-1112H8-Ab2 1112H8C12 VH

<400> SEQUENCE: 70

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Thr Asp Ala
            20                  25                  30

Trp Met Asn Trp Val Arg Gln Ser Pro Glu Lys Gly Leu Glu Trp Ile
        35                  40                  45

Ala Glu Ile Arg Asn Lys Ala His Asn Tyr Ala Thr Tyr Tyr Ala Glu
    50                  55                  60

Ser Val Lys Gly Arg Phe Asp Ile Ser Gly Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Ile Tyr Ser Tyr Trp Gly Pro Gly Thr Leu Val Thr Val
            100                 105                 110

Ser Ala

<210> SEQ ID NO 71
<211> LENGTH: 4
<212> TYPE: PRT
<213> ORGANISM: Artificial Sequence
<220> FEATURE:
<223> OTHER INFORMATION: ACI-7067-1112H8-Ab2 1112H8C12 VH CDR1

<400> SEQUENCE: 71

```
Asp Ala Trp Met
1


<210> SEQ ID NO 72
<211> LENGTH: 19
<212> TYPE: PRT
<213> ORGANISM: Artificial Sequence
<220> FEATURE:
<223> OTHER INFORMATION: ACI-7067-1112H8-Ab2 1112H8C12 VH CDR2

<400> SEQUENCE: 72

Glu Ile Arg Asn Lys Ala His Asn Tyr Ala Thr Tyr Tyr Ala Glu Ser
1               5                   10                  15

Val Lys Gly


<210> SEQ ID NO 73
<211> LENGTH: 4
<212> TYPE: PRT
<213> ORGANISM: Artificial Sequence
<220> FEATURE:
<223> OTHER INFORMATION: ACI-7067-1112H8-Ab2 1112H8C12 VH CDR3
<220> FEATURE:
<221> NAME/KEY: VARIANT
<222> LOCATION: (1)..(1)
<223> OTHER INFORMATION: Xaa is any amino acid

<400> SEQUENCE: 73

Xaa Tyr Ser Tyr
1


<210> SEQ ID NO 74
<211> LENGTH: 107
<212> TYPE: PRT
<213> ORGANISM: Artificial Sequence
<220> FEATURE:
<223> OTHER INFORMATION: ACI-7067-1112H8-Ab2 1112H8C12 VL

<400> SEQUENCE: 74

Ser Ile Val Met Thr Gln Thr Pro Lys Phe Leu Leu Met Ser Pro Gly
1               5                   10                  15

Asp Arg Val Thr Met Thr Cys Thr Ala Ser Gln Ser Val Ser Asn Tyr
            20                  25                  30

Val Ala Trp Tyr Gln Gln Lys Pro Gly Gln Ser Pro Lys Leu Leu Ile
        35                  40                  45

Tyr Ser Ala Ser Asn Arg Phe Thr Gly Val Pro Asp Arg Phe Thr Gly
    50                  55                  60

Ser Gly Tyr Gly Thr Asp Phe Thr Phe Thr Ile Asn Thr Val Gln Thr
65                  70                  75                  80

Glu Asp Met Ala Val Tyr Phe Cys Gln Gln Asp Tyr Thr Ser Pro Tyr
                85                  90                  95

Thr Phe Gly Gly Gly Thr Lys Leu Glu Ile Lys
            100                 105


<210> SEQ ID NO 75
<211> LENGTH: 11
<212> TYPE: PRT
<213> ORGANISM: Artificial Sequence
<220> FEATURE:
<223> OTHER INFORMATION: ACI-7067-1112H8-Ab2 1112H8C12 VL CDR1

<400> SEQUENCE: 75

Thr Ala Ser Gln Ser Val Ser Asn Tyr Val Ala
1               5                   10
```

<210> SEQ ID NO 76
<211> LENGTH: 7
<212> TYPE: PRT
<213> ORGANISM: Artificial Sequence
<220> FEATURE:
<223> OTHER INFORMATION: ACI-7067-1112H8-Ab2 1112H8C12 VL CDR2

<400> SEQUENCE: 76

Ser Ala Ser Asn Arg Phe Thr
1               5

<210> SEQ ID NO 77
<211> LENGTH: 9
<212> TYPE: PRT
<213> ORGANISM: Artificial Sequence
<220> FEATURE:
<223> OTHER INFORMATION: ACI-7067-1112H8-Ab2 1112H8C12 VL CDR3

<400> SEQUENCE: 77

Gln Gln Asp Tyr Thr Ser Pro Tyr Thr
1               5

<210> SEQ ID NO 78
<211> LENGTH: 342
<212> TYPE: DNA
<213> ORGANISM: Artificial Sequence
<220> FEATURE:
<223> OTHER INFORMATION: ACI-7067-1112H8-Ab2 1112H8C12 VH

<400> SEQUENCE: 78
gaagtgaagc ttgaggagtc tggaggaggc ttggtgcaac ctggaggatc catgaaactc 60
tcttgtgctg cctctggatt cacttttact gacgcctgga tgaactgggt ccgccagtct 120
ccagaaaagg ggcttgagtg gattgctgaa attagaaaca aagctcataa ttatgcaaca 180
tactatgctg agtctgtgaa agggaggttc gacatctcag gagatgattc caaaagtagt 240
gtctacctgc aaatgaacaa cttgagagtt gaagacactg gcatttatta ctgtaccatt 300
tactcttact ggggcccagg gactctggtc actgtctctg ca 342

<210> SEQ ID NO 79
<211> LENGTH: 321
<212> TYPE: DNA
<213> ORGANISM: Artificial Sequence
<220> FEATURE:
<223> OTHER INFORMATION: ACI-7067-1112H8-Ab2 1112H8C12 VL

<400> SEQUENCE: 79
agtattgtga tgacccagac tcccaaattc ctgcttatgt caccaggaga cagggttacc 60
atgacctgca cggccagtca gagtgtgagt aattatgtgg cttggtacca acagaagcca 120
gggcagtctc ctaaactgct gatatactct gcatccaatc gcttcactgg agtccctgat 180
cgcttcactg gcagtggata tgggacggat ttcactttca ccatcaacac tgtgcagact 240
gaagacatgg cagtttattt ctgtcagcag gattacacct ctccgtacac gttcgggggg 300
gggaccaagc tggaaataaa a 321

<210> SEQ ID NO 80
<211> LENGTH: 120
<212> TYPE: PRT
<213> ORGANISM: Artificial Sequence
<220> FEATURE:
<223> OTHER INFORMATION: ACI-7067-1108B11-Ab2 1108B11D3 VH

<400> SEQUENCE: 80

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met His Trp Val Arg Gln Ala Pro Gly Lys Gly Leu Glu Trp Val
35 40 45

Ala Arg Ile Arg Ser Lys Gly Ser Asn Tyr Ala Thr Asn Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Arg Gly His Gly Ser Ser Tyr Phe Ser Tyr Trp Gly Gln
100 105 110

Gly Thr Leu Val Thr Val Ser Ala
115 120

<210> SEQ ID NO 81
<211> LENGTH: 5
<212> TYPE: PRT
<213> ORGANISM: Artificial Sequence
<220> FEATURE:
<223> OTHER INFORMATION: ACI-7067-1108B11-Ab2 1108B11D3 VH CDR1

<400> SEQUENCE: 81

Thr Tyr Ala Met His
1 5

<210> SEQ ID NO 82
<211> LENGTH: 19
<212> TYPE: PRT
<213> ORGANISM: Artificial Sequence
<220> FEATURE:
<223> OTHER INFORMATION: ACI-7067-1108B11-Ab2 1108B11D3 VH CDR2

<400> SEQUENCE: 82

Arg Ile Arg Ser Lys Gly Ser Asn Tyr Ala Thr Asn Tyr Ala Asp Ser
1 5 10 15

Val Lys Asp

<210> SEQ ID NO 83
<211> LENGTH: 9
<212> TYPE: PRT
<213> ORGANISM: Artificial Sequence
<220> FEATURE:
<223> OTHER INFORMATION: ACI-7067-1108B11-Ab2 1108B11D3 VH CDR3

<400> SEQUENCE: 83

Gly His Gly Ser Ser Tyr Phe Ser Tyr
1 5

<210> SEQ ID NO 84
<211> LENGTH: 106
<212> TYPE: PRT
<213> ORGANISM: Artificial Sequence
<220> FEATURE:
<223> OTHER INFORMATION: ACI-7067-1108B11-Ab2 1108B11D3 VL

<400> SEQUENCE: 84

Gln Ile Val Leu Thr Gln Ser Pro Ala Ile Met Ser Ala Ser Pro Gly
1 5 10 15

Glu Arg Ile Thr Met Thr Cys Ser Ala Asn Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Lys Ser His Pro Pro Thr
                85                  90                  95

Phe Gly Ala Gly Thr Lys Leu Glu Leu Lys
            100                 105

<210> SEQ ID NO 85
<211> LENGTH: 10
<212> TYPE: PRT
<213> ORGANISM: Artificial Sequence
<220> FEATURE:
<223> OTHER INFORMATION: ACI-7067-1108B11-Ab2 1108B11D3 VL CDR1

<400> SEQUENCE: 85

Ser Ala Asn Ser Ser Val Thr Tyr Met His
1               5                   10

<210> SEQ ID NO 86
<211> LENGTH: 7
<212> TYPE: PRT
<213> ORGANISM: Artificial Sequence
<220> FEATURE:
<223> OTHER INFORMATION: ACI-7067-1108B11-Ab2 1108B11D3 VL CDR2

<400> SEQUENCE: 86

Asp Thr Ser Asn Leu Ala Ser
1               5

<210> SEQ ID NO 87
<211> LENGTH: 9
<212> TYPE: PRT
<213> ORGANISM: Artificial Sequence
<220> FEATURE:
<223> OTHER INFORMATION: ACI-7067-1108B11-Ab2 1108B11D3 VL CDR3

<400> SEQUENCE: 87

Gln Gln Trp Lys Ser His Pro Pro Thr
1               5

<210> SEQ ID NO 88
<211> LENGTH: 360
<212> TYPE: DNA
<213> ORGANISM: Artificial Sequence
<220> FEATURE:
<223> OTHER INFORMATION: ACI-7067-1108B11-Ab2 1108B11D3 VH

<400> SEQUENCE: 88
gaggtgcagc ttgttgagtc tggtggagga ttggtgcagc ctaaaggatc attgaaactc     60
tcatgtgccg cctctggttt caccttcaat acctatgcca tgcactgggt ccgccaggct    120
ccaggaaagg gtttggaatg ggttgctcgc ataagaagta aaggtagtaa ttatgcaaca    180
aattatgccg attcagtgaa agacagattc accatctcca gagatgattc gcaaagcatg    240
ctctatctgc aaatgaacaa cctgaaaact gaggacacag ccatgtatta ctgtgtgaga    300
ggacacggta gtagctactt ttcttactgg ggccaaggga ctctggtcac tgtctctgca    360

<210> SEQ ID NO 89
<211> LENGTH: 318
<212> TYPE: DNA
<213> ORGANISM: Artificial Sequence
<220> FEATURE:
<223> OTHER INFORMATION: ACI-7067-1108B11-Ab2 1108B11D3 VL

<400> SEQUENCE: 89
caaattgttc tcacccagtc tccagcaatc atgtctgcat ctccagggga gaggatcacc 60
atgacctgca gtgccaactc aagtgttact tacatgcact ggtaccagca gaagtcaggc 120
acctccccca aaagatggat ttatgacaca tccaatctgg cttctggagt ccctgctcgc 180
ttcagtggca gtgggtctgg gacctcttac tctctcacaa tcagcagcat ggaggctgaa 240
gatgctgcca cttattactg ccagcagtgg aaaagtcacc cacccacgtt cggtgctggg 300
accaagctgg aactgaaa 318

<210> SEQ ID NO 90
<211> LENGTH: 119
<212> TYPE: PRT
<213> ORGANISM: Artificial Sequence
<220> FEATURE:
<223> OTHER INFORMATION: ACI-7067-1113D10-Ab1 1113D10E3D5 VH

<400> SEQUENCE: 90

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Leu His Trp Val Arg Gln Ala Pro Gly Lys Gly Leu Glu Trp Val
35 40 45

Ala Arg Ile Arg Ser Lys Ser Ser Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Gly Met Tyr
85 90 95

Tyr Cys Val Arg Gly Gly Val Ser Pro Phe Asp Tyr Trp Gly Gln Gly
100 105 110

Thr Thr Leu Thr Val Ser Ser
115

<210> SEQ ID NO 91
<211> LENGTH: 5
<212> TYPE: PRT
<213> ORGANISM: Artificial Sequence
<220> FEATURE:
<223> OTHER INFORMATION: ACI-7067-1113D10-Ab1 1113D10E3D5 VH CDR1

<400> SEQUENCE: 91

Thr Tyr Ala Leu His
1 5

<210> SEQ ID NO 92
<211> LENGTH: 19
<212> TYPE: PRT
<213> ORGANISM: Artificial Sequence
<220> FEATURE:
<223> OTHER INFORMATION: ACI-7067-1113D10-Ab1 1113D10E3D5 VH CDR2

<400> SEQUENCE: 92

```
Arg Ile Arg Ser Lys Ser Ser Asn Tyr Ala Thr Tyr Tyr Ala Asp Ser
1               5                   10                  15

Val Lys Asp


<210> SEQ ID NO 93
<211> LENGTH: 8
<212> TYPE: PRT
<213> ORGANISM: Artificial Sequence
<220> FEATURE:
<223> OTHER INFORMATION: ACI-7067-1113D10-Ab1 1113D10E3D5 VH CDR3

<400> SEQUENCE: 93

Gly Gly Val Ser Pro Phe Asp Tyr
1               5


<210> SEQ ID NO 94
<211> LENGTH: 106
<212> TYPE: PRT
<213> ORGANISM: Artificial Sequence
<220> FEATURE:
<223> OTHER INFORMATION: ACI-7067-1113D10-Ab1 1113D10E3D5 VL

<400> SEQUENCE: 94

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ser Ala Thr Tyr Tyr Cys Gln Gln Trp Ser Asn Asn Pro Pro Thr
                85                  90                  95

Phe Gly Gly Gly Thr Lys Leu Glu Ile Lys
            100                 105


<210> SEQ ID NO 95
<211> LENGTH: 10
<212> TYPE: PRT
<213> ORGANISM: Artificial Sequence
<220> FEATURE:
<223> OTHER INFORMATION: ACI-7067-1113D10-Ab1 1113D10E3D5 VL CDR1

<400> SEQUENCE: 95

Ser Ala Ser Ser Ser Val Ser Tyr Met His
1               5                   10


<210> SEQ ID NO 96
<211> LENGTH: 7
<212> TYPE: PRT
<213> ORGANISM: Artificial Sequence
<220> FEATURE:
<223> OTHER INFORMATION: ACI-7067-1113D10-Ab1 1113D10E3D5 VL CDR2

<400> SEQUENCE: 96

Asp Thr Ser Lys Leu Ala Ser
1               5


<210> SEQ ID NO 97
<211> LENGTH: 9
<212> TYPE: PRT
```

<213> ORGANISM: Artificial Sequence
<220> FEATURE:
<223> OTHER INFORMATION: ACI-7067-1113D10-Ab1 1113D10E3D5 VL CDR3

<400> SEQUENCE: 97

Gln Gln Trp Ser Asn Asn Pro Pro Thr
1 5

<210> SEQ ID NO 98
<211> LENGTH: 357
<212> TYPE: DNA
<213> ORGANISM: Artificial Sequence
<220> FEATURE:
<223> OTHER INFORMATION: ACI-7067-1113D10-Ab1 1113D10E3D5 VH

<400> SEQUENCE: 98
gaggtgcagc ttgttgagtc tggtggagga ttggtgcagc ctaaaggatc attgaaactc 60
tcatgtgccg cctctggttt caccttcaat acctatgccc tgcactgggt ccgccaggct 120
ccaggaaagg gtttggaatg ggttgctcgc ataagaagta aaagtagtaa ttatgcaaca 180
tattatgccg attcagtgaa agacagattc accatctcca gagatgattc acaaagcatg 240
ctctatctgc aaatgaacaa cctgaaaact gaggacacag gcatgtatta ctgtgtaaga 300
gggggtgttt ctccctttga ctactggggc caaggcacca ctctcacagt ctcctca 357

<210> SEQ ID NO 99
<211> LENGTH: 318
<212> TYPE: DNA
<213> ORGANISM: Artificial Sequence
<220> FEATURE:
<223> OTHER INFORMATION: ACI-7067-1113D10-Ab1 1113D10E3D5 VL

<400> SEQUENCE: 99
caaattgttc tcacccagtc tccagcaatc atgtctgcat ctccagggga gaaggtcacc 60
atgacctgca gtgccagctc aagtgtaagt tacatgcact ggtaccagca gaagtcaggc 120
acctccccca aaagatggat ttatgacaca tccaaactgg cttctggagt ccctgctcgc 180
ttcagtggca gtgggtctgg gacctcttac tctctcacaa tcagcagcat ggaggctgaa 240
gattctgcca cttattactg ccagcagtgg agtaataacc caccgacgtt cggtggaggc 300
accaagctgg aaatcaaa 318

<210> SEQ ID NO 100
<211> LENGTH: 113
<212> TYPE: PRT
<213> ORGANISM: Artificial Sequence
<220> FEATURE:
<223> OTHER INFORMATION: ACI-7067-1116F2-Ab1 1116F2A2 VH

<400> SEQUENCE: 100

Asp Val Gln Leu Gln Glu Ser Gly Pro Gly Phe Val Lys Pro Ser Gln
1 5 10 15

Ser Leu Ser Leu Thr Cys Ser Val Thr Gly Tyr Ser Ile Thr Arg Gly
20 25 30

Phe Tyr Trp Asn Trp Ile Arg Gln Phe Pro Gly Asn Lys Leu Glu Trp
35 40 45

Met Gly Tyr Ile Ser Asp Asp Gly Asn Ser Asn Tyr Asn Pro Ser Leu
50 55 60

Lys Asn Arg Ile Ser Ile Thr Arg Asp Thr Phe Lys Asn Gln Val Phe
65 70 75 80

Leu Arg Leu Asn Ser Val Thr Thr Glu Asp Thr Ala Thr Tyr Tyr Cys

```
                85                  90                  95

Thr Arg Gly Asp Leu Leu Trp Gly Gln Gly Thr Thr Leu Thr Val Ser
            100                 105                 110

Ser
```

<210> SEQ ID NO 101
<211> LENGTH: 6
<212> TYPE: PRT
<213> ORGANISM: Artificial Sequence
<220> FEATURE:
<223> OTHER INFORMATION: ACI-7067-1116F2-Ab1 1116F2A2 VH CDR1

<400> SEQUENCE: 101

```
Arg Gly Phe Tyr Trp Asn
1               5
```

<210> SEQ ID NO 102
<211> LENGTH: 16
<212> TYPE: PRT
<213> ORGANISM: Artificial Sequence
<220> FEATURE:
<223> OTHER INFORMATION: ACI-7067-1116F2-Ab1 1116F2A2 VH CDR2

<400> SEQUENCE: 102

```
Tyr Ile Ser Asp Asp Gly Asn Ser Asn Tyr Asn Pro Ser Leu Lys Asn
1               5                   10                  15
```

<210> SEQ ID NO 103
<211> LENGTH: 4
<212> TYPE: PRT
<213> ORGANISM: Artificial Sequence
<220> FEATURE:
<223> OTHER INFORMATION: ACI-7067-1116F2-Ab1 1116F2A2 VH CDR3

<400> SEQUENCE: 103

```
Gly Asp Leu Leu
1
```

<210> SEQ ID NO 104
<211> LENGTH: 112
<212> TYPE: PRT
<213> ORGANISM: Artificial Sequence
<220> FEATURE:
<223> OTHER INFORMATION: ACI-7067-1116F2-Ab1 1116F2A2 VL

<400> SEQUENCE: 104

```
Asp Val Val Met Thr Gln Thr Ala Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Ala Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 105

<211> LENGTH: 16
<212> TYPE: PRT
<213> ORGANISM: Artificial Sequence
<220> FEATURE:
<223> OTHER INFORMATION: ACI-7067-1116F2-Ab1 1116F2A2 VL CDR1

<400> SEQUENCE: 105

Lys Ser Ser Gln Ser Leu Leu Asp Ser Asp Gly Glu Thr Tyr Leu Asn
1 5 10 15

<210> SEQ ID NO 106
<211> LENGTH: 7
<212> TYPE: PRT
<213> ORGANISM: Artificial Sequence
<220> FEATURE:
<223> OTHER INFORMATION: ACI-7067-1116F2-Ab1 1116F2A2 VL CDR2

<400> SEQUENCE: 106

Leu Val Ser Lys Leu Asp Ser
1 5

<210> SEQ ID NO 107
<211> LENGTH: 9
<212> TYPE: PRT
<213> ORGANISM: Artificial Sequence
<220> FEATURE:
<223> OTHER INFORMATION: ACI-7067-1116F2-Ab1 1116F2A2 VL CDR3

<400> SEQUENCE: 107

Trp Gln Gly Thr His Phe Pro Gln Thr
1 5

<210> SEQ ID NO 108
<211> LENGTH: 339
<212> TYPE: DNA
<213> ORGANISM: Artificial Sequence
<220> FEATURE:
<223> OTHER INFORMATION: ACI-7067-1116F2-Ab1 1116F2A2 VH

<400> SEQUENCE: 108
gatgtacaac ttcaggagtc aggacctggc ttcgtgaaac cttctcagtc tctgtctctc 60
acctgctctg tcactggcta ctcaataacc agaggttttt actggaactg gatccgacag 120
tttccaggaa acaaactgga atggatgggc tacataagtg acgatggtaa tagtaactac 180
aatccctctc tcaaaaatcg aatctccatc actcgtgaca catttaagaa tcaggttttc 240
ctgaggttga actctgtgac tactgaggac actgccacat actattgtac aagaggagat 300
ctactttggg gccaaggcac cactctcaca gtctcctca 339

<210> SEQ ID NO 109
<211> LENGTH: 336
<212> TYPE: DNA
<213> ORGANISM: Artificial Sequence
<220> FEATURE:
<223> OTHER INFORMATION: ACI-7067-1116F2-Ab1 1116F2A2 VL

<400> SEQUENCE: 109
gatgttgtga tgacccagac tgcactcact ttgtcggtta ccattggaca accagcctcc 60
atctcttgca agtcaagtca aagcctctta gatagtgatg gagagacata tttgaattgg 120
ttgttacaga ggccaggcca gtctccaaag cgcctaatct atctggtgtc taaactggac 180
tctggagtcc ctgacaggtt cactggtagt ggatcaggga cagatttcgc actgaaaatc 240
agcagagtgg aggctgagga cttgggaatt tattattgct ggcaaggtac acattttcct 300
cagacgttcg gtggaggcac caagctggaa atcaaa 336

<210> SEQ ID NO 110
<211> LENGTH: 123
<212> TYPE: PRT
<213> ORGANISM: Artificial Sequence
<220> FEATURE:
<223> OTHER INFORMATION: ACI-7067-1206E5-Ab1 1206E5D2 VH

<400> SEQUENCE: 110

Gln Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Val Ile Ser Trp Val Lys Gln Gly Thr Gly Gln Gly Leu Glu Trp Ile
35 40 45

Gly Glu Ile Tyr Pro Gly Asn Asp Ser Thr Tyr Tyr Asn Glu Lys Phe
50 55 60

Lys Gly Lys Ala Thr Leu Thr Ala Asp Lys Ser Ser Asn Thr Ala Tyr
65 70 75 80

Met Gln Leu Ser Ser Leu Thr Ser Glu Asp Ser Ala Val Tyr Phe Cys
85 90 95

Ala Arg Glu Gly Val Ser Asn Gly Tyr Leu Tyr Leu Ser Met Asp Tyr
100 105 110

Trp Gly Gln Gly Thr Ser Val Thr Val Ser Ser
115 120

<210> SEQ ID NO 111
<211> LENGTH: 5
<212> TYPE: PRT
<213> ORGANISM: Artificial Sequence
<220> FEATURE:
<223> OTHER INFORMATION: ACI-7067-1206E5-Ab1 1206E5D2 VH CDR1

<400> SEQUENCE: 111

Asp Tyr Val Ile Ser
1 5

<210> SEQ ID NO 112
<211> LENGTH: 17
<212> TYPE: PRT
<213> ORGANISM: Artificial Sequence
<220> FEATURE:
<223> OTHER INFORMATION: ACI-7067-1206E5-Ab1 1206E5D2 VH CDR2

<400> SEQUENCE: 112

Glu Ile Tyr Pro Gly Asn Asp Ser Thr Tyr Tyr Asn Glu Lys Phe Lys
1 5 10 15

Gly

<210> SEQ ID NO 113
<211> LENGTH: 14
<212> TYPE: PRT
<213> ORGANISM: Artificial Sequence
<220> FEATURE:
<223> OTHER INFORMATION: ACI-7067-1206E5-Ab1 1206E5D2 VH CDR3

<400> SEQUENCE: 113

Glu Gly Val Ser Asn Gly Tyr Leu Tyr Leu Ser Met Asp Tyr
1 5 10

<210> SEQ ID NO 114

<211> LENGTH: 112
<212> TYPE: PRT
<213> ORGANISM: Artificial Sequence
<220> FEATURE:
<223> OTHER INFORMATION: ACI-7067-1206E5-Ab1 1206E5D2 VL

<400> SEQUENCE: 114

Asp Val Leu Met Thr Gln Thr Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asn Gly Lys Thr Tyr Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Val Gln Gly
85 90 95

Thr His Phe Pro Trp Thr Phe Gly Gly Gly Thr Lys Leu Glu Ile Lys
100 105 110

<210> SEQ ID NO 115
<211> LENGTH: 16
<212> TYPE: PRT
<213> ORGANISM: Artificial Sequence
<220> FEATURE:
<223> OTHER INFORMATION: ACI-7067-1206E5-Ab1 1206E5D2 VL CDR1

<400> SEQUENCE: 115

Lys Ser Ser Gln Ser Leu Leu Tyr Ser Asn Gly Lys Thr Tyr Leu Asn
1 5 10 15

<210> SEQ ID NO 116
<211> LENGTH: 7
<212> TYPE: PRT
<213> ORGANISM: Artificial Sequence
<220> FEATURE:
<223> OTHER INFORMATION: ACI-7067-1206E5-Ab1 1206E5D2 VL CDR2

<400> SEQUENCE: 116

Leu Val Ser Lys Leu Asp Ser
1 5

<210> SEQ ID NO 117
<211> LENGTH: 9
<212> TYPE: PRT
<213> ORGANISM: Artificial Sequence
<220> FEATURE:
<223> OTHER INFORMATION: ACI-7067-1206E5-Ab1 1206E5D2 VL CDR3

<400> SEQUENCE: 117

Val Gln Gly Thr His Phe Pro Trp Thr
1 5

<210> SEQ ID NO 118
<211> LENGTH: 369
<212> TYPE: DNA
<213> ORGANISM: Artificial Sequence
<220> FEATURE:
<223> OTHER INFORMATION: ACI-7067-1206E5-Ab1 1206E5D2 VH

<400> SEQUENCE: 118
caggttcagc tgcagcagtc tggacctgag ctggtgaagc ctggggcttc agtgaagatg 60

```
tcctgcaagg cttctggata cacattcact gactatgtta taagctgggt gaagcaggga    120

actggacagg gccttgagtg gattggagag atttatcctg gaaatgatag tacttactac    180

aatgagaagt tcaagggcaa ggccacactg actgcagaca aatcctccaa cacagcctac    240

atgcagctca gcagcctgac atctgaggac tctgcggtct atttctgtgc aagagagggg    300

gtctctaatg gttacctata tttgtctatg gactactggg gtcaaggaac ctcagtcacc    360

gtctcctca                                                            369


<210> SEQ ID NO 119
<211> LENGTH: 336
<212> TYPE: DNA
<213> ORGANISM: Artificial Sequence
<220> FEATURE:
<223> OTHER INFORMATION: ACI-7067-1206E5-Ab1 1206E5D2 VL

<400> SEQUENCE: 119

gatgttttga tgacccaaac tccactcact ttgtcggtta ccattggaca accagcctct     60

atctcttgca agtcaagtca gagcctctta tatagtaatg gaaaaaccta tttgaattgg    120

ttattacaga ggccaggcca gtctccaaag cgcctaatct atctggtgtc taaactggac    180

tctggagtcc ctgacaggtt cactggcagt ggatcaggaa cagattttac actgaaaatc    240

agcagagtgg aggctgagga tttgggagtt tattactgcg tgcaaggtac acattttccg    300

tggacgttcg gtggaggcac caagctggaa atcaaa                              336


<210> SEQ ID NO 120
<211> LENGTH: 14
<212> TYPE: PRT
<213> ORGANISM: Unknown
<220> FEATURE:
<223> OTHER INFORMATION: Organism of the class Mammalia

<400> SEQUENCE: 120

Met Asp Val Phe Met Lys Gly Leu Ser Lys Ala Lys Glu Gly
1               5                   10


<210> SEQ ID NO 121
<211> LENGTH: 15
<212> TYPE: PRT
<213> ORGANISM: Unknown
<220> FEATURE:
<223> OTHER INFORMATION: Organism of the class Mammalia

<400> SEQUENCE: 121

Met Asp Val Phe Met Lys Gly Leu Ser Lys Ala Lys Glu Gly Val
1               5                   10                  15


<210> SEQ ID NO 122
<211> LENGTH: 15
<212> TYPE: PRT
<213> ORGANISM: Unknown
<220> FEATURE:
<223> OTHER INFORMATION: Organism of the class Mammalia

<400> SEQUENCE: 122

Lys Ala Lys Glu Gly Val Val Ala Ala Ala Glu Lys Thr Lys Gln
1               5                   10                  15


<210> SEQ ID NO 123
<211> LENGTH: 15
<212> TYPE: PRT
<213> ORGANISM: Unknown
```

<220> FEATURE:
<223> OTHER INFORMATION: Organism of the class Mammalia

<400> SEQUENCE: 123

Ala Glu Lys Thr Lys Gln Gly Val Ala Glu Ala Ala Gly Lys Thr
1 5 10 15

<210> SEQ ID NO 124
<211> LENGTH: 15
<212> TYPE: PRT
<213> ORGANISM: Unknown
<220> FEATURE:
<223> OTHER INFORMATION: Organism of the class Mammalia

<400> SEQUENCE: 124

Glu Ala Ala Gly Lys Thr Lys Glu Gly Val Leu Tyr Val Gly Ser
1 5 10 15

<210> SEQ ID NO 125
<211> LENGTH: 15
<212> TYPE: PRT
<213> ORGANISM: Unknown
<220> FEATURE:
<223> OTHER INFORMATION: Organism of the class Mammalia

<400> SEQUENCE: 125

Val Leu Tyr Val Gly Ser Lys Thr Lys Glu Gly Val Val His Gly
1 5 10 15

<210> SEQ ID NO 126
<211> LENGTH: 15
<212> TYPE: PRT
<213> ORGANISM: Unknown
<220> FEATURE:
<223> OTHER INFORMATION: Organism of the class Mammalia

<400> SEQUENCE: 126

Glu Gly Val Val His Gly Val Ala Thr Val Ala Glu Lys Thr Lys
1 5 10 15

<210> SEQ ID NO 127
<211> LENGTH: 15
<212> TYPE: PRT
<213> ORGANISM: Unknown
<220> FEATURE:
<223> OTHER INFORMATION: Organism of the class Mammalia

<400> SEQUENCE: 127

Val Ala Glu Lys Thr Lys Glu Gln Val Thr Asn Val Gly Gly Ala
1 5 10 15

<210> SEQ ID NO 128
<211> LENGTH: 15
<212> TYPE: PRT
<213> ORGANISM: Unknown
<220> FEATURE:
<223> OTHER INFORMATION: Organism of the class Mammalia

<400> SEQUENCE: 128

Thr Asn Val Gly Gly Ala Val Val Thr Gly Val Thr Ala Val Ala
1 5 10 15

<210> SEQ ID NO 129
<211> LENGTH: 15
<212> TYPE: PRT
<213> ORGANISM: Unknown
<220> FEATURE:

<223> OTHER INFORMATION: Organism of the class Mammalia

<400> SEQUENCE: 129

Gly Val Thr Ala Val Ala Gln Lys Thr Val Glu Gly Ala Gly Ser
1 5 10 15

<210> SEQ ID NO 130
<211> LENGTH: 15
<212> TYPE: PRT
<213> ORGANISM: Unknown
<220> FEATURE:
<223> OTHER INFORMATION: Organism of the class Mammalia

<400> SEQUENCE: 130

Val Glu Gly Ala Gly Ser Ile Ala Ala Ala Thr Gly Phe Val Lys
1 5 10 15

<210> SEQ ID NO 131
<211> LENGTH: 15
<212> TYPE: PRT
<213> ORGANISM: Unknown
<220> FEATURE:
<223> OTHER INFORMATION: Organism of the class Mammalia

<400> SEQUENCE: 131

Ala Thr Gly Phe Val Lys Lys Asp Gln Leu Gly Lys Asn Glu Glu
1 5 10 15

<210> SEQ ID NO 132
<211> LENGTH: 15
<212> TYPE: PRT
<213> ORGANISM: Unknown
<220> FEATURE:
<223> OTHER INFORMATION: Organism of the class Mammalia

<400> SEQUENCE: 132

Leu Gly Lys Asn Glu Glu Gly Ala Pro Gln Glu Gly Ile Leu Glu
1 5 10 15

<210> SEQ ID NO 133
<211> LENGTH: 15
<212> TYPE: PRT
<213> ORGANISM: Unknown
<220> FEATURE:
<223> OTHER INFORMATION: Organism of the class Mammalia

<400> SEQUENCE: 133

Gln Glu Gly Ile Leu Glu Asp Met Pro Val Asp Pro Asp Asn Glu
1 5 10 15

<210> SEQ ID NO 134
<211> LENGTH: 15
<212> TYPE: PRT
<213> ORGANISM: Unknown
<220> FEATURE:
<223> OTHER INFORMATION: Organism of the class Mammalia

<400> SEQUENCE: 134

Val Asp Pro Asp Asn Glu Ala Tyr Glu Met Pro Ser Glu Glu Gly
1 5 10 15

<210> SEQ ID NO 135
<211> LENGTH: 14
<212> TYPE: PRT
<213> ORGANISM: Unknown
<220> FEATURE:
<223> OTHER INFORMATION: Organism of the class Mammalia

<400> SEQUENCE: 135

Met Pro Ser Glu Glu Gly Tyr Gln Asp Tyr Glu Pro Glu Ala
1               5                   10

<210> SEQ ID NO 136
<211> LENGTH: 8
<212> TYPE: PRT
<213> ORGANISM: Unknown
<220> FEATURE:
<223> OTHER INFORMATION: Organism of the class Mammalia

<400> SEQUENCE: 136

Gly Val Ala Thr Val Ala Glu Lys
1               5

<210> SEQ ID NO 137
<211> LENGTH: 40
<212> TYPE: PRT
<213> ORGANISM: Unknown
<220> FEATURE:
<223> OTHER INFORMATION: Organism of the class Mammalia

<400> SEQUENCE: 137

Thr Val Glu Gly Ala Gly Ser Ile Ala Ala Ala Thr Gly Phe Val Lys
1               5                   10                  15

Lys Asp Gln Leu Gly Lys Asn Glu Glu Gly Ala Pro Gln Glu Gly Ile
            20                  25                  30

Leu Glu Asp Met Pro Val Asp Pro
        35                  40

<210> SEQ ID NO 138

<400> SEQUENCE: 138

000

<210> SEQ ID NO 139

<400> SEQUENCE: 139

000

<210> SEQ ID NO 140
<211> LENGTH: 121
<212> TYPE: PRT
<213> ORGANISM: Artificial Sequence
<220> FEATURE:
<223> OTHER INFORMATION: ACI-7079-2501G2-Ab2 2501G2E5 VH

<400> SEQUENCE: 140

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Asn Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Thr Lys Ser Asn Asn Phe Ala Thr Tyr Tyr Ala His
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

```
Tyr Cys Val Arg Gln Gly Leu Ala Tyr Tyr Ala Met Asp Tyr Trp Gly
            100                 105                 110

Gln Gly Thr Ser Val Thr Val Ser Ser
        115                 120


<210> SEQ ID NO 141
<211> LENGTH: 5
<212> TYPE: PRT
<213> ORGANISM: Artificial Sequence
<220> FEATURE:
<223> OTHER INFORMATION: ACI-7079-2501G2-Ab2 2501G2E5 VH CDR1

<400> SEQUENCE: 141

Thr Tyr Ala Met Asn
1               5


<210> SEQ ID NO 142
<211> LENGTH: 19
<212> TYPE: PRT
<213> ORGANISM: Artificial Sequence
<220> FEATURE:
<223> OTHER INFORMATION: ACI-7079-2501G2-Ab2 2501G2E5 VH CDR2

<400> SEQUENCE: 142

Arg Ile Arg Thr Lys Ser Asn Asn Phe Ala Thr Tyr Tyr Ala His Ser
1               5                   10                  15

Val Lys Asp


<210> SEQ ID NO 143
<211> LENGTH: 10
<212> TYPE: PRT
<213> ORGANISM: Artificial Sequence
<220> FEATURE:
<223> OTHER INFORMATION: ACI-7079-2501G2-Ab2 2501G2E5 VH CDR3

<400> SEQUENCE: 143

Gln Gly Leu Ala Tyr Tyr Ala Met Asp Tyr
1               5                   10


<210> SEQ ID NO 144
<211> LENGTH: 112
<212> TYPE: PRT
<213> ORGANISM: Artificial Sequence
<220> FEATURE:
<223> OTHER INFORMATION: ACI-7079-2501G2-Ab2 2501G2E5 VL

<400> SEQUENCE: 144

Asp Val Leu Met Thr Gln Thr Pro Leu Ser Leu Pro Val Ser Leu Gly
1               5                   10                  15

Asp Gln Val Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Gln Gly Pro Leu Thr Phe Gly Ala Gly Thr Lys Leu Glu Leu Lys
            100                 105                 110
```

<210> SEQ ID NO 145
<211> LENGTH: 16
<212> TYPE: PRT
<213> ORGANISM: Artificial Sequence
<220> FEATURE:
<223> OTHER INFORMATION: ACI-7079-2501G2-Ab2 2501G2E5 VL CDR1

<400> SEQUENCE: 145

Arg Ser Ser Gln Thr Ile Val His Ser Asn Gly Asn Thr Tyr Leu Glu
1 5 10 15

<210> SEQ ID NO 146
<211> LENGTH: 7
<212> TYPE: PRT
<213> ORGANISM: Artificial Sequence
<220> FEATURE:
<223> OTHER INFORMATION: ACI-7079-2501G2-Ab2 2501G2E5 VL CDR2

<400> SEQUENCE: 146

Lys Val Ser Asn Arg Phe Ser
1 5

<210> SEQ ID NO 147
<211> LENGTH: 9
<212> TYPE: PRT
<213> ORGANISM: Artificial Sequence
<220> FEATURE:
<223> OTHER INFORMATION: ACI-7079-2501G2-Ab2 2501G2E5 VL CDR3

<400> SEQUENCE: 147

Phe Gln Gly Ser Gln Gly Pro Leu Thr
1 5

<210> SEQ ID NO 148
<211> LENGTH: 363
<212> TYPE: DNA
<213> ORGANISM: Artificial Sequence
<220> FEATURE:
<223> OTHER INFORMATION: ACI-7079-2501G2-Ab2 2501G2E5 VH

<400> SEQUENCE: 148
gaggtgcagc ttgttgagtc tggtggagga ttggtgcagc ctaaagggtc attgaaactc 60
tcatgtgcag cctctggatt caacttcaat acctatgcca tgaactgggt ccgccaggct 120
ccaggaaagg gtttggaatg ggttgctcgc ataagaacta aaagtaataa ttttgcaaca 180
tattatgccc attcagtgaa agacagattc accatctcca gagatgattc agaaagcatg 240
ctctatctgc aaatgaacaa cttgaaaact gaggacacag ccatgtatta ctgtgtgaga 300
cagggactag cctactatgc tatggactac tggggtcaag gaacctcagt caccgtctcc 360
tca 363

<210> SEQ ID NO 149
<211> LENGTH: 336
<212> TYPE: DNA
<213> ORGANISM: Artificial Sequence
<220> FEATURE:
<223> OTHER INFORMATION: ACI-7079-2501G2-Ab2 2501G2E5 VL

<400> SEQUENCE: 149
gatgttttga tgacccaaac tccactctcc ctgcctgtca gtcttggaga tcaagtctcc 60
atctcttgca gatctagtca aaccattgta catagtaatg gaaacaccta tttagaatgg 120
tacctgcaga aaccaggcca gtctccaaag ctcctgatct acaaagtttc caaccgattt 180

```
tctggggtcc cagacaggtt cagtggcagt ggatcaggga cagatttcac actcaagatc    240

agcagagtgg aggctgagga tctgggagtt tattactgct ttcaaggttc acaaggtccg    300

ctcacgttcg gtgctgggac caaactggag ctgaaa                              336


<210> SEQ ID NO 150
<211> LENGTH: 113
<212> TYPE: PRT
<213> ORGANISM: Artificial Sequence
<220> FEATURE:
<223> OTHER INFORMATION: ACI-7079-2503C6-Ab1 2503C6H9 VH

<400> SEQUENCE: 150

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Leu Phe Pro Gly Asn Lys Leu Glu Trp
        35                  40                  45

Leu Gly Tyr Ile Asn Tyr Asp Gly Ser Asn Asn Phe Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Ser Glu Asp Thr Ala Thr Tyr Phe Cys
                85                  90                  95

Leu Arg Gly Asp Trp Asp Trp Gly Gln Gly Thr Leu Val Thr Val Ser
            100                 105                 110

Ala


<210> SEQ ID NO 151
<211> LENGTH: 6
<212> TYPE: PRT
<213> ORGANISM: Artificial Sequence
<220> FEATURE:
<223> OTHER INFORMATION: ACI-7079-2503C6-Ab1 2503C6H9 VH CDR1

<400> SEQUENCE: 151

Ser Gly Tyr Tyr Trp Asn
1               5


<210> SEQ ID NO 152
<211> LENGTH: 16
<212> TYPE: PRT
<213> ORGANISM: Artificial Sequence
<220> FEATURE:
<223> OTHER INFORMATION: ACI-7079-2503C6-Ab1 2503C6H9 VH CDR2

<400> SEQUENCE: 152

Tyr Ile Asn Tyr Asp Gly Ser Asn Asn Phe Asn Pro Ser Leu Lys Asn
1               5                   10                  15


<210> SEQ ID NO 153
<211> LENGTH: 4
<212> TYPE: PRT
<213> ORGANISM: Artificial Sequence
<220> FEATURE:
<223> OTHER INFORMATION: ACI-7079-2503C6-Ab1 2503C6H9 VH CDR3

<400> SEQUENCE: 153

Gly Asp Trp Asp
1
```

<210> SEQ ID NO 154
<211> LENGTH: 112
<212> TYPE: PRT
<213> ORGANISM: Artificial Sequence
<220> FEATURE:
<223> OTHER INFORMATION: ACI-7079-2503C6-Ab1 2503C6H9 VL

<400> SEQUENCE: 154

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asp Gly Glu Thr Tyr Leu Asn Trp Leu Leu Gln Arg Pro Gly Gln Ser
35 40 45

Pro Lys Arg Leu Ile Cys Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Trp Gln Gly
85 90 95

Thr His Phe Pro Gln Thr Phe Gly Gly Gly Thr Arg Leu Glu Ile Lys
100 105 110

<210> SEQ ID NO 155
<211> LENGTH: 16
<212> TYPE: PRT
<213> ORGANISM: Artificial Sequence
<220> FEATURE:
<223> OTHER INFORMATION: ACI-7079-2503C6-Ab1 2503C6H9 VL CDR1

<400> SEQUENCE: 155

Lys Ser Ser Gln Ser Leu Leu Asp Ser Asp Gly Glu Thr Tyr Leu Asn
1 5 10 15

<210> SEQ ID NO 156
<211> LENGTH: 7
<212> TYPE: PRT
<213> ORGANISM: Artificial Sequence
<220> FEATURE:
<223> OTHER INFORMATION: ACI-7079-2503C6-Ab1 2503C6H9 VL CDR2

<400> SEQUENCE: 156

Leu Val Ser Lys Leu Asp Ser
1 5

<210> SEQ ID NO 157
<211> LENGTH: 9
<212> TYPE: PRT
<213> ORGANISM: Artificial Sequence
<220> FEATURE:
<223> OTHER INFORMATION: ACI-7079-2503C6-Ab1 2503C6H9 VL CDR3

<400> SEQUENCE: 157

Trp Gln Gly Thr His Phe Pro Gln Thr
1 5

<210> SEQ ID NO 158
<211> LENGTH: 339
<212> TYPE: DNA
<213> ORGANISM: Artificial Sequence
<220> FEATURE:
<223> OTHER INFORMATION: ACI-7079-2503C6-Ab1 2503C6H9 VH

<400> SEQUENCE: 158
gatgtacagc ttcaggagtc aggacctggc ctcgtgaaac cttctcagtc tctgtctctc 60
acctgctctg tcactggcta ctccatcacc agtggttatt actggaactg gatccgacta 120
tttccaggaa acaaactgga atggctgggc tacataaact acgatggtag caataacttc 180
aacccatctc tcaaaaatcg aatctccatc actcgtgaca catctaagaa ccagtttttc 240
ctgaaattga attctgtgac ttctgaggac acagccacat atttctgttt aagaggggac 300
tgggactggg gccaagggac tctggtcact gtctctgca 339

<210> SEQ ID NO 159
<211> LENGTH: 336
<212> TYPE: DNA
<213> ORGANISM: Artificial Sequence
<220> FEATURE:
<223> OTHER INFORMATION: ACI-7079-2503C6-Ab1 2503C6H9 VL

<400> SEQUENCE: 159
gatgttgtga tgacccagac tccactcact ttgtcggtta ccattggaca accagcctcc 60
atctcttgca agtcaagtca gagcctctta gatagtgatg gagagacata tttgaattgg 120
ttgttacaga ggccaggcca gtctccaaag cgcctaatct gtctggtgtc taaactggac 180
tctggagtcc ctgacaggtt cactggcagt ggatcaggga cagatttcac actgaaaatc 240
agcagagtgg aggctgagga tttgggagtt tattattgct ggcaaggtac acattttcct 300
cagacgttcg gtggaggcac caggctggaa atcaaa 336

<210> SEQ ID NO 160
<211> LENGTH: 114
<212> TYPE: PRT
<213> ORGANISM: Artificial Sequence
<220> FEATURE:
<223> OTHER INFORMATION: ACI-7079-2504A6-Ab1 2504A6C8 VH

<400> SEQUENCE: 160

Gln Val Gln Leu Gln Gln Ser Gly Val Glu Leu Ala Arg Pro Gly Ala
1 5 10 15

Ser Val Lys Leu Ser Cys Lys Ala Ser Gly Tyr Thr Phe Thr Ser Tyr
20 25 30

Gly Ile Ser Trp Val Lys Gln Arg Thr Gly Gln Gly Leu Lys Trp Ile
35 40 45

Gly Glu Ile Tyr Pro Gly Ser Gly Asn Thr Tyr Tyr Asn Glu Lys Phe
50 55 60

Lys Gly Lys Ala Thr Leu Thr Ala Asp Lys Ser Ser Ser Thr Ala Tyr
65 70 75 80

Met Glu Leu Arg Ser Leu Thr Ser Glu Asp Ser Ala Val Tyr Phe Cys
85 90 95

Ala Thr Asp Tyr Asp Ala Tyr Trp Gly Gln Gly Thr Thr Leu Thr Val
100 105 110

Ser Ser

<210> SEQ ID NO 161
<211> LENGTH: 5
<212> TYPE: PRT
<213> ORGANISM: Artificial Sequence
<220> FEATURE:
<223> OTHER INFORMATION: ACI-7079-2504A6-Ab1 2504A6C8 VH CDR1

<400> SEQUENCE: 161

Ser Tyr Gly Ile Ser
1 5

<210> SEQ ID NO 162
<211> LENGTH: 17
<212> TYPE: PRT
<213> ORGANISM: Artificial Sequence
<220> FEATURE:
<223> OTHER INFORMATION: ACI-7079-2504A6-Ab1 2504A6C8 VH CDR2

<400> SEQUENCE: 162

```
Glu Ile Tyr Pro Gly Ser Gly Asn Thr Tyr Tyr Asn Glu Lys Phe Lys
1               5                   10                  15

Gly
```

<210> SEQ ID NO 163
<211> LENGTH: 5
<212> TYPE: PRT
<213> ORGANISM: Artificial Sequence
<220> FEATURE:
<223> OTHER INFORMATION: ACI-7079-2504A6-Ab1 2504A6C8 VH CDR3

<400> SEQUENCE: 163

```
Asp Tyr Asp Ala Tyr
1               5
```

<210> SEQ ID NO 164
<211> LENGTH: 112
<212> TYPE: PRT
<213> ORGANISM: Artificial Sequence
<220> FEATURE:
<223> OTHER INFORMATION: ACI-7079-2504A6-Ab1 2504A6C8 VL

<400> SEQUENCE: 164

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110
```

<210> SEQ ID NO 165
<211> LENGTH: 16
<212> TYPE: PRT
<213> ORGANISM: Artificial Sequence
<220> FEATURE:
<223> OTHER INFORMATION: ACI-7079-2504A6-Ab1 2504A6C8 VL CDR1

<400> SEQUENCE: 165

```
Arg Ser Ser Gln Ser Leu Val His Ser Asn Gly Asn Thr Tyr Leu His
1               5                   10                  15
```

<210> SEQ ID NO 166
<211> LENGTH: 7
<212> TYPE: PRT
<213> ORGANISM: Artificial Sequence
<220> FEATURE:

<223> OTHER INFORMATION: ACI-7079-2504A6-Ab1 2504A6C8 VL CDR2

<400> SEQUENCE: 166

Lys Val Ser Asn Arg Phe Ser
1 5

<210> SEQ ID NO 167
<211> LENGTH: 9
<212> TYPE: PRT
<213> ORGANISM: Artificial Sequence
<220> FEATURE:
<223> OTHER INFORMATION: ACI-7079-2504A6-Ab1 2504A6C8 VL CDR3

<400> SEQUENCE: 167

Ser Gln Ser Thr His Val Pro Leu Thr
1 5

<210> SEQ ID NO 168
<211> LENGTH: 342
<212> TYPE: DNA
<213> ORGANISM: Artificial Sequence
<220> FEATURE:
<223> OTHER INFORMATION: ACI-7079-2504A6-Ab1 2504A6C8 VH

<400> SEQUENCE: 168
caggttcagc tgcagcagtc tggagttgag ctggcgaggc ctggggcttc agtgaaactg 60
tcctgcaagg cttctggcta caccttcaca agctatggta taagctgggt gaagcagaga 120
actggacagg gccttaagtg gattggagag atttatcctg gaagtggtaa tacttactac 180
aatgagaagt tcaagggcaa ggccacactg actgcagaca aatcctccag cacagcgtac 240
atggagctcc gcagcctgac gtctgaggac tctgcggtct atttctgtgc aaccgattac 300
gacgcctact ggggccaagg caccactctc acagtctcct ca 342

<210> SEQ ID NO 169
<211> LENGTH: 336
<212> TYPE: DNA
<213> ORGANISM: Artificial Sequence
<220> FEATURE:
<223> OTHER INFORMATION: ACI-7079-2504A6-Ab1 2504A6C8 VL

<400> SEQUENCE: 169
gatgttgtga tgacccaaac tccactctcc ctgcctgtca gtcttggaga tcaagcctcc 60
atctcttgca gatctagtca gagccttgta cacagtaatg gaaacaccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tatttctgct ctcaaagtac acatgttccg 300
ctcacgttcg gtgctgggac caagctggag ctgaaa 336

<210> SEQ ID NO 170
<211> LENGTH: 120
<212> TYPE: PRT
<213> ORGANISM: Artificial Sequence
<220> FEATURE:
<223> OTHER INFORMATION: ACI-7079-2506E2-Ab2 2506E2G4 VH

<400> SEQUENCE: 170

Gln Val Gln Leu Gln Gln Ser Gly Pro Glu Leu Val Arg Pro Gly Ala
1 5 10 15

Ser Val Lys Ile Ser Cys Lys Ala Ser Gly Tyr Ala Phe Ser Asn Ser
20 25 30

```
Trp Met Asn Trp Val Lys Gln Arg Pro Gly Lys Gly Leu Glu Trp Ile
        35                  40                  45

Gly Arg Ile Phe Pro Gly Asp Gly Asp Thr Tyr Tyr Asp Gly Lys Phe
    50                  55                  60

Lys Gly Lys Val Lys Leu Thr Thr Asp Lys Phe Ser Asn Thr Ala Tyr
65                  70                  75                  80

Met Gln Leu Arg Ser Leu Thr Ser Glu Asp Ser Ala Val Tyr Phe Cys
                85                  90                  95

Ala Arg Trp Gly Gly Thr Asn Asp Glu Trp Phe Ala His Trp Gly Gln
            100                 105                 110

Gly Thr Leu Val Thr Val Ser Val
        115                 120


<210> SEQ ID NO 171
<211> LENGTH: 5
<212> TYPE: PRT
<213> ORGANISM: Artificial Sequence
<220> FEATURE:
<223> OTHER INFORMATION: ACI-7079-2506E2-Ab2 2506E2G4 VH CDR1

<400> SEQUENCE: 171

Asn Ser Trp Met Asn
1               5


<210> SEQ ID NO 172
<211> LENGTH: 17
<212> TYPE: PRT
<213> ORGANISM: Artificial Sequence
<220> FEATURE:
<223> OTHER INFORMATION: ACI-7079-2506E2-Ab2 2506E2G4 VH CDR2

<400> SEQUENCE: 172

Arg Ile Phe Pro Gly Asp Gly Asp Thr Tyr Tyr Asp Gly Lys Phe Lys
1               5                   10                  15

Gly


<210> SEQ ID NO 173
<211> LENGTH: 11
<212> TYPE: PRT
<213> ORGANISM: Artificial Sequence
<220> FEATURE:
<223> OTHER INFORMATION: ACI-7079-2506E2-Ab2 2506E2G4 VH CDR3

<400> SEQUENCE: 173

Trp Gly Gly Thr Asn Asp Glu Trp Phe Ala His
1               5                   10


<210> SEQ ID NO 174
<211> LENGTH: 111
<212> TYPE: PRT
<213> ORGANISM: Artificial Sequence
<220> FEATURE:
<223> OTHER INFORMATION: ACI-7079-2506E2-Ab2 2506E2G4 VL

<400> SEQUENCE: 174

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Arg Asn Ser Tyr Met His Trp Tyr Gln Gln Lys Pro Arg Gln Pro Pro
        35                  40                  45
```

Lys Leu Leu Ile Lys Tyr Ala Ser Asn Leu Glu Ser Gly Val Pro Ala
50 55 60

Arg Phe Ser Gly Ser Gly Ser Gly Ala Asp Phe Thr Leu Asn Ile His
65 70 75 80

Pro Val Glu Glu Glu Asp Thr Ala Thr Tyr Tyr Cys Gln His Ser Trp
85 90 95

Asp Ile Pro Leu Thr Phe Gly Thr Gly Thr Lys Leu Glu Leu Ser
100 105 110

<210> SEQ ID NO 175
<211> LENGTH: 15
<212> TYPE: PRT
<213> ORGANISM: Artificial Sequence
<220> FEATURE:
<223> OTHER INFORMATION: ACI-7079-2506E2-Ab2 2506E2G4 VL CDR1

<400> SEQUENCE: 175

Arg Ala Ser Gln Ser Val Ser Thr Ser Arg Asn Ser Tyr Met His
1 5 10 15

<210> SEQ ID NO 176
<211> LENGTH: 7
<212> TYPE: PRT
<213> ORGANISM: Artificial Sequence
<220> FEATURE:
<223> OTHER INFORMATION: ACI-7079-2506E2-Ab2 2506E2G4 VL CDR2

<400> SEQUENCE: 176

Tyr Ala Ser Asn Leu Glu Ser
1 5

<210> SEQ ID NO 177
<211> LENGTH: 9
<212> TYPE: PRT
<213> ORGANISM: Artificial Sequence
<220> FEATURE:
<223> OTHER INFORMATION: ACI-7079-2506E2-Ab2 2506E2G4 VL CDR3

<400> SEQUENCE: 177

Gln His Ser Trp Asp Ile Pro Leu Thr
1 5

<210> SEQ ID NO 178
<211> LENGTH: 360
<212> TYPE: DNA
<213> ORGANISM: Artificial Sequence
<220> FEATURE:
<223> OTHER INFORMATION: ACI-7079-2506E2-Ab2 2506E2G4 VH

<400> SEQUENCE: 178
caggttcagt tgcagcagtc tggacctgag ctggtgaggc ctggggcctc agtgaagatt 60
tcctgcaagg cttctggcta cgcattcagt aactcctgga tgaactgggt gaagcagagg 120
cctggaaagg gtcttgagtg gattggacgg atttttcctg gagatggaga tacttactac 180
gatgggaagt tcaagggcaa ggtcaaactg acaacagaca aattctccaa cacagcctac 240
atgcaactcc gcagcctgac atctgaggac tctgcggtct acttctgtgc aagatggggg 300
ggtactaacg atgagtggtt tgctcactgg ggccaaggga ctctggtcac tgtctctgta 360

<210> SEQ ID NO 179
<211> LENGTH: 333
<212> TYPE: DNA
<213> ORGANISM: Artificial Sequence
<220> FEATURE:

<223> OTHER INFORMATION: ACI-7079-2506E2-Ab2 2506E2G4 VL

<400> SEQUENCE: 179

```
gacattgtgc tgacacagtc tcctgcttcc ttaactgtat ctctggggca gagggccacc      60

atctcatgca gggccagcca aagtgtcagt acatctagga atagttatat gcactggtac     120

caacagaaac caagacagcc acccaaactc ctcatcaagt atgcatccaa cctagaatct     180

ggggtccctg ccaggttcag tggcagtggg tctggggcag acttcaccct caacatccat     240

cctgtggagg aggaggatac tgcaacatat tactgtcagc acagttggga tattccgctc     300

acgttcggta ctgggaccaa gctggagctg agt                                  333
```

<210> SEQ ID NO 180
<211> LENGTH: 114
<212> TYPE: PRT
<213> ORGANISM: Artificial Sequence
<220> FEATURE:
<223> OTHER INFORMATION: ACI-7079-2506F3-Ab1 2506F3E12 VH

<400> SEQUENCE: 180

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Ile Asn Tyr Asn Gln Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Ser Ala Val Tyr Tyr Cys
                85                  90                  95

Ala Arg Gly Met Met Asp Tyr Trp Gly Gln Gly Thr Ser Val Thr Val
            100                 105                 110

Ser Ser
```

<210> SEQ ID NO 181
<211> LENGTH: 5
<212> TYPE: PRT
<213> ORGANISM: Artificial Sequence
<220> FEATURE:
<223> OTHER INFORMATION: ACI-7079-2506F3-Ab1 2506F3E12 VH CDR1

<400> SEQUENCE: 181

```
Thr Tyr Trp Met Gln
1               5
```

<210> SEQ ID NO 182
<211> LENGTH: 17
<212> TYPE: PRT
<213> ORGANISM: Artificial Sequence
<220> FEATURE:
<223> OTHER INFORMATION: ACI-7079-2506F3-Ab1 2506F3E12 VH CDR2

<400> SEQUENCE: 182

```
Glu Ile Asp Pro Ser Asp Ser Tyr Ile Asn Tyr Asn Gln Lys Phe Lys
1               5                   10                  15

Gly
```

<210> SEQ ID NO 183

<211> LENGTH: 5
<212> TYPE: PRT
<213> ORGANISM: Artificial Sequence
<220> FEATURE:
<223> OTHER INFORMATION: ACI-7079-2506F3-Ab1 2506F3E12 VH CDR3

<400> SEQUENCE: 183

```
Gly Met Met Asp Tyr
1               5
```

<210> SEQ ID NO 184
<211> LENGTH: 112
<212> TYPE: PRT
<213> ORGANISM: Artificial Sequence
<220> FEATURE:
<223> OTHER INFORMATION: ACI-7079-2506F3-Ab1 2506F3E12 VL

<400> SEQUENCE: 184

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Lys Gly
                85                  90                  95

Ser His Val Pro Tyr Thr Phe Gly Gly Gly Thr Lys Leu Glu Ile Lys
            100                 105                 110
```

<210> SEQ ID NO 185
<211> LENGTH: 16
<212> TYPE: PRT
<213> ORGANISM: Artificial Sequence
<220> FEATURE:
<223> OTHER INFORMATION: ACI-7079-2506F3-Ab1 2506F3E12 VL CDR1

<400> SEQUENCE: 185

```
Arg Ser Ser Gln Ser Ile Val His Ser Asn Gly Asn Thr Tyr Leu Glu
1               5                   10                  15
```

<210> SEQ ID NO 186
<211> LENGTH: 7
<212> TYPE: PRT
<213> ORGANISM: Artificial Sequence
<220> FEATURE:
<223> OTHER INFORMATION: ACI-7079-2506F3-Ab1 2506F3E12 VL CDR2

<400> SEQUENCE: 186

```
Lys Val Ser Asn Arg Phe Ser
1               5
```

<210> SEQ ID NO 187
<211> LENGTH: 9
<212> TYPE: PRT
<213> ORGANISM: Artificial Sequence
<220> FEATURE:
<223> OTHER INFORMATION: ACI-7079-2506F3-Ab1 2506F3E12 VL CDR3

<400> SEQUENCE: 187

```
Phe Lys Gly Ser His Val Pro Tyr Thr
```

1 5

<210> SEQ ID NO 188
<211> LENGTH: 342
<212> TYPE: DNA
<213> ORGANISM: Artificial Sequence
<220> FEATURE:
<223> OTHER INFORMATION: ACI-7079-2506F3-Ab1 2506F3E12 VH

<400> SEQUENCE: 188
caggtccaac tgcagcagcc tggggctgag cttgtgaagc ctggggcttc agtgaagctg 60
tcctgcaagg cttctggcta caccttcacc acctactgga tgcagtgggt aaaacagagg 120
cctggacagg gccttgagtg gatcggagag attgatcctt ctgatagcta tattaactac 180
aatcaaaagt tcaagggcaa ggccacattg actgtagaca catcctccag cacagccttc 240
atgcagctca gcagcctgac atctgaggac tctgcggtct attactgtgc aagggggatg 300
atggactact ggggtcaagg aacctcagtc accgtctcct ca 342

<210> SEQ ID NO 189
<211> LENGTH: 336
<212> TYPE: DNA
<213> ORGANISM: Artificial Sequence
<220> FEATURE:
<223> OTHER INFORMATION: ACI-7079-2506F3-Ab1 2506F3E12 VL

<400> SEQUENCE: 189
gatgttttga tgacccaaac tccactctcc ctgcctgtca gtcttggaga tcaagcctcc 60
atctcttgca gatctagtca gagcattgta catagtaatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttaaaggttc acatgttccg 300
tacacgttcg gaggggggac caagctggaa ataaaa 336

<210> SEQ ID NO 190
<211> LENGTH: 120
<212> TYPE: PRT
<213> ORGANISM: Artificial Sequence
<220> FEATURE:
<223> OTHER INFORMATION: ACI-7079-2507B3-Ab1 2507B3G8 VH

<400> SEQUENCE: 190

Glu Val Gln Leu Val Glu Ser Gly Gly Gly Leu Val Gln Pro Lys Gly
1 5 10 15

Ser Leu Lys Val Ser Cys Ala Ala Ser Gly Phe Thr Phe Lys Thr Tyr
20 25 30

Ala Met His Trp Val Arg Gln Ala Pro Gly Lys Gly Leu Glu Trp Val
35 40 45

Ala Arg Ile Arg Ser Glu Asn Ser Asn Phe Ala Lys Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met His Thr Leu Lys Thr Glu Asp Thr Ala Ile Tyr
85 90 95

Tyr Cys Val Arg Gly Tyr Asn Gly Ser Ser Leu Asp Tyr Trp Gly Gln
100 105 110

Gly Thr Thr Leu Thr Val Ser Ser
115 120

<210> SEQ ID NO 191
<211> LENGTH: 5
<212> TYPE: PRT
<213> ORGANISM: Artificial Sequence
<220> FEATURE:
<223> OTHER INFORMATION: ACI-7079-2507B3-Ab1 2507B3G8 VH CDR1

<400> SEQUENCE: 191

Thr Tyr Ala Met His
1 5

<210> SEQ ID NO 192
<211> LENGTH: 19
<212> TYPE: PRT
<213> ORGANISM: Artificial Sequence
<220> FEATURE:
<223> OTHER INFORMATION: ACI-7079-2507B3-Ab1 2507B3G8 VH CDR2

<400> SEQUENCE: 192

Arg Ile Arg Ser Glu Asn Ser Asn Phe Ala Lys Tyr Tyr Ala Asp Ser
1 5 10 15

Val Lys Asp

<210> SEQ ID NO 193
<211> LENGTH: 9
<212> TYPE: PRT
<213> ORGANISM: Artificial Sequence
<220> FEATURE:
<223> OTHER INFORMATION: ACI-7079-2507B3-Ab1 2507B3G8 VH CDR3

<400> SEQUENCE: 193

Gly Tyr Asn Gly Ser Ser Leu Asp Tyr
1 5

<210> SEQ ID NO 194
<211> LENGTH: 106
<212> TYPE: PRT
<213> ORGANISM: Artificial Sequence
<220> FEATURE:
<223> OTHER INFORMATION: ACI-7079-2507B3-Ab1 2507B3G8 VL

<400> SEQUENCE: 194

Gln Ile Val Leu Thr Gln Ser Pro Ala Ile Met Ser Ala Phe Pro Gly
1 5 10 15

Glu Arg Val Thr Met Thr Cys Ser Ala Ser Ser Ser Val Asn Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Gly
50 55 60

Gly Ser Gly Thr Ser Tyr Ser Leu Thr Ile Ser Asn Met Glu Ala Glu
65 70 75 80

Asp Ala Ala Thr Tyr Tyr Cys Gln Gln Trp Arg Ser Asn Pro Pro Thr
85 90 95

Phe Gly Gly Gly Thr Lys Leu Glu Ile Lys
100 105

<210> SEQ ID NO 195
<211> LENGTH: 10
<212> TYPE: PRT
<213> ORGANISM: Artificial Sequence
<220> FEATURE:

<223> OTHER INFORMATION: ACI-7079-2507B3-Ab1 2507B3G8 VL CDR1

<400> SEQUENCE: 195

Ser Ala Ser Ser Ser Val Asn Tyr Met His
1 5 10

<210> SEQ ID NO 196
<211> LENGTH: 7
<212> TYPE: PRT
<213> ORGANISM: Artificial Sequence
<220> FEATURE:
<223> OTHER INFORMATION: ACI-7079-2507B3-Ab1 2507B3G8 VL CDR2

<400> SEQUENCE: 196

Asp Thr Ser Lys Leu Ala Ser
1 5

<210> SEQ ID NO 197
<211> LENGTH: 9
<212> TYPE: PRT
<213> ORGANISM: Artificial Sequence
<220> FEATURE:
<223> OTHER INFORMATION: ACI-7079-2507B3-Ab1 2507B3G8 VL CDR3

<400> SEQUENCE: 197

Gln Gln Trp Arg Ser Asn Pro Pro Thr
1 5

<210> SEQ ID NO 198
<211> LENGTH: 360
<212> TYPE: DNA
<213> ORGANISM: Artificial Sequence
<220> FEATURE:
<223> OTHER INFORMATION: ACI-7079-2507B3-Ab1 2507B3G8 VH

<400> SEQUENCE: 198
gaggtgcagc ttgttgagtc tggtggagga ttggtgcagc ctaaaggatc attgaaagtc 60
tcatgtgccg cctctggttt caccttcaag acctatgcca tgcactgggt ccgccaggct 120
ccgggaaagg gtttggaatg ggttgctcgc ataagaagtg aaaacagtaa ttttgcaaaa 180
tattatgccg attcagtgaa agacagattc accatctcca gagatgattc acaaagtatg 240
ctctatctgc aaatgcacac cctgaaaact gaggacacag ccatctatta ttgtgtaagg 300
ggatataacg gcagtagcct tgactactgg ggccaaggca ccactctcac agtctcctca 360

<210> SEQ ID NO 199
<211> LENGTH: 318
<212> TYPE: DNA
<213> ORGANISM: Artificial Sequence
<220> FEATURE:
<223> OTHER INFORMATION: ACI-7079-2507B3-Ab1 2507B3G8 VL

<400> SEQUENCE: 199
caaattgttc tcacccagtc tccagcaatc atgtctgcat ttccagggga gagggtcacc 60
atgacctgca gtgccagctc aagtgtaaat tacatgcact ggtaccagca gaagtccggc 120
acctccccca aaagatggat ttatgacaca tccaaactgg cttctggagt ccctgctcgc 180
ttcagtggcg gtgggtctgg gacctcttac tctctcacaa tcagcaacat ggaggctgaa 240
gatgctgcca cttattactg ccagcagtgg agaagtaatc cacccacttt cggagggggg 300
accaagctgg aaataaaa 318

<210> SEQ ID NO 200

<211> LENGTH: 113
<212> TYPE: PRT
<213> ORGANISM: Artificial Sequence
<220> FEATURE:
<223> OTHER INFORMATION: ACI-7079-2511B3-Ab3 2511B3B12 VH

<400> SEQUENCE: 200

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Ser Tyr
            20                  25                  30

Tyr Tyr Trp Asn Trp Ile Arg Gln Phe Pro Gly Asn Lys Leu Glu Trp
        35                  40                  45

Met Ala Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Thr Arg Gly Asp Trp Asp Trp Gly Gln Gly Thr Leu Val Thr Val Ser
            100                 105                 110

Ala
```

<210> SEQ ID NO 201
<211> LENGTH: 6
<212> TYPE: PRT
<213> ORGANISM: Artificial Sequence
<220> FEATURE:
<223> OTHER INFORMATION: ACI-7079-2511B3-Ab3 2511B3B12 VH CDR1

<400> SEQUENCE: 201

```
Ser Tyr Tyr Tyr Trp Asn
1               5
```

<210> SEQ ID NO 202
<211> LENGTH: 16
<212> TYPE: PRT
<213> ORGANISM: Artificial Sequence
<220> FEATURE:
<223> OTHER INFORMATION: ACI-7079-2511B3-Ab3 2511B3B12 VH CDR2

<400> SEQUENCE: 202

```
Tyr Ile Ser Tyr Asp Gly Ser Asn Asn Tyr Asn Pro Ser Leu Lys Asn
1               5                   10                  15
```

<210> SEQ ID NO 203
<211> LENGTH: 4
<212> TYPE: PRT
<213> ORGANISM: Artificial Sequence
<220> FEATURE:
<223> OTHER INFORMATION: ACI-7079-2511B3-Ab3 2511B3B12 VH CDR3

<400> SEQUENCE: 203

```
Gly Asp Trp Asp
1
```

<210> SEQ ID NO 204
<211> LENGTH: 112
<212> TYPE: PRT
<213> ORGANISM: Artificial Sequence
<220> FEATURE:
<223> OTHER INFORMATION: ACI-7079-2511B3-Ab3 2511B3B12 VL

<400> SEQUENCE: 204

```
Asp Val Val Met Thr Gln Thr Pro Leu Thr Leu Ser Leu Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Glu Ser Gly Val Pro
    50                  55                  60

Asp Arg Phe Thr Gly Ser Gly Ser Gly Thr Val Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110


<210> SEQ ID NO 205
<211> LENGTH: 16
<212> TYPE: PRT
<213> ORGANISM: Artificial Sequence
<220> FEATURE:
<223> OTHER INFORMATION: ACI-7079-2511B3-Ab3 2511B3B12 VL CDR1

<400> SEQUENCE: 205

Lys Ser Ser Gln Ser Leu Leu Asp Ser Asp Gly Glu Thr Tyr Leu Asn
1               5                   10                  15


<210> SEQ ID NO 206
<211> LENGTH: 7
<212> TYPE: PRT
<213> ORGANISM: Artificial Sequence
<220> FEATURE:
<223> OTHER INFORMATION: ACI-7079-2511B3-Ab3 2511B3B12 VL CDR2

<400> SEQUENCE: 206

Leu Val Ser Lys Leu Glu Ser
1               5


<210> SEQ ID NO 207
<211> LENGTH: 9
<212> TYPE: PRT
<213> ORGANISM: Artificial Sequence
<220> FEATURE:
<223> OTHER INFORMATION: ACI-7079-2511B3-Ab3 2511B3B12 VL CDR3

<400> SEQUENCE: 207

Trp Gln Gly Thr His Phe Pro Gln Thr
1               5


<210> SEQ ID NO 208
<211> LENGTH: 339
<212> TYPE: DNA
<213> ORGANISM: Artificial Sequence
<220> FEATURE:
<223> OTHER INFORMATION: ACI-7079-2511B3-Ab3- 2511B3B12 VH

<400> SEQUENCE: 208

gatgtacagc ttcaggaatc aggacctggc ctcgtgaaac cttctcagtc tctgtctctc      60

acctgctctg tcactggctt ctccatcacc agttattatt actggaactg gatccggcag     120

tttccaggaa acaaactgga atggatggcc tacataagct acgatggtag caataactac     180

aacccatctc tcaaaaatcg aatctccatc actcgtgaca catctaagaa ccagtttttc     240
```

ctgaagttga attctgtgac tactgaggac acagccacat attactgtac aagaggggac 300
tgggactggg gccaagggac tctggtcact gtctctgca 339

<210> SEQ ID NO 209
<211> LENGTH: 336
<212> TYPE: DNA
<213> ORGANISM: Artificial Sequence
<220> FEATURE:
<223> OTHER INFORMATION: ACI-7079-2511B3-Ab3- 2511B3B12 VL

<400> SEQUENCE: 209
gatgttgtga tgacccagac tccactcact ttgtcgctta ccattggaca accagcctcc 60
atctcttgca agtcaagtca gagcctctta gatagtgatg gagagacata tttgaattgg 120
ttgttacaga ggccaggtca gtctccaaag cgcctaatct atctggtgtc taaactggaa 180
tctggagtcc ctgacaggtt cactggcagt ggatcaggga cagttttcac actgaaaatc 240
agcagagtgg aggctgagga tttgggagtt tattattgct ggcaagggac acattttcct 300
cagacgttcg gtggaggcac caagctggaa atcaaa 336

<210> SEQ ID NO 210
<211> LENGTH: 113
<212> TYPE: PRT
<213> ORGANISM: Artificial Sequence
<220> FEATURE:
<223> OTHER INFORMATION: ACI-7079-2601B6-Ab1 2601B6D2 VH

<400> SEQUENCE: 210

Glu Ile Gln Leu Gln Gln Ser Gly Ala Glu Leu Val Arg Pro Gly Ala
1 5 10 15

Ser Val Lys Leu Ser Cys Thr Thr Ser Gly Phe Asn Ile Lys Asp Asp
20 25 30

Tyr Ile His Trp Val Lys Gln Arg Pro Glu Gln Gly Leu Glu Trp Ile
35 40 45

Gly Trp Ile Asp Pro Glu Asn Gly Asp Thr Asp Tyr Ala Ser Lys Phe
50 55 60

Gln Gly Lys Ala Thr Ile Thr Ala Asp Thr Ser Ser Asn Thr Ala Tyr
65 70 75 80

Leu His Leu Ser Ser Leu Thr Ser Glu Asp Ala Ala Val Tyr Phe Cys
85 90 95

Thr Thr Arg Gly Phe Gly Tyr Trp Gly Gln Gly Thr Leu Val Thr Val
100 105 110

Ser

<210> SEQ ID NO 211
<211> LENGTH: 5
<212> TYPE: PRT
<213> ORGANISM: Artificial Sequence
<220> FEATURE:
<223> OTHER INFORMATION: ACI-7079-2601B6-Ab1 2601B6D2 VH CDR1

<400> SEQUENCE: 211

Asp Asp Tyr Ile His
1 5

<210> SEQ ID NO 212
<211> LENGTH: 17
<212> TYPE: PRT
<213> ORGANISM: Artificial Sequence
<220> FEATURE:
<223> OTHER INFORMATION: ACI-7079-2601B6-Ab1 2601B6D2 VH CDR2

<400> SEQUENCE: 212

Trp Ile Asp Pro Glu Asn Gly Asp Thr Asp Tyr Ala Ser Lys Phe Gln
1               5                   10                  15

Gly

<210> SEQ ID NO 213
<211> LENGTH: 5
<212> TYPE: PRT
<213> ORGANISM: Artificial Sequence
<220> FEATURE:
<223> OTHER INFORMATION: ACI-7079-2601B6-Ab1 2601B6D2 VH CDR3

<400> SEQUENCE: 213

Arg Gly Phe Gly Tyr
1               5

<210> SEQ ID NO 214
<211> LENGTH: 107
<212> TYPE: PRT
<213> ORGANISM: Artificial Sequence
<220> FEATURE:
<223> OTHER INFORMATION: ACI-7079-2601B6-Ab1 2601B6D2 VL

<400> SEQUENCE: 214

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Asn Val
            20                  25                  30

Val Ala Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Gly Ser Gly Thr Glu Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 215
<211> LENGTH: 11
<212> TYPE: PRT
<213> ORGANISM: Artificial Sequence
<220> FEATURE:
<223> OTHER INFORMATION: ACI-7079-2601B6-Ab1 2601B6D2 VL CDR1

<400> SEQUENCE: 215

Lys Ala Ser Gln Asp Val Gly Asn Val Val Ala
1               5                   10

<210> SEQ ID NO 216
<211> LENGTH: 7
<212> TYPE: PRT
<213> ORGANISM: Artificial Sequence
<220> FEATURE:
<223> OTHER INFORMATION: ACI-7079-2601B6-Ab1 2601B6D2 VL CDR2

<400> SEQUENCE: 216

Trp Ala Ser Ser Arg His Thr
1               5

<210> SEQ ID NO 217
<211> LENGTH: 9
<212> TYPE: PRT
<213> ORGANISM: Artificial Sequence
<220> FEATURE:
<223> OTHER INFORMATION: ACI-7079-2601B6-Ab1 2601B6D2 VL CDR3

<400> SEQUENCE: 217

Gln Gln Tyr Ser Ser Tyr Pro Leu Thr
1 5

<210> SEQ ID NO 218
<211> LENGTH: 339
<212> TYPE: DNA
<213> ORGANISM: Artificial Sequence
<220> FEATURE:
<223> OTHER INFORMATION: ACI-7079-2601B6-Ab1 2601B6D2 VH

<400> SEQUENCE: 218
gagattcaac tgcagcagtc tggggctgag cttgtgaggc caggggcctc agtcaagttg 60
tcctgcacaa cttccggctt taacattaaa gacgactata ttcactgggt gaagcagagg 120
cctgaacagg gcctggagtg gattggatgg attgatcctg agaatggtga tactgattat 180
gcctcgaagt tccagggcaa ggccactata acagcagaca catcctccaa cacagcctac 240
ctgcacctca gcagcctgac atcagaggac gctgccgtct atttctgtac tacaagagga 300
tttggttact ggggccaagg gactctggtc actgtctct 339

<210> SEQ ID NO 219
<211> LENGTH: 321
<212> TYPE: DNA
<213> ORGANISM: Artificial Sequence
<220> FEATURE:
<223> OTHER INFORMATION: ACI-7079-2601B6-Ab1 2601B6D2 VL

<400> SEQUENCE: 219
gacattgtga tgacccagtc tcacaaattc atgtccacat cagtaggaga cagggtcagc 60
atcacctgca aggccagtca ggatgtgggt aatgttgttg cctggtatca acagaaacca 120
ggacaatctc ctaaactact gatttactgg gcatcctccc ggcacactgg agtccctgat 180
cgcttcacag gcagtggatc tgggacagaa ttcactctca ccattagcaa tgtgcagtct 240
gaagacttgg cagattattt ctgtcagcaa tatagcagct atccgctcac gttcggtgct 300
gggaccaagc tggagctgaa g 321

<210> SEQ ID NO 220
<211> LENGTH: 120
<212> TYPE: PRT
<213> ORGANISM: Artificial Sequence
<220> FEATURE:
<223> OTHER INFORMATION: ACI-7079-2602G4-Ab4 2602G4H1 VH

<400> SEQUENCE: 220

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Lys Thr Tyr
20 25 30

Ala Met His Trp Val Arg Gln Ala Pro Gly Lys Gly Leu Glu Trp Val
35 40 45

Ala Arg Ile Arg Ser Lys Gly Ser Asp Tyr Ala Thr Tyr Tyr Ala Asp
50 55 60

Ser Val Lys Asp Arg Phe Thr Ile Ser Arg Asp Asp Ser Gln Ser Met

```
65                  70                  75                  80

Leu Tyr Leu Gln Met Asn Asn Leu Lys Thr Glu Asp Thr Ala Met Tyr
                85                  90                  95

Phe Cys Val Arg Gly Gly Ala Asp Ser Trp Phe Ala Tyr Trp Gly Gln
            100                 105                 110

Gly Thr Leu Val Thr Val Ser Thr
        115                 120


<210> SEQ ID NO 221
<211> LENGTH: 5
<212> TYPE: PRT
<213> ORGANISM: Artificial Sequence
<220> FEATURE:
<223> OTHER INFORMATION: ACI-7079-2602G4-Ab4 2602G4H1 VH CDR1

<400> SEQUENCE: 221

Thr Tyr Ala Met His
1               5


<210> SEQ ID NO 222
<211> LENGTH: 19
<212> TYPE: PRT
<213> ORGANISM: Artificial Sequence
<220> FEATURE:
<223> OTHER INFORMATION: ACI-7079-2602G4-Ab4 2602G4H1 VH CDR2

<400> SEQUENCE: 222

Arg Ile Arg Ser Lys Gly Ser Asp Tyr Ala Thr Tyr Tyr Ala Asp Ser
1               5                   10                  15

Val Lys Asp


<210> SEQ ID NO 223
<211> LENGTH: 9
<212> TYPE: PRT
<213> ORGANISM: Artificial Sequence
<220> FEATURE:
<223> OTHER INFORMATION: ACI-7079-2602G4-Ab4 2602G4H1 VH CDR3

<400> SEQUENCE: 223

Gly Gly Ala Asp Ser Trp Phe Ala Tyr
1               5


<210> SEQ ID NO 224
<211> LENGTH: 106
<212> TYPE: PRT
<213> ORGANISM: Artificial Sequence
<220> FEATURE:
<223> OTHER INFORMATION: ACI-7079-2602G4-Ab4 2602G4H1 VL

<400> SEQUENCE: 224

Gln Ile Val Leu Thr Gln Ser Pro Ala Ile Met Ser Ala Ser Pro Gly
1               5                   10                  15

Glu Arg Ile Thr Met Thr Cys Thr Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Ala Ser Tyr Thr Leu Thr Ile Ser Ser Met Glu Ala Glu
65                  70                  75                  80

Asp Ala Ala Thr Tyr Tyr Cys Gln Gln Trp Asn Arg Asn Pro Pro Thr
                85                  90                  95
```

Phe Gly Gly Gly Thr Gln Leu Ala Ile Lys
100 105

<210> SEQ ID NO 225
<211> LENGTH: 10
<212> TYPE: PRT
<213> ORGANISM: Artificial Sequence
<220> FEATURE:
<223> OTHER INFORMATION: ACI-7079-2602G4-Ab4 2602G4H1 VL CDR1

<400> SEQUENCE: 225

Thr Ala Ser Ser Ser Val Ser Tyr Met His
1 5 10

<210> SEQ ID NO 226
<211> LENGTH: 7
<212> TYPE: PRT
<213> ORGANISM: Artificial Sequence
<220> FEATURE:
<223> OTHER INFORMATION: ACI-7079-2602G4-Ab4 2602G4H1 VL CDR2

<400> SEQUENCE: 226

Asp Thr Ser Lys Leu Ala Ser
1 5

<210> SEQ ID NO 227
<211> LENGTH: 9
<212> TYPE: PRT
<213> ORGANISM: Artificial Sequence
<220> FEATURE:
<223> OTHER INFORMATION: ACI-7079-2602G4-Ab4 2602G4H1 VL CDR3

<400> SEQUENCE: 227

Gln Gln Trp Asn Arg Asn Pro Pro Thr
1 5

<210> SEQ ID NO 228
<211> LENGTH: 360
<212> TYPE: DNA
<213> ORGANISM: Artificial Sequence
<220> FEATURE:
<223> OTHER INFORMATION: ACI-7079-2602G4-Ab4 2602G4H1 VH

<400> SEQUENCE: 228
gaggtgcagc ttgttgagtc tggtggagga ttggtgcagc ctaaaggatc attgaaactc 60
tcatgtgccg cctctggttt caccttcaag acctatgcca tgcactgggt ccgccaggct 120
ccaggaaagg gtttggaatg ggttgctcgc ataagaagta aaggtagtga ttatgcaaca 180
tattatgccg attcagtgaa ggacagattc accatctcca gagatgattc acaaagcatg 240
ctctatctgc aaatgaacaa cctgaaaact gaggatacag ccatgtattt ctgtgtgaga 300
gggggtgctg actcctggtt tgcttactgg ggccaaggga ctctggtcac tgtctctaca 360

<210> SEQ ID NO 229
<211> LENGTH: 318
<212> TYPE: DNA
<213> ORGANISM: Artificial Sequence
<220> FEATURE:
<223> OTHER INFORMATION: ACI-7079-2602G4-Ab4 2602G4H1 VL

<400> SEQUENCE: 229
caaattgttc tcacccagtc tccagcaatc atgtctgcat ctccagggga gaggatcacc 60
atgacctgca ctgccagctc aagtgtaagt tacatgcact ggtaccagca gaagtcaggc 120

```
acctccccca aaagatggat ttatgacaca tccaaactgg cttctggagt ccctgctcgc    180

ttcagtggca gtgggtctgg ggcctcttat actctcacaa tcagcagcat ggaggctgaa    240

gatgctgcca cttattactg ccagcagtgg aatcgtaacc caccgacgtt cggtggaggc    300

acccagctgg caatcaaa                                                  318


<210> SEQ ID NO 230
<211> LENGTH: 114
<212> TYPE: PRT
<213> ORGANISM: Artificial Sequence
<220> FEATURE:
<223> OTHER INFORMATION: ACI-7079-2603C1-Ab3 2603C1H6 VH

<400> SEQUENCE: 230

Gln Val Gln Leu Gln Gln Pro Gly Ala Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Thr Lys Gln Arg Pro Gly Gln Gly Leu Glu Trp Ile
        35                  40                  45

Gly Glu Ile Asp Pro Ser Asp Ser Tyr Ala Asn Tyr Asn Gln Lys Phe
    50                  55                  60

Lys Gly Lys Ala Thr Leu Thr Val Asp Lys Tyr Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Leu Tyr Asp Gly Pro Ser Tyr Trp Gly Gln Gly Thr Leu Val Thr
            100                 105                 110

Val Ser


<210> SEQ ID NO 231
<211> LENGTH: 5
<212> TYPE: PRT
<213> ORGANISM: Artificial Sequence
<220> FEATURE:
<223> OTHER INFORMATION: ACI-7079-2603C1-Ab3 2603C1H6 VH CDR1

<400> SEQUENCE: 231

Ser Tyr Trp Met Gln
1               5


<210> SEQ ID NO 232
<211> LENGTH: 17
<212> TYPE: PRT
<213> ORGANISM: Artificial Sequence
<220> FEATURE:
<223> OTHER INFORMATION: ACI-7079-2603C1-Ab3 2603C1H6 VH CDR2

<400> SEQUENCE: 232

Glu Ile Asp Pro Ser Asp Ser Tyr Ala Asn Tyr Asn Gln Lys Phe Lys
1               5                   10                  15

Gly


<210> SEQ ID NO 233
<211> LENGTH: 6
<212> TYPE: PRT
<213> ORGANISM: Artificial Sequence
<220> FEATURE:
<223> OTHER INFORMATION: ACI-7079-2603C1-Ab3 2603C1H6 VH CDR3

<400> SEQUENCE: 233
```

```
Tyr Asp Gly Pro Ser Tyr
1               5


<210> SEQ ID NO 234
<211> LENGTH: 106
<212> TYPE: PRT
<213> ORGANISM: Artificial Sequence
<220> FEATURE:
<223> OTHER INFORMATION: ACI-7079-2603C1-Ab3 2603C1H6 VL

<400> SEQUENCE: 234

Glu Asn Val Leu Thr Gln Ser Pro Ala Ile Met Ser Ala Ser Pro Gly
1               5                   10                  15

Glu Lys Val Thr Met Thr Cys Ser Ala Gly Ser Ser Val Ser Tyr Met
            20                  25                  30

His Trp Phe Gln Gln Lys Ser Ser Thr Ser Pro Lys Leu Trp Ile Tyr
        35                  40                  45

Asp Thr Ser Lys Leu Pro Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Tyr Thr
                85                  90                  95

Phe Gly Gly Gly Thr Lys Leu Glu Ile Lys
            100                 105


<210> SEQ ID NO 235
<211> LENGTH: 10
<212> TYPE: PRT
<213> ORGANISM: Artificial Sequence
<220> FEATURE:
<223> OTHER INFORMATION: ACI-7079-2603C1-Ab3 2603C1H6 VL CDR1

<400> SEQUENCE: 235

Ser Ala Gly Ser Ser Val Ser Tyr Met His
1               5                   10


<210> SEQ ID NO 236
<211> LENGTH: 7
<212> TYPE: PRT
<213> ORGANISM: Artificial Sequence
<220> FEATURE:
<223> OTHER INFORMATION: ACI-7079-2603C1-Ab3 2603C1H6 VL CDR2

<400> SEQUENCE: 236

Asp Thr Ser Lys Leu Pro Ser
1               5


<210> SEQ ID NO 237
<211> LENGTH: 9
<212> TYPE: PRT
<213> ORGANISM: Artificial Sequence
<220> FEATURE:
<223> OTHER INFORMATION: ACI-7079-2603C1-Ab3 2603C1H6 VL CDR3

<400> SEQUENCE: 237

Phe Gln Gly Ser Gly Tyr Pro Tyr Thr
1               5


<210> SEQ ID NO 238
<211> LENGTH: 342
<212> TYPE: DNA
<213> ORGANISM: Artificial Sequence
<220> FEATURE:
```

<223> OTHER INFORMATION: ACI-7079-2603C1-Ab3 2603C1H6 VH

<400> SEQUENCE: 238
caggtccaac tgcagcaacc tggggctgac cttgtgaagc ctggggcttc agtgaagctg 60
tcctgtaagg cttctggcta caccttcacc agttactgga tgcagtggac aaaacagagg 120
cctggacagg gccttgagtg gatcggagag attgatcctt ctgatagcta tgctaactac 180
aatcaaaagt tcaagggcaa ggccacattg actgttgaca aatattccag cacagcctac 240
atgcagctca acagcctgac atctgaggac tctgcggtct attactgtgc cctctatgat 300
ggtccctctt actggggcca agggactctg gtcactgtct ct 342

<210> SEQ ID NO 239
<211> LENGTH: 318
<212> TYPE: DNA
<213> ORGANISM: Artificial Sequence
<220> FEATURE:
<223> OTHER INFORMATION: ACI-7079-2603C1-Ab3 2603C1H6 VL

<400> SEQUENCE: 239
gaaaatgttc tcacccagtc tccagcaatc atgtctgcat ctccagggga aaaggtcacc 60
atgacctgca gtgccggctc aagtgtaagt tacatgcact ggttccaaca gaagtcaagc 120
acctccccca aactctggat ttatgacaca tccaaactgc cttctggagt cccaggtcgc 180
ttcagtggca gtgggtctgg aaactcttac tctctcacga tcagcagcat ggaggctgaa 240
gatgttgcca cttattactg ttttcagggg agtgggtacc cgtacacgtt cggagggggg 300
accaagctgg aaataaaa 318

<210> SEQ ID NO 240
<211> LENGTH: 120
<212> TYPE: PRT
<213> ORGANISM: Artificial Sequence
<220> FEATURE:
<223> OTHER INFORMATION: ACI-7079-2603F3-Ab1 2603F3H3 VH

<400> SEQUENCE: 240

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Gly Ser Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Gly Asp Ser Trp Phe Ala Tyr Trp Gly Gln
            100                 105                 110

Gly Thr Leu Val Thr Val Ser Ala
        115                 120

<210> SEQ ID NO 241
<211> LENGTH: 5
<212> TYPE: PRT
<213> ORGANISM: Artificial Sequence
<220> FEATURE:
<223> OTHER INFORMATION: ACI-7079-2603F3-Ab1 2603F3H3 VH CDR1

<400> SEQUENCE: 241

Thr Tyr Ala Met His
1 5

<210> SEQ ID NO 242
<211> LENGTH: 19
<212> TYPE: PRT
<213> ORGANISM: Artificial Sequence
<220> FEATURE:
<223> OTHER INFORMATION: ACI-7079-2603F3-Ab1 2603F3H3 VH CDR2

<400> SEQUENCE: 242

Arg Ile Arg Ser Lys Gly Ser Asn Tyr Ala Thr Tyr Tyr Ala Asp Ser
1 5 10 15

Val Lys Asp

<210> SEQ ID NO 243
<211> LENGTH: 9
<212> TYPE: PRT
<213> ORGANISM: Artificial Sequence
<220> FEATURE:
<223> OTHER INFORMATION: ACI-7079-2603F3-Ab1 2603F3H3 VH CDR3

<400> SEQUENCE: 243

Gly Gly Gly Asp Ser Trp Phe Ala Tyr
1 5

<210> SEQ ID NO 244
<211> LENGTH: 106
<212> TYPE: PRT
<213> ORGANISM: Artificial Sequence
<220> FEATURE:
<223> OTHER INFORMATION: ACI-7079-2603F3-Ab1 2603F3H3 VL

<400> SEQUENCE: 244

Gln Ile Val Leu Thr Gln Ser Pro Ala Ile Met Ser Ala Ser Pro Gly
1 5 10 15

Glu Arg Val Thr Met Thr Cys Thr Ala Ser Ser Ser Val Ser Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Ser
50 55 60

Gly Ser Gly Ala Ser Tyr Thr Leu Thr Ile Ser Ser Met Glu Ala Glu
65 70 75 80

Asp Ala Ala Thr Tyr Tyr Cys Gln Gln Trp Asn Ser Asn Pro Pro Thr
85 90 95

Phe Gly Gly Gly Thr Gln Leu Ala Ile Lys
100 105

<210> SEQ ID NO 245
<211> LENGTH: 10
<212> TYPE: PRT
<213> ORGANISM: Artificial Sequence
<220> FEATURE:
<223> OTHER INFORMATION: ACI-7079-2603F3-Ab1 2603F3H3 VL CDR1

<400> SEQUENCE: 245

Thr Ala Ser Ser Ser Val Ser Tyr Met His
1 5 10

<210> SEQ ID NO 246
<211> LENGTH: 7
<212> TYPE: PRT
<213> ORGANISM: Artificial Sequence
<220> FEATURE:
<223> OTHER INFORMATION: ACI-7079-2603F3-Ab1 2603F3H3 VL CDR2

<400> SEQUENCE: 246

Asp Thr Ser Lys Leu Ala Ser
1               5

<210> SEQ ID NO 247
<211> LENGTH: 9
<212> TYPE: PRT
<213> ORGANISM: Artificial Sequence
<220> FEATURE:
<223> OTHER INFORMATION: ACI-7079-2603F3-Ab1 2603F3H3 VL CDR3

<400> SEQUENCE: 247

Gln Gln Trp Asn Ser Asn Pro Pro Thr
1               5

<210> SEQ ID NO 248
<211> LENGTH: 360
<212> TYPE: DNA
<213> ORGANISM: Artificial Sequence
<220> FEATURE:
<223> OTHER INFORMATION: ACI-7079-2603F3-Ab1 2603F3H3 VH

<400> SEQUENCE: 248
gaggtgcagc ttgttgagtc tggtggagga ttggtgcagc ctaaaggatc attgaaactc 60
tcatgtgccg cctctggttt caccttcaat acctatgcca tgcactgggt ccgccaggct 120
ccaggaaagg gtttggaatg ggttgctcgc ataagaagta aaggtagtaa ttatgcaaca 180
tattatgccg attcagtgaa agacagattc accatctcca gagatgattc acaaagcatg 240
ctctatctgc aaatgaacaa cctgaaaact gaggacacag ccatgtatta ctgtgtgaga 300
gggggtggtg actcctggtt tgcttactgg ggccaaggga ctctggtcac tgtctctgca 360

<210> SEQ ID NO 249
<211> LENGTH: 318
<212> TYPE: DNA
<213> ORGANISM: Artificial Sequence
<220> FEATURE:
<223> OTHER INFORMATION: ACI-7079-2603F3-Ab1 2603F3H3 VL

<400> SEQUENCE: 249
caaattgttc tcacccagtc tccagcaatc atgtctgcat ctccagggga gagggtcacc 60
atgacctgca ctgccagctc aagtgtaagt tacatgcact ggtaccagca gaagtcaggc 120
acctccccca aaagatggat ttatgacaca tccaaactgg cttctggagt ccctgctcgc 180
ttcagtggca gtgggtctgg ggcctcttat actctcacaa tcagcagcat ggaggctgaa 240
gatgctgcca cttattactg ccagcagtgg aatagtaacc caccgacgtt cggtggaggc 300
acccagctgg caatcaaa 318

<210> SEQ ID NO 250
<211> LENGTH: 120
<212> TYPE: PRT
<213> ORGANISM: Artificial Sequence
<220> FEATURE:
<223> OTHER INFORMATION: ACI-7079-2605B3-Ab2 2605B3D1 VH

<400> SEQUENCE: 250

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ile Phe Lys Thr Tyr
            20                  25                  30

Ala Met His Trp Val Arg Gln Ala Pro Gly Lys Gly Leu Glu Trp Val
        35                  40                  45

Ala Arg Ile Arg Ser Lys Gly Gly Asn Tyr Ala Thr Tyr Phe Ala Asp
    50                  55                  60

Ser Val Lys Asp Arg Phe Thr Ile Ser Arg Asp Asp Ser Gln Asn Met
65                  70                  75                  80

Leu Tyr Leu Gln Val Asn Asn Leu Lys Ile Glu Asp Thr Ala Met Tyr
                85                  90                  95

Phe Cys Val Arg Gly Gly Asn Tyr Ser Trp Phe Ala Tyr Trp Gly Gln
            100                 105                 110

Gly Thr Leu Val Thr Val Ser Ala
        115                 120


<210> SEQ ID NO 251
<211> LENGTH: 5
<212> TYPE: PRT
<213> ORGANISM: Artificial Sequence
<220> FEATURE:
<223> OTHER INFORMATION: ACI-7079-2605B3-Ab2 2605B3D1 VH CDR1

<400> SEQUENCE: 251

Thr Tyr Ala Met His
1               5


<210> SEQ ID NO 252
<211> LENGTH: 19
<212> TYPE: PRT
<213> ORGANISM: Artificial Sequence
<220> FEATURE:
<223> OTHER INFORMATION: ACI-7079-2605B3-Ab2 2605B3D1 VH CDR2

<400> SEQUENCE: 252

Arg Ile Arg Ser Lys Gly Gly Asn Tyr Ala Thr Tyr Phe Ala Asp Ser
1               5                   10                  15

Val Lys Asp


<210> SEQ ID NO 253
<211> LENGTH: 9
<212> TYPE: PRT
<213> ORGANISM: Artificial Sequence
<220> FEATURE:
<223> OTHER INFORMATION: ACI-7079-2605B3-Ab2 2605B3D1 VH CDR3

<400> SEQUENCE: 253

Gly Gly Asn Tyr Ser Trp Phe Ala Tyr
1               5


<210> SEQ ID NO 254
<211> LENGTH: 106
<212> TYPE: PRT
<213> ORGANISM: Artificial Sequence
<220> FEATURE:
<223> OTHER INFORMATION: ACI-7079-2605B3-Ab2 2605B3D1 VL

<400> SEQUENCE: 254

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
```

20 25 30

His Trp Tyr Gln Gln Lys Ser Gly Thr Ser Pro Lys Arg Trp Ile Tyr
35 40 45

Asp Thr Ser Gln Leu Ala Ser Gly Val Pro Ala Arg Phe Ser Gly Ser
50 55 60

Gly Ser Gly Thr Ser His Ser Leu Thr Ile Ser Ser Met Glu Thr Glu
65 70 75 80

Asp Ala Ala Thr Tyr Tyr Cys Gln Gln Trp Thr Arg Asn Pro Pro Thr
85 90 95

Phe Gly Gly Gly Thr Lys Leu Ala Ile Lys
100 105

<210> SEQ ID NO 255
<211> LENGTH: 10
<212> TYPE: PRT
<213> ORGANISM: Artificial Sequence
<220> FEATURE:
<223> OTHER INFORMATION: ACI-7079-2605B3-Ab2 2605B3D1 VL CDR1

<400> SEQUENCE: 255

Ser Ala Ser Ser Ser Val Thr Tyr Met His
1 5 10

<210> SEQ ID NO 256
<211> LENGTH: 7
<212> TYPE: PRT
<213> ORGANISM: Artificial Sequence
<220> FEATURE:
<223> OTHER INFORMATION: ACI-7079-2605B3-Ab2 2605B3D1 VL CDR2

<400> SEQUENCE: 256

Asp Thr Ser Gln Leu Ala Ser
1 5

<210> SEQ ID NO 257
<211> LENGTH: 8
<212> TYPE: PRT
<213> ORGANISM: Artificial Sequence
<220> FEATURE:
<223> OTHER INFORMATION: ACI-7079-2605B3-Ab2 2605B3D1 VL CDR3

<400> SEQUENCE: 257

Gln Gln Trp Thr Arg Asn Pro Pro
1 5

<210> SEQ ID NO 258
<211> LENGTH: 360
<212> TYPE: DNA
<213> ORGANISM: Unknown
<220> FEATURE:
<223> OTHER INFORMATION: Organism of the class Mammalia

<400> SEQUENCE: 258
gaggtgcagc ttgttgagtc tggtggagga ttggtgcagc ctaaaggatc attgaaactc 60
tcatgtgccg cctctggttt catctttaaa acctatgcca tgcattgggt ccgccaggct 120
ccaggaaagg gtttggaatg ggttgctcga ataagaagta aaggtggtaa ttatgcaaca 180
tattttgccg attcagtgaa agacagattc accatctcca gagatgattc acaaaatatg 240
ctctatctgc aagtgaacaa cctgaaaatt gaggacacag ccatgtattt ctgtgtgaga 300
gggggtaatt actcctggtt tgcttactgg ggccaaggga ctctggtcac tgtctctgca 360

<210> SEQ ID NO 259
<211> LENGTH: 318
<212> TYPE: DNA
<213> ORGANISM: Unknown
<220> FEATURE:
<223> OTHER INFORMATION: Organism of the class Mammalia

<400> SEQUENCE: 259
caaattgttc tcacccagtc tccagcaatc atgtctgctt ctccagggga gaaggtcacc 60
atgacctgca gtgccagctc aagtgtaact tacatgcatt ggtaccagca gaagtcaggc 120
acctccccca aaagatggat ttatgacaca tcccaactgg cttctggagt ccctgctcgc 180
ttcagtggca gtgggtctgg gacctctcac tctctcacaa tcagcagcat ggagactgaa 240
gatgctgcca cttattactg ccaacaatgg actagaaacc caccgacgtt cggtggaggc 300
accaagctgg caatcaaa 318

<210> SEQ ID NO 260
<211> LENGTH: 119
<212> TYPE: PRT
<213> ORGANISM: Artificial Sequence
<220> FEATURE:
<223> OTHER INFORMATION: ACI-7079-2606A6-Ab2 2606A6D5 VH

<400> SEQUENCE: 260

Gln Val Gln Leu Gln Gln Ser Gly Pro Glu Leu Val Lys Pro Gly Ala
1 5 10 15

Ser Val Lys Ile Ser Cys Lys Ala Ser Gly Phe Ala Phe Ser Ser Ser
20 25 30

Trp Met Asn Trp Val Lys Gln Arg Pro Gly Lys Gly Leu Glu Trp Val
35 40 45

Gly Arg Ile Phe Pro Gly Asp Gly Asp Thr Asn Tyr Asp Arg Lys Phe
50 55 60

Lys Asp Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Trp Thr Gly Gly Tyr Asp Trp Phe Ala Tyr Trp Gly Gln Gly
100 105 110

Thr Leu Val Thr Val Ser Ala
115

<210> SEQ ID NO 261
<211> LENGTH: 5
<212> TYPE: PRT
<213> ORGANISM: Artificial Sequence
<220> FEATURE:
<223> OTHER INFORMATION: ACI-7079-2606A6-Ab2 2606A6D5 VH CDR1

<400> SEQUENCE: 261

Ser Ser Trp Met Asn
1 5

<210> SEQ ID NO 262
<211> LENGTH: 17
<212> TYPE: PRT
<213> ORGANISM: Artificial Sequence
<220> FEATURE:
<223> OTHER INFORMATION: ACI-7079-2606A6-Ab2 2606A6D5 VH CDR2

<400> SEQUENCE: 262

Arg Ile Phe Pro Gly Asp Gly Asp Thr Asn Tyr Asp Arg Lys Phe Lys 1 5 10 15

Asp

<210> SEQ ID NO 263
<211> LENGTH: 10
<212> TYPE: PRT
<213> ORGANISM: Artificial Sequence
<220> FEATURE:
<223> OTHER INFORMATION: ACI-7079-2606A6-Ab2 2606A6D5 VH CDR3

<400> SEQUENCE: 263

Trp Thr Gly Gly Tyr Asp Trp Phe Ala Tyr
1 5 10

<210> SEQ ID NO 264
<211> LENGTH: 111
<212> TYPE: PRT
<213> ORGANISM: Artificial Sequence
<220> FEATURE:
<223> OTHER INFORMATION: ACI-7079-2606A6-Ab2 2606A6D5 VL

<400> SEQUENCE: 264

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Thr Ser
20 25 30

Asn Tyr Asn Tyr Leu His Trp Tyr Gln Gln Lys Pro Gly Gln Pro Pro
35 40 45

Lys Leu Leu Ile Thr Tyr Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Gly Asp Thr Ala Thr Tyr Tyr Cys Gln His Ser Trp
85 90 95

Glu Ile Pro Leu Thr Phe Gly Ala Gly Thr Lys Leu Glu Leu Lys
100 105 110

<210> SEQ ID NO 265
<211> LENGTH: 15
<212> TYPE: PRT
<213> ORGANISM: Artificial Sequence
<220> FEATURE:
<223> OTHER INFORMATION: ACI-7079-2606A6-Ab2 2606A6D5 VL CDR1

<400> SEQUENCE: 265

Arg Ala Ser Gln Ser Val Ser Thr Ser Asn Tyr Asn Tyr Leu His
1 5 10 15

<210> SEQ ID NO 266
<211> LENGTH: 7
<212> TYPE: PRT
<213> ORGANISM: Artificial Sequence
<220> FEATURE:
<223> OTHER INFORMATION: ACI-7079-2606A6-Ab2 2606A6D5 VL CDR2

<400> SEQUENCE: 266

Tyr Ala Ser Asn Leu Glu Ser
1 5

<210> SEQ ID NO 267
<211> LENGTH: 9
<212> TYPE: PRT
<213> ORGANISM: Artificial Sequence
<220> FEATURE:
<223> OTHER INFORMATION: ACI-7079-2606A6-Ab2 2606A6D5 VL CDR3

<400> SEQUENCE: 267

Gln His Ser Trp Glu Ile Pro Leu Thr
1               5

<210> SEQ ID NO 268
<211> LENGTH: 357
<212> TYPE: DNA
<213> ORGANISM: Artificial Sequence
<220> FEATURE:
<223> OTHER INFORMATION: ACI-7079-2606A6-Ab2 2606A6D5 VH

<400> SEQUENCE: 268
caggttcagc tgcaacagtc tggacctgag ctggtgaagc ctggggcctc agtgaagatt 60
tcctgcaagg cttctggctt cgcattcagt agctcctgga tgaactgggt gaagcagagg 120
cctggaaagg gtcttgagtg ggttggacgg atttttcctg gagatggaga tactaactac 180
gataggaagt tcaaggacaa ggccacactg actgcagaca aatcctccag cacagcctac 240
atgcaactca gcagcctgac atctgaggac tctgcggtct acttctgtgc aagatggacg 300
gggggttacg actggtttgc ttactggggc caagggactc tggtcactgt ctctgca 357

<210> SEQ ID NO 269
<211> LENGTH: 333
<212> TYPE: DNA
<213> ORGANISM: Artificial Sequence
<220> FEATURE:
<223> OTHER INFORMATION: ACI-7079-2606A6-Ab2 2606A6D5 VL

<400> SEQUENCE: 269
gacattgtgc tgacacagtc tcctgcttcc ttagctgtat ctctggggca gagggccacc 60
atctcatgca gggccagcca aagtgtcagt acatctaact ataattatct tcactggtac 120
caacagaaac caggacagcc acccaaactc ctcatcacgt atgcatccaa cctagaatct 180
ggggtccctg ccaggttcag tggcagtggg tctgggacag acttcaccct caacatccat 240
cctgtggagg agggagatac tgcaacatat tactgtcaac acagttggga gattccgctc 300
acgttcggtg ctgggaccaa gctggagctg aaa 333

<210> SEQ ID NO 270
<211> LENGTH: 117
<212> TYPE: PRT
<213> ORGANISM: Artificial Sequence
<220> FEATURE:
<223> OTHER INFORMATION: ACI-7079-2509E5-Ab2 2509E5E5 VH

<400> SEQUENCE: 270

Glu Val Gln Leu Gln Gln Ser Gly Pro Glu Leu Val Lys Pro Gly Ala
1               5                   10                  15

Ser Leu Lys Met Ser Cys Lys Ala Ser Gly Tyr Ser Phe Thr Asp Tyr
            20                  25                  30

Asn Met His Trp Val Lys Gln Ser Arg Gly Lys Ser Leu Glu Trp Ile
        35                  40                  45

Gly Tyr Ile Asn Pro Asn Asn Gly Val Pro Thr Tyr Lys Gln Lys Phe
    50                  55                  60

Lys Gly Arg Ala Thr Leu Thr Val Asn Gln Ser Ser Ser Thr Ala Tyr
65                  70                  75                  80

Met Glu Ile Arg Ser Leu Thr Ser Glu Asp Ser Ala Val Tyr Tyr Cys
                85                  90                  95

```
Thr Arg Gly Gly Asp His Arg Phe Ala Tyr Trp Gly Gln Gly Thr Leu
            100                 105                 110

Val Thr Val Ser Ala
        115


<210> SEQ ID NO 271
<211> LENGTH: 5
<212> TYPE: PRT
<213> ORGANISM: Artificial Sequence
<220> FEATURE:
<223> OTHER INFORMATION: ACI-7079-2509E5-Ab2 2509E5E5 VH CDR1

<400> SEQUENCE: 271

Asp Tyr Asn Met His
1               5


<210> SEQ ID NO 272
<211> LENGTH: 17
<212> TYPE: PRT
<213> ORGANISM: Artificial Sequence
<220> FEATURE:
<223> OTHER INFORMATION: ACI-7079-2509E5-Ab2 2509E5E5 VH CDR2

<400> SEQUENCE: 272

Tyr Ile Asn Pro Asn Asn Gly Val Pro Thr Tyr Lys Gln Lys Phe Lys
1               5                   10                  15

Gly


<210> SEQ ID NO 273
<211> LENGTH: 8
<212> TYPE: PRT
<213> ORGANISM: Artificial Sequence
<220> FEATURE:
<223> OTHER INFORMATION: ACI-7079-2509E5-Ab2 2509E5E5 VH CDR3

<400> SEQUENCE: 273

Gly Gly Asp His Arg Phe Ala Tyr
1               5


<210> SEQ ID NO 274
<211> LENGTH: 111
<212> TYPE: PRT
<213> ORGANISM: Artificial Sequence
<220> FEATURE:
<223> OTHER INFORMATION: ACI-7079-2509E5-Ab2 2509E5E5 VL

<400> SEQUENCE: 274

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Phe Ser Phe Val Asn Trp Phe Gln Gln Lys Pro Gly Gln Pro Pro
        35                  40                  45

Lys Leu Leu Ile Tyr Ser Ala Ser Tyr Lys Gly Ser Gly Val Pro Val
    50                  55                  60

Arg Phe Ser Gly Ser Gly Ser Gly Thr Asp Phe Ser Leu Ser Ile His
65                  70                  75                  80

Pro Met Glu Ala Asp Asp Thr Ala Met Tyr Phe Cys Gln Gln Asn Lys
                85                  90                  95

Glu Val Pro Leu Thr Phe Gly Ala Gly Thr Lys Leu Glu Leu Lys
            100                 105                 110
```

<210> SEQ ID NO 275
<211> LENGTH: 15
<212> TYPE: PRT
<213> ORGANISM: Artificial Sequence
<220> FEATURE:
<223> OTHER INFORMATION: ACI-7079-2509E5-Ab2 2509E5E5 VL CDR1

<400> SEQUENCE: 275

Arg Ala Ser Glu Ser Val Asp Tyr Tyr Gly Phe Ser Phe Val Asn
1               5                   10                  15

<210> SEQ ID NO 276
<211> LENGTH: 7
<212> TYPE: PRT
<213> ORGANISM: Artificial Sequence
<220> FEATURE:
<223> OTHER INFORMATION: ACI-7079-2509E5-Ab2 2509E5E5 VL CDR2

<400> SEQUENCE: 276

Ser Ala Ser Tyr Lys Gly Ser
1               5

<210> SEQ ID NO 277
<211> LENGTH: 9
<212> TYPE: PRT
<213> ORGANISM: Artificial Sequence
<220> FEATURE:
<223> OTHER INFORMATION: ACI-7079-2509E5-Ab2 2509E5E5 VL CDR3

<400> SEQUENCE: 277

Gln Gln Asn Lys Glu Val Pro Leu Thr
1               5

<210> SEQ ID NO 278
<211> LENGTH: 351
<212> TYPE: DNA
<213> ORGANISM: Artificial Sequence
<220> FEATURE:
<223> OTHER INFORMATION: ACI-7079-2509E5-Ab2 2509E5E5 VH

<400> SEQUENCE: 278
gaggtccagc tgcaacagtc tggacctgaa ctggtgaagc ctggggcttc gctgaagatg 60
tcctgcaagg cttctggata ctcattcact gactacaaca tgcactgggt gaaacagagc 120
cgtggaaaga gccttgagtg gattggatat attaacccta acaatggtgt tcccacgtat 180
aagcagaagt tcaagggcag ggccaccttg actgtaaacc agtcctccag cacagcctac 240
atggagatcc gcagcctgac atcggaagat tctgcagtct attactgtac aagagggggt 300
gatcaccggt ttgcttactg gggccaaggg actctggtca ctgtctctgc a 351

<210> SEQ ID NO 279
<211> LENGTH: 333
<212> TYPE: DNA
<213> ORGANISM: Artificial Sequence
<220> FEATURE:
<223> OTHER INFORMATION: ACI-7079-2509E5-Ab2 2509E5E5 VL

<400> SEQUENCE: 279
gacattgtgc tgacccaatc tccagcttct ttggctgtgt ctctagggca gagggccacc 60
atctcctgca gagccagcga aagtgttgat tattatggct ttagttttgt gaactggttc 120
caacagaaac caggacagcc acccaaactc ctcatctata gtgcgtccta caaaggatcc 180
ggggtccctg tcaggttcag tggcagtggg tctgggacag acttcagtct cagcatccat 240

```
cctatggagg cggatgatac tgcaatgtat ttctgtcagc aaaataagga ggttccgctc    300

acgttcggtg ctgggaccaa gctggagctg aaa                                 333


<210> SEQ ID NO 280
<211> LENGTH: 120
<212> TYPE: PRT
<213> ORGANISM: Artificial Sequence
<220> FEATURE:
<223> OTHER INFORMATION: ACI-7079-2501B11-Ab3 2501B11C7 VH

<400> SEQUENCE: 280

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Phe
            20                  25                  30

Trp Met Asn Trp Met Lys Gln Arg Pro Gly Lys Gly Leu Glu Trp Ile
        35                  40                  45

Gly Arg Ile Tyr Pro Gly Asp Gly Asp Ala His Tyr Asn Gly Glu Phe
    50                  55                  60

Lys Gly Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Lys Gly Asp Phe Tyr Gly Ser Asn Tyr Asp Tyr Trp Gly Gln
            100                 105                 110

Gly Thr Thr Leu Thr Val Ser Ser
        115                 120


<210> SEQ ID NO 281
<211> LENGTH: 4
<212> TYPE: PRT
<213> ORGANISM: Artificial Sequence
<220> FEATURE:
<223> OTHER INFORMATION: ACI-7079-2501B11-Ab3 2501B11C7 VH CDR1

<400> SEQUENCE: 281

Ser Phe Trp Met
1


<210> SEQ ID NO 282
<211> LENGTH: 17
<212> TYPE: PRT
<213> ORGANISM: Artificial Sequence
<220> FEATURE:
<223> OTHER INFORMATION: ACI-7079-2501B11-Ab3 2501B11C7 VH CDR2

<400> SEQUENCE: 282

Arg Ile Tyr Pro Gly Asp Gly Asp Ala His Tyr Asn Gly Glu Phe Lys
1               5                   10                  15

Gly


<210> SEQ ID NO 283
<211> LENGTH: 11
<212> TYPE: PRT
<213> ORGANISM: Artificial Sequence
<220> FEATURE:
<223> OTHER INFORMATION: ACI-7079-2501B11-Ab3 2501B11C7 VH CDR3

<400> SEQUENCE: 283

Lys Gly Asp Phe Tyr Gly Ser Asn Tyr Asp Tyr
1               5                   10
```

<210> SEQ ID NO 284
<211> LENGTH: 109
<212> TYPE: PRT
<213> ORGANISM: Artificial Sequence
<220> FEATURE:
<223> OTHER INFORMATION: ACI-7079-2501B11-Ab3 2501B11C7 VL

<400> SEQUENCE: 284

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Arg Leu Thr Val Leu
            100                 105
```

<210> SEQ ID NO 285
<211> LENGTH: 14
<212> TYPE: PRT
<213> ORGANISM: Artificial Sequence
<220> FEATURE:
<223> OTHER INFORMATION: ACI-7079-2501B11-Ab3 2501B11C7 VL CDR1

<400> SEQUENCE: 285

```
Arg Ser Ser Thr Gly Ala Val Thr Thr Ser Asn Tyr Ala Asn
1               5                   10
```

<210> SEQ ID NO 286
<211> LENGTH: 7
<212> TYPE: PRT
<213> ORGANISM: Artificial Sequence
<220> FEATURE:
<223> OTHER INFORMATION: ACI-7079-2501B11-Ab3 2501B11C7 VL CDR2

<400> SEQUENCE: 286

```
Gly Thr Asn Asn Arg Ala Pro
1               5
```

<210> SEQ ID NO 287
<211> LENGTH: 9
<212> TYPE: PRT
<213> ORGANISM: Artificial Sequence
<220> FEATURE:
<223> OTHER INFORMATION: ACI-7079-2501B11-Ab3 2501B11C7 VL CDR3

<400> SEQUENCE: 287

```
Ala Leu Trp Tyr Ser Asn His Leu Val
1               5
```

<210> SEQ ID NO 288
<211> LENGTH: 360
<212> TYPE: DNA
<213> ORGANISM: Artificial Sequence
<220> FEATURE:
<223> OTHER INFORMATION: ACI-7079-2501B11-Ab3 2501B11C7 VH

<400> SEQUENCE: 288

```
caggttcagc tgcagcagtc tggacctgag ctggtgaagc ctggggcctc agtgaagatt     60

tcctgcaagg cttctggcta cgcattcagt agtttctgga tgaactggat gaaacagagg    120

cctggaaagg gtcttgagtg gattggacgg atttatcctg gagatggaga tgctcactac    180

aatggggagt tcaagggcag ggccacactg actgcagaca aatcctccag cacagcctac    240

atgcaactca gcagcctgac atctgaggac tctgcggtct acttctgtgc aagaaagggg    300

gatttctacg gtagtaacta cgactattgg ggccaaggca ccactctcac agtctcctca    360


<210> SEQ ID NO 289
<211> LENGTH: 327
<212> TYPE: DNA
<213> ORGANISM: Artificial Sequence
<220> FEATURE:
<223> OTHER INFORMATION: ACI-7079-2501B11-Ab3 2501B11C7 VL

<400> SEQUENCE: 289

caggctgttg tgactcagga atctgcactc accacatcac ctggtgaaac agtcacactc     60

acttgtcgct caagtactgg ggctgttaca actagtaact atgccaactg ggtccaagaa    120

aaaccagatc atttattcac tggtctaata ggtggtacca acaaccgagc tccaggtgtt    180

cctgccagat tctcaggctc cctgattgga gacaaggctg ccctcaccat cacaggggca    240

cagactgagg atgaggcaat atatttctgt gctctatggt acagcaacca tttggtgttc    300

ggtggaggaa ccagactgac tgtccta                                        327


<210> SEQ ID NO 290
<211> LENGTH: 120
<212> TYPE: PRT
<213> ORGANISM: Artificial Sequence
<220> FEATURE:
<223> OTHER INFORMATION: ACI-7079-2501D10-Ab1 2501D10C3 VH

<400> SEQUENCE: 290

Glu Val Gln Leu Val Glu Ser Gly Gly Gly Leu Val Gln Pro Lys Gly
1               5                   10                  15

Ser Leu Lys Val Ser Cys Ala Ala Ser Gly Phe Thr Phe Lys Thr Tyr
            20                  25                  30

Ala Met His Trp Val Arg Gln Ala Pro Gly Lys Gly Leu Glu Trp Val
        35                  40                  45

Ala Arg Ile Arg Ser Glu Asn Ser Asn Phe Ala Lys Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Tyr Asn Gly Ser Ser Leu Asp Tyr Trp Gly Gln
            100                 105                 110

Gly Thr Thr Leu Thr Val Ser Ser
        115                 120


<210> SEQ ID NO 291
<211> LENGTH: 5
<212> TYPE: PRT
<213> ORGANISM: Artificial Sequence
<220> FEATURE:
<223> OTHER INFORMATION: ACI-7079-2501D10-Ab1 2501D10C3 VH CDR1

<400> SEQUENCE: 291
```

Thr Tyr Ala Met His
1 5

<210> SEQ ID NO 292
<211> LENGTH: 19
<212> TYPE: PRT
<213> ORGANISM: Artificial Sequence
<220> FEATURE:
<223> OTHER INFORMATION: ACI-7079-2501D10-Ab1 2501D10C3 VH CDR2

<400> SEQUENCE: 292

Arg Ile Arg Ser Glu Asn Ser Asn Phe Ala Lys Tyr Tyr Ala Asp Ser
1 5 10 15

Val Lys Asp

<210> SEQ ID NO 293
<211> LENGTH: 9
<212> TYPE: PRT
<213> ORGANISM: Artificial Sequence
<220> FEATURE:
<223> OTHER INFORMATION: ACI-7079-2501D10-Ab1 2501D10C3 VH CDR3

<400> SEQUENCE: 293

Gly Tyr Asn Gly Ser Ser Leu Asp Tyr
1 5

<210> SEQ ID NO 294
<211> LENGTH: 106
<212> TYPE: PRT
<213> ORGANISM: Artificial Sequence
<220> FEATURE:
<223> OTHER INFORMATION: ACI-7079-2501D10-Ab1 2501D10C3 VL

<400> SEQUENCE: 294

Gln Ile Val Leu Thr Gln Ser Pro Ala Ile Met Ser Ala Phe Pro Gly
1 5 10 15

Glu Arg Val Thr Met Thr Cys Ser Ala Ser Ser Ser Val Asn Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Gly
50 55 60

Gly Ser Gly Thr Ser Tyr Ser Leu Thr Ile Ser Asn Met Glu Ala Glu
65 70 75 80

Asp Ala Ala Thr Tyr Tyr Cys Gln Gln Trp Arg Ser Asn Pro Pro Thr
85 90 95

Phe Gly Gly Gly Thr Lys Leu Glu Ile Lys
100 105

<210> SEQ ID NO 295
<211> LENGTH: 10
<212> TYPE: PRT
<213> ORGANISM: Artificial Sequence
<220> FEATURE:
<223> OTHER INFORMATION: ACI-7079-2501D10-Ab1 2501D10C3 VL CDR1

<400> SEQUENCE: 295

Ser Ala Ser Ser Ser Val Asn Tyr Met His
1 5 10

<210> SEQ ID NO 296
<211> LENGTH: 7
<212> TYPE: PRT

<213> ORGANISM: Artificial Sequence
<220> FEATURE:
<223> OTHER INFORMATION: ACI-7079-2501D10-Ab1 2501D10C3 VL CDR2

<400> SEQUENCE: 296

Asp Thr Ser Lys Leu Ala Ser
1 5

<210> SEQ ID NO 297
<211> LENGTH: 9
<212> TYPE: PRT
<213> ORGANISM: Artificial Sequence
<220> FEATURE:
<223> OTHER INFORMATION: ACI-7079-2501D10-Ab1 2501D10C3 VL CDR3

<400> SEQUENCE: 297

Gln Gln Trp Arg Ser Asn Pro Pro Thr
1 5

<210> SEQ ID NO 298
<211> LENGTH: 360
<212> TYPE: DNA
<213> ORGANISM: Artificial Sequence
<220> FEATURE:
<223> OTHER INFORMATION: ACI-7079-2501D10-Ab1 2501D10C3 VH

<400> SEQUENCE: 298
gaggtgcagc ttgttgagtc tggtggagga ttggtgcagc ctaaaggatc attgaaagtc 60
tcatgtgccg cctctggttt caccttcaag acctatgcca tgcactgggt ccgccaggct 120
ccgggaaagg gtttggaatg ggttgctcgc ataagaagtg aaaacagtaa ttttgcaaaa 180
tattatgccg attcagtgaa ggacagattc accatctcca gagatgattc acaaagtatg 240
ctctatctgc aaatgaacaa cctgaaaact gaggacacag ccatgtatta ttgtgtaagg 300
ggatataacg gcagtagcct tgactactgg ggccaaggca ccactctcac agtctcctca 360

<210> SEQ ID NO 299
<211> LENGTH: 318
<212> TYPE: DNA
<213> ORGANISM: Artificial Sequence
<220> FEATURE:
<223> OTHER INFORMATION: ACI-7079-2501D10-Ab1 2501D10C3 VL

<400> SEQUENCE: 299
caaattgttc tcacccagtc tccagcaatc atgtctgcat ttccagggga gagggtcacc 60
atgacctgca gtgccagctc aagtgtaaat tacatgcact ggtaccagca gaagtccggc 120
acctccccca aaagatggat ttatgacaca tccaaactgg cttctggagt ccctgctcgc 180
ttcagtggcg gtgggtctgg gacctcttac tctctcacaa tcagcaacat ggaggctgaa 240
gatgctgcca cttattactg ccagcagtgg agaagtaatc cacccacttt cggagggggg 300
accaagctgg aaataaaa 318

<210> SEQ ID NO 300
<211> LENGTH: 117
<212> TYPE: PRT
<213> ORGANISM: Artificial Sequence
<220> FEATURE:
<223> OTHER INFORMATION: ACI-7087-4119E10-Ab2 4119E10D12 VH

<400> SEQUENCE: 300

Gln Val Gln Leu Gln Gln Ser Gly Ala Glu Leu Val Arg Pro Gly Ala
1 5 10 15

```
Ser Val Thr Leu Ser Cys Lys Ala Ser Gly Tyr Thr Phe Ser Asp Tyr
            20                  25                  30

Glu Met Asn Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ser Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Leu Leu Ile Asp Phe Asp Tyr Trp Gly Gln Gly Thr Thr
            100                 105                 110

Leu Thr Val Ser Ser
        115


<210> SEQ ID NO 301
<211> LENGTH: 5
<212> TYPE: PRT
<213> ORGANISM: Artificial Sequence
<220> FEATURE:
<223> OTHER INFORMATION: ACI-7087-4119E10-Ab2 4119E10D12 VH CDR1

<400> SEQUENCE: 301

Asp Tyr Glu Met Asn
1               5


<210> SEQ ID NO 302
<211> LENGTH: 17
<212> TYPE: PRT
<213> ORGANISM: Artificial Sequence
<220> FEATURE:
<223> OTHER INFORMATION: ACI-7087-4119E10-Ab2 4119E10D12 VH CDR2

<400> SEQUENCE: 302

Ala Ile Asp Pro Glu Thr Gly Gly Thr Ala Tyr Asn Gln Lys Phe Lys
1               5                   10                  15

Gly


<210> SEQ ID NO 303
<211> LENGTH: 8
<212> TYPE: PRT
<213> ORGANISM: Artificial Sequence
<220> FEATURE:
<223> OTHER INFORMATION: ACI-7087-4119E10-Ab2 4119E10D12 VH CDR3

<400> SEQUENCE: 303

Phe Leu Leu Ile Asp Phe Asp Tyr
1               5


<210> SEQ ID NO 304
<211> LENGTH: 112
<212> TYPE: PRT
<213> ORGANISM: Artificial Sequence
<220> FEATURE:
<223> OTHER INFORMATION: ACI-7087-4119E10-Ab2 4119E10D12 VL

<400> SEQUENCE: 304

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Lys Lys Ala Gly Gln Ser
```

```
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Glu Leu Glu Ile Lys
            100                 105                 110


<210> SEQ ID NO 305

<400> SEQUENCE: 305

000


<210> SEQ ID NO 306

<400> SEQUENCE: 306

000


<210> SEQ ID NO 307
<211> LENGTH: 9
<212> TYPE: PRT
<213> ORGANISM: Artificial Sequence
<220> FEATURE:
<223> OTHER INFORMATION: ACI-7087-4119E10-Ab2 4119E10D12 VL CDR3

<400> SEQUENCE: 307

Phe Gln Gly Ser His Val Pro Tyr Thr
1               5


<210> SEQ ID NO 308
<211> LENGTH: 351
<212> TYPE: DNA
<213> ORGANISM: Artificial Sequence
<220> FEATURE:
<223> OTHER INFORMATION: ACI-7087-4119E10-Ab2 4119E10D12 VH

<400> SEQUENCE: 308

caggttcaac tgcagcagtc tggggctgag ctggtgaggc ctggggcttc agtgacgctg      60

tcctgcaagg cttcgggcta cacattttct gactatgaaa tgaactgggt gaagcagaca     120

cctgtgcatg gcctggaatg gattggagct attgatcctg aaactggtgg tactgcctac     180

aatcagaagt tcaagggcaa ggccatactg acttcagaca aatcctccag cacagcctac     240

atggagctcc gcagcctgac atctgaggac tctgccgtct attactgtac aagattcctg     300

ttaatcgact ttgactattg gggccaaggc accactctca cagtctcctc a              351


<210> SEQ ID NO 309
<211> LENGTH: 336
<212> TYPE: DNA
<213> ORGANISM: Artificial Sequence
<220> FEATURE:
<223> OTHER INFORMATION: ACI-7087-4119E10-Ab2 4119E10D12 VL

<400> SEQUENCE: 309

gatgtcttga tgacccaaac tccactctcc ctgcctgtca gtcttggaga tcaagcctcc      60

atctcttgca gatctagtca gagcattgta catagtaatg gaaacaccta tttagaatgg     120

tacctgaaga aagcaggcca gtctccaaag gtcctgatct acaaagtttc caaccgattt     180
```

```
tctggggtcc cagacaggtt cagtggcagt ggatcaggga cagatttcac actcaaaatc    240

agcagggtgg aggctgagga tctgggagtt tattactgct ttcaaggttc acatgttccg    300

tacacattcg gaggggggac cgagctggaa ataaaa                              336


<210> SEQ ID NO 310
<211> LENGTH: 113
<212> TYPE: PRT
<213> ORGANISM: Artificial Sequence
<220> FEATURE:
<223> OTHER INFORMATION: ACI-7087-4125E6-Ab1 4125E6D5 VH

<400> SEQUENCE: 310

Gln Val Gln Leu Gln Gln Pro Gly Thr Glu Leu Val Lys Pro Gly Ala
1               5                   10                  15

Ser Val Arg Leu Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Gly Leu Thr Ser Glu Asp Ser Ala Val Tyr Tyr Cys
                85                  90                  95

Ala Thr Gly Leu His Tyr Trp Gly Gln Gly Thr Thr Leu Thr Val Ser
            100                 105                 110

Ser


<210> SEQ ID NO 311
<211> LENGTH: 5
<212> TYPE: PRT
<213> ORGANISM: Artificial Sequence
<220> FEATURE:
<223> OTHER INFORMATION: ACI-7087-4125E6-Ab1 4125E6D5 VH CDR1

<400> SEQUENCE: 311

Ser Tyr Trp Met His
1               5


<210> SEQ ID NO 312
<211> LENGTH: 17
<212> TYPE: PRT
<213> ORGANISM: Artificial Sequence
<220> FEATURE:
<223> OTHER INFORMATION: ACI-7087-4125E6-Ab1 4125E6D5 VH CDR2

<400> SEQUENCE: 312

Asn Ile Asn Pro Ser Asn Gly Gly Thr Asn Tyr Asn Glu Lys Phe Lys
1               5                   10                  15

Asn


<210> SEQ ID NO 313
<211> LENGTH: 4
<212> TYPE: PRT
<213> ORGANISM: Artificial Sequence
<220> FEATURE:
<223> OTHER INFORMATION: ACI-7087-4125E6-Ab1 4125E6D5 VH CDR3

<400> SEQUENCE: 313

Gly Leu His Tyr
1
```

<210> SEQ ID NO 314
<211> LENGTH: 107
<212> TYPE: PRT
<213> ORGANISM: Artificial Sequence
<220> FEATURE:
<223> OTHER INFORMATION: ACI-7087-4125E6-Ab1 4125E6D5 VL

<400> SEQUENCE: 314

```
Asp Ile Gln Met Thr Gln Ser Pro Ser Ser Leu Ser Ala Ser Leu Gly
1               5                   10                  15

Glu Arg Val Thr Leu Thr Cys Arg Ala Ser Gln Asp Ile Gly Asn Tyr
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Phe Ala Ser Ser Pro Leu
                85                  90                  95

Thr Phe Gly Pro Gly Thr Lys Leu Glu Leu Lys
            100                 105
```

<210> SEQ ID NO 315
<211> LENGTH: 11
<212> TYPE: PRT
<213> ORGANISM: Artificial Sequence
<220> FEATURE:
<223> OTHER INFORMATION: ACI-7087-4125E6-Ab1 4125E6D5 VL CDR1

<400> SEQUENCE: 315

```
Arg Ala Ser Gln Asp Ile Gly Asn Tyr Leu Asn
1               5                   10
```

<210> SEQ ID NO 316

<400> SEQUENCE: 316

000

<210> SEQ ID NO 317

<400> SEQUENCE: 317

000

<210> SEQ ID NO 318
<211> LENGTH: 339
<212> TYPE: DNA
<213> ORGANISM: Artificial Sequence
<220> FEATURE:
<223> OTHER INFORMATION: ACI-7087-4125E6-Ab1 4125E6D5 VH

<400> SEQUENCE: 318

```
caggtccaac tgcagcagcc tgggactgaa ctggtgaagc ctggggcttc agtgaggctg      60

tcctgcaagg cttctggcta cgccttcacc agctactgga tgcactgggt gaagcagagg     120

cctggacaag gccttgagtg gattggaaat attaatccta gcaatggtgg tactaactac     180

aatgagaagt tcaagaacaa ggccacactg actgtagaca aatcctccag cacagcctat     240

atgcagctca gcggcctgac atctgaggac tctgcggtct attattgtgc aacgggcctt     300
```

```
cactactggg gccaaggcac cactctcaca gtctcctca                        339


<210> SEQ ID NO 319
<211> LENGTH: 321
<212> TYPE: DNA
<213> ORGANISM: Artificial Sequence
<220> FEATURE:
<223> OTHER INFORMATION: ACI-7087-4125E6-Ab1 4125E6D5 VL

<400> SEQUENCE: 319

gacatccaga tgacccagtc tccatcctcc ttatctgcct ctctgggaga aagagtcact     60

ctcacttgtc gggcaagtca ggacattggt aattacttaa actggcttca gcaggaacca    120

gatggaacta ttaaacgcct gatctacgcc acatccagtt tagattctgg tgtccccaaa    180

aggttcagtg gcagtaggtc tgggtcagat tattctctca ccatcagcag ccttgagtct    240

gaagattttg tagactatta ctgtctacaa tttgctagtt ctccgctcac gttcggtcct    300

gggaccaaac tggaactgaa a                                               321


<210> SEQ ID NO 320
<211> LENGTH: 117
<212> TYPE: PRT
<213> ORGANISM: Artificial Sequence
<220> FEATURE:
<223> OTHER INFORMATION: ACI-7088-4301D5-Ab2 4301D5B10 VH

<400> SEQUENCE: 320

Gln Val Gln Leu Gln Gln Ser Gly Pro Glu Leu Val Arg Pro Gly Ala
1               5                   10                  15

Ser Val Lys Ile Ser Cys Lys Ala Ser Gly Tyr Arg Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Asp Asn Thr Lys His Asn Asp Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Tyr Asp Val Gly Phe Gly Tyr Trp Gly Gln Gly Thr Leu
            100                 105                 110

Val Thr Val Ser Ser
        115


<210> SEQ ID NO 321
<211> LENGTH: 5
<212> TYPE: PRT
<213> ORGANISM: Artificial Sequence
<220> FEATURE:
<223> OTHER INFORMATION: ACI-7088-4301D5-Ab2 4301D5B10 VH CDR1

<400> SEQUENCE: 321

Ser Tyr Tyr Ile His
1               5


<210> SEQ ID NO 322
<211> LENGTH: 17
<212> TYPE: PRT
<213> ORGANISM: Artificial Sequence
<220> FEATURE:
<223> OTHER INFORMATION: ACI-7088-4301D5-Ab2 4301D5B10 VH CDR2
```

<400> SEQUENCE: 322

Trp Ile Tyr Pro Gly Ser Asp Asn Thr Lys His Asn Asp Lys Phe Lys
1 5 10 15

Gly

<210> SEQ ID NO 323
<211> LENGTH: 8
<212> TYPE: PRT
<213> ORGANISM: Artificial Sequence
<220> FEATURE:
<223> OTHER INFORMATION: ACI-7088-4301D5-Ab2 4301D5B10 VH CDR3

<400> SEQUENCE: 323

Asp Tyr Asp Val Gly Phe Gly Tyr
1 5

<210> SEQ ID NO 324
<211> LENGTH: 111
<212> TYPE: PRT
<213> ORGANISM: Artificial Sequence
<220> FEATURE:
<223> OTHER INFORMATION: ACI-7088-4301D5-Ab2 4301D5B10 VL

<400> SEQUENCE: 324

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Asn Tyr
20 25 30

Gly Ile Ser Phe Met Asn Trp Phe Gln Gln Lys Pro Gly Gln Pro Pro
35 40 45

Lys Leu Leu Ile Tyr Ala Ala Ser Asn Gln Gly Ser Gly Val Pro Ala
50 55 60

Arg Phe Ser Gly Ile Gly Ser Gly Thr Asp Phe Ser Leu Asn Ile His
65 70 75 80

Pro Met Glu Glu Asp Asp Thr Ala Met Tyr Phe Cys Gln Gln Ser Gln
85 90 95

Glu Val Pro Leu Thr Phe Gly Ala Gly Thr Lys Leu Glu Leu Lys
100 105 110

<210> SEQ ID NO 325
<211> LENGTH: 15
<212> TYPE: PRT
<213> ORGANISM: Artificial Sequence
<220> FEATURE:
<223> OTHER INFORMATION: ACI-7088-4301D5-Ab2 4301D5B10 VL CDR1

<400> SEQUENCE: 325

Arg Ala Ser Glu Ser Val Asp Asn Tyr Gly Ile Ser Phe Met Asn
1 5 10 15

<210> SEQ ID NO 326
<211> LENGTH: 7
<212> TYPE: PRT
<213> ORGANISM: Artificial Sequence
<220> FEATURE:
<223> OTHER INFORMATION: ACI-7088-4301D5-Ab2 4301D5B10 VL CDR2

<400> SEQUENCE: 326

Ala Ala Ser Asn Gln Gly Ser
1 5

<210> SEQ ID NO 327

<211> LENGTH: 9
<212> TYPE: PRT
<213> ORGANISM: Artificial Sequence
<220> FEATURE:
<223> OTHER INFORMATION: ACI-7088-4301D5-Ab2 4301D5B10 VL CDR3

<400> SEQUENCE: 327

Gln Gln Ser Gln Glu Val Pro Leu Thr
1 5

<210> SEQ ID NO 328
<211> LENGTH: 351
<212> TYPE: DNA
<213> ORGANISM: Artificial Sequence
<220> FEATURE:
<223> OTHER INFORMATION: ACI-7088-4301D5-Ab2 4301D5B10 VH

<400> SEQUENCE: 328
caggtccagc tgcagcagtc tggacctgag ctggtgaggc ctggggcttc agtgaagata 60
tcctgcaagg cttctggcta caggttcaca agctactata tacactgggt gaagcagagg 120
cctggacagg gacttgagtg gattggatgg atttatcctg gaagtgataa tactaagcac 180
aatgacaagt tcaagggcaa ggccacactg acggcagaca catcctccag cactgcctac 240
atgcagctca gcagcctaac atctgaggac tctgcggtct atttctgtgc aagagactac 300
gacgtggggt ttggttactg gggccaaggg actctggtca ctgtctctgc a 351

<210> SEQ ID NO 329
<211> LENGTH: 333
<212> TYPE: DNA
<213> ORGANISM: Artificial Sequence
<220> FEATURE:
<223> OTHER INFORMATION: ACI-7088-4301D5-Ab2 4301D5B10 VL

<400> SEQUENCE: 329
gacattgtgc tgacccaatc tccagcttct ttggctgtgt ctctagggca gagggccacc 60
atctcctgca gagccagcga aagtgttgat aattatggca ttagttttat gaactggttc 120
caacagaaac caggacagcc acccaaactc ctcatctatg ctgcatccaa ccaaggatcc 180
ggggtccctg ccaggtttag tggcattggg tctgggacag acttcagcct caacatccat 240
cctatggagg aggatgatac tgcaatgtat ttctgtcagc aaagtcagga ggttccgctc 300
acgttcggtg ctgggaccaa gctggagctg aaa 333

<210> SEQ ID NO 330
<211> LENGTH: 113
<212> TYPE: PRT
<213> ORGANISM: Artificial Sequence
<220> FEATURE:
<223> OTHER INFORMATION: ACI-7088-4301E12-Ab2 4301E12B9 VH

<400> SEQUENCE: 330

Asp Val Gln Leu Gln Glu Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Asp Asp Gly Ser Lys Asn Tyr Asn Pro Ser Leu
50 55 60

Lys Asn Arg Ile Ser Ile Thr Arg Asp Thr Ser Lys Asn Gln Leu Phe
65 70 75 80

```
Met Lys Leu Asn Ser Val Thr Thr Glu Asp Thr Ala Thr Tyr Tyr Cys
                85                  90                  95

Ala Arg Gly Asp Ser Arg Leu Gly Gln Gly Thr Leu Val Thr Val Ser
            100                 105                 110

Ala


<210> SEQ ID NO 331

<400> SEQUENCE: 331

000


<210> SEQ ID NO 332
<211> LENGTH: 16
<212> TYPE: PRT
<213> ORGANISM: Artificial Sequence
<220> FEATURE:
<223> OTHER INFORMATION: ACI-7088-4301E12-Ab2 4301E12B9 VH CDR2

<400> SEQUENCE: 332

Tyr Ile Ser Asp Asp Gly Ser Lys Asn Tyr Asn Pro Ser Leu Lys Asn
1               5                   10                  15


<210> SEQ ID NO 333
<211> LENGTH: 4
<212> TYPE: PRT
<213> ORGANISM: Artificial Sequence
<220> FEATURE:
<223> OTHER INFORMATION: ACI-7088-4301E12-Ab2 4301E12B9 VH CDR3

<400> SEQUENCE: 333

Gly Asp Ser Arg
1


<210> SEQ ID NO 334
<211> LENGTH: 112
<212> TYPE: PRT
<213> ORGANISM: Artificial Sequence
<220> FEATURE:
<223> OTHER INFORMATION: ACI-7088-4301E12-Ab2 4301E12B9 VL

<400> SEQUENCE: 334

Asp Val Val Leu Thr Gln Thr Pro Leu Thr Leu Ser Val Thr Ile Gly
1               5                   10                  15

Gln Pro Ala Ser Ile Ser Cys Arg Ser Ser Gln Asn Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Ile
            100                 105                 110


<210> SEQ ID NO 335
<211> LENGTH: 16
<212> TYPE: PRT
<213> ORGANISM: Artificial Sequence
<220> FEATURE:
```

<223> OTHER INFORMATION: ACI-7088-4301E12-Ab2 4301E12B9 VL CDR1

<400> SEQUENCE: 335

Arg Ser Ser Gln Asn Leu Leu Asp Ser Asp Gly Glu Thr Tyr Leu Asn
1 5 10 15

<210> SEQ ID NO 336
<211> LENGTH: 7
<212> TYPE: PRT
<213> ORGANISM: Artificial Sequence
<220> FEATURE:
<223> OTHER INFORMATION: ACI-7088-4301E12-Ab2 4301E12B9 VL CDR2

<400> SEQUENCE: 336

Leu Val Ser Glu Leu Asp Ser
1 5

<210> SEQ ID NO 337

<400> SEQUENCE: 337

000

<210> SEQ ID NO 338
<211> LENGTH: 339
<212> TYPE: DNA
<213> ORGANISM: Artificial Sequence
<220> FEATURE:
<223> OTHER INFORMATION: ACI-7088-4301E12-Ab2 4301E12B9 VH

<400> SEQUENCE: 338
gatgtacagc ttcaggagtc aggacctggc ctcgtgaaac cttctcagtc tctgtctctc 60
acctgctctg tcactggcta ctccatcacc agtggttatt actggaactg gatccggcag 120
tttccaggaa acaaactgga atggatgggc tacataagcg acgatggtag taaaaattac 180
aacccatctc tcaaaaatcg aatctccatc actcgtgaca catctaagaa ccagcttttc 240
atgaagttga attctgtgac tactgaggac acagccacat attactgtgc aagaggcgat 300
tcccgcctgg gccaagggac tctggtcact gtctctgca 339

<210> SEQ ID NO 339
<211> LENGTH: 336
<212> TYPE: DNA
<213> ORGANISM: Artificial Sequence
<220> FEATURE:
<223> OTHER INFORMATION: ACI-7088-4301E12-Ab2 4301E12B9 VL

<400> SEQUENCE: 339
gatgttgtgt tgacccagac tccactcact ttgtcggtta ccattggaca accagcctcc 60
atctcttgca ggtcaagtca gaacctctta gatagtgatg gagagacata tttgaattgg 120
ttgttacaga ggccaggcca gtctccaaag cgcctaatct atctggtgtc tgagctggac 180
tctggagtcc ctgacaggtt cactggcagt ggatcaggga cagatttcac actgaaaatc 240
agcagagtgg aggctgagga tttgggagtt tattattgct ggcaaggtac acattttcct 300
cagacgttcg gtggaggcac caagctggaa atcatt 336

<210> SEQ ID NO 340
<211> LENGTH: 117
<212> TYPE: PRT
<213> ORGANISM: Artificial Sequence
<220> FEATURE:
<223> OTHER INFORMATION: ACI-7088-4301H3-Ab2 4301H3A5 VH

<400> SEQUENCE: 340

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ala Asp Tyr
            20                  25                  30

Phe Met Asn Trp Val Lys Gln Ser His Gly Lys Ser Leu Glu Trp Ile
        35                  40                  45

Gly Asp Ile Asn Pro Asn Asn Gly Gly Thr Thr Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Arg Asn Tyr Ala Met Asp Tyr Trp Gly Gln Gly Thr Ser
            100                 105                 110

Val Thr Val Ser Ser
        115

<210> SEQ ID NO 341
<211> LENGTH: 5
<212> TYPE: PRT
<213> ORGANISM: Artificial Sequence
<220> FEATURE:
<223> OTHER INFORMATION: ACI-7088-4301H3-Ab2 VH CDR1

<400> SEQUENCE: 341

Asp Tyr Phe Met Asn
1               5

<210> SEQ ID NO 342
<211> LENGTH: 17
<212> TYPE: PRT
<213> ORGANISM: Artificial Sequence
<220> FEATURE:
<223> OTHER INFORMATION: ACI-7088-4301H3-Ab2 4301H3A5 VH CDR2

<400> SEQUENCE: 342

Asp Ile Asn Pro Asn Asn Gly Gly Thr Thr Tyr Asn Gln Lys Phe Lys
1               5                   10                  15

Gly

<210> SEQ ID NO 343
<211> LENGTH: 8
<212> TYPE: PRT
<213> ORGANISM: Artificial Sequence
<220> FEATURE:
<223> OTHER INFORMATION: ACI-7088-4301H3-Ab2 4301H3A5 VH CDR3

<400> SEQUENCE: 343

Gly Arg Asn Tyr Ala Met Asp Tyr
1               5

<210> SEQ ID NO 344
<211> LENGTH: 112
<212> TYPE: PRT
<213> ORGANISM: Artificial Sequence
<220> FEATURE:
<223> OTHER INFORMATION: ACI-7088-4301H3-Ab2 4301H3A5 VL

<400> SEQUENCE: 344

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
20 25 30

Arg Thr Arg Lys Asn Tyr Leu Ala Trp Tyr Gln Gln Lys Pro Gly Gln
35 40 45

Ser Pro Lys Leu Leu Ile Tyr Ser Ala Ser Thr Arg Glu Ser Gly Val
50 55 60

Pro Asp Arg Phe Thr Gly Ser Gly Phe Gly Thr Asp Phe Thr Leu Thr
65 70 75 80

Ile Ser Ser Val Gln Ala Glu Asp Leu Ala Val Tyr Tyr Cys Lys Gln
85 90 95

Ser Tyr Asp Leu Trp Thr Phe Gly Gly Gly Thr Lys Leu Glu Ile Lys
100 105 110

<210> SEQ ID NO 345
<211> LENGTH: 17
<212> TYPE: PRT
<213> ORGANISM: Artificial Sequence
<220> FEATURE:
<223> OTHER INFORMATION: ACI-7088-4301H3-Ab2 4301H3A5 VL CDR1

<400> SEQUENCE: 345

Lys Ser Ser Gln Ser Leu Leu Asn Ser Arg Thr Arg Lys Asn Tyr Leu
1 5 10 15

Ala

<210> SEQ ID NO 346
<211> LENGTH: 7
<212> TYPE: PRT
<213> ORGANISM: Artificial Sequence
<220> FEATURE:
<223> OTHER INFORMATION: ACI-7088-4301H3-Ab2 4301H3A5 VL CDR2

<400> SEQUENCE: 346

Ser Ala Ser Thr Arg Glu Ser
1 5

<210> SEQ ID NO 347
<211> LENGTH: 8
<212> TYPE: PRT
<213> ORGANISM: Artificial Sequence
<220> FEATURE:
<223> OTHER INFORMATION: ACI-7088-4301H3-Ab2 4301H3A5 VL CDR3

<400> SEQUENCE: 347

Lys Gln Ser Tyr Asp Leu Trp Thr
1 5

<210> SEQ ID NO 348
<211> LENGTH: 351
<212> TYPE: DNA
<213> ORGANISM: Artificial Sequence
<220> FEATURE:
<223> OTHER INFORMATION: ACI-7088-4301H3-Ab2 4301H3A5 VH

<400> SEQUENCE: 348
gaggtccagc tgcaacaatc tggacctgaa ctggtgaagc ctggggcttc agtgaagata 60
tcttgtaagg cttctggata cacgttcgct gactacttca tgaactgggt gaagcagagc 120
catggaaaga gccttgagtg gattggagat attaatccta acaatggtgg tactacctac 180
aaccagaagt tcaagggcaa ggccacattg actgtagaca agtcctccaa cacagcctac 240
atggagctcc gcagcctgac atctgaggac tctgcagtct actactgtgc aagaggtaga 300
aactacgcta tggactactg gggtcaagga acctcagtca ccgtctcctc a 351

<210> SEQ ID NO 349
<211> LENGTH: 336
<212> TYPE: DNA
<213> ORGANISM: Artificial Sequence
<220> FEATURE:
<223> OTHER INFORMATION: ACI-7088-4301H3-Ab2 4301H3A5 VL

<400> SEQUENCE: 349
gacattgtga tgtcacagtc tccatcctcc ctggctgtgt cagcaggaga gaaggtcact 60
atgagctgca aatccagtca gagtctcctc aacagtagaa cccgaaagaa ttatttggct 120
tggtaccagc agaaaccagg gcagtctcct aaattgttga tctactcggc atccactagg 180
gaatctgggg tccctgatcg cttcacaggc agtggatttg ggacagattt cactctcacc 240
atcagcagtg tgcaggctga ggacctggca gtttattact gcaagcaatc ttatgatctg 300
tggacgttcg gtggaggcac caagctggaa atcaaa 336

<210> SEQ ID NO 350
<211> LENGTH: 119
<212> TYPE: PRT
<213> ORGANISM: Artificial Sequence
<220> FEATURE:
<223> OTHER INFORMATION: ACI-7088-4303A1-Ab1 4303A1E7 VH

<400> SEQUENCE: 350

Glu Val Gln Leu Gln Gln Ser Gly Ala Glu Leu Val Arg Pro Gly Ala
1 5 10 15

Ser Val Lys Leu Ser Cys Thr Ala Ser Gly Phe Asn Ile Lys Asp Asp
20 25 30

Tyr Met His Trp Val Lys Gln Arg Pro Glu Gln Gly Leu Glu Trp Ile
35 40 45

Gly Trp Ile Asp Pro Glu Asn Gly Asp Ser Glu Tyr Ala Ser Lys Phe
50 55 60

Gln Gly Lys Ala Thr Met Thr Ala Asp Thr Ser Ser Asn Thr Ala Tyr
65 70 75 80

Leu Gln Leu Ser Ser Leu Thr Ser Glu Asp Thr Ala Val Tyr Tyr Cys
85 90 95

Lys Thr Trp Gly Thr Ala Gln Ala Leu Phe Pro Tyr Trp Gly Gln Gly
100 105 110

Thr Leu Val Thr Val Ser Ala
115

<210> SEQ ID NO 351
<211> LENGTH: 5
<212> TYPE: PRT
<213> ORGANISM: Artificial Sequence
<220> FEATURE:
<223> OTHER INFORMATION: ACI-7088-4303A1-Ab1 4303A1E7 VH CDR1

<400> SEQUENCE: 351

Asp Asp Tyr Met His
1 5

<210> SEQ ID NO 352
<211> LENGTH: 17
<212> TYPE: PRT
<213> ORGANISM: Artificial Sequence
<220> FEATURE:
<223> OTHER INFORMATION: ACI-7088-4303A1-Ab1 4303A1E7 VH CDR2

<400> SEQUENCE: 352

Trp Ile Asp Pro Glu Asn Gly Asp Ser Glu Tyr Ala Ser Lys Phe Gln
1               5                   10                  15

Gly

<210> SEQ ID NO 353
<211> LENGTH: 10
<212> TYPE: PRT
<213> ORGANISM: Artificial Sequence
<220> FEATURE:
<223> OTHER INFORMATION: ACI-7088-4303A1-Ab1 4303A1E7 VH CDR3

<400> SEQUENCE: 353

Trp Gly Thr Ala Gln Ala Leu Phe Pro Tyr
1               5                   10

<210> SEQ ID NO 354
<211> LENGTH: 107
<212> TYPE: PRT
<213> ORGANISM: Artificial Sequence
<220> FEATURE:
<223> OTHER INFORMATION: ACI-7088-4303A1-Ab1 4303A1E7 VL

<400> SEQUENCE: 354

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ser
            20                  25                  30

Val Gly Trp Tyr Gln Gln Lys Ala Gly Gln Ser Pro Lys Leu Leu Ile
        35                  40                  45

His Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Gln Gln Tyr Arg Ser Tyr Pro Leu
                85                  90                  95

Thr Phe Gly Ala Gly Thr Lys Leu Glu Leu Lys
            100                 105

<210> SEQ ID NO 355
<211> LENGTH: 11
<212> TYPE: PRT
<213> ORGANISM: Artificial Sequence
<220> FEATURE:
<223> OTHER INFORMATION: ACI-7088-4303A1-Ab1 4303A1E7 VL CDR1

<400> SEQUENCE: 355

Lys Ala Ser Gln Asn Val Gly Thr Ser Val Gly
1               5                   10

<210> SEQ ID NO 356
<211> LENGTH: 7
<212> TYPE: PRT
<213> ORGANISM: Artificial Sequence
<220> FEATURE:
<223> OTHER INFORMATION: ACI-7088-4303A1-Ab1 4303A1E7 VL CDR2

<400> SEQUENCE: 356

Ser Ala Ser Asn Arg Tyr Thr
1               5

<210> SEQ ID NO 357
<211> LENGTH: 9
<212> TYPE: PRT
<213> ORGANISM: Artificial Sequence
<220> FEATURE:
<223> OTHER INFORMATION: ACI-7088-4303A1-Ab1 4303A1E7 VL CDR3

<400> SEQUENCE: 357

Gln Gln Tyr Arg Ser Tyr Pro Leu Thr
1               5

<210> SEQ ID NO 358
<211> LENGTH: 357
<212> TYPE: DNA
<213> ORGANISM: Artificial Sequence
<220> FEATURE:
<223> OTHER INFORMATION: ACI-7088-4303A1-Ab1 4303A1E7 VH

<400> SEQUENCE: 358
gaggttcagc tgcagcagtc tggggctgaa cttgtgaggc caggggcctc agtcaagttg 60
tcctgcacag cttctggctt taacattaaa gacgactata tgcactgggt gaaacagagg 120
cctgaacagg gcctggagtg gattggatgg attgatcctg agaatggtga ttctgaatat 180
gcctcgaagt tccagggcaa ggccactatg acagcagaca catcctccaa cacagcctac 240
ctgcaactca gcagcctgac atctgaggac actgccgtct attattgtaa aacatggggg 300
acagctcagg ccctctttcc ttactggggc caagggactc tggtcactgt ctctgca 357

<210> SEQ ID NO 359
<211> LENGTH: 321
<212> TYPE: DNA
<213> ORGANISM: Artificial Sequence
<220> FEATURE:
<223> OTHER INFORMATION: ACI-7088-4303A1-Ab1 4303A1E7 VL

<400> SEQUENCE: 359
gacattgtga tgacccagtc tcaaaaattc atgtccacat cagtaggaga cagggtcagc 60
atcacctgca aggccagtca gaatgtgggt acttctgtag gctggtatca acaaaaagca 120
ggacaatctc ctaaactact gattcactcg gcatctaatc ggtacactgg agtccctgat 180
cgcttcacag gcagtggatc tgggacagat ttcactctca ccatcaacaa tatgcagtct 240
gaagacctgg cagattattt ctgccagcaa tatagaagtt atccgctcac gttcggtgct 300
gggaccaagc tggagctgaa a 321

<210> SEQ ID NO 360
<211> LENGTH: 117
<212> TYPE: PRT
<213> ORGANISM: Artificial Sequence
<220> FEATURE:
<223> OTHER INFORMATION: ACI-7088-4303A3-Ab1 4303A3E4 VH

<400> SEQUENCE: 360

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Val Ile Asp Pro Glu Thr Gly Gly Ala Val Gln Asn Gln Lys Phe
    50                  55                  60

Lys Gly Lys Ala Ile Leu Thr Ala Asp Asn Ser Ser Ser Thr Ala Tyr

```
65                  70                  75                  80

Met Asp Leu Arg Ser Leu Thr Ser Glu Asp Ser Ala Val Tyr Asn Cys
                85                  90                  95

Ala Met Gly Ala Ala Leu Arg Leu Ala Tyr Trp Gly Gln Gly Thr Leu
            100                 105                 110

Val Thr Val Ser Ser
        115


<210> SEQ ID NO 361
<211> LENGTH: 5
<212> TYPE: PRT
<213> ORGANISM: Artificial Sequence
<220> FEATURE:
<223> OTHER INFORMATION: ACI-7088-4303A3-Ab1 4303A3E4 VH CDR1

<400> SEQUENCE: 361

Asp Tyr Glu Met His
1               5


<210> SEQ ID NO 362
<211> LENGTH: 17
<212> TYPE: PRT
<213> ORGANISM: Artificial Sequence
<220> FEATURE:
<223> OTHER INFORMATION: ACI-7088-4303A3-Ab1 4303A3E4 VH CDR2

<400> SEQUENCE: 362

Val Ile Asp Pro Glu Thr Gly Gly Ala Val Gln Asn Gln Lys Phe Lys
1               5                   10                  15

Gly


<210> SEQ ID NO 363
<211> LENGTH: 8
<212> TYPE: PRT
<213> ORGANISM: Artificial Sequence
<220> FEATURE:
<223> OTHER INFORMATION: ACI-7088-4303A3-Ab1 4303A3E4 VH CDR3

<400> SEQUENCE: 363

Gly Ala Ala Leu Arg Leu Ala Tyr
1               5


<210> SEQ ID NO 364
<211> LENGTH: 112
<212> TYPE: PRT
<213> ORGANISM: Artificial Sequence
<220> FEATURE:
<223> OTHER INFORMATION: ACI-7088-4303A3-Ab1 4303A3E4 VL

<400> SEQUENCE: 364

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Ser Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95
```

Ser His Val Pro Phe Thr Phe Gly Ser Gly Thr Lys Leu Glu Ile Lys
100 105 110

<210> SEQ ID NO 365
<211> LENGTH: 16
<212> TYPE: PRT
<213> ORGANISM: Artificial Sequence
<220> FEATURE:
<223> OTHER INFORMATION: ACI-7088-4303A3-Ab1 4303A3E4 VL CDR1

<400> SEQUENCE: 365

Arg Ser Ser Gln Ser Ile Val His Ser Asn Gly Asn Ser Tyr Leu Glu
1 5 10 15

<210> SEQ ID NO 366

<400> SEQUENCE: 366

000

<210> SEQ ID NO 367
<211> LENGTH: 9
<212> TYPE: PRT
<213> ORGANISM: Artificial Sequence
<220> FEATURE:
<223> OTHER INFORMATION: ACI-7088-4303A3-Ab1 4303A3E4 VL CDR3

<400> SEQUENCE: 367

Phe Gln Gly Ser His Val Pro Phe Thr
1 5

<210> SEQ ID NO 368
<211> LENGTH: 351
<212> TYPE: DNA
<213> ORGANISM: Artificial Sequence
<220> FEATURE:
<223> OTHER INFORMATION: ACI-7088-4303A3-Ab1 4303A3E4 VH

<400> SEQUENCE: 368
caggttcaac tgcagcagtc tggggctgag ctggtgaggc ctggggcttc agtgacgctg 60
tcctgcaagg cttcgggcta cacatttact gactatgaaa tgcactgggt gaaacagaca 120
cctgtgcatg gcctggagtg gattggagtt attgatcctg aaactggtgg tgctgtccag 180
aatcagaagt tcaagggcaa ggccatactg actgcagaca attcctccag cacagcctac 240
atggacctcc gcagcctgac atctgaggac tctgccgtct ataactgtgc aatgggtgcg 300
gcattacggc ttgcttactg gggccaaggg actctggtca ctgtctctgc a 351

<210> SEQ ID NO 369
<211> LENGTH: 336
<212> TYPE: DNA
<213> ORGANISM: Artificial Sequence
<220> FEATURE:
<223> OTHER INFORMATION: ACI-7088-4303A3-Ab1 4303A3E4 VL

<400> SEQUENCE: 369
gatgttttga tgacccaaac tccactctcc ctgcctgtca gtcttggaga tcaagcctcc 60
atctcttgca gatctagtca gagcattgta catagtaatg gaaactccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
aacagagtgg aggctgagga tctgggagtt tattactgct ttcaaggttc acatgttcca 300
ttcacgttcg gctcggggac aaagttggaa ataaaa 336

<210> SEQ ID NO 370
<211> LENGTH: 123
<212> TYPE: PRT
<213> ORGANISM: Artificial Sequence
<220> FEATURE:
<223> OTHER INFORMATION: ACI-7088-4303B6-Ab2 4303B6C11 VH

<400> SEQUENCE: 370

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Asp Ile Asn Pro Asn Asn Gly Gly Thr Thr Tyr Asn Gln Lys Phe
50 55 60

Lys Asp Lys Ala Thr Leu Thr Val Asp Arg Ser Ser Ser Thr Ala Tyr
65 70 75 80

Met Glu Leu Arg Ser Leu Thr Ser Gly Asp Ser Ala Val Tyr Tyr Cys
85 90 95

Ala Arg Ser Gly Tyr Ser Gly Ser Arg Leu Tyr Tyr Ala Met Asp Tyr
100 105 110

Trp Ser Gln Gly Ser Ser Val Thr Val Ser Ser
115 120

<210> SEQ ID NO 371
<211> LENGTH: 5
<212> TYPE: PRT
<213> ORGANISM: Artificial Sequence
<220> FEATURE:
<223> OTHER INFORMATION: ACI-7088-4303B6-Ab2 4303B6C11

<400> SEQUENCE: 371

Asp Tyr Tyr Met Asn
1 5

<210> SEQ ID NO 372
<211> LENGTH: 17
<212> TYPE: PRT
<213> ORGANISM: Artificial Sequence
<220> FEATURE:
<223> OTHER INFORMATION: ACI-7088-4303B6-Ab2 4303B6C11 VH CDR2

<400> SEQUENCE: 372

Asp Ile Asn Pro Asn Asn Gly Gly Thr Thr Tyr Asn Gln Lys Phe Lys
1 5 10 15

Asp

<210> SEQ ID NO 373
<211> LENGTH: 14
<212> TYPE: PRT
<213> ORGANISM: Artificial Sequence
<220> FEATURE:
<223> OTHER INFORMATION: ACI-7088-4303B6-Ab2 4303B6C11 VH CDR3

<400> SEQUENCE: 373

Ser Gly Tyr Ser Gly Ser Arg Leu Tyr Tyr Ala Met Asp Tyr
1 5 10

<210> SEQ ID NO 374

<211> LENGTH: 112
<212> TYPE: PRT
<213> ORGANISM: Artificial Sequence
<220> FEATURE:
<223> OTHER INFORMATION: ACI-7088-4303B6-Ab2 4303B6C11 VL

<400> SEQUENCE: 374

Asp Ile Val Met Ser Gln Ser Pro Ser Ser Leu Ala Val Ser Ala Arg
1 5 10 15

Glu Lys Val Thr Met Ser Cys Lys Ser Ser Gln Ser Leu Leu Asn Ser
20 25 30

Arg Thr Arg Lys Asn Tyr Leu Ala Trp Tyr Gln Gln Lys Pro Gly Gln
35 40 45

Ser Pro Lys Leu Leu Ile Phe Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Lys Gln
85 90 95

Ser Tyr Asp Leu Trp Thr Phe Gly Gly Gly Thr Lys Leu Glu Ile Lys
100 105 110

<210> SEQ ID NO 375

<400> SEQUENCE: 375

000

<210> SEQ ID NO 376
<211> LENGTH: 7
<212> TYPE: PRT
<213> ORGANISM: Artificial Sequence
<220> FEATURE:
<223> OTHER INFORMATION: ACI-7088-4303B6-Ab2 4303B6C11 VL CDR2

<400> SEQUENCE: 376

Trp Ala Ser Thr Arg Glu Ser
1 5

<210> SEQ ID NO 377

<400> SEQUENCE: 377

000

<210> SEQ ID NO 378
<211> LENGTH: 369
<212> TYPE: DNA
<213> ORGANISM: Artificial Sequence
<220> FEATURE:
<223> OTHER INFORMATION: ACI-7088-4303B6-Ab2 4303B6C11 VH

<400> SEQUENCE: 378
gaggtccagc tgcaacaatc tggacctgag ctggtgaagc ctggggcttc agtgaagata 60
tcctgtaagg cttctggata cacgttcact gactactaca tgaactgggt gaagcagagc 120
catggaaaga gccttgagtg gattggagat attaatccta acaatggtgg tactacctac 180
aaccagaagt tcaaggacaa ggccacattg actgtggaca ggtcctccag cacagcctac 240
atggaactcc gcagcctgac atctggggac tctgcagtct attactgtgc aagatcgggg 300
tactccggta gtcgcctcta ctatgctatg gactactgga gtcaaggatc ctcagtcacc 360
gtctcctca 369

<210> SEQ ID NO 379
<211> LENGTH: 336
<212> TYPE: DNA
<213> ORGANISM: Artificial Sequence
<220> FEATURE:
<223> OTHER INFORMATION: ACI-7088-4303B6-Ab2 4303B6C11 VL

<400> SEQUENCE: 379
gacattgtga tgtcacagtc tccatcctcc ctggctgtgt cagcacgaga gaaggtcact 60
atgagctgca aatccagtca gagtctgctc aacagtagaa cccgaaagaa ctacttggct 120
tggtaccagc agaaaccagg gcagtctcct aaactgctga tcttctgggc ttccactagg 180
gaatctgggg tccctgatcg cttcactggc agtggatctg ggacagattt cactctcacc 240
atcagcagtg tgcaggctga agacctggca gtttattact gcaaacaatc ttatgatctg 300
tggacgttcg gtggcggcac caagctggaa atcaaa 336

<210> SEQ ID NO 380
<211> LENGTH: 119
<212> TYPE: PRT
<213> ORGANISM: Artificial Sequence
<220> FEATURE:
<223> OTHER INFORMATION: ACI-7088-4303H6-Ab1 4303H6D7 VH

<400> SEQUENCE: 380

Glu Val Gln Leu Gln Gln Ser Gly Ala Glu Leu Val Arg Pro Gly Ala
1 5 10 15

Ser Val Lys Leu Ser Cys Thr Ala Ser Gly Phe Asn Ile Gln Asp Asp
20 25 30

Tyr Met His Trp Val Lys Gln Arg Pro Glu Gln Gly Leu Glu Trp Ile
35 40 45

Gly Trp Ile Asp Pro Glu Asn Gly Asp Thr Glu Tyr Ala Ser Lys Phe
50 55 60

Gln Gly Lys Ala Thr Leu Thr Ala Asp Thr Ser Ser Asn Thr Ala Tyr
65 70 75 80

Leu Gln Leu Ser Arg Leu Thr Ser Glu Asp Thr Ala Val Tyr Tyr Cys
85 90 95

Thr Thr Ala Gly Ser Gly Val Gln Leu Phe Asp Tyr Trp Gly Gln Gly
100 105 110

Thr Thr Leu Thr Val Ser Ala
115

<210> SEQ ID NO 381

<400> SEQUENCE: 381

000

<210> SEQ ID NO 382
<211> LENGTH: 17
<212> TYPE: PRT
<213> ORGANISM: Artificial Sequence
<220> FEATURE:
<223> OTHER INFORMATION: ACI-7088-4303H6-Ab1 4303H6D7 VH CDR2

<400> SEQUENCE: 382

Trp Ile Asp Pro Glu Asn Gly Asp Thr Glu Tyr Ala Ser Lys Phe Gln
1 5 10 15

Gly

<210> SEQ ID NO 383
<211> LENGTH: 10
<212> TYPE: PRT
<213> ORGANISM: Artificial Sequence
<220> FEATURE:
<223> OTHER INFORMATION: ACI-7088-4303H6-Ab1 4303H6D7 VH CDR3

<400> SEQUENCE: 383

```
Ala Gly Ser Gly Val Gln Leu Phe Asp Tyr
1               5                   10
```

<210> SEQ ID NO 384
<211> LENGTH: 107
<212> TYPE: PRT
<213> ORGANISM: Artificial Sequence
<220> FEATURE:
<223> OTHER INFORMATION: ACI-7088-4303H6-Ab1 4303H6D7 VL

<400> SEQUENCE: 384

```
Asp Ile Leu Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Ser Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Arg Tyr Pro Leu
                85                  90                  95

Thr Phe Gly Ala Gly Thr Lys Leu Glu Leu Lys
            100                 105
```

<210> SEQ ID NO 385
<211> LENGTH: 11
<212> TYPE: PRT
<213> ORGANISM: Artificial Sequence
<220> FEATURE:
<223> OTHER INFORMATION: ACI-7088-4303H6-Ab1 4303H6D7 VL CDR1

<400> SEQUENCE: 385

```
Lys Ala Ser Gln Asn Val Gly Thr Asn Val Ala
1               5                   10
```

<210> SEQ ID NO 386
<211> LENGTH: 7
<212> TYPE: PRT
<213> ORGANISM: Artificial Sequence
<220> FEATURE:
<223> OTHER INFORMATION: ACI-7088-4303H6-Ab1 4303H6D7 VL CDR2

<400> SEQUENCE: 386

```
Ser Ala Ser Ser Arg Tyr Ser
1               5
```

<210> SEQ ID NO 387
<211> LENGTH: 9
<212> TYPE: PRT
<213> ORGANISM: Artificial Sequence
<220> FEATURE:
<223> OTHER INFORMATION: ACI-7088-4303H6-Ab1 4303H6D7 VL CDR3

<400> SEQUENCE: 387

Gln Gln Tyr Asn Arg Tyr Pro Leu Thr
1 5

<210> SEQ ID NO 388
<211> LENGTH: 357
<212> TYPE: DNA
<213> ORGANISM: Artificial Sequence
<220> FEATURE:
<223> OTHER INFORMATION: ACI-7088-4303H6-Ab1 4303H6D7 VH

<400> SEQUENCE: 388
gaggttcagc tgcagcagtc tggggctgag cttgtgaggc caggggcctc agtcaagttg 60
tcctgcacag cttctggctt taacattcaa gacgactata tgcactgggt gaagcagagg 120
cctgaacagg gcctggagtg gattggttgg attgatcctg agaatggtga tactgaatat 180
gcctcgaaat tccagggcaa ggccacttta acagcagaca catcctccaa cacagcctac 240
ctgcagctca gcagactgac atctgaggac actgccgtct attactgtac tacagcgggc 300
tcaggcgtcc aactctttga ctactggggc caaggcacca ctctcacagt ctcctca 357

<210> SEQ ID NO 389
<211> LENGTH: 321
<212> TYPE: DNA
<213> ORGANISM: Artificial Sequence
<220> FEATURE:
<223> OTHER INFORMATION: ACI-7088-4303H6-Ab1 4303H6D7 VL

<400> SEQUENCE: 389
gacattttga tgacccagtc tcaaaaattc atgtccacat cagtaggaga cagggtcagc 60
gtcacctgca aggccagtca gaatgtgggt actaatgtag cctggtatca acagaaacca 120
gggcaatctc ctaaaccact gatttcctcg gcatcctccc ggtacagtgg cgtccctgat 180
cgcttcacag gcagtggatc tgggacagat ttcactctca ccatcagcaa tgtgcagtct 240
gaagacttgg cagactattt ctgtcagcaa tataaccgct atcctctcac gttcggtgct 300
gggaccaagc tggagctgaa a 321

<210> SEQ ID NO 390
<211> LENGTH: 119
<212> TYPE: PRT
<213> ORGANISM: Artificial Sequence
<220> FEATURE:
<223> OTHER INFORMATION: ACI-7088-4305H7-Ab1 4305H7A4 VH

<400> SEQUENCE: 390

Glu Val Gln Leu Gln Gln Ser Gly Ala Glu Leu Val Arg Pro Gly Ala
1 5 10 15

Ser Val Lys Leu Ser Cys Thr Ala Ser Gly Phe Asn Ile Lys Asp Asp
20 25 30

Tyr Met His Trp Val Lys Gln Arg Pro Glu Gln Gly Leu Glu Trp Ile
35 40 45

Gly Trp Ile Asp Pro Glu Asn Gly Asp Thr Glu Tyr Ala Ser Lys Phe
50 55 60

Gln Gly Lys Ala Thr Met Ile Ala Asp Thr Ser Ser Asn Thr Ala Tyr
65 70 75 80

Leu Gln Leu Ser Ser Leu Thr Ser Glu Asp Thr Ala Val Tyr Tyr Cys
85 90 95

Lys Thr Trp Gly Thr Thr Gln Ala Leu Phe Pro Tyr Trp Gly Gln Gly
100 105 110

```
Thr Leu Val Thr Val Ser Ser
        115


<210> SEQ ID NO 391

<400> SEQUENCE: 391

000


<210> SEQ ID NO 392

<400> SEQUENCE: 392

000


<210> SEQ ID NO 393
<211> LENGTH: 10
<212> TYPE: PRT
<213> ORGANISM: Artificial Sequence
<220> FEATURE:
<223> OTHER INFORMATION: ACI-7088-4305H7-Ab1 4305H7A4 VH CDR3

<400> SEQUENCE: 393

Trp Gly Thr Thr Gln Ala Leu Phe Pro Tyr
1               5                   10


<210> SEQ ID NO 394
<211> LENGTH: 107
<212> TYPE: PRT
<213> ORGANISM: Artificial Sequence
<220> FEATURE:
<223> OTHER INFORMATION: ACI-7088-4305H7-Ab1 4305H7A4 VL

<400> SEQUENCE: 394

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Gly Trp Tyr Gln Gln Lys Ala Gly Gln Ser Pro Lys Leu Leu Ile
        35                  40                  45

His Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Gln Gln Tyr Arg Ser Tyr Pro Leu
                85                  90                  95

Thr Phe Gly Ala Gly Thr Lys Leu Glu Leu Lys
            100                 105


<210> SEQ ID NO 395
<211> LENGTH: 11
<212> TYPE: PRT
<213> ORGANISM: Artificial Sequence
<220> FEATURE:
<223> OTHER INFORMATION: ACI-7088-4305H7-Ab1 4305H7A4 VL CDR1

<400> SEQUENCE: 395

Lys Ala Ser Gln Asn Val Gly Thr Ala Val Gly
1               5                   10


<210> SEQ ID NO 396

<400> SEQUENCE: 396
```

000

<210> SEQ ID NO 397

<400> SEQUENCE: 397

000

<210> SEQ ID NO 398
<211> LENGTH: 357
<212> TYPE: DNA
<213> ORGANISM: Artificial Sequence
<220> FEATURE:
<223> OTHER INFORMATION: ACI-7088-4305H7-Ab1 4305H7A4 VH

<400> SEQUENCE: 398
gaggttcagc tgcagcagtc tggggctgaa cttgtgaggc caggggcctc agtcaagttg 60
tcctgcacag cttctggctt taacattaaa gacgactata tgcactgggt gaagcagagg 120
cctgaacagg gcctggagtg gattggatgg attgatcctg agaatggtga tactgaatat 180
gcctcgaagt tccagggcaa ggccactatg atagcagaca catcctccaa cacagcctac 240
ctgcaactca gcagcctgac atctgaggac actgccgtct attattgtaa aacatggggg 300
acaactcagg ccctctttcc ttactggggc caagggactc tggtcactgt ctctgca 357

<210> SEQ ID NO 399
<211> LENGTH: 321
<212> TYPE: DNA
<213> ORGANISM: Artificial Sequence
<220> FEATURE:
<223> OTHER INFORMATION: ACI-7088-4305H7-Ab1 4305H7A4 VL

<400> SEQUENCE: 399
gacattgtga tgacccagtc tcaaaaattc atgtccacat cagtaggaga cagggtcagc 60
atcacctgca aggccagtca gaatgtgggt actgctgtag gctggtatca acaaaaagca 120
ggacaatctc ctaaactact gattcactcg gcatccaatc ggtacactgg agtccctgat 180
cgcttcacag gcagtggatc tgggacagat ttcactctca ccatcaacaa tatgcagtct 240
gaagacctgg cagattattt ctgccagcaa tatagaagtt atccgctcac gttcggtgct 300
gggaccaagc tggagctgaa a 321

<210> SEQ ID NO 400
<211> LENGTH: 119
<212> TYPE: PRT
<213> ORGANISM: Artificial Sequence
<220> FEATURE:
<223> OTHER INFORMATION: ACI-7088-4317A4-Ab1 4317A4D2 VH

<400> SEQUENCE: 400

Glu Val Gln Leu Gln Gln Ser Gly Ala Glu Leu Val Arg Pro Gly Ala
1 5 10 15

Ser Val Lys Leu Ser Cys Thr Ala Ser Gly Phe Asn Ile Lys Asp Asp
20 25 30

Tyr Met His Trp Val Lys Gln Arg Pro Glu Gln Gly Leu Glu Trp Ile
35 40 45

Gly Trp Ile Asp Pro Glu Asn Gly Asp Thr Glu Tyr Ala Ser Lys Phe
50 55 60

Gln Gly Lys Ala Thr Met Thr Ala Asp Thr Ser Ser Asn Thr Ala Tyr
65 70 75 80

Leu Gln Leu Ser Ser Leu Thr Ser Glu Asp Thr Ala Val Tyr Tyr Cys

```
                85                  90                  95

Lys Thr Trp Gly Thr Thr Gln Ala Leu Phe Pro Tyr Trp Gly Gln Gly
            100                 105                 110

Thr Leu Val Thr Val Ser Ala
        115


<210> SEQ ID NO 401

<400> SEQUENCE: 401

000


<210> SEQ ID NO 402

<400> SEQUENCE: 402

000


<210> SEQ ID NO 403

<400> SEQUENCE: 403

000


<210> SEQ ID NO 404
<211> LENGTH: 107
<212> TYPE: PRT
<213> ORGANISM: Artificial Sequence
<220> FEATURE:
<223> OTHER INFORMATION: ACI-7088-4317A4-Ab1 4317A4D2 VL

<400> SEQUENCE: 404

Asp Ile Val Met Thr Gln Ser Gln Lys Phe Met Tyr Thr Ser Val Gly
1               5                   10                  15

Asp Arg Val Ser Ile Thr Cys Lys Ala Ser Gln Asn Val Gly Asn Ala
            20                  25                  30

Val Gly Trp Tyr Gln Gln Lys Ala Gly Gln Ser Pro Lys Leu Leu Ile
        35                  40                  45

His Ser Ala Ser Asn Arg Tyr Thr Gly Val Pro Asp Arg Phe Thr Gly
    50                  55                  60

Thr Gly Ser Gly Thr Asp Phe Thr Leu Thr Ile Asn Asn Met Gln Ser
65                  70                  75                  80

Glu Asp Leu Ala Asp Tyr Phe Cys Gln Gln Tyr Arg Ser Tyr Pro Leu
                85                  90                  95

Thr Phe Gly Ala Gly Thr Lys Leu Glu Leu Lys
            100                 105


<210> SEQ ID NO 405
<211> LENGTH: 11
<212> TYPE: PRT
<213> ORGANISM: Artificial Sequence
<220> FEATURE:
<223> OTHER INFORMATION: ACI-7088-4317A4-Ab1 4317A4D2 VL CDR1

<400> SEQUENCE: 405

Lys Ala Ser Gln Asn Val Gly Asn Ala Val Gly
1               5                   10


<210> SEQ ID NO 406

<400> SEQUENCE: 406

000
```

<210> SEQ ID NO 407

<400> SEQUENCE: 407

000

<210> SEQ ID NO 408
<211> LENGTH: 357
<212> TYPE: DNA
<213> ORGANISM: Artificial Sequence
<220> FEATURE:
<223> OTHER INFORMATION: ACI-7088-4317A4-Ab1 4317A4D2 VH

<400> SEQUENCE: 408
gaggttcagc tgcagcagtc tggggctgaa cttgtgaggc caggggcctc agtcaagttg 60
tcctgcacag cttctggctt taacattaaa gacgactata tgcactgggt gaagcagagg 120
cctgaacagg gcctggagtg gattggatgg attgatcctg agaatggtga tactgaatat 180
gcctcgaagt tccagggcaa ggccactatg acagcagaca catcctccaa cacagcctac 240
ctgcaactca gcagcctgac atctgaggac actgccgtct attattgtaa aacatggggg 300
acaactcagg ccctctttcc ttactggggc caagggactc tggtcactgt ctctgca 357

<210> SEQ ID NO 409
<211> LENGTH: 321
<212> TYPE: DNA
<213> ORGANISM: Artificial Sequence
<220> FEATURE:
<223> OTHER INFORMATION: ACI-7088-4317A4-Ab1 4317A4D2 VL

<400> SEQUENCE: 409
gacattgtga tgacccagtc tcaaaagttc atgtacacat cagtgggaga cagggtcagc 60
atcacctgca aggccagtca gaatgtgggt aatgctgtag gctggtatca acaaaaagca 120
ggacaatctc ctaaactact gattcactcg gcatccaatc ggtacactgg agtccctgat 180
cgcttcacag gcactggatc tgggacagat ttcactctca ccatcaacaa tatgcagtct 240
gaagacctgg cagattattt ctgccagcaa tatagaagtt atccgctcac gttcggtgct 300
gggaccaagc tggagctgaa a 321

<210> SEQ ID NO 410
<211> LENGTH: 113
<212> TYPE: PRT
<213> ORGANISM: Artificial Sequence
<220> FEATURE:
<223> OTHER INFORMATION: ACI-7089-4409F1-Ab1 4409F1A8 VH

<400> SEQUENCE: 410

Asp Val Gln Leu Gln Glu Ser Gly Pro Gly Leu Val Lys Pro Ser Gln
1 5 10 15

Ser Leu Ser Leu Thr Cys Ser Val Thr Gly Tyr Ser Ile Thr Arg Gly
20 25 30

Tyr Tyr Trp Asn Trp Ile Arg Gln Phe Pro Gly Asn Lys Leu Glu Trp
35 40 45

Met Gly Tyr Ile Ser Tyr Asp Gly Ser Asn Asn Tyr Asn Pro Ser Leu
50 55 60

Arg Asn Arg Ile Ser Ile Thr Arg Asp Thr Ser Lys Asn Gln Phe Phe
65 70 75 80

Leu Lys Leu Lys Ser Val Thr Thr Glu Asp Thr Ala Thr Tyr Phe Cys
85 90 95

```
Ala Arg Gly Asp Ser Asn Trp Gly Gln Gly Thr Thr Leu Thr Val Ser
            100                 105                 110

Ala


<210> SEQ ID NO 411
<211> LENGTH: 6
<212> TYPE: PRT
<213> ORGANISM: Artificial Sequence
<220> FEATURE:
<223> OTHER INFORMATION: ACI-7089-4409F1-Ab1 4409F1A8 VH CDR1

<400> SEQUENCE: 411

Arg Gly Tyr Tyr Trp Asn
1               5


<210> SEQ ID NO 412
<211> LENGTH: 16
<212> TYPE: PRT
<213> ORGANISM: Artificial Sequence
<220> FEATURE:
<223> OTHER INFORMATION: ACI-7089-4409F1-Ab1 4409F1A8 VH CDR2

<400> SEQUENCE: 412

Tyr Ile Ser Tyr Asp Gly Ser Asn Asn Tyr Asn Pro Ser Leu Arg Asn
1               5                   10                  15


<210> SEQ ID NO 413
<211> LENGTH: 4
<212> TYPE: PRT
<213> ORGANISM: Artificial Sequence
<220> FEATURE:
<223> OTHER INFORMATION: ACI-7089-4409F1-Ab1 4409F1A8 VH CDR3

<400> SEQUENCE: 413

Gly Asp Ser Asn
1


<210> SEQ ID NO 414
<211> LENGTH: 112
<212> TYPE: PRT
<213> ORGANISM: Artificial Sequence
<220> FEATURE:
<223> OTHER INFORMATION: ACI-7089-4409F1-Ab1 4409F1A8 VL

<400> SEQUENCE: 414

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110


<210> SEQ ID NO 415
```

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418
<211> LENGTH: 339
<212> TYPE: DNA
<213> ORGANISM: Artificial Sequence
<220> FEATURE:
<223> OTHER INFORMATION: ACI-7089-4409F1-Ab1 4409F1A8 VH

<400> SEQUENCE: 418
gatgtacagc ttcaggagtc aggacctggc ctcgtgaaac cttctcagtc tctgtctctc 60
acctgctctg tcactggcta ctccatcacc aggggttatt actggaactg gatccggcag 120
tttccaggaa acaaactgga atggatgggc tacataagct acgatggtag caataactac 180
aacccatctc tcagaaatcg aatctccatc actcgtgaca catctaagaa ccagtttttc 240
ctgaagttga aatctgtgac tactgaggac acagccacat atttctgtgc aagaggggat 300
agtaactggg gccaaggcac cactctcaca gtctcctca 339

<210> SEQ ID NO 419
<211> LENGTH: 336
<212> TYPE: DNA
<213> ORGANISM: Artificial Sequence
<220> FEATURE:
<223> OTHER INFORMATION: ACI-7089-4409F1-Ab1 4409F1A8 VL

<400> SEQUENCE: 419
gatgttgtga tgacccagac tccactcact ttgtcggtta ccattggaca accagcctcc 60
atctcttgca agtcaagtca gagcctctta gatagtgatg gagagacata tttgaattgg 120
ttgttacaga ggccaggcca gtctccaaag cgcctaatct atctggtgtc taaactggac 180
tctggagtcc ctgacaggtt cactggtagt ggatcaggga cagatttcac actgaaaatc 240
agcagagtgg aggctgagga tttgggagtt tattattgct ggcaaggtac acattttcct 300
cagacgttcg gtggaggcac caagttggaa atcaaa 336

<210> SEQ ID NO 420
<211> LENGTH: 112
<212> TYPE: PRT
<213> ORGANISM: Artificial Sequence
<220> FEATURE:
<223> OTHER INFORMATION: ACI-7089-4415G5-Ab1 4415G5A11 VH

<400> SEQUENCE: 420

Gln Val Gln Leu Gln Gln Ser Gly Ala Glu Leu Ala Arg Pro Gly Ala
1 5 10 15

Ser Val Lys Val Ser Cys Lys Ala Ser Gly Tyr Thr Phe Thr Ser Ser
20 25 30

Gly Ile Ser Trp Leu Lys His Arg Thr Gly Gln Gly Leu Glu Trp Ile

```
        35                  40                  45

Gly Asp Ile Tyr Pro Arg Ser Gly Asn Thr Tyr Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Ser Gly Asn Tyr Trp Gly Gln Gly Thr Thr Leu Thr Val Ser Ala
            100                 105                 110


<210> SEQ ID NO 421
<211> LENGTH: 5
<212> TYPE: PRT
<213> ORGANISM: Artificial Sequence
<220> FEATURE:
<223> OTHER INFORMATION: ACI-7089-4415G5-Ab1 4415G5A11 VH CDR1

<400> SEQUENCE: 421

Ser Ser Gly Ile Ser
1               5


<210> SEQ ID NO 422
<211> LENGTH: 17
<212> TYPE: PRT
<213> ORGANISM: Artificial Sequence
<220> FEATURE:
<223> OTHER INFORMATION: ACI-7089-4415G5-Ab1 4415G5A11 VH CDR2

<400> SEQUENCE: 422

Asp Ile Tyr Pro Arg Ser Gly Asn Thr Tyr Tyr Asn Glu Lys Phe Lys
1               5                   10                  15

Asp


<210> SEQ ID NO 423

<400> SEQUENCE: 423

000


<210> SEQ ID NO 424
<211> LENGTH: 112
<212> TYPE: PRT
<213> ORGANISM: Artificial Sequence
<220> FEATURE:
<223> OTHER INFORMATION: ACI-7089-4415G5-Ab1 4415G5A11 VL

<400> SEQUENCE: 424

Asp Ile Val Ile Thr Gln Asp Asp Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Leu Glu Tyr Pro Leu Thr Phe Gly Ala Gly Thr Lys Leu Glu Leu Lys
            100                 105                 110
```

<210> SEQ ID NO 425
<211> LENGTH: 16
<212> TYPE: PRT
<213> ORGANISM: Artificial Sequence
<220> FEATURE:
<223> OTHER INFORMATION: ACI-7089-4415G5-Ab1 4415G5A11 VL CDR1

<400> SEQUENCE: 425

Arg Ser Ser Lys Ser Leu Leu Tyr Lys Asp Gly Lys Thr Tyr Leu Asn
1 5 10 15

<210> SEQ ID NO 426
<211> LENGTH: 7
<212> TYPE: PRT
<213> ORGANISM: Artificial Sequence
<220> FEATURE:
<223> OTHER INFORMATION: ACI-7089-4415G5-Ab1 4415G5A11 VL CDR2

<400> SEQUENCE: 426

Leu Met Ser Thr Arg Ala Ser
1 5

<210> SEQ ID NO 427
<211> LENGTH: 9
<212> TYPE: PRT
<213> ORGANISM: Artificial Sequence
<220> FEATURE:
<223> OTHER INFORMATION: ACI-7089-4415G5-Ab1 4415G5A11 VL CDR2

<400> SEQUENCE: 427

Gln Gln Leu Leu Glu Tyr Pro Leu Thr
1 5

<210> SEQ ID NO 428
<211> LENGTH: 336
<212> TYPE: DNA
<213> ORGANISM: Artificial Sequence
<220> FEATURE:
<223> OTHER INFORMATION: ACI-7089-4415G5-Ab1 4415G5A11 VH

<400> SEQUENCE: 428
caggttcagc tgcagcagtc tggagctgag ctggcgaggc ctggggcttc agtgaaggtg 60
tcctgcaagg cttctggcta caccttcaca agctctggta taagctggtt gaagcacaga 120
actggacagg gccttgagtg gattggagac atttatccta gaagtggtaa tacttactac 180
aatgagaaat tcaaggacaa ggccacactg actgcagaca aatcctccag cacggcgtac 240
atggagctcc gcagcctgac atctgaggac tctgcggtct atttctgtgc aagtggtaac 300
tactggggcc aaggcaccac tctcacagtc tcctca 336

<210> SEQ ID NO 429
<211> LENGTH: 336
<212> TYPE: DNA
<213> ORGANISM: Artificial Sequence
<220> FEATURE:
<223> OTHER INFORMATION: ACI-7089-4415G5-Ab1 4415G5A11

<400> SEQUENCE: 429
gatattgtga taacccagga tgacctctcc aatcctgtca cttctggaga atcagtttcc 60
atctcctgca ggtctagtaa gagtctccta tataaggatg ggaagacata cttgaattgg 120
tttctgcaga gaccaggaca atctcctcag ctcctgatct atttgatgtc cacccgtgca 180
tcaggagtct cagaccggtt tagtggcagt gggtcaggaa cagatttcac cctggaaatc 240
agtagagtga aggctgagga tgtgggtgtg tattactgtc aacaactttt agagtatccg 300
ctcacgttcg gtgctgggac caagctggag ctgaaa 336

<210> SEQ ID NO 430
<211> LENGTH: 114
<212> TYPE: PRT
<213> ORGANISM: Artificial Sequence
<220> FEATURE:
<223> OTHER INFORMATION: ACI-7089-4417G6-Ab1 4417G6B12 VH

<400> SEQUENCE: 430

Gln Val Gln Leu Gln Gln Ser Gly Ala Glu Leu Val Arg Pro Gly Ala
1 5 10 15

Ser Val Thr Leu Ser Cys Lys Ala Ser Gly Tyr Thr Phe Thr Gly Tyr
20 25 30

Glu Met His Lys Gln Thr Pro Val His Gly Leu Glu Trp Ile Gly Ala
35 40 45

Ile Asp Pro Glu Thr Gly Gly Thr Ala Tyr Ile Gln Lys Phe Lys Gly
50 55 60

Lys Ala Thr Leu Thr Ala Asp Lys Ser Ser Ser Thr Ala Tyr Met Glu
65 70 75 80

Leu Arg Ser Leu Thr Ser Glu Asp Ser Ala Val Tyr Tyr Cys Thr Arg
85 90 95

Gly Trp Asp Tyr Phe Asp Tyr Trp Gly Gln Gly Thr Thr Leu Thr Val
100 105 110

Ser Ala

<210> SEQ ID NO 431
<211> LENGTH: 5
<212> TYPE: PRT
<213> ORGANISM: Artificial Sequence
<220> FEATURE:
<223> OTHER INFORMATION: ACI-7089-4417G6-Ab1 4417G6B12 VH CDR1

<400> SEQUENCE: 431

Gly Tyr Glu Met His
1 5

<210> SEQ ID NO 432
<211> LENGTH: 17
<212> TYPE: PRT
<213> ORGANISM: Artificial Sequence
<220> FEATURE:
<223> OTHER INFORMATION: ACI-7089-4417G6-Ab1 4417G6B12 VH CDR2

<400> SEQUENCE: 432

Ala Ile Asp Pro Glu Thr Gly Gly Thr Ala Tyr Ile Gln Lys Phe Lys
1 5 10 15

Gly

<210> SEQ ID NO 433
<211> LENGTH: 7
<212> TYPE: PRT
<213> ORGANISM: Artificial Sequence
<220> FEATURE:
<223> OTHER INFORMATION: ACI-7089-4417G6-Ab1 4417G6B12 VH CDR3

<400> SEQUENCE: 433

Gly Trp Asp Tyr Phe Asp Tyr
1 5

<210> SEQ ID NO 434
<211> LENGTH: 112
<212> TYPE: PRT
<213> ORGANISM: Artificial Sequence
<220> FEATURE:
<223> OTHER INFORMATION: ACI-7089-4417G6-Ab1 4417G6B12 VL

<400> SEQUENCE: 434

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Phe Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 435
<211> LENGTH: 16
<212> TYPE: PRT
<213> ORGANISM: Artificial Sequence
<220> FEATURE:
<223> OTHER INFORMATION: ACI-7089-4417G6-Ab1 4417G6B12 VL CDR1

<400> SEQUENCE: 435

```
Arg Ser Ser Gln Ser Leu Leu His Ser Asn Gly Phe Thr Tyr Leu His
1               5                   10                  15
```

<210> SEQ ID NO 436
<211> LENGTH: 7
<212> TYPE: PRT
<213> ORGANISM: Artificial Sequence
<220> FEATURE:
<223> OTHER INFORMATION: ACI-7089-4417G6-Ab1 4417G6B12 VL CDR2

<400> SEQUENCE: 436

```
Arg Val Ser Asn Arg Phe Ser
1               5
```

<210> SEQ ID NO 437
<211> LENGTH: 9
<212> TYPE: PRT
<213> ORGANISM: Artificial Sequence
<220> FEATURE:
<223> OTHER INFORMATION: ACI-7089-4417G6-Ab1 4417G6B12 VL CDR3

<400> SEQUENCE: 437

```
Ser Gln Ser Thr His Val Pro Tyr Thr
1               5
```

<210> SEQ ID NO 438
<211> LENGTH: 348
<212> TYPE: DNA
<213> ORGANISM: Artificial Sequence
<220> FEATURE:
<223> OTHER INFORMATION: ACI-7089-4417G6-Ab1 4417G6B12 VH

<400> SEQUENCE: 438
caggttcaac tgcagcagtc tggggctgag ttggtgaggc ctggggcttc agtgacgctg 60
tcctgcaagg cttcgggcta cacatttact ggctatgaaa tgcactgggt gaagcagaca 120
cctgtgcatg gcctggaatg gattggagct attgatcctg aaaccggtgg aactgcctat 180
attcagaagt tcaagggcaa ggccacactg actgcagaca aatcctccag cacagcctac 240
atggagctcc gcagcctgac atctgaggac tctgccgtct attactgtac aagaggctgg 300
gactattttg actactgggg ccaaggcacc actctcacag tctcctca 348

<210> SEQ ID NO 439
<211> LENGTH: 336
<212> TYPE: DNA
<213> ORGANISM: Artificial Sequence
<220> FEATURE:
<223> OTHER INFORMATION: ACI-7089-4417G6-Ab1 4417G6B12 VL

<400> SEQUENCE: 439
gatgttgtga tgacccaaac tccactctcc ctgcctgtca gtcttggaga tcaagcctcc 60
atctcttgca gatctagtca gagccttcta cacagtaatg gattcaccta tttacattgg 120
tacctgcaga agccaggcca gtctccaaag ctcctgatct acagagtttc caatcgattt 180
tctggggtcc cagacaggtt cagtggcagt ggatcaggga cagatttcac actcaagatc 240
agcagagtgg aggctgagga tctgggagtt tatttctgct ctcaaagtac acatgttccg 300
tacacgttcg gaggggggac caagctggaa ataaaa 336

<210> SEQ ID NO 440
<211> LENGTH: 113
<212> TYPE: PRT
<213> ORGANISM: Artificial Sequence
<220> FEATURE:
<223> OTHER INFORMATION: ACI-7089-4418C5-Ab1 4418C5G1 VH

<400> SEQUENCE: 440

Asp Gly Gln Leu Gln Glu Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Asn Tyr Asp Gly Ser Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Phe Asn Phe Val Thr Thr Glu Asp Thr Ala Thr Tyr Tyr Cys
85 90 95

Val Arg Gly Asp Val Tyr Trp Gly Gln Gly Thr Thr Leu Thr Val Ser
100 105 110

Ser

<210> SEQ ID NO 441

<400> SEQUENCE: 441

000

<210> SEQ ID NO 442
<211> LENGTH: 16
<212> TYPE: PRT

<213> ORGANISM: Artificial Sequence
<220> FEATURE:
<223> OTHER INFORMATION: ACI-7089-4418C5-Ab1 4418C5G1 VH CDR2

<400> SEQUENCE: 442

Tyr Ile Asn Tyr Asp Gly Ser Asn Asn Tyr Asn Pro Ser Leu Lys Asn
1               5                   10                  15

<210> SEQ ID NO 443
<211> LENGTH: 4
<212> TYPE: PRT
<213> ORGANISM: Artificial Sequence
<220> FEATURE:
<223> OTHER INFORMATION: ACI-7089-4418C5-Ab1 4418C5G1 VH CDR3

<400> SEQUENCE: 443

Gly Asp Val Tyr
1

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448
<211> LENGTH: 339
<212> TYPE: DNA
<213> ORGANISM: Artificial Sequence
<220> FEATURE:
<223> OTHER INFORMATION: ACI-7089-4418C5-Ab1 4418C5G1 VH

<400> SEQUENCE: 448
gatggacaac ttcaggagtc aggacctggc ctcgtgaaac cttctcagtc tctgtctctc 60
acctgctctg tcactggcta ctccatcacc agtggatatt actggaactg gatccggcag 120
tttccaggaa acaaactgga atggatgggc tacataaact acgatggtag caataactac 180
aacccatctc tcaaaaatcg aatctccatc actcgtgaca catctaagaa tcagtttttc 240
ctgaagttca attttgtgac tactgaggac acagccacat attactgtgt gagggggac 300 gtctactggg gccaaggcac cactctcaca gtctcctca 339

<210> SEQ ID NO 449
<211> LENGTH: 336
<212> TYPE: DNA
<213> ORGANISM: Artificial Sequence
<220> FEATURE:
<223> OTHER INFORMATION: ACI-7089-4418C5-Ab1 4418C5G1 VL

<400> SEQUENCE: 449

```
gatgttgtga tgacccagac tccactcact ttgtcggtta ccattggaca accagcctcc     60
atctcttgca agtcaagtca gagcctctta gatagtgatg gagagacata tttgaattgg    120
ttattacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
cagacgttcg gtggaggcac caagctggaa atcaaa                              336
```

<210> SEQ ID NO 450
<211> LENGTH: 112
<212> TYPE: PRT
<213> ORGANISM: Artificial Sequence
<220> FEATURE:
<223> OTHER INFORMATION: ACI-7089-4418F6-Ab1 4418F6G7 VH

<400> SEQUENCE: 450

```
Gln Val Gln Leu Gln Gln Ser Gly Ala Glu Leu Ala Arg Pro Gly Ala
1               5                   10                  15

Ser Val Lys Val Ser Cys Lys Ala Ser Gly Tyr Thr Phe Thr Ser Ser
            20                  25                  30

Gly Ile Ser Trp Leu Lys His Arg Thr Gly Gln Gly Leu Glu Trp Ile
        35                  40                  45

Gly Asp Ile Tyr Pro Arg Ser Gly Asn Thr Tyr Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ser Ser Gly Asn Tyr Trp Gly Gln Gly Thr Thr Leu Thr Val Ser Ser
            100                 105                 110
```

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458
<211> LENGTH: 336
<212> TYPE: DNA
<213> ORGANISM: Artificial Sequence
<220> FEATURE:
<223> OTHER INFORMATION: ACI-7089-4418F6-Ab1 4418F6G7 VH

<400> SEQUENCE: 458
caggttcagc tgcagcagtc tggagctgag ctggcgaggc ctggggcttc agtgaaggtg 60
tcctgcaagg cttctggcta caccttcaca agttctggta taagctggtt gaagcacaga 120
actggacagg gccttgagtg gattggagac atttatccta gaagtggtaa tacttactac 180
aatgagaaat tcaaggacaa ggccacactg actgcagaca aatcctccag cacggcgtac 240
atggagctcc gcagcctgac atctgaggac tctgcggtct atttctgttc aagtggtaac 300
tactggggcc aaggcaccac tctcacagtc tcctca 336

<210> SEQ ID NO 459
<211> LENGTH: 336
<212> TYPE: DNA
<213> ORGANISM: Artificial Sequence
<220> FEATURE:
<223> OTHER INFORMATION: ACI-7089-4418F6-Ab1 4418F6G7 VL

<400> SEQUENCE: 459
gatattgtga taacccagga tgacctctcc aatcctgtca cttctggaga atcagtttcc 60
atctcctgta ggtctagtaa gagtctccta tataaggatg ggaagacata cttgaattgg 120
tttctgcaga gaccaggaca atctcctcag ctcctgatct atttgatgtc cacccgtgca 180
tcaggagtct cagaccggtt tagtggcagt gggtcaggaa cagatttcac cctggaaatc 240
agtagagtga aggctgagga tgtgggtgtg tattactgtc aacaactttt agagtatccg 300
ctcacgttcg gtgctgggac caagctggag ctgaaa 336

<210> SEQ ID NO 460
<211> LENGTH: 114
<212> TYPE: PRT
<213> ORGANISM: Artificial Sequence
<220> FEATURE:
<223> OTHER INFORMATION: ACI-8033-5A12-Ab1 917.5A12A11C9 VH

<400> SEQUENCE: 460

Gln Val His Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

```
Ala Arg Ile Tyr Pro Gly Ser Gly Asn Thr Tyr Tyr Asn Glu Lys Phe
    50                  55                  60

Lys Gly Arg Ala Thr Leu Ser Ala Glu Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Val Val Gly Tyr Tyr Gly Ala Trp Gly Gln Gly Thr Thr Leu Thr Val
            100                 105                 110

Ser Ser


<210> SEQ ID NO 461
<211> LENGTH: 5
<212> TYPE: PRT
<213> ORGANISM: Artificial Sequence
<220> FEATURE:
<223> OTHER INFORMATION: ACI-8033-5A12-Ab1 917.5A12A11C9 VH CDR1

<400> SEQUENCE: 461

Asp Tyr Tyr Ile Asn
1               5


<210> SEQ ID NO 462
<211> LENGTH: 17
<212> TYPE: PRT
<213> ORGANISM: Artificial Sequence
<220> FEATURE:
<223> OTHER INFORMATION: ACI-8033-5A12-Ab1 917.5A12A11C9 VH CDR2

<400> SEQUENCE: 462

Arg Ile Tyr Pro Gly Ser Gly Asn Thr Tyr Tyr Asn Glu Lys Phe Lys
1               5                   10                  15

Gly


<210> SEQ ID NO 463
<211> LENGTH: 5
<212> TYPE: PRT
<213> ORGANISM: Artificial Sequence
<220> FEATURE:
<223> OTHER INFORMATION: ACI-8033-5A12-Ab1 917.5A12A11C9 VH CDR3

<400> SEQUENCE: 463

Gly Tyr Tyr Gly Ala
1               5


<210> SEQ ID NO 464
<211> LENGTH: 112
<212> TYPE: PRT
<213> ORGANISM: Artificial Sequence
<220> FEATURE:
<223> OTHER INFORMATION: ACI-8033-5A12-Ab1 917.5A12A11C9 VL

<400> SEQUENCE: 464

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Lys Thr His Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110


<210> SEQ ID NO 465
<211> LENGTH: 16
<212> TYPE: PRT
<213> ORGANISM: Artificial Sequence
<220> FEATURE:
<223> OTHER INFORMATION: ACI-8033-5A12-Ab1 917.5A12A11C9 VL CDR1

<400> SEQUENCE: 465

Arg Ser Ser Gln Ser Leu Val His Ser Asn Gly Lys Thr His Leu His
1               5                   10                  15


<210> SEQ ID NO 466

<400> SEQUENCE: 466

000


<210> SEQ ID NO 467
<211> LENGTH: 9
<212> TYPE: PRT
<213> ORGANISM: Artificial Sequence
<220> FEATURE:
<223> OTHER INFORMATION: ACI-8033-5A12-Ab1 917.5A12A11C9 VL CDR3

<400> SEQUENCE: 467

Ser Gln Ser Thr His Val Pro Trp Thr
1               5


<210> SEQ ID NO 468
<211> LENGTH: 342
<212> TYPE: DNA
<213> ORGANISM: Artificial Sequence
<220> FEATURE:
<223> OTHER INFORMATION: ACI-8033-5A12-Ab1 917.5A12A11C9 VH

<400> SEQUENCE: 468

caggtccacc tgaagcagtc tggggctgac ctggtgaggc ctggggcttc agtgaagctg      60

tcctgcaagg cgtctggcta cactttcact gactactata taaactgggt gaagcagagg     120

cctggacagg gacttgagtg gattgcaagg atttatcctg gaagtggtaa tacttactac     180

aatgagaagt tcaagggcag ggccacactg agtgcagaaa aatcctccac cactgcctac     240

atgcagctca gcagcctgac atctgaggac tctgctgtct atttctgtgt agtggggtac     300

tacggtgcct ggggccaagg caccactctc acagtctcct ca                        342


<210> SEQ ID NO 469
<211> LENGTH: 336
<212> TYPE: DNA
<213> ORGANISM: Artificial Sequence
<220> FEATURE:
<223> OTHER INFORMATION: ACI-8033-5A12-Ab1 917.5A12A11C9 VL

<400> SEQUENCE: 469

gatgttgtga tgacccaaac tccactctcc ctgcctgtca gtcttggaga tcaagcctcc      60

atctcttgta gatctagtca gagccttgta cacagtaatg gaaaaaccca tttacattgg     120

tacctgcaga agccaggcca gtctccaaag ctcctgatct ataaagtttc caaccgattt     180

tctggggtcc cagacaggtt cagtggcagt ggatcaggga cagatttcac actcaagatc     240
```

agcagagtgg aggctgagga tctgggagtt tatttctgct ctcaaagtac acatgttccg 300
tggacgttcg gtggaggcac caagctggaa atcaaa 336

<210> SEQ ID NO 470
<211> LENGTH: 115
<212> TYPE: PRT
<213> ORGANISM: Artificial Sequence
<220> FEATURE:
<223> OTHER INFORMATION: ACI-8033-25A3-Ab1 917.25A3E9F6 VH

<400> SEQUENCE: 470

Glu Val Gln Leu Val Glu Ser Gly Gly Gly Leu Val Gln Pro Lys Gly
1 5 10 15

Ser Leu Lys Leu Ser Cys Ala Ala Ser Gly Phe Ser Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Phe Ala Thr Tyr Tyr Ala Asp
50 55 60

Ser Val Lys Asp Arg Phe Thr Ile Ser Arg Asp Glu Ser Glu Ser Met
65 70 75 80

Leu Tyr Leu Gln Met Asn Asn Leu Lys Thr Glu Asp Thr Ala Met Tyr
85 90 95

Tyr Cys Val Arg Ser Phe Asp Tyr Trp Gly Gln Gly Thr Thr Leu Thr
100 105 110

Val Ser Ser
115

<210> SEQ ID NO 471

<400> SEQUENCE: 471

000

<210> SEQ ID NO 472
<211> LENGTH: 19
<212> TYPE: PRT
<213> ORGANISM: Artificial Sequence
<220> FEATURE:
<223> OTHER INFORMATION: ACI-8033-25A3-Ab1 917.25A3E9F6 VH CDR2

<400> SEQUENCE: 472

Arg Ile Arg Ser Lys Ser Asn Asn Phe Ala Thr Tyr Tyr Ala Asp Ser
1 5 10 15

Val Lys Asp

<210> SEQ ID NO 473
<211> LENGTH: 4
<212> TYPE: PRT
<213> ORGANISM: Artificial Sequence
<220> FEATURE:
<223> OTHER INFORMATION: ACI-8033-25A3-Ab1 917.25A3E9F6 VH CDR3

<400> SEQUENCE: 473

Ser Phe Asp Tyr
1

<210> SEQ ID NO 474
<211> LENGTH: 107
<212> TYPE: PRT
<213> ORGANISM: Artificial Sequence
<220> FEATURE:
<223> OTHER INFORMATION: ACI-8033-25A3-Ab1 917.25A3E9F6 VL

<400> SEQUENCE: 474

Asp Ile Lys Met Thr Gln Ser Pro Ser Ser Met Tyr Ala Ser Leu Gly
1 5 10 15

Glu Arg Val Thr Ile Thr Cys Lys Ala Ser Gln Asp Ile Asn Ser Tyr
20 25 30

Leu Ser Trp Phe Gln Gln Lys Pro Gly Lys Ser Pro Lys Thr Leu Ile
35 40 45

Tyr Arg Ala Lys Arg Leu Val Asp Gly Val Pro Ser Arg Phe Ser Gly
50 55 60

Ser Gly Ser Gly Gln Asp Tyr Ser Leu Thr Ile Ser Ser Leu Glu Tyr
65 70 75 80

Glu Asp Met Gly Ile Tyr Tyr Cys Leu Gln Tyr Asp Glu Phe Pro Phe
85 90 95

Thr Phe Gly Ser Gly Thr Lys Leu Glu Ile Lys
100 105

<210> SEQ ID NO 475
<211> LENGTH: 11
<212> TYPE: PRT
<213> ORGANISM: Artificial Sequence
<220> FEATURE:
<223> OTHER INFORMATION: ACI-8033-25A3-Ab1 917.25A3E9F6 VL CDR1

<400> SEQUENCE: 475

Lys Ala Ser Gln Asp Ile Asn Ser Tyr Leu Ser
1 5 10

<210> SEQ ID NO 476
<211> LENGTH: 7
<212> TYPE: PRT
<213> ORGANISM: Artificial Sequence
<220> FEATURE:
<223> OTHER INFORMATION: ACI-8033-25A3-Ab1 917.25A3E9F6 VL CDR2

<400> SEQUENCE: 476

Arg Ala Lys Arg Leu Val Asp
1 5

<210> SEQ ID NO 477
<211> LENGTH: 9
<212> TYPE: PRT
<213> ORGANISM: Artificial Sequence
<220> FEATURE:
<223> OTHER INFORMATION: ACI-8033-25A3-Ab1 917.25A3E9F6 VL CDR3

<400> SEQUENCE: 477

Leu Gln Tyr Asp Glu Phe Pro Phe Thr
1 5

<210> SEQ ID NO 478
<211> LENGTH: 345
<212> TYPE: DNA
<213> ORGANISM: Artificial Sequence
<220> FEATURE:
<223> OTHER INFORMATION: ACI-8033-25A3-Ab1 917.25A3E9F6 VH

<400> SEQUENCE: 478
gaggtgcagc ttgttgagtc tggtggagga ttggtgcagc ctaaagggtc attgaaactc 60
tcatgtgcag cctctggatt cagcttcaat acctacgcca tgaactgggt ccgccaggct 120

```
ccaggaaagg gtttggaatg ggttgctcgc ataagaagta aaagtaataa ttttgcaaca    180

tattatgccg attcagtgaa agacagattc accatctcca gagatgaatc agaaagcatg    240

ctctatctgc aaatgaacaa cttgaaaact gaggacacag ccatgtatta ctgtgtgagg    300

tcctttgact actggggcca aggcaccact ctcacagtct cctca                    345


<210> SEQ ID NO 479
<211> LENGTH: 321
<212> TYPE: DNA
<213> ORGANISM: Artificial Sequence
<220> FEATURE:
<223> OTHER INFORMATION: ACI-8033-25A3-Ab1 917.25A3E9F6 VL

<400> SEQUENCE: 479

gacatcaaga tgacccagtc tccatcttcc atgtatgcat ctctaggaga gagagtcact     60

atcacttgca aggcgagtca ggacattaat agctatttaa gctggttcca gcagaaacca    120

gggaaatctc ctaagaccct aatctatcgt gcaaaaagat tggtagatgg ggtcccatca    180

aggttcagtg gcagtggatc tgggcaagat tattctctca ccatcagcag cctggagtat    240

gaagatatgg gaatttatta ttgtctacag tatgatgagt ttccattcac gttcggctcg    300

gggacaaagt tggaaataaa a                                              321


<210> SEQ ID NO 480
<211> LENGTH: 119
<212> TYPE: PRT
<213> ORGANISM: Artificial Sequence
<220> FEATURE:
<223> OTHER INFORMATION: ACI-8033-1G10-Ab1 917.1G10A10F6 VH

<400> SEQUENCE: 480

Asp Val Gln Leu Gln Glu Ser Gly Pro Gly Leu Val Lys Pro Ser Gln
1               5                   10                  15

Thr Val Phe Leu Thr Cys Thr Val Thr Gly Ile Ser Ile Thr Thr Gly
            20                  25                  30

Asn Tyr Arg Trp Ser Trp Ile Arg Gln Phe Pro Gly Asn Lys Leu Glu
        35                  40                  45

Trp Ile Gly Tyr Ile Tyr Tyr Ser Gly Thr Ile Thr Tyr Asn Pro Ser
    50                  55                  60

Leu Thr Ser Arg Thr Thr Ile Thr Arg Asp Thr Pro Lys Asn Gln Phe
65                  70                  75                  80

Phe Leu Glu Met Asn Ser Leu Thr Ala Glu Asp Thr Ala Thr Tyr Tyr
                85                  90                  95

Cys Ala Arg Ile Tyr Tyr Gly Asn Ala Met Asp Tyr Trp Gly Gln Gly
            100                 105                 110

Thr Ser Val Thr Val Ser Ser
        115


<210> SEQ ID NO 481
<211> LENGTH: 7
<212> TYPE: PRT
<213> ORGANISM: Artificial Sequence
<220> FEATURE:
<223> OTHER INFORMATION: ACI-8033-1G10-Ab1 917.1G10A10F6 VH CDR1

<400> SEQUENCE: 481

Thr Gly Asn Tyr Arg Trp Ser
1               5


<210> SEQ ID NO 482
```

<211> LENGTH: 16
<212> TYPE: PRT
<213> ORGANISM: Artificial Sequence
<220> FEATURE:
<223> OTHER INFORMATION: ACI-8033-1G10-Ab1 917.1G10A10F6 VH CDR2

<400> SEQUENCE: 482

Tyr Ile Tyr Tyr Ser Gly Thr Ile Thr Tyr Asn Pro Ser Leu Thr Ser
1 5 10 15

<210> SEQ ID NO 483
<211> LENGTH: 9
<212> TYPE: PRT
<213> ORGANISM: Artificial Sequence
<220> FEATURE:
<223> OTHER INFORMATION: ACI-8033-1G10-Ab1 917.1G10A10F6 VH CDR3

<400> SEQUENCE: 483

Ile Tyr Tyr Gly Asn Ala Met Asp Tyr
1 5

<210> SEQ ID NO 484
<211> LENGTH: 112
<212> TYPE: PRT
<213> ORGANISM: Artificial Sequence
<220> FEATURE:
<223> OTHER INFORMATION: ACI-8033-1G10-Ab1 917.1G10A10F6 VL

<400> SEQUENCE: 484

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro His Thr Phe Gly Gly Gly Thr Lys Leu Glu Ile Lys
100 105 110

<210> SEQ ID NO 485

<400> SEQUENCE: 485

000

<210> SEQ ID NO 486

<400> SEQUENCE: 486

000

<210> SEQ ID NO 487
<211> LENGTH: 9
<212> TYPE: PRT
<213> ORGANISM: Artificial Sequence
<220> FEATURE:
<223> OTHER INFORMATION: ACI-8033-1G10-Ab1 917.1G10A10F6 VL CDR3

<400> SEQUENCE: 487

```
Ser Gln Ser Thr His Val Pro His Thr
1               5


<210> SEQ ID NO 488
<211> LENGTH: 357
<212> TYPE: DNA
<213> ORGANISM: Artificial Sequence
<220> FEATURE:
<223> OTHER INFORMATION: ACI-8033-1G10-Ab1 917.1G10A10F6 VH

<400> SEQUENCE: 488

gatgtgcagc ttcaggagtc aggacctggc ctggtgaaac cttctcagac agtgttcctc     60

acctgcactg tcactggcat ttccatcacc actggaaatt acaggtggag ctggatccgg    120

cagtttccag gaaacaaact ggagtggata gggtacatat actacagtgg taccattacc    180

tacaatccat ctctcacaag tcgaaccacc atcactagag acactcccaa gaaccagttc    240

ttcctggaaa tgaactcttt gactgctgag gacacagcca catactactg tgcacggatt    300

tactacggta atgctatgga ctactggggt caaggaacct cagtcaccgt ctcctca       357


<210> SEQ ID NO 489
<211> LENGTH: 336
<212> TYPE: DNA
<213> ORGANISM: Artificial Sequence
<220> FEATURE:
<223> OTHER INFORMATION: ACI-8033-1G10-Ab1 917.1G10A10F6 VL

<400> SEQUENCE: 489

gatgttgtga tgacccaaac tccactctcc ctgcctgtca gtcttggaga tcaagcctcc     60

atctcttgca gatctagtca gagccttgta cacagtaatg gaaacaccta tttacattgg    120

tacctgcaga agccaggcca gtctccaaag ctcctgatct acaaagtttc caaccgattt    180

tctggggtcc cagacaggtt cagtggcagt ggatcaggga cagatttcac actcaagatc    240

agcagagtgg aggctgagga tctgggagtt tatttctgct ctcaaagtac acatgttcct    300

cacacgttcg gaggggggac caagctggaa ataaaa                              336


<210> SEQ ID NO 490
<211> LENGTH: 115
<212> TYPE: PRT
<213> ORGANISM: Artificial Sequence
<220> FEATURE:
<223> OTHER INFORMATION: ACI-8033-19A2-Ab1 917.19A2E9E5 VH

<400> SEQUENCE: 490

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Val Asp
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Leu Tyr
                85                  90                  95

Tyr Cys Val Ser Glu Ser Ala Tyr Trp Gly Gln Gly Thr Leu Val Thr
            100                 105                 110

Val Ser Ala
```

115

<210> SEQ ID NO 491

<400> SEQUENCE: 491

000

<210> SEQ ID NO 492
<211> LENGTH: 19
<212> TYPE: PRT
<213> ORGANISM: Artificial Sequence
<220> FEATURE:
<223> OTHER INFORMATION: ACI-8033-19A2-Ab1 917.19A2E9E5 VH CDR2

<400> SEQUENCE: 492

Arg Ile Arg Ser Lys Ser Asn Asn Tyr Ala Thr Tyr Tyr Val Asp Ser
1 5 10 15

Val Lys Asp

<210> SEQ ID NO 493
<211> LENGTH: 4
<212> TYPE: PRT
<213> ORGANISM: Artificial Sequence
<220> FEATURE:
<223> OTHER INFORMATION: ACI-8033-19A2-Ab1 917.19A2E9E5 VH CDR3

<400> SEQUENCE: 493

Glu Ser Ala Tyr
1

<210> SEQ ID NO 494
<211> LENGTH: 112
<212> TYPE: PRT
<213> ORGANISM: Artificial Sequence
<220> FEATURE:
<223> OTHER INFORMATION: ACI-8033-19A2-Ab1 917.19A2E9E5 VL

<400> SEQUENCE: 494

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu Tyr Trp Tyr Leu Gln Lys Pro Gly Gln Ser
35 40 45

Pro Lys Leu Leu Ile Tyr Lys Val Ser Asn Arg Leu Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Phe Thr Phe Gly Ser Gly Thr Lys Leu Glu Ile Lys
100 105 110

<210> SEQ ID NO 495
<211> LENGTH: 16
<212> TYPE: PRT
<213> ORGANISM: Artificial Sequence
<220> FEATURE:
<223> OTHER INFORMATION: ACI-8033-19A2-Ab1 917.19A2E9E5 VL CDR1

<400> SEQUENCE: 495

Arg Ser Ser Gln Ser Leu Val His Ser Asn Gly Asn Thr Tyr Leu Tyr

-continued 1               5                   10                  15

<210> SEQ ID NO 496
<211> LENGTH: 7
<212> TYPE: PRT
<213> ORGANISM: Artificial Sequence
<220> FEATURE:
<223> OTHER INFORMATION: ACI-8033-19A2-Ab1 917.19A2E9E5 VL CDR2

<400> SEQUENCE: 496

Lys Val Ser Asn Arg Leu Ser
1               5

<210> SEQ ID NO 497
<211> LENGTH: 9
<212> TYPE: PRT
<213> ORGANISM: Artificial Sequence
<220> FEATURE:
<223> OTHER INFORMATION: ACI-8033-19A2-Ab1 917.19A2E9E5 VL CDR3

<400> SEQUENCE: 497

Ser Gln Ser Thr His Val Pro Phe Thr
1               5

<210> SEQ ID NO 498
<211> LENGTH: 345
<212> TYPE: DNA
<213> ORGANISM: Artificial Sequence
<220> FEATURE:
<223> OTHER INFORMATION: ACI-8033-19A2-Ab1 917.19A2E9E5 VH

<400> SEQUENCE: 498
gaggtgcaac ttgttgagtc tggtggagga ttggtgcagc ctaaagggtc attgaaactc 60
tcatgtgcag cctctggatt cagcttcaat acctacgcca tgaactgggt ccgccaggct 120
ccaggaaagg gtttggaatg ggttgctcgc ataagaagta aaagtaataa ttatgcaaca 180
tattatgtcg attcagtgaa agacagattc accatctcca gagatgattc agaaagcatg 240
ctctatctgc aaatgaacaa cttgaaaact gaggacacag ccctgtatta ctgtgtgagc 300
gaatccgctt actggggcca agggactctg gtcactgtct ctgca 345

<210> SEQ ID NO 499
<211> LENGTH: 336
<212> TYPE: DNA
<213> ORGANISM: Artificial Sequence
<220> FEATURE:
<223> OTHER INFORMATION: ACI-8033-19A2-Ab1 917.19A2E9E5 VL

<400> SEQUENCE: 499
gatgttgtga tgacccaaac tccactctcc ctgcctgtca gtcttggaga tcaagcctcc 60
atctcttgca gatctagtca gagccttgta cacagtaatg gaaacaccta tttatattgg 120
tacctgcaga agccaggcca gtctccaaag ctcctgatct acaaagtttc caaccgactt 180
tctggggtcc cagacaggtt cagtggcagt ggatcaggga cagatttcac actcaagatc 240
agcagagtgg aggctgagga tctgggagtt tatttctgct ctcaaagtac acatgttcca 300
ttcacgttcg gctcggggac aaagttggaa ataaaa 336

<210> SEQ ID NO 500
<211> LENGTH: 113
<212> TYPE: PRT
<213> ORGANISM: Artificial Sequence
<220> FEATURE:
<223> OTHER INFORMATION: ACI-8033-8C10-Ab1 917.8C10C6G3 VH

<400> SEQUENCE: 500

Asp Val Gln Leu Gln Glu Ser Gly Pro Gly Leu Val Lys Pro Ser Gln
1 5 10 15

Ser Leu Ser Leu Thr Cys Ser Val Thr Gly Gln Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Asn Asp Gly Ser Ser Lys Thr Asn Pro Ser Leu
50 55 60

Thr Asn Arg Ile Ser Val Thr Arg Asp Thr Ser Lys Asn Gln Val Phe
65 70 75 80

Leu Lys Leu Lys Ser Val Thr Thr Glu Asp Thr Ala Thr Tyr Tyr Cys
85 90 95

Val Arg Gly Asp Gln His Trp Gly Gln Gly Thr Ala Leu Thr Val Ser
100 105 110

Ser

<210> SEQ ID NO 501

<400> SEQUENCE: 501

000

<210> SEQ ID NO 502
<211> LENGTH: 16
<212> TYPE: PRT
<213> ORGANISM: Artificial Sequence
<220> FEATURE:
<223> OTHER INFORMATION: ACI-8033-8C10-Ab1 917.8C10C6G3 VH CDR2

<400> SEQUENCE: 502

Tyr Ile Ser Asn Asp Gly Ser Ser Lys Thr Asn Pro Ser Leu Thr Asn
1 5 10 15

<210> SEQ ID NO 503
<211> LENGTH: 4
<212> TYPE: PRT
<213> ORGANISM: Artificial Sequence
<220> FEATURE:
<223> OTHER INFORMATION: ACI-8033-8C10-Ab1 917.8C10C6G3 VH CDR2

<400> SEQUENCE: 503

Gly Asp Gln His
1

<210> SEQ ID NO 504
<211> LENGTH: 112
<212> TYPE: PRT
<213> ORGANISM: Artificial Sequence
<220> FEATURE:
<223> OTHER INFORMATION: ACI-8033-8C10-Ab1 917.8C10C6G3 VL

<400> SEQUENCE: 504

Asp Val Val Leu Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asp Gly Glu Thr Tyr Leu Asn Trp Leu Leu Gln Arg Pro Gly Gln Ser
35 40 45

Pro Lys Arg Leu Ile Tyr Leu Val Ser Glu Leu Asp Ser Gly Val Ser

```
    50                  55                  60

Asp Arg Phe Thr Gly Ser Gly Ser Gly Thr Asp Phe Thr Leu Lys Ile
65                  70                  75                  80

Ser Arg Leu Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508
<211> LENGTH: 339
<212> TYPE: DNA
<213> ORGANISM: Artificial Sequence
<220> FEATURE:
<223> OTHER INFORMATION: ACI-8033-8C10-Ab1 917.8C10C6G3 VH

<400> SEQUENCE: 508

```
gatgtacagc ttcaggagtc aggacctggc ctcgtgaaac cttctcagtc tctgtctctc     60

acctgctctg tcactggcca atccatcacc agtggttatt actggaactg gatccggcaa    120

tttccaggaa acaaactgga atggatgggc tacataagca acgatggtag cagtaaaacc    180

aacccatctc tcacaaatcg aatctccgtc actcgtgaca catctaagaa ccaggttttc    240

ctgaagttga aatctgtgac tactgaggac acagccacat attactgtgt aagaggggac    300

cagcactggg gccaaggcac cgctctcaca gtctcctca                           339
```

<210> SEQ ID NO 509
<211> LENGTH: 336
<212> TYPE: DNA
<213> ORGANISM: Artificial Sequence
<220> FEATURE:
<223> OTHER INFORMATION: ACI-8033-8C10-Ab1 917.8C10C6G3 VL

<400> SEQUENCE: 509

```
gatgttgtgt tgacccagac tccactcact ttgtcagtta ccattgggca accagcctcc     60

atctcttgca agtcaagtca gagcctctta gatagtgatg gagagacata tttgaattgg    120

ttgttacaga ggccaggcca gtctccaaag cgcctaatct atctggtgtc tgaactggac    180

tctggagtct ctgacaggtt cactggcagt ggttcaggga cagatttcac actgaaaatc    240

agcagactgg aggctgagga tttgggagtt tattattgct ggcaaggtac acattttcct    300

cagacgttcg gtggaggcac caagctggaa atcaaa                              336
```

<210> SEQ ID NO 510
<211> LENGTH: 120

<212> TYPE: PRT
<213> ORGANISM: Artificial Sequence
<220> FEATURE:
<223> OTHER INFORMATION: ACI-8033-7A2-Ab1 917.7A2B6A9 VH

<400> SEQUENCE: 510

Gln Val Gln Leu Gln Gln Pro Gly Thr Glu Leu Val Lys Pro Gly Ala
1               5                   10                  15

Ser Val Asn Leu Pro Cys Lys Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Asn Val Asn Pro Asn Asn Ser Asp Ser Asn Tyr Asn Glu Lys Phe
    50                  55                  60

Lys Arg Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Ser Pro Tyr Tyr Gly Gly Arg Tyr Leu Asp Tyr Trp Gly Gln
            100                 105                 110

Gly Thr Thr Leu Thr Val Ser Ser
        115                 120

<210> SEQ ID NO 511

<400> SEQUENCE: 511

000

<210> SEQ ID NO 512
<211> LENGTH: 17
<212> TYPE: PRT
<213> ORGANISM: Artificial Sequence
<220> FEATURE:
<223> OTHER INFORMATION: ACI-8033-7A2-Ab1 917.7A2B6A9 VH CDR2

<400> SEQUENCE: 512

Asn Val Asn Pro Asn Asn Ser Asp Ser Asn Tyr Asn Glu Lys Phe Lys
1               5                   10                  15

Arg

<210> SEQ ID NO 513
<211> LENGTH: 11
<212> TYPE: PRT
<213> ORGANISM: Artificial Sequence
<220> FEATURE:
<223> OTHER INFORMATION: ACI-8033-7A2-Ab1 917.7A2B6A9 VH CDR3

<400> SEQUENCE: 513

Ser Pro Tyr Tyr Gly Gly Arg Tyr Leu Asp Tyr
1               5                   10

<210> SEQ ID NO 514
<211> LENGTH: 113
<212> TYPE: PRT
<213> ORGANISM: Artificial Sequence
<220> FEATURE:
<223> OTHER INFORMATION: ACI-8033-7A2-Ab1 917.7A2B6A9 VL

<400> SEQUENCE: 514

Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Arg
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Phe Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Leu Thr Phe Gly Ala Gly Thr Lys Leu Glu Leu
100 105 110

Lys

<210> SEQ ID NO 515
<211> LENGTH: 17
<212> TYPE: PRT
<213> ORGANISM: Artificial Sequence
<220> FEATURE:
<223> OTHER INFORMATION: ACI-8033-7A2-Ab1 917.7A2B6A9 VL CDR1

<400> SEQUENCE: 515

Lys Ser Ser Gln Ser Leu Leu Tyr Arg Ser Asn Gln Lys Asn Tyr Leu
1 5 10 15

Ala

<210> SEQ ID NO 516
<211> LENGTH: 7
<212> TYPE: PRT
<213> ORGANISM: Artificial Sequence
<220> FEATURE:
<223> OTHER INFORMATION: ACI-8033-7A2-Ab1 917.7A2B6A9 VL CDR2

<400> SEQUENCE: 516

Trp Ala Phe Thr Arg Glu Ser
1 5

<210> SEQ ID NO 517
<211> LENGTH: 9
<212> TYPE: PRT
<213> ORGANISM: Artificial Sequence
<220> FEATURE:
<223> OTHER INFORMATION: ACI-8033-7A2-Ab1 917.7A2B6A9 VL CDR3

<400> SEQUENCE: 517

Gln Gln Tyr Tyr Ser Tyr Pro Leu Thr
1 5

<210> SEQ ID NO 518
<211> LENGTH: 360
<212> TYPE: DNA
<213> ORGANISM: Artificial Sequence
<220> FEATURE:
<223> OTHER INFORMATION: ACI-8033-7A2-Ab1 917.7A2B6A9 VH

<400> SEQUENCE: 518
caggtccaac tacagcagcc tgggactgaa ctggtgaagc ctggggcttc agtgaacctg 60
ccctgcaagg cttctggcta caccttcacc agctactgga tgcactgggt gaagcagagg 120
cctggtcaag gccttgattg gattggaaat gttaatccta acaatagtga tagtaattac 180
aatgagaagt tcaagaggaa ggccacactg actgtagaca aatcctccag cacagcctac 240
atgcacctca gcagcctgac atctgaggac tctgcggtct attattgtgc aagatctcct 300
tactacggtg gccgttacct tgactactgg ggccaaggca ccactctcac agtctcctca 360

<210> SEQ ID NO 519
<211> LENGTH: 339
<212> TYPE: DNA
<213> ORGANISM: Artificial Sequence
<220> FEATURE:
<223> OTHER INFORMATION: ACI-8033-7A2-Ab1 917.7A2B6A9 VL

<400> SEQUENCE: 519
gacattgtga tgtcacagtc tccatcctcc ctagctgtgt cagttggaga gaaggttact 60
atgacctgca agtccagtca gagcctttta tatagaagca atcaaaagaa ctacttggcc 120
tggtaccagc agaaaccagg acagtctcct aaactgttga tttactgggc attcactagg 180
gaatctgggg tccctgatcg cttcacaggc agtggatctg ggacagattt cactctcacc 240
atcagcagtg tgaaggctga agacctggca gtttattact gtcagcaata ttatagctat 300
cctctcacgt tcggtgctgg gaccaagctg gagctgaaa 339

<210> SEQ ID NO 520
<211> LENGTH: 114
<212> TYPE: PRT
<213> ORGANISM: Artificial Sequence
<220> FEATURE:
<223> OTHER INFORMATION: ACI-8033-1A12-Ab1 917.1A12C1B4 VH

<400> SEQUENCE: 520

Gln Val His Leu Lys Gln Ser Gly Ala Asp Leu Val Arg Pro Gly Ala
1 5 10 15

Ser Val Lys Leu Ser Cys Lys Ala Ser Gly Tyr Ser Phe Thr Asp Phe
20 25 30

Tyr Ile Asn Trp Val Lys Gln Thr Pro Gly Gln Gly Leu Glu Trp Ile
35 40 45

Ala Arg Ile Tyr Pro Gly Asn Asn Asn Thr Phe Tyr Asn Glu Lys Phe
50 55 60

Lys Gly Lys Ala Thr Leu Ser Ala Glu Lys Ser Ser Thr Thr Ala Tyr
65 70 75 80

Met Gln Leu Ser Ser Leu Thr Ser Glu Asp Ser Ala Val Tyr Phe Cys
85 90 95

Val Val Gly Tyr Tyr Gly Ala Trp Gly Gln Gly Thr Thr Leu Thr Val
100 105 110

Ser Ser

<210> SEQ ID NO 521
<211> LENGTH: 5
<212> TYPE: PRT
<213> ORGANISM: Artificial Sequence
<220> FEATURE:
<223> OTHER INFORMATION: ACI-8033-1A12-Ab1 917.1A12C1B4 VH CDR1

<400> SEQUENCE: 521

Asp Phe Tyr Ile Asn
1 5

<210> SEQ ID NO 522
<211> LENGTH: 17
<212> TYPE: PRT
<213> ORGANISM: Artificial Sequence
<220> FEATURE:
<223> OTHER INFORMATION: ACI-8033-1A12-Ab1 917.1A12C1B4 VH CDR2

<400> SEQUENCE: 522

Arg Ile Tyr Pro Gly Asn Asn Asn Thr Phe Tyr Asn Glu Lys Phe Lys
1 5 10 15

Gly

<210> SEQ ID NO 523

<400> SEQUENCE: 523

000

<210> SEQ ID NO 524
<211> LENGTH: 112
<212> TYPE: PRT
<213> ORGANISM: Artificial Sequence
<220> FEATURE:
<223> OTHER INFORMATION: ACI-8033-1A12-Ab1 917.1A12C1B4 VL

<400> SEQUENCE: 524

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr His Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Phe Tyr Phe Cys Ser Gln Ser
85 90 95

Thr His Val Pro Trp Thr Phe Gly Gly Gly Thr Lys Leu Glu Ile Lys
100 105 110

<210> SEQ ID NO 525
<211> LENGTH: 16
<212> TYPE: PRT
<213> ORGANISM: Artificial Sequence
<220> FEATURE:
<223> OTHER INFORMATION: ACI-8033-1A12-Ab1 917.1A12C1B4 VL CDR1

<400> SEQUENCE: 525

Arg Ser Ser Gln Ser Leu Val His Ser Asn Gly Asn Thr His Leu His
1 5 10 15

<210> SEQ ID NO 526

<400> SEQUENCE: 526

000

<210> SEQ ID NO 527

<400> SEQUENCE: 527

000

<210> SEQ ID NO 528
<211> LENGTH: 342
<212> TYPE: DNA
<213> ORGANISM: Artificial Sequence
<220> FEATURE:

<223> OTHER INFORMATION: ACI-8033-1A12-Ab1 917.1A12C1B4 VH

<400> SEQUENCE: 528

```
caggtccacc tgaagcagtc tggggctgac ctggtgaggc ctggggcttc agtgaagctg     60

tcctgcaagg cgtctggcta cagtttcact gacttttata taaattgggt gaagcagacg    120

cctggacagg gacttgagtg gattgcgagg atttatcctg gaaataataa tactttctac    180

aatgagaaat tcaagggcaa ggccacactg agtgcagaaa aatcctccac cactgcctac    240

atgcagctca gcagcctgac atctgaggac tctgctgtct atttctgtgt agtggggtac    300

tacggtgcct ggggccaagg caccactctc acagtctcct ca                       342
```

<210> SEQ ID NO 529
<211> LENGTH: 336
<212> TYPE: DNA
<213> ORGANISM: Artificial Sequence
<220> FEATURE:
<223> OTHER INFORMATION: ACI-8033-1A12-Ab1 917.1A12C1B4 VL

<400> SEQUENCE: 529

```
gatgttgtga tgacccaaac tccactctcc ctgcctgtca gtcttggaga tcaagcctcc     60

atctcttgca gatctagtca gagccttgta cacagtaatg gaaacaccca tttgcattgg    120

tacctgcaga agccaggcca gtctccaaag ctcctgatct ataaagtttc caaccgattt    180

tctggggtcc cagacaggtt cagtggcagt ggatcaggga cagatttcac actcaagatc    240

agcagagtgg aggctgagga tctaggattt tatttctgct ctcaaagtac acatgttccg    300

tggacgttcg gtggaggcac caagctggaa atcaaa                              336
```

<210> SEQ ID NO 530
<211> LENGTH: 125
<212> TYPE: PRT
<213> ORGANISM: Artificial Sequence
<220> FEATURE:
<223> OTHER INFORMATION: ACI-8033-4F3-Ab1 917.4F3F4G6 VH

<400> SEQUENCE: 530

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Thr Gly Thr Asn Ser Tyr Asn Gln Lys Phe
    50                  55                  60

Lys Gly Arg Ala Ser Leu Thr Val Asp Lys Phe Ser Ser Ala Ala Tyr
65                  70                  75                  80

Met Glu Leu Arg Ser Leu Thr Ser Glu Asp Ser Ala Val Tyr Tyr Cys
                85                  90                  95

Ala Arg Thr Gly Tyr Gly Asp Pro Ile Ser Ser Tyr Tyr Tyr Ala Leu
            100                 105                 110

Asp Tyr Trp Gly Gln Gly Thr Ser Val Thr Val Ser Ser
        115                 120                 125
```

<210> SEQ ID NO 531

<400> SEQUENCE: 531

000

<210> SEQ ID NO 532
<211> LENGTH: 17
<212> TYPE: PRT
<213> ORGANISM: Artificial Sequence
<220> FEATURE:
<223> OTHER INFORMATION: ACI-8033-4F3-Ab1 917.4F3F4G6 VH CDR2

<400> SEQUENCE: 532

Asp Ile Asn Pro Asn Thr Gly Thr Asn Ser Tyr Asn Gln Lys Phe Lys
1 5 10 15

Gly

<210> SEQ ID NO 533
<211> LENGTH: 16
<212> TYPE: PRT
<213> ORGANISM: Artificial Sequence
<220> FEATURE:
<223> OTHER INFORMATION: ACI-8033-4F3-Ab1 917.4F3F4G6 VH CDR3

<400> SEQUENCE: 533

Thr Gly Tyr Gly Asp Pro Ile Ser Ser Tyr Tyr Tyr Ala Leu Asp Tyr
1 5 10 15

<210> SEQ ID NO 534
<211> LENGTH: 112
<212> TYPE: PRT
<213> ORGANISM: Artificial Sequence
<220> FEATURE:
<223> OTHER INFORMATION: ACI-8033-4F3-Ab1 917.4F3F4G6 VL

<400> SEQUENCE: 534

Asp Ile Val Met Ser Gln Ser Pro Ser Ser Leu Ala Val Ser Ala Gly
1 5 10 15

Glu Lys Val Thr Met Ser Cys Lys Ser Ser Gln Ser Leu Leu Asn Ser
20 25 30

Arg Thr Arg Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Lys Gln
85 90 95

Ser Tyr Asn Leu Trp Thr Phe Gly Gly Gly Thr Lys Leu Glu Ile Lys
100 105 110

<210> SEQ ID NO 535

<400> SEQUENCE: 535

000

<210> SEQ ID NO 536

<400> SEQUENCE: 536

000

<210> SEQ ID NO 537
<211> LENGTH: 8
<212> TYPE: PRT
<213> ORGANISM: Artificial Sequence
<220> FEATURE:

<223> OTHER INFORMATION: ACI-8033-4F3-Ab1 917.4F3F4G6 VL CDR3

<400> SEQUENCE: 537

Lys Gln Ser Tyr Asn Leu Trp Thr
1 5

<210> SEQ ID NO 538
<211> LENGTH: 375
<212> TYPE: DNA
<213> ORGANISM: Artificial Sequence
<220> FEATURE:
<223> OTHER INFORMATION: ACI-8033-4F3-Ab1 917.4F3F4G6 VH

<400> SEQUENCE: 538
gaggtccagc tgcaacaatc tggacctgag ctggtgaagc ctggggcttc agtgaagata 60
tcctgtaagg cttctggata cacgttcact gactactaca tgaactgggt gaagcagagc 120
catggaaaga gccttgaatg gattggagat attaatccta acactggtac taatagctac 180
aaccagaagt tcaagggcag ggcctcactg actgtagaca agttctccag cgcagcctac 240
atggagctcc gcagcctgac atctgaggac tctgcagtct attactgtgc aagaaccggc 300
tatggcgacc ctatttcctc atattactat gctctggact actggggtca aggaacctca 360
gtcaccgtct cctca 375

<210> SEQ ID NO 539
<211> LENGTH: 336
<212> TYPE: DNA
<213> ORGANISM: Artificial Sequence
<220> FEATURE:
<223> OTHER INFORMATION: ACI-8033-4F3-Ab1 917.4F3F4G6 VL

<400> SEQUENCE: 539
gacattgtga tgtcacagtc tccatcctcc ctggctgtgt cagcaggaga gaaggtcact 60
atgagctgca aatccagtca gagtctgctc aacagtagaa cccgaaagaa ctacttggct 120
tggtaccagc agaaaccagg gcagtctcct aaactgctga tctactgggc atccactagg 180
gaatctgggg tccctgatcg cttcacaggc agtggatctg ggacagattt cactctcacc 240
atcagcagtg tgcaggctga agacctggca gtttattact gcaagcaatc ttataatctg 300
tggacgttcg gtggaggcac caagctggaa atcaaa 336

<210> SEQ ID NO 540
<211> LENGTH: 117
<212> TYPE: PRT
<213> ORGANISM: Artificial Sequence
<220> FEATURE:
<223> OTHER INFORMATION: ACI-8033-17F5-Ab1 917.17F5F5G9 VH

<400> SEQUENCE: 540

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Phe Met Asn Trp Val Lys Gln Ser His Gly Lys Ser Leu Glu Trp Ile
35 40 45

Gly Asp Ile Asn Pro Asn Ile Asp Val Thr Asn Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys

```
                85                  90                  95

Ala Arg Gly Arg Asp Tyr Ala Met Asp Phe Trp Gly Gln Gly Thr Ser
            100                 105                 110

Val Thr Val Ser Ser
        115


<210> SEQ ID NO 541

<400> SEQUENCE: 541

000


<210> SEQ ID NO 542
<211> LENGTH: 17
<212> TYPE: PRT
<213> ORGANISM: Artificial Sequence
<220> FEATURE:
<223> OTHER INFORMATION: ACI-8033-17F5-Ab1 917.17F5F5G9 VH CDR2

<400> SEQUENCE: 542

Asp Ile Asn Pro Asn Ile Asp Val Thr Asn Tyr Asn Gln Lys Phe Lys
1               5                   10                  15

Gly


<210> SEQ ID NO 543
<211> LENGTH: 8
<212> TYPE: PRT
<213> ORGANISM: Artificial Sequence
<220> FEATURE:
<223> OTHER INFORMATION: ACI-8033-17F5-Ab1 917.17F5F5G9 VH CDR3

<400> SEQUENCE: 543

Gly Arg Asp Tyr Ala Met Asp Phe
1               5


<210> SEQ ID NO 544
<211> LENGTH: 112
<212> TYPE: PRT
<213> ORGANISM: Artificial Sequence
<220> FEATURE:
<223> OTHER INFORMATION: ACI-8033-17F5-Ab1 917.17F5F5G9 VL

<400> SEQUENCE: 544

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Leu Trp Thr Phe Gly Gly Gly Thr Lys Leu Glu Ile Lys
            100                 105                 110


<210> SEQ ID NO 545

<400> SEQUENCE: 545
```

000

<210> SEQ ID NO 546

<400> SEQUENCE: 546

000

<210> SEQ ID NO 547

<400> SEQUENCE: 547

000

<210> SEQ ID NO 548
<211> LENGTH: 351
<212> TYPE: DNA
<213> ORGANISM: Artificial Sequence
<220> FEATURE:
<223> OTHER INFORMATION: ACI-8033-17F5-Ab1 917.17F5F5G9 VH

<400> SEQUENCE: 548
gaggtccaac tgcaacaatc tggacctgag ctggtgaagc ctggggcttc agtgaagata 60
tcctgtaagg cttctggata cacgttcact gactacttca tgaactgggt gaagcagagc 120
catggaaaga gccttgagtg gattggagat attaatccta acattgatgt tactaactac 180
aaccagaagt tcaagggcaa ggccacattg actgtagaca agtcctccag cacagcctac 240
atggagctcc gcagcctgac atctgaggac tctgcagtct attactgtgc aagagggcgg 300
gactatgcta tggacttctg gggtcaagga acctcagtca ccgtctcctc a 351

<210> SEQ ID NO 549
<211> LENGTH: 336
<212> TYPE: DNA
<213> ORGANISM: Artificial Sequence
<220> FEATURE:
<223> OTHER INFORMATION: ACI-8033-17F5-Ab1 917.17F5F5G9 VL

<400> SEQUENCE: 549
gacattgtga tgtcacagtc tccatcctcc ctggctgtgt cagcaggaga gaaggtcact 60
atgagctgca aatccagtca gagtctgctc aacagtagaa cccgaaagaa ctacttggct 120
tggtaccagc agaaaccagg gcagtctcct aaactgctga tctactgggc atccactagg 180
gaatctgggg tccctgatcg cttcacaggc agtggatctg ggacagattt caccctcacc 240
atcagcagtg tgcaggctga agacctggca gtttattact gcaagcaatc ttatgatctg 300
tggacgttcg gtggaggcac caagctggaa atcaaa 336

<210> SEQ ID NO 550
<211> LENGTH: 116
<212> TYPE: PRT
<213> ORGANISM: Artificial Sequence
<220> FEATURE:
<223> OTHER INFORMATION: ACI-8033-18C11-Ab1 917.18C11A11F10 VH

<400> SEQUENCE: 550

Gln Val Gln Leu Gln Gln Pro Gly Ala Glu Leu Val Lys Pro Gly Ala
1 5 10 15

Ser Val Lys Met Ser Cys Lys Ala Ala Gly Tyr Thr Phe Ser Ser Tyr
20 25 30

Trp Ile Thr Trp Val Arg Gln Arg Pro Gly Gln Gly Leu Asp Trp Ile
35 40 45

```
Gly Asp Ile Tyr Pro Gly Gly Gly Val Thr Asn Tyr Asn Glu Lys Phe
    50                  55                  60

Lys Thr Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Ala Gln Thr Thr Phe Ala Tyr Trp Gly Gln Gly Thr Leu Val
            100                 105                 110

Thr Val Ser Ala
        115


<210> SEQ ID NO 551
<211> LENGTH: 5
<212> TYPE: PRT
<213> ORGANISM: Artificial Sequence
<220> FEATURE:
<223> OTHER INFORMATION: ACI-8033-18C11-Ab1 917.18C11A11F10 VH CDR1

<400> SEQUENCE: 551

Ser Tyr Trp Ile Thr
1               5


<210> SEQ ID NO 552
<211> LENGTH: 17
<212> TYPE: PRT
<213> ORGANISM: Artificial Sequence
<220> FEATURE:
<223> OTHER INFORMATION: ACI-8033-18C11-Ab1 917.18C11A11F10 VH CDR2

<400> SEQUENCE: 552

Asp Ile Tyr Pro Gly Gly Gly Val Thr Asn Tyr Asn Glu Lys Phe Lys
1               5                   10                  15

Thr


<210> SEQ ID NO 553
<211> LENGTH: 7
<212> TYPE: PRT
<213> ORGANISM: Artificial Sequence
<220> FEATURE:
<223> OTHER INFORMATION: ACI-8033-18C11-Ab1 917.18C11A11F10 VH CDR3

<400> SEQUENCE: 553

Ala Gln Thr Thr Phe Ala Tyr
1               5


<210> SEQ ID NO 554
<211> LENGTH: 112
<212> TYPE: PRT
<213> ORGANISM: Artificial Sequence
<220> FEATURE:
<223> OTHER INFORMATION: ACI-8033-18C11-Ab1 917.18C11A11F10 VL

<400> SEQUENCE: 554

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Asn
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110


<210> SEQ ID NO 555
<211> LENGTH: 16
<212> TYPE: PRT
<213> ORGANISM: Artificial Sequence
<220> FEATURE:
<223> OTHER INFORMATION: ACI-8033-18C11-Ab1 917.18C11A11F10 VL CDR1

<400> SEQUENCE: 555

Arg Ser Ser Gln Asn Ile Val His Asn Asn Gly Asn Thr Tyr Leu Glu
1               5                   10                  15


<210> SEQ ID NO 556

<400> SEQUENCE: 556

000


<210> SEQ ID NO 557
<211> LENGTH: 9
<212> TYPE: PRT
<213> ORGANISM: Artificial Sequence
<220> FEATURE:
<223> OTHER INFORMATION: ACI-8033-18C11-Ab1 917.18C11A11F10 VL CDR3

<400> SEQUENCE: 557

Phe Gln Gly Ser His Val Pro Arg Thr
1               5


<210> SEQ ID NO 558
<211> LENGTH: 348
<212> TYPE: DNA
<213> ORGANISM: Artificial Sequence
<220> FEATURE:
<223> OTHER INFORMATION: ACI-8033-18C11-Ab1 917.18C11A11F10 VH

<400> SEQUENCE: 558

caggtccaac tccagcagcc tggggctgag cttgtgaagc ctggggcttc agtgaagatg      60

tcctgcaagg ctgctggcta caccttcagc agctactgga taacctgggt gaggcagagg     120

cctggacaag gccttgactg gattggagat atttatcctg gtggaggtgt tactaactac     180

aatgagaagt tcaagaccaa ggccacactg actgtagaca catcctccag cacagcctac     240

atgcagctca gcagcctgac atctgaggac tctgcggtct attactgtgc gacagctcag     300

actacgtttg cttactgggg ccaagggact ctggtcactg tctctgca                  348


<210> SEQ ID NO 559
<211> LENGTH: 336
<212> TYPE: DNA
<213> ORGANISM: Artificial Sequence
<220> FEATURE:
<223> OTHER INFORMATION: ACI-8033-18C11-Ab1 917.18C11A11F10 VL

<400> SEQUENCE: 559

gatgttttga tgacccaaac tccactgtcc ctgcctgtca gtcttggaga tcaagcctcc      60

atctcttgca gatctagtca gaacattgta cataataatg gaaacaccta tttagaatgg     120

tacctgcaga aaccaggcca gtctccaaag ctcctgatct acaaagtttc caaccgattt     180
```

```
tctggggtcc cagacaggtt cagtggcagt ggatcaggga cagatttcac actcaagatc    240

agcagagtgg aggctgagga tctgggagtt tattactgct ttcaaggttc acatgttcct    300

cggacgttcg gtggaggcac caagctggaa atcaaa                              336


<210> SEQ ID NO 560
<211> LENGTH: 116
<212> TYPE: PRT
<213> ORGANISM: Artificial Sequence
<220> FEATURE:
<223> OTHER INFORMATION: ACI-8033-18D12-Ab1 917.18D12F10D6 VH

<400> SEQUENCE: 560

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Arg Gln Arg Pro Gly Gln Gly Leu Asp Trp Ile
        35                  40                  45

Gly Asp Ile Tyr Pro Gly Gly Gly Val Thr Asn Tyr Asn Glu Lys Phe
    50                  55                  60

Lys Thr Lys Ala Thr Leu Thr Val Asp Thr Ser Ser Ser Thr Ala Tyr
65                  70                  75                  80

Met His Leu Ser Ser Leu Thr Ser Glu Asp Ser Ala Val Tyr Phe Cys
                85                  90                  95

Ala Thr Ala Gln Thr Thr Phe Ala His Trp Gly Gln Gly Thr Leu Val
            100                 105                 110

Thr Val Ser Ala
        115


<210> SEQ ID NO 561

<400> SEQUENCE: 561

000


<210> SEQ ID NO 562

<400> SEQUENCE: 562

000


<210> SEQ ID NO 563
<211> LENGTH: 7
<212> TYPE: PRT
<213> ORGANISM: Artificial Sequence
<220> FEATURE:
<223> OTHER INFORMATION: ACI-8033-18D12-Ab1 917.18D12F10D6 VH CDR3

<400> SEQUENCE: 563

Ala Gln Thr Thr Phe Ala His
1               5


<210> SEQ ID NO 564
<211> LENGTH: 112
<212> TYPE: PRT
<213> ORGANISM: Artificial Sequence
<220> FEATURE:
<223> OTHER INFORMATION: ACI-8033-18D12-Ab1 917.18D12F10D6 VL

<400> SEQUENCE: 564

Asp Val Leu Met Thr Gln Thr Pro Leu Ser Leu Pro Val Ser Leu Gly
1               5                   10                  15
```

Asp Gln Ala Ser Ile Ser Cys Arg Ser Ser Gln Asn Ile Ala His Asn
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Arg Thr Phe Gly Gly Gly Thr Lys Leu Glu Ile Lys
100 105 110

<210> SEQ ID NO 565
<211> LENGTH: 16
<212> TYPE: PRT
<213> ORGANISM: Artificial Sequence
<220> FEATURE:
<223> OTHER INFORMATION: ACI-8033-18D12-Ab1 917.18D12F10D6 VL CDR1

<400> SEQUENCE: 565

Arg Ser Ser Gln Asn Ile Ala His Asn Asn Gly Asn Thr Tyr Leu Glu
1 5 10 15

<210> SEQ ID NO 566

<400> SEQUENCE: 566

000

<210> SEQ ID NO 567

<400> SEQUENCE: 567

000

<210> SEQ ID NO 568
<211> LENGTH: 348
<212> TYPE: DNA
<213> ORGANISM: Artificial Sequence
<220> FEATURE:
<223> OTHER INFORMATION: ACI-8033-18D12-Ab1 917.18D12F10D6 VH

<400> SEQUENCE: 568
caggtccaac tccagcagcc tggggctgag cttgtgaagc ctggggcttc agtgaagatg 60
tcctgcaagg cttctggcta caccttcacc agctactgga taacctgggt gaggcagagg 120
cctggacaag gccttgactg gattggagat atttatcctg gtggaggtgt tactaactac 180
aatgagaagt tcaagaccaa ggccacactg actgtagaca catcctccag cacagcctac 240
atgcacctca gcagcctgac atctgaggac tctgcggtct atttctgtgc gacagctcag 300
actacgtttg ctcactgggg ccaagggact ctggtcactg tctctgca 348

<210> SEQ ID NO 569
<211> LENGTH: 336
<212> TYPE: PRT
<213> ORGANISM: Artificial Sequence
<220> FEATURE:
<223> OTHER INFORMATION: ACI-8033-18D12-Ab1 917.18D12F10D6 VL

<400> SEQUENCE: 569

Gly Ala Thr Gly Thr Thr Thr Thr Gly Ala Thr Gly Ala Cys Cys Cys

```
1               5                   10                  15

Ala Ala Ala Cys Thr Cys Cys Ala Cys Thr Cys Thr Cys Cys Cys Thr
            20                  25                  30

Gly Cys Cys Cys Gly Thr Cys Ala Gly Thr Cys Thr Thr Gly Gly Ala
        35                  40                  45

Gly Ala Thr Cys Ala Ala Gly Cys Cys Thr Cys Cys Ala Thr Cys Thr
    50                  55                  60

Cys Thr Thr Gly Cys Ala Gly Ala Thr Cys Thr Ala Gly Thr Cys Ala
65                  70                  75                  80

Gly Ala Ala Thr Ala Thr Thr Gly Cys Ala Cys Ala Thr Ala Ala Thr
                85                  90                  95

Ala Ala Thr Gly Gly Ala Ala Ala Cys Ala Cys Cys Thr Ala Thr Thr
            100                 105                 110

Thr Ala Gly Ala Ala Thr Gly Gly Thr Ala Cys Cys Thr Gly Cys Ala
        115                 120                 125

Gly Ala Ala Ala Cys Cys Ala Gly Gly Cys Cys Ala Gly Thr Cys Thr
    130                 135                 140

Cys Cys Ala Ala Ala Gly Cys Thr Cys Cys Thr Gly Ala Thr Cys Thr
145                 150                 155                 160

Ala Cys Ala Ala Ala Gly Thr Thr Thr Cys Cys Ala Ala Cys Cys Gly
                165                 170                 175

Ala Thr Thr Thr Thr Cys Thr Gly Gly Gly Gly Thr Cys Cys Cys Ala
            180                 185                 190

Gly Ala Cys Ala Gly Gly Thr Thr Cys Ala Gly Thr Gly Gly Cys Ala
        195                 200                 205

Gly Thr Gly Gly Ala Thr Cys Ala Gly Gly Gly Ala Cys Ala Gly Ala
    210                 215                 220

Thr Thr Thr Cys Ala Cys Ala Cys Thr Cys Ala Ala Gly Ala Thr Cys
225                 230                 235                 240

Ala Gly Cys Ala Gly Ala Gly Thr Gly Gly Ala Gly Gly Cys Thr Gly
                245                 250                 255

Ala Gly Gly Ala Thr Cys Thr Gly Gly Gly Ala Gly Thr Thr Thr Ala
            260                 265                 270

Thr Thr Ala Cys Thr Gly Cys Thr Thr Thr Cys Ala Ala Gly Gly Thr
        275                 280                 285

Thr Cys Ala Cys Ala Thr Gly Thr Thr Cys Cys Thr Cys Gly Gly Ala
    290                 295                 300

Cys Gly Thr Thr Cys Gly Gly Thr Gly Gly Ala Gly Gly Cys Ala Cys
305                 310                 315                 320

Cys Ala Ala Gly Cys Thr Gly Gly Ala Ala Ala Thr Cys Ala Ala Ala
                325                 330                 335
```

<210> SEQ ID NO 570
<211> LENGTH: 113
<212> TYPE: PRT
<213> ORGANISM: Artificial Sequence
<220> FEATURE:
<223> OTHER INFORMATION: ACI-8033-1F8-Ab1 917.1F8D8E4 VH

<400> SEQUENCE: 570

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Asn Trp Ile Arg Gln Phe Pro Gly Asn Lys Leu Glu Trp
```

```
        35                  40                  45

Met Gly Tyr Ile Ser Tyr Asp Gly Ser Asn Asn Tyr Asn Pro Ser Leu
    50                  55                  60

Lys Asn Arg Ile Ser Ile Ile Arg Asp Thr Ser Lys Asn Gln Phe Phe
65                  70                  75                  80

Leu Lys Leu Lys Ser Val Thr Ser Glu Asp Thr Ala Thr Tyr Tyr Cys
                85                  90                  95

Val Arg Gly Asp Val Asp Trp Gly Gln Gly Thr Thr Leu Thr Val Ser
            100                 105                 110

Ser


<210> SEQ ID NO 571
<211> LENGTH: 6
<212> TYPE: PRT
<213> ORGANISM: Artificial Sequence
<220> FEATURE:
<223> OTHER INFORMATION: ACI-8033-1F8-Ab1 917.1F8D8E4 VH CDR1

<400> SEQUENCE: 571

Ser Gly Phe Tyr Trp Asn
1               5


<210> SEQ ID NO 572

<400> SEQUENCE: 572

000


<210> SEQ ID NO 573
<211> LENGTH: 4
<212> TYPE: PRT
<213> ORGANISM: Artificial Sequence
<220> FEATURE:
<223> OTHER INFORMATION: ACI-8033-1F8-Ab1 917.1F8D8E4 VH CDR3

<400> SEQUENCE: 573

Gly Asp Val Asp
1


<210> SEQ ID NO 574
<211> LENGTH: 112
<212> TYPE: PRT
<213> ORGANISM: Artificial Sequence
<220> FEATURE:
<223> OTHER INFORMATION: ACI-8033-1F8-Ab1 917.1F8D8E4 VL

<400> SEQUENCE: 574

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Phe Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Pro Glu Asp Leu Gly Val Tyr Tyr Cys Trp Gln Gly
                85                  90                  95

Thr His Phe Pro Gln Thr Leu Gly Gly Gly Thr Lys Leu Glu Ile Lys
            100                 105                 110
```

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578
<211> LENGTH: 339
<212> TYPE: DNA
<213> ORGANISM: Artificial Sequence
<220> FEATURE:
<223> OTHER INFORMATION: ACI-8033-1F8-Ab1 917.1F8D8E4 VH

<400> SEQUENCE: 578
gatgtacagc ttcaggagtc aggacctggc ctcgtgaaac cttctcagtc tctgtctctc 60
acctgctctg tcactggcta ctccatcacc agtgggtttt actggaactg gatccggcaa 120
tttccaggaa ataaactgga atggatgggc tacataagct acgatggtag caataactac 180
aacccatctc tcaaaaatcg aatctccatt attcgtgaca catctaagaa ccagtttttc 240
ctgaagttga aatctgtgac ttctgaggac acagccacat attattgtgt aagaggggac 300
gtcgactggg gccaaggcac cactctcact gtctcctca 339

<210> SEQ ID NO 579
<211> LENGTH: 336
<212> TYPE: DNA
<213> ORGANISM: Artificial Sequence
<220> FEATURE:
<223> OTHER INFORMATION: ACI-8033-1F8-Ab1 917.1F8D8E4 VL

<400> SEQUENCE: 579
gatgttgtga tgacccagac tccactcact ttgtcggtca ccattggaca accagcctcc 60
atctcttgca agtcaagtca gagcctctta gatagtgatg gagagacata tttgaattgg 120
ttgtttcaga ggccaggcca gtctccaaag cgcctaatct atctggtgtc taaactggac 180
tctggagtcc ctgacaggtt cactggcagt ggatcaggga cagatttcac actgaaaatc 240
agcagagtgg agcctgagga tttgggagtt tattattgct ggcaaggtac acattttcct 300
cagacgctcg gtggaggcac caagctggaa atcaaa 336

<210> SEQ ID NO 580
<211> LENGTH: 120
<212> TYPE: PRT
<213> ORGANISM: Artificial Sequence
<220> FEATURE:
<223> OTHER INFORMATION: ACI-8033-22E5-Ab1 917.22E5C5F7 VH

<400> SEQUENCE: 580

Glu Val Gln Leu Val Glu Ser Gly Gly Asp Leu Val Lys Pro Gly Gly
1 5 10 15

```
Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Asn Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Leu Arg Arg Asp Gly Trp Tyr Phe Asp Val Trp Gly Thr
            100                 105                 110

Gly Thr Thr Val Thr Val Ser Ser
        115                 120


<210> SEQ ID NO 581
<211> LENGTH: 5
<212> TYPE: PRT
<213> ORGANISM: Artificial Sequence
<220> FEATURE:
<223> OTHER INFORMATION: ACI-8033-22E5-Ab1 917.22E5C5F7 VH CDR1

<400> SEQUENCE: 581

Ser Tyr Gly Met Ser
1               5


<210> SEQ ID NO 582
<211> LENGTH: 17
<212> TYPE: PRT
<213> ORGANISM: Artificial Sequence
<220> FEATURE:
<223> OTHER INFORMATION: ACI-8033-22E5-Ab1 917.22E5C5F7 VH CDR2

<400> SEQUENCE: 582

Thr Ile Ser Asn Gly Gly Ser Tyr Thr Tyr Tyr Pro Asp Ser Val Lys
1               5                   10                  15

Gly


<210> SEQ ID NO 583
<211> LENGTH: 11
<212> TYPE: PRT
<213> ORGANISM: Artificial Sequence
<220> FEATURE:
<223> OTHER INFORMATION: ACI-8033-22E5-Ab1 917.22E5C5F7 VH CDR3

<400> SEQUENCE: 583

Gln Leu Arg Arg Asp Gly Trp Tyr Phe Asp Val
1               5                   10


<210> SEQ ID NO 584
<211> LENGTH: 108
<212> TYPE: PRT
<213> ORGANISM: Artificial Sequence
<220> FEATURE:
<223> OTHER INFORMATION: ACI-8033-22E5-Ab1 917.22E5C5F7 VL

<400> SEQUENCE: 584

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Lys Leu His Trp Tyr Gln Gln Lys Ser Glu Thr Ser Pro Lys Leu Trp
```

```
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Lys
            100                 105


<210> SEQ ID NO 585
<211> LENGTH: 12
<212> TYPE: PRT
<213> ORGANISM: Artificial Sequence
<220> FEATURE:
<223> OTHER INFORMATION: ACI-8033-22E5-Ab1 917.22E5C5F7 VL CDR1

<400> SEQUENCE: 585

Ser Val Ser Ser Ser Ile Ser Ser Ser Lys Leu His
1               5                   10


<210> SEQ ID NO 586
<211> LENGTH: 7
<212> TYPE: PRT
<213> ORGANISM: Artificial Sequence
<220> FEATURE:
<223> OTHER INFORMATION: ACI-8033-22E5-Ab1 917.22E5C5F7 VL CDR2

<400> SEQUENCE: 586

Gly Thr Ser Asn Leu Ala Ser
1               5


<210> SEQ ID NO 587
<211> LENGTH: 9
<212> TYPE: PRT
<213> ORGANISM: Artificial Sequence
<220> FEATURE:
<223> OTHER INFORMATION: ACI-8033-22E5-Ab1 917.22E5C5F7 VL CDR3

<400> SEQUENCE: 587

Gln Gln Trp Ser Ser Tyr Pro Leu Thr
1               5


<210> SEQ ID NO 588
<211> LENGTH: 360
<212> TYPE: DNA
<213> ORGANISM: Artificial Sequence
<220> FEATURE:
<223> OTHER INFORMATION: ACI-8033-22E5-Ab1 917.22E5C5F7 VH

<400> SEQUENCE: 588

gaggtgcaac tagtggagtc tgggggagac ttagtgaagc ctggagggtc cctgaaactc      60

tcctgtgcag cctctggatt cactttcagt agctatggca tgtcttgggt tcgccagact     120

ccagacaaga ggctggagtg ggtcgcaacc attagtaatg gtggtagtta cacctactat     180

ccagacagtg tgaaggggcg attcaccatc tccagagaca atgccaagaa caccctgtac     240

ctgcaaatga gcagtctgaa gtctgaggac acagccatgt attactgtgc aagacaatta     300

cgacgggacg gttggtactt cgatgtctgg ggcacaggga ccacggtcac cgtctcctca     360


<210> SEQ ID NO 589
<211> LENGTH: 324
<212> TYPE: DNA
```

<213> ORGANISM: Artificial Sequence
<220> FEATURE:
<223> OTHER INFORMATION: ACI-8033-22E5-Ab1 917.22E5C5F7 VL

<400> SEQUENCE: 589
gaaattgtgc tcacccagtc tccagcactc atggctgcat ctccagggga gaaggtcacc 60
atcacctgca gtgtcagctc aagtataagt tccagcaagt tgcactggta ccagcagaag 120
tcagaaacct cccccaaact ctggatttat ggcacatcca acctggcttc tggagtccct 180
gttcgcttca gtggcagtgg atctgggacc tcttattctc tcacaatcag cagcatggag 240
gctgaagatg ctgccactta ttactgtcaa cagtggagta gttacccact cacgttcggt 300
gctgggacca agctggagct gaaa 324

<210> SEQ ID NO 590
<211> LENGTH: 115
<212> TYPE: PRT
<213> ORGANISM: Artificial Sequence
<220> FEATURE:
<223> OTHER INFORMATION: ACI-8033-27D8-Ab1 917.27D8E1H10E10 VH

<400> SEQUENCE: 590

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Ser Asn Asn Phe Ala Thr Tyr Tyr Ala Asp
50 55 60

Ser Val Lys Asp Arg Phe Thr Ile Ser Arg Asp Glu Ser Glu Ser Met
65 70 75 80

Leu Tyr Leu Gln Met Asn Asn Leu Lys Ala Glu Asp Thr Ala Met Tyr
85 90 95

Tyr Cys Val Arg Ser Phe Asp Tyr Trp Gly Gln Gly Thr Thr Leu Thr
100 105 110

Val Ser Ser
115

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598
<211> LENGTH: 345
<212> TYPE: DNA
<213> ORGANISM: Artificial Sequence
<220> FEATURE:
<223> OTHER INFORMATION: ACI-8033-27D8-Ab1 917.27D8E1H10E10 VH

<400> SEQUENCE: 598
gaggtgcagc ttgttgagtc tggtggagga ttggtgcagc ctaaagggtc attgaaactc 60
tcatgtgcag cctctggatt caccttcaat acctacgcca tgaactgggt ccgccaggct 120
ccaggaaagg gtttggaatg ggttgctcgc ataagaagta aaagtaataa ttttgcaaca 180
tattatgccg attcagtgaa agacagattc accatctcca gagatgaatc agaaagcatg 240
ctctatctgc aaatgaacaa cttgaaagct gaggacacag ccatgtatta ctgtgtgagg 300
tcctttgact actggggcca aggcaccact ctcacagtct cctca 345

<210> SEQ ID NO 599

<400> SEQUENCE: 599

000

<210> SEQ ID NO 600
<211> LENGTH: 116
<212> TYPE: PRT
<213> ORGANISM: Artificial Sequence
<220> FEATURE:
<223> OTHER INFORMATION: ACI-8033-21C8-Ab1 917.21C8E4C8 VH

<400> SEQUENCE: 600

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Trp Ile Thr Trp Val Arg Gln Arg Pro Gly Gln Gly Leu Asp Trp Ile
35 40 45

Gly Asp Ile Tyr Pro Gly Gly Gly Val Thr Asn Tyr Asn Glu Lys Phe
50 55 60

Lys Thr Lys Ala Thr Leu Thr Val Asp Thr Ser Ser Ser Thr Ala Tyr
65 70 75 80

Met His Leu Ser Ser Leu Thr Ser Glu Asp Ser Ala Val Tyr Phe Cys
85 90 95

```
Ala Thr Ala Gln Thr Thr Phe Ala Tyr Trp Gly Gln Gly Thr Leu Val
            100                 105                 110

Thr Val Ser Ala
        115


<210> SEQ ID NO 601

<400> SEQUENCE: 601

000


<210> SEQ ID NO 602

<400> SEQUENCE: 602

000


<210> SEQ ID NO 603

<400> SEQUENCE: 603

000


<210> SEQ ID NO 604

<400> SEQUENCE: 604

000


<210> SEQ ID NO 605

<400> SEQUENCE: 605

000


<210> SEQ ID NO 606

<400> SEQUENCE: 606

000


<210> SEQ ID NO 607

<400> SEQUENCE: 607

000


<210> SEQ ID NO 608
<211> LENGTH: 348
<212> TYPE: DNA
<213> ORGANISM: Artificial Sequence
<220> FEATURE:
<223> OTHER INFORMATION: ACI-8033-21C8-Ab1 917.21C8E4C8 VH

<400> SEQUENCE: 608

caggtccaac tccagcagcc tggggctgag cttgtgaagc ctggggcttc agtgaagatg      60

tcctgcaagg cttctggcta caccttcacc agctactgga taacctgggt gaggcagagg     120

cctggacaag gccttgactg gattggagat atttatcctg gtggaggtgt tactaactac     180

aatgagaagt tcaagaccaa ggccacactg actgtagaca catcctccag cacagcctac     240

atgcacctca gcagcctgac atctgaggac tctgcggtct atttctgtgc gacagctcag     300

actacgtttg cttactgggg ccaagggact ctggtcactg tctctgca                  348


<210> SEQ ID NO 609
```

<211> LENGTH: 336
<212> TYPE: DNA
<213> ORGANISM: Artificial Sequence
<220> FEATURE:
<223> OTHER INFORMATION: ACI-8033-21C8-Ab1 917.21C8E4C8 VL

<400> SEQUENCE: 609
gatgttttga tgacccaaac tccactctcc ctgcctgtca gtcttggaga tcaagcctcc 60
atctcttgca gatctagtca gaacattgta cataataatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttcct 300
cggacgttcg gtggaggcac caagctggaa atcaaa 336

<210> SEQ ID NO 610
<211> LENGTH: 121
<212> TYPE: PRT
<213> ORGANISM: Artificial Sequence
<220> FEATURE:
<223> OTHER INFORMATION: hACI-7067-1101C8-Ab2_H1 VH

<400> SEQUENCE: 610

Glu Val Gln Leu Val Glu Ser Gly Gly Gly Leu Val Gln Pro Gly Gly
1 5 10 15

Ser Leu Lys Leu Ser Cys Ala Ala Ser Gly Phe Ser Phe Asn Ile Tyr
20 25 30

Ala Met Asn Trp Val Arg Gln Ala Pro Gly Lys Gly Leu Glu Trp Val
35 40 45

Ala Arg Ile Arg Ser Lys Ser Asn Ala Tyr Ala Thr Tyr Tyr Ala Ala
50 55 60

Ser Val Lys Gly Arg Phe Thr Ile Ser Arg Asp Asp Ser Lys Asn Thr
65 70 75 80

Leu Tyr Leu Gln Met Asn Asn Leu Lys Thr Glu Asp Thr Ala Val Tyr
85 90 95

Tyr Cys Val Arg Val Gly Leu Arg Phe Tyr Ala Met Asp Tyr Trp Gly
100 105 110

Gln Gly Thr Leu Val Thr Val Ser Ser
115 120

<210> SEQ ID NO 611

<400> SEQUENCE: 611

000

<210> SEQ ID NO 612
<211> LENGTH: 19
<212> TYPE: PRT
<213> ORGANISM: Artificial Sequence
<220> FEATURE:
<223> OTHER INFORMATION: hACI-7067-1101C8-Ab2_H1 VH CDR2

<400> SEQUENCE: 612

Arg Ile Arg Ser Lys Ser Asn Ala Tyr Ala Thr Tyr Tyr Ala Ala Ser
1 5 10 15

Val Lys Gly

<210> SEQ ID NO 613

<400> SEQUENCE: 613

000

<210> SEQ ID NO 614
<211> LENGTH: 112
<212> TYPE: PRT
<213> ORGANISM: Artificial Sequence
<220> FEATURE:
<223> OTHER INFORMATION: hACI-7067-1101C8-Ab2_L1 VL

<400> SEQUENCE: 614

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Ala Asn Thr Tyr Leu Glu Trp Tyr Gln Gln Arg Pro Gly Gln Ser
35 40 45

Pro Arg Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser Gln Gly Pro Leu Thr Phe Gly Gln Gly Thr Lys Leu Glu Ile Lys
100 105 110

<210> SEQ ID NO 615
<211> LENGTH: 16
<212> TYPE: PRT
<213> ORGANISM: Artificial Sequence
<220> FEATURE:
<223> OTHER INFORMATION: hACI-7067-1101C8-Ab2_L1 VL CDR1

<400> SEQUENCE: 615

Arg Ser Ser Gln Ser Ile Val His Ser Asn Ala Asn Thr Tyr Leu Glu
1 5 10 15

<210> SEQ ID NO 616

<400> SEQUENCE: 616

000

<210> SEQ ID NO 617

<400> SEQUENCE: 617

000

<210> SEQ ID NO 618
<211> LENGTH: 363
<212> TYPE: DNA
<213> ORGANISM: Artificial Sequence
<220> FEATURE:
<223> OTHER INFORMATION: hACI-7067-1101C8-Ab2_H1 VH

<400> SEQUENCE: 618
gaggtgcagc tggtggagag cggaggagga ctggtccagc ccggcggatc tctgaaactg 60
agctgcgccg ccagcggctt cagcttcaac atctacgcca tgaactgggt gaggcaagcc 120
cccggcaaag gactggagtg ggtggctaga atcagaagca agagcaacgc ctacgccacc 180
tactacgccg cctccgtgaa gggaagattc accatctcta gagacgacag caagaacaca 240
ctgtatctgc agatgaacaa tctgaagacc gaggacaccg ccgtgtacta ctgcgtgaga 300
gtgggactga ggttctacgc catggactac tggggccaag gcacactggt gacagtgagc 360
tcc 363

<210> SEQ ID NO 619
<211> LENGTH: 336
<212> TYPE: DNA
<213> ORGANISM: Artificial Sequence
<220> FEATURE:
<223> OTHER INFORMATION: hACI-7067-1101C8-Ab2_L1 VL

<400> SEQUENCE: 619
gacgtggtga tgacccagag ccctctgtct ctgcccgtga cactgggaca acccgcctcc 60
atcagctgca gatccagcca gtccatcgtg cacagcaacg ccaacaccta tctggagtgg 120
taccagcaga gacccggcca gagccctagg ctgctgatct acaaggtgtc caatagattc 180
agcggcgtgc ccgacagatt cagcggaagc ggcagcggca cagacttcac actgaagatc 240
agcagagtgg aggccgagga cctcggcgtg tactattgct ttcaaggcag ccaaggccct 300
ctgacctttg gacaaggcac caagctggag atcaag 336

<210> SEQ ID NO 620
<211> LENGTH: 121
<212> TYPE: PRT
<213> ORGANISM: Artificial Sequence
<220> FEATURE:
<223> OTHER INFORMATION: hACI-7067-1101C8-Ab2_H2 VH

<400> SEQUENCE: 620

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Val Arg Val Gly Leu Arg Phe Tyr Ala Met Asp Tyr Trp Gly
            100                 105                 110

Gln Gly Thr Leu Val Thr Val Ser Ser
        115                 120

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624
<211> LENGTH: 112
<212> TYPE: PRT
<213> ORGANISM: Artificial Sequence
<220> FEATURE:
<223> OTHER INFORMATION: hACI-7067-1101C8-Ab2_L2 VL

<400> SEQUENCE: 624

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Ala Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Gln Gly Pro Leu Thr Phe Gly Gln Gly Thr Lys Leu Glu Ile Lys
            100                 105                 110
```

<210> SEQ ID NO 625
<211> LENGTH: 16
<212> TYPE: PRT
<213> ORGANISM: Artificial Sequence
<220> FEATURE:
<223> OTHER INFORMATION: hACI-7067-1101C8-Ab2_L2 VL CDR1

<400> SEQUENCE: 625

```
Arg Ser Ser Gln Ser Leu Val His Ser Asn Ala Asn Thr Tyr Leu Glu
1               5                   10                  15
```

<210> SEQ ID NO 626

<400> SEQUENCE: 626

000

<210> SEQ ID NO 627

<400> SEQUENCE: 627

000

<210> SEQ ID NO 628
<211> LENGTH: 363
<212> TYPE: DNA
<213> ORGANISM: Artificial Sequence
<220> FEATURE:
<223> OTHER INFORMATION: hACI-7067-1101C8-Ab2_H2 VH

<400> SEQUENCE: 628

```
gaggtgcagc tggtggagag cggaggagga ctggtccagc ccggcggatc tctgaaactg     60

agctgcgccg ccagcggctt cagcttcaac atctacgcca tgaactgggt gaggcaagcc    120

cccggcaaag gactggagtg ggtgggaaga atcagaagca agagcaacgc ctacgccacc    180
```

```
tactacgccg cctccgtgaa gggaagattc accatctcta gagacgacag caagaacaca    240

ctgtatctgc agatgaacaa tctgaagacc gaggacaccg ccgtgtacta ctgcgtgaga    300

gtgggactga ggttctacgc catggactac tggggccaag gcacactggt gacagtgagc    360

tcc                                                                  363
```

<210> SEQ ID NO 629
<211> LENGTH: 336
<212> TYPE: DNA
<213> ORGANISM: Artificial Sequence
<220> FEATURE:
<223> OTHER INFORMATION: hACI-7067-1101C8-Ab2_L2 VL

<400> SEQUENCE: 629

```
gacgtggtga tgacccagag ccctctgtct ctgcccgtga cactgggaca acccgcctcc     60

atcagctgca gatccagcca gtccctggtg cacagcaacg ccaacaccta tctggagtgg    120

taccagcaga gacccggcca gagccctagg ctgctgatct acaaggtgtc caatagattc    180

agcggcgtgc ccgacagatt cagcggaagc ggcagcggca cagacttcac actgaagatc    240

agcagagtgg aggccgagga cctcggcgtg tactattgct ttcaaggcag ccaaggccct    300

ctgacctttg gacaaggcac caagctggag atcaag                              336
```

<210> SEQ ID NO 630
<211> LENGTH: 121
<212> TYPE: PRT
<213> ORGANISM: Artificial Sequence
<220> FEATURE:
<223> OTHER INFORMATION: hACI-7067-1101C8-Ab2_H3 VH

<400> SEQUENCE: 630

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg Val Gly Leu Arg Phe Tyr Ala Met Asp Tyr Trp Gly
            100                 105                 110

Gln Gly Thr Leu Val Thr Val Ser Ser
        115                 120
```

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634
<211> LENGTH: 112
<212> TYPE: PRT
<213> ORGANISM: Artificial Sequence
<220> FEATURE:
<223> OTHER INFORMATION: hACI-7067-1101C8-Ab2_L3 VL

<400> SEQUENCE: 634

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Glu Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Gln Gly Pro Leu Thr Phe Gly Gln Gly Thr Lys Leu Glu Ile Lys
            100                 105                 110
```

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638
<211> LENGTH: 363
<212> TYPE: DNA
<213> ORGANISM: Artificial Sequence
<220> FEATURE:
<223> OTHER INFORMATION: hACI-7067-1101C8-Ab2_H3 VH

<400> SEQUENCE: 638

```
gaggtgcagc tggtggagag cggaggagga ctggtccagc ccggcggatc tctgaaactg      60

agctgcgccg ccagcggctt cagcttcaac atctacgcca tgaactgggt gaggcaagcc     120

cccggcaaag gactggagtg ggtgggaaga atcagaagca agagcaacgc ctacgccacc     180

tactacgccg cctccgtgaa gggaagattc accatctcta gagacgacag caagaacaca     240

gcttatctgc agatgaacaa tctgaagacc gaggacaccg ccgtgtacta ctgcgtgaga     300

gtgggactga ggttctacgc catggactac tggggccaag gcacactggt gacagtgagc     360
```

tcc 363

<210> SEQ ID NO 639
<211> LENGTH: 336
<212> TYPE: DNA
<213> ORGANISM: Artificial Sequence
<220> FEATURE:
<223> OTHER INFORMATION: hACI-7067-1101C8-Ab2_L3 VL

<400> SEQUENCE: 639
gacgtggtga tgacccagag ccctctgtct ctgcccgtga cactgggaca acccgcctcc 60
atcagctgca gatccagcca gtccatcgtg cacagcaacg ccaacaccta tctggagtgg 120
ttccagcaga gacccggcca gagccctagg ctgctgatct acaaggtgtc caatagattc 180
agcggcgtgc ccgacagatt cagcggaagc ggcagcggca cagacttcac actgaagatc 240
agcagagtgg aggccgagga cctcggcgtg tactattgct ttcaaggcag ccaaggccct 300
ctgacctttg gacaaggcac caagctggag atcaag 336

<210> SEQ ID NO 640
<211> LENGTH: 121
<212> TYPE: PRT
<213> ORGANISM: Artificial Sequence
<220> FEATURE:
<223> OTHER INFORMATION: hACI-7067-1101C8-Ab2_H4 VH

<400> SEQUENCE: 640

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Ile Tyr
20 25 30

Ala Met Asn Trp Val Arg Gln Ala Pro Gly Lys Gly Leu Glu Trp Val
35 40 45

Gly Arg Ile Arg Ser Lys Ser Asn Ala Tyr Ala Thr Tyr Tyr Ala Ala
50 55 60

Ser Val Lys Gly Arg Phe Thr Ile Ser Arg Asp Asp Ser Lys Asn Thr
65 70 75 80

Leu Tyr Leu Gln Met Asn Asn Leu Lys Thr Glu Asp Thr Ala Val Tyr
85 90 95

Tyr Cys Val Arg Val Gly Leu Arg Phe Tyr Ala Met Asp Tyr Trp Gly
100 105 110

Gln Gly Thr Leu Val Thr Val Ser Ser
115 120

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644
<211> LENGTH: 112
<212> TYPE: PRT
<213> ORGANISM: Artificial Sequence
<220> FEATURE:
<223> OTHER INFORMATION: hACI-7067-1101C8-Ab2_L4 VL

<400> SEQUENCE: 644

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asn Ala Asn Thr Tyr Leu Glu Trp Phe Gln Gln Arg Pro Gly Gln Ser
35 40 45

Pro Arg Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser Gln Gly Pro Leu Thr Phe Gly Gln Gly Thr Lys Leu Glu Ile Lys
100 105 110

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648
<211> LENGTH: 363
<212> TYPE: DNA
<213> ORGANISM: Artificial Sequence
<220> FEATURE:
<223> OTHER INFORMATION: hACI-7067-1101C8-Ab2_H4 VH

<400> SEQUENCE: 648
gaggtgcagc tggtggagag cggaggagga ctggtccagc ccggcggatc tctgaaactg 60
agctgcgccg ccagcggctt caccttcaac atctacgcca tgaactgggt gaggcaagcc 120
cccggcaaag gactggagtg ggtgggaaga atcagaagca agagcaacgc ctacgccacc 180
tactacgccg cctccgtgaa gggaagattc accatctcta gagacgacag caagaacaca 240
ctgtatctgc agatgaacaa tctgaagacc gaggacaccg ccgtgtacta ctgcgtgaga 300
gtgggactga ggttctacgc catggactac tggggccaag gcacactggt gacagtgagc 360
tcc 363

<210> SEQ ID NO 649

<211> LENGTH: 336
<212> TYPE: DNA
<213> ORGANISM: Artificial Sequence
<220> FEATURE:
<223> OTHER INFORMATION: hACI-7067-1101C8-Ab2_L4 VL

<400> SEQUENCE: 649
gatgtggtga tgacccagag ccctctgtct ctgcccgtga cactgggcca gcccgccagc 60
atcagctgca gatccagcca gtctctggtg cacagcaacg ccaacaccta tctggagtgg 120
ttccagcaga gacccggcca gtcccctagg ctgctgatct acaaggtctc caatagattc 180
agcggcgtgc ccgacagatt tagcggcagc ggaagcggca ccgactttac actgaagatc 240
agcagagtgg aggctgagga tctgggcgtg tactactgct ttcaaggcag ccaaggccct 300
ctgacctttg gccaaggcac caagctggag atcaag 336

<210> SEQ ID NO 650
<211> LENGTH: 121
<212> TYPE: PRT
<213> ORGANISM: Artificial Sequence
<220> FEATURE:
<223> OTHER INFORMATION: hACI-7067-1101C8-Ab2_H5

<400> SEQUENCE: 650

Glu Val Gln Leu Val Glu Ser Gly Gly Gly Leu Val Gln Pro Gly Gly
1 5 10 15

Ser Leu Lys Leu Ser Cys Ala Ala Ser Gly Phe Ser Phe Asn Ile Tyr
20 25 30

Ala Met Asn Trp Val Arg Gln Ala Pro Gly Lys Gly Leu Glu Trp Val
35 40 45

Gly Arg Ile Arg Ser Lys Ser Asn Ala Tyr Ala Thr Tyr Tyr Ala Ala
50 55 60

Ser Val Lys Gly Arg Phe Thr Ile Ser Arg Asp Asp Ser Lys Asn Thr
65 70 75 80

Leu Tyr Leu Gln Met Asn Asn Leu Lys Thr Glu Asp Thr Ala Val Tyr
85 90 95

Tyr Cys Thr Arg Val Gly Leu Arg Phe Tyr Ala Met Asp Tyr Trp Gly
100 105 110

Gln Gly Thr Leu Val Thr Val Ser Ser
115 120

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658
<211> LENGTH: 363
<212> TYPE: DNA
<213> ORGANISM: Artificial Sequence
<220> FEATURE:
<223> OTHER INFORMATION: hACI-7067-1101C8-Ab2_H5 VH

<400> SEQUENCE: 658
gaggtgcagc tggtggagag cggaggagga ctggtccagc ccggcggatc tctgaaactg 60
agctgcgccg ccagcggctt cagcttcaac atctacgcca tgaactgggt gaggcaagcc 120
cccggcaaag gactggagtg ggtgggaaga atcagaagca agagcaacgc ctacgccacc 180
tactacgccg cctccgtgaa gggaagattc accatctcta gagacgacag caagaacaca 240
ctgtatctgc agatgaacaa tctgaagacc gaggacaccg ccgtgtacta ctgcaccaga 300
gtgggactga ggttctacgc catggactac tggggccaag gcacactggt gacagtgagc 360
tcc 363

<210> SEQ ID NO 659

<400> SEQUENCE: 659

000

<210> SEQ ID NO 660
<211> LENGTH: 121
<212> TYPE: PRT
<213> ORGANISM: Artificial Sequence
<220> FEATURE:
<223> OTHER INFORMATION: hACI-7067-1101C8-Ab2_H6 VH

<400> SEQUENCE: 660

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

```
Leu Tyr Leu Gln Met Asn Asn Leu Lys Thr Glu Asp Thr Ala Val Tyr
                85                  90                  95

Tyr Cys Val Arg Val Gly Leu Arg Phe Tyr Ala Ser Asp Tyr Trp Gly
            100                 105                 110

Gln Gly Thr Leu Val Thr Val Ser Ser
        115                 120


<210> SEQ ID NO 661

<400> SEQUENCE: 661

000


<210> SEQ ID NO 662

<400> SEQUENCE: 662

000


<210> SEQ ID NO 663
<211> LENGTH: 10
<212> TYPE: PRT
<213> ORGANISM: Artificial Sequence
<220> FEATURE:
<223> OTHER INFORMATION: hACI-7067-1101C8-Ab2_H6 VH CDR3

<400> SEQUENCE: 663

Val Gly Leu Arg Phe Tyr Ala Ser Asp Tyr
1               5                   10


<210> SEQ ID NO 664

<400> SEQUENCE: 664

000


<210> SEQ ID NO 665

<400> SEQUENCE: 665

000


<210> SEQ ID NO 666

<400> SEQUENCE: 666

000


<210> SEQ ID NO 667

<400> SEQUENCE: 667

000


<210> SEQ ID NO 668
<211> LENGTH: 363
<212> TYPE: DNA
<213> ORGANISM: Artificial Sequence
<220> FEATURE:
<223> OTHER INFORMATION: hACI-7067-1101C8-Ab2_H6 VH

<400> SEQUENCE: 668

gaggtgcagc tggtggaaag cggcggcgga ctggtgcaac ccggcggatc tctgaagctg      60

agctgtgccg ccagcggctt cagcttcaac atctacgcca tgaactgggt gagacaagcc     120
```

```
cccggcaaag gactggaatg ggtggccaga attagaagca agtccaacgc ctacgccacc    180

tactacgccg ccagcgtgaa gggcagattc accatctcta gagacgacag caagaacaca    240

ctgtatctgc agatgaacaa tctgaagacc gaggacaccg ccgtgtacta ctgcgtgagg    300

gtgggactga gattctacgc cagcgactac tggggccaag gcacactggt gaccgtgtcc    360

agc                                                                  363
```

```
<210> SEQ ID NO 669

<400> SEQUENCE: 669

000


<210> SEQ ID NO 670
<211> LENGTH: 121
<212> TYPE: PRT
<213> ORGANISM: Artificial Sequence
<220> FEATURE:
<223> OTHER INFORMATION: hACI-7067-1101C8-Ab2_H7 VH

<400> SEQUENCE: 670

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Asn Leu Lys Thr Glu Asp Thr Ala Val Tyr
            85                  90                  95

Tyr Cys Val Arg Val Gly Leu Arg Phe Tyr Ala Thr Asp Tyr Trp Gly
            100                 105                 110

Gln Gly Thr Leu Val Thr Val Ser Ser
        115                 120


<210> SEQ ID NO 671

<400> SEQUENCE: 671

000


<210> SEQ ID NO 672

<400> SEQUENCE: 672

000


<210> SEQ ID NO 673
<211> LENGTH: 10
<212> TYPE: PRT
<213> ORGANISM: Artificial Sequence
<220> FEATURE:
<223> OTHER INFORMATION: hACI-7067-1101C8-Ab2_H7 VH CDR3

<400> SEQUENCE: 673

Val Gly Leu Arg Phe Tyr Ala Thr Asp Tyr
1               5                   10
```

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678
<211> LENGTH: 363
<212> TYPE: DNA
<213> ORGANISM: Artificial Sequence
<220> FEATURE:
<223> OTHER INFORMATION: hACI-7067-1101C8-Ab2_H7 VH

<400> SEQUENCE: 678
gaggtgcagc tggtggaaag cggcggcgga ctggtgcaac ccggcggatc tctgaagctg 60
agctgtgccg ccagcggctt cagcttcaac atctacgcca tgaactgggt gagacaagcc 120
cccggcaaag gactggaatg ggtggccaga attagaagca agtccaacgc ctacgccacc 180
tactacgccg ccagcgtgaa gggcagattc accatctcta gagacgacag caagaacaca 240
ctgtatctgc agatgaacaa tctgaagacc gaggacaccg ccgtgtacta ctgcgtgagg 300
gtgggactga gattctacgc caccgactac tggggccaag gcacactggt gaccgtgtcc 360
agc 363

<210> SEQ ID NO 679

<400> SEQUENCE: 679

000

<210> SEQ ID NO 680
<211> LENGTH: 121
<212> TYPE: PRT
<213> ORGANISM: Artificial Sequence
<220> FEATURE:
<223> OTHER INFORMATION: hACI-7067-1101C8-Ab2_H8 VH

<400> SEQUENCE: 680

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65 70 75 80

Leu Tyr Leu Gln Met Asn Asn Leu Lys Thr Glu Asp Thr Ala Val Tyr
85 90 95

Tyr Cys Thr Arg Val Gly Leu Arg Phe Tyr Ala Leu Asp Tyr Trp Gly
100 105 110

Gln Gly Thr Leu Val Thr Val Ser Ser
115 120

<210> SEQ ID NO 681

<400> SEQUENCE: 681

000

<210> SEQ ID NO 682

<400> SEQUENCE: 682

000

<210> SEQ ID NO 683
<211> LENGTH: 10
<212> TYPE: PRT
<213> ORGANISM: Artificial Sequence
<220> FEATURE:
<223> OTHER INFORMATION: hACI-7067-1101C8-Ab2_H8 VH CDR3

<400> SEQUENCE: 683

Val Gly Leu Arg Phe Tyr Ala Leu Asp Tyr
1 5 10

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688
<211> LENGTH: 363
<212> TYPE: DNA
<213> ORGANISM: Artificial Sequence
<220> FEATURE:
<223> OTHER INFORMATION: hACI-7067-1101C8-Ab2_H8 VH

<400> SEQUENCE: 688
gaggtgcagc tggtggaaag cggcggagga ctggtgcaac ccggcggatc tctgaagctg 60

```
agctgtgccg cctccggctt cagcttcaac atctacgcca tgaactgggt gaggcaagcc    120

cccggcaagg gactggagtg ggtgggcaga atcagaagca agagcaacgc ctacgccacc    180

tactacgccg ccagcgtgaa gggaagattc accatctcta gagacgacag caagaacaca    240

ctgtatctgc agatgaacaa tctgaagacc gaggacaccg ccgtgtacta ctgcacaaga    300

gtgggactga gattctacgc tctggactac tggggccaag gcacactggt gaccgtgagc    360

agc                                                                  363
```

<210> SEQ ID NO 689

<400> SEQUENCE: 689

000

<210> SEQ ID NO 690
<211> LENGTH: 121
<212> TYPE: PRT
<213> ORGANISM: Artificial Sequence
<220> FEATURE:
<223> OTHER INFORMATION: hACI-7067-1101C8-Ab2_H9 VH

<400> SEQUENCE: 690

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Thr Arg Val Gly Leu Arg Phe Tyr Ala Met Asp Tyr Trp Gly
            100                 105                 110

Gln Gly Thr Leu Val Thr Val Ser Ser
        115                 120
```

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698
<211> LENGTH: 363
<212> TYPE: DNA
<213> ORGANISM: Artificial Sequence
<220> FEATURE:
<223> OTHER INFORMATION: hACI-7067-1101C8-Ab2_H9 VH

<400> SEQUENCE: 698
gaggtgcagc tggtggaaag cggcggagga ctggtgcaac ccggcggatc tctgaagctg 60
agctgtgccg cctccggctt caccttcaac atctacgcca tgaactgggt gaggcaagcc 120
cccggcaagg gactggagtg ggtgggcaga atcagaagca agagcaacgc ctacgccacc 180
tactacgccg ccagcgtgaa gggaagattc accatctcta gagacgacag caagaacaca 240
ctgtatctgc agatgaacaa tctgaagacc gaggacaccg ccgtgtacta ctgcacaaga 300
gtgggactga gattctacgc tatggactac tggggccaag gcacactggt gaccgtgagc 360
agc 363

<210> SEQ ID NO 699

<400> SEQUENCE: 699

000

<210> SEQ ID NO 700
<211> LENGTH: 121
<212> TYPE: PRT
<213> ORGANISM: Artificial Sequence
<220> FEATURE:
<223> OTHER INFORMATION: hACI-7067-1101C8-Ab2_H10 VH

<400> SEQUENCE: 700

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Ile Tyr
20 25 30

Ala Met Asn Trp Val Arg Gln Ala Pro Gly Lys Gly Leu Glu Trp Val
35 40 45

Gly Arg Ile Arg Ser Lys Ser Asn Ala Tyr Ala Thr Tyr Tyr Ala Ala
50 55 60

Ser Val Lys Gly Arg Phe Thr Ile Ser Arg Asp Asp Ser Lys Asn Thr
65 70 75 80

Leu Tyr Leu Gln Met Asn Asn Leu Lys Thr Glu Asp Thr Ala Val Tyr
85 90 95

Tyr Cys Thr Arg Val Gly Leu Arg Phe Tyr Ala Leu Asp Tyr Trp Gly
100 105 110

Gln Gly Thr Leu Val Thr Val Ser Ser
115 120

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708
<211> LENGTH: 363
<212> TYPE: DNA
<213> ORGANISM: Artificial Sequence
<220> FEATURE:
<223> OTHER INFORMATION: hACI-7067-1101C8-Ab2_H10 VH

<400> SEQUENCE: 708
gaggtgcagc tggtggaaag cggcggagga ctggtgcaac ccggcggatc tctgaagctg 60
agctgtgccg cctccggctt caccttcaac atctacgcca tgaactgggt gaggcaagcc 120
cccggcaagg gactggagtg ggtgggcaga atcagaagca agagcaacgc ctacgccacc 180
tactacgccg ccagcgtgaa gggaagattc accatctcta gagacgacag caagaacaca 240
ctgtatctgc agatgaacaa tctgaagacc gaggacaccg ccgtgtacta ctgcacaaga 300

```
gtgggactga gattctacgc tctggactac tggggccaag gcacactggt gaccgtgagc    360

agc                                                                   363

<210> SEQ ID NO 709

<400> SEQUENCE: 709

000


<210> SEQ ID NO 710
<211> LENGTH: 121
<212> TYPE: PRT
<213> ORGANISM: Artificial Sequence
<220> FEATURE:
<223> OTHER INFORMATION: hACI-7067-1101C8-Ab2_H11 VH

<400> SEQUENCE: 710

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Thr Arg Val Gly Leu Arg Phe Tyr Ala Met Asp Tyr Trp Gly
            100                 105                 110

Gln Gly Thr Leu Val Thr Val Ser Ser
        115                 120


<210> SEQ ID NO 711

<400> SEQUENCE: 711

000


<210> SEQ ID NO 712

<400> SEQUENCE: 712

000


<210> SEQ ID NO 713

<400> SEQUENCE: 713

000


<210> SEQ ID NO 714

<400> SEQUENCE: 714

000


<210> SEQ ID NO 715

<400> SEQUENCE: 715

000
```

<210> SEQ ID NO 716

<400> SEQUENCE: 716

000

<210> SEQ ID NO 717

<400> SEQUENCE: 717

000

<210> SEQ ID NO 718
<211> LENGTH: 363
<212> TYPE: DNA
<213> ORGANISM: Artificial Sequence
<220> FEATURE:
<223> OTHER INFORMATION: hACI-7067-1101C8-Ab2_H11 VH

<400> SEQUENCE: 718
gaggtgcagc tggtggagag cggaggcgga ctggtgcaac ccggcggatc tctgaaactg 60
agctgtgccg ccagcggctt caccttcaac atctacgcca tgaactgggt gagacaagcc 120
cccggcaagg gactggagtg ggtgggcaga attagaagca agagcaacgc ctacgccacc 180
tactacgccg ccagcgtcaa gggaagattc accatctcta gagacgacag caagaacacc 240
gcctatctgc agatgaacaa tctgaagacc gaggacaccg ccgtgtacta ctgcaccaga 300
gtgggactga ggttctacgc catggactac tggggccaag gcacactggt gaccgtgagc 360
tcc 363

<210> SEQ ID NO 719

<400> SEQUENCE: 719

000

<210> SEQ ID NO 720
<211> LENGTH: 121
<212> TYPE: PRT
<213> ORGANISM: Artificial Sequence
<220> FEATURE:
<223> OTHER INFORMATION: hACI-7067-1101C8-Ab2_H12 VH

<400> SEQUENCE: 720

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Ile Tyr
20 25 30

Ala Met Asn Trp Val Arg Gln Ala Pro Gly Lys Gly Leu Glu Trp Val
35 40 45

Gly Arg Ile Arg Ser Lys Ser Asn Ala Tyr Ala Thr Tyr Tyr Ala Ala
50 55 60

Ser Val Lys Gly Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Thr Arg Val Gly Leu Arg Phe Tyr Ala Leu Asp Tyr Trp Gly
100 105 110

Gln Gly Thr Leu Val Thr Val Ser Ser
115 120

-continued

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728
<211> LENGTH: 363
<212> TYPE: DNA
<213> ORGANISM: Artificial Sequence
<220> FEATURE:
<223> OTHER INFORMATION: hACI-7067-1101C8-Ab2_H12 VH

<400> SEQUENCE: 728
gaggtgcagc tggtggaaag cggcggagga ctggtgcaac ccggcggatc tctgaagctg 60
agctgtgccg cctccggctt caccttcaac atctacgcca tgaactgggt gaggcaagcc 120
cccggcaagg gactggagtg ggtgggcaga atcagaagca agagcaacgc ctacgccacc 180
tactacgccg ccagcgtgaa gggaagattc accatctcta gagacgacag caagaacaca 240
gcttatctgc agatgaacaa tctgaagacc gaggacaccg ccgtgtacta ctgcacaaga 300
gtgggactga gattctacgc tctggactac tggggccaag gcacactggt gaccgtgagc 360
agc 363

MOLECULES FOR THERAPY AND DIAGNOSIS

INCORPORATION BY REFERENCE OF SEQUENCE LISTING PROVIDED AS A TEXT FILE

A Sequence Listing is provided herewith in a text file, BOULT-037_SEQ_LIST_ST25, created on May 16, 2022 and having a size of 298,415 bytes. The contents of the text file are incorporated herein by reference in its entirety.

FIELD OF THE INVENTION

The present invention relates to novel molecules that can be employed for the prevention, alleviation, treatment and/or diagnosis of diseases, disorders and abnormalities associated with alpha-synuclein (a-synuclein, A-synuclein, aSynuclein, A-syn, a-syn, aSyn, a-syn) aggregates including, but not limited to, Lewy bodies and/or Lewy neurites, such as Parkinson's disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease. The invention relates to alpha-synuclein binding molecules, in particular to alpha-synuclein antibodies or an antigen-binding fragment thereof or a derivative thereof and uses thereof. The present molecules can also be used for determining a predisposition to such a disorder, disease or abnormality, monitoring residual disorder, disease or abnormality, or predicting the responsiveness of a patient who is suffering from such a disorder, disease or abnormality to the treatment with a certain medicament.

BACKGROUND OF THE INVENTION

Many degenerative diseases are associated with extracellular or intracellular deposits of amyloid or amyloid-like proteins that contribute to the pathogenesis as well as to the progression of the disease. The best characterized amyloid protein that forms extracellular aggregates is amyloid beta (Aβ).

Amyloid-like proteins that form mainly intracellular aggregates, include, but are not limited to alpha-synuclein, tau, and huntingtin (htt). Diseases involving alpha-synuclein aggregates are generally listed as synucleinopathies (or a-synucleinopathies) and these include, but are not limited to, Parkinson's disease (PD). Synucleinopathies include Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), diffuse Lewy body disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, and Down syndrome. Synucleinopathies with neuronal and glial aggregates of alpha-synuclein include but are not limited to multiple system atrophy (Shy-Drager syndrome, striatonigral degeneration and olivopontocerebellar atrophy). Other diseases that may have alpha-synuclein-immunoreactive lesions include traumatic brain injury, chronic traumatic encephalopathy, dementia puglistica, tauopathies (Pick's disease, frontotemporal dementia, progressive supranuclear palsy, corticobasal degeneration and Niemann-Pick type C1 disease, frontotemporal dementia with Parkinsonism linked to chromosome 17), motor neuron disease, Huntington's disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Creutzfeldt-Jakob disease, ataxia telangiectatica, Meige's syndrome, subacute sclerosing panencephalitis, Gerstmann-Straussler-Scheinker disease, inclusion-body myositis, Gaucher disease, Krabbe disease as well as other lysosomal storage disorders (including Kufor-Rakeb syndrome and Sanfilippo syndrome) and rapid eye movement (REM) sleep behavior disorder (Jellinger, Mov Disord 2003, 18 Suppl. 6, S2-12; Galvin et al., JAMA Neurology 2001, 58 (2), 186-190; Kovari et al., Acta Neuropathol. 2007, 114 (3), 295-8; Saito et al., J Neuropathol Exp Neurol. 2004, 63 (4), 323-328; McKee et al., Brain, 2013, 136 (Pt 1), 43-64; Puschmann et al., Parkinsonism Relat Disord 2012, 18S1, S24-S27; Usenovic et al., J Neurosci. 2012, 32 (12), 4240-4246; Winder-Rhodes et al., Mov Disord. 2012, 27 (2), 312-315; Ferman et al., J Int Neuropsychol Soc. 2002, 8 (7), 907-914; Smith et al., J Pathol. 2014; 232:509-521, Lippa et al., Ann Neurol. 1999 March;45 (3): 353-7; Schmitz et al., Mol Neurobiol. 2018 Aug. 22; Charles et al., Neurosci Lett. 2000 Jul. 28;289 (1): 29-32; Wilhelmsen et al., Arch Neurol. 2004 March;61 (3): 398-406; Yamaguchi et al., J Neuropathol Exp Neurol. 2004, 80th annual meeting, vol. 63; Askanas et al., J Neuropathol Exp Neurol. 2000 July;59 (7): 592-8).

Alpha-synuclein is a 140 amino acid long, cytosolic protein abundantly and predominantly expressed in the CNS and localized in pre-synaptic terminals (Burre J., J Parkinsons Dis. 2015;5 (4): 699-713). Alpha-synuclein is a natively unfolded protein but adopts secondary structure of mostly helical nature upon association with lipid vesicles or membranes (Iwai et al., Biochemistry 1995, 34 (32), 10139-10145). The physiological function of alpha-synuclein still remains elusive. Because of the association of alpha-synuclein to synaptic vesicles and its presynaptic localization it is suggested that it regulates synaptic activity and plasticity, neurotransmitter release, dopamine production and metabolism, vesicle trafficking, synaptic vesicle pool maintenance and chaperone-like activity (Cabin et al., J Neurosci. 2002; 22:8797-8807; Chandra et al., Cell. 2005; 123:383-396).

The sequence of alpha-synuclein can be divided into three main domains: 1) the N-terminal region comprising of residues 1-60, which contains 11-mer amphipathic imperfect repeat residues with highly conserved hexamer (KTKEGV). This region has been implicated in regulating alpha-synuclein association to lipid membranes and its internalization; 2) the hydrophobic Non-Amyloid beta Component (NAC) domain spanning residues 61-95; which is essential for alpha-synuclein fibrillization; and 3) the C-terminal region spanning residues 96-140 which is highly acidic and proline-rich, has no distinct structural propensity.

Alpha-synuclein has been shown to undergo several post translational modifications, including truncations, phosphorylation, ubiquitination, sumoylation, oxidation, nitration, acetylation, glycation, glycosylation, and/or transglutaminase covalent cross linking (Fujiwara et al., Nat Cell Biol 2002, 4 (2), 160-164; Hasegawa et al., J Biol Chem 2002, 277 (50), 49071-49076; Li et al., Proc Natl Acad Sci USA 2005, 102 (6), 2162-2167; Oueslati et al., Prog Brain Res 2010, 183, 115-145; Schmid et al., J Biol Chem 2009, 284 (19), 13128-13142; Dorval et al., J Biol Chem. 2006, 281 (15): 9919-24; Ruzafa et al., PlosOne 2017 12 (5): e0178576; Ischiropoulos et al., Ann N Y Acad Sci. 2003, 991, 93-100; Munch et al., J Chem Neuroanat. 2000; 20:253-257; Marotta et al., Chembiochem. 2012; 13:2665-2670). The majority of these modifications involve residues within the C-terminal region.

Several phosphorylation sites have been detected in the carboxyl-terminal region on Tyr-125,-133, and -136, and on Ser-129 (Negro et al., FASEB J 2002, 16 (2), 210-212). Extensive and selective phosphorylation of alpha-synuclein at Ser-129 is evident in synucleinopathy lesions, including Lewy bodies (Fujiwara et al., Nat Cell Biol 2002, 4 (2); 160-164). Other post-translational modifications in the carboxyl-terminal, including glycosylation on Ser-129 (McLean et al., Neurosci Lett 2002, 323 (3), 219-223) and nitration on Tyr-125,-133, and-136 (Takahashi et al., Brain Res 2002, 938 (1-2), 73-80), may affect aggregation of alpha-synuclein. Truncation of the carboxyl-terminal region by proteolysis has been reported to play a role in alpha-synuclein fibrillogenesis in various neurodegenerative diseases (Rochet et al., Biochemistry 2000, 39 (35), 10619-10626). Full-length as well as partially truncated and insoluble aggregates of alpha-synuclein have been detected in highly purified Lewy bodies (Crowther et al., FEBS Lett 1998, 436 (3), 309-312).

Abnormal protein aggregation is a common feature in aging brain and in several neurodegenerative diseases, even though a clear role in the disease process remains to be defined. In in vitro models, alpha-synuclein readily assembles into filaments resembling those isolated from brain of patients with Lewy Body dementia and familial PD (Crowther et al., FEBS Lett 1998, 436 (3), 309-312). Alpha-synuclein and its mutated forms (e.g. A53T and A30P) have a random coil conformation and do not form significant secondary structures in aqueous solution at low concentrations; however, at higher concentrations they are prone to self-aggregate, producing amyloid fibrils (Wood et al., J Biol Chem 1999, 274 (28), 19509-19512). Several differences in the aggregation behavior of the PD-linked mutants and the wild-type protein have been documented. Monomeric alpha-synuclein aggregates in vitro form stable fibrils via a metastable oligomeric (i.e., protofibril) state (Volles et al., Biochemistry 2002, 41 (14), 4595-4602).

Parkinson's disease (PD) is the most common neurodegenerative motor disorder. PD is mainly an idiopathic disease, although in at least 5% of the PD patients the pathology is linked to mutations in one or several specific genes. Several point mutations have been described in the alpha-synuclein gene (A30P, E46K, H50Q, G51D, A53T) which cause familial PD with autosomal dominant inheritance. Furthermore, duplications and triplications of the alpha-synuclein gene have been described in patients that developed PD underlining the role of alpha-synuclein in PD pathogenesis (Lesage et al., Hum. Mol. Genet., 2009, 18, R48-59). The pathogenesis of PD remains elusive, however, growing evidence suggests a role for the pathogenic folding of the alpha-synuclein protein that leads to the formation of amyloid-like fibrils. Indeed, the hallmarks of PD are the presence of intracellular alpha-synuclein aggregate structures called Lewy Bodies in the nigral neurons, as well as the death of dopaminergic neurons in the substantia nigra and elsewhere. Alpha-synuclein is a natively unfolded presynaptic protein that can misfold and aggregate into larger oligomeric and fibrillar forms which are linked to the pathogenesis of PD. Studies have implicated small soluble oligomeric and protofibrillar forms of alpha-synuclein as the most neurotoxic species (Lashuel et al., J. Mol. Biol., 2002, 322, 1089-102), however the precise role of alpha-synuclein in the neuronal cell toxicity remains to be clarified (review: Cookson, Annu. Rev. Biochem., 2005, 74, 29-52).

Recent evidence from cellular and animal models suggests that pathological and/or aggregated alpha-synuclein can spread from one neuron to another. Once inside the new cell alpha-synuclein aggregates act as seeds, recruiting endogenous alpha-synuclein and advancing protein aggregation (Luk et al., Science. 2012, 338 (6109): 949-5; Tran et al., Cell Rep. 2014, 7 (6): 2054-65). Moreover, the transynaptic spreading of pathological and/or aggregated alpha-synuclein could explain the progressive advancing of Lewy pathology through defined anatomical connected brain areas in PD that was first described by Braak and colleagues (Braak et al., Neurobiol. Aging. 2003; 24:197-211).

Consequently, the cell-to-cell spreading of pathological and/or aggregated alpha-synuclein renders immunotherapy as a compelling target for new therapeutic approaches aiming to alleviate, treat, retard or halt the progression of PD and other synucleinopathies. Antibodies described herein inhibit and/or delay seeded and/or spontaneous alpha-synuclein aggregation, and this functional feature would allow them to bind to alpha-synuclein seeds in the extracellular space to either neutralize the seeds and consequently delay or inhibit the propagation of alpha-synuclein aggregates or facilitate the clearance of these spreading species. The development of such therapies for PD and other synucleinopathies would addresses an unmet medical need since currently only symptomatic treatments are available.

The diagnosis of Parkinson's disease is largely clinical and depends on the presence of a specific set of symptoms and signs (the initial core feature being bradykinesia, rigidity, rest tremor and postural instability), a slowly progressive course, and a response to drug treatment. The final confirmation of the diagnosis is made by post-mortem neuropathological analysis. Strategies are being developed to apply recent advances of the cause of Parkinson's disease to the development of biochemical biomarkers as well as imaging biomarkers (Schapira, Curr Opin Neurol 2013; 26 (4): 395-400). Such biomarkers that have been investigated in different body fluids (cerebrospinal fluid (CSF), plasma, saliva) include alpha-synuclein levels but also DJ-1, Tau and Abeta, as well as neurofilaments proteins, interleukins, osteopontin and hypocrontin (Schapira, Curr Opin Neurol 2013; 26 (4): 395-400), but so far none of these biomarkers alone or in combination can be used as a determinant diagnostic test. Antibodies for diagnostic application that selectively recognize and bind to certain pathological structures of alpha-synuclein would have the potential to be used as biomarkers with high sensitivity and specificity. To our knowledge no approved biomarker for monitoring pathological alpha-synuclein levels is currently on the market or available for clinical trials despite a crucial needs for Parkinson's disease research and drug development (Eberling et al., J Parkinsons Dis. 2013; 3 (4): 565-7).

PRIOR ART

WO2017/207739 provides antibodies that specifically bind human alpha-synuclein with a high affinity and reduces alpha-synuclein spreading in vivo.

SUMMARY OF THE INVENTION

It is an object of the present invention to provide alpha-synuclein binding molecules that can be employed to treat, alleviate and/or prevent a disease, disorder or abnormality associated with alpha-synuclein aggregates, such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In another aspect, it is an object of the present invention to provide molecules that can be employed to diagnose, monitor disease progression of, and/or monitor drug activity against, a disease, disorder or abnormality associated with alpha-synuclein aggregates including, but not limited to, Lewy bodies, Lewy neurites and/or glial cytoplasmic inclusions, such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

The invention generally relates to an alpha-synuclein binding molecule, which inhibits and/or delays seeded and/or spontaneous alpha-synuclein aggregation.

In one embodiment, the invention relates to an alpha-synuclein binding molecule, which (i) inhibits and/or delays seeded and/or spontaneous alpha-synuclein aggregation; and (ii) is capable of recognizing and binding to pathological and/or aggregated alpha-synuclein, particularly human alpha-synuclein, in vitro and/or in vivo.

Accordingly, the invention relates in its broadest aspect to binding molecules, in particular antibodies or antigen-binding fragments thereof, which bind alpha-synuclein. In a preferred embodiment of the invention, the binding molecules, in particular antibodies or antigen-binding fragments thereof, inhibit and/or delay the aggregation of seeded and/or spontaneous alpha-synuclein aggregation and are capable of recognizing and binding to pathological and/or aggregated alpha-synuclein, particularly human alpha-synuclein, in vitro and/or in vivo. Alpha-synuclein is a soluble protein that has the propensity to spontaneously aggregate and form soluble oligomers or soluble/insoluble protofibrils or mature fibrils or detergent-insoluble aggregates under certain conditions. Seeded alpha-synuclein aggregation is the aggregation accelerated by pathological alpha-synuclein, so called "seeds".

The alpha-synuclein binding molecules of the invention, in particular antibodies or antigen-binding fragments thereof, block cell-to-cell spreading and/or delay and/or inhibit the aggregation of alpha-synuclein protein or fragments thereof. Thus, an alpha-synuclein binding molecule within the present invention inhibits and/or delays seeded and/or spontaneous alpha-synuclein aggregation; and is capable of recognizing and binding to pathological and/or aggregated alpha-synuclein, particularly human alpha-synuclein, in vitro and in vivo. An alpha-synuclein binding molecule within the present invention inhibits and/or delays seeded and/or spontaneous alpha-synuclein aggregation; and is capable of recognizing and binding to pathological and/or aggregated alpha-synuclein, particularly human alpha-synuclein, in vitro or in vivo.

It is preferred within the invention that the alpha-synuclein binding molecule, in particular the antibody or antigen-binding fragment thereof, additionally has one or more, preferably two or more, more preferably 3 or more, more preferably 4 or more, even more preferably all of the functional features (i) to (vi):

(i) reduces the pathological alpha-synuclein levels in vivo; and/or (ii) reduces the phosphorylated alpha-synuclein levels in vivo; and/or (iii) reduces and/or delays the aggregation and/or seeding of pathological alpha-synuclein in vivo; and/or (iv) demonstrates a recovery in neuronal loss in vivo; and/or (v) decreases pathological alpha-synuclein spreading in vivo; and/or (vi) reduces and/or delays the cellular uptake of pathological and/or aggregated alpha-synuclein in vivo.

It is preferred within the invention that the alpha-synuclein binding molecule, in particular the antibody or antigen-binding fragment thereof, additionally has one or more, preferably two or more, more preferably 3 or more, more preferably 4 or more, even more preferably all of the functional features (i) to (vi):

(i) reduces the pathological alpha-synuclein levels in vitro; and/or (ii) reduces the phosphorylated alpha-synuclein levels in vitro; and/or (iii) reduces and/or delays the aggregation and/or seeding of pathological alpha-synuclein in vitro; and/or (iv) demonstrates a recovery in neuronal loss in vitro; and/or (v) decreases pathological alpha-synuclein spreading in vitro; and/or (vi) reduces and/or delays the cellular uptake of pathological and/or aggregated alpha-synuclein in vitro.

In particular alpha-synuclein binding molecules of the invention, in particular antibodies or antigen-binding fragments thereof, inhibit and/or delay aggregation of alpha-synuclein protein or fragments thereof.

In one embodiment, alpha-synuclein binding molecules of the invention, in particular antibodies or antigen-binding fragments thereof, inhibit the formation of alpha-synuclein aggregates, including but not limited to, Lewy Bodies, Lewy Neurites, and/or glial cytoplasmic inclusions.

The alpha-synuclein binding molecules, especially antibodies or antigen-binding fragments thereof, of the invention may selectively bind aggregated alpha-synuclein and/or pathological alpha-synuclein in preference to non-aggregated alpha-synuclein and/or non-pathological alpha-synuclein (such as monomeric alpha-synuclein).

In some embodiments of the invention, the antibody is a monoclonal antibody. In some embodiments, the antibody is a murine, murinized, human, humanized, or chimeric antibody.

In some embodiments of the invention, the antibody, or antigen-binding fragment or derivative thereof having a binding characteristic of an antibody described herein, is an antibody having the variable regions VH and/or VL of the amino acid sequences, respectively, set forth in SEQ ID NO: 10 and SEQ ID NO: 14; SEQ ID NO: 20 and SEQ ID NO: 24; SEQ ID NO: 30 and SEQ ID NO: 34; SEQ ID NO: 40 and SEQ ID NO: 44; SEQ ID NO: 50 and SEQ ID NO: 54; SEQ ID NO: 60 and SEQ ID NO: 64; SEQ ID NO: 70 and SEQ ID NO: 74; SEQ ID NO: 30 and SEQ ID NO: 84; SEQ ID NO: 90 and SEQ ID NO: 94; SEQ ID NO: 100 and SEQ ID NO: 104; SEQ ID NO: 110 and SEQ ID NO: 114; SEQ ID NO: 280 and SEQ ID NO: 284; SEQ ID NO: 290 and SEQ ID NO: 194; SEQ ID NO: 140 and SEQ ID NO: 144; SEQ ID NO: 150 and SEQ ID NO: 154; SEQ ID NO: 160 and SEQ ID NO: 164; SEQ ID NO: 170 and SEQ ID NO: 174; SEQ ID NO: 180 and SEQ ID NO: 184; SEQ ID NO: 190 and SEQ ID NO: 194; SEQ ID NO: 200 and SEQ ID NO: 204; SEQ ID NO: 210 and SEQ ID NO: 214; SEQ ID NO: 220 and SEQ ID NO: 224; SEQ ID NO: 230 and SEQ ID NO: 234; SEQ ID NO: 240 and SEQ ID NO: 244; SEQ ID NO: 250 and SEQ ID NO: 254; SEQ ID NO: 260 and SEQ ID NO: 264; SEQ ID NO: 270 and SEQ ID NO: 274; SEQ ID NO: 300 and SEQ ID NO: 304; SEQ ID NO: 310 and SEQ ID NO: 314; SEQ ID NO: 320 and SEQ ID NO: 324; SEQ ID NO: 330 and SEQ ID NO: 334; SEQ ID NO: 340 and SEQ ID NO: 344; SEQ ID NO: 350 and SEQ ID NO: 354; SEQ ID NO: 360 and SEQ ID NO: 364; SEQ ID NO: 370 and SEQ ID NO: 374; SEQ ID NO: 380 and SEQ ID NO: 384; SEQ ID NO: 390 and SEQ ID NO: 394; SEQ ID NO: 400 and SEQ ID NO: 404; SEQ ID NO: 410 and SEQ ID NO: 414; SEQ ID NO: 420 and SEQ ID NO: 424; SEQ ID NO: 430 and SEQ ID NO: 434; SEQ ID NO: 440 and SEQ ID NO: 414; SEQ ID NO: 450 and SEQ ID NO: 424; SEQ ID NO: 460 and SEQ ID NO: 464; SEQ ID NO: 470 and SEQ ID NO: 474; SEQ ID NO: 480 and SEQ ID NO: 484; SEQ ID NO: 490 and SEQ ID NO: 494; SEQ ID NO: 500 and SEQ ID NO: 504; SEQ ID NO: 510 and SEQ ID NO: 514; SEQ ID NO: 520 and SEQ ID NO: 524; SEQ ID NO: 530 and SEQ ID NO: 534; SEQ ID NO: 540 and SEQ ID NO: 544; SEQ ID NO: 550 and SEQ ID NO: 554; SEQ ID NO: 560 and SEQ ID NO: 564; SEQ ID NO: 570 and SEQ ID NO: 574; SEQ ID NO: 580 and SEQ ID NO: 584; SEQ ID NO: 590 and SEQ ID NO: 474; SEQ ID NO: 600 and SEQ ID NO: 554; SEQ ID NO: 610 and SEQ ID NO: 614; SEQ ID NO: 610 and SEQ ID NO: 624; SEQ ID NO: 610 and SEQ ID NO: 634; SEQ ID NO: 610 and SEQ ID NO: 644; SEQ ID NO: 620 and SEQ ID NO: 614; SEQ ID NO: 620 and SEQ ID NO: 624; SEQ ID NO: 620 and SEQ ID NO: 634; SEQ ID NO: 620 and SEQ ID NO: 644; SEQ ID NO: 630 and SEQ ID NO: 614; SEQ ID NO: 630 and SEQ ID NO: 624; SEQ ID NO: 630 and SEQ ID NO: 634; SEQ ID NO: 630 and SEQ ID NO: 644; SEQ ID NO: 640 and SEQ ID NO: 614; SEQ ID NO: 640 and SEQ ID NO: 624; SEQ ID NO: 640 and SEQ ID NO: 634; SEQ ID NO: 640 and SEQ ID NO: 644; SEQ ID NO: 650 and SEQ ID NO: 614; SEQ ID NO: 650 and SEQ ID NO: 624; SEQ ID NO: 650 and SEQ ID NO: 634; SEQ ID NO: 650 and SEQ ID NO: 644; SEQ ID NO: 660 and SEQ ID NO: 614; SEQ ID NO: 670 and SEQ ID NO: 614; SEQ ID NO: 680 and SEQ ID NO: 614; SEQ ID NO: 690 and SEQ ID NO: 614; SEQ ID NO: 690 and SEQ ID NO: 624; SEQ ID NO: 700 and SEQ ID NO: 614; SEQ ID NO: 700 and SEQ ID NO: 624; SEQ ID NO: 710 and SEQ ID NO: 614; SEQ ID NO: 710 and SEQ ID NO: 624; SEQ ID NO: 720 and SEQ ID NO: 614; SEQ ID NO: 720 and SEQ ID NO: 624.

The invention therefore also provides an alpha-synuclein binding antibody having the variable regions VH and/or VL of the amino acid sequences, respectively, set forth in SEQ ID NO: 10 and SEQ ID NO: 14; SEQ ID NO: 20 and SEQ ID NO: 24; SEQ ID NO: 30 and SEQ ID NO: 34; SEQ ID NO: 40 and SEQ ID NO: 44; SEQ ID NO: 50 and SEQ ID NO: 54; SEQ ID NO: 60 and SEQ ID NO: 64; SEQ ID NO: 70 and SEQ ID NO: 74; SEQ ID NO: 30 and SEQ ID NO: 84; SEQ ID NO: 90 and SEQ ID NO: 94; SEQ ID NO: 100 and SEQ ID NO: 104; SEQ ID NO: 110 and SEQ ID NO: 114; SEQ ID NO: 280 and SEQ ID NO: 284; SEQ ID NO: 290 and SEQ ID NO: 194; SEQ ID NO: 140 and SEQ ID NO: 144; SEQ ID NO: 150 and SEQ ID NO: 154; SEQ ID NO: 160 and SEQ ID NO: 164; SEQ ID NO: 170 and SEQ ID NO: 174; SEQ ID NO: 180 and SEQ ID NO: 184; SEQ ID NO: 190 and SEQ ID NO: 194; SEQ ID NO: 200 and SEQ ID NO: 204; SEQ ID NO: 210 and SEQ ID NO: 214; SEQ ID NO: 220 and SEQ ID NO: 224; SEQ ID NO: 230 and SEQ ID NO: 234; SEQ ID NO: 240 and SEQ ID NO: 244; SEQ ID NO: 250 and SEQ ID NO: 254; SEQ ID NO: 260 and SEQ ID NO: 264; SEQ ID NO: 270 and SEQ ID NO: 274 SEQ ID NO: 300 and SEQ ID NO: 304; SEQ ID NO: 310 and SEQ ID NO: 314; SEQ ID NO: 320 and SEQ ID NO: 324; SEQ ID NO: 330 and SEQ ID NO: 334; SEQ ID NO: 340 and SEQ ID NO: 344; SEQ ID NO: 350 and SEQ ID NO: 354; SEQ ID NO: 360 and SEQ ID NO: 364; SEQ ID NO: 370 and SEQ ID NO: 374; SEQ ID NO: 380 and SEQ ID NO: 384; SEQ ID NO: 390 and SEQ ID NO: 394; SEQ ID NO: 400 and SEQ ID NO: 404; SEQ ID NO: 410 and SEQ ID NO: 414; SEQ ID NO: 420 and SEQ ID NO: 424; SEQ ID NO: 430 and SEQ ID NO: 434; SEQ ID NO: 440 and SEQ ID NO: 414; SEQ ID NO: 450 and SEQ ID NO: 424; SEQ ID NO: 460 and SEQ ID NO: 464; SEQ ID NO: 470 and SEQ ID NO: 474; SEQ ID NO: 480 and SEQ ID NO: 484; SEQ ID NO: 490 and SEQ ID NO: 494; SEQ ID NO: 500 and SEQ ID NO: 504; SEQ ID NO: 510 and SEQ ID NO: 514; SEQ ID NO: 520 and SEQ ID NO: 524; SEQ ID NO: 530 and SEQ ID NO: 534; SEQ ID NO: 540 and SEQ ID NO: 544; SEQ ID NO: 550 and SEQ ID NO: 554; SEQ ID NO: 560 and SEQ ID NO: 564; SEQ ID NO: 570 and SEQ ID NO: 574; SEQ ID NO: 580 and SEQ ID NO: 584; SEQ ID NO: 590 and SEQ ID NO: 474; SEQ ID NO: 600 and SEQ ID NO: 554; SEQ ID NO: 610 and SEQ ID NO: 614; SEQ ID NO: 610 and SEQ ID NO: 624; SEQ ID NO: 610 and SEQ ID NO: 634; SEQ ID NO: 610 and SEQ ID NO: 644; SEQ ID NO: 620 and SEQ ID NO: 614; SEQ ID NO: 620 and SEQ ID NO: 624; SEQ ID NO: 620 and SEQ ID NO: 634; SEQ ID NO: 620 and SEQ ID NO: 644; SEQ ID NO: 630 and SEQ ID NO: 614; SEQ ID NO: 630 and SEQ ID NO: 624; SEQ ID NO: 630 and SEQ ID NO: 634; SEQ ID NO: 630 and SEQ ID NO: 644; SEQ ID NO: 640 and SEQ ID NO: 614; SEQ ID NO: 640 and SEQ ID NO: 624; SEQ ID NO: 640 and SEQ ID NO: 634; SEQ ID NO: 640 and SEQ ID NO: 644; SEQ ID NO: 650 and SEQ ID NO: 614; SEQ ID NO: 650 and SEQ ID NO: 624; SEQ ID NO: 650 and SEQ ID NO: 634; SEQ ID NO: 650 and SEQ ID NO: 644; SEQ ID NO: 660 and SEQ ID NO: 614; SEQ ID NO: 670 and SEQ ID NO: 614; SEQ ID NO: 680 and SEQ ID NO: 614; SEQ ID NO: 690 and SEQ ID NO: 614; SEQ ID NO: 690 and SEQ ID NO: 624; SEQ ID NO: 700 and SEQ ID NO: 614; SEQ ID NO: 700 and SEQ ID NO: 624; SEQ ID NO: 710 and SEQ ID NO: 614; SEQ ID NO: 710 and SEQ ID NO: 624; SEQ ID NO: 720 and SEQ ID NO: 614; SEQ ID NO: 720 and SEQ ID NO: 624.

In some embodiments, the antibody comprises:

a) VH-CDR1 comprising the amino acid sequence of SEQ ID NO: 11; VH-CDR2 comprising the amino acid sequence of SEQ ID NO: 12; and VH-CDR3 comprising the amino acid sequence of SEQ ID NO: 13; VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) VH-CDR1 comprising the amino acid sequence of SEQ ID NO: 21; VH-CDR2 comprising the amino acid sequence of SEQ ID NO: 22; and VH-CDR3 comprising the amino acid sequence YSY; VL-CDR1 comprising the amino acid sequence of SEQ ID NO: 25; VL-CDR2 comprising the amino acid sequence of SEQ ID NO: 26; and VL-CDR3 comprising the amino acid sequence of SEQ ID NO: 27; or c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43; VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47; or e) VH-CDR1 comprising the amino acid sequence of SEQ ID NO: 21; VH-CDR2 comprising the amino acid sequence of SEQ ID NO: 52; and VH-CDR3 comprising the amino acid sequence YSF; VL-CDR1 comprising the amino acid sequence of SEQ ID NO: 55; VL-CDR2 comprising the amino acid sequence of SEQ ID NO: 56; and VL-CDR3 comprising the amino acid sequence of SEQ ID NO: 27; or f) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 43; VL-CDR1 comprising the amino acid sequence of SEQ ID NO: 65; VL-CDR2 comprising the amino acid sequence of SEQ ID NO: 46; and VL-CDR3 comprising the amino acid sequence of SEQ ID NO: 67; or g) VH-CDR1 comprising the amino acid sequence of SEQ ID NO: 21; VH-CDR2 comprising the amino acid sequence of SEQ ID NO: 72; and VH-CDR3 comprising the amino acid sequence YSY; VL-CDR1 comprising the amino acid sequence of SEQ ID NO: 75; VL-CDR2 comprising the amino acid sequence of SEQ ID NO: 76; and VL-CDR3 comprising the amino acid sequence of SEQ ID NO: 77; or h) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 85; VL-CDR2 comprising the amino acid sequence of SEQ ID NO: 36; and VL-CDR3 comprising the amino acid sequence of SEQ ID NO: 87; or i) VH-CDR1 comprising the amino acid sequence of SEQ ID NO: 91; VH-CDR2 comprising the amino acid sequence of SEQ ID NO: 92; and VH-CDR3 comprising the amino acid sequence of SEQ ID NO: 93; VL-CDR1 comprising the amino acid sequence of SEQ ID NO: 95; VL-CDR2 comprising the amino acid sequence of SEQ ID NO: 96; and VL-CDR3 comprising the amino acid sequence of SEQ ID NO: 97; or j) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or k) VH-CDR1 comprising the amino acid sequence of SEQ ID NO: 111; VH-CDR2 comprising the amino acid sequence of SEQ ID NO: 112; and VH-CDR3 comprising the amino acid sequence of SEQ ID NO: 113; VL-CDR1 comprising the amino acid sequence of SEQ ID NO: 115; VL-CDR2 comprising the amino acid sequence of SEQ ID NO: 106; and VL-CDR3 comprising the amino acid sequence of SEQ ID NO: 117; or l) VH-CDR1 comprising the amino acid sequence of SEQ ID NO: 281; VH-CDR2 comprising the amino acid sequence of SEQ ID NO: 282; and VH-CDR3 comprising the amino acid sequence of SEQ ID NO: 283; VL-CDR1 comprising the amino acid sequence of SEQ ID NO: 285; VL-CDR2 comprising the amino acid sequence of SEQ ID NO: 286; and VL-CDR3 comprising the amino acid sequence of SEQ ID NO: 287; or m) VH-CDR1 comprising the amino acid sequence of SEQ ID NO: 31; VH-CDR2 comprising the amino acid sequence of SEQ ID NO: 192; and VH-CDR3 comprising the amino acid sequence of SEQ ID NO: 193; VL-CDR1 comprising the amino acid sequence of SEQ ID NO: 195; VL-CDR2 comprising the amino acid sequence of SEQ ID NO: 96; and VL-CDR3 comprising the amino acid sequence of SEQ ID NO: 197; or n) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; VL-CDR1 comprising the amino acid sequence of SEQ ID NO: 145; VL-CDR2 comprising the amino acid sequence of SEQ ID NO: 16; and VL-CDR3 comprising the amino acid sequence of SEQ ID NO: 17; or o) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or p) VH-CDR1 comprising the amino acid sequence of SEQ ID NO: 161; VH-CDR2 comprising the amino acid sequence of SEQ ID NO: 162; and VH-CDR3 comprising the amino acid sequence of SEQ ID NO: 163; VL-CDR1 comprising the amino acid sequence of SEQ ID NO: 165; VL-CDR2 comprising the amino acid sequence of SEQ ID NO: 16; and VL-CDR3 comprising the amino acid sequence of SEQ ID NO: 167; or q) VH-CDR1 comprising the amino acid sequence of SEQ ID NO: 171; VH-CDR2 comprising the amino acid sequence of SEQ ID NO: 172; and VH-CDR3 comprising the amino acid sequence of SEQ ID NO: 173; VL-CDR1 comprising the amino acid sequence of SEQ ID NO: 175; VL-CDR2 comprising the amino acid sequence of SEQ ID NO: 176; and VL-CDR3 comprising the amino acid sequence of SEQ ID NO: 177; or r) VH-CDR1 comprising the amino acid sequence of SEQ ID NO: 181; VH-CDR2 comprising the amino acid sequence of SEQ ID NO: 182; and VH-CDR3 comprising the amino acid sequence of SEQ ID NO: 183; VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 187; or s) VH-CDR1 comprising the amino acid sequence of SEQ ID NO: 201; VH-CDR2 comprising the amino acid sequence of SEQ ID NO: 202; and VH-CDR3 comprising the amino acid sequence of SEQ ID NO: 153; VL-CDR1 comprising the amino acid sequence of SEQ ID NO: 105; VL-CDR2 comprising the amino acid sequence of SEQ ID NO: 206; and VL-CDR3 comprising the amino acid sequence of SEQ ID NO: 107; or t) VH-CDR1 comprising the amino acid sequence of SEQ ID NO: 211; VH-CDR2 comprising the amino acid sequence of SEQ ID NO: 212; and VH-CDR3 comprising the amino acid sequence of SEQ ID NO: 213; VL-CDR1 comprising the amino acid sequence of SEQ ID NO: 215; VL-CDR2 comprising the amino acid sequence of SEQ ID NO: 216; and VL-CDR3 comprising the amino acid sequence of SEQ ID NO: 217; or u) VH-CDR1 comprising the amino acid sequence of SEQ ID NO: 31; VH-CDR2 comprising the amino acid sequence of SEQ ID NO: 222; and VH-CDR3 comprising the amino acid sequence of SEQ ID NO: 223; VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 227; or v) VH-CDR1 comprising the amino acid sequence of SEQ ID NO: 231; VH-CDR2 comprising the amino acid sequence of SEQ ID NO: 232; and VH-CDR3 comprising the amino acid sequence of SEQ ID NO: 233; VL-CDR1 comprising the amino acid sequence of SEQ ID NO: 235; VL-CDR2 comprising the amino acid sequence of SEQ ID NO: 236; and VL-CDR3 comprising the amino acid sequence of SEQ ID NO: 237; or w) VH-CDR1 comprising the amino acid sequence of SEQ ID NO: 31; VH-CDR2 comprising the amino acid sequence of SEQ ID NO: 242; and VH-CDR3 comprising the amino acid sequence of SEQ ID NO: 243; VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 247; or x) VH-CDR1 comprising the amino acid sequence of SEQ ID NO: 31; VH-CDR2 comprising the amino acid sequence of SEQ ID NO: 252; and VH-CDR3 comprising the amino acid sequence of SEQ ID NO: 253; VL-CDR1 comprising the amino acid sequence of SEQ ID NO: 255; VL-CDR2 comprising the amino acid sequence of SEQ ID NO: 256; and VL-CDR3 comprising the amino acid sequence of SEQ ID NO: 257;or y) VH-CDR1 comprising the amino acid sequence of SEQ ID NO: 261; VH-CDR2 comprising the amino acid sequence of SEQ ID NO: 262; and VH-CDR3 comprising the amino acid sequence of SEQ ID NO: 263; VL-CDR1 comprising the amino acid sequence of SEQ ID NO: 265; VL-CDR2 comprising the amino acid sequence of SEQ ID NO: 176; and VL-CDR3 comprising the amino acid sequence of SEQ ID NO: 267; or z) VH-CDR1 comprising the amino acid sequence of SEQ ID NO: 271; VH-CDR2 comprising the amino acid sequence of SEQ ID NO: 272; and VH-CDR3 comprising the amino acid sequence of SEQ ID NO: 273; VL-CDR1 comprising the amino acid sequence of SEQ ID NO: 275; VL-CDR2 comprising the amino acid sequence of SEQ ID NO: 276; and VL-CDR3 comprising the amino acid sequence of SEQ ID NO: 277; or aa) VH-CDR1 comprising the amino acid sequence of SEQ ID NO: 301; VH-CDR2 comprising the amino acid sequence of SEQ ID NO: 302; and VH-CDR3 comprising the amino acid sequence of SEQ ID NO: 303; VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 307; or bb) VH-CDR1 comprising the amino acid sequence of SEQ ID NO: 311; VH-CDR2 comprising the amino acid sequence of SEQ ID NO: 312; and VH-CDR3 comprising the amino acid sequence of SEQ ID NO: 313; VL-CDR1 comprising the amino acid sequence of SEQ ID NO: 315; VL-CDR2 comprising the amino acid sequence of SEQ ID NO: 46; and VL-CDR3 comprising the amino acid sequence of SEQ ID NO: 67; or cc) VH-CDR1 comprising the amino acid sequence of SEQ ID NO: 321; VH-CDR2 comprising the amino acid sequence of SEQ ID NO: 322; and VH-CDR3 comprising the amino acid sequence of SEQ ID NO: 323; VL-CDR1 comprising the amino acid sequence of SEQ ID NO: 325; VL-CDR2 comprising the amino acid sequence of SEQ ID NO: 326; and VL-CDR3 comprising the amino acid sequence of SEQ ID NO: 327; or dd) VH-CDR1 comprising the amino acid sequence of SEQ ID NO: 151; VH-CDR2 comprising the amino acid sequence of SEQ ID NO: 332; and VH-CDR3 comprising the amino acid sequence of SEQ ID NO: 333; VL-CDR1 comprising the amino acid sequence of SEQ ID NO: 335; VL-CDR2 comprising the amino acid sequence of SEQ ID NO: 336; and VL-CDR3 comprising the amino acid sequence of SEQ ID NO: 107; or or ee) VH-CDR1 comprising the amino acid sequence of SEQ ID NO: 341; VH-CDR2 comprising the amino acid sequence of SEQ ID NO: 342; and VH-CDR3 comprising the amino acid sequence of SEQ ID NO: 343; VL-CDR1 comprising the amino acid sequence of SEQ ID NO: 345; VL-CDR2 comprising the amino acid sequence of SEQ ID NO: 346; and VL-CDR3 comprising the amino acid sequence of SEQ ID NO: 347; or ff) VH-CDR1 comprising the amino acid sequence of SEQ ID NO: 351; VH-CDR2 comprising the amino acid sequence of SEQ ID NO: 352; and VH-CDR3 comprising the amino acid sequence of SEQ ID NO: 353; VL-CDR1 comprising the amino acid sequence of SEQ ID NO: 355; VL-CDR2 comprising the amino acid sequence of SEQ ID NO: 356; and VL-CDR3 comprising the amino acid sequence of SEQ ID NO: 357; or gg) VH-CDR1 comprising the amino acid sequence of SEQ ID NO: 361; VH-CDR2 comprising the amino acid sequence of SEQ ID NO: 362; and VH-CDR3 comprising the amino acid sequence of SEQ ID NO: 363; VL-CDR1 comprising the amino acid sequence of SEQ ID NO: 365; VL-CDR2 comprising the amino acid sequence of SEQ ID NO: 16; and VL-CDR3 comprising the amino acid sequence of SEQ ID NO: 367; or hh) VH-CDR1 comprising the amino acid sequence of SEQ ID NO: 371; VH-CDR2 comprising the amino acid sequence of SEQ ID NO: 372; and VH-CDR3 comprising the amino acid sequence of SEQ ID NO: 373; VL-CDR1 comprising the amino acid sequence of SEQ ID NO: 345; VL-CDR2 comprising the amino acid sequence of SEQ ID NO: 376; and VL-CDR3 comprising the amino acid sequence of SEQ ID NO: 347; or ii) VH-CDR1 comprising the amino acid sequence of SEQ ID NO: 351; VH-CDR2 comprising the amino acid sequence of SEQ ID NO: 382; and VH-CDR3 comprising the amino acid sequence of SEQ ID NO: 383; VL-CDR1 comprising the amino acid sequence of SEQ ID NO: 385; VL-CDR2 comprising the amino acid sequence of SEQ ID NO: 386; and VL-CDR3 comprising the amino acid sequence of SEQ ID NO: 387; or jj) VH-CDR1 comprising the amino acid sequence of SEQ ID NO: 351; VH-CDR2 comprising the amino acid sequence of SEQ ID NO: 382; and VH-CDR3 comprising the amino acid sequence of SEQ ID NO: 393; VL-CDR1 comprising the amino acid sequence of SEQ ID NO: 395; VL-CDR2 comprising the amino acid sequence of SEQ ID NO: 356; and VL-CDR3 comprising the amino acid sequence of SEQ ID NO: 357; or kk) VH-CDR1 comprising the amino acid sequence of SEQ ID NO: 351; VH-CDR2 comprising the amino acid sequence of SEQ ID NO: 382; and VH-CDR3 comprising the amino acid sequence of SEQ ID NO: 393; VL-CDR1 comprising the amino acid sequence of SEQ ID NO: 405; VL-CDR2 comprising the amino acid sequence of SEQ ID NO: 356; and VL-CDR3 comprising the amino acid sequence of SEQ ID NO: 357; or ll) VH-CDR1 comprising the amino acid sequence of SEQ ID NO: 411; VH-CDR2 comprising the amino acid sequence of SEQ ID NO: 412; and VH-CDR3 comprising the amino acid sequence of SEQ ID NO: 413; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or mm) VH-CDR1 comprising the amino acid sequence of SEQ ID NO: 421; VH-CDR2 comprising the amino acid sequence of SEQ ID NO: 422; and VH-CDR3 comprising the amino acid sequence GNY; VL-CDR1 comprising the amino acid sequence of SEQ ID NO: 425; VL-CDR2 comprising the amino acid sequence of SEQ ID NO: 426; and VL-CDR3 comprising the amino acid sequence of SEQ ID NO: 427; or nn) VH-CDR1 comprising the amino acid sequence of SEQ ID NO: 431; VH-CDR2 comprising the amino acid sequence of SEQ ID NO: 432; and VH-CDR3 comprising the amino acid sequence of SEQ ID NO: 433; VL-CDR1 comprising the amino acid sequence of SEQ ID NO: 435; VL-CDR2 comprising the amino acid sequence of SEQ ID NO: 436; and VL-CDR3 comprising the amino acid sequence of SEQ ID NO: 437; or oo) VH-CDR1 comprising the amino acid sequence of SEQ ID NO: 151; VH-CDR2 comprising the amino acid sequence of SEQ ID NO: 442; and VH-CDR3 comprising the amino acid sequence of SEQ ID NO: 443; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or pp) VH-CDR1 comprising the amino acid sequence of SEQ ID NO: 461; VH-CDR2 comprising the amino acid sequence of SEQ ID NO: 462; and VH-CDR3 comprising the amino acid sequence of SEQ ID NO: 463; VL-CDR1 comprising the amino acid sequence of SEQ ID NO: 465; VL-CDR2 comprising the amino acid sequence of SEQ ID NO: 16; and VL-CDR3 comprising the amino acid sequence of SEQ ID NO: 467; or qq) VH-CDR1 comprising the amino acid sequence of SEQ ID NO: 141; VH-CDR2 comprising the amino acid sequence of SEQ ID NO: 472; and VH-CDR3 comprising the amino acid sequence of SEQ ID NO: 473; VL-CDR1 comprising the amino acid sequence of SEQ ID NO: 475; VL-CDR2 comprising the amino acid sequence of SEQ ID NO: 476; and VL-CDR3 comprising the amino acid sequence of SEQ ID NO: 477; or rr) VH-CDR1 comprising the amino acid sequence of SEQ ID NO: 481; VH-CDR2 comprising the amino acid sequence of SEQ ID NO: 482; and VH-CDR3 comprising the amino acid sequence of SEQ ID NO: 483; VL-CDR1 comprising the amino acid sequence of SEQ ID NO: 165; VL-CDR2 comprising the amino acid sequence of SEQ ID NO: 16; and VL-CDR3 comprising the amino acid sequence of SEQ ID NO: 487; or ss) VH-CDR1 comprising the amino acid sequence of SEQ ID NO: 141; VH-CDR2 comprising the amino acid sequence of SEQ ID NO: 492; and VH-CDR3 comprising the amino acid sequence of SEQ ID NO: 493; VL-CDR1 comprising the amino acid sequence of SEQ ID NO: 495; VL-CDR2 comprising the amino acid sequence of SEQ ID NO: 496; and VL-CDR3 comprising the amino acid sequence of SEQ ID NO: 497; or tt) VH-CDR1 comprising the amino acid sequence of SEQ ID NO: 151; VH-CDR2 comprising the amino acid sequence of SEQ ID NO: 502; and VH-CDR3 comprising the amino acid sequence of SEQ ID NO: 503; VL-CDR1 comprising the amino acid sequence of SEQ ID NO: 105; VL-CDR2 comprising the amino acid sequence of SEQ ID NO: 336; and VL-CDR3 comprising the amino acid sequence of SEQ ID NO: 107; or uu) VH-CDR1 comprising the amino acid sequence of SEQ ID NO: 311; VH-CDR2 comprising the amino acid sequence of SEQ ID NO: 512; and VH-CDR3 comprising the amino acid sequence of SEQ ID NO: 513; VL-CDR1 comprising the amino acid sequence of SEQ ID NO: 515; VL-CDR2 comprising the amino acid sequence of SEQ ID NO: 516; and VL-CDR3 comprising the amino acid sequence of SEQ ID NO: 517; or vv) VH-CDR1 comprising the amino acid sequence of SEQ ID NO: 521; VH-CDR2 comprising the amino acid sequence of SEQ ID NO: 522; and VH-CDR3 comprising the amino acid sequence of SEQ ID NO: 463; VL-CDR1 comprising the amino acid sequence of SEQ ID NO: 525; VL-CDR2 comprising the amino acid sequence of SEQ ID NO: 16; and VL-CDR3 comprising the amino acid sequence of SEQ ID NO: 467; or ww) VH-CDR1 comprising the amino acid sequence of SEQ ID NO: 371; VH-CDR2 comprising the amino acid sequence of SEQ ID NO: 532; and VH-CDR3 comprising the amino acid sequence of SEQ ID NO: 533; VL-CDR1 comprising the amino acid sequence of SEQ ID NO: 345; VL-CDR2 comprising the amino acid sequence of SEQ ID NO: 376; and VL-CDR3 comprising the amino acid sequence of SEQ ID NO: 537; or xx) VH-CDR1 comprising the amino acid sequence of SEQ ID NO: 341; VH-CDR2 comprising the amino acid sequence of SEQ ID NO: 542; and VH-CDR3 comprising the amino acid sequence of SEQ ID NO: 543; VL-CDR1 comprising the amino acid sequence of SEQ ID NO: 345; VL-CDR2 comprising the amino acid sequence of SEQ ID NO: 376; and VL-CDR3 comprising the amino acid sequence of SEQ ID NO: 347; or yy) VH-CDR1 comprising the amino acid sequence of SEQ ID NO: 551; VH-CDR2 comprising the amino acid sequence of SEQ ID NO: 552; and VH-CDR3 comprising the amino acid sequence of SEQ ID NO: 553; VL-CDR1 comprising the amino acid sequence of SEQ ID NO: 555; VL-CDR2 comprising the amino acid sequence of SEQ ID NO: 16; and VL-CDR3 comprising the amino acid sequence of SEQ ID NO: 557; or zz) VH-CDR1 comprising the amino acid sequence of SEQ ID NO: 551; VH-CDR2 comprising the amino acid sequence of SEQ ID NO: 552; and VH-CDR3 comprising the amino acid sequence of SEQ ID NO: 563; VL-CDR1 comprising the amino acid sequence of SEQ ID NO: 565; VL-CDR2 comprising the amino acid sequence of SEQ ID NO: 16; and VL-CDR3 comprising the amino acid sequence of SEQ ID NO: 557; or aaa) VH-CDR1 comprising the amino acid sequence of SEQ ID NO: 571; VH-CDR2 comprising the amino acid sequence of SEQ ID NO: 202; and VH-CDR3 comprising the amino acid sequence of SEQ ID NO: 573; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or bbb) VH-CDR1 comprising the amino acid sequence of SEQ ID NO: 581; VH-CDR2 comprising the amino acid sequence of SEQ ID NO: 582; and VH-CDR3 comprising the amino acid sequence of SEQ ID NO: 583; VL-CDR1 comprising the amino acid sequence of SEQ ID NO: 585; VL-CDR2 comprising the amino acid sequence of SEQ ID NO: 586; and VL-CDR3 comprising the amino acid sequence of SEQ ID NO: 587; or ccc) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 13; VL-CDR1 comprising the amino acid sequence of SEQ ID NO: 615; VL-CDR2 comprising the amino acid sequence of SEQ ID NO: 16; and VL-CDR3 comprising the amino acid sequence of SEQ ID NO: 17; or ddd) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 13; VL-CDR1 comprising the amino acid sequence of SEQ ID NO: 625; VL-CDR2 comprising the amino acid sequence of SEQ ID NO: 16; and VL-CDR3 comprising the amino acid sequence of SEQ ID NO: 17; or eee) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 663; VL-CDR1 comprising the amino acid sequence of SEQ ID NO: 615; VL-CDR2 comprising the amino acid sequence of SEQ ID NO: 16; and VL-CDR3 comprising the amino acid sequence of SEQ ID NO: 17; or fff) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 673; VL-CDR1 comprising the amino acid sequence of SEQ ID NO: 615; VL-CDR2 comprising the amino acid sequence of SEQ ID NO: 16; and VL-CDR3 comprising the amino acid sequence of SEQ ID NO: 17; or ggg) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 683; VL-CDR1 comprising the amino acid sequence of SEQ ID NO: 615; VL-CDR2 comprising the amino acid sequence of SEQ ID NO: 16; and VL-CDR3 comprising the amino acid sequence of SEQ ID NO: 17; or hhh) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 683; VL-CDR1 comprising the amino acid sequence of SEQ ID NO: 625; VL-CDR2 comprising the amino acid sequence of SEQ ID NO: 16; and VL-CDR3 comprising the amino acid sequence of SEQ ID NO: 17.

These alpha-synuclein binding antibodies may constitute separate aspects of the invention.

In some embodiments, an isolated nucleic acid is provided, wherein the isolated nucleic acid encodes an antibody, or an antigen-binding fragment or derivative thereof, described herein. In some embodiments, a host cell is provided, wherein the host cell comprises an isolated nucleic acid that encodes an antibody, or an antigen-binding fragment or derivative thereof, described herein. In some embodiments, a method of producing an antibody, or an antigen-binding fragment or derivative thereof, is provided, comprising culturing the host cell under conditions suitable for producing the antibody, or the antigen-binding fragment or the derivative thereof.

In some embodiments, an immunoconjugate is provided, wherein the immunoconjugate comprises an isolated antibody, antigen-binding fragment or derivative thereof, described herein and a therapeutic agent. In some embodiments, a labeled antibody, antigen-binding fragment or derivative thereof, is provided, comprising an antibody antigen-binding fragment or derivative thereof, described herein and a detectable label.

In some embodiments, a pharmaceutical composition is provided, comprising an isolated antibody, antigen-binding fragment or derivative thereof, described herein and a pharmaceutically acceptable carrier and/or excipient.

As used herein, the term "isolated" means that the chemical compound, e.g. the nucleic acid or antibody, may have been separated and/or recovered from its natural environment. Within the present invention, the chemical compound is preferably chemically synthesized, or synthesized in a cellular system different from the cell from which it naturally originates, and is thus "isolated" from its naturally associated components. The chemical compound may be isolated from its natural environment by e.g. purification or produced by means of a technical process (including but not limited to e.g. gene synthesis, polymerase chain reaction (PCR), vector purification and protein (antibody) purification). Such chemical compound may be, in particular, a nucleic acid, DNA-, RNA-, or cDNA-sequence, or a peptide, antibody or protein.

The present invention is not limited to an isolated antibody in accordance with the above definition, but also relates to an antibody as such irrespective of its origin.

The same applies to peptides, nucleic acids, DNA, RNA and/or cDNA sequences provided by the present invention, which are encompassed in isolated form, as defined above, or in any other form.

In some embodiments, a method of preventing, alleviating and/or treating a disease, disorder or abnormality associated with alpha-synuclein aggregates or pathological alpha-synuclein, such as Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17 and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder, is provided. According to one embodiment, the methods of the invention comprise administering an effective concentration or an effective amount of a binding molecule, particularly an antibody, or an antigen-binding fragment or derivative thereof, of the invention binding alpha-synuclein (e.g., a full-length antibody or an alpha-synuclein binding fragment or derivative of an antibody) as described herein to a subject in need thereof.

In some embodiments, a method of retaining motor capabilities or improving motor deficits of a subject suffering from a synucleopathy, including reducing bradykinesia, rigidity, resting tremor or postural instability is provided, comprising administering an antibody, or an antigen-binding fragment or derivative thereof, described herein or a pharmaceutical composition comprising an antibody, or antigen-binding fragment or derivative thereof, described herein to a subject in need thereof.

In some embodiments, a method of retaining or increasing cognitive capacity of a subject suffering from a synucleopathy is provided, comprising administering an antibody, or antigen-binding fragment or derivative thereof, described herein or a pharmaceutical composition comprising an antibody, or antigen-binding fragment or derivative thereof, described herein to a subject in need thereof.

In some embodiments, an isolated antibody, or an antigen-binding fragment or derivative thereof, described herein is provided for use as a medicament. In some embodiments, an isolated antibody, or an antigen-binding fragment or derivative thereof, described herein is provided for use in alleviating, preventing and/or treating a synucleinopathy in a subject. In some embodiments, use of an antibody, or an antigen-binding fragment or derivative thereof, described herein is provided for manufacture of a medicament for preventing, alleviating and/or treating a disease, a disorder and/or abnormality associated with alpha-synuclein aggregates.

In some embodiments, the disease, disorder and/or abnormality associated with alpha-synuclein aggregate is a synucleinopathy. In some embodiments, the synucleinopathy is Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17 and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder.

More particularly, the synucleinopathy is selected from Parkinson's Disease, Multiple System Atrophy, Lewy Body dementia (LBD; dementia with Lewy bodies (DLB) ("pure" Lewy body dementia), Parkinson's disease dementia (PDD)), and Diffuse Lewy Body Disease.

In some embodiments, a method of detecting alpha-synuclein aggregates including, but not limited to, Lewy bodies, Lewy neurites and/or glial cytoplasmic inclusions, is provided, comprising contacting a sample with an antibody, or antigen-binding fragment or derivative thereof, described herein and detecting the presence of aggregates using methods known in the art. In some embodiments, the sample is a brain sample, a cerebrospinal fluid sample, or a blood sample.

In some embodiments, a method for evaluating an alpha-synuclein binding molecule for the capability of inhibiting and/or delaying the seeded and/or spontaneous alpha-synuclein aggregation is provided, the method comprising the steps of: bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and determining the time to reach half-maximum signal of the detectable dye, particularly the signal of fluorescent dye, relative to the seeded aggregation in the absence of binding molecule, wherein an increase in time to reach half-maximum signal of the detectable dye in the presence of binding molecule relative to the seeded aggregation in the absence of binding molecule indicates that the alpha-synuclein binding molecule is capable of inhibiting and/or delaying the seeded and/or spontaneous alpha-synuclein aggregation.

In further embodiments, a method for selecting/screening an alpha-synuclein binding molecule capable of inhibiting and/or delaying the seeded and/or spontaneous alpha-synuclein aggregation is provided, the method comprising the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and selecting the alpha-synuclein binding molecule as being able to inhibit and/or delay seeded and/or spontaneous alpha-synuclein aggregation based on the signal of the detectable dye, in particular the fluorescent dye, determined in the absence and presence of the alpha-synuclein binding molecule.

In some embodiments, the method of evaluating or selecting an alpha-synuclein binding molecule capable of inhibiting and/or delaying the seeded and/or spontaneous alpha-synuclein aggregation is provided, wherein the detectable dye is thioflavin (ThT), which binds to the beta-sheet structure of the aggregated protein.

In some embodiments, the method of evaluating or selecting an alpha-synuclein binding molecule capable of inhibiting and/or delaying the seeded and/or spontaneous alpha-synuclein aggregation is provided, wherein the alpha-synuclein monomeric protein is covalently linked to the detectable dye, in particular the fluorescent dye, and/or wherein the signal of the detectable dye, in particular the fluorescent dye, is quenching of signal/fluorescence emission upon formation of the protein aggregates. Other detection methods are also envisaged within the scope of the present invention, including, for example, fluorescence resonance energy transfer (FRET) assays or the like. Dyes, in particular fluorescent dyes, are known to the person skilled in the art. Examples include for example green fluorescent protein, yellow fluorescent protein and the like.

In some embodiments, an alpha-synuclein binding molecule is evaluated as capable of inhibiting and/or delaying seeded and/or spontaneous alpha-synuclein aggregation or is selected, respectively, if in step d) of the invention the seeded and/or spontaneous alpha-synuclein aggregation is inhibited and/or delayed by at least 10%, 20%, 30%, 40%, 50%, 60%, 70%, 80%, 90%, 100%, 200%, or 300% in the presence of the alpha-synuclein binding molecule as compared to in the absence of the alpha-synuclein binding molecule. Alternatively, an alpha-synuclein binding molecule may be evaluated as capable of inhibiting and/or delaying seeded and/or spontaneous alpha-synuclein aggregation if the alpha-synuclein binding molecule causes an at least 10 percent increase in aggregation half-time (T½ values) of seeded aggregation relative to the seeded aggregation in the absence of binding molecule.

In some embodiments, a method for determining or evaluating an alpha-synuclein binding molecule for the capability of delaying and/or inhibiting seeded alpha-synuclein aggregation comprises the steps of:

(i) incubating cells containing and/or expressing a monomeric alpha-synuclein reporter protein with a composition comprising the alpha-synuclein binding molecule and a transduction reagent able to deliver alpha-synuclein binding molecules into cells, (ii) incubating the cells with a composition comprising alpha-synuclein aggregates (seeds) and a transduction reagent; and (iii) determine de novo aggregates of the alpha-synuclein reporter protein to determine or evaluate the capability of the alpha-synuclein binding molecule to delay and/or inhibit seeded alpha-synuclein aggregation.

In the method for determining or evaluating an alpha-synuclein binding molecule for the capability of delaying and/or inhibiting seeded alpha-synuclein aggregation, the composition comprising the alpha-synuclein binding molecule and a transduction reagent is pre-mixed prior to incubation with cells containing and/or expressing a monomeric alpha-synuclein reporter protein. In some embodiments, a method for determining or evaluating an alpha-synuclein binding molecule for the capability of delaying and/or inhibiting cellular uptake of pathological and/or aggregated alpha-synuclein comprises the steps of:

(i) incubating cells containing and/or expressing monomeric alpha-synuclein with an alpha-synuclein binding molecule, (ii) incubating the cells with alpha-synuclein aggregates (seeds); and (iii) determine de novo aggregates of alpha-synuclein to determine or evaluate the capability of the alpha-synuclein binding molecule to delay and/or inhibit cellular uptake of pathological and/or aggregated alpha-synuclein.

In some embodiments of the invention, the alpha-synuclein binding molecule for the method of determining or evaluating an alpha-synuclein binding molecule for the capability of delaying and/or inhibiting the seeded alpha-synuclein aggregation comprises preferably an alpha-synuclein antibody or an antigen-binding fragment or derivative thereof, more preferably an antibody or an antigen-binding fragment or derivative thereof of the invention.

In some embodiments of the invention, the transduction reagents under (i) and (ii) of the method of determining or evaluating an alpha-synuclein binding molecule for the capability of delaying and/or inhibiting the seeded alpha-synuclein aggregation can be the same or different, preferably the transduction reagents are different, more preferably the transduction reagent under (i) comprises Ab-DeliverIN™ and the transduction reagent under (ii) comprises Lipofectamine™ 2000.

In some embodiments of the invention, the step (iii) of the method of determining or evaluating an alpha-synuclein binding molecule for the capability of delaying and/or inhibiting the seeded alpha-synuclein aggregation comprises immunohistochemistry, microscopy, biochemical or flow cytometry detection methods, preferably immunohistochemistry, more preferably immunohistochemistry wherein by measuring fluorescence of the fluorescently labelled alpha-synuclein as expressed by said cells.

In some embodiments of the invention, a method for determining or evaluating an alpha-synuclein binding molecule for the capability of delaying and/or inhibiting the seeded alpha-synuclein aggregation comprises the steps of:

(i) incubating cells containing and/or expressing a monomeric alpha-synuclein reporter protein with a composition comprising the alpha-synuclein binding molecule and a transduction reagent able to deliver alpha-synuclein binding molecules into cells, (ii) incubating the cells with a composition comprising alpha-synuclein aggregates (seeds) and a transduction reagent; and (iii) determining de novo aggregation of the alpha-synuclein reporter protein to determine or evaluate the capability of the alpha-synuclein binding molecule to delay and/or inhibit seeded alpha-synuclein aggregation, wherein the incubation time in step (i) is up to 12 hours, preferably 5 hours and wherein the incubation time in step (ii) is at least 12 hours, preferably 96 hours, and wherein the transduction reagent under (i) is Ab-DeliverIN™ and wherein the transduction reagent under (ii) is Lipofectamine™ 2000.

Accordingly, in the context of the present invention, the term "transduction reagent" (or "transfection reagent") as used herein refers mainly to a formulation that is capable of forming non-covalent complexes with a molecule of interest to be transported intracellularly. Example of transduction reagent includes but is not limited to Ab-DeliverIN™, Lipofectamine™ 2000, Xfect™ Transfection Reagent, Via-Fect™ Transfection Reagent, Polyethylenimine (PEI) cellular transfection reagent or FuGENE™.

In some embodiments, an alpha-synuclein binding molecule is evaluated as capable of delaying and/or inhibiting seeded alpha-synuclein aggregation using the methods of the present invention if the seeded alpha-synuclein aggregation is delayed and/or inhibited by at least 10%, 20%, 30%, 40%, 50%, 60%, 70%, 80%, 90%, 100%, 200%, or 300% in the presence of the alpha-synuclein binding molecule as compared to in the absence of the alpha-synuclein binding molecule to be evaluated. Alternatively, an alpha-synuclein binding molecule may be evaluated as capable of delaying and/or inhibiting seeded alpha-synuclein aggregation if the alpha-synuclein binding molecule causes an at least 10% reduction of the level of aggregated alpha-synuclein relative to the level of aggregated alpha-synuclein in the absence of binding molecule.

Within the scope of the present invention, alpha-synuclein may have the sequence of SEQ ID NO: 1. Alpha-synuclein aggregates are multimeric beta-sheet rich assemblies of alpha-synuclein monomers that can form either soluble oligomers or soluble/insoluble protofibrils or mature fibrils which coalesce into intracellular deposits detected as a range of Lewy pathologies in Parkinson's disease and other synucleinopathies. Alpha-synuclein under physiological conditions does not adopt an ordered tertiary structure, rather it is classified as a natively unfolded protein which can exist as a mixture of dynamic and flexible structural conformations.

Misfolded alpha-synuclein can form multimeric intermediate oligomeric structures which eventually assemble into highly-ordered fibrillar aggregates.

The term "aggregated alpha-synuclein" as used herein, refers to insoluble or soluble oligomeric and/or polymeric structures composed of alpha-synuclein misfolded monomers and/or multimers and/or assemblies of monomers.

Pathological alpha-synuclein is misfolded or aggregated or post-translationally modified alpha-synuclein that is the main component of Lewy pathologies; Lewy pathologies can be detected as having the following morphologies: Lewy bodies, Lewy neurites, premature Lewy bodies or pale bodies, perikaryal deposits with diffuse, granular, punctate or pleomorphic patterns. Moreover, pathological alpha-synuclein is the major component of intracellular fibrillary inclusions detected in oligodendrocytes also referred to as glial cytoplasmic inclusions and in neuronal somata, axons and nuclei (referred to as neuronal cytoplasmic inclusions) that are the histological hallmarks of multiple system atrophy. Pathological alpha-synuclein in Lewy pathologies often displays substantial increase in post-translational modifications such as phosphorylation, ubiquitination, nitration, and truncation.

Seeds are multimeric beta-sheet rich structures which are composed of alpha-synuclein could be also (i.e. in addition to alpha-synuclein) composed of other amyloidogenic proteins (e.g. Tau, Amyloid β) which can accelerate the aggregation kinetics of alpha-synuclein by elongating the growing multimer and/or by acting as templates for the nucleation of monomers on the seed surface.

Spontaneous aggregation of alpha-synuclein is the aggregation process that progresses without the addition of seeds. Alpha-synuclein is a soluble protein that has the propensity to spontaneously aggregate and form soluble oligomers or soluble/insoluble protofibrils or mature fibrils or detergent-insoluble aggregates under certain conditions.

Lewy bodies are abnormal aggregates of protein that develop inside nerve cells in Parkinson's disease (PD), Lewy body dementia and other synucleinopathies. Lewy bodies appear as spherical masses that displace other cell components. Morphologically, Lewy bodies can be classified as being brainstem or cortical type. Classic brainstem Lewy bodies are eosinophilic cytoplasmic inclusions consisting of a dense core surrounded by a halo of 5-10-nm-wide radiating fibrils, the primary structural component of which is alpha-synuclein; cortical Lewy bodies differ by lacking a halo. The presence of Lewy bodies is a hallmark of Parkinson's disease.

Lewy neurites are abnormal neuronal processes in diseased neurons, containing granular material, abnormal alpha-synuclein filaments similar to those found in Lewy bodies, dot-like, varicose structures and axonal spheroids. Like Lewy bodies, Lewy neurites are a feature of a-synucleinopathies such as dementia with Lewy bodies, Parkinson's disease, and multiple system atrophy.

Glial cytoplasmic inclusions (also referred to as Papp-Lantos inclusions) consist of insoluble alpha-synuclein filamentous aggregates detected in oligodendrocytes in the white matter of multiple system atrophy brains. Alpha-synuclein aggregates in neuronal somata, axons and nuclei, referred to as neuronal cytoplasmic inclusions, are characteristic cytopathological features of multiple system atrophy. The detection of glial cytoplasmic inclusions is considered a hallmark for the neuropathological diagnosis of multiple system atrophy.

An alpha-synuclein binding molecule is a molecule that binds to the pathological and/or aggregated alpha-synuclein protein, such as an alpha-synuclein antibody or fragment thereof, at a specific recognition site, or epitope. Antigen-binding molecules of the invention bind to an epitope within the amino acid sequence of SEQ ID NO: 1. The epitope may be a linear epitope or a non-linear epitope. Preferably antigen-binding molecules of the invention bind to an epitope within amino acids residues 1-15 (SEQ ID NO: 121), 10-24 (SEQ ID NO: 122), 28-42 (SEQ ID NO: 124), 36-40 (SEQ ID NO: 2), 37-51 (SEQ ID NO: 125), 51-57 (SEQ ID NO: 3), 51-58 (SEQ ID NO: 136), 65-74 (SEQ ID NO: 4), 65-81 (SEQ ID NO: 5), 81-120 (SEQ ID NO:137), 82-96 (SEQ ID NO: 130), 91-105 (SEQ ID NO: 131), 93-95 (GFV), 100-114 (SEQ ID NO:132), 109-123 (SEQ ID NO: 133), 118-132 (SEQ ID NO: 134), 124-131 (SEQ ID NO: 7), 127-140 (SEQ ID NO: 135), 128-135 (SEQ ID NO: 8) or 131-140 (SEQ ID NO: 9) of human alpha-synuclein of SEQ ID NO: 1. More preferably, antigen-binding molecules of the invention bind to an epitope within amino acids residues 124-131 (SEQ ID NO: 7), 128-135 (SEQ ID NO: 8) or 131-140 (SEQ ID NO: 9) of human alpha-synuclein of SEQ ID NO: 1. Even more preferably, antigen-binding molecules of the invention may bind to an epitope comprising amino acids 126 and 127 of human alpha-synuclein of SEQ ID NO: 1 as critical residues for binding. In another embodiment, antigen-binding molecules of the invention bind to a non-linear epitope within amino acids residues of human alpha-synuclein of SEQ ID NO: 1.

Other alpha-synuclein binding molecules may also include multivalent molecules, multispecific molecules (e.g., diabodies or biparatopic antibodies), fusion molecules, aptamers, AVIMER® proteins, or other naturally occurring or recombinantly created molecules. Illustrative antigen-binding molecules useful in the present invention include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, designed ankyrin repeat proteins (WO 2002/020565), AFFIBODY™ molecules (WO 1995/001937), AVIMER® proteins (WO 2004/044011; WO 2005/040229), ADNECTIN™ molecules (WO 2002/032925) and FYNOMER® molecules (WO 2013/135588).

An "antigen binding molecule," as used herein, is any molecule that can specifically or selectively bind to an antigen. A binding molecule may include or be an antibody or a fragment thereof. An alpha-synuclein binding molecule is a molecule that binds to the alpha-synuclein protein, such as an alpha-synuclein antibody or fragment thereof, at a specific recognition site, epitope.

The terms "alpha-synuclein antibody", "anti-alpha-synuclein antibody" and "an antibody that binds to pathological and/or aggregated alpha-synuclein" or simply "antibody" as used herein refer to an antibody that is capable of binding pathological alpha-synuclein and/or aggregated alpha-synuclein, including, but not limited to, Lewy bodies, Lewy Neurites or glial cytoplasmic inclusions with sufficient affinity such that the antibody is useful as a therapeutic and/or diagnostic agent in targeting alpha-synuclein. In one embodiment, the extent of binding of an alpha-synuclein antibody of the invention to an unrelated, non-alpha-synuclein protein is less than about 10% of the binding of the antibody to alpha-synuclein as measured, e.g., by a radioimmunoassay (RIA).

In general, the term "antibody" is used herein in the broadest sense and encompasses various antibody structures, including but not limited to monoclonal antibodies, polyclonal antibodies, multispecific antibodies (e.g., bispecific antibodies), fully-human antibodies and antibody fragments so long as they exhibit the desired antigen-binding activity. Antibodies within the present invention may also be chimeric antibodies (especially mouse VH and VL regions fused with human constant domains), recombinant antibodies, antigen-binding fragments of recombinant antibodies, humanized antibodies or antibodies displayed upon the surface of a phage or displayed upon the surface of a chimeric antigen receptor (CAR) T-cell.

An "antigen-binding fragment" of an antibody refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F (ab') 2. The term "antibody" also comprises but is not limited to fully-human antibodies, chimeric antibodies, humanized antibodies, CDR-grafted antibodies and antibody constructs, like single chain Fvs (scFv) or antibody-fusion proteins.

Humanized antibodies are modified antibodies that are also referred to as reshaped human antibodies. A humanized antibody is constructed by transferring the CDRs of an antibody derived from an immunized animal to the complementarity determining regions of a human antibody. Conventional genetic recombination techniques for such purposes are known (see European Patent Application Publication No. EP 239400; International Publication No. WO 96/02576; Sato K. et al., Cancer Research 1993, 53:851-856; International Publication No. WO 99/51743).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. VH-CDR, or CDR-H depicts a CDR region of a variable heavy chain and VL-CDR or CDR-L relates to a CDR region of a variable light chain.

VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J., Mol. Biol. 196 (1987), 901-917 or Chothia, Nature 342 (1989), 877-883.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F (ab') 2 molecule.

A "F(ab') 2 fragment" contains two light chains and two heavy chains containing a portion of the constant region between the CH1 and CH2 domains, such that an interchain disulfide bond is formed between the two heavy chains. A F (ab') 2 fragment thus is composed of two Fab' fragments that are held together by a disulfide bond between the two heavy chains.

The "Fv region" comprises the variable regions from both the heavy and light chains, but lacks the constant regions.

Accordingly, in the context of this invention, antibody molecules or antigen-binding fragments thereof are provided, which are humanized and can successfully be employed in pharmaceutical compositions.

An "antibody that binds to an epitope" within a defined region of a protein is an antibody that requires the presence of one or more of the amino acids within that region for binding to the protein.

In certain embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 20% of the binding to unaltered protein. In some embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. In certain embodiments, binding of the antibody is determined by FACS, WB or by a suitable binding assay such as ELISA.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of alpha-synuclein. Said binding/interaction is also understood to define a "specific recognition". The term "specifically recognizing" means in accordance with this invention that the antibody is capable of specifically interacting with and/or binding to at least two amino acids of alpha-synuclein as defined herein (also known as "critical residues"), in particular interacting with/binding to at least two amino acids within residues 1-15 (SEQ ID NO: 121), 10-24 (SEQ ID NO: 122), 28-42 (SEQ ID NO: 124), 36-40 (SEQ ID NO: 2), 37-51 (SEQ ID NO:125), 51-57 (SEQ ID NO: 3), 51-58 (SEQ ID NO: 136), 65-74 (SEQ ID NO: 4), 65-81 (SEQ ID NO: 5), 81-120 (SEQ ID NO:137), 82-96 (SEQ ID NO: 130), 91-105 (SEQ ID NO: 131), 93-95 (GFV), 100-114 (SEQ ID NO:132), 109-123 (SEQ ID NO: 133), 118-132 (SEQ ID NO: 134), 124-131 (SEQ ID NO: 7), 127-140 (SEQ ID NO: 135), 128-135 (SEQ ID NO: 8) or 131-140 (SEQ ID NO: 9) of human alpha-synuclein of SEQ ID NO: 1. The residues may form a linear or a non-linear epitope. Preferably, antigen-binding molecule of the invention bind to an epitope within amino acids residues 124-131 (SEQ ID NO: 7), 128-135 (SEQ ID NO: 8) or 131-140 (SEQ ID NO: 9) of human alpha-synuclein of SEQ ID NO: 1. Even more preferably, antigen-binding molecules of the invention may bind to an epitope comprising amino acids 126 and 127 of human alpha-synuclein of SEQ ID NO: 1 as critical residues for binding. The antigen binding molecules of the invention may also bind to a non-linear epitope within amino acids residues of human alpha-synuclein of SEQ ID NO: 1.

Cross-reactivity of antigen-binding molecules, in particular a panel of antibodies or antigen-binding fragments thereof under investigation may be tested, for example, by assessing binding of said panel of antibodies or antigen-binding fragments thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly) peptide of interest as well as to a number of more or less (structurally and/or functionally) closely related (poly) peptides. Only those constructs (i.e. antibodies, antigen-binding fragments thereof and the like) that bind to the certain structure of alpha-synuclein as defined herein, e.g., a specific epitope or (poly) peptide/protein of alpha-synuclein as defined herein but do not or do not essentially bind to any of the other epitope or (poly) peptides of the same alpha-synuclein, are considered specific for the epitope or (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIACORE™), analytical ultracentrifugation, isothermal titration calorimetry, fluorescence anisotropy, fluorescence spectroscopy or by radiolabeled ligand binding assays.

Accordingly, specificity can be determined experimentally by methods known in the art and methods as described herein. Such methods comprise, but are not limited to Western Blots, ELISA-, RIA-, ECL-, IRMA-tests and peptide scans.

It may be understood by a person skilled in the art that the epitopes may be comprised in the alpha-synuclein protein, but may also be comprised in a degradation product thereof or may be a chemically synthesized peptide. The amino acid positions are only indicated to demonstrate the position of the corresponding amino acid sequence in the sequence of the alpha-synuclein protein. The invention encompasses all peptides comprising the epitope. The peptide may be a part of a polypeptide of more than 100 amino acids in length or may be a small peptide of less than 100, preferably less than 50, more preferably less than 25 amino acids, even more preferably less than 18 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophor), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane. In order to test whether an antibody in question and the antibody of the present invention recognize the same or similar epitope, many assays are known in the art, some of which (e.g. "alanine scanning mutagenesis") is described in below in example.

Whether an antibody recognizes the same epitope as or an epitope overlapping with an epitope that is recognized by another antibody as provided herein can be confirmed by competition between the two antibodies against the epitope. Competition between the antibodies can be evaluated by competitive binding assays using means such as enzyme-linked immunosorbent assay (ELISA), fluorescence energy transfer method (FRET), and fluorometric microvolume assay technology (FMAT®). The amount of antibodies bound to an antigen indirectly correlate with the binding ability of candidate competitor antibodies (test antibodies) that competitively bind to the same or overlapping epitope. In other words, as the amount of or the affinity of test antibodies against the same or overlapping epitope increases, the amount of antibodies bound to the antigen decreases, and the amount of test antibodies bound to the antigen increases. Specifically, the appropriately labeled antibodies and test antibodies are simultaneously added to the antigens, and then the bound antibodies are detected using the label. The amount of the antibodies bound to the antigen can be easily determined by labeling the antibodies in advance. This label is not particularly limited, and the labeling method is selected according to the assay technique used. Specific examples of the labeling method include fluorescent labeling, radiolabeling, and enzyme labeling.

Herein, the "antibody that binds to the overlapping epitope" or "antibody that binds to the same epitope" refers to a test antibody that can reduce the amount of binding of the labeled antibody by at least 50% at a concentration that is usually 100 times higher, preferably 80 times higher, more preferably 50 times higher, even more preferably 30 times higher, and still more preferably 10 times higher than a concentration of the non-labeled antibody at which binding of the non-labeled antibody reduces the amount of binding of the labeled antibody by 50% (IC50). The epitope recognized by the antibody can be analyzed by methods known to those skilled in the art, and for example, it can be performed by Western blotting and such.

In some embodiments, the antibody comprises:

a) a Heavy Chain Variable Region (VH) comprising the sequence of SEQ ID NO: 10 or a heavy chain variable region (VH) having at least 96%, 97%, 98%, or 99%, sequence identity to the amino acid sequence of SEQ ID NO: 10; or b) a Heavy Chain Variable Region (VH) comprising the sequence of SEQ ID NO: 20 or a heavy chain variable region (VH) having at least 96%, 97%, 98%, or 99%, sequence identity to the amino acid sequence of SEQ ID NO: 20; or c) a Heavy Chain Variable Region (VH) comprising the sequence of SEQ ID NO: 30 or a heavy chain variable region (VH) having at least 94%, 95%, 96%, 97%, 98%, or 99%, sequence identity to the amino acid sequence of SEQ ID NO: 30; or d) a Heavy Chain Variable Region (VH) comprising the sequence of SEQ ID NO: 40 or a heavy chain variable region (VH) having at least 94%, 95%, 96%, 97%, 98%, or 99%, sequence identity to the amino acid sequence of SEQ ID NO: 40; or e) a Heavy Chain Variable Region (VH) comprising the sequence of SEQ ID NO: 50 or a heavy chain variable region (VH) having at least 90%, 91%, 92%, 93%, 94%, 95%, 96%, 97%, 98%, or 99%, sequence identity to the amino acid sequence of SEQ ID NO: 50; or f) a Heavy Chain Variable Region (VH) comprising the sequence of SEQ ID NO: 60 or a heavy chain variable region (VH) having at least 89%, 90%, 91%, 92%, 93%, 94%, 95%, 96%, 97%, 98%, or 99% sequence identity to the amino acid sequence of SEQ ID NO: 60; or g) a Heavy Chain Variable Region (VH) comprising the sequence of SEQ ID NO: 70 or a heavy chain variable region (VH) having at least 91%, 92%, 93%, 94%, 95%, 96%, 97%, 98%, or 99% sequence identity to the amino acid sequence of SEQ ID NO: 70; or h) a Heavy Chain Variable Region (VH) comprising the sequence of SEQ ID NO: 90 or a heavy chain variable region (VH) having at least 94%, 95%, 96%, 97%, 98%, or 99% sequence identity to the amino acid sequence of SEQ ID NO: 90; or i) a Heavy Chain Variable Region (VH) comprising the sequence of SEQ ID NO: 100 or a heavy chain variable region (VH) having at least 87%, 88%, 89%, 90%, 91%, 92%, 93%, 94%, 95%, 96%, 97%, 98%, or 99% sequence identity to the amino acid sequence of SEQ ID NO: 100; or j) a Heavy Chain Variable Region (VH) comprising the sequence of SEQ ID NO: 110 or a heavy chain variable region (VH) having at least 97%, 98%, or 99% sequence identity to the amino acid sequence of SEQ ID NO: 110; or k) a Heavy Chain Variable Region (VH) comprising the sequence of SEQ ID NO: 280 or a heavy chain variable region (VH) having at least 91%, 92%, 93%, 94%, 95%, 96%, 97%, 98%, or 99% sequence identity to the amino acid sequence of SEQ ID NO: 280; or l) a Heavy Chain Variable Region (VH) comprising the sequence of SEQ ID NO: 290 or a heavy chain variable region (VH) having at least 91%, 92%, 93%, 94%, 95%, 96%, 97%, 98% or 99% sequence identity to the amino acid sequence of SEQ ID NO: 290; or m) a Heavy Chain Variable Region (VH) comprising the sequence of SEQ ID NO: 140 or a heavy chain variable region (VH) having at least 94%, 95%, 96%, 97%, 98% or 99% sequence identity to the amino acid sequence of SEQ ID NO: 140; or n) a Heavy Chain Variable Region (VH) comprising the sequence of SEQ ID NO: 150 or a heavy chain variable region (VH) having at least 90%, 91%, 92%, 93%, 94%, 95%, 96%, 97%, 98% or 99% sequence identity to the amino acid sequence of SEQ ID NO: 150; or o) a Heavy Chain Variable Region (VH) comprising the sequence of SEQ ID NO: 160 or a heavy chain variable region (VH) having at least 97%, 98% or 99% sequence identity to the amino acid sequence of SEQ ID NO: 160; or p) a Heavy Chain Variable Region (VH) comprising the sequence of SEQ ID NO: 170 or a heavy chain variable region (VH) having at least least 84%, 85%, 86%, 87%, 88%, 89%, 90%, 91%, 92%, 93%, 94%, 95%, 96%, 97%, 98% or 99% sequence identity to the amino acid sequence of SEQ ID NO: 170; or q) a Heavy Chain Variable Region (VH) comprising the sequence of SEQ ID NO: 180 or a heavy chain variable region (VH) having at least 93%, 94%, 95%, 96%, 97%, 98% or 99% sequence identity to the amino acid sequence of SEQ ID NO: 180; or r) a Heavy Chain Variable Region (VH) comprising the sequence of SEQ ID NO: 190 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 190; or s) a Heavy Chain Variable Region (VH) comprising the sequence of SEQ ID NO: 200 or a heavy chain variable region (VH) having at least 93%, 94%, 95%, 96%, 97%, 98% or 99% sequence identity to the amino acid sequence of SEQ ID NO: 200; or t) a Heavy Chain Variable Region (VH) comprising the sequence of SEQ ID NO: 210 or a heavy chain variable region (VH) having at least 91%, 92%, 93%, 94%, 95%, 96%, 97%, 98% or 99% sequence identity to the amino acid sequence of SEQ ID NO: 210; or u) a Heavy Chain Variable Region (VH) comprising the sequence of SEQ ID NO: 220 or a heavy chain variable region (VH) having at least 97%, 98% or 99% sequence identity to the amino acid sequence of SEQ ID NO: 220; or v) a Heavy Chain Variable Region (VH) comprising the sequence of SEQ ID NO: 230 or a heavy chain variable region (VH) having at least 90%, 91%, 92%, 93%, 94%, 95%, 96%, 97%, 98% or 99% sequence identity to the amino acid sequence of SEQ ID NO: 230; or w) a Heavy Chain Variable Region (VH) comprising the sequence of SEQ ID NO: 240 or a heavy chain variable region (VH) having at least 96%, 97%, 98% or 99% sequence identity to the amino acid sequence of SEQ ID NO: 240; or x) a Heavy Chain Variable Region (VH) comprising the sequence of SEQ ID NO: 250 or a heavy chain variable region (VH) having at least 90%, 91%, 92%, 93%, 94%, 95%, 96%, 97%, 98% or 99% sequence identity to the amino acid sequence of SEQ ID NO: 250; or y) a Heavy Chain Variable Region (VH) comprising the sequence of SEQ ID NO: 260 or a heavy chain variable region (VH) having at least 92%, 93%, 94%, 95%, 96%, 97%, 98% or 99% sequence identity to the amino acid sequence of SEQ ID NO: 260; or z) a Heavy Chain Variable Region (VH) comprising the sequence of SEQ ID NO: 270 or a heavy chain variable region (VH) having at least 85%, 86%, 87%, 88%, 89%, 90%, 91%, 92%, 93%, 94%, 95%, 96%, 97%, 98% or 99% sequence identity to the amino acid sequence of SEQ ID NO: 270; or aa) a Heavy Chain Variable Region (VH) comprising the sequence of SEQ ID NO: 300 or a heavy chain variable region (VH) having at least 97%, 98% or 99% sequence identity to the amino acid sequence of SEQ ID NO: 300; or bb) a Heavy Chain Variable Region (VH) comprising the sequence of SEQ ID NO: 310 or a heavy chain variable region (VH) having at least 94%, 95%, 96%, 97%, 98% or 99% sequence identity to the amino acid sequence of SEQ ID NO: 310; or cc) a Heavy Chain Variable Region (VH) comprising the sequence of SEQ ID NO: 320 or a heavy chain variable region (VH) having at least 94%, 95%, 96%, 97%, 98% or 99% sequence identity to the amino acid sequence of SEQ ID NO: 320; or dd) a Heavy Chain Variable Region (VH) comprising the sequence of SEQ ID NO: 330 or a heavy chain variable region (VH) having at least 96%, 97%, 98% or 99% sequence identity to the amino acid sequence of SEQ ID NO: 330; or ee) a Heavy Chain Variable Region (VH) comprising the sequence of SEQ ID NO: 340 or a heavy chain variable region (VH) having at least 93%, 94%, 95%, 96%, 97%, 98% or 99% sequence identity to the amino acid sequence of SEQ ID NO: 340; or ff) a Heavy Chain Variable Region (VH) comprising the sequence of SEQ ID NO: 350 or a heavy chain variable region (VH) having at least 92%, 93%, 94%, 95%, 96%, 97%, 98% or 99% sequence identity to the amino acid sequence of SEQ ID NO: 350; or gg) a Heavy Chain Variable Region (VH) comprising the sequence of SEQ ID NO: 360 or a heavy chain variable region (VH) having at least 93%, 94%, 95%, 96%, 97%, 98% or 99% sequence identity to the amino acid sequence of SEQ ID NO: 360; or hh) a Heavy Chain Variable Region (VH) comprising the sequence of SEQ ID NO: 370 or a heavy chain variable region (VH) having at least 90%, 91%, 92%, 93%, 94%, 95%, 96%, 97%, 98% or 99% sequence identity to the amino acid sequence of SEQ ID NO: 370; or ii) a Heavy Chain Variable Region (VH) comprising the sequence of SEQ ID NO: 380 or a heavy chain variable region (VH) having at least 92%, 93%, 94%, 95%, 96%, 97%, 98% or 99% sequence identity to the amino acid sequence of SEQ ID NO: 380; or jj) a Heavy Chain Variable Region (VH) comprising the sequence of SEQ ID NO: 390 or a heavy chain variable region (VH) having at least 91%, 92%, 93%, 94%, 95%, 96%, 97%, 98% or 99% sequence identity to the amino acid sequence of SEQ ID NO: 390; or kk) a Heavy Chain Variable Region (VH) comprising the sequence of SEQ ID NO: 400 or a heavy chain variable region (VH) having at least 93%, 94%, 95%, 96%, 97%, 98% or 99% sequence identity to the amino acid sequence of SEQ ID NO: 400; or ll) a Heavy Chain Variable Region (VH) comprising the sequence of SEQ ID NO: 410 or a heavy chain variable region (VH) having at least 92%, 93%, 94%, 95%, 96%, 97%, 98% or 99% sequence identity to the amino acid sequence of SEQ ID NO: 410; or mm) a Heavy Chain Variable Region (VH) comprising the sequence of SEQ ID NO: 420 or a heavy chain variable region (VH) having at least 94%, 95%, 96%, 97%, 98% or 99% sequence identity to the amino acid sequence of SEQ ID NO: 420; or nn) a Heavy Chain Variable Region (VH) comprising the sequence of SEQ ID NO: 430 or a heavy chain variable region (VH) having at least 96%, 97%, 98% or 99% sequence identity to the amino acid sequence of SEQ ID NO: 430; or oo) a Heavy Chain Variable Region (VH) comprising the sequence of SEQ ID NO: 440 or a heavy chain variable region (VH) having at least 93%, 94%, 95%, 96%, 97%, 98% or 99% sequence identity to the amino acid sequence of SEQ ID NO: 440; or pp) a Heavy Chain Variable Region (VH) comprising the sequence of SEQ ID NO: 450 or a heavy chain variable region (VH) having at least 93%, 94%, 95%, 96%, 97%, 98% or 99% sequence identity to the amino acid sequence of SEQ ID NO: 450; or qq) a Heavy Chain Variable Region (VH) comprising the sequence of SEQ ID NO: 460 or a heavy chain variable region (VH) having at least 94%, 95%, 96%, 97%, 98% or 99% sequence identity to the amino acid sequence of SEQ ID NO: 460; or rr) a Heavy Chain Variable Region (VH) comprising the sequence of SEQ ID NO: 470 or a heavy chain variable region (VH) having at least 96%, 97%, 98% or 99% sequence identity to the amino acid sequence of SEQ ID NO: 470; or ss) a Heavy Chain Variable Region (VH) comprising the sequence of SEQ ID NO: 480 or a heavy chain variable region (VH) having at least 98% or 99% sequence identity to the amino acid sequence of SEQ ID NO: 480; or tt) a Heavy Chain Variable Region (VH) comprising the sequence of SEQ ID NO: 490 or a heavy chain variable region (VH) having at least 98% or 99% sequence identity to the amino acid sequence of SEQ ID NO: 490; or uu) a Heavy Chain Variable Region (VH) comprising the sequence of SEQ ID NO: 500 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 500; or vv) a Heavy Chain Variable Region (VH) comprising the sequence of SEQ ID NO: 510 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 510; or ww) a Heavy Chain Variable Region (VH) comprising the sequence of SEQ ID NO: 520 or a heavy chain variable region (VH) having at least 89%, 90%, 91%, 92%, 93%, 94%, 95%, 96%, 97%, 98% or 99% sequence identity to the amino acid sequence of SEQ ID NO: 520; or xx) a Heavy Chain Variable Region (VH) comprising the sequence of SEQ ID NO: 530 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 530; or yy) a Heavy Chain Variable Region (VH) comprising the sequence of SEQ ID NO: 540 or a heavy chain variable region (VH) having at least 91%, 92%, 93%, 94%, 95%, 96%, 97%, 98% or 99% sequence identity to the amino acid sequence of SEQ ID NO: 540; or zz) a Heavy Chain Variable Region (VH) comprising the sequence of SEQ ID NO: 550 or a heavy chain variable region (VH) having at least 89%, 90%, 91%, 92%, 93%, 94%, 95%, 96%, 97%, 98% or 99% sequence identity to the amino acid sequence of SEQ ID NO: 550; or aaa) a Heavy Chain Variable Region (VH) comprising the sequence of SEQ ID NO: 560 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 560; or bbb) a Heavy Chain Variable Region (VH) comprising the sequence of SEQ ID NO: 570 or a heavy chain variable region (VH) having at least 92%, 93%, 94%, 95%, 96%, 97%, 98% or 99% sequence identity to the amino acid sequence of SEQ ID NO: 570; or ccc) a Heavy Chain Variable Region (VH) comprising the sequence of SEQ ID NO: 580 or a heavy chain variable region (VH) having at least 95%, 96%, 97%, 98% or 99% sequence identity to the amino acid sequence of SEQ ID NO: 580; or ddd) a Heavy Chain Variable Region (VH) comprising the sequence of SEQ ID NO: 590 or a heavy chain variable region (VH) having at least 95%, 96%, 97%, 98% or 99% sequence identity to the amino acid sequence of SEQ ID NO: 590; or eee) a Heavy Chain Variable Region (VH) comprising the sequence of SEQ ID NO: 600 or a heavy chain variable region (VH) having at least 89%, 90%, 91%, 92%, 93%, 94%, 95%, 96%, 97%, 98% or 99% sequence identity to the amino acid sequence of SEQ ID NO: 600; or fff) a Heavy Chain Variable Region (VH) comprising the sequence of SEQ ID NO: 610 or a heavy chain variable region (VH) having at least 90%, 91%, 92%, 93%, 94%, 95%, 96%, 97%, 98% or 99% sequence identity to the amino acid sequence of SEQ ID NO: 610; or ggg) a Heavy Chain Variable Region (VH) comprising the sequence of SEQ ID NO: 620 or a heavy chain variable region (VH) having at least 89%, 90%, 91%, 92%, 93%, 94%, 95%, 96%, 97%, 98% or 99% sequence identity to the amino acid sequence of SEQ ID NO: 620; or hhh) a Heavy Chain Variable Region (VH) comprising the sequence of SEQ ID NO: 630 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 630; or iii) a Heavy Chain Variable Region (VH) comprising the sequence of SEQ ID NO: 640 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 640; or jjj) a Heavy Chain Variable Region (VH) comprising the sequence of SEQ ID NO: 650 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 650; or kkk) a Heavy Chain Variable Region (VH) comprising the sequence of SEQ ID NO: 660 or a heavy chain variable region (VH) having at least 89%, 90%, 91%, 92%, 93%, 94%, 95%, 96%, 97%, 98% or 99% sequence identity to the amino acid sequence of SEQ ID NO: 660; or lll) a Heavy Chain Variable Region (VH) comprising the sequence of SEQ ID NO: 670 or a heavy chain variable region (VH) having at least 89%, 90%, 91%, 92%, 93%, 94%, 95%, 96%, 97%, 98% or 99% sequence identity to the amino acid sequence of SEQ ID NO: 670; or mmm) a Heavy Chain Variable Region (VH) comprising the sequence of SEQ ID NO: 680 or a heavy chain variable region (VH) having at least 87%, 88%, 89%, 90%, 91%, 92%, 93%, 94%, 95%, 96%, 97%, 98% or 99% sequence identity to the amino acid sequence of SEQ ID NO: 680; or nnn) a Heavy Chain Variable Region (VH) comprising the sequence of SEQ ID NO: 690 or a heavy chain variable region (VH) having at least 87%, 88%, 89%, 90%, 91%, 92%, 93%, 94%, 95%, 96%, 97%, 98% or 99% sequence identity to the amino acid sequence of SEQ ID NO: 690; or ooo) a Heavy Chain Variable Region (VH) comprising the sequence of SEQ ID NO: 700 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 700; or ppp) a Heavy Chain Variable Region (VH) comprising the sequence of SEQ ID NO: 710 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 710; or qqq) a Heavy Chain Variable Region (VH) comprising the sequence of SEQ ID NO: 720 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 720.

In some embodiments, the antibody comprises:

a) a Light Chain Variable Region (VL) comprising the sequence of SEQ ID NO: 14 or a light chain variable region (VL) having at least 99% sequence identity to the amino acid sequence of SEQ ID NO: 14; or b) a Light Chain Variable Region (VL) comprising the sequence of SEQ ID NO: 24 or a light chain variable region (VL) having at least 93%, 94%, 95%, 96%, 97%, 98%, or 99% sequence identity to the amino acid sequence of SEQ ID NO: 24; or c) a Light Chain Variable Region (VL) comprising the sequence of SEQ ID NO: 34 or a light chain variable region (VL) having at least 98%, or 99% sequence identity to the amino acid sequence of SEQ ID NO: 34; or d) a Light Chain Variable Region (VL) comprising the sequence of SEQ ID NO: 44 or a light chain variable region (VL) having at least 94%, 95%, 96%, 97%, 98%, or 99% sequence identity to the amino acid sequence of SEQ ID NO: 44; or e) a Light Chain Variable Region (VL) comprising the sequence of SEQ ID NO: 54 or a light chain variable region (VL) having at least 93%, 94%, 95%, 96%, 97%, 98%, or 99% sequence identity to the amino acid sequence of SEQ ID NO: 54; or f) a Light Chain Variable Region (VL) comprising the sequence of SEQ ID NO: 64 or a light chain variable region (VL) having at least 96%, 97%, 98%, or 99% sequence identity to the amino acid sequence of SEQ ID NO: 64; or g) a Light Chain Variable Region (VL) comprising the sequence of SEQ ID NO: 74 or a light chain variable region (VL) having at least 90%, 91%, 92%, 93%, 94%, 95%, 96%, 97%, 98%, or 99% sequence identity to the amino acid sequence of SEQ ID NO: 74; or h) a Light Chain Variable Region (VL) comprising the sequence of SEQ ID NO: 84 or a light chain variable region (VL) having at least 94%, 95%, 96%, 97%, 98%, or 99% sequence identity to the amino acid sequence of SEQ ID NO: 84; or i) a Light Chain Variable Region (VL) comprising the sequence of SEQ ID NO: 94 or a light chain variable region (VL) having at least 99% sequence identity to the amino acid sequence of SEQ ID NO: 94; or j) a Light Chain Variable Region (VL) comprising the sequence of SEQ ID NO: 104 or a light chain variable region (VL) having at least 98% or 99% sequence identity to the amino acid sequence of SEQ ID NO: 104; or k) a Light Chain Variable Region (VL) comprising the sequence of SEQ ID NO: 114; or l) a Light Chain Variable Region (VL) comprising the sequence of SEQ ID NO: 284; or m) a Light Chain Variable Region (VL) comprising the sequence of SEQ ID NO: 194 or a light chain variable region (VL) having at least 95%, 96%, 97%, 98% or 99% sequence identity to the amino acid sequence of SEQ ID NO: 194; or n) a Light Chain Variable Region (VL) comprising the sequence of SEQ ID NO: 144 or a light chain variable region (VL) having at least 97%, 98% or 99% sequence identity to the amino acid sequence of SEQ ID NO: 144; or o) a Light Chain Variable Region (VL) comprising the sequence of SEQ ID NO: 154 or a light chain variable region (VL) having at least 98% or 99% sequence identity to the amino acid sequence of SEQ ID NO: 154; or p) a Light Chain Variable Region (VL) comprising the sequence of SEQ ID NO: 174 or a light chain variable region (VL) having at least 93%, 94%, 95%, 96%, 97%, 98% or 99% sequence identity to the amino acid sequence of SEQ ID NO: 174; or q) a Light Chain Variable Region (VL) comprising the sequence of SEQ ID NO: 184; or r) a Light Chain Variable Region (VL) comprising the sequence of SEQ ID NO: 204 or a light chain variable region (VL) having at least 97%, 98% or 99% sequence identity to the amino acid sequence of SEQ ID NO: 204; or s) a Light Chain Variable Region (VL) comprising the sequence of SEQ ID NO: 214 or a light chain variable region (VL) having at least 97%, 98% or 99% sequence identity to the amino acid sequence of SEQ ID NO: 214; or t) a Light Chain Variable Region (VL) comprising the sequence of SEQ ID NO: 224 or a light chain variable region (VL) having at least 92%, 93%, 94%, 95%, 96%, 97%, 98% or 99% sequence identity to the amino acid sequence of SEQ ID NO: 224; or u) a Light Chain Variable Region (VL) comprising the sequence of SEQ ID NO: 234 or a light chain variable region (VL) having at least 97%, 98% or 99% sequence identity to the amino acid sequence of SEQ ID NO: 234; or v) a Light Chain Variable Region (VL) comprising the sequence of SEQ ID NO: 244 or a light chain variable region (VL) having at least 94%, 95%, 96%, 97%, 98% or 99% sequence identity to the amino acid sequence of SEQ ID NO: 244; or w) a Light Chain Variable Region (VL) comprising the sequence of SEQ ID NO: 254 or a light chain variable region (VL) having at least 94%, 95%, 96%, 97%, 98% or 99% sequence identity to the amino acid sequence of SEQ ID NO: 254; or x) a Light Chain Variable Region (VL) comprising the sequence of SEQ ID NO: 264 or a light chain variable region (VL) having at least 96%, 97%, 98% or 99% sequence identity to the amino acid sequence of SEQ ID NO: 264; or y) a Light Chain Variable Region (VL) comprising the sequence of SEQ ID NO: 274 or a light chain variable region (VL) having at least 91%, 92%, 93%, 94%, 95%, 96%, 97%, 98% or 99% sequence identity to the amino acid sequence of SEQ ID NO: 274; or z) a Light Chain Variable Region (VL) comprising the sequence of SEQ ID NO: 304 or a light chain variable region (VL) having at least 97%, 98% or 99% sequence identity to the amino acid sequence of SEQ ID NO: 304; or aa) a Light Chain Variable Region (VL) comprising the sequence of SEQ ID NO: 314 or a light chain variable region (VL) having at least 96%, 97%, 98% or 99% sequence identity to the amino acid sequence of SEQ ID NO: 314; or bb) a Light Chain Variable Region (VL) comprising the sequence of SEQ ID NO: 324 or a light chain variable region (VL) having at least 99% sequence identity to the amino acid sequence of SEQ ID NO: 324; or cc) a Light Chain Variable Region (VL) comprising the sequence of SEQ ID NO: 334 or a light chain variable region (VL) having at least 97%, 98% or 99% sequence identity to the amino acid sequence of SEQ ID NO: 334; or dd) a Light Chain Variable Region (VL) comprising the sequence of SEQ ID NO: 344 or a light chain variable region (VL) having at least 98% or 99% sequence identity to the amino acid sequence of SEQ ID NO: 344; or ee) a Light Chain Variable Region (VL) comprising the sequence of SEQ ID NO: 354 or a light chain variable region (VL) having at least 95%, 96%, 97%, 98% or 99% sequence identity to the amino acid sequence of SEQ ID NO: 354; or ff) a Light Chain Variable Region (VL) comprising the sequence of SEQ ID NO: 364 or a light chain variable region (VL) having at least 99% sequence identity to the amino acid sequence of SEQ ID NO: 364; or gg) a Light Chain Variable Region (VL) comprising the sequence of SEQ ID NO: 374 or a light chain variable region (VL) having at least 98% or 99% sequence identity to the amino acid sequence of SEQ ID NO: 374; or hh) a Light Chain Variable Region (VL) comprising the sequence of SEQ ID NO: 384 or a light chain variable region (VL) having at least 95%, 96%, 97%, 98% or 99% sequence identity to the amino acid sequence of SEQ ID NO: 384; or ii) a Light Chain Variable Region (VL) comprising the sequence of SEQ ID NO: 394 or a light chain variable region (VL) having at least 96%, 97%, 98% or 99% sequence identity to the amino acid sequence of SEQ ID NO: 394; or jj) a Light Chain Variable Region (VL) comprising the sequence of SEQ ID NO: 404 or a light chain variable region (VL) having at least 93%, 94%, 95%, 96%, 97%, 98% or 99% sequence identity to the amino acid sequence of SEQ ID NO: 404; or kk) a Light Chain Variable Region (VL) comprising the sequence of SEQ ID NO: 414; or ll) a Light Chain Variable Region (VL) comprising the sequence of SEQ ID NO: 424 or a light chain variable region (VL) having at least 99% sequence identity to the amino acid sequence of SEQ ID NO: 424; or mm) a Light Chain Variable Region (VL) comprising the sequence of SEQ ID NO: 434 or a light chain variable region (VL) having at least 98% or 99% sequence identity to the amino acid sequence of SEQ ID NO: 434; or nn) a Light Chain Variable Region (VL) comprising the sequence of SEQ ID NO: 464 or a light chain variable region (VL) having at least 99% sequence identity to the amino acid sequence of SEQ ID NO: 464; or oo) a Light Chain Variable Region (VL) comprising the sequence of SEQ ID NO: 474 or a light chain variable region (VL) having at least 99% sequence identity to the amino acid sequence of SEQ ID NO: 474; or pp) a Light Chain Variable Region (VL) comprising the sequence of SEQ ID NO: 484; or qq) a Light Chain Variable Region (VL) comprising the sequence of SEQ ID NO: 494 or a light chain variable region (VL) having at least 99% sequence identity to the amino acid sequence of SEQ ID NO: 494; or rr) a Light Chain Variable Region (VL) comprising the sequence of SEQ ID NO: 504 or a light chain variable region (VL) having at least 97%, 98% or 99% sequence identity to the amino acid sequence of SEQ ID NO: 504; or ss) a Light Chain Variable Region (VL) comprising the sequence of SEQ ID NO: 514 or a light chain variable region (VL) having at least 98% or 99% sequence identity to the amino acid sequence of SEQ ID NO: 514; or tt) a Light Chain Variable Region (VL) comprising the sequence of SEQ ID NO: 524 or a light chain variable region (VL) having at least 99% sequence identity to the amino acid sequence of SEQ ID NO: 524; or uu) a Light Chain Variable Region (VL) comprising the sequence of SEQ ID NO: 544; or vv) a Light Chain Variable Region (VL) comprising the sequence of SEQ ID NO: 554 or a light chain variable region (VL) having at least 99% sequence identity to the amino acid sequence of SEQ ID NO: 554; or ww) a Light Chain Variable Region (VL) comprising the sequence of SEQ ID NO: 564 or a light chain variable region (VL) having at least 98% or 99% sequence identity to the amino acid sequence of SEQ ID NO: 564; or xx) a Light Chain Variable Region (VL) comprising the sequence of SEQ ID NO: 574 or a light chain variable region (VL) having at least 97%, 98% or 99% sequence identity to the amino acid sequence of SEQ ID NO: 574; or yy) a Light Chain Variable Region (VL) comprising the sequence of SEQ ID NO: 584 or a light chain variable region (VL) having at least 99% sequence identity to the amino acid sequence of SEQ ID NO: 584; or zz) a Light Chain Variable Region (VL) comprising the sequence of SEQ ID NO: 614 or a light chain variable region (VL) having at least 94%, 95%, 96%, 97%, 98% or 99% sequence identity to the amino acid sequence of SEQ ID NO: 614; or aaa) a Light Chain Variable Region (VL) comprising the sequence of SEQ ID NO: 624 or a light chain variable region (VL) having at least 93%, 94%, 95%, 96%, 97%, 98% or 99% sequence identity to the amino acid sequence of SEQ ID NO: 624; or bbb) a Light Chain Variable Region (VL) comprising the sequence of SEQ ID NO: 634 or a light chain variable region (VL) having at least 93%, 94%, 95%, 96%, 97%, 98% or 99% sequence identity to the amino acid sequence of SEQ ID NO: 634; or ccc) a Light Chain Variable Region (VL) comprising the sequence of SEQ ID NO: 644 or a light chain variable region (VL) having at least 92%, 93%, 94%, 95%, 96%, 97%, 98% or 99% sequence identity to the amino acid sequence of SEQ ID NO: 644.

In some embodiments, the antibody comprises:

a) a Heavy Chain Variable Region (VH) comprising the sequence of SEQ ID NO: 10 and a Light Chain Variable Region (VL) comprising the sequence of SEQ ID NO: 14; or b) a Heavy Chain Variable Region (VH) comprising the sequence of SEQ ID NO: 20 and a Light Chain Variable Region (VL) comprising the sequence of SEQ ID NO: 24; or c) a Heavy Chain Variable Region (VH) comprising the sequence of SEQ ID NO: 30; and a Light Chain Variable Region (VL) comprising the sequence of SEQ ID NO: 34; or d) a Heavy Chain Variable Region (VH) comprising the sequence of SEQ ID NO: 40; and a Light Chain Variable Region (VL) comprising the sequence of SEQ ID NO: 44; or e) a Heavy Chain Variable Region (VH) comprising the sequence of SEQ ID NO: 50; and a Light Chain Variable Region (VL) comprising the sequence of SEQ ID NO: 54; or f) a Heavy Chain Variable Region (VH) comprising the sequence of SEQ ID NO: 60; and a Light Chain Variable Region (VL) comprising the sequence of SEQ ID NO: 64; or g) a Heavy Chain Variable Region (VH) comprising the sequence of SEQ ID NO: 70; and a Light Chain Variable Region (VL) comprising the sequence of SEQ ID NO: 74; or h) a Heavy Chain Variable Region (VH) comprising the sequence of SEQ ID NO: 30; and a Light Chain Variable Region (VL) comprising the sequence of SEQ ID NO: 84; or i) a Heavy Chain Variable Region (VH) comprising the sequence of SEQ ID NO: 90; and a Light Chain Variable Region (VL) comprising the sequence of SEQ ID NO: 94; or j) a Heavy Chain Variable Region (VH) comprising the sequence of SEQ ID NO: 100; and a Light Chain Variable Region (VL) comprising the sequence of SEQ ID NO: 104; or k) a Heavy Chain Variable Region (VH) comprising the sequence of SEQ ID NO: 110; and a Light Chain Variable Region (VL) comprising the sequence of SEQ ID NO: 114; or l) a Heavy Chain Variable Region (VH) comprising the sequence of SEQ ID NO: 280; and a Light Chain Variable Region (VL) comprising the sequence of SEQ ID NO: 284; or m) a Heavy Chain Variable Region (VH) comprising the sequence of SEQ ID NO: 290; and a Light Chain Variable Region (VL) comprising the sequence of SEQ ID NO: 194; or n) a Heavy Chain Variable Region (VH) comprising the sequence of SEQ ID NO: 140; and a Light Chain Variable Region (VL) comprising the sequence of SEQ ID NO: 144; or 0) a Heavy Chain Variable Region (VH) comprising the sequence of SEQ ID NO: 150; and a Light Chain Variable Region (VL) comprising the sequence of SEQ ID NO: 154; or p) a Heavy Chain Variable Region (VH) comprising the sequence of SEQ ID NO: 160; and a Light Chain Variable Region (VL) comprising the sequence of SEQ ID NO: 164; or q) a Heavy Chain Variable Region (VH) comprising the sequence of SEQ ID NO: 170; and a Light Chain Variable Region (VL) comprising the sequence of SEQ ID NO: 174; or r) a Heavy Chain Variable Region (VH) comprising the sequence of SEQ ID NO: 180; and a Light Chain Variable Region (VL) comprising the sequence of SEQ ID NO: 184; or s) a Heavy Chain Variable Region (VH) comprising the sequence of SEQ ID NO: 190; and a Light Chain Variable Region (VL) comprising the sequence of SEQ ID NO: 194; or t) a Heavy Chain Variable Region (VH) comprising the sequence of SEQ ID NO: 200; and a Light Chain Variable Region (VL) comprising the sequence of SEQ ID NO: 204; or u) a Heavy Chain Variable Region (VH) comprising the sequence of SEQ ID NO: 210; and a Light Chain Variable Region (VL) comprising the sequence of SEQ ID NO: 214; or v) a Heavy Chain Variable Region (VH) comprising the sequence of SEQ ID NO: 220; and a Light Chain Variable Region (VL) comprising the sequence of SEQ ID NO: 224; or w) a Heavy Chain Variable Region (VH) comprising the sequence of SEQ ID NO: 230; and a Light Chain Variable Region (VL) comprising the sequence of SEQ ID NO: 234;

x) a Heavy Chain Variable Region (VH) comprising the sequence of SEQ ID NO: 240; and a Light Chain Variable Region (VL) comprising the sequence of SEQ ID NO: 244; or y) a Heavy Chain Variable Region (VH) comprising the sequence of SEQ ID NO: 250; and a Light Chain Variable Region (VL) comprising the sequence of SEQ ID NO: 254; or z) a Heavy Chain Variable Region (VH) comprising the sequence of SEQ ID NO: 260; and a Light Chain Variable Region (VL) comprising the sequence of SEQ ID NO: 264; or aa) a Heavy Chain Variable Region (VH) comprising the sequence of SEQ ID NO: 270; and a Light Chain Variable Region (VL) comprising the sequence of SEQ ID NO: 274; or bb) a Heavy Chain Variable Region (VH) comprising the sequence of SEQ ID NO: 300 and a Light Chain Variable Region (VL) comprising the sequence of SEQ ID NO: 304; or cc) a Heavy Chain Variable Region (VH) comprising the sequence of SEQ ID NO: 310 and a Light Chain Variable Region (VL) comprising the sequence of SEQ ID NO: 314; or dd) a Heavy Chain Variable Region (VH) comprising the sequence of SEQ ID NO: 320 and a Light Chain Variable Region (VL) comprising the sequence of SEQ ID NO: 324; or ee) a Heavy Chain Variable Region (VH) comprising the sequence of SEQ ID NO: 330 and a Light Chain Variable Region (VL) comprising the sequence of SEQ ID NO: 334; or ff) a Heavy Chain Variable Region (VH) comprising the sequence of SEQ ID NO: 340 and a Light Chain Variable Region (VL) comprising the sequence of SEQ ID NO: 344; or gg) a Heavy Chain Variable Region (VH) comprising the sequence of SEQ ID NO: 350 and a Light Chain Variable Region (VL) comprising the sequence of SEQ ID NO: 354; or hh) a Heavy Chain Variable Region (VH) comprising the sequence of SEQ ID NO: 360 and a Light Chain Variable Region (VL) comprising the sequence of SEQ ID NO: 364; or ii) a Heavy Chain Variable Region (VH) comprising the sequence of SEQ ID NO: 370 and a Light Chain Variable Region (VL) comprising the sequence of SEQ ID NO: 374; or jj) a Heavy Chain Variable Region (VH) comprising the sequence of SEQ ID NO: 380 and a Light Chain Variable Region (VL) comprising the sequence of SEQ ID NO: 384; or kk) a Heavy Chain Variable Region (VH) comprising the sequence of SEQ ID NO: 390 and a Light Chain Variable Region (VL) comprising the sequence of SEQ ID NO: 394; or ll) a Heavy Chain Variable Region (VH) comprising the sequence of SEQ ID NO: 400 and a Light Chain Variable Region (VL) comprising the sequence of SEQ ID NO: 404; or mm) a Heavy Chain Variable Region (VH) comprising the sequence of SEQ ID NO: 410 and a Light Chain Variable Region (VL) comprising the sequence of SEQ ID NO: 414; or nn) a Heavy Chain Variable Region (VH) comprising the sequence of SEQ ID NO: 420 and a Light Chain Variable Region (VL) comprising the sequence of SEQ ID NO: 424; or oo) a Heavy Chain Variable Region (VH) comprising the sequence of SEQ ID NO: 430 and a Light Chain Variable Region (VL) comprising the sequence of SEQ ID NO: 434; or pp) a Heavy Chain Variable Region (VH) comprising the sequence of SEQ ID NO: 440 and a Light Chain Variable Region (VL) comprising the sequence of SEQ ID NO: 414; or qq) a Heavy Chain Variable Region (VH) comprising the sequence of SEQ ID NO: 450 and a Light Chain Variable Region (VL) comprising the sequence of SEQ ID NO: 424; or rr) a Heavy Chain Variable Region (VH) comprising the sequence of SEQ ID NO: 460 and a Light Chain Variable Region (VL) comprising the sequence of SEQ ID NO: 464; or ss) a Heavy Chain Variable Region (VH) comprising the sequence of SEQ ID NO: 470 and a Light Chain Variable Region (VL) comprising the sequence of SEQ ID NO: 474; or tt) a Heavy Chain Variable Region (VH) comprising the sequence of SEQ ID NO: 480 and a Light Chain Variable Region (VL) comprising the sequence of SEQ ID NO: 484; or uu) a Heavy Chain Variable Region (VH) comprising the sequence of SEQ ID NO: 490 and a Light Chain Variable Region (VL) comprising the sequence of SEQ ID NO: 494; or vv) a Heavy Chain Variable Region (VH) comprising the sequence of SEQ ID NO: 500 and a Light Chain Variable Region (VL) comprising the sequence of SEQ ID NO: 504; or ww) a Heavy Chain Variable Region (VH) comprising the sequence of SEQ ID NO: 510 and a Light Chain Variable Region (VL) comprising the sequence of SEQ ID NO: 514; or xx) a Heavy Chain Variable Region (VH) comprising the sequence of SEQ ID NO: 520 and a Light Chain Variable Region (VL) comprising the sequence of SEQ ID NO: 524; or yy) a Heavy Chain Variable Region (VH) comprising the sequence of SEQ ID NO: 530 and a Light Chain Variable Region (VL) comprising the sequence of SEQ ID NO: 534; or zz) a Heavy Chain Variable Region (VH) comprising the sequence of SEQ ID NO: 540 and a Light Chain Variable Region (VL) comprising the sequence of SEQ ID NO: 544; or aaa) a Heavy Chain Variable Region (VH) comprising the sequence of SEQ ID NO: 550 and a Light Chain Variable Region (VL) comprising the sequence of SEQ ID NO: 554; or bbb) a Heavy Chain Variable Region (VH) comprising the sequence of SEQ ID NO: 560 and a Light Chain Variable Region (VL) comprising the sequence of SEQ ID NO: 564; or ccc) a Heavy Chain Variable Region (VH) comprising the sequence of SEQ ID NO: 570 and a Light Chain Variable Region (VL) comprising the sequence of SEQ ID NO: 574; or ddd) a Heavy Chain Variable Region (VH) comprising the sequence of SEQ ID NO: 580 and a Light Chain Variable Region (VL) comprising the sequence of SEQ ID NO: 584; or eee) a Heavy Chain Variable Region (VH) comprising the sequence of SEQ ID NO: 590 and a Light Chain Variable Region (VL) comprising the sequence of SEQ ID NO: 474; or fff) a Heavy Chain Variable Region (VH) comprising the sequence of SEQ ID NO: 600 and a Light Chain Variable Region (VL) comprising the sequence of SEQ ID NO: 554; or ggg) a Heavy Chain Variable Region (VH) comprising the sequence of SEQ ID NO: 610 and a Light Chain Variable Region (VL) comprising the sequence of SEQ ID NO: 614; or hhh) a Heavy Chain Variable Region (VH) comprising the sequence of SEQ ID NO: 610 and a Light Chain Variable Region (VL) comprising the sequence of SEQ ID NO: 624; or iii) a Heavy Chain Variable Region (VH) comprising the sequence of SEQ ID NO: 610 and a Light Chain Variable Region (VL) comprising the sequence of SEQ ID NO: 634; or jjj) a Heavy Chain Variable Region (VH) comprising the sequence of SEQ ID NO: 610 and a Light Chain Variable Region (VL) comprising the sequence of SEQ ID NO: 644; or kkk) a Heavy Chain Variable Region (VH) comprising the sequence of SEQ ID NO: 620 and a Light Chain Variable Region (VL) comprising the sequence of SEQ ID NO: 614; or lll) a Heavy Chain Variable Region (VH) comprising the sequence of SEQ ID NO: 620 and a Light Chain Variable Region (VL) comprising the sequence of SEQ ID NO: 624; or mmm) a Heavy Chain Variable Region (VH) comprising the sequence of SEQ ID NO: 620 and a Light Chain Variable Region (VL) comprising the sequence of SEQ ID NO: 634; or nnn) a Heavy Chain Variable Region (VH) comprising the sequence of SEQ ID NO: 620 and a Light Chain Variable Region (VL) comprising the sequence of SEQ ID NO: 644; or ooo) a Heavy Chain Variable Region (VH) comprising the sequence of SEQ ID NO: 630 and a Light Chain Variable Region (VL) comprising the sequence of SEQ ID NO: 614; or ppp) a Heavy Chain Variable Region (VH) comprising the sequence of SEQ ID NO: 630 and a Light Chain Variable Region (VL) comprising the sequence of SEQ ID NO: 624; or (bbb a Heavy Chain Variable Region (VH) comprising the sequence of SEQ ID NO: 630 and a Light Chain Variable Region (VL) comprising the sequence of SEQ ID NO: 634; or rrr) a Heavy Chain Variable Region (VH) comprising the sequence of SEQ ID NO: 630 and a Light Chain Variable Region (VL) comprising the sequence of SEQ ID NO: 644; or sss) a Heavy Chain Variable Region (VH) comprising the sequence of SEQ ID NO: 640 and a Light Chain Variable Region (VL) comprising the sequence of SEQ ID NO: 614; or ttt) a Heavy Chain Variable Region (VH) comprising the sequence of SEQ ID NO: 640 and a Light Chain Variable Region (VL) comprising the sequence of SEQ ID NO: 624; or uuu) a Heavy Chain Variable Region (VH) comprising the sequence of SEQ ID NO: 640 and a Light Chain Variable Region (VL) comprising the sequence of SEQ ID NO: 634; or vvv) a Heavy Chain Variable Region (VH) comprising the sequence of SEQ ID NO: 640 and a Light Chain Variable Region (VL) comprising the sequence of SEQ ID NO: 644; or www) a Heavy Chain Variable Region (VH) comprising the sequence of SEQ ID NO: 650 and a Light Chain Variable Region (VL) comprising the sequence of SEQ ID NO: 614; or xxx) a Heavy Chain Variable Region (VH) comprising the sequence of SEQ ID NO: 650 and a Light Chain Variable Region (VL) comprising the sequence of SEQ ID NO: 624; or yyy) a Heavy Chain Variable Region (VH) comprising the sequence of SEQ ID NO: 650 and a Light Chain Variable Region (VL) comprising the sequence of SEQ ID NO: 634; or zzz) a Heavy Chain Variable Region (VH) comprising the sequence of SEQ ID NO: 650 and a Light Chain Variable Region (VL) comprising the sequence of SEQ ID NO: 644; or aaaa) a Heavy Chain Variable Region (VH) comprising the sequence of SEQ ID NO: 660 and a Light Chain Variable Region (VL) comprising the sequence of SEQ ID NO: 614; or bbbb) a Heavy Chain Variable Region (VH) comprising the sequence of SEQ ID NO: 670 and a Light Chain Variable Region (VL) comprising the sequence of SEQ ID NO: 614; or cccc) a Heavy Chain Variable Region (VH) comprising the sequence of SEQ ID NO: 680 and a Light Chain Variable Region (VL) comprising the sequence of SEQ ID NO: 614; or dddd) a Heavy Chain Variable Region (VH) comprising the sequence of SEQ ID NO: 690 and a Light Chain Variable Region (VL) comprising the sequence of SEQ ID NO: 614; or eeee) a Heavy Chain Variable Region (VH) comprising the sequence of SEQ ID NO: 690 and a Light Chain Variable Region (VL) comprising the sequence of SEQ ID NO: 624; or ffff) a Heavy Chain Variable Region (VH) comprising the sequence of SEQ ID NO: 700 and a Light Chain Variable Region (VL) comprising the sequence of SEQ ID NO: 614; or gggg) a Heavy Chain Variable Region (VH) comprising the sequence of SEQ ID NO: 700 and a Light Chain Variable Region (VL) comprising the sequence of SEQ ID NO: 624; or hhhh) a Heavy Chain Variable Region (VH) comprising the sequence of SEQ ID NO: 710 and a Light Chain Variable Region (VL) comprising the sequence of SEQ ID NO: 614; or iiii) a Heavy Chain Variable Region (VH) comprising the sequence of SEQ ID NO: 710 and a Light Chain Variable Region (VL) comprising the sequence of SEQ ID NO: 624; or jjjj) a Heavy Chain Variable Region (VH) comprising the sequence of SEQ ID NO: 720 and a Light Chain Variable Region (VL) comprising the sequence of SEQ ID NO: 614; or kkkk) a Heavy Chain Variable Region (VH) comprising the sequence of SEQ ID NO: 720 and a Light Chain Variable Region (VL) comprising the sequence of SEQ ID NO: 624.

In some embodiments, the antibody comprises:

a) a Heavy Chain Variable Region (VH) comprising the sequence of SEQ ID NO: 10 or a heavy chain variable region (VH) having at least 96%, 97%, 98%, or 99% sequence identity to the amino acid sequence of SEQ ID NO: 10; and a Light Chain Variable Region (VL) comprising the sequence of SEQ ID NO: 14 or a light chain variable region (VL) having at least 99% sequence identity to the amino acid sequence of SEQ ID NO: 14;

b) a Heavy Chain Variable Region (VH) comprising the sequence of SEQ ID NO: 20 or a heavy chain variable region (VH) having at least 96%, 97%, 98%, or 99% sequence identity to the amino acid sequence of SEQ ID NO: 20; and a Light Chain Variable Region (VL) comprising the sequence of SEQ ID NO: 24 or a light chain variable region (VL) having at least 93%, 94%, 95%, 96%, 97%, 98%, or 99% sequence identity to the amino acid sequence of SEQ ID NO: 24;

c) a Heavy Chain Variable Region (VH) comprising the sequence of SEQ ID NO: 30 or a heavy chain variable region (VH) having at least 94%, 95%, 96%, 97%, 98%, or 99% sequence identity to the amino acid sequence of SEQ ID NO: 30; and a Light Chain Variable Region (VL) comprising the sequence of SEQ ID NO: 34 or a light chain variable region (VL) having at least 98%, or 99% sequence identity to the amino acid sequence of SEQ ID NO: 34;

d) a Heavy Chain Variable Region (VH) comprising the sequence of SEQ ID NO: 40 or a heavy chain variable region (VH) having at least 94%, 95%, 96%, 97%, 98%, or 99% sequence identity to the amino acid sequence of SEQ ID NO: 40; and a Light Chain Variable Region (VL) comprising the sequence of SEQ ID NO: 44 or a light chain variable region (VL) having at least 94%, 95%, 96%, 97%, 98%, or 99% sequence identity to the amino acid sequence of SEQ ID NO: 44;

e) a Heavy Chain Variable Region (VH) comprising the sequence of SEQ ID NO: 50 or a heavy chain variable region (VH) having at least 90%, 91%, 92%, 93%, 94%, 95%, 96%, 97%, 98%, or 99% sequence identity to the amino acid sequence of SEQ ID NO: 50; and a Light Chain Variable Region (VL) comprising the sequence of SEQ ID NO: 54 or a light chain variable region (VL) having at least 93%, 94%, 95%, 96%, 97%, 98%, or 99% sequence identity to the amino acid sequence of SEQ ID NO: 54;

f) a Heavy Chain Variable Region (VH) comprising the sequence of SEQ ID NO: 60 or a heavy chain variable region (VH) having at least 89%, 90%, 91%, 92%, 93%, 94%, 95%, 96%, 97%, 98%, or 99% sequence identity to the amino acid sequence of SEQ ID NO: 60; and a Light Chain Variable Region (VL) comprising the sequence of SEQ ID NO: 64 or a light chain variable region (VL) having at least 96%, 97%, 98%, or 99% sequence identity to the amino acid sequence of SEQ ID NO: 64;

g) a Heavy Chain Variable Region (VH) comprising the sequence of SEQ ID NO: 70 or a heavy chain variable region (VH) having at least 91%, 92%, 93%, 94%, 95%, 96%, 97%, 98%, or 99% sequence identity to the amino acid sequence of SEQ ID NO: 70; and a Light Chain Variable Region (VL) comprising the sequence of SEQ ID NO: 74 or a light chain variable region (VL) having at least 90%, 91%, 92%, 93%, 94%, 95%, 96%, 97%, 98%, or 99% sequence identity to the amino acid sequence of SEQ ID NO: 74;

h) a Heavy Chain Variable Region (VH) comprising the sequence of SEQ ID NO: 30 or a heavy chain variable region (VH) having at least 94%, 95%, 96%, 97%, 98%, or 99% sequence identity to the amino acid sequence of SEQ ID NO: 30; and a Light Chain Variable Region (VL) comprising the sequence of SEQ ID NO: 84 or a light chain variable region (VL) having at least 94%, 95%, 96%, 97%, 98%, or 99% sequence identity to the amino acid sequence of SEQ ID NO: 84;

i) a Heavy Chain Variable Region (VH) comprising the sequence of SEQ ID NO: 90 or a heavy chain variable region (VH) having at least 94%, 95%, 96%, 97%, 98%, or 99% sequence identity to the amino acid sequence of SEQ ID NO: 90; and a Light Chain Variable Region (VL) comprising the sequence of SEQ ID NO: 94 or a light chain variable region (VL) having at least 99%, sequence identity to the amino acid sequence of SEQ ID NO: 94; or j) a Heavy Chain Variable Region (VH) comprising the sequence of SEQ ID NO: 100 or a heavy chain variable region (VH) having at least 87%, 88,%, 89%, 90%, 91%, 92%, 93%, 94%, 95%, 96%, 97%, 98%, or 99% sequence identity to the amino acid sequence of SEQ ID NO: 100; and a Light Chain Variable Region (VL) comprising the sequence of SEQ ID NO: 104 or a light chain variable region (VL) having at least 98% or 99% sequence identity to the amino acid sequence of SEQ ID NO: 104; or k) a Heavy Chain Variable Region (VH) comprising the sequence of SEQ ID NO: 110 or a heavy chain variable region (VH) having at least 97%, 98%, or 99% sequence identity to the amino acid sequence of SEQ ID NO: 110; and a Light Chain Variable Region (VL) comprising the sequence of SEQ ID NO: 114; or l).a Heavy Chain Variable Region (VH) comprising the sequence of SEQ ID NO: 280 or a heavy chain variable region (VH) having at least 91%, 92%, 93%, 94%, 95%, 96%, 97%, 98% or 99% sequence identity to the amino acid sequence of SEQ ID NO: 280; and a Light Chain Variable Region (VL) comprising the sequence of SEQ ID NO: 284; or m) a Heavy Chain Variable Region (VH) comprising the sequence of SEQ ID NO: 290 or a heavy chain variable region (VH) having at least 91%, 92%, 93%, 94%, 95%, 96%, 97%, 98% or 99% sequence identity to the amino acid sequence of SEQ ID NO: 290; and a Light Chain Variable Region (VL) comprising the sequence of SEQ ID NO: 194 or a light chain variable region (VL) having at least 95%, 96%, 97%, 98% or 99% sequence identity to the amino acid sequence of SEQ ID NO: 194; or n) a Heavy Chain Variable Region (VH) comprising the sequence of SEQ ID NO: 140 or a heavy chain variable region (VH) having at least 94%, 95%, 96%, 97%, 98% or 99% sequence identity to the amino acid sequence of SEQ ID NO: 140; and a Light Chain Variable Region (VL) comprising the sequence of SEQ ID NO: 144 or a light chain variable region (VL) having at least 97%, 98% or 99% sequence identity to the amino acid sequence of SEQ ID NO: 144; or o) a Heavy Chain Variable Region (VH) comprising the sequence of SEQ ID NO: 150 or a heavy chain variable region (VH) having at least 90%, 91%, 92%, 93%, 94%, 95%, 96%, 97%, 98% or 99% sequence identity to the amino acid sequence of SEQ ID NO: 150; and a Light Chain Variable Region (VL) comprising the sequence of SEQ ID NO: 154 or a light chain variable region (VL) having at least 98% or 99% sequence identity to the amino acid sequence of SEQ ID NO: 154; or p) a Heavy Chain Variable Region (VH) comprising the sequence of SEQ ID NO: 160 or a heavy chain variable region (VH) having at least 97%, 98% or 99% sequence identity to the amino acid sequence of SEQ ID NO: 160; and a Light Chain Variable Region (VL) comprising the sequence of SEQ ID NO: 164; or q) a Heavy Chain Variable Region (VH) comprising the sequence of SEQ ID NO: 170 or a heavy chain variable region (VH) having at least least 84%, 85%, 86%, 87%, 88%, 89%, 90%, 91%, 92%, 93%, 94%, 95%, 96%, 97%, 98% or 99% sequence identity to the amino acid sequence of SEQ ID NO: 170; and a Light Chain Variable Region (VL) comprising the sequence of SEQ ID NO: 174 or a light chain variable region (VL) having at least 93%, 94%, 95%, 96%, 97%, 98% or 99% sequence identity to the amino acid sequence of SEQ ID NO: 174; or r) a Heavy Chain Variable Region (VH) comprising the sequence of SEQ ID NO: 180 or a heavy chain variable region (VH) having at least 93%, 94%, 95%, 96%, 97%, 98% or 99% sequence identity to the amino acid sequence of SEQ ID NO: 180; and a Light Chain Variable Region (VL) comprising the sequence of SEQ ID NO: 184; or s) a Heavy Chain Variable Region (VH) comprising the sequence of SEQ ID NO: 190 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 190; and a Light Chain Variable Region (VL) comprising the sequence of SEQ ID NO: 194 or a light chain variable region (VL) having at least 95%, 96%, 97%, 98% or 99% sequence identity to the amino acid sequence of SEQ ID NO: 194; or t) a Heavy Chain Variable Region (VH) comprising the sequence of SEQ ID NO: 200 or a heavy chain variable region (VH) having at least 93%, 94%, 95%, 96%, 97%, 98% or 99% sequence identity to the amino acid sequence of SEQ ID NO: 200; and a Light Chain Variable Region (VL) comprising the sequence of SEQ ID NO: 204 or a light chain variable region (VL) having at least 97%, 98% or 99% sequence identity to the amino acid sequence of SEQ ID NO: 204; or u) a Heavy Chain Variable Region (VH) comprising the sequence of SEQ ID NO: 210 or a heavy chain variable region (VH) having at least 91%, 92%, 93%, 94%, 95%, 96%, 97%, 98% or 99% sequence identity to the amino acid sequence of SEQ ID NO: 210; and a Light Chain Variable Region (VL) comprising the sequence of SEQ ID NO: 214 or a light chain variable region (VL) having at least 97%, 98% or 99% sequence identity to the amino acid sequence of SEQ ID NO: 214; or v) a Heavy Chain Variable Region (VH) comprising the sequence of SEQ ID NO: 220 or a heavy chain variable region (VH) having at least 97%, 98% or 99% sequence identity to the amino acid sequence of SEQ ID NO: 220; and a Light Chain Variable Region (VL) comprising the sequence of SEQ ID NO: 224 or a light chain variable region (VL) having at least 92%, 93%, 94%, 95%, 96%, 97%, 98% or 99% sequence identity to the amino acid sequence of SEQ ID NO: 224; or w) a Heavy Chain Variable Region (VH) comprising the sequence of SEQ ID NO: 230 or a heavy chain variable region (VH) having at least 90%, 91%, 92%, 93%, 94%, 95%, 96%, 97%, 98% or 99% sequence identity to the amino acid sequence of SEQ ID NO: 230; and a Light Chain Variable Region (VL) comprising the sequence of SEQ ID NO: 234 or a light chain variable region (VL) having at least 97%, 98% or 99% sequence identity to the amino acid sequence of SEQ ID NO: 234; or x) a Heavy Chain Variable Region (VH) comprising the sequence of SEQ ID NO: 240 or a heavy chain variable region (VH) having at least 96%, 97%, 98% or 99% sequence identity to the amino acid sequence of SEQ ID NO: 240; and a Light Chain Variable Region (VL) comprising the sequence of SEQ ID NO: 244 or a light chain variable region (VL) having at least 94%, 95%, 96%, 97%, 98% or 99% sequence identity to the amino acid sequence of SEQ ID NO: 244; or y) a Heavy Chain Variable Region (VH) comprising the sequence of SEQ ID NO: 250 or a heavy chain variable region (VH) having at least 90%, 91%, 92%, 93%, 94%, 95%, 96%, 97%, 98% or 99% sequence identity to the amino acid sequence of SEQ ID NO: 250; and a Light Chain Variable Region (VL) comprising the sequence of SEQ ID NO: 254 or a light chain variable region (VL) having at least 94%, 95%, 96%, 97%, 98% or 99% sequence identity to the amino acid sequence of SEQ ID NO: 254; or z) a Heavy Chain Variable Region (VH) comprising the sequence of SEQ ID NO: 260 or a heavy chain variable region (VH) having at least 92%, 93%, 94%, 95%, 96%, 97%, 98% or 99% sequence identity to the amino acid sequence of SEQ ID NO: 260; and a Light Chain Variable Region (VL) comprising the sequence of SEQ ID NO: 264 or a light chain variable region (VL) having at least 96%, 97%, 98% or 99% sequence identity to the amino acid sequence of SEQ ID NO: 264; or aa) a Heavy Chain Variable Region (VH) comprising the sequence of SEQ ID NO: 270 or a heavy chain variable region (VH) having at least 85%, 86%, 87%, 88%, 89%, 90%, 91%, 92%, 93%, 94%, 95%, 96%, 97%, 98% or 99% sequence identity to the amino acid sequence of SEQ ID NO: 270; and a Light Chain Variable Region (VL) comprising the sequence of SEQ ID NO: 274 or a light chain variable region (VL) having at least 91%, 92%, 93%, 94%, 95%, 96%, 97%, 98% or 99% sequence identity to the amino acid sequence of SEQ ID NO: 274; or bb) a Heavy Chain Variable Region (VH) comprising the sequence of SEQ ID NO: 300 or a heavy chain variable region (VH) having at least 97%, 98% or 99% sequence identity to the amino acid sequence of SEQ ID NO: 300; and a Light Chain Variable Region (VL) comprising the sequence of SEQ ID NO: 304 or a light chain variable region (VL) having at least 97%, 98% or 99% sequence identity to the amino acid sequence of SEQ ID NO: 304; or cc) a Heavy Chain Variable Region (VH) comprising the sequence of SEQ ID NO: 310 or a heavy chain variable region (VH) having at least 94%, 95%, 96%, 97%, 98% or 99% sequence identity to the amino acid sequence of SEQ ID NO: 310; and a Light Chain Variable Region (VL) comprising the sequence of SEQ ID NO: 314 or a light chain variable region (VL) having at least 96%, 97%, 98% or 99% sequence identity to the amino acid sequence of SEQ ID NO: 314; or dd) a Heavy Chain Variable Region (VH) comprising the sequence of SEQ ID NO: 320 or a heavy chain variable region (VH) having at least 94%, 95%, 96%, 97%, 98% or 99% sequence identity to the amino acid sequence of SEQ ID NO: 320; and a Light Chain Variable Region (VL) comprising the sequence of SEQ ID NO: 324 or a light chain variable region (VL) having at least 99% sequence identity to the amino acid sequence of SEQ ID NO: 324; or ee) a Heavy Chain Variable Region (VH) comprising the sequence of SEQ ID NO: 330 or a heavy chain variable region (VH) having at least 96%, 97%, 98% or 99% sequence identity to the amino acid sequence of SEQ ID NO: 330; and a Light Chain Variable Region (VL) comprising the sequence of SEQ ID NO: 334 or a light chain variable region (VL) having at least 97%, 98% or 99% sequence identity to the amino acid sequence of SEQ ID NO: 334; or ff) a Heavy Chain Variable Region (VH) comprising the sequence of SEQ ID NO: 340 or a heavy chain variable region (VH) having at least 93%, 94%, 95%, 96%, 97%, 98% or 99% sequence identity to the amino acid sequence of SEQ ID NO: 340; and a Light Chain Variable Region (VL) comprising the sequence of SEQ ID NO: 344 or a light chain variable region (VL) having at least 98% or 99% sequence identity to the amino acid sequence of SEQ ID NO: 344; or gg) a Heavy Chain Variable Region (VH) comprising the sequence of SEQ ID NO: 350 or a heavy chain variable region (VH) having at least 92%, 93%, 94%, 95%, 96%, 97%, 98% or 99% sequence identity to the amino acid sequence of SEQ ID NO: 350; and a Light Chain Variable Region (VL) comprising the sequence of SEQ ID NO: 354 or a light chain variable region (VL) having at least 95%, 96%, 97%, 98% or 99% sequence identity to the amino acid sequence of SEQ ID NO: 354; or hh) a Heavy Chain Variable Region (VH) comprising the sequence of SEQ ID NO: 360 or a heavy chain variable region (VH) having at least 93%, 94%, 95%, 96%, 97%, 98% or 99% sequence identity to the amino acid sequence of SEQ ID NO: 360; and a Light Chain Variable Region (VL) comprising the sequence of SEQ ID NO: 364 or a light chain variable region (VL) having at least 99% sequence identity to the amino acid sequence of SEQ ID NO: 364; or ii) a Heavy Chain Variable Region (VH) comprising the sequence of SEQ ID NO: 370 or a heavy chain variable region (VH) having at least 90%, 91%, 92%, 93%, 94%, 95%, 96%, 97%, 98% or 99% sequence identity to the amino acid sequence of SEQ ID NO: 370; and a Light Chain Variable Region (VL) comprising the sequence of SEQ ID NO: 374 or a light chain variable region (VL) having at least 98% or 99% sequence identity to the amino acid sequence of SEQ ID NO: 374; or jj) a Heavy Chain Variable Region (VH) comprising the sequence of SEQ ID NO: 380 or a heavy chain variable region (VH) having at least 92%, 93%, 94%, 95%, 96%, 97%, 98% or 99% sequence identity to the amino acid sequence of SEQ ID NO: 380; and a Light Chain Variable Region (VL) comprising the sequence of SEQ ID NO: 384 or a light chain variable region (VL) having at least 95%, 96%, 97%, 98% or 99% sequence identity to the amino acid sequence of SEQ ID NO: 384; or kk) a Heavy Chain Variable Region (VH) comprising the sequence of SEQ ID NO: 390 or a heavy chain variable region (VH) having at least 91%, 92%, 93%, 94%, 95%, 96%, 97%, 98% or 99% sequence identity to the amino acid sequence of SEQ ID NO: 390; and a Light Chain Variable Region (VL) comprising the sequence of SEQ ID NO: 394 or a light chain variable region (VL) having at least 96%, 97%, 98% or 99% sequence identity to the amino acid sequence of SEQ ID NO: 394; or ll) a Heavy Chain Variable Region (VH) comprising the sequence of SEQ ID NO: 400 or a heavy chain variable region (VH) having at least 93%, 94%, 95%, 96%, 97%, 98% or 99% sequence identity to the amino acid sequence of SEQ ID NO: 400; and a Light Chain Variable Region (VL) comprising the sequence of SEQ ID NO: 404 or a light chain variable region (VL) having at least 93%, 94%, 95%, 96%, 97%, 98% or 99% sequence identity to the amino acid sequence of SEQ ID NO: 404; or mm) a Heavy Chain Variable Region (VH) comprising the sequence of SEQ ID NO: 410 or a heavy chain variable region (VH) having at least 92%, 93%, 94%, 95%, 96%, 97%, 98% or 99% sequence identity to the amino acid sequence of SEQ ID NO: 410; and a Light Chain Variable Region (VL) comprising the sequence of SEQ ID NO: 414; or nn) a Heavy Chain Variable Region (VH) comprising the sequence of SEQ ID NO: 420 or a heavy chain variable region (VH) having at least 94%, 95%, 96%, 97%, 98% or 99% sequence identity to the amino acid sequence of SEQ ID NO: 420; and a Light Chain Variable Region (VL) comprising the sequence of SEQ ID NO: 424 or a light chain variable region (VL) having at least 99% sequence identity to the amino acid sequence of SEQ ID NO: 424; or oo) a Heavy Chain Variable Region (VH) comprising the sequence of SEQ ID NO: 430 or a heavy chain variable region (VH) having at least 96%, 97%, 98% or 99% sequence identity to the amino acid sequence of SEQ ID NO: 430; and a Light Chain Variable Region (VL) comprising the sequence of SEQ ID NO: 434 or a light chain variable region (VL) having at least 98% or 99% sequence identity to the amino acid sequence of SEQ ID NO: 434; or pp) a Heavy Chain Variable Region (VH) comprising the sequence of SEQ ID NO: 440 or a heavy chain variable region (VH) having at least 93%, 94%, 95%, 96%, 97%, 98% or 99% sequence identity to the amino acid sequence of SEQ ID NO: 440; and a Light Chain Variable Region (VL) comprising the sequence of SEQ ID NO: 414; or qq) a Heavy Chain Variable Region (VH) comprising the sequence of SEQ ID NO: 450 or a heavy chain variable region (VH) having at least 93%, 94%, 95%, 96%, 97%, 98% or 99% sequence identity to the amino acid sequence of SEQ ID NO: 450; and a Light Chain Variable Region (VL) comprising the sequence of SEQ ID NO: 424 or a light chain variable region (VL) having at least 99% sequence identity to the amino acid sequence of SEQ ID NO: 424; or rr) a Heavy Chain Variable Region (VH) comprising the sequence of SEQ ID NO: 460 or a heavy chain variable region (VH) having at least 94%, 95%, 96%, 97%, 98% or 99% sequence identity to the amino acid sequence of SEQ ID NO: 460; and a Light Chain Variable Region (VL) comprising the sequence of SEQ ID NO: 464 or a light chain variable region (VL) having at least 99% sequence identity to the amino acid sequence of SEQ ID NO: 464; or ss) a Heavy Chain Variable Region (VH) comprising the sequence of SEQ ID NO: 470 or a heavy chain variable region (VH) having at least 96%, 97%, 98% or 99% sequence identity to the amino acid sequence of SEQ ID NO: 470; and a Light Chain Variable Region (VL) comprising the sequence of SEQ ID NO: 474 or a light chain variable region (VL) having at least 99% sequence identity to the amino acid sequence of SEQ ID NO: 474; or tt) a Heavy Chain Variable Region (VH) comprising the sequence of SEQ ID NO: 480 or a heavy chain variable region (VH) having at least 98% or 99% sequence identity to the amino acid sequence of SEQ ID NO: 480; and a Light Chain Variable Region (VL) comprising the sequence of SEQ ID NO: 484; or uu) a Heavy Chain Variable Region (VH) comprising the sequence of SEQ ID NO: 490 or a heavy chain variable region (VH) having at least 98% or 99% sequence identity to the amino acid sequence of SEQ ID NO: 490; and a Light Chain Variable Region (VL) comprising the sequence of SEQ ID NO: 494 or a light chain variable region (VL) having at least 99% sequence identity to the amino acid sequence of SEQ ID NO: 494; or vv) a Heavy Chain Variable Region (VH) comprising the sequence of SEQ ID NO: 500 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 500; and a Light Chain Variable Region (VL) comprising the sequence of SEQ ID NO: 504 or a light chain variable region (VL) having at least 97%, 98% or 99% sequence identity to the amino acid sequence of SEQ ID NO: 504; or ww) a Heavy Chain Variable Region (VH) comprising the sequence of SEQ ID NO: 510 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 510; and a Light Chain Variable Region (VL) comprising the sequence of SEQ ID NO: 514 or a light chain variable region (VL) having at least 98% or 99% sequence identity to the amino acid sequence of SEQ ID NO: 514; or xx) a Heavy Chain Variable Region (VH) comprising the sequence of SEQ ID NO: 520 or a heavy chain variable region (VH) having at least 89%, 90%, 91%, 92%, 93%, 94%, 95%, 96%, 97%, 98% or 99% sequence identity to the amino acid sequence of SEQ ID NO: 520; and a Light Chain Variable Region (VL) comprising the sequence of SEQ ID NO: 524 or a light chain variable region (VL) having at least 99% sequence identity to the amino acid sequence of SEQ ID NO: 524; or yy) a Heavy Chain Variable Region (VH) comprising the sequence of SEQ ID NO: 530 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 530; and a Light Chain Variable Region (VL) comprising the sequence of SEQ ID NO: 534; or zz) a Heavy Chain Variable Region (VH) comprising the sequence of SEQ ID NO: 540 or a heavy chain variable region (VH) having at least 91%, 92%, 93%, 94%, 95%, 96%, 97%, 98% or 99% sequence identity to the amino acid sequence of SEQ ID NO: 540; and a Light Chain Variable Region (VL) comprising the sequence of SEQ ID NO: 544; or aaa) a Heavy Chain Variable Region (VH) comprising the sequence of SEQ ID NO: 550 or a heavy chain variable region (VH) having at least 89%, 90%, 91%, 92%, 93%, 94%, 95%, 96%, 97%, 98% or 99% sequence identity to the amino acid sequence of SEQ ID NO: 550; and a Light Chain Variable Region (VL) comprising the sequence of SEQ ID NO: 554 or a light chain variable region (VL) having at least 99% sequence identity to the amino acid sequence of SEQ ID NO: 554; or bbb) a Heavy Chain Variable Region (VH) comprising the sequence of SEQ ID NO: 560 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 560; and a Light Chain Variable Region (VL) comprising the sequence of SEQ ID NO: 564 or a light chain variable region (VL) having at least 98% or 99% sequence identity to the amino acid sequence of SEQ ID NO: 564; or ccc) a Heavy Chain Variable Region (VH) comprising the sequence of SEQ ID NO: 570 or a heavy chain variable region (VH) having at least 92%, 93%, 94%, 95%, 96%, 97%, 98% or 99% sequence identity to the amino acid sequence of SEQ ID NO: 570; and a Light Chain Variable Region (VL) comprising the sequence of SEQ ID NO: 574 or a light chain variable region (VL) having at least 97%, 98% or 99% sequence identity to the amino acid sequence of SEQ ID NO: 574; or ddd) a Heavy Chain Variable Region (VH) comprising the sequence of SEQ ID NO: 580 or a heavy chain variable region (VH) having at least 95%, 96%, 97%, 98% or 99% sequence identity to the amino acid sequence of SEQ ID NO: 580; and a Light Chain Variable Region (VL) comprising the sequence of SEQ ID NO: 584 or a light chain variable region (VL) having at least 99% sequence identity to the amino acid sequence of SEQ ID NO: 584; or eee) a Heavy Chain Variable Region (VH) comprising the sequence of SEQ ID NO: 590 or a heavy chain variable region (VH) having at least 95%, 96%, 97%, 98% or 99% sequence identity to the amino acid sequence of SEQ ID NO: 590; and a Light Chain Variable Region (VL) comprising the sequence of SEQ ID NO: 474 or a light chain variable region (VL) having at least 99% sequence identity to the amino acid sequence of SEQ ID NO: 474; or fff) a Heavy Chain Variable Region (VH) comprising the sequence of SEQ ID NO: 600 or a heavy chain variable region (VH) having at least 89%, 90%, 91%, 92%, 93%, 94%, 95%, 96%, 97%, 98% or 99% sequence identity to the amino acid sequence of SEQ ID NO: 600; and a Light Chain Variable Region (VL) comprising the sequence of SEQ ID NO: 554 or a light chain variable region (VL) having at least 99% sequence identity to the amino acid sequence of SEQ ID NO: 554; or ggg) a Heavy Chain Variable Region (VH) comprising the sequence of SEQ ID NO: 610 or a heavy chain variable region (VH) having at least 90%, 91%, 92%, 93%, 94%, 95%, 96%, 97%, 98% or 99% sequence identity to the amino acid sequence of SEQ ID NO: 610; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or hhh) a Heavy Chain Variable Region (VH) comprising the sequence of SEQ ID NO: 610 or a heavy chain variable region (VH) having at least 90%, 91%, 92%, 93%, 94%, 95%, 96%, 97%, 98% or 99% sequence identity to the amino acid sequence of SEQ ID NO: 610; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or iii) a Heavy Chain Variable Region (VH) comprising the sequence of SEQ ID NO: 610 or a heavy chain variable region (VH) having at least 90%, 91%, 92%, 93%, 94%, 95%, 96%, 97%, 98% or 99% sequence identity to the amino acid sequence of SEQ ID NO: 610; and a Light Chain Variable Region (VL) comprising the sequence of SEQ ID NO: 634 or a light chain variable region (VL) having at least 93%, 94%, 95%, 96%, 97%, 98% and 99% sequence identity to the amino acid sequence of SEQ ID NO: 634; or jjj) a Heavy Chain Variable Region (VH) comprising the sequence of SEQ ID NO: 610 or a heavy chain variable region (VH) having at least 90%, 91%, 92%, 93%, 94%, 95%, 96%, 97%, 98% or 99% sequence identity to the amino acid sequence of SEQ ID NO: 610; and a Light Chain Variable Region (VL) comprising the sequence of SEQ ID NO: 644 or a light chain variable region (VL) having at least 92%, 93%, 94%, 95%, 96%, 97%, 98% and 99% sequence identity to the amino acid sequence of SEQ ID NO: 644; or kkk) a Heavy Chain Variable Region (VH) comprising the sequence of SEQ ID NO: 620 or a heavy chain variable region (VH) having at least 89%, 90%, 91%, 92%, 93%, 94%, 95%, 96%, 97%, 98% or 99% sequence identity to the amino acid sequence of SEQ ID NO: 620; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or lll) a Heavy Chain Variable Region (VH) comprising the sequence of SEQ ID NO: 620 or a heavy chain variable region (VH) having at least 89%, 90%, 91%, 92%, 93%, 94%, 95%, 96%, 97%, 98% or 99% sequence identity to the amino acid sequence of SEQ ID NO: 620; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or mmm) a Heavy Chain Variable Region (VH) comprising the sequence of SEQ ID NO: 620 or a heavy chain variable region (VH) having at least 89%, 90%, 91%, 92%, 93%, 94%, 95%, 96%, 97%, 98% or 99% sequence identity to the amino acid sequence of SEQ ID NO: 620; and a Light Chain Variable Region (VL) comprising the sequence of SEQ ID NO: 634 or a light chain variable region (VL) having at least 93%, 94%, 95%, 96%, 97%, 98% and 99% sequence identity to the amino acid sequence of SEQ ID NO: 634; or nnn) a Heavy Chain Variable Region (VH) comprising the sequence of SEQ ID NO: 620 or a heavy chain variable region (VH) having at least 89%, 90%, 91%, 92%, 93%, 94%, 95%, 96%, 97%, 98% or 99% sequence identity to the amino acid sequence of SEQ ID NO: 620; and a Light Chain Variable Region (VL) comprising the sequence of SEQ ID NO: 644 or a light chain variable region (VL) having at least 92%, 93%, 94%, 95%, 96%, 97%, 98% and 99% sequence identity to the amino acid sequence of SEQ ID NO: 644; or ooo) a Heavy Chain Variable Region (VH) comprising the sequence of SEQ ID NO: 630 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 630; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or ppp) a Heavy Chain Variable Region (VH) comprising the sequence of SEQ ID NO: 630 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 630; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or qqq) a Heavy Chain Variable Region (VH) comprising the sequence of SEQ ID NO: 630 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 630; and a Light Chain Variable Region (VL) comprising the sequence of SEQ ID NO: 634 or a light chain variable region (VL) having at least 93%, 94%, 95%, 96%, 97%, 98% and 99% sequence identity to the amino acid sequence of SEQ ID NO: 634; or rrr) a Heavy Chain Variable Region (VH) comprising the sequence of SEQ ID NO: 630 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 630; and a Light Chain Variable Region (VL) comprising the sequence of SEQ ID NO: 644 or a light chain variable region (VL) having at least 92%, 93%, 94%, 95%, 96%, 97%, 98% and 99% sequence identity to the amino acid sequence of SEQ ID NO: 644; or sss) a Heavy Chain Variable Region (VH) comprising the sequence of SEQ ID NO: 640 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 640; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or ttt) a Heavy Chain Variable Region (VH) comprising the sequence of SEQ ID NO: 640 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 640; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or uuu) a Heavy Chain Variable Region (VH) comprising the sequence of SEQ ID NO: 640 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 640; and a Light Chain Variable Region (VL) comprising the sequence of SEQ ID NO: 634 or a light chain variable region (VL) having at least 93%, 94%, 95%, 96%, 97%, 98% and 99% sequence identity to the amino acid sequence of SEQ ID NO: 634; or vvv) a Heavy Chain Variable Region (VH) comprising the sequence of SEQ ID NO: 640 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 640; and a Light Chain Variable Region (VL) comprising the sequence of SEQ ID NO: 644 or a light chain variable region (VL) having at least 92%, 93%, 94%, 95%, 96%, 97%, 98% and 99% sequence identity to the amino acid sequence of SEQ ID NO: 644; or www) a Heavy Chain Variable Region (VH) comprising the sequence of SEQ ID NO: 650 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 650; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or xxx) a Heavy Chain Variable Region (VH) comprising the sequence of SEQ ID NO: 650 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 650; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or yyy) a Heavy Chain Variable Region (VH) comprising the sequence of SEQ ID NO: 650 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 650; and a Light Chain Variable Region (VL) comprising the sequence of SEQ ID NO: 634 or a light chain variable region (VL) having at least 93%, 94%, 95%, 96%, 97%, 98% and 99% sequence identity to the amino acid sequence of SEQ ID NO: 634; or zzz) a Heavy Chain Variable Region (VH) comprising the sequence of SEQ ID NO: 650 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 650; and a Light Chain Variable Region (VL) comprising the sequence of SEQ ID NO: 644 or a light chain variable region (VL) having at least 92%, 93%, 94%, 95%, 96%, 97%, 98% and 99% sequence identity to the amino acid sequence of SEQ ID NO: 644; or aaaa) a Heavy Chain Variable Region (VH) comprising the sequence of SEQ ID NO: 660 or a heavy chain variable region (VH) having at least 89%, 90%, 91%, 92%, 93%, 94%, 95%, 96%, 97%, 98% or 99% sequence identity to the amino acid sequence of SEQ ID NO: 660; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or bbbb) a Heavy Chain Variable Region (VH) comprising the sequence of SEQ ID NO: 670 or a heavy chain variable region (VH) having at least 89%, 90%, 91%, 92%, 93%, 94%, 95%, 96%, 97%, 98% or 99% sequence identity to the amino acid sequence of SEQ ID NO: 670; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or cccc) a Heavy Chain Variable Region (VH) comprising the sequence of SEQ ID NO: 680 or a heavy chain variable region (VH) having at least 87%, 88%, 89%, 90%, 91%, 92%, 93%, 94%, 95%, 96%, 97%, 98% or 99% sequence identity to the amino acid sequence of SEQ ID NO: 680; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or dddd) a Heavy Chain Variable Region (VH) comprising the sequence of SEQ ID NO: 690 or a heavy chain variable region (VH) having at least 87%, 88%, 89%, 90%, 91%, 92%, 93%, 94%, 95%, 96%, 97%, 98% or 99% sequence identity to the amino acid sequence of SEQ ID NO: 690; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or eeee) a Heavy Chain Variable Region (VH) comprising the sequence of SEQ ID NO: 690 or a heavy chain variable region (VH) having at least 87%, 88%, 89%, 90%, 91%, 92%, 93%, 94%, 95%, 96%, 97%, 98% or 99% sequence identity to the amino acid sequence of SEQ ID NO: 690; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or ffff) a Heavy Chain Variable Region (VH) comprising the sequence of SEQ ID NO: 700 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 700; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or gggg) a Heavy Chain Variable Region (VH) comprising the sequence of SEQ ID NO: 700 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 700; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or hhhh) a Heavy Chain Variable Region (VH) comprising the sequence of SEQ ID NO: 710 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 710; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or iiii) a Heavy Chain Variable Region (VH) comprising the sequence of SEQ ID NO: 710 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 710; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624; or jjjj) a Heavy Chain Variable Region (VH) comprising the sequence of SEQ ID NO: 720 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 720; and a Light Chain Variable Region (VL) comprising the sequence of SEQ ID NO: 614 or a light chain variable region (VL) having at least 94%, 95%, 96%, 97%, 98% and 99% sequence identity to the amino acid sequence of SEQ ID NO: 614; or kkkk) a Heavy Chain Variable Region (VH) comprising the sequence of SEQ ID NO: 720 or a heavy chain variable region (VH) having at least 86%, 87%, 88%, 89%, 90%, 91%, 92%, 93%, 94%, 95%, 96%, 97%, 98% or 99% sequence identity to the amino acid sequence of SEQ ID NO: 720; and a Light Chain Variable Region (VL) comprising the sequence of SEQ ID NO: 624 or a light chain variable region (VL) having at least 93%, 94%, 95%, 96%, 97%, 98% and 99% sequence identity to the amino acid sequence of SEQ ID NO: 624.

In some embodiments, the antibody comprises:

a) VH-CDR1 comprising the amino acid sequence of SEQ ID NO: 11; VH-CDR2 comprising the amino acid sequence of SEQ ID NO: 12; and VH-CDR3 comprising the amino acid sequence of SEQ ID NO: 13;

b) VH-CDR1 comprising the amino acid sequence of SEQ ID NO: 21; VH-CDR2 comprising the amino acid sequence of SEQ ID NO: 22; and VH-CDR3 comprising the amino acid sequence YSY;

c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33;

d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43;

e) VH-CDR1 comprising the amino acid sequence of SEQ ID NO: 21; VH-CDR2 comprising the amino acid sequence of SEQ ID NO: 52; and VH-CDR3 comprising the amino acid sequence YSF;

f) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 43;

g) VH-CDR1 comprising the amino acid sequence of SEQ ID NO: 21; VH-CDR2 comprising the amino acid sequence of SEQ ID NO: 72; and VH-CDR3 comprising the amino acid sequence YSY;

h) VH-CDR1 comprising the amino acid sequence of SEQ ID NO: 91; VH-CDR2 comprising the amino acid sequence of SEQ ID NO: 92; and VH-CDR3 comprising the amino acid sequence of SEQ ID NO: 93; or i) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; or j) VH-CDR1 comprising the amino acid sequence of SEQ ID NO: 111; VH-CDR2 comprising the amino acid sequence of SEQ ID NO: 112; and VH-CDR3 comprising the amino acid sequence of SEQ ID NO: 113; or k) VH-CDR1 comprising the amino acid sequence of SEQ ID NO: 281; VH-CDR2 comprising the amino acid sequence of SEQ ID NO: 282; and VH-CDR3 comprising the amino acid sequence of SEQ ID NO: 283; or l) VH-CDR1 comprising the amino acid sequence of SEQ ID NO:31; VH-CDR2 comprising the amino acid sequence of SEQ ID NO: 192; and VH-CDR3 comprising the amino acid sequence of SEQ ID NO: 193; or m) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; or n) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153; or o) VH-CDR1 comprising the amino acid sequence of SEQ ID NO: 161; VH-CDR2 comprising the amino acid sequence of SEQ ID NO: 162; and VH-CDR3 comprising the amino acid sequence of SEQ ID NO: 163; or p) VH-CDR1 comprising the amino acid sequence of SEQ ID NO: 171; VH-CDR2 comprising the amino acid sequence of SEQ ID NO: 172; and VH-CDR3 comprising the amino acid sequence of SEQ ID NO: 173; or q) VH-CDR1 comprising the amino acid sequence of SEQ ID NO: 181; VH-CDR2 comprising the amino acid sequence of SEQ ID NO: 182; and VH-CDR3 comprising the amino acid sequence of SEQ ID NO: 183; or r) VH-CDR1 comprising the amino acid sequence of SEQ ID NO: 201; VH-CDR2 comprising the amino acid sequence of SEQ ID NO: 202; and VH-CDR3 comprising the amino acid sequence of SEQ ID NO: 153; or s) VH-CDR1 comprising the amino acid sequence of SEQ ID NO: 211; VH-CDR2 comprising the amino acid sequence of SEQ ID NO: 212; and VH-CDR3 comprising the amino acid sequence of SEQ ID NO: 213; or t) VH-CDR1 comprising the amino acid sequence of SEQ ID NO: 31; VH-CDR2 comprising the amino acid sequence of SEQ ID NO: 222; and VH-CDR3 comprising the amino acid sequence of SEQ ID NO: 223; or u) VH-CDR1 comprising the amino acid sequence of SEQ ID NO: 231; VH-CDR2 comprising the amino acid sequence of SEQ ID NO: 232; and VH-CDR3 comprising the amino acid sequence of SEQ ID NO: 233; or v) VH-CDR1 comprising the amino acid sequence of SEQ ID NO: 31; VH-CDR2 comprising the amino acid sequence of SEQ ID NO: 242; and VH-CDR3 comprising the amino acid sequence of SEQ ID NO: 243; or w) VH-CDR1 comprising the amino acid sequence of SEQ ID NO: 31; VH-CDR2 comprising the amino acid sequence of SEQ ID NO: 252; and VH-CDR3 comprising the amino acid sequence of SEQ ID NO: 253; or x) VH-CDR1 comprising the amino acid sequence of SEQ ID NO: 261; VH-CDR2 comprising the amino acid sequence of SEQ ID NO: 262; and VH-CDR3 comprising the amino acid sequence of SEQ ID NO: 263; or y) VH-CDR1 comprising the amino acid sequence of SEQ ID NO: 271; VH-CDR2 comprising the amino acid sequence of SEQ ID NO: 272; and VH-CDR3 comprising the amino acid sequence of SEQ ID NO: 273; or z) VH-CDR1 comprising the amino acid sequence of SEQ ID NO: 301; VH-CDR2 comprising the amino acid sequence of SEQ ID NO: 302; and VH-CDR3 comprising the amino acid sequence of SEQ ID NO: 303; or aa) VH-CDR1 comprising the amino acid sequence of SEQ ID NO: 311; VH-CDR2 comprising the amino acid sequence of SEQ ID NO: 312; and VH-CDR3 comprising the amino acid sequence of SEQ ID NO: 313; or bb) VH-CDR1 comprising the amino acid sequence of SEQ ID NO: 321; VH-CDR2 comprising the amino acid sequence of SEQ ID NO: 322; and VH-CDR3 comprising the amino acid sequence of SEQ ID NO: 323; or cc) VH-CDR1 comprising the amino acid sequence of SEQ ID NO: 151; VH-CDR2 comprising the amino acid sequence of SEQ ID NO: 332; and VH-CDR3 comprising the amino acid sequence of SEQ ID NO: 333; or dd) VH-CDR1 comprising the amino acid sequence of SEQ ID NO: 341; VH-CDR2 comprising the amino acid sequence of SEQ ID NO: 342; and VH-CDR3 comprising the amino acid sequence of SEQ ID NO: 343; or ee) VH-CDR1 comprising the amino acid sequence of SEQ ID NO: 351; VH-CDR2 comprising the amino acid sequence of SEQ ID NO: 352; and VH-CDR3 comprising the amino acid sequence of SEQ ID NO: 353; or ff) VH-CDR1 comprising the amino acid sequence of SEQ ID NO: 361; VH-CDR2 comprising the amino acid sequence of SEQ ID NO: 362; and VH-CDR3 comprising the amino acid sequence of SEQ ID NO: 363; or gg) VH-CDR1 comprising the amino acid sequence of SEQ ID NO: 371; VH-CDR2 comprising the amino acid sequence of SEQ ID NO: 372; and VH-CDR3 comprising the amino acid sequence of SEQ ID NO: 373; or hh) VH-CDR1 comprising the amino acid sequence of SEQ ID NO: 351; VH-CDR2 comprising the amino acid sequence of SEQ ID NO: 382; and VH-CDR3 comprising the amino acid sequence of SEQ ID NO: 383; or ii) VH-CDR1 comprising the amino acid sequence of SEQ ID NO: 351; VH-CDR2 comprising the amino acid sequence of SEQ ID NO: 382; and VH-CDR3 comprising the amino acid sequence of SEQ ID NO: 393; or jj) VH-CDR1 comprising the amino acid sequence of SEQ ID NO: 411; VH-CDR2 comprising the amino acid sequence of SEQ ID NO: 412; and VH-CDR3 comprising the amino acid sequence of SEQ ID NO: 413; or kk) VH-CDR1 comprising the amino acid sequence of SEQ ID NO: 421; VH-CDR2 comprising the amino acid sequence of SEQ ID NO: 422; and VH-CDR3 comprising the amino acid sequence GNY; or ll) VH-CDR1 comprising the amino acid sequence of SEQ ID NO: 431; VH-CDR2 comprising the amino acid sequence of SEQ ID NO: 432; and VH-CDR3 comprising the amino acid sequence of SEQ ID NO: 433; or mm) VH-CDR1 comprising the amino acid sequence of SEQ ID NO: 151; VH-CDR2 comprising the amino acid sequence of SEQ ID NO: 442; and VH-CDR3 comprising the amino acid sequence of SEQ ID NO: 443; or nn) VH-CDR1 comprising the amino acid sequence of SEQ ID NO: 461; VH-CDR2 comprising the amino acid sequence of SEQ ID NO: 462; and VH-CDR3 comprising the amino acid sequence of SEQ ID NO: 463; or oo) VH-CDR1 comprising the amino acid sequence of SEQ ID NO: 141; VH-CDR2 comprising the amino acid sequence of SEQ ID NO: 472; and VH-CDR3 comprising the amino acid sequence of SEQ ID NO: 473; or pp) VH-CDR1 comprising the amino acid sequence of SEQ ID NO: 481; VH-CDR2 comprising the amino acid sequence of SEQ ID NO: 482; and VH-CDR3 comprising the amino acid sequence of SEQ ID NO: 483; or qq) VH-CDR1 comprising the amino acid sequence of SEQ ID NO: 141; VH-CDR2 comprising the amino acid sequence of SEQ ID NO: 492; and VH-CDR3 comprising the amino acid sequence of SEQ ID NO: 493; or rr) VH-CDR1 comprising the amino acid sequence of SEQ ID NO: 151; VH-CDR2 comprising the amino acid sequence of SEQ ID NO: 502; and VH-CDR3 comprising the amino acid sequence of SEQ ID NO: 503; or ss) VH-CDR1 comprising the amino acid sequence of SEQ ID NO: 311; VH-CDR2 comprising the amino acid sequence of SEQ ID NO: 512; and VH-CDR3 comprising the amino acid sequence of SEQ ID NO: 513; or tt) VH-CDR1 comprising the amino acid sequence of SEQ ID NO: 521; VH-CDR2 comprising the amino acid sequence of SEQ ID NO: 522; and VH-CDR3 comprising the amino acid sequence of SEQ ID NO: 463; or uu) VH-CDR1 comprising the amino acid sequence of SEQ ID NO: 371; VH-CDR2 comprising the amino acid sequence of SEQ ID NO: 532; and VH-CDR3 comprising the amino acid sequence of SEQ ID NO: 533; or vv) VH-CDR1 comprising the amino acid sequence of SEQ ID NO: 341; VH-CDR2 comprising the amino acid sequence of SEQ ID NO: 542; and VH-CDR3 comprising the amino acid sequence of SEQ ID NO: 543; or ww) VH-CDR1 comprising the amino acid sequence of SEQ ID NO: 551; VH-CDR2 comprising the amino acid sequence of SEQ ID NO: 552; and VH-CDR3 comprising the amino acid sequence of SEQ ID NO: 553; or xx) VH-CDR1 comprising the amino acid sequence of SEQ ID NO: 551; VH-CDR2 comprising the amino acid sequence of SEQ ID NO: 552; and VH-CDR3 comprising the amino acid sequence of SEQ ID NO: 563; or yy) VH-CDR1 comprising the amino acid sequence of SEQ ID NO: 571; VH-CDR2 comprising the amino acid sequence of SEQ ID NO: 202; and VH-CDR3 comprising the amino acid sequence of SEQ ID NO: 573; or zz) VH-CDR1 comprising the amino acid sequence of SEQ ID NO: 581; VH-CDR2 comprising the amino acid sequence of SEQ ID NO: 582; and VH-CDR3 comprising the amino acid sequence of SEQ ID NO: 583; or aaa) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 13; or bbb) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 663; or ccc) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 673; or ddd) VH-CDR1 comprising the amino acid sequence of SEQ ID NO: 11; VH-CDR2 comprising the amino acid sequence of SEQ ID NO: 612; and VH-CDR3 comprising the amino acid sequence of SEQ ID NO: 683.

In some embodiments, the antibody comprises:

a) VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17;

b) VL-CDR1 comprising the amino acid sequence of SEQ ID NO: 25; VL-CDR2 comprising the amino acid sequence of SEQ ID NO: 26; and VL-CDR3 comprising the amino acid sequence of SEQ ID NO: 27;

c) VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37;

d) VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47;

e) VL-CDR1 comprising the amino acid sequence of SEQ ID NO: 55; VL-CDR2 comprising the amino acid sequence of SEQ ID NO: 56; and VL-CDR3 comprising the amino acid sequence of SEQ ID NO: 27;

f) VL-CDR1 comprising the amino acid sequence of SEQ ID NO: 65; VL-CDR2 comprising the amino acid sequence of SEQ ID NO: 46; and VL-CDR3 comprising the amino acid sequence of SEQ ID NO: 67;

g) VL-CDR1 comprising the amino acid sequence of SEQ ID NO: 75; VL-CDR2 comprising the amino acid sequence of SEQ ID NO: 76; and VL-CDR3 comprising the amino acid sequence of SEQ ID NO: 77;

h) VL-CDR1 comprising the amino acid sequence of SEQ ID NO: 85; VL-CDR2 comprising the amino acid sequence of SEQ ID NO: 36; and VL-CDR3 comprising the amino acid sequence of SEQ ID NO: 87;

i) VL-CDR1 comprising the amino acid sequence of SEQ ID NO: 95; VL-CDR2 comprising the amino acid sequence of SEQ ID NO: 96; and VL-CDR3 comprising the amino acid sequence of SEQ ID NO: 97;

j) VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or k) VL-CDR1 comprising the amino acid sequence of SEQ ID NO: 115; VL-CDR2 comprising the amino acid sequence of SEQ ID NO: 106; and VL-CDR3 comprising the amino acid sequence of SEQ ID NO: 117; or l) VL-CDR1 comprising the amino acid sequence of SEQ ID NO: 285; VL-CDR2 comprising the amino acid sequence of SEQ ID NO: 286; and VL-CDR3 comprising the amino acid sequence of SEQ ID NO: 287; or m) VL-CDR1 comprising the amino acid sequence of SEQ ID NO: 195; VL-CDR2 comprising the amino acid sequence of SEQ ID NO: 96; and VL-CDR3 comprising the amino acid sequence of SEQ ID NO: 197; or n) VL-CDR1 comprising the amino acid sequence of SEQ ID NO: 145; VL-CDR2 comprising the amino acid sequence of SEQ ID NO: 16; and VL-CDR3 comprising the amino acid sequence of SEQ ID NO: 17; or o) VL-CDR1 comprising the amino acid sequence of SEQ ID NO: 165; VL-CDR2 comprising the amino acid sequence of SEQ ID NO: 16; and VL-CDR3 comprising the amino acid sequence of SEQ ID NO: 167; or p) VL-CDR1 comprising the amino acid sequence of SEQ ID NO: 175; VL-CDR2 comprising the amino acid sequence of SEQ ID NO: 176; and VL-CDR3 comprising the amino acid sequence of SEQ ID NO: 177; or q) VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 187; or r) VL-CDR1 comprising the amino acid sequence of SEQ ID NO: 105; VL-CDR2 comprising the amino acid sequence of SEQ ID NO: 206; and VL-CDR3 comprising the amino acid sequence of SEQ ID NO: 107; or s) VL-CDR1 comprising the amino acid sequence of SEQ ID NO: 215; VL-CDR2 comprising the amino acid sequence of SEQ ID NO: 216; and VL-CDR3 comprising the amino acid sequence of SEQ ID NO: 217; or t) VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 227 u) VL-CDR1 comprising the amino acid sequence of SEQ ID NO: 235; VL-CDR2 comprising the amino acid sequence of SEQ ID NO: 236; and VL-CDR3 comprising the amino acid sequence of SEQ ID NO: 237; or v) VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 247; or w) VL-CDR1 comprising the amino acid sequence of SEQ ID NO: 255; VL-CDR2 comprising the amino acid sequence of SEQ ID NO: 256; and VL-CDR3 comprising the amino acid sequence of SEQ ID NO: 257; or x) VL-CDR1 comprising the amino acid sequence of SEQ ID NO: 265; VL-CDR2 comprising the amino acid sequence of SEQ ID NO: 176; and VL-CDR3 comprising the amino acid sequence of SEQ ID NO: 267; or y) VL-CDR1 comprising the amino acid sequence of SEQ ID NO: 275; VL-CDR2 comprising the amino acid sequence of SEQ ID NO: 276; and VL-CDR3 comprising the amino acid sequence of SEQ ID NO: 277; or z) VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 307; or aa) VL-CDR1 comprising the amino acid sequence of SEQ ID NO: 315; VL-CDR2 comprising the amino acid sequence of SEQ ID NO: 46; and VL-CDR3 comprising the amino acid sequence of SEQ ID NO: 67; or bb) VL-CDR1 comprising the amino acid sequence of SEQ ID NO: 325; VL-CDR2 comprising the amino acid sequence of SEQ ID NO: 326; and VL-CDR3 comprising the amino acid sequence of SEQ ID NO: 327; or cc) VL-CDR1 comprising the amino acid sequence of SEQ ID NO: 335; VL-CDR2 comprising the amino acid sequence of SEQ ID NO: 336; and VL-CDR3 comprising the amino acid sequence of SEQ ID NO: 107; or dd) VL-CDR1 comprising the amino acid sequence of SEQ ID NO: 345; VL-CDR2 comprising the amino acid sequence of SEQ ID NO: 346; and VL-CDR3 comprising the amino acid sequence of SEQ ID NO: 347; or ee) VL-CDR1 comprising the amino acid sequence of SEQ ID NO: 355; VL-CDR2 comprising the amino acid sequence of SEQ ID NO: 356; and VL-CDR3 comprising the amino acid sequence of SEQ ID NO: 357; or ff) VL-CDR1 comprising the amino acid sequence of SEQ ID NO: 365; VL-CDR2 comprising the amino acid sequence of SEQ ID NO: 16; and VL-CDR3 comprising the amino acid sequence of SEQ ID NO: 367; or gg) VL-CDR1 comprising the amino acid sequence of SEQ ID NO: 345; VL-CDR2 comprising the amino acid sequence of SEQ ID NO: 376; and VL-CDR3 comprising the amino acid sequence of SEQ ID NO: 347; or hh) VL-CDR1 comprising the amino acid sequence of SEQ ID NO: 385; VL-CDR2 comprising the amino acid sequence of SEQ ID NO: 386; and VL-CDR3 comprising the amino acid sequence of SEQ ID NO: 387; or ii) VL-CDR1 comprising the amino acid sequence of SEQ ID NO: 395; VL-CDR2 comprising the amino acid sequence of SEQ ID NO: 356; and VL-CDR3 comprising the amino acid sequence of SEQ ID NO: 357; or jj) VL-CDR1 comprising the amino acid sequence of SEQ ID NO: 405; VL-CDR2 comprising the amino acid sequence of SEQ ID NO: 356; and VL-CDR3 comprising the amino acid sequence of SEQ ID NO: 357; or kk) VL-CDR1 comprising the amino acid sequence of SEQ ID NO: 425; VL-CDR2 comprising the amino acid sequence of SEQ ID NO: 426; and VL-CDR3 comprising the amino acid sequence of SEQ ID NO: 427; or ll) VL-CDR1 comprising the amino acid sequence of SEQ ID NO: 435; VL-CDR2 comprising the amino acid sequence of SEQ ID NO: 436; and VL-CDR3 comprising the amino acid sequence of SEQ ID NO: 437; or mm) VL-CDR1 comprising the amino acid sequence of SEQ ID NO: 465; VL-CDR2 comprising the amino acid sequence of SEQ ID NO: 16; and VL-CDR3 comprising the amino acid sequence of SEQ ID NO: 467; or nn) VL-CDR1 comprising the amino acid sequence of SEQ ID NO: 475; VL-CDR2 comprising the amino acid sequence of SEQ ID NO: 476; and VL-CDR3 comprising the amino acid sequence of SEQ ID NO: 477; or oo) VL-CDR1 comprising the amino acid sequence of SEQ ID NO: 165; VL-CDR2 comprising the amino acid sequence of SEQ ID NO: 16; and VL-CDR3 comprising the amino acid sequence of SEQ ID NO: 487; or pp) VL-CDR1 comprising the amino acid sequence of SEQ ID NO: 495; VL-CDR2 comprising the amino acid sequence of SEQ ID NO: 496; and VL-CDR3 comprising the amino acid sequence of SEQ ID NO: 497; or qq) VL-CDR1 comprising the amino acid sequence of SEQ ID NO: 105; VL-CDR2 comprising the amino acid sequence of SEQ ID NO: 336; and VL-CDR3 comprising the amino acid sequence of SEQ ID NO: 107; or rr) VL-CDR1 comprising the amino acid sequence of SEQ ID NO: 515; VL-CDR2 comprising the amino acid sequence of SEQ ID NO: 516; and VL-CDR3 comprising the amino acid sequence of SEQ ID NO: 517; or ss) VL-CDR1 comprising the amino acid sequence of SEQ ID NO: 525; VL-CDR2 comprising the amino acid sequence of SEQ ID NO: 16; and VL-CDR3 comprising the amino acid sequence of SEQ ID NO: 467; or tt) VL-CDR1 comprising the amino acid sequence of SEQ ID NO: 345; VL-CDR2 comprising the amino acid sequence of SEQ ID NO: 376; and VL-CDR3 comprising the amino acid sequence of SEQ ID NO: 347; or uu) VL-CDR1 comprising the amino acid sequence of SEQ ID NO: 555; VL-CDR2 comprising the amino acid sequence of SEQ ID NO: 16; and VL-CDR3 comprising the amino acid sequence of SEQ ID NO: 557; or vv) VL-CDR1 comprising the amino acid sequence of SEQ ID NO: 565; VL-CDR2 comprising the amino acid sequence of SEQ ID NO: 16; and VL-CDR3 comprising the amino acid sequence of SEQ ID NO: 557; or ww) VL-CDR1 comprising the amino acid sequence of SEQ ID NO: 585; VL-CDR2 comprising the amino acid sequence of SEQ ID NO: 586; and VL-CDR3 comprising the amino acid sequence of SEQ ID NO: 587; or xx) VL-CDR1 comprising the amino acid sequence of SEQ ID NO: 615; VL-CDR2 comprising the amino acid sequence of SEQ ID NO: 16; and VL-CDR3 comprising the amino acid sequence of SEQ ID NO: 17; or yy) VL-CDR1 comprising the amino acid sequence of SEQ ID NO: 625; VL-CDR2 comprising the amino acid sequence of SEQ ID NO: 16; and VL-CDR3 comprising the amino acid sequence of SEQ ID NO: 17.

In some embodiments, the antibody comprises:

a) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 12; a VH-CDR3 comprising an amino acid sequence having at least 80%, 90%, 95% or 100% sequence identity to SEQ ID NO: 13; a VL-CDR1 comprising the amino acid sequence of SEQ ID NO: 15; a VL-CDR2 comprising the amino acid sequence having of SEQ ID NO: 16; and a VL-CDR3 comprising the amino acid sequence of sequence identity to SEQ ID NO: 17; or b) VH-CDR1 comprising an amino acid sequence having at least 80%, 90%, 95% or 100% sequence identity to SEQ ID NO: 21; a VH-CDR2 comprising an amino acid sequence having at least 80%, 90%, 95% or 100% sequence identity to SEQ ID NO: 22; a VH-CDR3 comprising an amino acid sequence having at least 80%, 90%, 95% or 100% sequence identity to the amino acid sequence YSY; a VL-CDR1 comprising the amino acid sequence of SEQ ID NO: 25; a VL-CDR2 comprising the amino acid sequence of SEQ ID NO: 26; and a VL-CDR3 comprising the amino acid sequence of sequence identity to SEQ ID NO: 27; or c) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 32; a VH-CDR3 comprising an amino acid sequence having at least 80%, 90%, 95% or 100% sequence identity to SEQ ID NO: 33; a VL-CDR1 comprising the amino acid sequence of SEQ ID NO: 35; a VL-CDR2 comprising the amino acid sequence of SEQ ID NO: 36; and a VL-CDR3 comprising the amino acid sequence of SEQ ID NO: 37; or d) VH-CDR1 comprising an amino acid sequence having at least 80%, 90%, 95% or 100% sequence identity to SEQ ID NO: 41; a VH-CDR2 comprising an amino acid sequence having at least 80%, 90%, 95% or 100% sequence identity to SEQ ID NO: 42; a VH-CDR3 comprising an amino acid sequence having at least 80%, 90%, 95% or 100% sequence identity to SEQ ID NO: 43; a VL-CDR1 comprising the amino acid sequence of SEQ ID NO: 45; a VL-CDR2 comprising the amino acid sequence of SEQ ID NO: 46; and a VL-CDR3 comprising the amino acid sequence of SEQ ID NO: 47; or e) VH-CDR1 comprising an amino acid sequence having at least 80%, 90%, 95% or 100% sequence identity to SEQ ID NO: 21; a VH-CDR2 comprising an amino acid sequence having at least 80%, 90%, 95% or 100% sequence identity to SEQ ID NO: 52; a VH-CDR3 comprising an amino acid sequence having at least 80%, 90%, 95% or 100% sequence identity to the amino acid sequence YSF; a VL-CDR1 comprising the amino acid sequence of SEQ ID NO: 55; a VL-CDR2 comprising the amino acid sequence of SEQ ID NO: 56; and a VL-CDR3 comprising the amino acid sequence of SEQ ID NO: 27; or f) VH-CDR1 comprising an amino acid sequence having at least 80%, 90%, 95% or 100% sequence identity to SEQ ID NO: 61; a VH-CDR2 comprising an amino acid sequence having at least 80%, 90%, 95% or 100% sequence identity to SEQ ID NO: 62; a VH-CDR3 comprising an amino acid sequence having at least 80%, 90%, 95% or 100% sequence identity to SEQ ID NO: 43; a VL-CDR1 comprising the amino acid sequence of SEQ ID NO: 65; a VL-CDR2 comprising the amino acid sequence of SEQ ID NO: 46; and a VL-CDR3 comprising the amino acid sequence of SEQ ID NO: 67; or g) VH-CDR1 comprising an amino acid sequence having at least 80%, 90%, 95% or 100% sequence identity to SEQ ID NO: 21; a VH-CDR2 comprising an amino acid sequence having at least 80%, 90%, 95% or 100% sequence identity to SEQ ID NO: 72; a VH-CDR3 comprising an amino acid sequence having at least 80%, 90%, 95% or 100% sequence identity to the amino acid sequence YSY; a VL-CDR1 comprising the amino acid sequence of SEQ ID NO: 75; a VL-CDR2 comprising the amino acid sequence of SEQ ID NO: 76; and a VL-CDR3 comprising the amino acid sequence of SEQ ID NO: 77; or h) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 32; a VH-CDR3 comprising an amino acid sequence having at least 80%, 90%, 95% or 100% sequence identity to SEQ ID NO: 33; a VL-CDR1 comprising the amino acid sequence of SEQ ID NO: 85; a VL-CDR2 comprising the amino acid sequence of SEQ ID NO: 36; and a VL-CDR3 comprising the amino acid sequence of SEQ ID NO: 87; or i) VH-CDR1 comprising an amino acid sequence having at least 80%, 90%, 95% or 100% sequence identity to SEQ ID NO: 91; a VH-CDR2 comprising an amino acid sequence having at least 80%, 90%, 95% or 100% sequence identity to SEQ ID NO: 92; and a VH-CDR3 comprising an amino acid sequence having at least 80%, 90%, 95% or 100% sequence identity to SEQ ID NO: 93; a VL-CDR1 comprising the amino acid sequence of SEQ ID NO: 95; a VL-CDR2 comprising the amino acid sequence of SEQ ID NO: 96; and a VL-CDR3 comprising the amino acid sequence of SEQ ID NO: 97; or j) VH-CDR1 comprising an amino acid sequence having at least 80%, 90%, 95% or 100% sequence identity to SEQ ID NO: 101; a VH-CDR2 comprising an amino acid sequence having at least 80%, 90%, 95% or 100% sequence identity to SEQ ID NO: 102; a VH-CDR3 comprising an amino acid sequence having at least 80%, 90%, 95% or 100% sequence identity to SEQ ID NO: 103; or a VL-CDR1 comprising the amino acid sequence of SEQ ID NO: 105; a VL-CDR2 comprising the amino acid sequence of SEQ ID NO: 106; and a VL-CDR3 comprising the amino acid sequence of SEQ ID NO: 107; or k) VH-CDR1 comprising an amino acid sequence having at least 80%, 90%, 95% or 100% sequence identity to SEQ ID NO: 111; a VH-CDR2 comprising an amino acid sequence having at least 80%, 90%, 95% or 100% sequence identity to SEQ ID NO: 112; a VH-CDR3 comprising an amino acid sequence having at 80%, 90%, 95% or 100% sequence identity to SEQ ID NO: 113; a VL-CDR1 comprising the amino acid sequence of SEQ ID NO: 115; a VL-CDR2 comprising the amino acid sequence of SEQ ID NO: 106; and a VL-CDR3 comprising the amino acid sequence of SEQ ID NO: 117; or l) VH-CDR1 comprising an amino acid sequence having at least 80%, 90%, 95% or 100% sequence identity to SEQ ID NO: 281; a VH-CDR2 comprising an amino acid sequence having at least 80%, 90%, 95% or 100% sequence identity to SEQ ID NO: 282; a VH-CDR3 comprising an amino acid sequence having at least 80%, 90%, 95% or 100% sequence identity to SEQ ID NO: 283; a VL-CDR1 comprising the amino acid sequence of SEQ ID NO: 285; a VL-CDR2 comprising the amino acid sequence having of SEQ ID NO: 286; and a VL-CDR3 comprising the amino acid sequence of sequence identity to SEQ ID NO: 287; or m) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 192; a VH-CDR3 comprising an amino acid sequence having at least 80%, 90%, 95% or 100% sequence identity to SEQ ID NO: 193; a VL-CDR1 comprising the amino acid sequence of SEQ ID NO: 195; a VL-CDR2 comprising the amino acid sequence having of SEQ ID NO: 96; and a VL-CDR3 comprising the amino acid sequence of sequence identity to SEQ ID NO: 197; or n) VH-CDR1 comprising an amino acid sequence having at least 80%, 90%, 95% or 100% sequence identity to SEQ ID NO: 141; a VH-CDR2 comprising an amino acid sequence having at least 80%, 90%, 95% or 100% sequence identity to SEQ ID NO: 142; a VH-CDR3 comprising an amino acid sequence having at least 80%, 90%, 95% or 100% sequence identity to SEQ ID NO: 143; a VL-CDR1 comprising the amino acid sequence of SEQ ID NO: 145; a VL-CDR2 comprising the amino acid sequence having of SEQ ID NO: 16; and a VL-CDR3 comprising the amino acid sequence of sequence identity to SEQ ID NO: 17; or o) VH-CDR1 comprising an amino acid sequence having at least 80%, 90%, 95% or 100% sequence identity to SEQ ID NO: 151; a VH-CDR2 comprising an amino acid sequence having at least 80%, 90%, 95% or 100% sequence identity to SEQ ID NO: 152; a VH-CDR3 comprising an amino acid sequence having at least 80%, 90%, 95% or 100% sequence identity to SEQ ID NO: 153; a VL-CDR1 comprising the amino acid sequence of SEQ ID NO: 105; a VL-CDR2 comprising the amino acid sequence having of SEQ ID NO: 106; and a VL-CDR3 comprising the amino acid sequence of sequence identity to SEQ ID NO: 107; or p) VH-CDR1 comprising an amino acid sequence having at least 80%, 90%, 95% or 100% sequence identity to SEQ ID NO: 161; a VH-CDR2 comprising an amino acid sequence having at least 80%, 90%, 95% or 100% sequence identity to SEQ ID NO: 162; a VH-CDR3 comprising an amino acid sequence having at least 80%, 90%, 95% or 100% sequence identity to SEQ ID NO: 163; a VL-CDR1 comprising the amino acid sequence of SEQ ID NO: 165; a VL-CDR2 comprising the amino acid sequence having of SEQ ID NO: 16; and a VL-CDR3 comprising the amino acid sequence of sequence identity to SEQ ID NO: 167; or) VH-CDR1 comprising an amino acid sequence having at least 80%, 90%, 95% or 100% sequence identity to SEQ ID NO: 171; a VH-CDR2 comprising an amino acid sequence having at least 80%, 90%, 95% or 100% sequence identity to SEQ ID NO: 172; a VH-CDR3 comprising an amino acid sequence having at least 80%, 90%, 95% or 100% sequence identity to SEQ ID NO: 173; a VL-CDR1 comprising the amino acid sequence of SEQ ID NO: 175; a VL-CDR2 comprising the amino acid sequence having of SEQ ID NO: 176; and a VL-CDR3 comprising the amino acid sequence of sequence identity to SEQ ID NO: 177; or r) VH-CDR1 comprising an amino acid sequence having at least 80%, 90%, 95% or 100% sequence identity to SEQ ID NO: 181; a VH-CDR2 comprising an amino acid sequence having at least 80%, 90%, 95% or 100% sequence identity to SEQ ID NO: 182; a VH-CDR3 comprising an amino acid sequence having at least 80%, 90%, 95% or 100% sequence identity to SEQ ID NO: 183; a VL-CDR1 comprising the amino acid sequence of SEQ ID NO: 15; a VL-CDR2 comprising the amino acid sequence having of SEQ ID NO: 16; and a VL-CDR3 comprising the amino acid sequence of sequence identity to SEQ ID NO: 187; or s) VH-CDR1 comprising an amino acid sequence having at least 80%, 90%, 95% or 100% sequence identity to SEQ ID NO: 201; a VH-CDR2 comprising an amino acid sequence having at least 80%, 90%, 95% or 100% sequence identity to SEQ ID NO: 202; a VH-CDR3 comprising an amino acid sequence having at least 80%, 90%, 95% or 100% sequence identity to SEQ ID NO: 153; a VL-CDR1 comprising the amino acid sequence of SEQ ID NO: 105; a VL-CDR2 comprising the amino acid sequence having of SEQ ID NO: 206; and a VL-CDR3 comprising the amino acid sequence of sequence identity to SEQ ID NO: 107; or t) VH-CDR1 comprising an amino acid sequence having at least 80%, 90%, 95% or 100% sequence identity to SEQ ID NO: 211; a VH-CDR2 comprising an amino acid sequence having at least 80%, 90%, 95% or 100% sequence identity to SEQ ID NO: 212; a VH-CDR3 comprising an amino acid sequence having at least 80%, 90%, 95% or 100% sequence identity to SEQ ID NO: 213; a VL-CDR1 comprising the amino acid sequence of SEQ ID NO: 215; a VL-CDR2 comprising the amino acid sequence having of SEQ ID NO: 216; and a VL-CDR3 comprising the amino acid sequence of sequence identity to SEQ ID NO: 217; or u) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 222; a VH-CDR3 comprising an amino acid sequence having at least 80%, 90%, 95% or 100% sequence identity to SEQ ID NO: 223; a VL-CDR1 comprising the amino acid sequence of SEQ ID NO: 225; a VL-CDR2 comprising the amino acid sequence having of SEQ ID NO: 96; and a VL-CDR3 comprising the amino acid sequence of sequence identity to SEQ ID NO: 227; or v) VH-CDR1 comprising an amino acid sequence having at least 80%, 90%, 95% or 100% sequence identity to SEQ ID NO: 231; a VH-CDR2 comprising an amino acid sequence having at least 80%, 90%, 95% or 100% sequence identity to SEQ ID NO: 232; a VH-CDR3 comprising an amino acid sequence having at least 80%, 90%, 95% or 100% sequence identity to SEQ ID NO: 233; a VL-CDR1 comprising the amino acid sequence of SEQ ID NO: 235; a VL-CDR2 comprising the amino acid sequence having of SEQ ID NO: 236; and a VL-CDR3 comprising the amino acid sequence of sequence identity to SEQ ID NO: 237; or w) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 242; a VH-CDR3 comprising an amino acid sequence having at least 80%, 90%, 95% or 100% sequence identity to SEQ ID NO: 243; a VL-CDR1 comprising the amino acid sequence of SEQ ID NO: 225; a VL-CDR2 comprising the amino acid sequence having of SEQ ID NO: 96; and a VL-CDR3 comprising the amino acid sequence of sequence identity to SEQ ID NO: 247; or x) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 252; a VH-CDR3 comprising an amino acid sequence having at least 80%, 90%, 95% or 100% sequence identity to SEQ ID NO: 253; a VL-CDR1 comprising the amino acid sequence of SEQ ID NO: 255; a VL-CDR2 comprising the amino acid sequence having of SEQ ID NO: 256; and a VL-CDR3 comprising the amino acid sequence of sequence identity to SEQ ID NO: 257; or y) VH-CDR1 comprising an amino acid sequence having at least 80%, 90%, 95% or 100% sequence identity to SEQ ID NO: 261; a VH-CDR2 comprising an amino acid sequence having at least 80%, 90%, 95% or 100% sequence identity to SEQ ID NO: 262; a VH-CDR3 comprising an amino acid sequence having at least 80%, 90%, 95% or 100% sequence identity to SEQ ID NO: 263; a VL-CDR1 comprising the amino acid sequence of SEQ ID NO: 265; a VL-CDR2 comprising the amino acid sequence having of SEQ ID NO: 176; and a VL-CDR3 comprising the amino acid sequence of sequence identity to SEQ ID NO: 267; or z) VH-CDR1 comprising an amino acid sequence having at least 80%, 90%, 95% or 100% sequence identity to SEQ ID NO: 271; a VH-CDR2 comprising an amino acid sequence having at least 80%, 90%, 95% or 100% sequence identity to SEQ ID NO: 272; a VH-CDR3 comprising an amino acid sequence having at least 80%, 90%, 95% or 100% sequence identity to SEQ ID NO: 273; a VL-CDR1 comprising the amino acid sequence of SEQ ID NO: 275; a VL-CDR2 comprising the amino acid sequence having of SEQ ID NO: 276; and a VL-CDR3 comprising the amino acid sequence of sequence identity to SEQ ID NO: 277; or aa) VH-CDR1 comprising an amino acid sequence having at least 80%, 90%, 95% or 100% sequence identity to SEQ ID NO: 301; a VH-CDR2 comprising an amino acid sequence having at least 80%, 90%, 95% or 100% sequence identity to SEQ ID NO: 302; a VH-CDR3 comprising an amino acid sequence having at least 80%, 90%, 95% or 100% sequence identity to SEQ ID NO: 303; a VL-CDR1 comprising the amino acid sequence of SEQ ID NO: 15; a VL-CDR2 comprising the amino acid sequence having of SEQ ID NO: 16; and a VL-CDR3 comprising the amino acid sequence of sequence identity to SEQ ID NO: 307; or bb) VH-CDR1 comprising an amino acid sequence having at least 80%, 90%, 95% or 100% sequence identity to SEQ ID NO: 311; a VH-CDR2 comprising an amino acid sequence having at least 80%, 90%, 95% or 100% sequence identity to SEQ ID NO: 312; a VH-CDR3 comprising an amino acid sequence having at least 80%, 90%, 95% or 100% sequence identity to SEQ ID NO: 313; a VL-CDR1 comprising the amino acid sequence of SEQ ID NO: 315; a VL-CDR2 comprising the amino acid sequence having of SEQ ID NO: 46; and a VL-CDR3 comprising the amino acid sequence of sequence identity to SEQ ID NO: 67; or cc) VH-CDR1 comprising an amino acid sequence having at least 80%, 90%, 95% or 100% sequence identity to SEQ ID NO: 321; a VH-CDR2 comprising an amino acid sequence having at least 80%, 90%, 95% or 100% sequence identity to SEQ ID NO: 322; a VH-CDR3 comprising an amino acid sequence having at least 80%, 90%, 95% or 100% sequence identity to SEQ ID NO: 323; a VL-CDR1 comprising the amino acid sequence of SEQ ID NO: 325; a VL-CDR2 comprising the amino acid sequence having of SEQ ID NO: 326; and a VL-CDR3 comprising the amino acid sequence of sequence identity to SEQ ID NO: 327; or dd) VH-CDR1 comprising an amino acid sequence having at least 80%, 90%, 95% or 100% sequence identity to SEQ ID NO: 151; a VH-CDR2 comprising an amino acid sequence having at least 80%, 90%, 95% or 100% sequence identity to SEQ ID NO: 332; a VH-CDR3 comprising an amino acid sequence having at least 80%, 90%, 95% or 100% sequence identity to SEQ ID NO: 333; a VL-CDR1 comprising the amino acid sequence of SEQ ID NO: 335; a VL-CDR2 comprising the amino acid sequence having of SEQ ID NO: 336; and a VL-CDR3 comprising the amino acid sequence of sequence identity to SEQ ID NO: 107; or ee) VH-CDR1 comprising an amino acid sequence having at least 80%, 90%, 95% or 100% sequence identity to SEQ ID NO: 341; a VH-CDR2 comprising an amino acid sequence having at least 80%, 90%, 95% or 100% sequence identity to SEQ ID NO: 342; a VH-CDR3 comprising an amino acid sequence having at least 80%, 90%, 95% or 100% sequence identity to SEQ ID NO: 343; a VL-CDR1 comprising the amino acid sequence of SEQ ID NO: 345; a VL-CDR2 comprising the amino acid sequence having of SEQ ID NO: 346; and a VL-CDR3 comprising the amino acid sequence of sequence identity to SEQ ID NO: 347; or ff) VH-CDR1 comprising an amino acid sequence having at least 80%, 90%, 95% or 100% sequence identity to SEQ ID NO: 351; a VH-CDR2 comprising an amino acid sequence having at least 80%, 90%, 95% or 100% sequence identity to SEQ ID NO: 352; a VH-CDR3 comprising an amino acid sequence having at least 80%, 90%, 95% or 100% sequence identity to SEQ ID NO: 353; a VL-CDR1 comprising the amino acid sequence of SEQ ID NO: 355; a VL-CDR2 comprising the amino acid sequence having of SEQ ID NO: 356; and a VL-CDR3 comprising the amino acid sequence of sequence identity to SEQ ID NO: 357; or gg) VH-CDR1 comprising an amino acid sequence having at least 80%, 90%, 95% or 100% sequence identity to SEQ ID NO: 361; a VH-CDR2 comprising an amino acid sequence having at least 80%, 90%, 95% or 100% sequence identity to SEQ ID NO: 362; a VH-CDR3 comprising an amino acid sequence having at least 80%, 90%, 95% or 100% sequence identity to SEQ ID NO: 363; a VL-CDR1 comprising the amino acid sequence of SEQ ID NO: 365; a VL-CDR2 comprising the amino acid sequence having of SEQ ID NO: 16; and a VL-CDR3 comprising the amino acid sequence of sequence identity to SEQ ID NO: 367; or hh) VH-CDR1 comprising an amino acid sequence having at least 80%, 90%, 95% or 100% sequence identity to SEQ ID NO: 371; a VH-CDR2 comprising an amino acid sequence having at least 80%, 90%, 95% or 100% sequence identity to SEQ ID NO: 372; a VH-CDR3 comprising an amino acid sequence having at least 80%, 90%, 95% or 100% sequence identity to SEQ ID NO: 373; a VL-CDR1 comprising the amino acid sequence of SEQ ID NO: 345; a VL-CDR2 comprising the amino acid sequence having of SEQ ID NO: 376; and a VL-CDR3 comprising the amino acid sequence of sequence identity to SEQ ID NO: 347; or ii) VH-CDR1 comprising an amino acid sequence having at least 80%, 90%, 95% or 100% sequence identity to SEQ ID NO: 351; a VH-CDR2 comprising an amino acid sequence having at least 80%, 90%, 95% or 100% sequence identity to SEQ ID NO: 382; a VH-CDR3 comprising an amino acid sequence having at least 80%, 90%, 95% or 100% sequence identity to SEQ ID NO: 383; a VL-CDR1 comprising the amino acid sequence of SEQ ID NO: 385; a VL-CDR2 comprising the amino acid sequence having of SEQ ID NO: 386; and a VL-CDR3 comprising the amino acid sequence of sequence identity to SEQ ID NO: 387; or jj) VH-CDR1 comprising an amino acid sequence having at least 80%, 90%, 95% or 100% sequence identity to SEQ ID NO: 351; a VH-CDR2 comprising an amino acid sequence having at least 80%, 90%, 95% or 100% sequence identity to SEQ ID NO: 382; a VH-CDR3 comprising an amino acid sequence having at least 80%, 90%, 95% or 100% sequence identity to SEQ ID NO: 393; a VL-CDR1 comprising the amino acid sequence of SEQ ID NO: 395; a VL-CDR2 comprising the amino acid sequence having of SEQ ID NO: 356; and a VL-CDR3 comprising the amino acid sequence of sequence identity to SEQ ID NO: 357; or kk) VH-CDR1 comprising an amino acid sequence having at least 80%, 90%, 95% or 100% sequence identity to SEQ ID NO: 351; a VH-CDR2 comprising an amino acid sequence having at least 80%, 90%, 95% or 100% sequence identity to SEQ ID NO: 382; a VH-CDR3 comprising an amino acid sequence having at least 80%, 90%, 95% or 100% sequence identity to SEQ ID NO: 393; a VL-CDR1 comprising the amino acid sequence of SEQ ID NO: 405; a VL-CDR2 comprising the amino acid sequence having of SEQ ID NO: 356; and a VL-CDR3 comprising the amino acid sequence of sequence identity to SEQ ID NO: 357; or ll) VH-CDR1 comprising an amino acid sequence having at least 80%, 90%, 95% or 100% sequence identity to SEQ ID NO: 411; a VH-CDR2 comprising an amino acid sequence having at least 80%, 90%, 95% or 100% sequence identity to SEQ ID NO: 412; a VH-CDR3 comprising an amino acid sequence having at least 80%, 90%, 95% or 100% sequence identity to SEQ ID NO: 413; a VL-CDR1 comprising the amino acid sequence of SEQ ID NO: 105; a VL-CDR2 comprising the amino acid sequence having of SEQ ID NO: 106; and a VL-CDR3 comprising the amino acid sequence of sequence identity to SEQ ID NO: 107; or mm) VH-CDR1 comprising an amino acid sequence having at least 80%, 90%, 95% or 100% sequence identity to SEQ ID NO: 421; a VH-CDR2 comprising an amino acid sequence having at least 80%, 90%, 95% or 100% sequence identity to SEQ ID NO: 422; a VH-CDR3 comprising an amino acid sequence having at least 80%, 90%, 95% or 100% sequence identity to the amino acid sequence GNY; a VL-CDR1 comprising the amino acid sequence of SEQ ID NO: 425; a VL-CDR2 comprising the amino acid sequence having of SEQ ID NO: 426; and a VL-CDR3 comprising the amino acid sequence of sequence identity to SEQ ID NO: 427; or nn) VH-CDR1 comprising an amino acid sequence having at least 80%, 90%, 95% or 100% sequence identity to SEQ ID NO: 431; a VH-CDR2 comprising an amino acid sequence having at least 80%, 90%, 95% or 100% sequence identity to SEQ ID NO: 432; a VH-CDR3 comprising an amino acid sequence having at least 80%, 90%, 95% or 100% sequence identity to SEQ ID NO: 433; a VL-CDR1 comprising the amino acid sequence of SEQ ID NO: 435; a VL-CDR2 comprising the amino acid sequence having of SEQ ID NO: 436; and a VL-CDR3 comprising the amino acid sequence of sequence identity to SEQ ID NO: 437; or oo) VH-CDR1 comprising an amino acid sequence having at least 80%, 90%, 95% or 100% sequence identity to SEQ ID NO: 151; a VH-CDR2 comprising an amino acid sequence having at least 80%, 90%, 95% or 100% sequence identity to SEQ ID NO: 442; a VH-CDR3 comprising an amino acid sequence having at least 80%, 90%, 95% or 100% sequence identity to SEQ ID NO: 443; a VL-CDR1 comprising the amino acid sequence of SEQ ID NO: 105; a VL-CDR2 comprising the amino acid sequence having of SEQ ID NO: 106; and a VL-CDR3 comprising the amino acid sequence of sequence identity to SEQ ID NO: 107; or pp) VH-CDR1 comprising an amino acid sequence having at least 80%, 90%, 95% or 100% sequence identity to SEQ ID NO: 461; a VH-CDR2 comprising an amino acid sequence having at least 80%, 90%, 95% or 100% sequence identity to SEQ ID NO: 462; a VH-CDR3 comprising an amino acid sequence having at least 80%, 90%, 95% or 100% sequence identity to SEQ ID NO: 463; a VL-CDR1 comprising the amino acid sequence of SEQ ID NO: 465; a VL-CDR2 comprising the amino acid sequence having of SEQ ID NO: 16; and a VL-CDR3 comprising the amino acid sequence of sequence identity to SEQ ID NO: 467; or qq) VH-CDR1 comprising an amino acid sequence having at least 80%, 90%, 95% or 100% sequence identity to SEQ ID NO: 141; a VH-CDR2 comprising an amino acid sequence having at least 80%, 90%, 95% or 100% sequence identity to SEQ ID NO: 472; a VH-CDR3 comprising an amino acid sequence having at least 80%, 90%, 95% or 100% sequence identity to SEQ ID NO: 473; a VL-CDR1 comprising the amino acid sequence of SEQ ID NO: 475; a VL-CDR2 comprising the amino acid sequence having of SEQ ID NO: 476; and a VL-CDR3 comprising the amino acid sequence of sequence identity to SEQ ID NO: 477; or rr) VH-CDR1 comprising an amino acid sequence having at least 80%, 90%, 95% or 100% sequence identity to SEQ ID NO: 481; a VH-CDR2 comprising an amino acid sequence having at least 80%, 90%, 95% or 100% sequence identity to SEQ ID NO: 482; a VH-CDR3 comprising an amino acid sequence having at least 80%, 90%, 95% or 100% sequence identity to SEQ ID NO: 483; a VL-CDR1 comprising the amino acid sequence of SEQ ID NO: 165; a VL-CDR2 comprising the amino acid sequence having of SEQ ID NO: 16; and a VL-CDR3 comprising the amino acid sequence of sequence identity to SEQ ID NO: 487; or ss) VH-CDR1 comprising an amino acid sequence having at least 80%, 90%, 95% or 100% sequence identity to SEQ ID NO: 141; a VH-CDR2 comprising an amino acid sequence having at least 80%, 90%, 95% or 100% sequence identity to SEQ ID NO: 492; a VH-CDR3 comprising an amino acid sequence having at least 80%, 90%, 95% or 100% sequence identity to SEQ ID NO: 493; a VL-CDR1 comprising the amino acid sequence of SEQ ID NO: 495; a VL-CDR2 comprising the amino acid sequence having of SEQ ID NO: 496; and a VL-CDR3 comprising the amino acid sequence of sequence identity to SEQ ID NO: 497; or tt) VH-CDR1 comprising an amino acid sequence having at least 80%, 90%, 95% or 100% sequence identity to SEQ ID NO: 151; a VH-CDR2 comprising an amino acid sequence having at least 80%, 90%, 95% or 100% sequence identity to SEQ ID NO: 502; a VH-CDR3 comprising an amino acid sequence having at least 80%, 90%, 95% or 100% sequence identity to SEQ ID NO: 503; a VL-CDR1 comprising the amino acid sequence of SEQ ID NO: 105; a VL-CDR2 comprising the amino acid sequence having of SEQ ID NO: 336; and a VL-CDR3 comprising the amino acid sequence of sequence identity to SEQ ID NO: 107; or uu) VH-CDR1 comprising an amino acid sequence having at least 80%, 90%, 95% or 100% sequence identity to SEQ ID NO: 311; a VH-CDR2 comprising an amino acid sequence having at least 80%, 90%, 95% or 100% sequence identity to SEQ ID NO: 512; a VH-CDR3 comprising an amino acid sequence having at least 80%, 90%, 95% or 100% sequence identity to SEQ ID NO: 513; a VL-CDR1 comprising the amino acid sequence of SEQ ID NO: 515; a VL-CDR2 comprising the amino acid sequence having of SEQ ID NO: 516; and a VL-CDR3 comprising the amino acid sequence of sequence identity to SEQ ID NO: 517; or vv) VH-CDR1 comprising an amino acid sequence having at least 80%, 90%, 95% or 100% sequence identity to SEQ ID NO: 521; a VH-CDR2 comprising an amino acid sequence having at least 80%, 90%, 95% or 100% sequence identity to SEQ ID NO: 522; a VH-CDR3 comprising an amino acid sequence having at least 80%, 90%, 95% or 100% sequence identity to SEQ ID NO: 463; a VL-CDR1 comprising the amino acid sequence of SEQ ID NO: 525; a VL-CDR2 comprising the amino acid sequence having of SEQ ID NO: 16; and a VL-CDR3 comprising the amino acid sequence of sequence identity to SEQ ID NO: 467; or ww) VH-CDR1 comprising an amino acid sequence having at least 80%, 90%, 95% or 100% sequence identity to SEQ ID NO: 371; a VH-CDR2 comprising an amino acid sequence having at least 80%, 90%, 95% or 100% sequence identity to SEQ ID NO: 532; a VH-CDR3 comprising an amino acid sequence having at least 80%, 90%, 95% or 100% sequence identity to SEQ ID NO: 533; a VL-CDR1 comprising the amino acid sequence of SEQ ID NO: 345; a VL-CDR2 comprising the amino acid sequence having of SEQ ID NO: 376; and a VL-CDR3 comprising the amino acid sequence of sequence identity to SEQ ID NO: 537; or xx) VH-CDR1 comprising an amino acid sequence having at least 80%, 90%, 95% or 100% sequence identity to SEQ ID NO: 341; a VH-CDR2 comprising an amino acid sequence having at least 80%, 90%, 95% or 100% sequence identity to SEQ ID NO: 542; a VH-CDR3 comprising an amino acid sequence having at least 80%, 90%, 95% or 100% sequence identity to SEQ ID NO: 543; a VL-CDR1 comprising the amino acid sequence of SEQ ID NO: 345; a VL-CDR2 comprising the amino acid sequence having of SEQ ID NO: 376; and a VL-CDR3 comprising the amino acid sequence of sequence identity to SEQ ID NO: 347; or yy) VH-CDR1 comprising an amino acid sequence having at least 80%, 90%, 95% or 100% sequence identity to SEQ ID NO: 551; a VH-CDR2 comprising an amino acid sequence having at least 80%, 90%, 95% or 100% sequence identity to SEQ ID NO: 552; a VH-CDR3 comprising an amino acid sequence having at least 80%, 90%, 95% or 100% sequence identity to SEQ ID NO: 553; a VL-CDR1 comprising the amino acid sequence of SEQ ID NO: 555; a VL-CDR2 comprising the amino acid sequence having of SEQ ID NO: 16; and a VL-CDR3 comprising the amino acid sequence of sequence identity to SEQ ID NO: 557; or zz) VH-CDR1 comprising an amino acid sequence having at least 80%, 90%, 95% or 100% sequence identity to SEQ ID NO: 551; a VH-CDR2 comprising an amino acid sequence having at least 80%, 90%, 95% or 100% sequence identity to SEQ ID NO: 552; a VH-CDR3 comprising an amino acid sequence having at least 80%, 90%, 95% or 100% sequence identity to SEQ ID NO: 563; a VL-CDR1 comprising the amino acid sequence of SEQ ID NO: 565; a VL-CDR2 comprising the amino acid sequence having of SEQ ID NO: 16; and a VL-CDR3 comprising the amino acid sequence of sequence identity to SEQ ID NO: 557; or aaa) VH-CDR1 comprising an amino acid sequence having at least 80%, 90%, 95% or 100% sequence identity to SEQ ID NO: 571; a VH-CDR2 comprising an amino acid sequence having at least 80%, 90%, 95% or 100% sequence identity to SEQ ID NO: 202; a VH-CDR3 comprising an amino acid sequence having at least 80%, 90%, 95% or 100% sequence identity to SEQ ID NO: 573; a VL-CDR1 comprising the amino acid sequence of SEQ ID NO: 105; a VL-CDR2 comprising the amino acid sequence having of SEQ ID NO: 106; and a VL-CDR3 comprising the amino acid sequence of sequence identity to SEQ ID NO: 107; or bbb) VH-CDR1 comprising an amino acid sequence having at least 80%, 90%, 95% or 100% sequence identity to SEQ ID NO: 581; a VH-CDR2 comprising an amino acid sequence having at least 80%, 90%, 95% or 100% sequence identity to SEQ ID NO: 582; a VH-CDR3 comprising an amino acid sequence having at least 80%, 90%, 95% or 100% sequence identity to SEQ ID NO: 583; a VL-CDR1 comprising the amino acid sequence of SEQ ID NO: 585; a VL-CDR2 comprising the amino acid sequence having of SEQ ID NO: 586; and a VL-CDR3 comprising the amino acid sequence of sequence identity to SEQ ID NO: 587; or ccc) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 13; a VL-CDR1 comprising the amino acid sequence of SEQ ID NO: 615; a VL-CDR2 comprising the amino acid sequence having of SEQ ID NO: 16; and a VL-CDR3 comprising the amino acid sequence of sequence identity to SEQ ID NO: 17; or ddd) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 13; a VL-CDR1 comprising the amino acid sequence of SEQ ID NO: 625; a VL-CDR2 comprising the amino acid sequence having of SEQ ID NO: 16; and a VL-CDR3 comprising the amino acid sequence of sequence identity to SEQ ID NO: 17; or eee) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 663; a VL-CDR1 comprising the amino acid sequence of SEQ ID NO: 615; a VL-CDR2 comprising the amino acid sequence having of SEQ ID NO: 16; and a VL-CDR3 comprising the amino acid sequence of sequence identity to SEQ ID NO: 17; or fff) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 673; a VL-CDR1 comprising the amino acid sequence of SEQ ID NO: 615; a VL-CDR2 comprising the amino acid sequence having of SEQ ID NO: 16; and a VL-CDR3 comprising the amino acid sequence of sequence identity to SEQ ID NO: 17; or ggg) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 683; a VL-CDR1 comprising the amino acid sequence of SEQ ID NO: 615; a VL-CDR2 comprising the amino acid sequence having of SEQ ID NO: 16; and a VL-CDR3 comprising the amino acid sequence of sequence identity to SEQ ID NO: 17; or hhh) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 612; a VH-CDR3 comprising an amino acid sequence having at least 80%, 90%, 95% or 100% sequence identity to SEQ ID NO: 683; a VL-CDR1 comprising the amino acid sequence of SEQ ID NO: 625; a VL-CDR2 comprising the amino acid sequence having of SEQ ID NO: 16; and a VL-CDR3 comprising the amino acid sequence of sequence identity to SEQ ID NO: 17.

In some embodiments, the antibody comprises:

a) VH-CDR1 comprising the amino acid sequence of SEQ ID NO: 11; a VH-CDR2 comprising the amino acid sequence of SEQ ID NO: 12; a VH-CDR3 comprising the amino acid sequence of SEQ ID NO: 13; a VL-CDR1 comprising an amino acid sequence having at least 80%, 90%, 95% or 100% sequence identity to SEQ ID NO: 15; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or b) VH-CDR1 comprising the amino acid sequence of SEQ ID NO: 21; a VH-CDR2 comprising the amino acid sequence of SEQ ID NO: 22; a VH-CDR3 comprising the amino acid sequence YSY; a VL-CDR1 comprising an amino acid sequence having at least 80%, 90%, 95% or 100% sequence identity to SEQ ID NO: 25; a VL-CDR2 comprising an amino acid sequence having at least 80%, 90%, 95% or 100% sequence identity to SEQ ID NO: 26; and a VL-CDR3 comprising an amino acid sequence having at least 80%, 90%, 95% or 100% sequence identity to SEQ ID NO: 27; or c) VH-CDR1 comprising the amino acid sequence of SEQ ID NO: 31; a VH-CDR2 comprising the amino acid sequence of SEQ ID NO: 32; a VH-CDR3 comprising the amino acid sequence of SEQ ID NO: 33; a VL-CDR1 comprising an amino acid sequence having at least 80%, 90%, 95% or 100% sequence identity to SEQ ID NO: 35; a VL-CDR2 comprising an amino acid sequence having at least 80%, 90%, 95% or 100% sequence identity to SEQ ID NO: 36; and a VL-CDR3 comprising an amino acid sequence having at least 80%, 90%, 95% or 100% sequence identity to SEQ ID NO: 37; or d) VH-CDR1 comprising the amino acid sequence of SEQ ID NO: 41; a VH-CDR2 comprising the amino acid sequence of SEQ ID NO: 42; a VH-CDR3 comprising the amino acid sequence of SEQ ID NO: 43; a VL-CDR1 comprising an amino acid sequence having at least 80%, 90%, 95% or 100% sequence identity to SEQ ID NO: 45; a VL-CDR2 comprising an amino acid sequence having at least 80%, 90%, 95% or 100% sequence identity to SEQ ID NO: 46; and a VL-CDR3 comprising an amino acid sequence having at least 80%, 90%, 95% or 100% sequence identity to SEQ ID NO: 47; or e) VH-CDR1 comprising the amino acid sequence of SEQ ID NO: 21; a VH-CDR2 comprising the amino acid sequence of SEQ ID NO: 52; a VH-CDR3 comprising the amino acid sequence YSF; a VL-CDR1 comprising an amino acid sequence having at least 80%, 90%, 95% or 100% sequence identity to SEQ ID NO: 55; a VL-CDR2 comprising an amino acid sequence having at least 80%, 90%, 95% or 100% sequence identity to SEQ ID NO: 56; and a VL-CDR3 comprising an amino acid sequence having at least 80%, 90%, 95% or 100% sequence identity to SEQ ID NO: 27; or f) VH-CDR1 comprising the amino acid sequence of SEQ ID NO: 61; a VH-CDR2 comprising the amino acid sequence of SEQ ID NO: 62; a VH-CDR3 comprising the amino acid sequence of SEQ ID NO: 43; a VL-CDR1 comprising an amino acid sequence having at least 80%, 90%, 95% or 100% sequence identity to SEQ ID NO: 65; a VL-CDR2 comprising an amino acid sequence having at least 80%, 90%, 95% or 100% sequence identity to SEQ ID NO: 46; and a VL-CDR3 comprising an amino acid sequence having at least 80%, 90%, 95% or 100% sequence identity to SEQ ID NO: 67; or g) VH-CDR1 comprising the amino acid sequence of SEQ ID NO: 21; a VH-CDR2 comprising the amino acid sequence of SEQ ID NO: 72; a VH-CDR3 comprising the amino acid sequence YSY; a VL-CDR1 comprising an amino acid sequence having at least 80%, 90%, 95% or 100% sequence identity to SEQ ID NO: 75; a VL-CDR2 comprising an amino acid sequence having at least 80%, 90%, 95% or 100% sequence identity to SEQ ID NO: 76; and a VL-CDR3 comprising an amino acid sequence having at least 80%, 90%, 95% or 100% sequence identity to SEQ ID NO: 77; or h) a VH-CDR1 comprising the amino acid sequence of SEQ ID NO: 31; a VH-CDR2 comprising the amino acid sequence of SEQ ID NO: 32; a VH-CDR3 comprising the amino acid sequence of SEQ ID NO: 33; a VL-CDR1 comprising an amino acid sequence having at least 80%, 90%, 95% or 100% sequence identity to SEQ ID NO: 85; a VL-CDR2 comprising an amino acid sequence having at least 80%, 90%, 95% or 100% sequence identity to SEQ ID NO: 36; and a VL-CDR3 comprising an amino acid sequence having at least 80%, 90%, 95% or 100% sequence identity to SEQ ID NO: 87; or i) VH-CDR1 comprising the amino acid sequence of SEQ ID NO: 91; a VH-CDR2 comprising the amino acid sequence of SEQ ID NO: 92; and a VH-CDR3 comprising the amino acid sequence of SEQ ID NO: 93; a VL-CDR1 comprising an amino acid sequence having at least 80%, 90%, 95% or 100% sequence identity to SEQ ID NO: 95; a VL-CDR2 comprising an amino acid sequence having at least 80%, 90%, 95% or 100% sequence identity to SEQ ID NO: 96; and a VL-CDR3 comprising an amino acid sequence having at least 80%, 90%, 95% or 100% sequence identity to SEQ ID NO: 97; or j) VH-CDR1 comprising the amino acid sequence of SEQ ID NO: 101; a VH-CDR2 comprising the amino acid sequence of SEQ ID NO: 102; a VH-CDR3 comprising the amino acid sequence of SEQ ID NO: 103; or a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; orVH-CDR1 comprising the amino acid sequence of SEQ ID NO: 111; a VH-CDR2 comprising the amino acid sequence of SEQ ID NO: 112; a VH-CDR3 comprising the amino acid sequence having of SEQ ID NO: 113; a VL-CDR1 comprising an amino acid sequence having at least 80%, 90%, 95% or 100% sequence identity to SEQ ID NO: 115; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 117; or l) VH-CDR1 comprising the amino acid sequence of SEQ ID NO: 281; a VH-CDR2 comprising the amino acid sequence of SEQ ID NO: 282; a VH-CDR3 comprising the amino acid sequence of SEQ ID NO: 283; a VL-CDR1 comprising an amino acid sequence having at least 80%, 90%, 95% or 100% sequence identity to SEQ ID NO: 285; a VL-CDR2 comprising an amino acid sequence having at least 80%, 90%, 95% or 100% sequence identity to SEQ ID NO: 286; and a VL-CDR3 comprising an amino acid sequence having at least 80%, 90%, 95% or 100% sequence identity to SEQ ID NO: 287; or m) VH-CDR1 comprising the amino acid sequence of SEQ ID NO: 31; a VH-CDR2 comprising the amino acid sequence of SEQ ID NO: 192; a VH-CDR3 comprising the amino acid sequence of SEQ ID NO: 193; a VL-CDR1 comprising an amino acid sequence having at least 80%, 90%, 95% or 100% sequence identity to SEQ ID NO: 195; a VL-CDR2 comprising an amino acid sequence having at least 80%, 90%, 95% or 100% sequence identity to SEQ ID NO: 96; and a VL-CDR3 comprising an amino acid sequence having at least 80%, 90%, 95% or 100% sequence identity to SEQ ID NO: 197; or n) VH-CDR1 comprising the amino acid sequence of SEQ ID NO: 141; a VH-CDR2 comprising the amino acid sequence of SEQ ID NO: 142; a VH-CDR3 comprising the amino acid sequence of SEQ ID NO: 143; a VL-CDR1 comprising an amino acid sequence having at least 80%, 90%, 95% or 100% sequence identity to SEQ ID NO: 145; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or o) VH-CDR1 comprising the amino acid sequence of SEQ ID NO: 151; a VH-CDR2 comprising the amino acid sequence of SEQ ID NO: 152; a VH-CDR3 comprising the amino acid sequence of SEQ ID NO: 153; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; or p) VH-CDR1 comprising the amino acid sequence of SEQ ID NO: 161; a VH-CDR2 comprising the amino acid sequence of SEQ ID NO: 162; a VH-CDR3 comprising the amino acid sequence of SEQ ID NO: 163; a VL-CDR1 comprising an amino acid sequence having at least 80%, 90%, 95% or 100% sequence identity to SEQ ID NO: 165; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 167; or q) VH-CDR1 comprising the amino acid sequence of SEQ ID NO: 171; a VH-CDR2 comprising the amino acid sequence of SEQ ID NO: 172; a VH-CDR3 comprising the amino acid sequence of SEQ ID NO: 173; a VL-CDR1 comprising an amino acid sequence having at least 80%, 90%, 95% or 100% sequence identity to SEQ ID NO: 175; a VL-CDR2 comprising an amino acid sequence having at least 80%, 90%, 95% or 100% sequence identity to SEQ ID NO: 176; and a VL-CDR3 comprising an amino acid sequence having at least 80%, 90%, 95% or 100% sequence identity to SEQ ID NO: 177; or r) VH-CDR1 comprising the amino acid sequence of SEQ ID NO: 181; a VH-CDR2 comprising the amino acid sequence of SEQ ID NO: 182; a VH-CDR3 comprising the amino acid sequence of SEQ ID NO: 183; a VL-CDR1 comprising an amino acid sequence having at least 80%, 90%, 95% or 100% sequence identity to SEQ ID NO: 15; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 187; or s) VH-CDR1 comprising the amino acid sequence of SEQ ID NO: 201; a VH-CDR2 comprising the amino acid sequence of SEQ ID NO: 202; a VH-CDR3 comprising the amino acid sequence of SEQ ID NO: 153; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 206; and a VL-CDR3 comprising an amino acid sequence having at least 80%, 90%, 95% or 100% sequence identity to SEQ ID NO: 107; or t) VH-CDR1 comprising the amino acid sequence of SEQ ID NO: 211; a VH-CDR2 comprising the amino acid sequence of SEQ ID NO: 212; a VH-CDR3 comprising the amino acid sequence of SEQ ID NO: 213; a VL-CDR1 comprising an amino acid sequence having at least 80%, 90%, 95% or 100% sequence identity to SEQ ID NO: 215; a VL-CDR2 comprising an amino acid sequence having at least 80%, 90%, 95% or 100% sequence identity to SEQ ID NO: 216; and a VL-CDR3 comprising an amino acid sequence having at least 80%, 90%, 95% or 100% sequence identity to SEQ ID NO: 217; or u) VH-CDR1 comprising the amino acid sequence of SEQ ID NO: 31; a VH-CDR2 comprising the amino acid sequence of SEQ ID NO: 222; a VH-CDR3 comprising the amino acid sequence of SEQ ID NO: 223; a VL-CDR1 comprising an amino acid sequence having at least 80%, 90%, 95% or 100% sequence identity to SEQ ID NO: 225; a VL-CDR2 comprising an amino acid sequence having at least 80%, 90%, 95% or 100% sequence identity to SEQ ID NO: 96; and a VL-CDR3 comprising an amino acid sequence having at least 80%, 90%, 95% or 100% sequence identity to SEQ ID NO: 227; or v) VH-CDR1 comprising the amino acid sequence of SEQ ID NO: 231; a VH-CDR2 comprising the amino acid sequence of SEQ ID NO: 232; a VH-CDR3 comprising the amino acid sequence of SEQ ID NO: 233; a VL-CDR1 comprising an amino acid sequence having at least 80%, 90%, 95% or 100% sequence identity to SEQ ID NO: 235; a VL-CDR2 comprising an amino acid sequence having at least 80%, 90%, 95% or 100% sequence identity to SEQ ID NO: 236; and a VL-CDR3 comprising an amino acid sequence having at least 80%, 90%, 95% or 100% sequence identity to SEQ ID NO: 237; or w) VH-CDR1 comprising the amino acid sequence of SEQ ID NO: 31; a VH-CDR2 comprising the amino acid sequence of SEQ ID NO: 242; a VH-CDR3 comprising the amino acid sequence of SEQ ID NO: 243; a VL-CDR1 comprising an amino acid sequence having at least 80%, 90%, 95% or 100% sequence identity to SEQ ID NO: 225; a VL-CDR2 comprising an amino acid sequence having at least 80%, 90%, 95% or 100% sequence identity to SEQ ID NO: 96; and a VL-CDR3 comprising an amino acid sequence having at least 80%, 90%, 95% or 100% sequence identity to SEQ ID NO: 247; or x) VH-CDR1 comprising the amino acid sequence of SEQ ID NO: 31; a VH-CDR2 comprising the amino acid sequence of SEQ ID NO: 252; a VH-CDR3 comprising the amino acid sequence of SEQ ID NO: 253; a VL-CDR1 comprising an amino acid sequence having at least 80%, 90%, 95% or 100% sequence identity to SEQ ID NO: 255; a VL-CDR2 comprising an amino acid sequence having at least 80%, 90%, 95% or 100% sequence identity to SEQ ID NO: 256; and a VL-CDR3 comprising an amino acid sequence having at least 80%, 90%, 95% or 100% sequence identity to SEQ ID NO: 257; or y) VH-CDR1 comprising the amino acid sequence of SEQ ID NO: 261; a VH-CDR2 comprising the amino acid sequence of SEQ ID NO: 262; a VH-CDR3 comprising the amino acid sequence of SEQ ID NO: 263; a VL-CDR1 comprising an amino acid sequence having at least 80%, 90%, 95% or 100% sequence identity to SEQ ID NO: 265; a VL-CDR2 comprising an amino acid sequence having at least 80%, 90%, 95% or 100% sequence identity to SEQ ID NO: 176; and a VL-CDR3 comprising an amino acid sequence having at least 80%, 90%, 95% or 100% sequence identity to SEQ ID NO: 267; or z) VH-CDR1 comprising the amino acid sequence of SEQ ID NO: 271; a VH-CDR2 comprising the amino acid sequence of SEQ ID NO: 272; a VH-CDR3 comprising the amino acid sequence of SEQ ID NO: 273; a VL-CDR1 comprising an amino acid sequence having at least 80%, 90%, 95% or 100% sequence identity to SEQ ID NO: 275; a VL-CDR2 comprising an amino acid sequence having at least 80%, 90%, 95% or 100% sequence identity to SEQ ID NO: 276; and a VL-CDR3 comprising an amino acid sequence having at least 80%, 90%, 95% or 100% sequence identity to SEQ ID NO: 277; or aa) VH-CDR1 comprising the amino acid sequence of SEQ ID NO: 301; a VH-CDR2 comprising the amino acid sequence of SEQ ID NO: 302; a VH-CDR3 comprising the amino acid sequence of SEQ ID NO: 303; a VL-CDR1 comprising an amino acid sequence having at least 80%, 90%, 95% or 100% sequence identity to SEQ ID NO: 15; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 307; or bb) VH-CDR1 comprising the amino acid sequence of SEQ ID NO: 311; a VH-CDR2 comprising the amino acid sequence of SEQ ID NO: 312; a VH-CDR3 comprising the amino acid sequence of SEQ ID NO: 313; a VL-CDR1 comprising an amino acid sequence having at least 80%, 90%, 95% or 100% sequence identity to SEQ ID NO: 315; a VL-CDR2 comprising an amino acid sequence having at least 80%, 90%, 95% or 100% sequence identity to SEQ ID NO: 46; and a VL-CDR3 comprising an amino acid sequence having at least 80%, 90%, 95% or 100% sequence identity to SEQ ID NO: 67; or cc) VH-CDR1 comprising the amino acid sequence of SEQ ID NO: 321; a VH-CDR2 comprising the amino acid sequence of SEQ ID NO: 322; a VH-CDR3 comprising the amino acid sequence of SEQ ID NO: 323; a VL-CDR1 comprising an amino acid sequence having at least 80%, 90%, 95% or 100% sequence identity to SEQ ID NO: 325; a VL-CDR2 comprising an amino acid sequence having at least 80%, 90%, 95% or 100% sequence identity to SEQ ID NO: 326; and a VL-CDR3 comprising an amino acid sequence having at least 80%, 90%, 95% or 100% sequence identity to SEQ ID NO: 327; or dd) VH-CDR1 comprising the amino acid sequence of SEQ ID NO: 151; a VH-CDR2 comprising the amino acid sequence of SEQ ID NO: 332; a VH-CDR3 comprising the amino acid sequence of SEQ ID NO: 333; a VL-CDR1 comprising an amino acid sequence having at least 80%, 90%, 95% or 100% sequence identity to SEQ ID NO: 335; a VL-CDR2 comprising an amino acid sequence having at least 80%, 90%, 95% or 100% sequence identity to SEQ ID NO: 336; and a VL-CDR3 comprising an amino acid sequence having at least 80%, 90%, 95% or 100% sequence identity to SEQ ID NO: 107; or ee) VH-CDR1 comprising the amino acid sequence of SEQ ID NO: 341; a VH-CDR2 comprising the amino acid sequence of SEQ ID NO: 342; a VH-CDR3 comprising the amino acid sequence of SEQ ID NO: 343; a VL-CDR1 comprising an amino acid sequence having at least 80%, 90%, 95% or 100% sequence identity to SEQ ID NO: 345; a VL-CDR2 comprising an amino acid sequence having at least 80%, 90%, 95% or 100% sequence identity to SEQ ID NO: 346; and a VL-CDR3 comprising an amino acid sequence having at least 80%, 90%, 95% or 100% sequence identity to SEQ ID NO: 347; or ff) VH-CDR1 comprising the amino acid sequence of SEQ ID NO: 351; a VH-CDR2 comprising the amino acid sequence of SEQ ID NO: 352; a VH-CDR3 comprising the amino acid sequence of SEQ ID NO: 353; a VL-CDR1 comprising an amino acid sequence having at least 80%, 90%, 95% or 100% sequence identity to SEQ ID NO: 355; a VL-CDR2 comprising an amino acid sequence having at least 80%, 90%, 95% or 100% sequence identity to SEQ ID NO: 356; and a VL-CDR3 comprising an amino acid sequence having at least 80%, 90%, 95% or 100% sequence identity to SEQ ID NO: 357; or gg) VH-CDR1 comprising the amino acid sequence of SEQ ID NO: 361; a VH-CDR2 comprising the amino acid sequence of SEQ ID NO: 362; a VH-CDR3 comprising the amino acid sequence of SEQ ID NO: 363; a VL-CDR1 comprising an amino acid sequence having at least 80%, 90%, 95% or 100% sequence identity to SEQ ID NO: 365; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 367; or hh) VH-CDR1 comprising the amino acid sequence of SEQ ID NO: 371; a VH-CDR2 comprising the amino acid sequence of SEQ ID NO: 372; a VH-CDR3 comprising the amino acid sequence of SEQ ID NO: 373; a VL-CDR1 comprising an amino acid sequence having at least 80%, 90%, 95% or 100% sequence identity to SEQ ID NO: 345; a VL-CDR2 comprising an amino acid sequence having at least 80%, 90%, 95% or 100% sequence identity to SEQ ID NO: 376; and a VL-CDR3 comprising an amino acid sequence having at least 80%, 90%, 95% or 100% sequence identity to SEQ ID NO: 347; or ii) VH-CDR1 comprising the amino acid sequence of SEQ ID NO: 351; a VH-CDR2 comprising the amino acid sequence of SEQ ID NO: 382; a VH-CDR3 comprising the amino acid sequence of SEQ ID NO: 383; a VL-CDR1 comprising an amino acid sequence having at least 80%, 90%, 95% or 100% sequence identity to SEQ ID NO: 385; a VL-CDR2 comprising an amino acid sequence having at least 80%, 90%, 95% or 100% sequence identity to SEQ ID NO: 386; and a VL-CDR3 comprising an amino acid sequence having at least 80%, 90%, 95% or 100% sequence identity to SEQ ID NO: 387; or jj) VH-CDR1 comprising the amino acid sequence of SEQ ID NO: 351; a VH-CDR2 comprising the amino acid sequence of SEQ ID NO: 382; a VH-CDR3 comprising the amino acid sequence of SEQ ID NO: 393; a VL-CDR1 comprising an amino acid sequence having at least 80%, 90%, 95% or 100% sequence identity to SEQ ID NO: 395; a VL-CDR2 comprising an amino acid sequence having at least 80%, 90%, 95% or 100% sequence identity to SEQ ID NO: 356; and a VL-CDR3 comprising an amino acid sequence having at least 80%, 90%, 95% or 100% sequence identity to SEQ ID NO: 357; or kk) VH-CDR1 comprising the amino acid sequence of SEQ ID NO: 351; a VH-CDR2 comprising the amino acid sequence of SEQ ID NO: 382; a VH-CDR3 comprising the amino acid sequence of SEQ ID NO: 393; a VL-CDR1 comprising an amino acid sequence having at least 80%, 90%, 95% or 100% sequence identity to SEQ ID NO: 405; a VL-CDR2 comprising an amino acid sequence having at least 80%, 90%, 95% or 100% sequence identity to SEQ ID NO: 356; and a VL-CDR3 comprising an amino acid sequence having at least 80%, 90%, 95% or 100% sequence identity to SEQ ID NO: 357; or ll) VH-CDR1 comprising the amino acid sequence of SEQ ID NO: 411; a VH-CDR2 comprising the amino acid sequence of SEQ ID NO: 412; a VH-CDR3 comprising the amino acid sequence of SEQ ID NO: 413; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; or mm) VH-CDR1 comprising the amino acid sequence of SEQ ID NO: 421; a VH-CDR2 comprising the amino acid sequence of SEQ ID NO: 422; a VH-CDR3 comprising the amino acid sequence GNY; a VL-CDR1 comprising an amino acid sequence having at least 80%, 90%, 95% or 100% sequence identity to SEQ ID NO: 425; a VL-CDR2 comprising an amino acid sequence having at least 80%, 90%, 95% or 100% sequence identity to SEQ ID NO: 426; and a VL-CDR3 comprising an amino acid sequence having at least 80%, 90%, 95% or 100% sequence identity to SEQ ID NO: 427; or nn) VH-CDR1 comprising the amino acid sequence of SEQ ID NO: 431; a VH-CDR2 comprising the amino acid sequence of SEQ ID NO: 432; a VH-CDR3 comprising the amino acid sequence of SEQ ID NO: 433; a VL-CDR1 comprising an amino acid sequence having at least 80%, 90%, 95% or 100% sequence identity to SEQ ID NO: 435; a VL-CDR2 comprising an amino acid sequence having at least 80%, 90%, 95% or 100% sequence identity to SEQ ID NO: 436; and a VL-CDR3 comprising an amino acid sequence having at least 80%, 90%, 95% or 100% sequence identity to SEQ ID NO: 437; or oo) VH-CDR1 comprising the amino acid sequence of SEQ ID NO: 151; a VH-CDR2 comprising the amino acid sequence of SEQ ID NO: 442; a VH-CDR3 comprising the amino acid sequence of SEQ ID NO: 443; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; or pp) VH-CDR1 comprising the amino acid sequence of SEQ ID NO: 461; a VH-CDR2 comprising the amino acid sequence of SEQ ID NO: 462; a VH-CDR3 comprising the amino acid sequence of SEQ ID NO: 463; a VL-CDR1 comprising an amino acid sequence having at least 80%, 90%, 95% or 100% sequence identity to SEQ ID NO: 465; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 467; or qq) VH-CDR1 comprising the amino acid sequence of SEQ ID NO: 141; a VH-CDR2 comprising the amino acid sequence of SEQ ID NO: 472; a VH-CDR3 comprising the amino acid sequence of SEQ ID NO:

473; a VL-CDR1 comprising an amino acid sequence having at least 80%, 90%, 95% or 100% sequence identity to SEQ ID NO: 475; a VL-CDR2 comprising an amino acid sequence having at least 80%, 90%, 95% or 100% sequence identity to SEQ ID NO: 476; and a VL-CDR3 comprising an amino acid sequence having at least 80%, 90%, 95% or 100% sequence identity to SEQ ID NO: 477; or rr) VH-CDR1 comprising the amino acid sequence of SEQ ID NO: 481; a VH-CDR2 comprising the amino acid sequence of SEQ ID NO: 482; a VH-CDR3 comprising the amino acid sequence of SEQ ID NO: 483; a VL-CDR1 comprising an amino acid sequence having at least 80%, 90%, 95% or 100% sequence identity to SEQ ID NO: 165; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 487; or ss) VH-CDR1 comprising the amino acid sequence of SEQ ID NO: 141; a VH-CDR2 comprising the amino acid sequence of SEQ ID NO: 492; a VH-CDR3 comprising the amino acid sequence of SEQ ID NO: 493; a VL-CDR1 comprising an amino acid sequence having at least 80%, 90%, 95% or 100% sequence identity to SEQ ID NO: 495; a VL-CDR2 comprising an amino acid sequence having at least 80%, 90%, 95% or 100% sequence identity to SEQ ID NO: 496; and a VL-CDR3 comprising an amino acid sequence having at least 80%, 90%, 95% or 100% sequence identity to SEQ ID NO: 497; or tt) VH-CDR1 comprising the amino acid sequence of SEQ ID NO: 151; a VH-CDR2 comprising the amino acid sequence of SEQ ID NO: 502; a VH-CDR3 comprising the amino acid sequence of SEQ ID NO: 503; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 336; and a VL-CDR3 comprising an amino acid sequence having at least 80%, 90%, 95% or 100% sequence identity to SEQ ID NO: 107; or uu) VH-CDR1 comprising the amino acid sequence of SEQ ID NO: 311; a VH-CDR2 comprising the amino acid sequence of SEQ ID NO: 512; a VH-CDR3 comprising the amino acid sequence of SEQ ID NO: 513; a VL-CDR1 comprising an amino acid sequence having at least 80%, 90%, 95% or 100% sequence identity to SEQ ID NO: 515; a VL-CDR2 comprising an amino acid sequence having at least 80%, 90%, 95% or 100% sequence identity to SEQ ID NO: 516; and a VL-CDR3 comprising an amino acid sequence having at least 80%, 90%, 95% or 100% sequence identity to SEQ ID NO: 517; or vv) VH-CDR1 comprising the amino acid sequence of SEQ ID NO: 521; a VH-CDR2 comprising the amino acid sequence of SEQ ID NO: 522; a VH-CDR3 comprising the amino acid sequence of SEQ ID NO: 463; a VL-CDR1 comprising an amino acid sequence having at least 80%, 90%, 95% or 100% sequence identity to SEQ ID NO: 525; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 467; or ww) VH-CDR1 comprising the amino acid sequence of SEQ ID NO: 371; a VH-CDR2 comprising the amino acid sequence of SEQ ID NO: 532; a VH-CDR3 comprising the amino acid sequence of SEQ ID NO: 533; a VL-CDR1 comprising an amino acid sequence having at least 80%, 90%, 95% or 100% sequence identity to SEQ ID NO: 345; a VL-CDR2 comprising an amino acid sequence having at least 80%, 90%, 95% or 100% sequence identity to SEQ ID NO: 376; and a VL-CDR3 comprising an amino acid sequence having at least 80%, 90%, 95% or 100% sequence identity to SEQ ID NO: 537; or xx) VH-CDR1 comprising the amino acid sequence of SEQ ID NO: 341; a VH-CDR2 comprising the amino acid sequence of SEQ ID NO: 542; a VH-CDR3 comprising the amino acid sequence of SEQ ID NO: 543; a VL-CDR1 comprising an amino acid sequence having at least 80%, 90%, 95% or 100% sequence identity to SEQ ID NO: 345; a VL-CDR2 comprising an amino acid sequence having at least 80%, 90%, 95% or 100% sequence identity to SEQ ID NO: 376; and a VL-CDR3 comprising an amino acid sequence having at least 80%, 90%, 95% or 100% sequence identity to SEQ ID NO: 347; or yy) VH-CDR1 comprising the amino acid sequence of SEQ ID NO: 551; a VH-CDR2 comprising the amino acid sequence of SEQ ID NO: 552; a VH-CDR3 comprising the amino acid sequence of SEQ ID NO: 553; a VL-CDR1 comprising an amino acid sequence having at least 80%, 90%, 95% or 100% sequence identity to SEQ ID NO: 555; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 557; or zz) VH-CDR1 comprising the amino acid sequence of SEQ ID NO: 551; a VH-CDR2 comprising the amino acid sequence of SEQ ID NO: 552; a VH-CDR3 comprising the amino acid sequence of SEQ ID NO: 563; a VL-CDR1 comprising an amino acid sequence having at least 80%, 90%, 95% or 100% sequence identity to SEQ ID NO: 565; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 557; or aaa) VH-CDR1 comprising the amino acid sequence of SEQ ID NO: 571; a VH-CDR2 comprising the amino acid sequence of SEQ ID NO: 202; a VH-CDR3 comprising the amino acid sequence of SEQ ID NO: 573; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; or bbb) VH-CDR1 comprising the amino acid sequence of SEQ ID NO: 581; a VH-CDR2 comprising the amino acid sequence of SEQ ID NO: 582; a VH-CDR3 comprising the amino acid sequence of SEQ ID NO:

583; a VL-CDR1 comprising an amino acid sequence having at least 80%, 90%, 95% or 100% sequence identity to SEQ ID NO: 585; a VL-CDR2 comprising an amino acid sequence having at least 80%, 90%, 95% or 100% sequence identity to SEQ ID NO: 586; and a VL-CDR3 comprising an amino acid sequence having at least 80%, 90%, 95% or 100% sequence identity to SEQ ID NO: 587; or ccc) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 13; a VL-CDR1 comprising an amino acid sequence having at least 80%, 90%, 95% or 100% sequence identity to SEQ ID NO: 615; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or ddd) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 13; a VL-CDR1 comprising an amino acid sequence having at least 80%, 90%, 95% or 100% sequence identity to SEQ ID NO: 625; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or eee) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 663; a VL-CDR1 comprising an amino acid sequence having at least 80%, 90%, 95% or 100% sequence identity to SEQ ID NO: 615; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or fff) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 673; a VL-CDR1 comprising an amino acid sequence having at least 80%, 90%, 95% or 100% sequence identity to SEQ ID NO: 615; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or ggg) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 683; a VL-CDR1 comprising an amino acid sequence having at least 80%, 90%, 95% or 100% sequence identity to SEQ ID NO: 615; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or hhh) VH-CDR1 comprising the amino acid sequence of SEQ ID NO: 11; a VH-CDR2 comprising the amino acid sequence of SEQ ID NO: 612; a VH-CDR3 comprising the amino acid sequence of SEQ ID NO: 683; a VL-CDR1 comprising an amino acid sequence having at least 80%, 90%, 95% or 100% sequence identity to SEQ ID NO: 625; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 12; (c) VH-CDR3 comprising the amino acid sequence of SEQ ID NO: 13; (d) VL-CDR1 comprising the amino acid sequence of SEQ ID NO: 15; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 21; (b) VH-CDR2 comprising the amino acid sequence of SEQ ID NO: 22; (c) VH-CDR3 comprising the amino acid sequence YSY; (d) VL-CDR1 comprising the amino acid sequence of SEQ ID NO: 25; (e) VL-CDR2 comprising the amino acid sequence of SEQ ID NO: 26; and (f) VL-CDR3 comprising the amino acid sequence of SEQ ID NO: 27.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 32; (c) VH-CDR3 comprising the amino acid sequence of SEQ ID NO: 33; (d) VL-CDR1 comprising the amino acid sequence of SEQ ID NO: 35; (e) VL-CDR2 comprising the amino acid sequence of SEQ ID NO: 36; and (f) VL-CDR3 comprising the amino acid sequence of SEQ ID NO: 37.

In some embodiments, an alpha-synuclein antibody comprises at least one, two, three, four, five, or six CDRs selected from (a) VH-CDR1 comprising the amino acid sequence of SEQ ID NO: 41; (b) VH-CDR2 comprising the amino acid sequence of SEQ ID NO: 42; (c) VH-CDR3 comprising the amino acid sequence of SEQ ID NO: 43; (d) VL-CDR1 comprising the amino acid sequence of SEQ ID NO: 45; (e) VL-CDR2 comprising the amino acid sequence of SEQ ID NO: 46; and (f) VL-CDR3 comprising the amino acid sequence of SEQ ID NO: 47.

In some embodiments, an alpha-synuclein antibody comprises at least one, two, three, four, five, or six CDRs selected from (a) VH-CDR1 comprising the amino acid sequence of SEQ ID NO: 21; (b) VH-CDR2 comprising the amino acid sequence of SEQ ID NO: 52; (c) VH-CDR3 comprising the amino acid sequence YSF; (d) VL-CDR1 comprising the amino acid sequence of SEQ ID NO: 55; (e) VL-CDR2 comprising the amino acid sequence of SEQ ID NO: 56; and (f) VL-CDR3 comprising the amino acid sequence of SEQ ID NO: 27.

In some embodiments, an alpha-synuclein antibody comprises at least one, two, three, four, five, or six CDRs selected from (a) VH-CDR1 comprising the amino acid sequence of SEQ ID NO: 61; (b) VH-CDR2 comprising the amino acid sequence of SEQ ID NO: 62; (c) VH-CDR3 comprising the amino acid sequence of SEQ ID NO: 43; (d) VL-CDR1 comprising the amino acid sequence of SEQ ID NO: 65; (e) VL-CDR2 comprising the amino acid sequence of SEQ ID NO: 46; and (f) VL-CDR3 comprising the amino acid sequence of SEQ ID NO: 67.

In some embodiments, an alpha-synuclein antibody comprises at least one, two, three, four, five, or six CDRs selected from (a) VH-CDR1 comprising the amino acid sequence of SEQ ID NO: 21; (b) VH-CDR2 comprising the amino acid sequence of SEQ ID NO: 72; (c) VH-CDR3 comprising the amino acid sequence YSY; (d) VL-CDR1 comprising the amino acid sequence of SEQ ID NO: 75; (e) VL-CDR2 comprising the amino acid sequence of SEQ ID NO: 76; and (f) VL-CDR3 comprising the amino acid sequence of SEQ ID NO: 77.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 32; (c) VH-CDR3 comprising the amino acid sequence of SEQ ID NO: 33; (d) VL-CDR1 comprising the amino acid sequence of SEQ ID NO: 85; (e) VL-CDR2 comprising the amino acid sequence of SEQ ID NO: 36; and (f) VL-CDR3 comprising the amino acid sequence of SEQ ID NO: 87.

In some embodiments, an alpha-synuclein antibody comprises at least one, two, three, four, five, or six CDRs selected from (a) VH-CDR1 comprising the amino acid sequence of SEQ ID NO: 91; (b) VH-CDR2 comprising the amino acid sequence of SEQ ID NO: 92; (c) VH-CDR3 comprising the amino acid sequence of SEQ ID NO: 93; (d) VL-CDR1 comprising the amino acid sequence of SEQ ID NO: 95; (e) VL-CDR2 comprising the amino acid sequence of SEQ ID NO: 96; and (f) VL-CDR3 comprising the amino acid sequence of SEQ ID NO: 97.

In some embodiments, an alpha-synuclein antibody comprises at least one, two, three, four, five, or six CDRs selected from (a) VH-CDR1 comprising the amino acid sequence of SEQ ID NO: 101; (b) VH-CDR2 comprising the amino acid sequence of SEQ ID NO: 102; (c) VH-CDR3 comprising the amino acid sequence of SEQ ID NO: 103; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 111; (b) VH-CDR2 comprising the amino acid sequence of SEQ ID NO: 112; (c) VH-CDR3 comprising the amino acid sequence of SEQ ID NO: 113; (d) VL-CDR1 comprising the amino acid sequence of SEQ ID NO: 115; (e) VL-CDR2 comprising the amino acid sequence of SEQ ID NO: 106; and (f) VL-CDR3 comprising the amino acid sequence of SEQ ID NO: 117.

In some embodiments, an alpha-synuclein antibody comprises at least one, two, three, four, five, or six CDRs selected from (a) VH-CDR1 comprising the amino acid sequence of SEQ ID NO: 281; (b) VH-CDR2 comprising the amino acid sequence of SEQ ID NO: 282; (c) VH-CDR3 comprising the amino acid sequence of SEQ ID NO: 283; (d) VL-CDR1 comprising the amino acid sequence of SEQ ID NO: 285; (e) VL-CDR2 comprising the amino acid sequence of SEQ ID NO: 286; and (f) VL-CDR3 comprising the amino acid sequence of SEQ ID NO: 287.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 192; (c) VH-CDR3 comprising the amino acid sequence of SEQ ID NO: 193; (d) VL-CDR1 comprising the amino acid sequence of SEQ ID NO: 195; (e) VL-CDR2 comprising the amino acid sequence of SEQ ID NO: 96; and (f) VL-CDR3 comprising the amino acid sequence of SEQ ID NO: 197.

In some embodiments, an alpha-synuclein antibody comprises at least one, two, three, four, five, or six CDRs selected from (a) VH-CDR1 comprising the amino acid sequence of SEQ ID NO: 141; (b) VH-CDR2 comprising the amino acid sequence of SEQ ID NO: 142; (c) VH-CDR3 comprising the amino acid sequence of SEQ ID NO: 143; (d) VL-CDR1 comprising the amino acid sequence of SEQ ID NO: 145; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 151; (b) VH-CDR2 comprising the amino acid sequence of SEQ ID NO: 152; (c) VH-CDR3 comprising the amino acid sequence of SEQ ID NO: 153; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, an alpha-synuclein antibody comprises at least one, two, three CDRs selected from (a) VH-CDR1 comprising the amino acid sequence of SEQ ID NO: 161; (b) VH-CDR2 comprising the amino acid sequence of SEQ ID NO: 162; (c) VH-CDR3 comprising the amino acid sequence of SEQ ID NO: 163.

In some embodiments, an alpha-synuclein antibody comprises at least four, five, or six CDRs selected from (a) VH-CDR1 comprising the amino acid sequence of SEQ ID NO: 161; (b) VH-CDR2 comprising the amino acid sequence of SEQ ID NO: 162; (c) VH-CDR3 comprising the amino acid sequence of SEQ ID NO: 163; (d) VL-CDR1 comprising the amino acid sequence of SEQ ID NO: 165; (e) VL-CDR2 comprising the amino acid sequence of SEQ ID NO: 16; and (f) VL-CDR3 comprising the amino acid sequence of SEQ ID NO: 167.

In some embodiments, an alpha-synuclein antibody comprises at least one, two, three, four, five, or six CDRs selected from (a) VH-CDR1 comprising the amino acid sequence of SEQ ID NO: 171; (b) VH-CDR2 comprising the amino acid sequence of SEQ ID NO: 172; (c) VH-CDR3 comprising the amino acid sequence of SEQ ID NO: 173; (d) VL-CDR1 comprising the amino acid sequence of SEQ ID NO: 175; (e) VL-CDR2 comprising the amino acid sequence of SEQ ID NO: 176; and (f) VL-CDR3 comprising the amino acid sequence of SEQ ID NO: 177.

In some embodiments, an alpha-synuclein antibody comprises at least one, two, three, four, five, or six CDRs selected from (a) VH-CDR1 comprising the amino acid sequence of SEQ ID NO: 181; (b) VH-CDR2 comprising the amino acid sequence of SEQ ID NO: 182; (c) VH-CDR3 comprising the amino acid sequence of SEQ ID NO: 183; (d) VL-CDR1 comprising the amino acid sequence of SEQ ID NO: 15; (e) VL-CDR2 comprising the amino acid sequence of SEQ ID NO: 16; and (f) VL-CDR3 comprising the amino acid sequence of SEQ ID NO: 187.

In some embodiments, an alpha-synuclein antibody comprises at least one, two, three, four, five, or six CDRs selected from (a) VH-CDR1 comprising the amino acid sequence of SEQ ID NO: 201; (b) VH-CDR2 comprising the amino acid sequence of SEQ ID NO: 202; (c) VH-CDR3 comprising the amino acid sequence of SEQ ID NO: 153; (d) VL-CDR1 comprising the amino acid sequence of SEQ ID NO: 105; (e) VL-CDR2 comprising the amino acid sequence of SEQ ID NO: 206; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 211; (b) VH-CDR2 comprising the amino acid sequence of SEQ ID NO: 212; (c) VH-CDR3 comprising the amino acid sequence of SEQ ID NO: 213; (d) VL-CDR1 comprising the amino acid sequence of SEQ ID NO: 215; (e) VL-CDR2 comprising the amino acid sequence of SEQ ID NO: 216; and (f) VL-CDR3 comprising the amino acid sequence of SEQ ID NO: 217.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 222; (c) VH-CDR3 comprising the amino acid sequence of SEQ ID NO: 223; (d) VL-CDR1 comprising the amino acid sequence of SEQ ID NO: 225; (e) VL-CDR2 comprising the amino acid sequence of SEQ ID NO: 96; and (f) VL-CDR3 comprising the amino acid sequence of SEQ ID NO: 227.

In some embodiments, an alpha-synuclein antibody comprises at least one, two, three, four, five, or six CDRs selected from (a) VH-CDR1 comprising the amino acid sequence of SEQ ID NO: 231; (b) VH-CDR2 comprising the amino acid sequence of SEQ ID NO: 232; (c) VH-CDR3 comprising the amino acid sequence of SEQ ID NO: 233; (d) VL-CDR1 comprising the amino acid sequence of SEQ ID NO: 235; (e) VL-CDR2 comprising the amino acid sequence of SEQ ID NO: 236; and (f) VL-CDR3 comprising the amino acid sequence of SEQ ID NO: 237.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 242; (c) VH-CDR3 comprising the amino acid sequence of SEQ ID NO: 243; (d) VL-CDR1 comprising the amino acid sequence of SEQ ID NO: 225; (e) VL-CDR2 comprising the amino acid sequence of SEQ ID NO: 96; and (f) VL-CDR3 comprising the amino acid sequence of SEQ ID NO: 247.

In some embodiments, an alpha-synuclein antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 252; (c) VH-CDR3 comprising the amino acid sequence of SEQ ID NO: 253; (d) VL-CDR1 comprising the amino acid sequence of SEQ ID NO: 255; (e) VL-CDR2 comprising the amino acid sequence of SEQ ID NO: 256; and (f) VL-CDR3 comprising the amino acid sequence of SEQ ID NO: 257.

In some embodiments, an alpha-synuclein antibody comprises at least one, two, three, four, five, or six CDRs selected from (a) VH-CDR1 comprising the amino acid sequence of SEQ ID NO: 261; (b) VH-CDR2 comprising the amino acid sequence of SEQ ID NO: 262; (c) VH-CDR3 comprising the amino acid sequence of SEQ ID NO: 263; (d) VL-CDR1 comprising the amino acid sequence of SEQ ID NO: 265; (e) VL-CDR2 comprising the amino acid sequence of SEQ ID NO: 176; and (f) VL-CDR3 comprising the amino acid sequence of SEQ ID NO: 267.

In some embodiments, an alpha-synuclein antibody comprises at least one, two, three, four, five, or six CDRs selected from (a) VH-CDR1 comprising the amino acid sequence of SEQ ID NO: 271; (b) VH-CDR2 comprising the amino acid sequence of SEQ ID NO: 272; (c) VH-CDR3 comprising the amino acid sequence of SEQ ID NO: 273; (d) VL-CDR1 comprising the amino acid sequence of SEQ ID NO: 275; (e) VL-CDR2 comprising the amino acid sequence of SEQ ID NO: 276; and (f) VL-CDR3 comprising the amino acid sequence of SEQ ID NO: 277.

In some embodiments, an alpha-synuclein antibody comprises at least one, two, three, four, five, or six CDRs selected from (a) VH-CDR1 comprising the amino acid sequence of SEQ ID NO: 301; (b) VH-CDR2 comprising the amino acid sequence of SEQ ID NO: 302; (c) VH-CDR3 comprising the amino acid sequence of SEQ ID NO: 303; (d) VL-CDR1 comprising the amino acid sequence of SEQ ID NO: 15; (e) VL-CDR2 comprising the amino acid sequence of SEQ ID NO: 16; and (f) VL-CDR3 comprising the amino acid sequence of SEQ ID NO: 307.

In some embodiments, an alpha-synuclein antibody comprises at least one, two, three, four, five, or six CDRs selected from (a) VH-CDR1 comprising the amino acid sequence of SEQ ID NO: 311; (b) VH-CDR2 comprising the amino acid sequence of SEQ ID NO: 312; (c) VH-CDR3 comprising the amino acid sequence of SEQ ID NO: 313; (d) VL-CDR1 comprising the amino acid sequence of SEQ ID NO: 315; (e) VL-CDR2 comprising the amino acid sequence of SEQ ID NO: 46; and (f) VL-CDR3 comprising the amino acid sequence of SEQ ID NO: 67.

In some embodiments, an alpha-synuclein antibody comprises at least one, two, three, four, five, or six CDRs selected from (a) VH-CDR1 comprising the amino acid sequence of SEQ ID NO: 321; (b) VH-CDR2 comprising the amino acid sequence of SEQ ID NO: 322; (c) VH-CDR3 comprising the amino acid sequence of SEQ ID NO: 323; (d) VL-CDR1 comprising the amino acid sequence of SEQ ID NO: 325; (e) VL-CDR2 comprising the amino acid sequence of SEQ ID NO: 326; and (f) VL-CDR3 comprising the amino acid sequence of SEQ ID NO: 327.

In some embodiments, an alpha-synuclein antibody comprises at least one, two, three, four, five, or six CDRs selected from (a) VH-CDR1 comprising the amino acid sequence of SEQ ID NO: 151; (b) VH-CDR2 comprising the amino acid sequence of SEQ ID NO: 332; (c) VH-CDR3 comprising the amino acid sequence of SEQ ID NO: 333; (d) VL-CDR1 comprising the amino acid sequence of SEQ ID NO: 335; (e) VL-CDR2 comprising the amino acid sequence of SEQ ID NO: 336; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 341; (b) VH-CDR2 comprising the amino acid sequence of SEQ ID NO: 342; (c) VH-CDR3 comprising the amino acid sequence of SEQ ID NO: 343; (d) VL-CDR1 comprising the amino acid sequence of SEQ ID NO: 345; (e) VL-CDR2 comprising the amino acid sequence of SEQ ID NO: 346; and (f) VL-CDR3 comprising the amino acid sequence of SEQ ID NO: 347.

In some embodiments, an alpha-synuclein antibody comprises at least one, two, three, four, five, or six CDRs selected from (a) VH-CDR1 comprising the amino acid sequence of SEQ ID NO: 351; (b) VH-CDR2 comprising the amino acid sequence of SEQ ID NO: 352; (c) VH-CDR3 comprising the amino acid sequence of SEQ ID NO: 353; (d) VL-CDR1 comprising the amino acid sequence of SEQ ID NO: 355; (e) VL-CDR2 comprising the amino acid sequence of SEQ ID NO: 356; and (f) VL-CDR3 comprising the amino acid sequence of SEQ ID NO: 357.

In some embodiments, an alpha-synuclein antibody comprises at least one, two, three, four, five, or six CDRs selected from (a) VH-CDR1 comprising the amino acid sequence of SEQ ID NO: 361; (b) VH-CDR2 comprising the amino acid sequence of SEQ ID NO: 362; (c) VH-CDR3 comprising the amino acid sequence of SEQ ID NO: 363; (d) VL-CDR1 comprising the amino acid sequence of SEQ ID NO: 365; (e) VL-CDR2 comprising the amino acid sequence of SEQ ID NO: 16; and (f) VL-CDR3 comprising the amino acid sequence of SEQ ID NO: 367.

In some embodiments, an alpha-synuclein antibody comprises at least one, two, three, four, five, or six CDRs selected from (a) VH-CDR1 comprising the amino acid sequence of SEQ ID NO: 371; (b) VH-CDR2 comprising the amino acid sequence of SEQ ID NO: 372; (c) VH-CDR3 comprising the amino acid sequence of SEQ ID NO: 373; (d) VL-CDR1 comprising the amino acid sequence of SEQ ID NO: 345; (e) VL-CDR2 comprising the amino acid sequence of SEQ ID NO: 376; and (f) VL-CDR3 comprising the amino acid sequence of SEQ ID NO: 347.

In some embodiments, an alpha-synuclein antibody comprises at least one, two, three, four, five, or six CDRs selected from (a) VH-CDR1 comprising the amino acid sequence of SEQ ID NO: 351; (b) VH-CDR2 comprising the amino acid sequence of SEQ ID NO: 382; (c) VH-CDR3 comprising the amino acid sequence of SEQ ID NO: 383; (d) VL-CDR1 comprising the amino acid sequence of SEQ ID NO: 385; (e) VL-CDR2 comprising the amino acid sequence of SEQ ID NO: 386; and (f) VL-CDR3 comprising the amino acid sequence of SEQ ID NO: 387.

In some embodiments, an alpha-synuclein antibody comprises at least one, two, three, four, five, or six CDRs selected from (a) VH-CDR1 comprising the amino acid sequence of SEQ ID NO: 351; (b) VH-CDR2 comprising the amino acid sequence of SEQ ID NO: 382; (c) VH-CDR3 comprising the amino acid sequence of SEQ ID NO: 393; (d) VL-CDR1 comprising the amino acid sequence of SEQ ID NO: 395; (e) VL-CDR2 comprising the amino acid sequence of SEQ ID NO: 356; and (f) VL-CDR3 comprising the amino acid sequence of SEQ ID NO: 357.

In some embodiments, an alpha-synuclein antibody comprises at least one, two, three, four, five, or six CDRs selected from (a) VH-CDR1 comprising the amino acid sequence of SEQ ID NO: 351; (b) VH-CDR2 comprising the amino acid sequence of SEQ ID NO: 382; (c) VH-CDR3 comprising the amino acid sequence of SEQ ID NO: 393; (d) VL-CDR1 comprising the amino acid sequence of SEQ ID NO: 405; (e) VL-CDR2 comprising the amino acid sequence of SEQ ID NO: 356; and (f) VL-CDR3 comprising the amino acid sequence of SEQ ID NO: 357.

In some embodiments, an alpha-synuclein antibody comprises at least one, two, three, four, five, or six CDRs selected from (a) VH-CDR1 comprising the amino acid sequence of SEQ ID NO: 411; (b) VH-CDR2 comprising the amino acid sequence of SEQ ID NO: 412; (c) VH-CDR3 comprising the amino acid sequence of SEQ ID NO: 413; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 421; (b) VH-CDR2 comprising the amino acid sequence of SEQ ID NO: 422; (c) VH-CDR3 comprising the amino acid sequence GNY; (d) VL-CDR1 comprising the amino acid sequence of SEQ ID NO: 425; (e) VL-CDR2 comprising the amino acid sequence of SEQ ID NO: 426; and (f) VL-CDR3 comprising the amino acid sequence of SEQ ID NO: 427.

In some embodiments, an alpha-synuclein antibody comprises at least one, two, three, four, five, or six CDRs selected from (a) VH-CDR1 comprising the amino acid sequence of SEQ ID NO: 431; (b) VH-CDR2 comprising the amino acid sequence of SEQ ID NO: 432; (c) VH-CDR3 comprising the amino acid sequence of SEQ ID NO: 433; (d) VL-CDR1 comprising the amino acid sequence of SEQ ID NO: 435; (e) VL-CDR2 comprising the amino acid sequence of SEQ ID NO: 436; and (f) VL-CDR3 comprising the amino acid sequence of SEQ ID NO: 437.

In some embodiments, an alpha-synuclein antibody comprises at least one, two, three, four, five, or six CDRs selected from (a) VH-CDR1 comprising the amino acid sequence of SEQ ID NO: 151; (b) VH-CDR2 comprising the amino acid sequence of SEQ ID NO: 442; (c) VH-CDR3 comprising the amino acid sequence of SEQ ID NO: 443; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 461; (b) VH-CDR2 comprising the amino acid sequence of SEQ ID NO: 462; (c) VH-CDR3 comprising the amino acid sequence of SEQ ID NO: 463; (d) VL-CDR1 comprising the amino acid sequence of SEQ ID NO: 465; (e) VL-CDR2 comprising the amino acid sequence of SEQ ID NO: 16; and (f) VL-CDR3 comprising the amino acid sequence of SEQ ID NO: 467.

In some embodiments, an alpha-synuclein antibody comprises at least one, two, three, four, five, or six CDRs selected from (a) VH-CDR1 comprising the amino acid sequence of SEQ ID NO: 141; (b) VH-CDR2 comprising the amino acid sequence of SEQ ID NO: 472; (c) VH-CDR3 comprising the amino acid sequence of SEQ ID NO: 473; (d) VL-CDR1 comprising the amino acid sequence of SEQ ID NO: 475; (e) VL-CDR2 comprising the amino acid sequence of SEQ ID NO: 476; and (f) VL-CDR3 comprising the amino acid sequence of SEQ ID NO: 477.

In some embodiments, an alpha-synuclein antibody comprises at least one, two, three, four, five, or six CDRs selected from (a) VH-CDR1 comprising the amino acid sequence of SEQ ID NO: 481; (b) VH-CDR2 comprising the amino acid sequence of SEQ ID NO: 482; (c) VH-CDR3 comprising the amino acid sequence of SEQ ID NO: 483; (d) VL-CDR1 comprising the amino acid sequence of SEQ ID NO: 165; (e) VL-CDR2 comprising the amino acid sequence of SEQ ID NO: 16; and (f) VL-CDR3 comprising the amino acid sequence of SEQ ID NO: 487.

In some embodiments, an alpha-synuclein antibody comprises at least one, two, three, four, five, or six CDRs selected from (a) VH-CDR1 comprising the amino acid sequence of SEQ ID NO: 141; (b) VH-CDR2 comprising the amino acid sequence of SEQ ID NO: 492; (c) VH-CDR3 comprising the amino acid sequence of SEQ ID NO: 493; (d) VL-CDR1 comprising the amino acid sequence of SEQ ID NO: 495; (e) VL-CDR2 comprising the amino acid sequence of SEQ ID NO: 496; and (f) VL-CDR3 comprising the amino acid sequence of SEQ ID NO: 497.

In some embodiments, an alpha-synuclein antibody comprises at least one, two, three, four, five, or six CDRs selected from (a) VH-CDR1 comprising the amino acid sequence of SEQ ID NO: 151; (b) VH-CDR2 comprising the amino acid sequence of SEQ ID NO: 502; (c) VH-CDR3 comprising the amino acid sequence of SEQ ID NO: 503; (d) VL-CDR1 comprising the amino acid sequence of SEQ ID NO: 105; (e) VL-CDR2 comprising the amino acid sequence of SEQ ID NO: 336; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 311; (b) VH-CDR2 comprising the amino acid sequence of SEQ ID NO: 512; (c) VH-CDR3 comprising the amino acid sequence of SEQ ID NO: 513; (d) VL-CDR1 comprising the amino acid sequence of SEQ ID NO: 515; (e) VL-CDR2 comprising the amino acid sequence of SEQ ID NO: 516; and (f) VL-CDR3 comprising the amino acid sequence of SEQ ID NO: 517.

In some embodiments, an alpha-synuclein antibody comprises at least one, two, three, four, five, or six CDRs selected from (a) VH-CDR1 comprising the amino acid sequence of SEQ ID NO: 521; (b) VH-CDR2 comprising the amino acid sequence of SEQ ID NO: 522; (c) VH-CDR3 comprising the amino acid sequence of SEQ ID NO: 463; (d) VL-CDR1 comprising the amino acid sequence of SEQ ID NO: 525; (e) VL-CDR2 comprising the amino acid sequence of SEQ ID NO: 16; and (f) VL-CDR3 comprising the amino acid sequence of SEQ ID NO: 467.

In some embodiments, an alpha-synuclein antibody comprises at least one, two or three CDRs selected from (a) VH-CDR1 comprising the amino acid sequence of SEQ ID NO: 371; (b) VH-CDR2 comprising the amino acid sequence of SEQ ID NO: 532; (c) VH-CDR3 comprising the amino acid sequence of SEQ ID NO: 533.

In some embodiments, an alpha-synuclein antibody comprises at least four, five, or six CDRs selected from (a) VH-CDR1 comprising the amino acid sequence of SEQ ID NO: 371; (b) VH-CDR2 comprising the amino acid sequence of SEQ ID NO: 532; (c) VH-CDR3 comprising the amino acid sequence of SEQ ID NO: 533; (d) VL-CDR1 comprising the amino acid sequence of SEQ ID NO: 345; (e) VL-CDR2 comprising the amino acid sequence of SEQ ID NO: 376; and (f) VL-CDR3 comprising the amino acid sequence of SEQ ID NO: 537.

In some embodiments, an alpha-synuclein antibody comprises at least one, two, three, four, five, or six CDRs selected from (a) VH-CDR1 comprising the amino acid sequence of SEQ ID NO: 341; (b) VH-CDR2 comprising the amino acid sequence of SEQ ID NO: 542; (c) VH-CDR3 comprising the amino acid sequence of SEQ ID NO: 543; (d) VL-CDR1 comprising the amino acid sequence of SEQ ID NO: 345; (e) VL-CDR2 comprising the amino acid sequence of SEQ ID NO: 376; and (f) VL-CDR3 comprising the amino acid sequence of SEQ ID NO: 347.

In some embodiments, an alpha-synuclein antibody comprises at least one, two, three, four, five, or six CDRs selected from (a) VH-CDR1 comprising the amino acid sequence of SEQ ID NO: 551; (b) VH-CDR2 comprising the amino acid sequence of SEQ ID NO: 552; (c) VH-CDR3 comprising the amino acid sequence of SEQ ID NO: 553; (d) VL-CDR1 comprising the amino acid sequence of SEQ ID NO: 555; (e) VL-CDR2 comprising the amino acid sequence of SEQ ID NO: 16; and (f) VL-CDR3 comprising the amino acid sequence of SEQ ID NO: 557.

In some embodiments, an alpha-synuclein antibody comprises at least one, two, three, four, five, or six CDRs selected from (a) VH-CDR1 comprising the amino acid sequence of SEQ ID NO: 551; (b) VH-CDR2 comprising the amino acid sequence of SEQ ID NO: 552; (c) VH-CDR3 comprising the amino acid sequence of SEQ ID NO: 563; (d) VL-CDR1 comprising the amino acid sequence of SEQ ID NO: 565; (e) VL-CDR2 comprising the amino acid sequence of SEQ ID NO: 16; and (f) VL-CDR3 comprising the amino acid sequence of SEQ ID NO: 557.

In some embodiments, an alpha-synuclein antibody comprises at least one, two, three, four, five, or six CDRs selected from (a) VH-CDR1 comprising the amino acid sequence of SEQ ID NO: 571; (b) VH-CDR2 comprising the amino acid sequence of SEQ ID NO: 202; (c) VH-CDR3 comprising the amino acid sequence of SEQ ID NO: 573; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, an alpha-synuclein antibody comprises at least one, two, three, four, five, or six CDRs selected from (a) VH-CDR1 comprising the amino acid sequence of SEQ ID NO: 581; (b) VH-CDR2 comprising the amino acid sequence of SEQ ID NO: 582; (c) VH-CDR3 comprising the amino acid sequence of SEQ ID NO: 583; (d) VL-CDR1 comprising the amino acid sequence of SEQ ID NO: 585; (e) VL-CDR2 comprising the amino acid sequence of SEQ ID NO: 586; and (f) VL-CDR3 comprising the amino acid sequence of SEQ ID NO: 587.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 13; (d) VL-CDR1 comprising the amino acid sequence of SEQ ID NO: 615; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 13; (d) VL-CDR1 comprising the amino acid sequence of SEQ ID NO: 625; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 663; (d) VL-CDR1 comprising the amino acid sequence of SEQ ID NO: 615; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 673; (d) VL-CDR1 comprising the amino acid sequence of SEQ ID NO: 615; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 683; (d) VL-CDR1 comprising the amino acid sequence of SEQ ID NO: 615; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 612; (c) VH-CDR3 comprising the amino acid sequence of SEQ ID NO: 683; (d) VL-CDR1 comprising the amino acid sequence of SEQ ID NO: 625; (e) VL-CDR2 comprising the amino acid sequence of SEQ ID NO: 16; and (f) VL-CDR3 comprising the amino acid sequence of SEQ ID NO: 17.

In some embodiments, an alpha-synuclein antibody comprises at least one, two, or three CDRs selected from (a) VH-CDR1 comprising the amino acid sequence selected from SEQ ID NO: 11, 21, 31, 41, 61, 91, 101, 111,141, 151, 161, 171, 181, 201, 211, 231, 261, 271, 281, 301, 311, 321, 341, 351, 361, 371, 411, 421, 431, 461, 481, 521, 551, 571 and 581, (b) VH-CDR2 comprising the amino acid sequence selected from SEQ ID NO: 12, 22, 32, 42, 52, 62, 72, 92, 102, 112, 142, 152, 162, 172, 182, 192, 202, 212, 222, 232, 242, 252, 262, 272, 282, 302, 312, 322, 332, 342, 352, 362, 372, 382, 412, 422, 432, 442, 462, 472, 482, 492, 502, 512, 522, 532, 542, 552, 582 and 612, (c) VH-CDR3 comprising the amino acid sequence selected from SEQ ID NO: 13, YSY, 33, 43, YSF, 93, 103, 113, 143, 153, 163, 173, 183, 193, 213, 223, 233, 243, 253, 263, 273, 283, 303, 313, 323, 333, 343, 353, 363, 373, 383, 393, 413, GNY, 433, 443, 463, 473, 483, 493, 503, 513, 533, 543, 553, 563, 573, 583, 663, 673 and 683.

In some embodiments, an alpha-synuclein antibody comprises at least one, two, or three CDRs selected from (a) VL-CDR1 comprising the amino acid sequence selected from SEQ ID NO: 15, 25, 35, 45, 55, 65, 75, 85, 95, 105, 115, 145, 165, 175, 195, 215, 225, 235, 255, 265, 275, 285, 315, 325, 335, 345, 355, 365, 385, 395, 405, 425, 435, 465, 475, 495, 515, 525, 555, 565, 585, 615 and 625, (b) VL-CDR2 comprising the amino acid sequence selected from SEQ ID NO: 16, 26, 36, 46, 56, 76, 96, 106, 176, 206, 216, 236, 256, 276, 286, 326, 336, 346, 356, 376, 386, 426, 436, 476, 496, 516 and 586, (c) VL-CDR3 comprising the amino acid sequence selected from SEQ ID NO: 17, 27, 37, 47, 67, 77, 87, 97, 107, 117, 167, 177, 187, 197, 217, 227, 237, 247, 257, 267, 277, 287, 307, 327, 347, 357, 367, 387, 427, 437, 467, 477, 487, 497, 517, 537, 557 and 587.

In another embodiment, the alpha-synuclein antibody comprises a heavy chain variable domain (VH) selected from SEQ ID NO: 10, 20, 30, 40, 50, 60, 70, 90, 100, 110, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710 and 720 including post-translational modifications of that sequence.

In a particular embodiment, the heavy chain variable domain (VH) comprises at least one, two, or three CDRs selected from (a) VH-CDR1 comprising the amino acid sequence selected from SEQ ID NO: 11, 21, 31, 41, 61, 91, 101, 111, 141, 151, 161, 171, 181, 201, 211, 231, 261 271, 281, 301, 311, 321, 341, 351, 361, 371, 411, 421, 431, 461, 481, 521, 551, 571 and 581, (b) VH-CDR2 comprising the amino acid sequence selected from SEQ ID NO: 12, 22, 32, 42, 52, 62, 72, 92, 102, 112, 142, 152, 162, 172, 182, 192, 202, 212, 222, 232, 242, 252, 262, 272, 282, 302, 312, 322, 332, 342, 352, 362, 372, 382, 412, 422, 432, 442, 462, 472, 482, 492, 502, 512, 522, 532, 542, 552, 582 and 612, (c) VH-CDR3 comprising the amino acid sequence selected from SEQ ID NO: 13, YSY, 33, 43, YSF, 93, 103, 113, 143, 153, 163, 173, 183, 193, 213, 223, 233, 243, 253, 263, 273, 283, 303, 313, 323, 333, 343, 353, 363, 373, 383, 393, 413, GNY, 433, 443, 463, 473, 483, 493, 503, 513, 533, 543, 553, 563, 573, 583, 663, 673 and 683. In another embodiment, the alpha-synuclein antibody comprises a light chain variable domain (VL) selected from SEQ ID NO: 14, 24, 34, 44, 54, 64, 74, 84, 94, 104, 114, 144, 154, 174, 184, 194, 204, 214, 224, 234, 244, 254, 264, 274, 284, 304, 314, 324, 334, 344, 354, 364, 374, 384, 394, 404, 414, 424, 434, 464, 474, 484, 494, 504, 514, 524, 544, 554, 564, 574, 584, 614, 624, 634 and 644 including post-translational modifications of that sequence.

In a particular embodiment, the light chain variable domain (VL) comprises at least one, two, or three CDRs selected from (a) VL-CDR1 comprising the amino acid sequence selected from SEQ ID NO: 15, 25, 35, 45, 55, 65, 75, 85, 95, 105, 115, 145, 165, 175, 195, 215, 225, 235, 255, 265, 275, 285, 315, 325, 335, 345, 355, 365, 385, 395, 405, 425, 435, 465, 475, 495, 515, 525, 555, 565, 585, 615 and 625 (b) VL-CDR2 comprising the amino acid sequence selected from SEQ ID NO: 16, 26, 36, 46, 56, 76, 96, 106, 176, 206, 216, 236, 256, 276, 286, 326, 336, 346, 356, 376, 386, 426, 436, 476, 496, 516 and 586, (c) VL-CDR3 comprising the amino acid sequence selected from SEQ ID NO: 17, 27, 37, 47, 67, 77, 87, 97, 107, 117, 167, 177, 187, 197, 217, 227, 237, 247, 257, 267, 277, 287, 307, 327, 347, 357, 367, 387, 427, 437, 467, 477, 487, 497, 517, 537, 557 and 587.

In some embodiments, the invention relates to an antibody selected from ACI-7067-1101C8-Ab2, ACI-7067-1102G3-Ab1, ACI-7067-1106A8-Ab2, ACI-7067-1107G5-Ab2, ACI-7067-1108H1-Ab1, ACI-7067-1111B12-Ab2, ACI-7067-1112H8-Ab2, ACI-7067-1108B11-Ab2, ACI-7067-1113D10-Ab1, ACI-7067-1116F2-Ab1, ACI-7067-1206E5-Ab1, ACI-7079-2501B11-Ab3, ACI-7079-2501D10-Ab1, ACI-7079-2501G2-Ab2, ACI-7079-2503C6-Ab1, ACI-7079-2504A6-Ab1, ACI-7079-2506E2-Ab2, ACI-7079-2506F3-Ab1, ACI-7079-2507B3-Ab1, ACI-7079-2511B3-Ab3, ACI-7079-2601B6-Ab1, ACI-7079-2602G4-Ab4, ACI-7079-2603C1-Ab3, ACI-7079-2603F3-Ab1, ACI-7079-2605B3-Ab2, ACI-7079-2606A6-Ab2, ACI-7079-2509E5-Ab2, ACI-7087-4119E10-Ab2, ACI-7087-4125E6-Ab1, ACI-7088-4301D5-Ab2, ACI-7088-4301E12-Ab2, ACI-7088-4301H3-Ab2, ACI-7088-4303A1-Ab1, ACI-7088-4303A3-Ab1, ACI-7088-4303B6-Ab2, ACI-7088-4303H6-Ab1, ACI-7088-4305H7-Ab1, ACI-7088-4317A4-Ab1, ACI-7089-4409F1-Ab1, ACI-7089-4415G5-Ab1, ACI-7089-4417G6-Ab1, ACI-7089-4418C5-Ab1, ACI-7089-4418F6-Ab1, ACI-8033-5A12-Ab1, ACI-8033-25A3-Ab1, ACI-8033-1G10-Ab1, ACI-8033-19A2-Ab1, ACI-8033-8C10-Ab1, ACI-8033-7A2-

Ab1, ACI-8033-1A12-Ab1, ACI-8033-4F3-Ab1, ACI-8033-17F5-Ab1, ACI-8033-18C11-Ab1, ACI-8033-18D12-Ab1, ACI-8033-1F8-Ab1, ACI-8033-22E5-Ab1, ACI-8033-27D8-Ab1, ACI-8033-21C8-Ab1, hACI-7067-1101C8-Ab2_H1L1, hACI-7067-1101C8-Ab2_H1L2, hACI-7067-1101C8-Ab2_H1L3, hACI-7067-1101C8-Ab2_H1L4, hACI-7067-1101C8-Ab2_H2L1, hACI-7067-1101C8-Ab2_H2L2, hACI-7067-1101C8-Ab2_H2L3, hACI-7067-1101C8-Ab2_H2L4, hACI-7067-1101C8-Ab2_H3L1, hACI-7067-1101C8-Ab2_H3L2, hACI-7067-1101C8-Ab2_H3L3, hACI-7067-1101C8-Ab2_H3L4, hACI-7067-1101C8-Ab2_H4L1, hACI-7067-1101C8-Ab2_H4L2, hACI-7067-1101C8-Ab2_H4L3, hACI-7067-1101C8-Ab2_H4L4, hACI-7067-1101C8-Ab2_H5L1, hACI-7067-1101C8-Ab2_H5L2, hACI-7067-1101C8-Ab2_H5L3, hACI-7067-1101C8-Ab2_H5L4, hACI-7067-1101C8-Ab2_H6L1, hACI-7067-1101C8-Ab2_H7L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1, hACI-7067-1101C8-Ab2_H10L2, hACI-7067-1101C8-Ab2_H11L1, hACI-7067-1101C8-Ab2_H11L2, hACI-7067-1101C8-Ab2_H12L1 and hACI-7067-1101C8-Ab2_H12L2. In certain preferred embodiments, the antibody may be selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1, hACI-7067-1101C8-Ab2_H10L2, hACI-7067-1101C8-Ab2_H11L1, hACI-7067-1101C8-Ab2_H11L2, hACI-7067-1101C8-Ab2_H12L1 and hACI-7067-1101C8-Ab2_H12L2. As demonstrated herein, these humanized antibodies display advantageous affinity to alpha synuclein, expression levels and sequence identity to the human acceptor framework. They all delay seeded aggregation. In certain preferred embodiments, the antibody may be selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2 and hACI-7067-1101C8-Ab2_H10L1. As demonstrated herein, these humanized antibodies display improved affinity against the aggregated form of alpha synuclein compared to the chimeric antibody cACI-7067-1101C8-Ab2. In certain preferred embodiments, the antibody may be selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1 and hACI-7067-1101C8-Ab2_H10L2. As demonstrated herein, these humanized antibodies display efficacy in delaying alpha synuclein aggregation compared to the chimeric antibody cACI-7067-1101C8-Ab2.

In some embodiments, an antibody binds to the same or similar epitope (totally or partially overlapping epitope) as an antibody selected from ACI-7067-1101C8-Ab2, ACI-7067-1102G3-Ab1, ACI-7067-1106A8-Ab2, ACI-7067-1107G5-Ab2, ACI-7067-1108H1-Ab1, ACI-7067-1111B12-Ab2, ACI-7067-1112H8-Ab2, ACI-7067-1108B11-Ab2, ACI-7067-1113D10-Ab1, ACI-7067-1116F2-Ab1, ACI-7067-1206E5-Ab1, ACI-7079-2501B11-Ab3, ACI-7079-2501D10-Ab1, ACI-7079-2501G2-Ab2, ACI-7079-2503C6-Ab1, ACI-7079-2504A6-Ab1, ACI-7079-2506E2-Ab2, ACI-7079-2506F3-Ab1, ACI-7079-2507B3-Ab1, ACI-7079-2511B3-Ab3, ACI-7079-2601B6-Ab1, ACI-7079-2602G4-Ab4, ACI-7079-2603C1-Ab3, ACI-7079-2603F3-Ab1, ACI-7079-2605B3-Ab2, ACI-7079-2606A6-Ab2, ACI-7079-2509E5-Ab2, ACI-7087-4119E10-Ab2, ACI-7087-4125E6-Ab1, ACI-7088-4301D5-Ab2, ACI-7088-4301E12-Ab2, ACI-7088-4301H3-Ab2, ACI-7088-4303A1-Ab1, ACI-7088-4303A3-Ab1, ACI-7088-4303B6-Ab2, ACI-7088-4303H6-Ab1, ACI-7088-4305H7-Ab1, ACI-7088-4317A4-Ab1, ACI-7089-4409F1-Ab1, ACI-7089-4415G5-Ab1, ACI-7089-4417G6-Ab1, ACI-7089-4418C5-Ab1, ACI-7089-4418F6-Ab1, ACI-8033-5A12-Ab1, ACI-8033-25A3-Ab1, ACI-8033-1G10-Ab1, ACI-8033-19A2-Ab1, ACI-8033-8C10-Ab1, ACI-8033-7A2-Ab1, ACI-8033-1A12-Ab1, ACI-8033-4F3-Ab1, ACI-8033-17F5-Ab1, ACI-8033-18C11-Ab1, ACI-8033-18D12-Ab1, ACI-8033-1F8-Ab1, ACI-8033-22E5-Ab1, ACI-8033-27D8-Ab1, ACI-8033-21C8-Ab1, hACI-7067-1101C8-Ab2_H1L1, hACI-7067-1101C8-Ab2_H1L2, hACI-7067-1101C8-Ab2_H1L3, hACI-7067-1101C8-Ab2_H1L4, hACI-7067-1101C8-Ab2_H2L1, hACI-7067-1101C8-Ab2_H2L2, hACI-7067-1101C8-Ab2_H2L3, hACI-7067-1101C8-Ab2_H2L4, hACI-7067-1101C8-Ab2_H3L1, hACI-7067-1101C8-Ab2_H3L2, hACI-7067-1101C8-Ab2_H3L3, hACI-7067-1101C8-Ab2_H3L4, hACI-7067-1101C8-Ab2_H4L1, hACI-7067-1101C8-Ab2_H4L2, hACI-7067-1101C8-Ab2_H4L3, hACI-7067-1101C8-Ab2_H4L4, hACI-7067-1101C8-Ab2_H5L1, hACI-7067-1101C8-Ab2_H5L2, hACI-7067-1101C8-Ab2_H5L3, hACI-7067-1101C8-Ab2_H5L4, hACI-7067-1101C8-Ab2_H6L1, hACI-7067-1101C8-Ab2_H7L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1, hACI-7067-1101C8-Ab2_H10L2, hACI-7067-1101C8-Ab2_H11L1, hACI-7067-1101C8-Ab2_H11L2, hACI-7067-1101C8-Ab2_H12L1 and hACI-7067-1101C8-Ab2_H12L2. In certain preferred embodiments, the antibody binds to the same or similar epitope (totally or partially overlapping epitope) as an antibody selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1, hACI-7067-1101C8-Ab2_H10L2, hACI-7067-1101C8-Ab2_H11L1, hACI-7067-1101C8-Ab2_H11L2, hACI-7067-1101C8-Ab2_H12L1 and hACI-7067-1101C8-Ab2_H12L2. As demonstrated herein, these humanized antibodies display advantageous affinity to alpha synuclein, expression levels and sequence identity to the human acceptor framework. They all delay seeded aggregation. In certain preferred embodiments, the antibody binds to the same or similar epitope (totally or partially overlapping epitope) as an antibody selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2 and hACI-7067-1101C8-Ab2_H10L1. As demonstrated herein, these humanized antibodies display improved affinity against the aggregated form of alpha synuclein compared to the chimeric antibody cACI-7067-1101C8-Ab2. In certain preferred embodiments, the antibody binds to the same or similar epitope (totally or partially overlapping epitope) as an antibody selected from hACI-7067-1101C8-Ab2_H5L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1 and hACI-7067-1101C8-Ab2_H10L2. As demonstrated herein, these humanized antibodies display efficacy in delaying alpha synuclein aggregation compared to the chimeric antibody cACI-7067-1101C8-Ab2.

In some embodiments, an isolated antibody is provided, wherein the isolated antibody binds to the same or similar epitope comprising the sequence SEQ ID NO: 2. In some embodiments, an isolated antibody is provided, wherein the isolated antibody binds to the same epitope comprising the sequence SEQ ID NO: 3. In some embodiments, an isolated antibody is provided, wherein the isolated antibody binds to the same epitope comprising the sequence SEQ ID NO: 4. In some embodiments, an isolated antibody is provided, wherein the isolated antibody binds to the same epitope comprising the sequence SEQ ID NO: 5. In some embodiments, an isolated antibody is provided, wherein the isolated antibody binds to the same epitope comprising the sequence comprising amino acids 93-95 of SEQ ID NO:1. In some embodiments, an isolated antibody is provided, wherein the isolated antibody binds to the same epitope comprising the sequence SEQ ID NO: 7. In some embodiments, an isolated antibody is provided, wherein the isolated antibody binds to the same epitope comprising the sequence SEQ ID NO: 8. In some embodiments, an isolated antibody is provided, wherein the isolated antibody binds to the same epitope comprising the sequence SEQ ID NO: 9. In some embodiments, an isolated antibody is provided, wherein the isolated antibody binds to the same or similar epitope comprising the sequence SEQ ID NO: 121. In some embodiments, an isolated antibody is provided, wherein the isolated antibody binds to the same or similar epitope comprising the sequence SEQ ID NO: 136. In some embodiments, an isolated antibody is provided, wherein the isolated antibody binds to the same or similar epitope comprising the sequence SEQ ID NO: 130. In some embodiments, an isolated antibody is provided, wherein the isolated antibody binds to the same or similar epitope comprising the sequence SEQ ID NO: 131. In some embodiments, an isolated antibody is provided, wherein the isolated antibody binds to the same or similar epitope comprising the sequence SEQ ID NO: 134. In some embodiments, an isolated antibody is provided, wherein the isolated antibody binds to the same or similar epitope comprising the sequence SEQ ID NO: 135. In some embodiments, an isolated antibody is provided, wherein the isolated antibody binds to the same or similar epitope comprising the sequence SEQ ID NO: 122. In some embodiments, an isolated antibody is provided, wherein the isolated antibody binds to the same or similar epitope comprising the sequence SEQ ID NO: 124. In some embodiments, an isolated antibody is provided, wherein the isolated antibody binds to the same or similar epitope comprising the sequence SEQ ID NO:

125. In some embodiments, an isolated antibody is provided, wherein the isolated antibody binds to the same or similar epitope comprising the sequence SEQ ID NO: 132. In some embodiments, an isolated antibody is provided, wherein the isolated antibody binds to the same or similar epitope comprising the sequence SEQ ID NO: 133. In some embodiments, an isolated antibody is provided, wherein the isolated antibody binds to the same or similar epitope comprising the sequence SEQ ID NO: 137. In some embodiments, an isolated antibody is provided wherein the isolated antibody binds to the same or similar non-linear epitope within amino acids residues of human alpha-synuclein of SEQ ID NO: 1. The term "the same or similar epitope" references any antibody provided herein.

Antibodies binding the same epitope as any of the antibodies provided herein are also part of the invention. In some embodiments, an isolated antibody is provided, wherein the isolated antibody binds to the same epitope comprising the sequence SEQ ID NO: 2. In some embodiments, an isolated antibody is provided, wherein the isolated antibody binds to the same epitope comprising the sequence SEQ ID NO: 3. In some embodiments, an isolated antibody is provided, wherein the isolated antibody binds to the same epitope comprising the sequence SEQ ID NO: 4. In some embodiments, an isolated antibody is provided, wherein the isolated antibody binds to the same epitope comprising the sequence SEQ ID NO: 5. In some embodiments, an isolated antibody is provided, wherein the isolated antibody binds to the same epitope comprising the sequence comprising amino acids 93-95 of SEQ ID NO:1. In some embodiments, an isolated antibody is provided, wherein the isolated antibody binds to the same epitope comprising the sequence SEQ ID NO: 7. In some embodiments, an isolated antibody is provided, wherein the isolated antibody binds to the same epitope comprising the sequence SEQ ID NO: 8. In some embodiments, an isolated antibody is provided, wherein the isolated antibody binds to the same epitope comprising the sequence SEQ ID NO: 9. In some embodiments, an isolated antibody is provided, wherein the isolated antibody binds to the same epitope comprising the sequence SEQ ID NO: 121. In some embodiments, an isolated antibody is provided, wherein the isolated antibody binds to the same epitope comprising the sequence SEQ ID NO: 136. In some embodiments, an isolated antibody is provided, wherein the isolated antibody binds to the same epitope comprising the sequence SEQ ID NO: 130. In some embodiments, an isolated antibody is provided, wherein the isolated antibody binds to the same epitope comprising the sequence SEQ ID NO: 131. In some embodiments, an isolated antibody is provided, wherein the isolated antibody binds to the same epitope comprising the sequence SEQ ID NO: 134. In some embodiments, an isolated antibody is provided, wherein the isolated antibody binds to the same epitope comprising the sequence SEQ ID NO: 135. In some embodiments, an isolated antibody is provided, wherein the isolated antibody binds to the same epitope comprising the sequence SEQ ID NO: 122. In some embodiments, an isolated antibody is provided, wherein the isolated antibody binds to the same epitope comprising the sequence SEQ ID NO: 124. In some embodiments, an isolated antibody is provided, wherein the isolated antibody binds to the same epitope comprising the sequence SEQ ID NO: 125. In some embodiments, an isolated antibody is provided, wherein the isolated antibody binds to the same epitope comprising the sequence SEQ ID NO: 132. In some embodiments, an isolated antibody is provided, wherein the isolated antibody binds to the same epitope comprising the sequence SEQ ID NO: 133. In some embodiments, an isolated antibody is provided, wherein the isolated antibody binds to the same epitope comprising the sequence SEQ ID NO: 137. In some embodiments, an isolated antibody is provided wherein the isolated antibody binds to the same non-linear epitope within amino acids residues of human alpha-synuclein of SEQ ID NO: 1. The term "the same epitope" references any antibody provided herein.

In accordance with the above, in certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

In certain embodiments, one or more amino acid modifications may be introduced into the Fc region of an antibody provided herein, thereby generating an Fc region variant. The Fc region variant may comprise a murine Fc region sequence (e.g.: IgG1, IgG2a or IgG2b) comprising an amino acid modification (e.g. substitution) at one or more amino acid positions. The Fc region variant may comprise a human Fc region sequence (e.g., a human IgG1, IgG2, IgG3 or IgG4 Fc region) comprising an amino acid modification (e.g. a substitution) at one or more amino acid positions (e.g. an IgG4 isotype including the S228P mutation).

In certain embodiments, the Fc region is mutated to increase its affinity to FcRn at pH 6.0 and consequently extend the antibody half-life. Antibodies with enhanced affinity to FcRn include those with substitution of one or more of Fc region residues 252, 253, 254, 256, 428, 434, including the so called YTE mutation with substitution M252Y/S254T/T256E (Dall'Acqua et al, J Immunol. 169: 5171-5180 (2002)) or LS mutation M428L/N434S (Zalevsky et al, Nat Biotechnol. 28 (2): 157-159 (2010)).

In certain embodiments, the invention contemplates an antibody variant that possesses some but not all effector functions, which make it a desirable candidate for applications in which the half life of the antibody in vivo is important yet certain effector functions (such as complement activation and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes and microglia express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)).

Antibodies with reduced effector function include those with substitution of one or more of Fc region residues 234, 235, 238, 265, 269, 270, 297, 327 and 329 (U.S. Pat. No. 6,737,056). Certain antibody variants with improved or diminished binding to FcRs are described. (See, e.g., U.S. Pat. No. 6,737,056; WO 2004/056312, and Shields et al., J. Biol. Chem. 9 (2): 6591-6604 (2001)). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581) or the so-called "DANG" FC mutant with substitution of residues 265 to alanine and 297 to Glycine. Alternatively, antibodies with reduced effector function include those with substitution of one or more of Fc region residues 234, 235 and 329, so-called "PG-LALA" Fc mutant with substitution of residues 234 and 235 to alanine and 329 to glycine (Lo, M. et al., Journal of Biochemistry, 292, 3900-3908). Other known mutations at position 234, 235 and 321, the so called™ mutant containing mutations L234F/L235E/P331S in the CH2 domain, can be used (Oganesyan et al. Acta Cryst. D64, 700-704. (2008)). Antibodies from the human IgG4 isotype include mutations S228P/L235E to stabilize the hinge and to reduce FgR binding (Schlothauer et al, PEDS, 29 (10): 457-466).

Other Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260, 5,624,821.

Antibodies may be produced using recombinant methods and compositions, e.g., as described in U.S. Pat. No. 4,816,567. In one embodiment, isolated nucleic acid encoding an alpha-synuclein antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20). In one embodiment, a method of making an anti-apha-synuclein antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an alpha-synuclein antibody, nucleic acid encoding an antibody, e.g., as described above, is isolated and inserted into one or more vectors for further cloning and/or expression in a host cell.

Suitable host cells for cloning or expression of antibody-encoding vectors include prokaryotic or eukaryotic cells described herein.

The present invention also relates to the production of specific antibodies against native polypeptides and recombinant polypeptides of alpha-synuclein. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of alpha-synuclein can be subcloned into an appropriate vector, wherein the recombinant polypeptide is to be expressed in an organism being suitable for its expression, for example in bacteria. Thus, the expressed recombinant protein can be injected into a mice and the resulting specific antibody can be, for example, obtained from the mice serum being provided by intra-cardiac blood puncture. Many other strategies are known in the art, such as the use of DNA vaccine strategies which is well-known in the art and encompass liposome-mediated delivery, by gene gun or jet injection and intramuscular or intradermal injection. Thus, antibodies directed against a polypeptide or a protein or an epitope of alpha-synuclein, in particular the epitope of the antibodies provided herein, can be obtained by directly immunizing the animal by directly injecting intramuscularly the vector expressing the desired polypeptide or a protein or an epitope of alpha-synuclein. The amount of obtained specific antibody can be quantified using an ELISA, which is also described herein below. Further methods for the production of antibodies are well known in the art, see, e.g. Harlow and Lane, "Antibodies, A Laboratory Manual", CSH Press, Cold Spring Harbor, 1988.

Accordingly, antibodies of the present invention can be produced by methods known to those skilled in the art. Specifically, DNA encoding the antibody of interest is inserted into an expression vector. Insertion into an expression vector is carried out such that the expression will take place under the control of expression regulatory regions such as enhancers and promoters. Next, host cells are transformed using this expression vector to express the antibodies. Appropriate combinations of the host and expression vector can be used in this step.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for the purpose of producing the antibody. For example, when the host is *E. coli* such as JM109, DH5a, HB101, or XL1-Blue, the expression vectors indispensably have a promoter that permits efficient expression in *E. coli*, for example, lacZ promoter (Ward et al., Nature (1989) 341, 544-546; and FASEB J (1992) 6, 2422-2427), araB promoter (Better et al., Science (1988) 240, 1041-1043), or T7 promoter. Examples of such vectors include the vectors mentioned above as well as pGEX-5X-1 (manufactured by Pharmacia), "QIAexpress system" (manufactured by QIAGEN), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S. P. et al., J. Bacteriol. (1987) 169, 4397) can be used as the signal sequence for polypeptide secretion. The vectors can be transferred to the host cells using, for example, calcium chloride methods or electroporation methods.

In addition to the *E. coli* expression vectors, examples of the vectors for producing the antibody of the present invention include mammal-derived expression vectors (e.g., pcDNA3 (manufactured by Invitrogen Corp.), pEGF-BOS (Nucleic Acids. Res. 1990, 18 (17), p5322), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, or NIH3T3 cells, the vectors indispensably have a promoter necessary for intracellular expression, for example, SV40 promoter (Mulligan et al., Nature (1979) 277, 108), MMTV-LTR promoter, EF1a promoter (Mizushima et al., Nucleic Acids Res (1990) 18, 5322), CAG promoter (Gene (1991) 108, 193), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, POPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having a gene which expresses an SV40 T antigen on their chromosomes to transform the cells with vectors having a replication origin of SV40 (pcD, etc.). Also, a replication origin derived from polyomavirus, adenovirus, bovine papillomavirus (BPV), or the like may be used. The expression vectors for increasing the number of gene copies in a host cell system can additionally contain a selection marker such as an aminoglycoside transferase (APH) gene, a thymidine kinase (TK) gene, an *E. coli* xanthine guanine phosphoribosyltransferase (Ecogpt) gene, or a dihydrofolate reductase (dhfr) gene.

The antibodies of the present invention obtained by the methods described above can be isolated from inside host cells or from outside of the cells (the medium, or such), and purified to practically pure and homogeneous antibodies. The antibodies can be separated and purified by methods routinely used for separating and purifying antibodies, and the type of method is not limited. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid-chromatography, for example, HPLC and FPLC. Columns used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The obtained antibodies can be purified to homogeneity. Separation and purification of the antibodies can be performed using separation and purification methods generally used for protein separation and purification. For example, the antibodies can be separated and purified by appropriately selecting and combining column chromatography such as affinity chromatography, filtration, ultrafiltration, salting-out, dialysis, SDS-polyacrylamide gel electrophoresis, isoelectric focusing, and such, without limitation (Antibodies: A Laboratory Manual. Ed Harlow and David Lane, Cold Spring Harbor Laboratory, 1988). Columns used for affinity chromatography include, for example, protein A columns and protein G columns.

Alpha-synuclein antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, immunofluorescence or immunohistochemistry.

In another aspect, competition assays may be used to identify an antibody that competes with any of the antibodies described herein for binding to aggregated or pathlological alpha-synuclein. In certain embodiments, such a competing antibody binds to the same or similar epitope (e.g., a linear or a conformational epitope with total or partial overlap) that is bound by an antibody described herein. Detailed exemplary methods for mapping an epitope to which an antibody binds are provided in Morris (1996) "Epitope Mapping Protocols," in Methods in Molecular Biology vol. 66 (Humana Press, Totowa, NJ).

The invention also provides immunoconjugates comprising an alpha-synuclein antibody provided herein conjugated to one or more therapeutic agents, such as chemotherapeutic agents or drugs, growth inhibitory agents, toxins (e.g., protein toxins, enzymatically active toxins of bacterial, fungal, plant, or animal origin, or fragments thereof), radioactive isotopes (i.e., a radioconjugate), blood brain barrier penetration moieties or detectable labels.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease or disorder or abnormality, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease, disorder or abnormality. In particular embodiments, the binding molecules of the invention are for preventing, slowing down, halting, retaining and/or improving the motor capabilities or motor deficits, cognitive capabilities or cognitive deficits, or behavioral impairements of a subject suffering from a synucleopathy. In further particular embodiments, the binding molecules of the invention are for improving motor capabilities, in particular facial expression, speech, ocular motor dysfunction, tremor at rest, action tremor, increased tone, rapid alternating movement of hands, finger tapping, leg agility, Heel-Shin test, arising from chair, posture, body sway and/or gait; improving cognitive deficits, in particular as measured by MoCA (Montreal Cognitive Assessment) or Addenbrookes Cognitive Examination; and/or improving behavioral impairments, in particular using NPI scale, wherein the synucleopathy is multiple system atrophy (MSA).

In a further embodiment, when the synucleopathy is Parkinson's disease, Lewy Body dementia (LBD; dementia with Lewy bodies (DLB) ("pure" Lewy body dementia), Parkinson's disease dementia (PDD)), or Diffuse Lewy Body Disease, the binding molecules of the invention are for: (i) improving motor capabilities, in particular activities of daily living (speech, salivation, swallowing, handwriting, cutting food and handling ustensils, dressing, hygiene, turning in bed and adjusting bed clothes, falling, freezing when walking, walking, tremor, sensory complaints related to Parkinsonism), motor examination (speech, facial expression, tremor at rest, action or postural tremor of hands, rigidity, finger taps, hand movements, rapid alternating movements of hands, leg agility, arising from chair, posture, gait, postural stability, body bradykinesia and hypokinesia, dyskinesias, clinical fluctuations), symptomatic orthostatis, repeated falls and syncope, and/or transient unexplained loss of consciousness; and/or (ii) improving cognitive deficits; and/or (iii) improving behavioral impairments, in particular behavior and mood (intellectual Impairment, thought disorder, depression, motivation/initiative), delusions, hallucinations, agitation/aggression, depression/dysphoria, anxiety, elation/euphoria, apathy/indifference, irritability/lability, motor disturbance, nighttime behavior, and/or appetite/eating, deficits of attention, executive functions, visuospatial ability, visual hallucination; and/or (iv) improving rapid eye movement (REM) sleep disorders, in particular insomnia, hypersomnolence.

In one embodiment, a pharmaceutical composition is provided comprising the antibody, antigen-binding fragment thereof or derivative thereof, as an active ingredient and a pharmaceutically acceptable carrier and/or excipient. For example, the antibody, antigen-binding fragment thereof or derivative thereof may be combined, as appropriate, with pharmaceutically acceptable carriers or media such as sterilized water or saline solution, vegetable oils, emulsifiers, suspensions, surfactants, stabilizers, flavoring agents, excipients, vehicles, preservatives, and binders, for example, and formulated into a pharmaceutical preparation. Examples of carriers include light anhydrous silicie acid, lactose, crystalline cellulose, mannitol, starch, cannellose calcium, carmellose sodium, hydroxypropylcellulose, hydroxypropylmethylcellulose, polyvinylacetal diethylaminoacetate, polyvinyl pyrrolidone, gelatin, medium chain fatty acid triglycerides, polyoxyethylene hydrogenated castor oil 60, sucrose, carboxymethyl cellulose, corn starch, and inorganic salts.

The amount of the active ingredient in these preparations can be set as appropriate within the designated range of doses.

In another embodiment, the present disclosure provides a product comprising at least (i) a container (e.g., an injection); (ii) a pharmaceutical composition comprising the antibody, antigen-binding fragment thereof or derivative thereof as an active ingredient within the container; and (iii) a document instructing that the antibody, antigen-binding fragment thereof or derivative thereof be administered according to a desired dosage regimen. Additionally, a label, a syringe, an injection needle, a pharmacologically acceptable medium, an alcohol cotton cloth, plaster, and the like may be additionally packaged, as appropriate, with this product. The container may be a bottle, a glass bottle, or a syringe, for example, and may be made of any of various materials such as glass and plastics. The container contains the pharmaceutical composition, and has an outlet sealed with a rubber stopper, for example. The container is provided with, for example, a label indicating that the pharmaceutical composition is for use in preventing or treating a selected pathological condition. In some cases, this label may describe the embodiment where the antibody, antigen-binding fragment thereof or derivative thereof is used in combination with an additional medicament.

An antibody, immunoconjugate, pharmaceutical composition of the invention (and any additional therapeutic agent) can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies, immunoconjugates, pharmaceutical compositions of the invention may be formulated, dosed, and administered in a fashion consistent with good medical practice. Factors for consideration in this context include the particular disease or disorder or abnormality being treated, the particular subject being treated, the clinical condition of the individual patient, the cause of the disease or disorder or abnormality, the site of delivery of the agent, the method of administration, the scheduling of administration, and other factors known to medical practitioners. The antibody or immunoconjugate need not be, but is optionally formulated with one or more agents currently used to prevent or treat the disease or disorder or abnormality in question. The effective amount of such other agents depends on the amount of antibody or immunoconjugate present in the formulation, the type of disease, or disorder or abnormality or treatment, and other factors discussed above. These are generally used in the same dosages and with administration routes as described herein, or in any dosage and by any route that is empirically/clinically determined to be appropriate.

It is understood that any of the above formulations or therapeutic methods may be carried out using both an immunoconjugate of the invention and an alpha-synuclein antibody.

In some embodiments, an isolated nucleic acid is provided, wherein the isolated nucleic acid encodes an antibody described herein.

In some embodiments, an isolated nucleic acid is provided, wherein the isolated nucleic acid comprises SEQ ID NO: 18 encoding an alpha-synuclein antibody. In some embodiments, an isolated nucleic acid is provided, wherein the isolated nucleic acid comprises SEQ ID NO: 28 encoding an alpha-synuclein antibody. In some embodiments, an isolated nucleic acid is provided, wherein the isolated nucleic acid comprises SEQ ID NO: 38 encoding an alpha-synuclein antibody. In some embodiments, an isolated nucleic acid is provided, wherein the isolated nucleic acid comprises SEQ ID NO: 48 encoding an alpha-synuclein antibody. In some embodiments, an isolated nucleic acid is provided, wherein the isolated nucleic acid comprises SEQ ID NO: 58 encoding an alpha-synuclein antibody. In some embodiments, an isolated nucleic acid is provided, wherein the isolated nucleic acid comprises SEQ ID NO: 68 encoding an alpha-synuclein antibody. In some embodiments, an isolated nucleic acid is provided, wherein the isolated nucleic acid comprises SEQ ID NO: 78 encoding an alpha-synuclein antibody. In some embodiments, an isolated nucleic acid is provided, wherein the isolated nucleic acid comprises SEQ ID NO: 98 encoding an alpha-synuclein antibody. In some embodiments, an isolated nucleic acid is provided, wherein the isolated nucleic acid comprises SEQ ID NO: 108 encoding an alpha-synuclein antibody. In some embodiments, an isolated nucleic acid is provided, wherein the isolated nucleic acid comprises SEQ ID NO: 118 encoding an alpha-synuclein antibody. In some embodiments, an isolated nucleic acid is provided, wherein the isolated nucleic acid comprises SEQ ID NO: 288 encoding an alpha-synuclein antibody. In some embodiments, an isolated nucleic acid is provided, wherein the isolated nucleic acid comprises SEQ ID NO: 298 encoding an alpha-synuclein antibody. In some embodiments, an isolated nucleic acid is provided, wherein the isolated nucleic acid comprises SEQ ID NO: 148 encoding an alpha-synuclein antibody. In some embodiments, an isolated nucleic acid is provided, wherein the isolated nucleic acid comprises SEQ ID NO: 158 encoding an alpha-synuclein antibody. In some embodiments, an isolated nucleic acid is provided, wherein the isolated nucleic acid comprises SEQ ID NO: 168 encoding an alpha-synuclein antibody. In some embodiments, an isolated nucleic acid is provided, wherein the isolated nucleic acid comprises SEQ ID NO: 178 encoding an alpha-synuclein antibody. In some embodiments, an isolated nucleic acid is provided, wherein the isolated nucleic acid comprises SEQ ID NO: 188 encoding an alpha-synuclein antibody. In some embodiments, an isolated nucleic acid is provided, wherein the isolated nucleic acid comprises SEQ ID NO: 198 encoding an alpha-synuclein antibody. In some embodiments, an isolated nucleic acid is provided, wherein the isolated nucleic acid comprises SEQ ID NO: 208 encoding an alpha-synuclein antibody. In some embodiments, an isolated nucleic acid is provided, wherein the isolated nucleic acid comprises SEQ ID NO: 218 encoding an alpha-synuclein antibody. In some embodiments, an isolated nucleic acid is provided, wherein the isolated nucleic acid comprises SEQ ID NO: 228 encoding an alpha-synuclein antibody. In some embodiments, an isolated nucleic acid is provided, wherein the isolated nucleic acid comprises SEQ ID NO: 238 encoding an alpha-synuclein antibody. In some embodiments, an isolated nucleic acid is provided, wherein the isolated nucleic acid comprises SEQ ID NO: 248 encoding an alpha-synuclein antibody. In some embodiments, an isolated nucleic acid is provided, wherein the isolated nucleic acid comprises SEQ ID NO: 258 encoding an alpha-synuclein antibody. In some embodiments, an isolated nucleic acid is provided, wherein the isolated nucleic acid comprises SEQ ID NO: 268 encoding an alpha-synuclein antibody. In some embodiments, an isolated nucleic acid is provided, wherein the isolated nucleic acid comprises SEQ ID NO: 278 encoding an alpha-synuclein antibody. In some embodiments, an isolated nucleic acid is provided, wherein the isolated nucleic acid comprises SEQ ID NO: 308 encoding an alpha-synuclein antibody. In some embodiments, an isolated nucleic acid is provided, wherein the isolated nucleic acid comprises SEQ ID NO: 318 encoding an alpha-synuclein antibody. In some embodiments, an isolated nucleic acid is provided, wherein the isolated nucleic acid comprises SEQ ID NO: 328 encoding an alpha-synuclein antibody. In some embodiments, an isolated nucleic acid is provided, wherein the isolated nucleic acid comprises SEQ ID NO: 338 encoding an alpha-synuclein antibody. In some embodiments, an isolated nucleic acid is provided, wherein the isolated nucleic acid comprises SEQ ID NO: 348 encoding an alpha-synuclein antibody. In some embodiments, an isolated nucleic acid is provided, wherein the isolated nucleic acid comprises SEQ ID NO: 358 encoding an alpha-synuclein antibody. In some embodiments, an isolated nucleic acid is provided, wherein the isolated nucleic acid comprises SEQ ID NO: 368 encoding an alpha-synuclein antibody. In some embodiments, an isolated nucleic acid is provided, wherein the isolated nucleic acid comprises SEQ ID NO: 378 encoding an alpha-synuclein antibody. In some embodiments, an isolated nucleic acid is provided, wherein the isolated nucleic acid comprises SEQ ID NO: 388 encoding an alpha-synuclein antibody. In some embodiments, an isolated nucleic acid is provided, wherein the isolated nucleic acid comprises SEQ ID NO: 398 encoding an alpha-synuclein antibody. In some embodiments, an isolated nucleic acid is provided, wherein the isolated nucleic acid comprises SEQ ID NO: 408 encoding an alpha-synuclein antibody. In some embodiments, an isolated nucleic acid is provided, wherein the isolated nucleic acid comprises SEQ ID NO: 418 encoding an alpha-synuclein antibody. In some embodiments, an isolated nucleic acid is provided, wherein the isolated nucleic acid comprises SEQ ID NO: 428 encoding an alpha-synuclein antibody. In some embodiments, an isolated nucleic acid is provided, wherein the isolated nucleic acid comprises SEQ ID NO: 438 encoding an alpha-synuclein antibody. In some embodiments, an isolated nucleic acid is provided, wherein the isolated nucleic acid comprises SEQ ID NO: 448 encoding an alpha-synuclein antibody. In some embodiments, an isolated nucleic acid is provided, wherein the isolated nucleic acid comprises SEQ ID NO: 458 encoding an alpha-synuclein antibody. In some embodiments, an isolated nucleic acid is provided, wherein the isolated nucleic acid comprises SEQ ID NO: 468 encoding an alpha-synuclein antibody. In some embodiments, an isolated nucleic acid is provided, wherein the isolated nucleic acid comprises SEQ ID NO: 478 encoding an alpha-synuclein antibody. In some embodiments, an isolated nucleic acid is provided, wherein the isolated nucleic acid comprises SEQ ID NO: 488 encoding an alpha-synuclein antibody. In some embodiments, an isolated nucleic acid is provided, wherein the isolated nucleic acid comprises SEQ ID NO: 498 encoding an alpha-synuclein antibody. In some embodiments, an isolated nucleic acid is provided, wherein the isolated nucleic acid comprises SEQ ID NO: 508 encoding an alpha-synuclein antibody. In some embodiments, an isolated nucleic acid is provided, wherein the isolated nucleic acid comprises SEQ ID NO: 518 encoding an alpha-synuclein antibody. In some embodiments, an isolated nucleic acid is provided, wherein the isolated nucleic acid comprises SEQ ID NO: 528 encoding an alpha-synuclein antibody. In some embodiments, an isolated nucleic acid is provided, wherein the isolated nucleic acid comprises SEQ ID NO: 538 encoding an alpha-synuclein antibody. In some embodiments, an isolated nucleic acid is provided, wherein the isolated nucleic acid comprises SEQ ID NO: 548 encoding an alpha-synuclein antibody. In some embodiments, an isolated nucleic acid is provided, wherein the isolated nucleic acid comprises SEQ ID NO: 558 encoding an alpha-synuclein antibody. In some embodiments, an isolated nucleic acid is provided, wherein the isolated nucleic acid comprises SEQ ID NO: 568 encoding an alpha-synuclein antibody. In some embodiments, an isolated nucleic acid is provided, wherein the isolated nucleic acid comprises SEQ ID NO: 578 encoding an alpha-synuclein antibody. In some embodiments, an isolated nucleic acid is provided, wherein the isolated nucleic acid comprises SEQ ID NO: 588 encoding an alpha-synuclein antibody. In some embodiments, an isolated nucleic acid is provided, wherein the isolated nucleic acid comprises SEQ ID NO: 598 encoding an alpha-synuclein antibody. In some embodiments, an isolated nucleic acid is provided, wherein the isolated nucleic acid comprises SEQ ID NO: 608 encoding an alpha-synuclein antibody. In some embodiments, an isolated nucleic acid is provided, wherein the isolated nucleic acid comprises SEQ ID NO: 618 encoding an alpha-synuclein antibody. In some embodiments, an isolated nucleic acid is provided, wherein the isolated nucleic acid comprises SEQ ID NO: 628 encoding an alpha-synuclein antibody. In some embodiments, an isolated nucleic acid is provided, wherein the isolated nucleic acid comprises SEQ ID NO: 638 encoding an alpha-synuclein antibody. In some embodiments, an isolated nucleic acid is provided, wherein the isolated nucleic acid comprises SEQ ID NO: 648 encoding an alpha-synuclein antibody. In some embodiments, an isolated nucleic acid is provided, wherein the isolated nucleic acid comprises SEQ ID NO: 658 encoding an alpha-synuclein antibody. In some embodiments, an isolated nucleic acid is provided, wherein the isolated nucleic acid comprises SEQ ID NO: 668 encoding an alpha-synuclein antibody. In some embodiments, an isolated nucleic acid is provided, wherein the isolated nucleic acid comprises SEQ ID NO: 678 encoding an alpha-synuclein antibody. In some embodiments, an isolated nucleic acid is provided, wherein the isolated nucleic acid comprises SEQ ID NO: 688 encoding an alpha-synuclein antibody. In some embodiments, an isolated nucleic acid is provided, wherein the isolated nucleic acid comprises SEQ ID NO: 698 encoding an alpha-synuclein antibody. In some embodiments, an isolated nucleic acid is provided, wherein the isolated nucleic acid comprises SEQ ID NO: 708 encoding an alpha-synuclein antibody. In some embodiments, an isolated nucleic acid is provided, wherein the isolated nucleic acid comprises SEQ ID NO: 718 encoding an alpha-synuclein antibody. In some embodiments, an isolated nucleic acid is provided, wherein the isolated nucleic acid comprises SEQ ID NO: 728 encoding an alpha-synuclein antibody.

In some embodiments, an isolated nucleic acid is provided, wherein the isolated nucleic acid comprises SEQ ID NO: 19 encoding an alpha-synuclein antibody. In some embodiments, an isolated nucleic acid is provided, wherein the isolated nucleic acid comprises SEQ ID NO: 29 encoding an alpha-synuclein antibody. In some embodiments, an isolated nucleic acid is provided, wherein the isolated nucleic acid comprises SEQ ID NO: 39 encoding an alpha-synuclein antibody. In some embodiments, an isolated nucleic acid is provided, wherein the isolated nucleic acid comprises SEQ ID NO: 49 encoding an alpha-synuclein antibody. In some embodiments, an isolated nucleic acid is provided, wherein the isolated nucleic acid comprises SEQ ID NO: 59 encoding an alpha-synuclein antibody. In some embodiments, an isolated nucleic acid is provided, wherein the isolated nucleic acid comprises SEQ ID NO: 69 encoding an alpha-synuclein antibody. In some embodiments, an isolated nucleic acid is provided, wherein the isolated nucleic acid comprises SEQ ID NO: 79 encoding an alpha-synuclein antibody. In some embodiments, an isolated nucleic acid is provided, wherein the isolated nucleic acid comprises SEQ ID NO: 89 encoding analpha-synuclein antibody. In some embodiments, an isolated nucleic acid is provided, wherein the isolated nucleic acid comprises SEQ ID NO: 99 encoding an alpha-synuclein antibody. In some embodiments, an isolated nucleic acid is provided, wherein the isolated nucleic acid comprises SEQ ID NO: 109 encoding an alpha-synuclein antibody. In some embodiments, an isolated nucleic acid is provided, wherein the isolated nucleic acid comprises SEQ ID NO: 119 encoding an alpha-synuclein antibody. In some embodiments, an isolated nucleic acid is provided, wherein the isolated nucleic acid comprises SEQ ID NO: 289 encoding an alpha-synuclein antibody. In some embodiments, an isolated nucleic acid is provided, wherein the isolated nucleic acid comprises SEQ ID NO: 199 encoding an alpha-synuclein antibody. In some embodiments, an isolated nucleic acid is provided, wherein the isolated nucleic acid comprises SEQ ID NO: 149 encoding an alpha-synuclein antibody. In some embodiments, an isolated nucleic acid is provided, wherein the isolated nucleic acid comprises SEQ ID NO: 159 encoding an alpha-synuclein antibody. In some embodiments, an isolated nucleic acid is provided, wherein the isolated nucleic acid comprises SEQ ID NO: 169 encoding an alpha-synuclein antibody. In some embodiments, an isolated nucleic acid is provided, wherein the isolated nucleic acid comprises SEQ ID NO: 179 encoding an alpha-synuclein antibody. In some embodiments, an isolated nucleic acid is provided, wherein the isolated nucleic acid comprises SEQ ID NO: 189 encoding an alpha-synuclein antibody. In some embodiments, an isolated nucleic acid is provided, wherein the isolated nucleic acid comprises SEQ ID NO: 209 encoding an alpha-synuclein antibody. In some embodiments, an isolated nucleic acid is provided, wherein the isolated nucleic acid comprises SEQ ID NO: 219 encoding an alpha-synuclein antibody. In some embodiments, an isolated nucleic acid is provided, wherein the isolated nucleic acid comprises SEQ ID NO: 229 encoding an alpha-synuclein antibody. In some embodiments, an isolated nucleic acid is provided, wherein the isolated nucleic acid comprises SEQ ID NO: 239 encoding an alpha-synuclein antibody. In some embodiments, an isolated nucleic acid is provided, wherein the isolated nucleic acid comprises SEQ ID NO: 249 encoding an alpha-synuclein antibody. In some embodiments, an isolated nucleic acid is provided, wherein the isolated nucleic acid comprises SEQ ID NO: 259 encoding an alpha-synuclein antibody. In some embodiments, an isolated nucleic acid is provided, wherein the isolated nucleic acid comprises SEQ ID NO: 269 encoding an alpha-synuclein antibody. In some embodiments, an isolated nucleic acid is provided, wherein the isolated nucleic acid comprises SEQ ID NO: 279 encoding an alpha-synuclein antibody. In some embodiments, an isolated nucleic acid is provided, wherein the isolated nucleic acid comprises SEQ ID NO: 309 encoding an alpha-synuclein antibody. In some embodiments, an isolated nucleic acid is provided, wherein the isolated nucleic acid comprises SEQ ID NO: 319 encoding an alpha-synuclein antibody. In some embodiments, an isolated nucleic acid is provided, wherein the isolated nucleic acid comprises SEQ ID NO: 329 encoding an alpha-synuclein antibody. In some embodiments, an isolated nucleic acid is provided, wherein the isolated nucleic acid comprises SEQ ID NO: 339 encoding an alpha-synuclein antibody. In some embodiments, an isolated nucleic acid is provided, wherein the isolated nucleic acid comprises SEQ ID NO: 349 encoding an alpha-synuclein antibody. In some embodiments, an isolated nucleic acid is provided, wherein the isolated nucleic acid comprises SEQ ID NO: 359 encoding an alpha-synuclein antibody. In some embodiments, an isolated nucleic acid is provided, wherein the isolated nucleic acid comprises SEQ ID NO: 369 encoding an alpha-synuclein antibody. In some embodiments, an isolated nucleic acid is provided, wherein the isolated nucleic acid comprises SEQ ID NO: 379 encoding an alpha-synuclein antibody. In some embodiments, an isolated nucleic acid is provided, wherein the isolated nucleic acid comprises SEQ ID NO: 389 encoding an alpha-synuclein antibody. In some embodiments, an isolated nucleic acid is provided, wherein the isolated nucleic acid comprises SEQ ID NO: 399 encoding an alpha-synuclein antibody. In some embodiments, an isolated nucleic acid is provided, wherein the isolated nucleic acid comprises SEQ ID NO: 409 encoding an alpha-synuclein antibody. In some embodiments, an isolated nucleic acid is provided, wherein the isolated nucleic acid comprises SEQ ID NO: 419 encoding an alpha-synuclein antibody. In some embodiments, an isolated nucleic acid is provided, wherein the isolated nucleic acid comprises SEQ ID NO: 429 encoding an alpha-synuclein antibody. In some embodiments, an isolated nucleic acid is provided, wherein the isolated nucleic acid comprises SEQ ID NO: 439 encoding an alpha-synuclein antibody. In some embodiments, an isolated nucleic acid is provided, wherein the isolated nucleic acid comprises SEQ ID NO: 449 encoding an alpha-synuclein antibody. In some embodiments, an isolated nucleic acid is provided, wherein the isolated nucleic acid comprises SEQ ID NO: 459 encoding an alpha-synuclein antibody. In some embodiments, an isolated nucleic acid is provided, wherein the isolated nucleic acid comprises SEQ ID NO: 469 encoding an alpha-synuclein antibody. In some embodiments, an isolated nucleic acid is provided, wherein the isolated nucleic acid comprises SEQ ID NO: 479 encoding an alpha-synuclein antibody. In some embodiments, an isolated nucleic acid is provided, wherein the isolated nucleic acid comprises SEQ ID NO: 489 encoding an alpha-synuclein antibody. In some embodiments, an isolated nucleic acid is provided, wherein the isolated nucleic acid comprises SEQ ID NO: 499 encoding an alpha-synuclein antibody. In some embodiments, an isolated nucleic acid is provided, wherein the isolated nucleic acid comprises SEQ ID NO: 509 encoding an alpha-synuclein antibody. In some embodiments, an isolated nucleic acid is provided, wherein the isolated nucleic acid comprises SEQ ID NO: 519 encoding an alpha-synuclein antibody. In some embodiments, an isolated nucleic acid is provided, wherein the isolated nucleic acid comprises SEQ ID NO: 529 encoding an alpha-synuclein antibody. In some embodiments, an isolated nucleic acid is provided, wherein the isolated nucleic acid comprises SEQ ID NO: 539 encoding an alpha-synuclein antibody. In some embodiments, an isolated nucleic acid is provided, wherein the isolated nucleic acid comprises SEQ ID NO: 549 encoding an alpha-synuclein antibody. In some embodiments, an isolated nucleic acid is provided, wherein the isolated nucleic acid comprises SEQ ID NO: 559 encoding an alpha-synuclein antibody. In some embodiments, an isolated nucleic acid is provided, wherein the isolated nucleic acid comprises SEQ ID NO: 569 encoding an alpha-synuclein antibody. In some embodiments, an isolated nucleic acid is provided, wherein the isolated nucleic acid comprises SEQ ID NO: 579 encoding an alpha-synuclein antibody. In some embodiments, an isolated nucleic acid is provided, wherein the isolated nucleic acid comprises SEQ ID NO: 589 encoding an alpha-synuclein antibody. In some embodiments, an isolated nucleic acid is provided, wherein the isolated nucleic acid comprises SEQ ID NO: 609 encoding an alpha-synuclein antibody. In some embodiments, an isolated nucleic acid is provided, wherein the isolated nucleic acid comprises SEQ ID NO: 619 encoding an alpha-synuclein antibody. In some embodiments, an isolated nucleic acid is provided, wherein the isolated nucleic acid comprises SEQ ID NO: 629 encoding an alpha-synuclein antibody. In some embodiments, an isolated nucleic acid is provided, wherein the isolated nucleic acid comprises SEQ ID NO: 639 encoding an alpha-synuclein antibody. In some embodiments, an isolated nucleic acid is provided, wherein the isolated nucleic acid comprises SEQ ID NO: 649 encoding an alpha-synuclein antibody.

In certain embodiments, a binding molecule or an antibody provided herein has a dissociation constant (KD) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M), in particular with respect to binding alpha-synuclein, in particular aggregated alpha-synuclein and/or pathological alpha-synuclein.

In certain embodiments, a binding molecule or an antibody provided herein has a dissociation constant (KD) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M), in particular with respect to binding pathological and/or aggregated alpha-synuclein, including but limited to protofibrils, fibrils, oligomers, Lewy Body, Lewy neurites and/or glial cytoplasmic inclusions.

In one embodiment, KD is measured using surface plasmon resonance assays using a BIACORE®-2000 or a BIACORE®-3000 (BIAcore, Inc., Piscataway, NJ) at 25° C. with immobilized antigen CM5 chips at −10 response units (RU).

In some embodiments, an antibody, particularly an isolated antibody of the invention as described herein that binds human alpha-synuclein is provided, wherein the antibody binds aggregated alpha-synuclein and/or pathological alpha-synuclein with a KD of less than 100 nM, less than 10 nM, less than 1 nM, less than 200 pM, less than 100 pM, or less than 10 pM. Preferably, the antibody of the invention binds aggregated alpha-synuclein and/or pathological alpha-synuclein with a KD of less than 100 nM, less than 10 nM, less than 1 nM, less than 200 pM, less than 100 pM, or less than 10 pM.

The binding molecules, especially antibodies, of the invention may selectively bind aggregated alpha-synuclein and/or pathological alpha-synuclein in preference to non-aggregated alpha-synuclein and/or non-pathological alpha-synuclein (such as monomeric alpha-synuclein). This selectivity may be measured in terms of dissociation (or "off") rates (kd). Thus, the binding molecules, especially antibodies, of the invention may display slower, preferably significantly slower, dissociation rates (kd) from aggregated alpha-synuclein and/or pathological alpha-synuclein (such as fibrillar alpha-synuclein) compared to non-aggregated alpha-synuclein and/or non-pathological alpha-synuclein (such as monomeric alpha-synuclein). For example, the binding molecules, especially antibodies, of the invention may display at least 10-fold, preferably at least 100-fold, and more preferably at least 1000-fold slower dissociation rates (kd) from aggregated alpha-synuclein and/or pathological alpha-synuclein (such as fibrillar alpha-synuclein) compared to non-aggregated alpha-synuclein and/or non-pathological alpha-synuclein (such as monomeric alpha-synuclein). This selectivity may be measured in terms of relative dissociation constant (KD). Thus, the binding molecules, especially antibodies, of the invention may display lower, preferably significantly lower, dissociation constants (KD) with respect to aggregated alpha-synuclein and/or pathological alpha-synuclein (such as fibrillar alpha-synuclein) compared to non-aggregated alpha-synuclein and/or non-pathological alpha-synuclein (such as monomeric alpha-synuclein). For example, the binding molecules, especially antibodies, of the invention may display at least 10-fold, more preferably at least 20-fold, and more preferably at least 100-fold lower dissociation constants (KD) with respect to aggregated alpha-synuclein and/or pathological alpha-synuclein (such as fibrillar alpha-synuclein) compared to non-aggregated alpha-synuclein and/or non-pathological alpha-synuclein (such as monomeric alpha-synuclein). KD and kd may be measured using surface plasmon resonance assays using a BIACORE®-2000 or a BIACORE®-3000 (BIAcore, Inc., Piscataway, NJ) at 25° C. with immobilized antigen CM5 chips at −10 response units (RU). Specific methodology is described in the Examples section herein (see "Affinity measurements on alpha-synuclein monomers and alpha-synuclein fibrils by SPR" and "Characterization of ACI-7067-1101C8-Ab2 humanized variants by Surface Plasmon resonance (SPR)"), which may be applied according to the invention as a reference method.

The binding molecules, especially antibodies, of the invention may inhibit and/or delay seeded and/or spontaneous alpha-synuclein aggregation with an $IC_{50}$ of ≤1 μM, ≤100 nM, ≤10 nM, ≤1 nM or ≤0.1 nM. The $IC_{50}$ may be obtained by measuring the percentage of de novo alpha-synuclein aggregates formed, relative to conditions in the absence of antibody, as a function of antibody concentration. Dose-response curves may be plotted and $IC_{50}$ values obtained using Equation 6. See FIG. 12 and the Examples describing the in vitro cellular model, which methodology applies mutatis mutandis. Alternatively, dose-response curves may be plotted and $IC_{50}$ values obtained using Equation 7. See FIG. 13 and the Examples describing the mouse primary cortical neuron experiments, which methodology applies mutatis mutandis.

The binding molecules, especially antibodies, of the invention may inhibit and/or delay seeded and/or spontaneous alpha-synuclein aggregation as quantified by a percent change in the aggregation half-time ($T_{1/2}$). Suitable methodology for measuring the aggregation half-time is provided herein, see the Examples "Inhibition or delay of seeded alpha-synuclein aggregation", which description can be applied mutatis mutandis. Antibodies of the invention significantly increase, such as at least a 10% increase in, $T_{1/2}$ values, as normalized to aggregation in the absence of antibody.

In some embodiments, an antibody, antigen-binding fragment thereof or derivative thereof, is provided which binds to human alpha-synuclein within an epitope comprised in SEQ ID NO: 1. In some particular embodiments, an antibody is provided which binds to human alpha-synuclein within amino acids residues 36-40 (SEQ ID NO: 2). In some particular embodiments, an antibody is provided which binds to human alpha-synuclein within amino acids residues 1-15 (SEQ ID NO: 121). In some particular embodiments, an antibody is provided which binds to human alpha-synuclein within amino acids residues 51-57 (SEQ ID NO: 3). In some particular embodiments, an antibody is provided which binds to human alpha-synuclein within amino acids residues 51-58 (SEQ ID NO: 136). In some particular embodiments, an antibody is provided which binds to human alpha-synuclein within amino acids residues 65-74 (SEQ ID NO: 4). In some particular embodiments, an antibody is provided which binds to human alpha-synuclein within amino acids residues 65-81 (SEQ ID NO: 5). In some particular embodiments, an antibody is provided which binds to human alpha-synuclein within amino acids residues 82-96 (SEQ ID NO: 130). In some particular embodiments, an antibody is provided which binds to human alpha-synuclein within amino acids residues 91-105 (SEQ ID NO: 131). In some particular embodiments, an antibody is provided which binds to human alpha-synuclein within amino acids residues 93-95 (GFV) of SEQ ID NO:1. In some particular embodiments, an antibody is provided which binds to human alpha-synuclein within amino acids residues 118-132 (SEQ ID NO: 134). In some particular embodiments, an antibody is provided which binds to human alpha-synuclein within amino acids residues 124-131 (SEQ ID NO: 7). In some particular embodiments, an antibody is provided which binds to human alpha-synuclein within amino acids residues 127-140 (SEQ ID NO: 135). In some particular embodiments, an antibody is provided which binds to human alpha-synuclein within amino acids residues 10-24 (SEQ ID NO: 122). In some particular embodiments, an antibody is provided which binds to human alpha-synuclein within amino acids residues 128-135 (SEQ ID NO: 8). In some particular embodiments, an antibody is provided which binds to human alpha-synuclein within amino acids residues 131-140 (SEQ ID NO: 9). In some particular embodiments, an antibody is provided which binds to human alpha-synuclein within amino acids residues 28-42 (SEQ ID NO: 124). In some particular embodiments, an antibody is provided which binds to human alpha-synuclein within amino acids residues 37-51 (SEQ ID NO: 125). In some particular embodiments, an antibody is provided which binds to human alpha-synuclein within amino acids residues 100-114 (SEQ ID NO: 132). In some particular embodiments, an antibody is provided which binds to human alpha-synuclein within amino acids residues 109-123 (SEQ ID NO: 133). In some particular embodiments, an antibody is provided which binds to human alpha-synuclein within amino acids residues 81-120 (SEQ ID NO: 137). In some embodiments, an antibody is provided which binds to a non-linear epitope within amino acids residues of human alpha-synuclein of SEQ ID NO: 1. More preferably, antigen-binding molecule of the invention bind to an epitope within amino acids residues 124-131 (SEQ ID NO: 7), 128-135 (SEQ ID NO: 8) or 131-140 (SEQ ID NO: 9) of human alpha-synuclein of SEQ ID NO: 1. Even more preferably, antigen-binding molecules of the invention may bind to an epitope comprising amino acids 126 and 127 of human alpha-synuclein of SEQ ID NO: 1 as critical residues for binding.

In some embodiments, an isolated antibody that binds to human alpha-synuclein is provided, wherein the antibody binds extracellular or cytoplasmic alpha-synuclein. In some embodiments an isolated antibody that binds to monomeric or aggregated alpha-synuclein. In some embodiments of the invention, the monomeric, oligomeric or aggregated alpha-synuclein is post-translationally modified, e.g. phosphorylated or nitrosylated. The invention also relates to compositions comprising a binding molecule, particularly an antibody of the invention (including alpha-synuclein antibody fragments and derivatives) as described herein and to therapeutic and diagnostic methods using such compositions in the prevention, diagnosis or treatment of a synucleopathy, wherein an effective amount of the binding molecule is administered to a patient in need thereof.

In certain embodiments, the alpha-synuclein antibodies described herein are useful for detecting the presence of alpha-synuclein in a biological sample. Such methods (specific examples of which are described herein) are typically performed in vitro using an isolated sample. However, they may be performed in vivo in some circumstances, where appropriate. In particular embodiments, the alpha-synuclein antibodies described herein are useful for detecting the presence of aggregated and/or pathological alpha-synuclein, inlcuding but not limited to Lewy bodies, Lewy neurites and/or glial cytoplasmic inclusions in a biological sample. The term "detecting" as used herein encompasses quantitative or qualitative detection. The biological sample (in all methods reliant upon such detecting) is typically a clinical sample from a mammalian, in particular human, subject. In certain embodiments, a biological sample comprises a cell or tissue, such as cerebrospinal fluid (CSF), a cell or tissue of the brain (e.g., brain cortex or hippocampus), or blood. In some embodiments, a biological sample is cerebrospinal fluid.

In some embodiments, an alpha-synuclein antibody described herein for use in a method of diagnosis or detection is provided. In a further aspect, a method of detecting the presence of alpha-synuclein in a biological sample is provided. In certain embodiments, the method comprises contacting the biological sample with an alpha-synuclein antibody as described herein under conditions permissive for binding of the alpha-synuclein antibody to alpha-synuclein, and detecting whether a complex is formed between the alpha-synuclein antibody and alpha-synuclein. Such method may be an in vitro and/or in vivo method. Further, the complex formed between the the alpha-synuclein antibody and alpha-synuclein in a test biological sample can be compared to the complex formed in a control biological sample (e.g., a biological sample from a healthy subject or subjects). The amount of the complex formed between the the alpha-synuclein antibody and alpha-synuclein in a test biological sample can also be quantified and compared to the amount of the complex formed in a control biological sample (e.g., a biological sample from a healthy subject or subjects) or to the average amount of the complex known to be formed in healthy subjects.

In some embodiments, an alpha-synuclein antibody described herein is used to select subjects eligible for therapy, including therapy with an alpha-synuclein antibody, e.g. where alpha-synuclein is a biomarker for selection of patients. For example, in some embodiments, an alpha-synuclein antibody is used to detect whether the subject has a disease, disorder or abnormality associated with alpha-synuclein aggregates including but not limited, Lewy bodies, Lewy neurites and/or Glial cytoplasic inclusions, or whether the subject is at high risk (or predisposed to) a disease or disorder or abnormality associated with alpha-synuclein aggregates including but not limited, Lewy bodies, Lewy neurites and/or Glial cytoplasic inclusions.

Exemplary diseases or disorders or abnormality that may be diagnosed using an antibody of the invention include diseases or disorders or abnormalities associated with alpha-synuclein aggregates including, but not limited, Lewy bodies, Lewy neurites and/or Glial cytoplasic inclusions, that are manifested in a cognitive deficit or behavioral impairment, or motor deficit or impairement such as bradykinesia, rigidity, resting tremor or postural instability. In particular, diseases or disorders or abnormality that may be diagnosed using an antibody, antigen-binding fragment thereof or derivative thereof, of the invention include synucleinopathies such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

Exemplary diseases or disorders or abnormality that may be prevented or treated using an antibody of the invention include diseases, disorders or abnormalities associated with alpha-synuclein aggregates including, but not limited, Lewy bodies, Lewy neurites and/or Glial cytoplasic inclusions, that are manifested in a cognitive deficit or behavioral impairment, or motor deficit or impairement such as bradykinesia, rigidity, resting tremor or postural instability. In particular, diseases or disorders or abnormality that may be diagnosed using an antibody, antigen-binding it thereof or derivative thereof, of the invention include synucleinopathies such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments, an immunoconjugate is provided, wherein the immunoconjugate comprises an isolated antibody described herein and a therapeutic agent.

In some embodiments, a labeled antibody is provided, comprising an antibody described herein and a detectable label.

In some embodiments the alpha-synuclein binding molecule of the present invention is linked to a detectable label.

In some embodiments the alpha-synuclein binding molecule is part of an immunoconjugate wherein the alpha-synuclein binding molecule is covalently linked to another suitable therapeutic agent.

In some embodiments an alpha-synuclein binding molecule is part of a pharmaceutical composition comprising an alpha-synuclein binding molecule, or an immunoconjugate wherein the alpha-synuclein binding molecule is covalently linked to another suitable therapeutic agent, or a composition comprising an alpha-synuclein specific binding molecule combined with a pharmaceutically acceptable carrier and/or excipient.

In some embodiments an alpha-synuclein binding molecule is part of a diagnostic kit comprising an alpha-synuclein specific binding molecule, or an immunoconjugate wherein the alpha-synuclein specific binding molecule is covalently linked to another suitable therapeutic agent, or a composition comprising an alpha-synuclein specific binding molecule and an alpha-synuclein agonist and cognate molecules, or alternately, antagonists of the same.

In some embodiments an alpha-synuclein binding molecule is used in an immunodiagnostic method for use in the prevention, diagnosis, alleviation of symptoms associated with, or treatment of a disease or disorder or abnormality associated with alpha-synuclein aggregates including, but not limited to, Lewy bodies, Lewy neurites, and/or glial cytoplasmic inclusions.

In some embodiments an alpha-synuclein binding molecule is part of an immunotherapeutic method for the prevention, alleviation of symptoms associated with, or treatment of a synucleinopathy, wherein an effective amount of the alpha-synuclein binding molecule, or an immunoconjugate wherein the alpha-synuclein binding molecule is covalently linked to another suitable therapeutic agent, or a composition comprising an alpha-synuclein binding molecule is administered to a patient in need thereof.

In some embodiments the alpha-synuclein binding molecule, or an immunoconjugate wherein the alpha-synuclein binding molecule is covalently linked to another suitable therapeutic agent, or a composition comprising an alpha-synuclein binding molecule is administered to a patient in need thereof is used to diagnose, prevent, alleviate, delay, inhibit or treat a disease, disorder or abnormality associated with alpha-synuclein aggregates, such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments the alpha-synuclein binding molecule, or an immunoconjugate wherein the alpha-synuclein specific binding molecule is covalently linked to another suitable therapeutic agent, or a composition comprising an alpha-synuclein binding molecule and an alpha-synuclein agonists and cognate molecules, or alternately, antagonists of the same is administered to a patient in need thereof is used in a method for diagnosing or monitoring a disease, disorder or abnormality associated with alpha-synuclein aggregates such as Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17 and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia a telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder.

In some embodiments an alpha-synuclein binding molecule is used in a method for diagnosing presymptomatic disease or disorder or abnormality, or for monitoring disease or disorder or abnormality progression and therapeutic efficacy of a drug, or for predicting responsiveness, or for selecting patients which are likely to respond to the treatment with an alpha-synuclein binding molecule. Said method is preferably performed using a sample of human blood or urine. Most preferably the method involves an ELISA-based or surface adapted assay.

In some embodiments an alpha-synuclein binding molecule is used in a method wherein an alpha-synuclein binding molecule of the present invention is contacted with a sample (e.g., blood, cerebrospinal fluid, or brain tissue) to detect, diagnose or monitor Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments an alpha-synuclein binding molecule is used in a method wherein an alpha-synuclein specific binding molecule of the present invention is contacted with a sample (e.g., blood, cerebrospinal fluid, or brain tissue) to detect, diagnose a disease or disorder or abnormality associated with alpha-synuclein aggregates, such as Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17 and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder.

In some embodiments an alpha-synuclein binding molecule, or an immunoconjugate wherein the alpha-synuclein binding molecule is covalently linked to another suitable therapeutic agent, or a composition comprising an alpha-synuclein binding molecule and an alpha-synuclein agonist and cognate molecules, or alternately, antagonists of the same is administered to a patient in need thereof is used for preventing, alleviating or treating a disease, disorder or abnormality associated with apha-synuclein aggregates or a synucleinoptahy or Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments an alpha-synuclein binding molecule, or an immunoconjugate wherein the alpha-synuclein binding molecule is covalently linked to another suitable therapeutic agent, or a composition comprising an alpha-synuclein binding molecule and an alpha-synuclein agonists and cognate molecules, or alternately, antagonists of the same is administered to a patient in need thereof is used for treating a disease or disorder or abnormality associated with alpha-synuclein aggregates, such as Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17 and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder.

In some embodiments an alpha-synuclein binding molecule, or an immunoconjugate wherein the alpha-synuclein binding molecule is covalently linked to another suitable therapeutic agent, or a composition comprising an alpha-synuclein specific binding molecule and an alpha-synuclein agonist and cognate molecules, or alternately, antagonists of the same is administered to a patient in need thereof is used for manufacturing a medicament for treating a disease, disorder or abnormality associated with alpha-synuclein aggregates, or a synucleinoptahy or Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments, an alpha-synuclein antibody or immunoconjugate for use as a medicament is provided. In some embodiments, an alpha-synuclein antibody or immunoconjugate for use in a method of treatment is provided. In certain embodiments, an anti-alpha-synuclein antibody or immunoconjugate for use in the prevention, diagnosis and/or treatment of a synucleinopathy is provided. In a preferred embodiment of the invention, an alpha-synuclein antibody or immunoconjugate is provided for use in the prevention, diagnosis and/or treatment of a disease, disorder or abnormality associated with alpha-synuclein aggregates, such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In some embodiments, the invention describes the use of an alpha-synuclein antibody or immunoconjugate in the manufacture or preparation of a medicament. In one such embodiment, the method further comprises administering to the individual an effective amount of at least one additional therapeutic agent.

Antibodies or immunoconjugates of the invention can be used either alone or in combination with other agents in a therapy. For instance, an antibody or immunoconjugate of the invention may be co-administered with at least one additional therapeutic agent.

In another aspect of the invention, an article of manufacture containing materials useful for the treatment, prevention and/or diagnosis of the disease or disorders or abnormality described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disease, disorder or abnormality and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

The methods of the invention may comprise administering at least one additional therapy, preferably wherein the additional therapy is selected from, but not limited to, neurological drugs, levodopa (e.g. sinemet®), catechol-O-methyl transferase inhibitors (e.g. entacapone, tolcapone), dopamine agonists, monoamine oxidase B inhibitors (e.g. rasagiline, selegiline) Amantadine, anticholinergic medication, anti-abeta antibodies, anti-Tau antibodies, Tau aggregation inhibitors, beta-amyloid aggregation inhibitors, anti-BACE1 antibodies, and BACE1 inhibitors.

The invention furthermore relates to a method of detecting aggregated and/or pathological alpha-synuclein, including, but not limited to Lewy neurites, Lewy Bodies and/or Glial cytoplasmic inclusions, comprising contacting a sample with the binding molecule of the invention, preferably wherein the sample is a brain sample, a cerebrospinal fluid sample, urine sample or a blood sample.

In some embodiments, the invention encompasses alpha-synuclein binding molecules, particularly antibodies of the invention as described herein that binds aggregated and/or pathological alpha-synuclein and the use of these molecules to diagnose, prevent, alleviate or treat a disease, disorder or abnormality associated with alpha-synuclein aggregates such as Parkinson's Disease, Multiple System Atrophy, Lewy Body dementia (LBD; dementia with Lewy bodies (DLB) ("pure" Lewy body dementia), Parkinson's disease dementia (PDD)), or Diffuse Lewy Body Disease.

In another embodiment, a binding molecule, particularly an antibody of the invention as described herein specific for alpha-synuclein is administered to prevent, alleviate or treat a disease, disorder or abnormality associated with alpha-synuclein aggregates selected from Parkinson's Disease, Multiple System Atrophy, Lewy Body dementia (LBD; dementia with Lewy bodies (DLB) ("pure" Lewy body dementia), Parkinson's disease dementia (PDD)), and Diffuse Lewy Body Disease.

In another embodiment, an binding molecules, in particular antibodies or antigen-binding fragments thereof as described herein, binding aggregated and/or pathological alpha-synuclein is contacted with a sample to detect, diagnose or monitor a disease, disorder or abnormality associated with alpha-synuclein aggregates selected from Parkinson's disease (sporadic, familial with alpha-synuclein mutations, familial with mutations other than alpha-synuclein, pure autonomic failure and Lewy body dysphagia), Lewy Body dementia (LBD; dementia with Lewy bodies (DLB) ("pure" Lewy body dementia), Parkinson's disease dementia (PDD)), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (Shy-Drager syndrome, striatonigral degeneration and olivopontocerebellar atrophy), inclusion-body myositis, traumatic brain injury, chronic traumatic encephalopathy, dementia pugilistica, tauopathies (Pick's disease, frontotemporal dementia, progressive supranuclear palsy, corticobasal degeneration, Frontotemporal dementia with Parkinsonism linked to chromosome 17, and Niemann-Pick type C1 disease), Down syndrome, Creutzfeldt-Jakob disease, Huntington's disease, motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, Gerstmann-Straussler-Scheinker disease, ataxia a telangiectatica, Meige's syndrome, subacute sclerosing panencephalitis, Gaucher disease, Krabbe disease as well as other lysosomal storage disorders (including Kufor-Rakeb syndrome and Sanfilippo syndrome), or rapid eye movement (REM) sleep behavior disorder.

The invention furthermore relates to methods for evaluating an alpha-synuclein binding molecule for the capability of inhibiting and/or delaying the seeded and/or spontaneous alpha-synuclein aggregation, comprising the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and determining the time to reach half-maximum signal of the detectable dye, particularly the signal of fluorescent dye, relative to the seeded aggregation in the absence of binding molecule. In an alternative or additional embodiment, the method for evaluating an alpha-synuclein binding molecule for the capability of inhibiting and/or delaying the seeded and/or spontaneous alpha-synuclein aggregation, may comprise the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and determining the time to reach half-maximum signal of the detectable dye, particularly the signal of fluorescent dye, wherein an increase in time to reach half-maximum signal of the detectable dye in the presence of binding molecule relative to the seeded aggregation in the absence of binding molecule indicates that the alpha-synuclein binding molecule is capable of inhibiting and/or delaying the seeded and/or spontaneous alpha-synuclein aggregation. In a further alternative or additional embodiment, the method for evaluating an alpha-synuclein binding molecule for the capability of inhibiting and/or delaying the seeded and/or spontaneous alpha-synuclein aggregation, may comprise the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and determining the time to reach half-maximum signal of the detectable dye, particularly the signal of fluorescent dye, and detecting the increase in time to reach half-maximum signal of the detectable dye in the presence of binding molecule relative to the seeded aggregation in the absence of binding molecule, indicating that the alpha-synuclein binding molecule inhibits and/or delays the seeded and/or spontaneous alpha-synuclein aggregation. In a yet further alternative or additional embodiment the method for evaluating an alpha-synuclein binding molecule for the capability of inhibiting and/or delaying the seeded and/or spontaneous alpha-synuclein aggregation, may comprise the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and measuring the increase in time to reach half-maximum signal of the detectable dye in the presence of the alpha-synuclein binding molecule relative to the seeded aggregation in the absence of binding molecule, as an indication of the binding molecule having capability of inhibiting and/or delaying the seeded and/or spontaneous alpha-synuclein aggregation.

The invention furthermore relates to a method for screening an alpha-synuclein binding molecule capable of inhibiting and/or delaying the seeded and/or spontaneous alpha-synuclein aggregation, comprising the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and selecting the alpha-synuclein binding molecule as being able to inhibit and/or delay seeded and/or spontaneous alpha-synuclein aggregation based on the signal of the detectable dye, in particular the fluorescent dye, determined in the absence and presence of the alpha-synuclein binding molecule.

The screening or evaluation methods provided herein may further comprise a step of providing alpha-synuclein binding molecules to be screened/evaluated. The binding molecules may for example be provided in form of a library, in particular an antibody library. The skilled person is well-aware of methods for providing binding molecule libraries and in particular antibody libraries. Alternatively, libraries may be obtained commercially before evaluation/screening.

The invention furthermore relates to an in vitro assay for screening for alpha-synuclein binding molecules for the capability of inhibiting and/or delaying the seeded and/or spontaneous alpha-synuclein aggregation, said assay comprising the steps of bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and selecting the alpha-synuclein binding molecule as being able to inhibit and/or delay seeded and/or spontaneous alpha-synuclein aggregation based on the signal of the detectable dye, in particular the fluorescent dye, determined in the absence and presence of the alpha-synuclein binding molecule. In an alternative or additional embodiment, the invention relates to an in vitro assay for evaluating an alpha-synuclein binding molecule for the capability of inhibiting and/or delaying the seeded and/or spontaneous alpha-synuclein aggregation, said assay comprising the steps of: bringing an alpha-synuclein binding molecule in contact with alpha-synuclein aggregates (seeds); allowing the alpha-synuclein binding molecule to bind to alpha-synuclein aggregates, to form an immunological complex; adding alpha-synuclein monomeric protein and a detectable dye, in particular a fluorescent dye, to the immunological complex; and determining the time to reach half-maximum signal of the detectable dye, particularly the signal of fluorescent dye, wherein an increase in time to reach half-maximum signal of the detectable dye in the presence of binding molecule relative to the seeded aggregation in the absence of binding molecule indicates that the alpha-synuclein binding molecule is capable of inhibiting and/or delaying the seeded and/or spontaneous alpha-synuclein aggregation. In a particular embodiment, the fluorescent dye is thioflavin.

The invention also relates to kits for use in screening or evaluating alpha-synuclein binding molecules, in particular antibodies. Such kits may comprise all necessary components for performing the herein provided methods and/or assays, such as, for example, buffers, detectable dyes, laboratory equipment, reaction containers, instructions and the like.

The invention also relates to methods for the prevention, alleviation or treatment of diseases, disorders and/or abnormalities associated with alpha-synuclein, particularly with pathological alpha-synuclein and/or aggregated alpha-synuclein, comprising administering an effective amount of an alpha-synuclein binding molecule, in particular an antibody, of the invention to a subject in need thereof.

FIGURES

FIG. 1: Antibody binding to human full-length recombinant alpha-synuclein. Binding to recombinant full-length alpha-synuclein for the antibodies derived from stable hybridoma clones was determined using an indirect ELISA. Antibodies were diluted from 1 μg/mL to 0.0005 μg/mL. Results are expressed in optical densities (O.D.), mean values of two technical replicates±SEM are shown. Commercial antibody Syn1 was used as a positive control.

Figure 2:
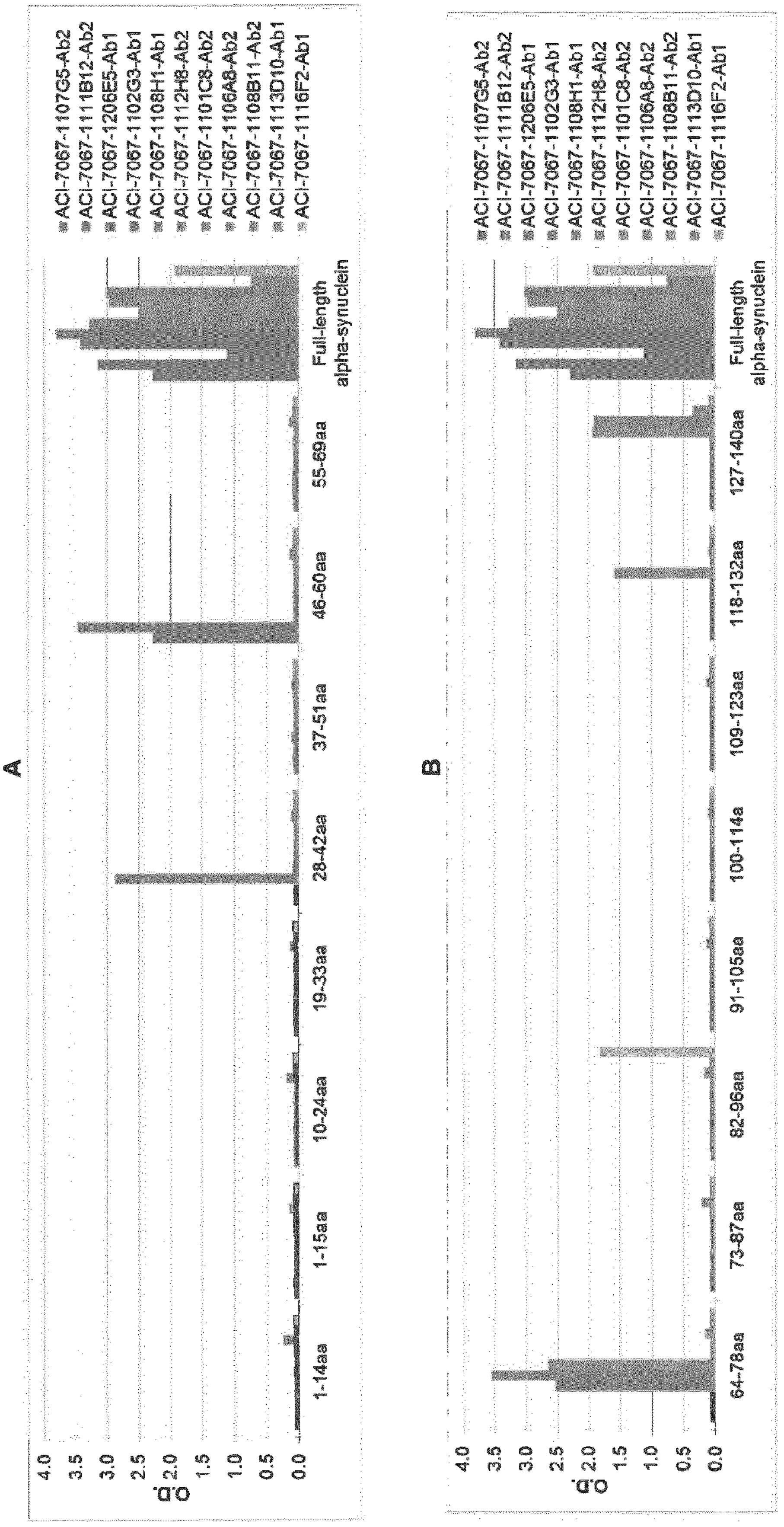

FIG. 2. Epitope mapping on alpha-synuclein. Epitope mapping for the antibodies derived from stable hybridoma clones was determined using an indirect ELISA on a library of 15-mer peptides covering the entire sequence of human alpha-synuclein from 1 to 140aa. (A) Results on peptides from 1 to 69aa and full-length alpha-synuclein. (B) Results on peptides from 64 to 140aa and full-length alpha-synuclein. Results are expressed as optical density (O.D.).

Each bar represents data for an individual antibody. Amino-acid sequence of alpha-synuclein indicated as shown in Table 3.

Figure 3:
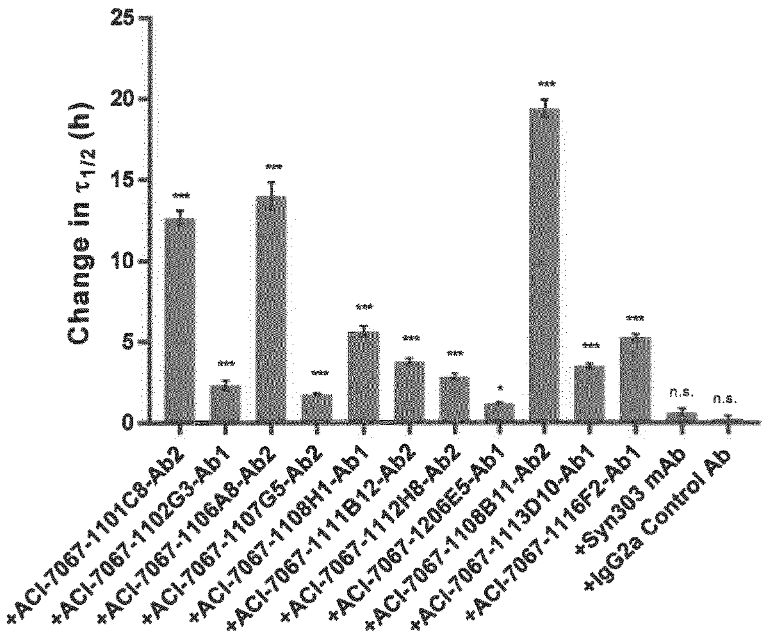
Figure 3:
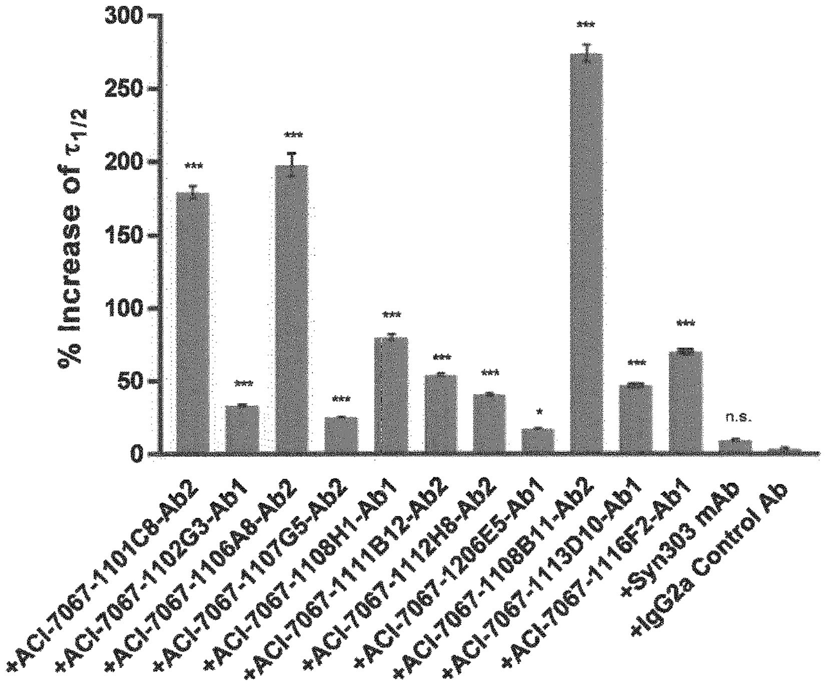

FIG. 3: Effect of mAbs on aggregation half-times in seeded a-syn aggregation. (A) Change in $T_{1/2}$ values, relative to no mAb control, from in vitro alpha-synuclein aggregations in the presence of the indicated mAbs at 3.28 μM. Error bars represent calculated SEM. Significance was determined using a one-way ANOVA (Dunnett's multiple comparisons test) versus aggregation with no antibody (no mAb) (n.s. not significant; (*) P<0.033; (***) P<0.001). (B) Percent increases of $T_{1/2}$ values, relative to the absence of antibody, are plotted for the seeded aggregations in the presence of the indicated mAb. Error bars represent the propagation of error (Equation 5). Significance was determined using a one-way ANOVA (Dunnett's multiple comparisons test) versus aggregation with IgG2a control Ab (n.s. not significant; (*) P<0.033; (***) P<0.001).

Figure 4:
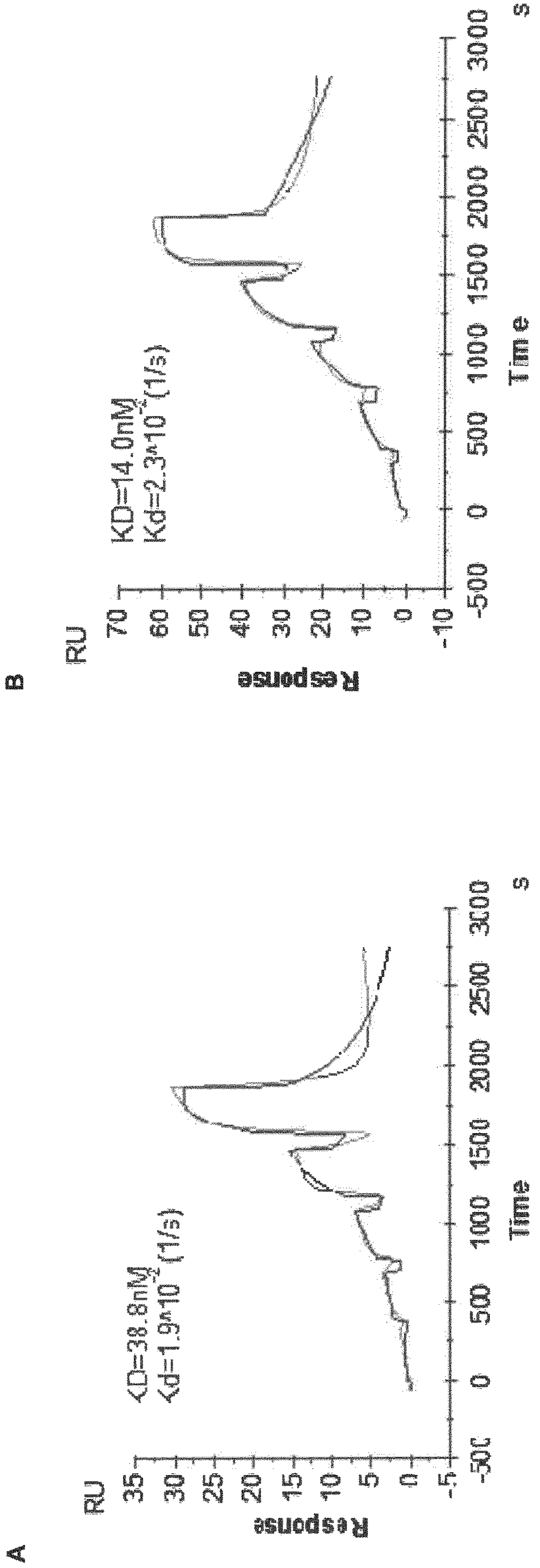
Figure 4:
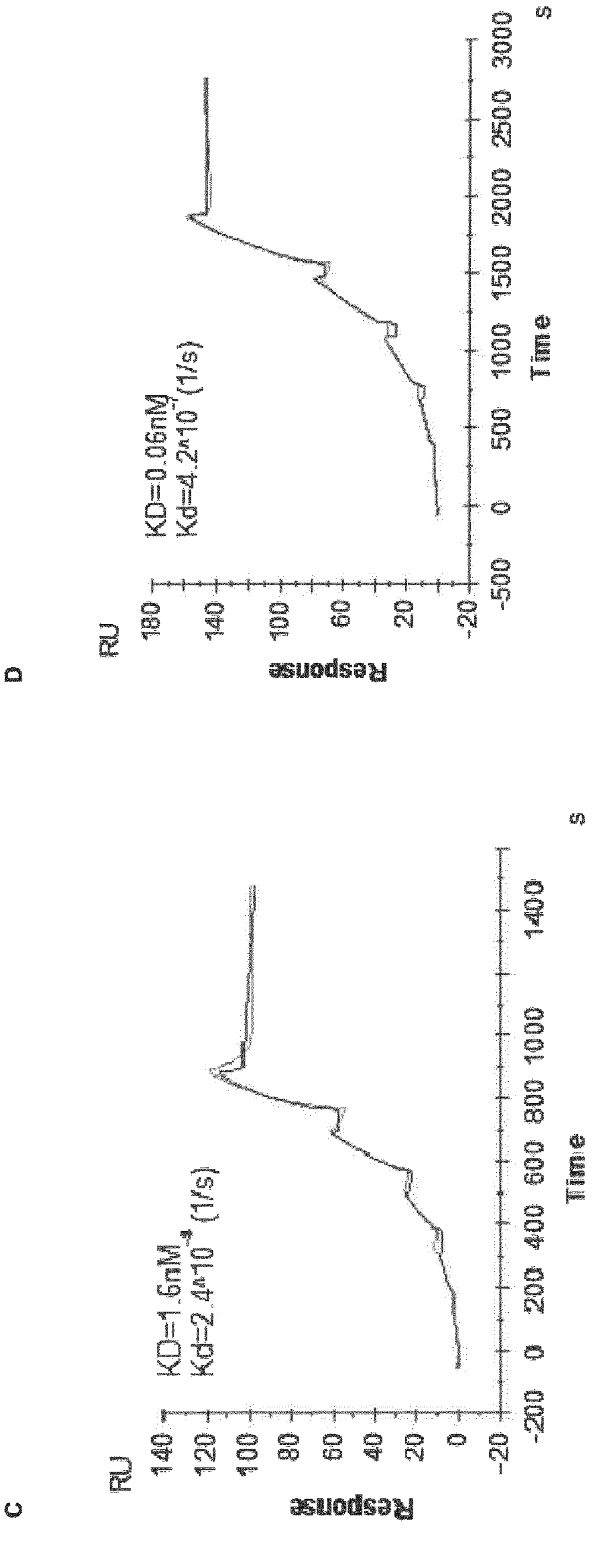

FIG. 4: Single-cycle kinetic sensograms of alpha-synuclein antibody responses to monomeric or fibrillar alpha-synuclein. (A) Sensogram from single-cycle kinetics of monomeric alpha-synuclein of ACI-7067-1101C8-Ab2 (black trace). (B) Sensogram from single-cycle kinetics of monomeric alpha-synuclein of ACI-7067-1113D10-Ab1 (black trace). (C) Sensogram from single-cycle kinetics of fibrillar alpha-synuclein of ACI-7067-1101C8-Ab2 (black trace). (D) Sensogram from single-cycle kinetics of fibrillar alpha-synuclein of ACI-7067-1113D10-Ab1 (black trace). 1:1 binding fits using a homogenous Langmuir model are shown overlaid (gray traces).

Figure 5:
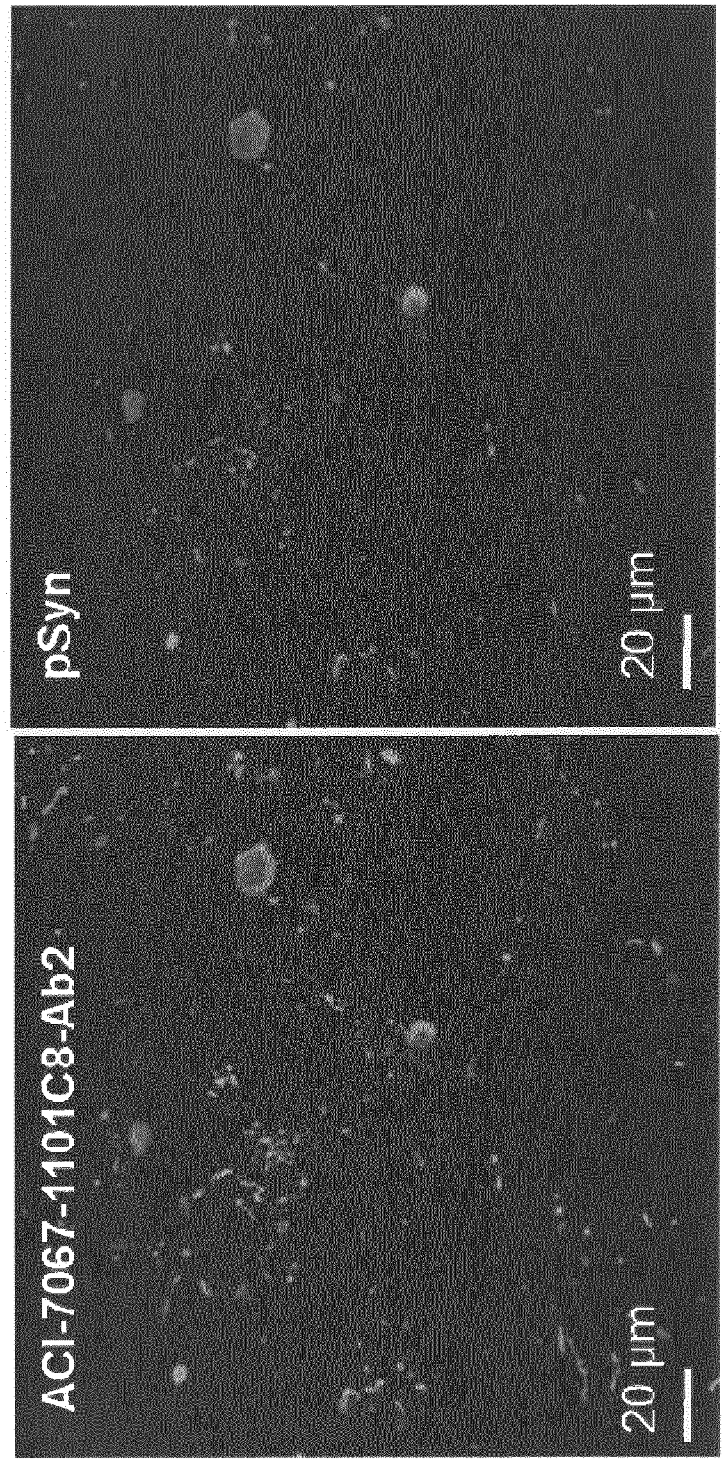
Figure 5:
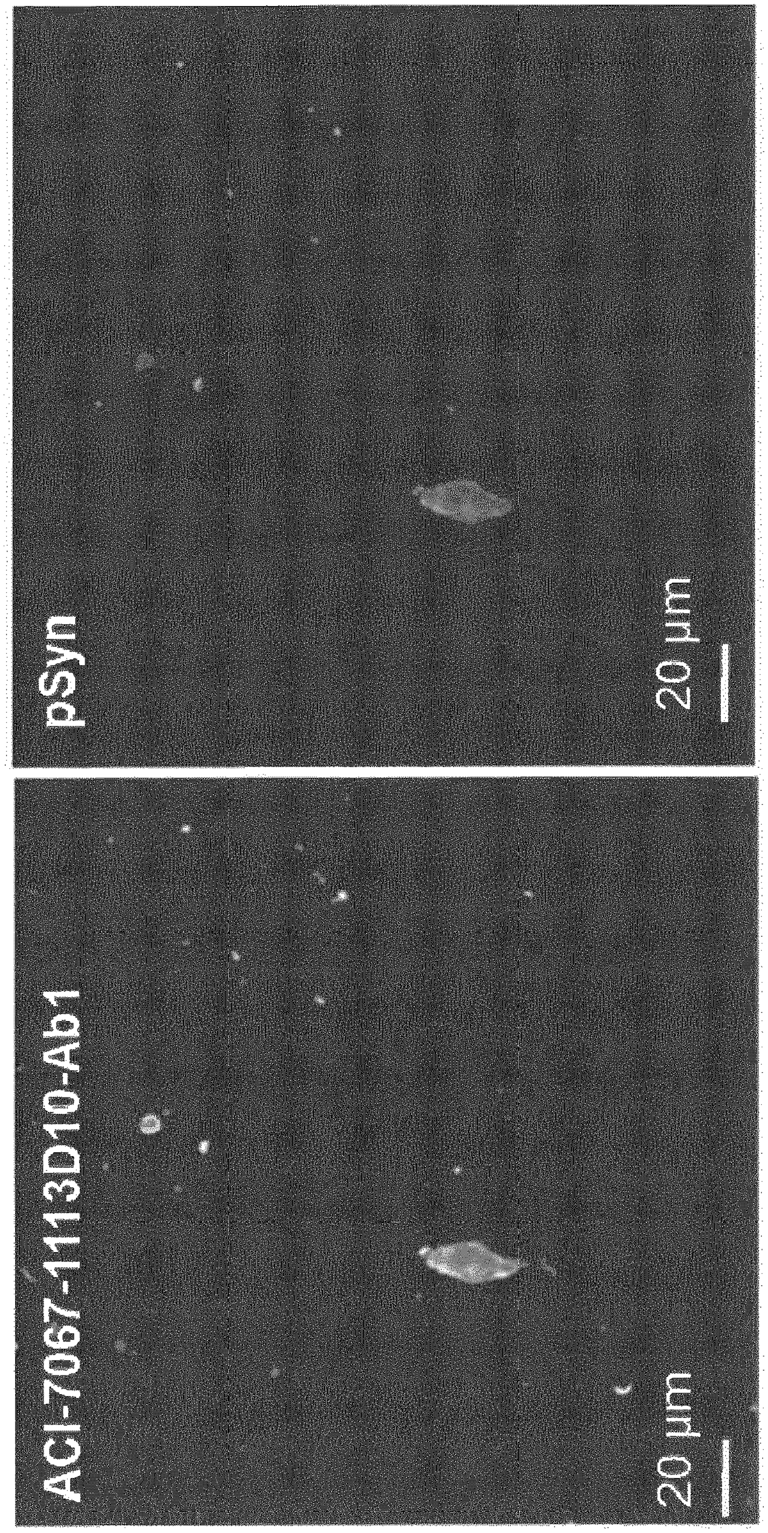
Figure 5:
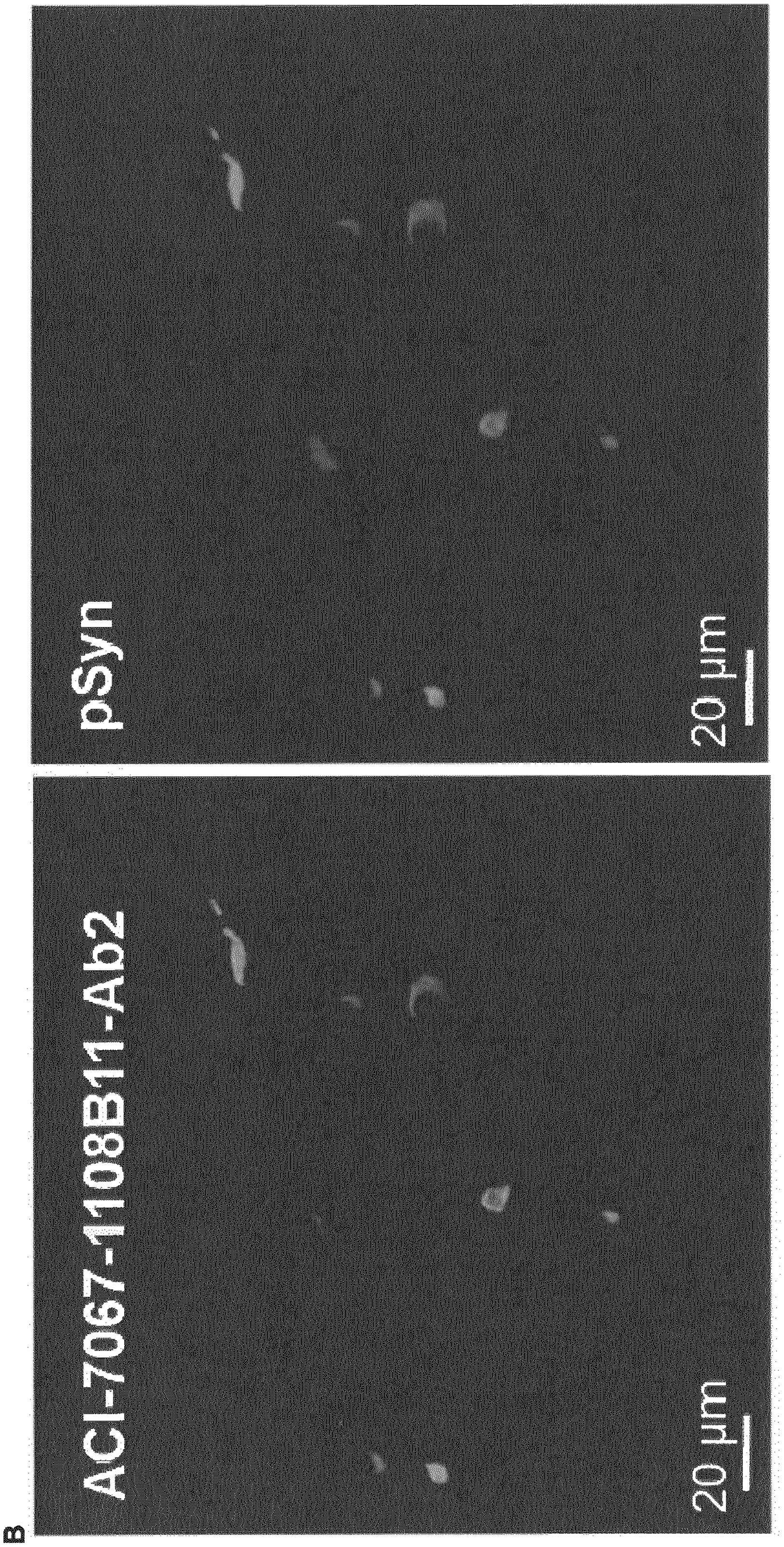
Figure 5:
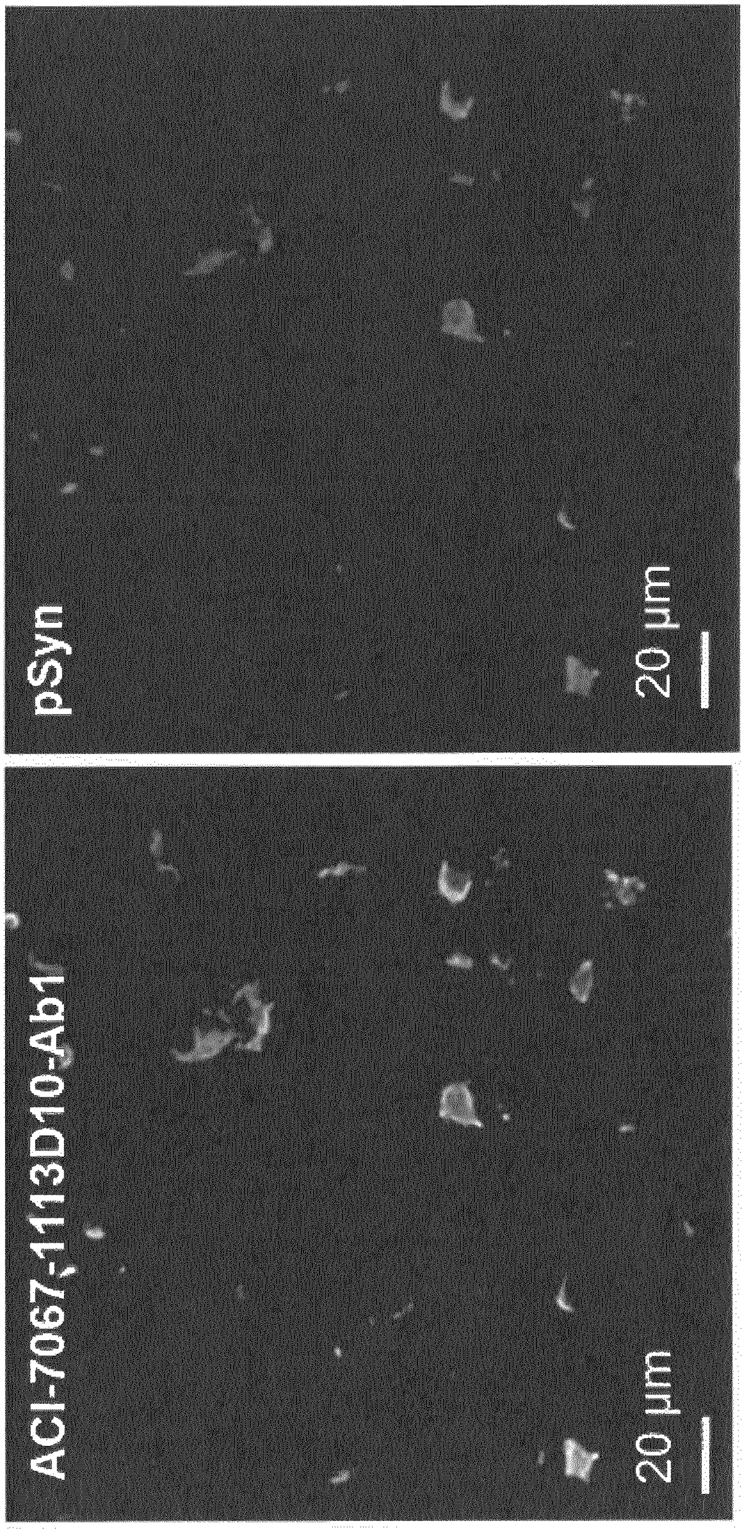

FIG. 5: Target engagement of alpha-synuclein antibodies in tissues from PD and MSA cases. (A) Representative images of immunostaining with alpha-synuclein antibodies for the detection of pathological alpha-synuclein aggregates in brain tissue from PD amygdala and (B) the medula oblongata of a MSA case. An antibody recognizing alpha-synuclein phosphorylated at Ser129, (pSyn) used as control for detecting pathological aggregated and phosphorylated alpha-synuclein.

Figure 6:
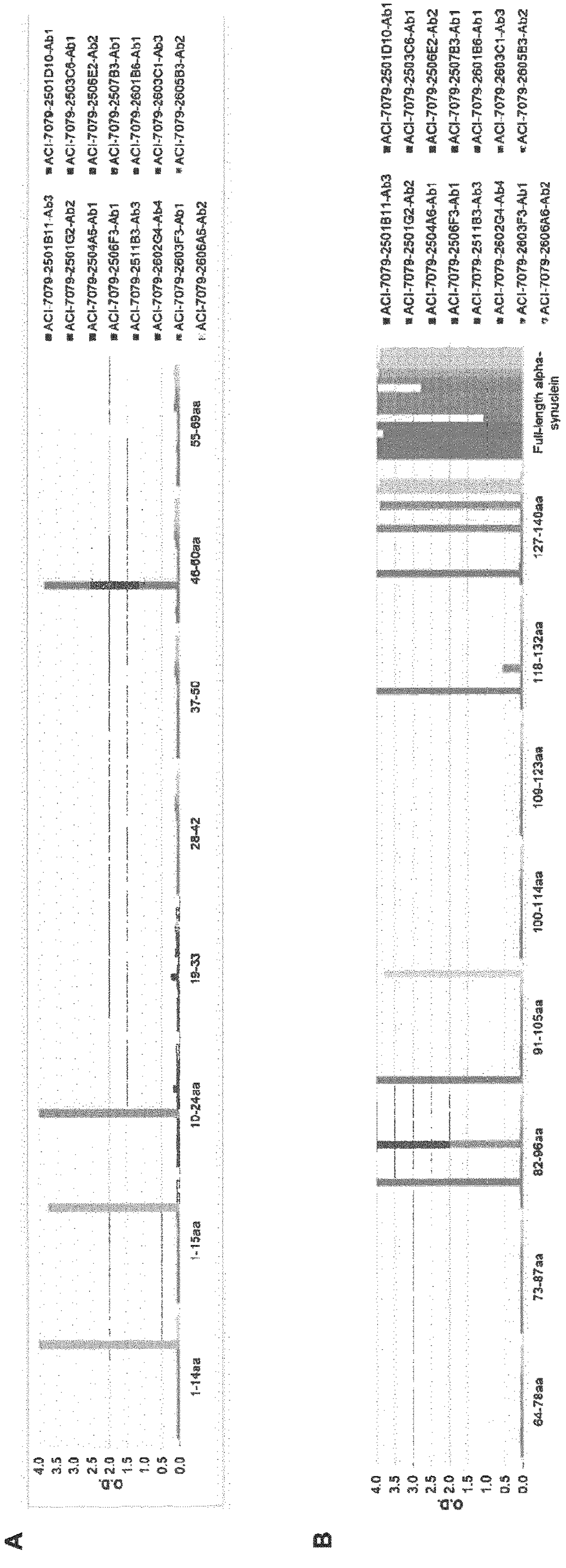

FIG. 6: Epitope mapping on alpha-synuclein. Epitope mapping for the antibodies derived from stable hybridoma clones was determined using an indirect ELISA on a library of 15-mer peptides covering the entire sequence of human alpha-synuclein from 1 to 140aa. (A) Results on peptides from 1 to 69aa and full-length alpha-synuclein. (B) Results on peptides from 64 to 140aa and full-length alpha-synuclein. Results are expressed as optical density (O.D.). Each bar represents data for an individual antibody. Amino-acid sequence of alpha-synuclein indicated as shown in Table 3.

Figure 7:
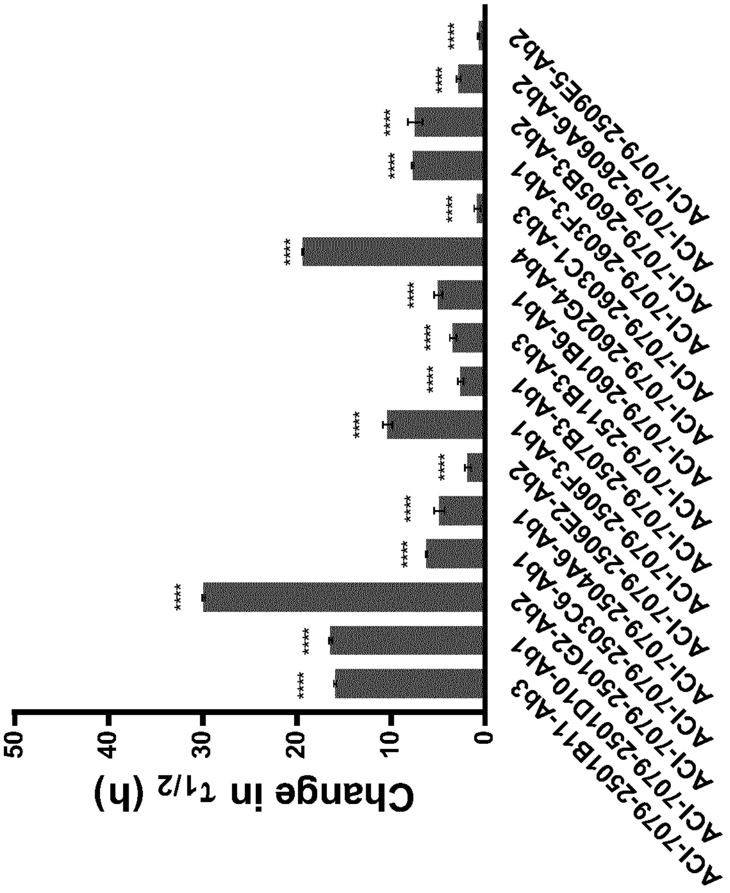
Figure 7:
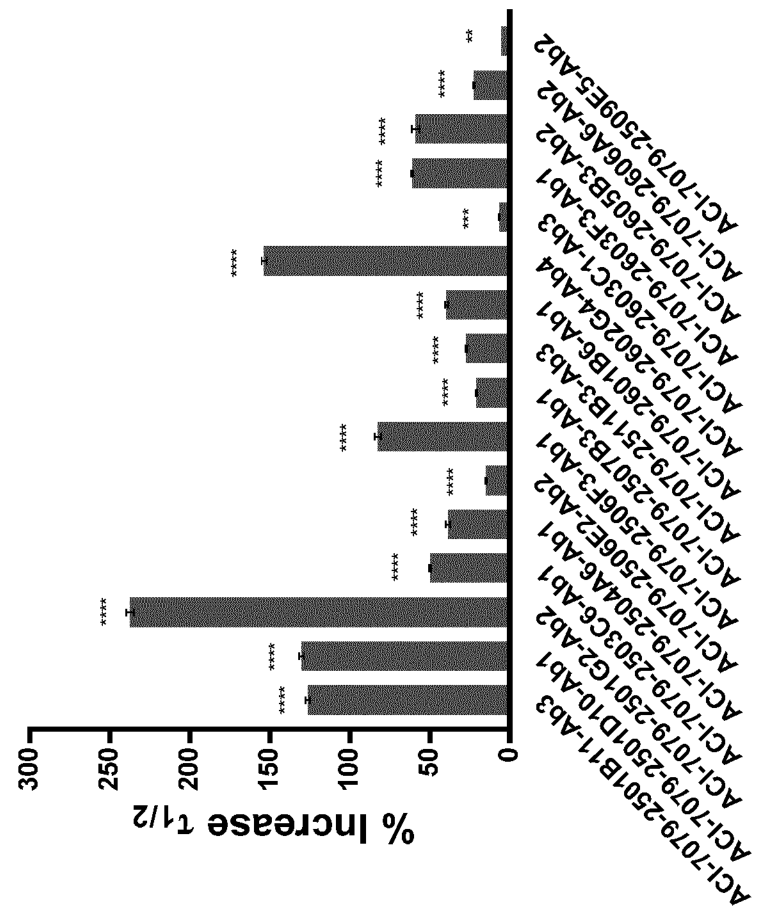

FIG. 7: Effect of alpha-synuclein antibodies (mAbs) on aggregation half-times in seeded a-syn aggregation. (A) Change in $T_{1/2}$ values, relative to no mAb control, from in vitro alpha-synuclein aggregations in the presence of the indicated mAbs at 3.28 μM. Error bars represent calculated SEM. Significance was determined using a one-way ANOVA (Dunnett's multiple comparisons test) versus aggregation with no antibody (no mAb) ((**) P<0.0001). (B) Percent increases of $T_{1/2}$ values, relative to the absence of antibody, are plotted for the seeded aggregations in the presence of the indicated mAb. Error bars represent the propagation of error (Equation 5). Significance was determined using a one-way ANOVA (Dunnett's multiple comparisons test) versus aggregation with no antibody control (n.s. not significant; () P<0.01; (*) P<0.0008, (**) P<0.0001).

FIG. 8-11: Efficacy of alpha-synuclein antibodies (mAbs) in an in vivo mouse model of Parkinson's disease. (FIG. 8) Percent change in body weight from baseline (Week 0) at Week 17 of human alpha-synuclein pre-formed fibrils (hPFFs) Vehicle treated control and alpha-synuclein antibodies ACI-7067-1101C8-Ab2, ACI-7067-1108B11-Ab2, or ACI-7067-1113D10-Ab1. Error bars represent calculated SD. Significance was determined using a Welch's t-test versus the hPFFs-Vehicle control group; (*) P<0.05; () P<0.01. (FIG. 9**A) Phosphorylated alpha-synuclein staining density in the piriform cortex contralateral to the injection site of (hPFFs) for vehicle treated control and alpha-synuclein antibodies ACI-7067-1101C8-Ab2, ACI-7067-1108B11-Ab2, or ACI-7067-1113D10-Ab1. Data is plotted as the geometric mean and error bars represent the calculated geometric SD. Significance was determined using a two-way ANOVA (corrected for cohorts) versus the hPFFS-Vehicle control group; (*) P<0.05. (FIG. 9B) Data from FIG. 9A plotted as the arithmetic mean and error bars represent the standard error of measurement. Significance was determined using a pairwise Mann-Whitney-test; (*) P<0.05. (FIG. 10) Phosphorylated alpha-synuclein staining density in the brainstem contralateral to the injection site of hPFFs for vehicle treated control and alpha-synuclein antibodies ACI-7067-1101C8-Ab2, ACI-7067-1108B11-Ab2, or ACI-7067-1113D10-Ab1. Data is plotted as the geometric mean and error bars represent the calculated geometric SD. Significance was determined using a two-way ANOVA (corrected for cohorts) versus the hPFFs-Vehicle control group; (*) P<0.05. (FIG. 11) NeuN neuronal staining density in the piriform cortex ipsilateral to the injection site of either phosphate buffered saline (PBS) or hPFFs treated controls or hPFFs treated with alpha-synuclein antibodies ACI-7067-1101C8-Ab2, ACI-7067-1108B11-Ab2, or ACI-7067-1113D10-Ab1. Data is plotted as the geometric mean and error bars represent the calculated geometric SD. Significance was determined using a two-way ANOVA (corrected for cohorts) versus the hPFFs-vehicle control group; (*) P<0.05; () P<0.01, (**) P<0.0001.

Figure 12:
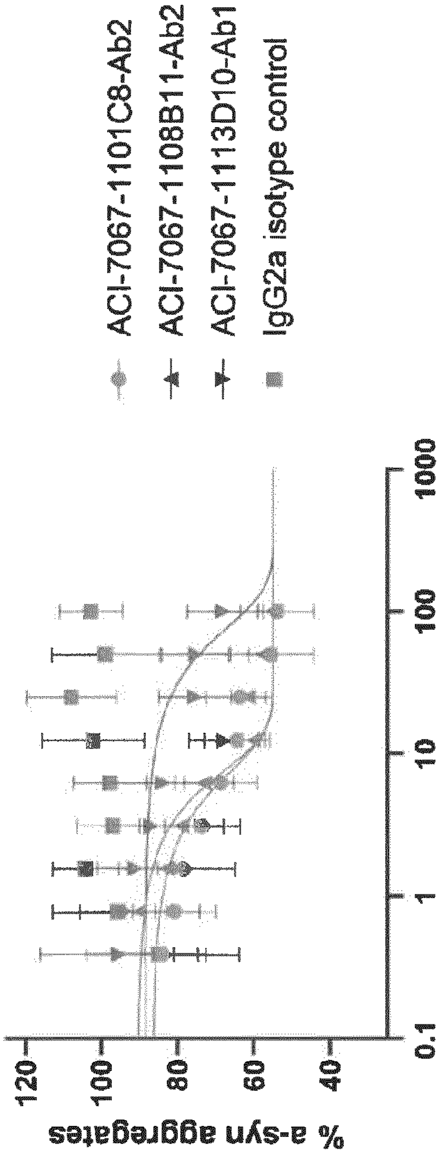

FIG. 12: Inhibition of alpha-synuclein seeding capacity and aggregation in an in vitro cellular model. Percentage of de novo alpha-synuclein aggregates formed, relative to conditions in the absence of antibody, as a function of antibody concentration. Error bars represent standard deviation. Dose-response curves were plotted and $IC_{50}$ values of 3.3 nM (ACI-7067-1101C8-Ab2), 4.5 nM (ACI-7067-1108B11-Ab2), and 39.6 nM (ACI-7067-1113D10-Ab1) were obtained using Equation 6.

Figure 13:
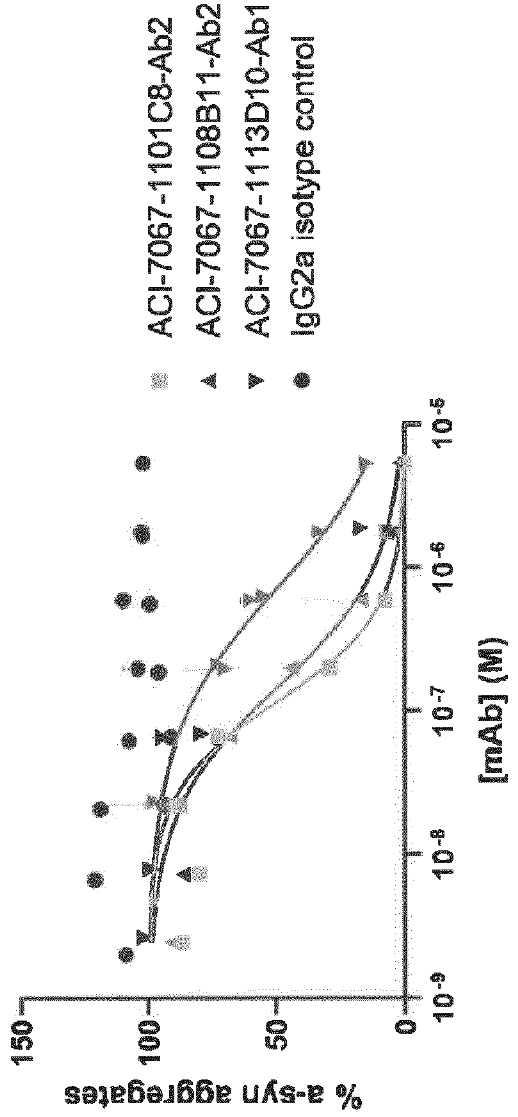

FIG. 13: Inhibition of alpha-synuclein seeding capacity, aggregation, and uptake in mouse primary cortical neurons. Percentage of de novo alpha-synuclein aggregates formed, relative to conditions in the absence of antibody, as a function of antibody concentration. Error bars represent standard deviation. Dose-response curves were plotted and $IC_{50}$ values of 114 nM (ACI-7067-1101C8-Ab2), 143 nM (ACI-7067-1108B11-Ab2), and 702 nM (ACI-7067-1113D10-Ab1) were obtained using Equation 7.

Figure 14:
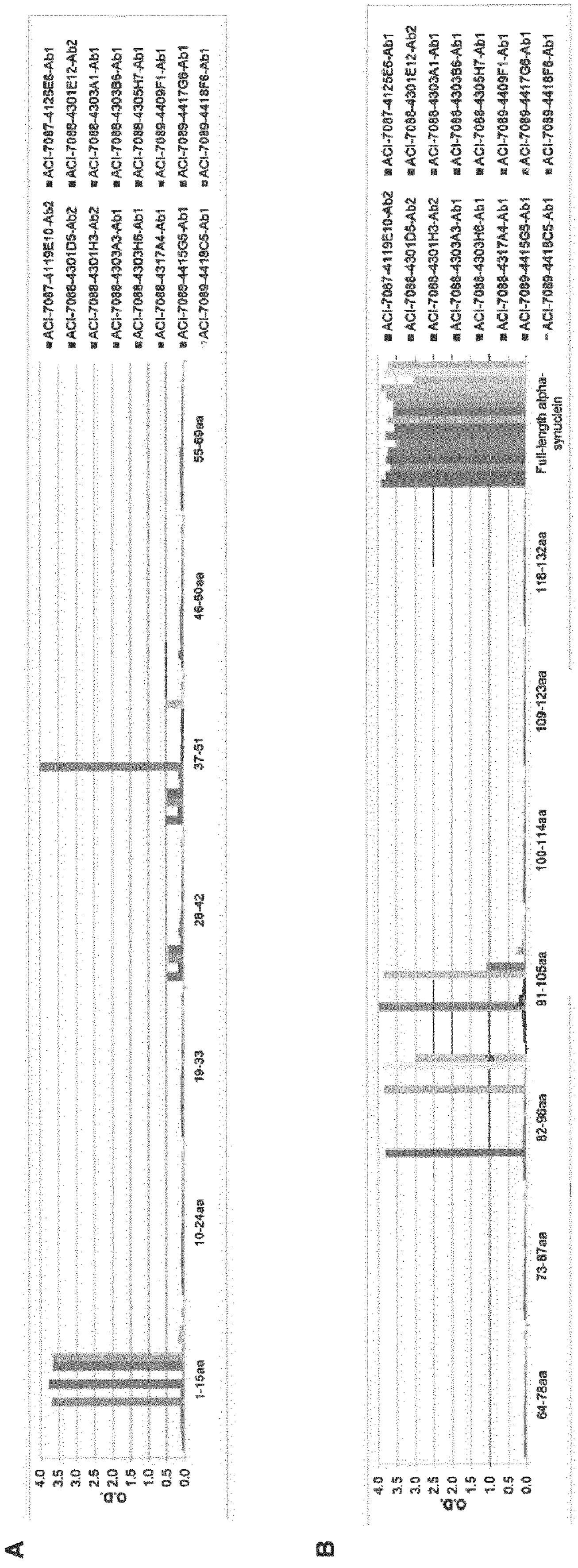

FIG. 14: Epitope mapping on alpha-synuclein. Epitope mapping for the antibodies derived from stable hybridoma clones was determined using an indirect ELISA on a library of 15-mer peptides covering the entire sequence of human alpha-synuclein from 1 to 140aa. (A) Results on peptides from 1 to 69aa and full-length alpha-synuclein. (B) Results on peptides from 64 to 140aa and full-length alpha-synuclein. Results are expressed as optical density (O.D.).

Each bar represents data for an individual antibody. Amino-acid sequence of alpha-synuclein indicated as shown in Table 3.

Figure 15:
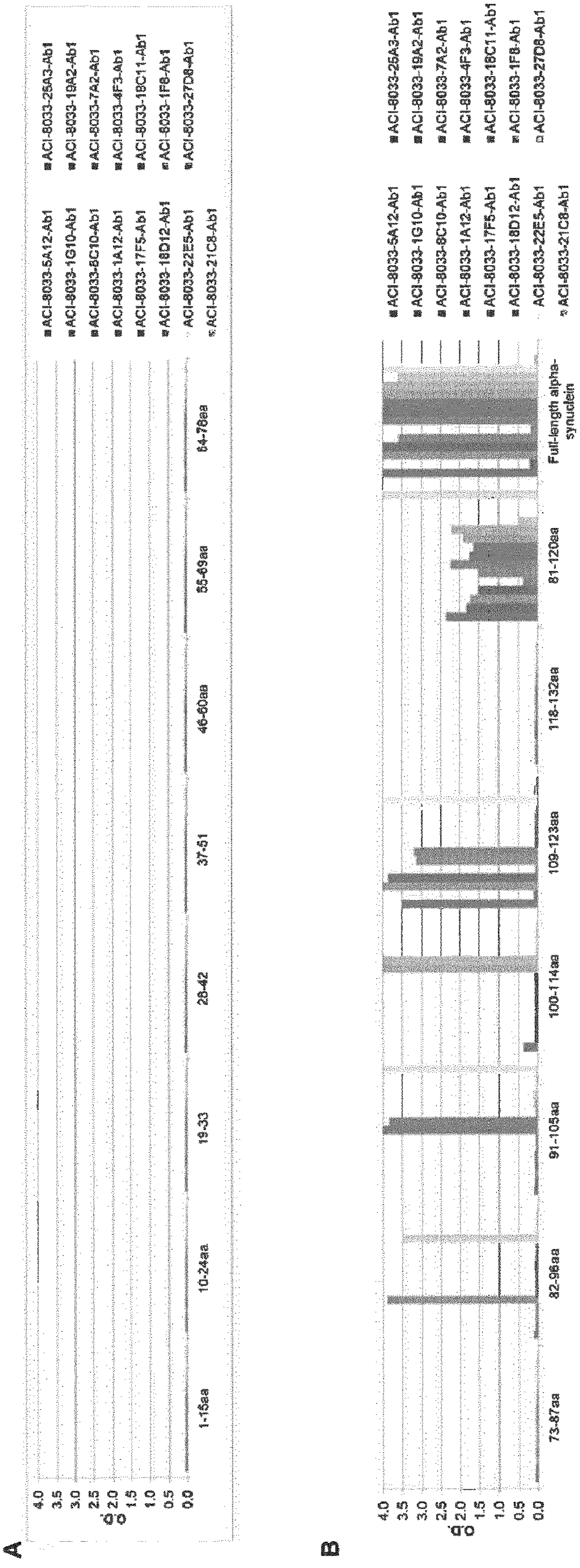

FIG. 15: Epitope mapping on alpha-synuclein. Epitope mapping for the antibodies derived from stable hybridoma clones was determined using an indirect ELISA on a library of 15-mer peptides covering the entire sequence of human alpha-synuclein from 1 to 140aa. (A) Results on peptides from 1 to 78aa and full-length alpha-synuclein. (B) Results on peptides from 73 to 140aa and full-length alpha-synuclein. Results are expressed as optical density (O.D.). Each bar represents data for an individual antibody. Amino-acid sequence of alpha-synuclein indicated as shown in Table 3.

Figure 16:
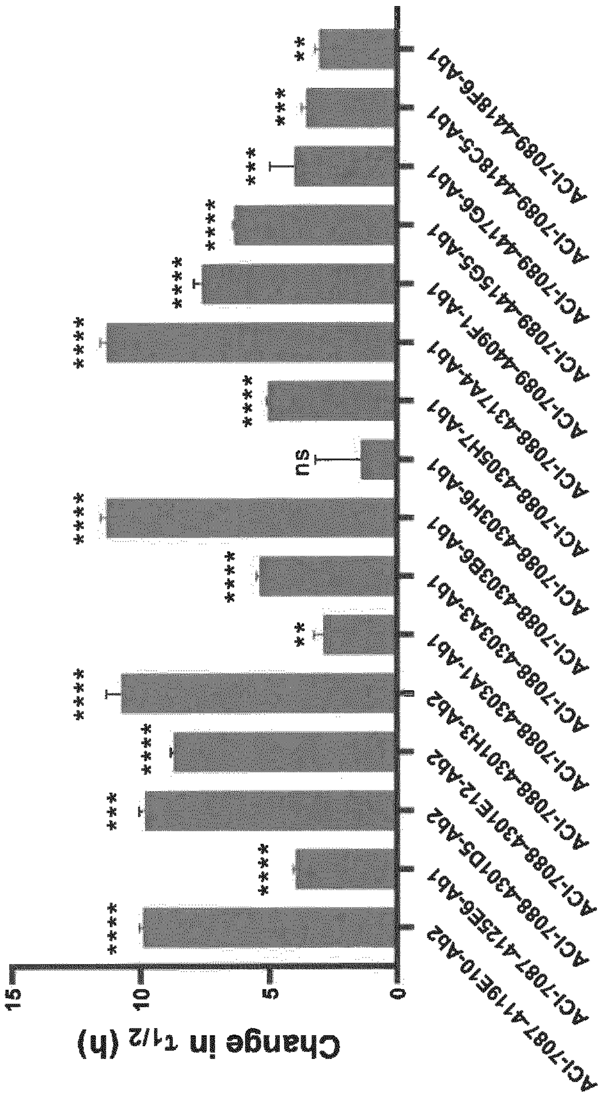
Figure 16:
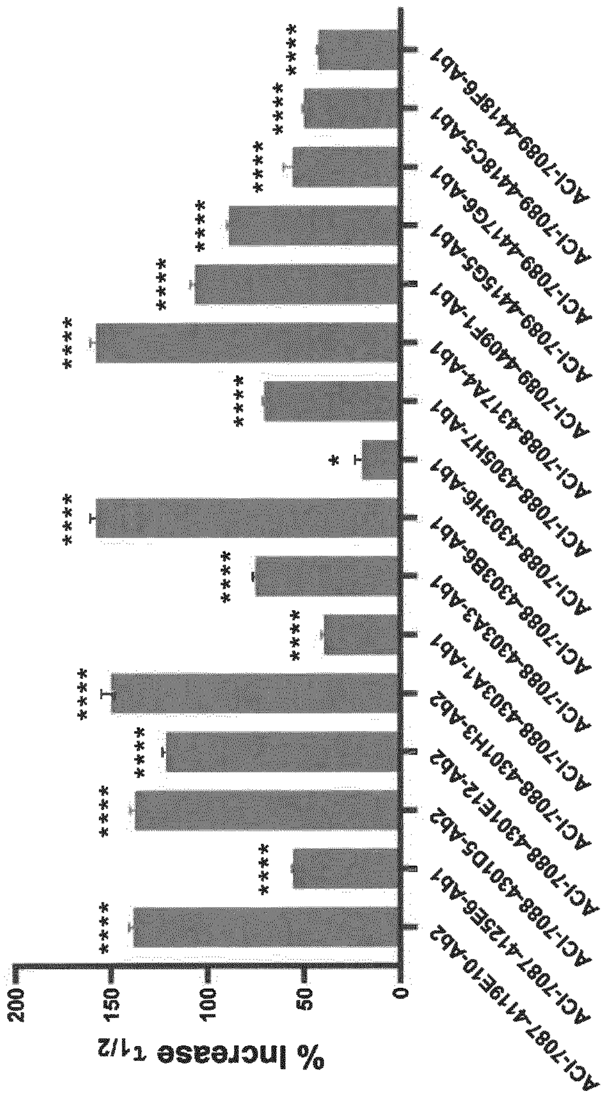
Figure 17:
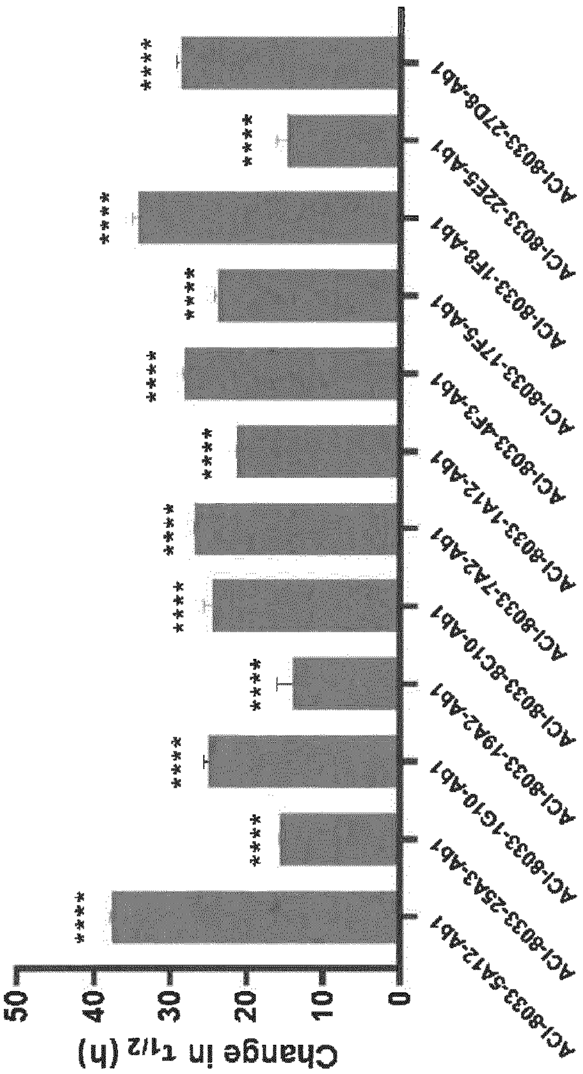
Figure 17:
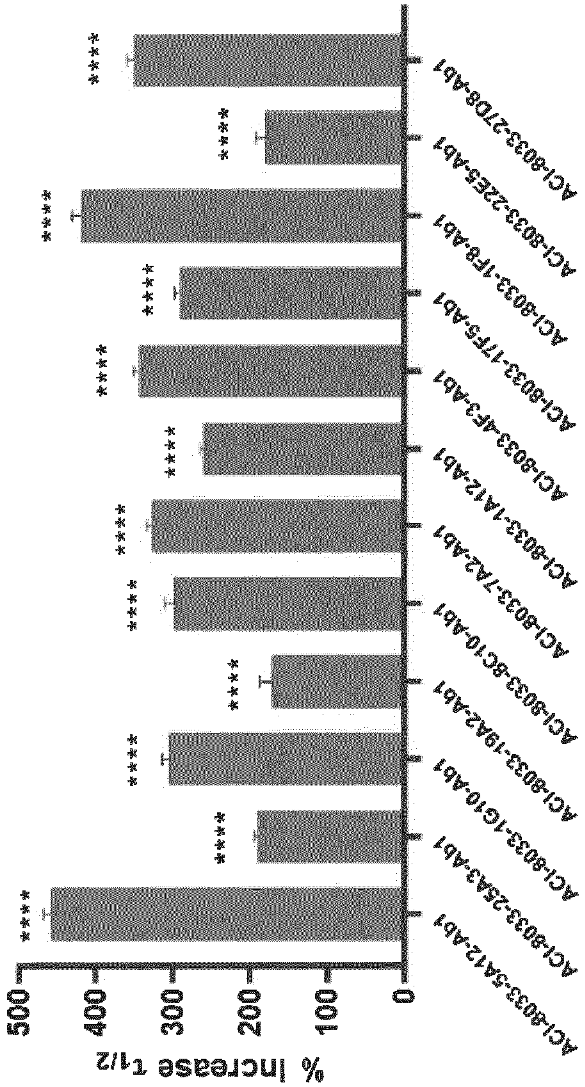

FIG. 16-17: Effect of alpha-synuclein antibodies (mAbs) on aggregation half-times in seeded a-syn aggregation. (A) Change in $T_{1/2}$ values, relative to no mAb control, from in vitro alpha-synuclein aggregations in the presence of the indicated mAbs at 3.28 μM. Error bars represent calculated SEM. Significance was determined using a one-way ANOVA (Dunnett's multiple comparisons test) versus aggregation with no antibody (no mAb) ((**) P<0.0001). (B) Percent increases of $T_{1/2}$ values, relative to the absence of antibody, are plotted for the seeded aggregations in the presence of the indicated mAb. Error bars represent the propagation of error (Equation 5). Significance was determined using a one-way ANOVA (Dunnett's multiple comparisons test) versus aggregation with no antibody control (n.s. not significant; () P<0.01; (*) P<0.0008, (**) P<0.0001).

Figure 18:
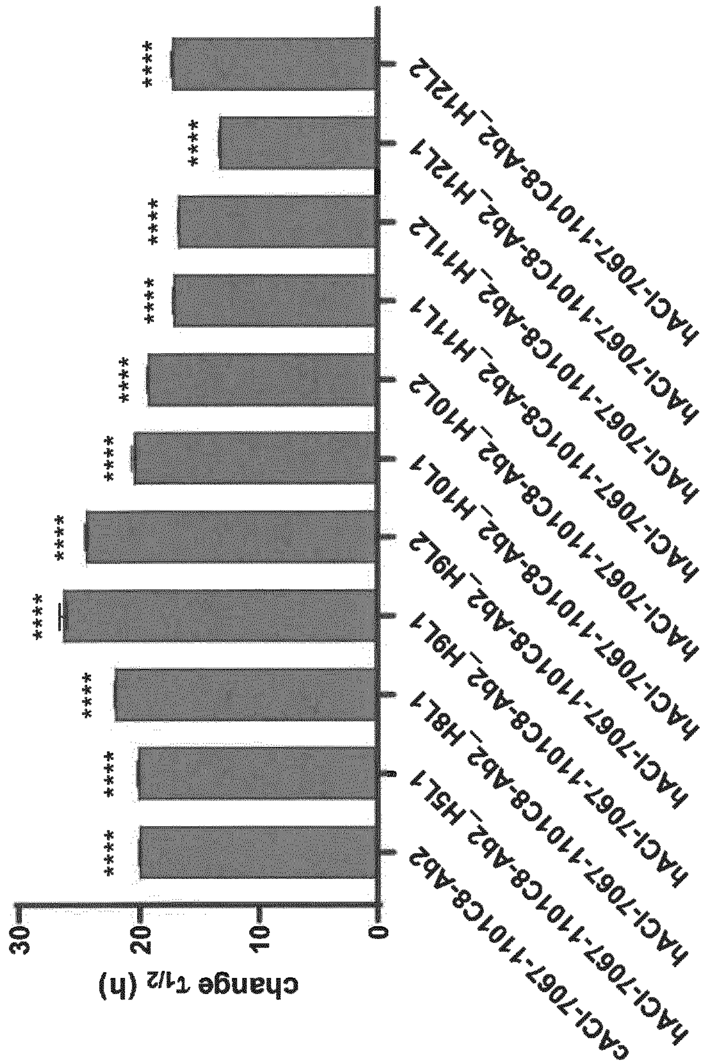
Figure 18:
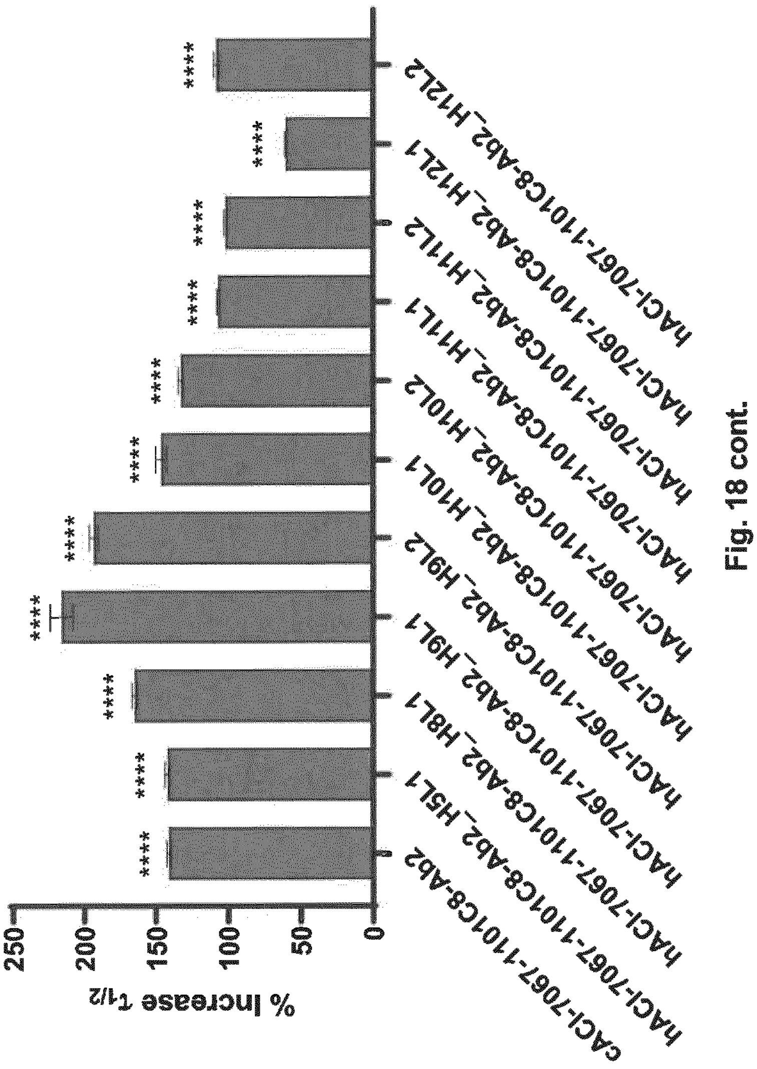

FIG. 18: Effect of ACI-7067-1101C8-Ab2 humanized variants mAbs on aggregation half-times in seeded a-syn aggregation. (A) Change in $T_{1/2}$ values, relative to the no mAb control, from in vitro alpha-synuclein aggregations in the presence of the indicated mAbs at 3.28 μM. Error bars represent calculated standard deviation. Significance was determined using a one-way ANOVA (Dunnett's multiple comparisons test) versus aggregation with no antibody (no mAb) ((**) P<0.0001). (B) Percent increases of $T_{1/2}$ values, relative to the absence of antibody, are plotted for the seeded aggregations in the presence of the indicated mAb. Error bars represent calculated SEM. Significance was determined using a one-way ANOVA (Dunnett's multiple comparisons test) versus aggregation with no antibody (no mAb) ((**) P<0.0001).

The invention will be further understood with reference to the following non-limiting examples:

EXAMPLES

Preparation of an alpha-synuclein liposomal vaccine composition

The liposome-based antigenic constructs were prepared according to the protocols published in WO2012/055933. The liposomal vaccine with human full-length alpha-synuclein protein as antigen was used for antibody generation (Table 2, SEQ ID NO: 1) or liposomal vaccine with alpha-synuclein peptide as antigen was used for antibody generation.

TABLE 2

| antigen description | | |
|---|---|---|
| | Definition | Amino acid sequence (1-letter code) |
| SEQ ID NO: 1 | FL-alpha-synuclein (140 aa) | MDVFMKGLSKAKEGVVAAAEKTKQGVA EAAGKTKEGVLYVGSKTKEGVVHGVAT VAEKTKEQVTNVGGAVVTGVTAVAQKT VEGAGSIAAATGFVKKDQLGKNEEGAP QEGILEDMPVDPDNEAYEMPSEEGYQD YEPEA |

Mouse Immunization

Female C57BL/6JOlaHsd and BALB/cOlaHsd mice (Envigo, USA) were vaccinated at 10 weeks of age. C57BL/6JOlaHsd substrain is known to have a spontaneous deletion of the alpha-synuclein gene. Mice were vaccinated with vaccine containing human full-length alpha-synuclein protein or alpha-synuclein peptide presented on the surface of liposomes in the presence of synthetic monophosphoryl hexa-acyl Lipid A 3-deacyl (3D-(6-acyl) PHAD®) (Avanti Polar Lipids, USA) as adjuvant.

Mice were vaccinated by subcutaneous injection (s.c.) on days 0, 5, 8, 21, 35, 84, and in some cases on day 14, 28, 63, 73 and 398. Mice were bled and heparinized plasma prepared 7 days before immunization (pre-immune plasma) and on days 14, 28, 40, 84, 90 and in some cases on day 7, 21, 35, 37, 73, 77 and 308 after first immunization. Mice used for myeloma fusion were additionally vaccinated with three or four daily booster injections by intraperitoneal injection (i.p.) of liposomal vaccines without adjuvant. Very high antigen-specific lgG responses were obtained in all immunized mice.

Isolation of clonal mouse hybridoma cell lines producing specific and high-affinity monoclonal antibodies Mice were euthanized and fusion with PAI myeloma cells was performed using splenocytes from immunized mice. For screening fusion products, cell culture supernatant was diluted 1:50 and analysed using Luminex bead-based multiplex assay (Luminex, The Netherlands). Luminex beads were conjugated to either full-length alpha-synuclein, alpha-synuclein peptide 1-60aa, alpha-synuclein peptide 1-95aa, alpha-synuclein peptide 61-140aa, or full-length beta-synuclein (irrelevant target), and with capturing IgGs with anti-mouse lgG-Fc antibodies specific for the IgG1, IgG2a, IgG2b, IgG2c, and IgG3 subclasses (Jackson Immunoresearch, USA). Luminex assay results binding to full-length alpha-synuclein identified 92 hits. In a second round of fusion of immunized mice splenocytes and PAI myeloma cells, 400 hits were identified by Luminex assay binding to full-length alpha-synuclein. Viable hybridomas were grown using serum-containing selection media, and the best hybridomas binding to full-length alpha-synuclein were then selected for subcloning. Following limiting dilution, the clonal hybridomas were grown in low immunoglobulin containing medium and stable colonies were selected for antibody screening and selection.

In another round of fusion of immunized mice splenocytes or lymph nodes (popliteals, axial, brachials, and inguinals) and X63/AG.8653 myeloma cells, 279 hits were identified by ELISA assay binding to alpha-synuclein peptide 1-120aa. Viable hybridomas were grown using serum-containing selection media, and the best hybridomas binding to alpha-synuclein peptide were then selected for subcloning. Following limiting dilution, the clonal hybridomas were grown in low immunoglobulin containing medium and stable colonies were selected for antibody screening and selection.

Antibody binding to human full-length alpha-synuclein

Antibody binding to human full-length alpha-synuclein was determined using an indirect ELISA. Full-length alpha-synuclein was diluted in carbonate/bicarbonate buffer pH 9.6 (Sigma, C3041) to a final concentration of 2.5 μg/ml and coated onto ELISA plates overnight at 4° C. After washing with PBS/0.05% Polyethylene glycol sorbitan monolaurate (Tween®20) and blocking for 1 hour at 37° C. (PBS/0.05% Tween®20/1% BSA), plates were incubated for 2 hours at 37° C. with three-fold dilution series of alpha-synuclein antibodies from 1 μg/mL to 0.0005 μg/mL using PBS/0.05% Tween®20/1% BSA as diluent. Dilution series (three-fold from 0.1 μg/mL to 0.0001 μg/mL) of Syn1 antibody (BD Biosciences, 610787; epitope 91-99aa) was used as positive control, where applicable. Next, plates were washed with PBS/0.05% Tween®20 and incubated for 2 hours at 37° C. with the detection antibody, anti-mouse IgG conjugated to alkaline phosphatase (Jackson Immunoresearch Laboratories Inc., 115-055-164,) at 1:1000 dilution. After final wash, plates were incubated 2 hours at 25° C. with 1 mg/ml of alkaline phosphatase substrate (p-nitrophenyl phosphate disodium hexahydrate; pNPP, S0942, Sigma) and read the absorbance optical density (O.D.) signal at 405 nm using an ELISA plate reader (Tecan, Switzerland). All generated antibodies show very good binding to human full-legnth alpha-synuclein (FIG. 1).

Epitope mapping on alpha-synuclein

Serum-free supernatants were harvested from stable hybridomas. The supernatants containing antibodies of interest were then screened by an indirect ELISA assay to determine epitopes. Epitopes were first determined using a library of 15-mer peptides covering the entire sequence of human alpha-synuclein protein, spanning amino acids (aa) 1-140 with 9aa offset and 6aa overlap. All peptides were synthesized biotinylated at N-terminus with aminohexanoic acid spacer except the N-terminal peptide 1-14aa (SEQ ID NO: 130) which was synthesized biotinylated at the C-terminus. Briefly, streptavidin-coated ELISA plates were blocked overnight at 4° C. (PBS/0.05% Tween®20/1% BSA) and then incubated for 1 hour at 25° C. with 0.25M of biotinylated full-length alpha-synuclein protein or biotinylated 15-mer peptides. Peptide sequences are provided in Table 3. Plates were washed with PBS/0.05% Tween®20 and then incubated with the hybridoma supernatants at 1/100 dilution for 1 hour at 25° C. Next, plates were washed with PBS/0.05% Tween®20 and incubated for 1 hour at 25° C. with the detection antibody, anti-mouse IgG conjugated to alkaline phosphatase (Jackson Immunoresearch Laboratories Inc., 115-055-164,) at 1:1000 dilution. After final wash, plates were incubated 2 hours at 25° C. with alkaline phosphatase substrate (p-nitrophenyl phosphate disodium hexahydrate; pNPP, S0942, Sigma) and read the absorbance optical density (O.D.) signal at 405 nm using an ELISA plate reader (Tecan, Switzerland). Tested antibodies were found to bind to one or more of the following peptides: 1-14aa, 1-15aa, $10^{-24}$aa, 28-42aa, 46-60aa, 64-78aa, 82-96aa, 91-105aa, 118-132aa, 127-140aa, or 81-120aa. For antibodies ACI-7079-2601B6-Ab1, ACI-7087-4125E6-Ab1, and ACI-7089-4415G5-Ab1 no linear epitope could be identified, no binding was observed to peptides of 15-mer length while antibodies bound to full-length alpha-synuclein. Results are shown in FIG. 2, FIG. 6 FIG. 14, and FIG. 15.

TABLE 3

Library of 15-mer peptides used for epitope mapping

| SEQ ID NO: | Sequence | aa alpha-synuclein sequence |
|---|---|---|
| 120 | MDVFMKGLSKAKEG | 1-14* |
| 121 | MDVFMKGLSKAKEGV | 1-15 |
| 122 | KAKEGVVAAAEKTKQ | 10-24 |
| 123 | AEKTKQGVAEAAGKT | 19-33 |
| 124 | EAAGKTKEGVLYVGS | 28-42 |
| 125 | VLYVGSKTKEGVVHG | 37-51 |
| 126 | EGVVHGVATVAEKTK | 46-60 |
| 127 | VAEKTKEQVTNVGGA | 55-69 |
| 128 | TNVGGAVVTGVTAVA | 64-78 |
| 129 | GVTAVAQKTVEGAGS | 73-87 |
| 130 | VEGAGSIAAATGFVK | 82-96 |
| 131 | ATGFVKKDQLGKNEE | 91-105 |
| 132 | LGKNEEGAPQEGILE | 100-114 |
| 133 | QEGILEDMPVDPDNE | 109-123 |
| 134 | VDPDNEAYEMPSEEG | 118-132 |
| 135 | MPSEEGYQDYEPEA | 127-140 |
| 137 | TVEGAGSIAAATGFVKKDQLGK NEEGAPQEGILEDMPVDP | 81-120 |

*Peptide biotinylated at C-terminus

Epitopes were further determined using a library of 8-mer peptides covering the alpha-synuclein sequences previously identified by indirect ELISA on a library of 15-mer peptides. The 8-mer peptides were designed with 1aa offset and 7aa overlap. Finally, for determining the critical residues for antibody binding an Alanine scanning library of peptides was utilized covering the alpha-synuclein sequences previously identified with the library of 15-mer peptides. The peptides of the Alanine scanning library were from 15 to 30 residues in length and synthesized with an alanine residue in each position substituting the natural residue in the sequence (except when the natural residue is alanine). All peptides were synthesized biotinylated at N-terminus with aminohexanoic acid spacer. For the indirect ELISA, streptavidin-coated ELISA plates were blocked overnight at 4° C. (PBS/0.05% Tween®20/1% BSA) and then incubated for 1 hour at 25° C. with 0.25UM of biotinylated peptides. Plates were washed with PBS/0.05% Tween®20 and then incubated with the hybridoma supernatants at 1/100 dilution for 1 hour at 25° C. Next, plates were washed with PBS/0.05% Tween®20 and incubated for 1 hour at 25° C. with the detection antibody, anti-mouse IgG conjugated to alkaline phosphatase (Jackson Immunoresearch Laboratories Inc., 115-055-164,) at 1:1000 dilution. After final wash, plates were incubated 2 hours at 25° C. with alkaline phosphatase substrate (p-nitrophenyl phosphate disodium hexahydrate; pNPP, S0942, Sigma) and read the absorbance optical density (O.D.) signal at 405 nm using an ELISA plate reader (Tecan, Switzerland). The binding epitopes for the antibodies are shown in Table 4.

TABLE 4

| Antibody binding epitopes | | | |
|---|---|---|---|
| Antibody Code | Hybridoma Code | Epitope (aa) | Critical residues (aa) - Alanine scanning library |
| ACI-7067-1206E5-Ab1 | 1206E5D2 | 36-40 (SEQ ID NO: 2) | 36-40 |
| ACI-7067-1107G5-Ab2 | 1107G5B6 | 51-57 (SEQ ID NO: 3) | 51-52, 55-57 |
| ACI-7067-1111 B12-Ab2 | 1111B12H10 | 51-57 (SEQ ID NO: 3) | 51-57 |
| ACI-7067-1108H1-Ab1 | 1108H1E1 | 65-74 (SEQ ID NO: 4) | 65, 68-70, 73-74 |
| ACI-7067-1112H8-Ab2 | 1112H8C12 | 65-74 (SEQ ID NO: 4) | 65, 68-71, 73-74 |
| ACI-7067-1102G3-Ab1 | 1102G3F2 | 65-81 (SEQ ID NO: 5) | 65, 68-70, 73-81 |
| ACI-7067-1116F2-Ab1 | 1116F2A2 | 93-95 | 93-95 |
| ACI-7067-1101C8-Ab2 | 1101C8F7 | 124-131 (SEQ ID NO: 7) | 126-127 |
| ACI-7067-1113D10-Ab1 | 1113D10E3D5 | 128-135 (SEQ ID NO: 8) | 128, 133, 135 |
| ACI-7067-1106A8-Ab2 | 1106A8H3 | 131-140 (SEQ ID NO: 9) | 135-136 |
| ACI-7067-1108B11-Ab2 | 1108B11D3 | 131-140 (SEQ ID NO: 9) | 135-136 |
| ACI-7079-2603C1-Ab3 | 2603C1H6 | 1-15 (SEQ ID NO: 121) | 14 |
| ACI-7079-2506F3-Ab1 | 2506F3E12 | 10-24 (SEQ ID NO: 122) | 14 |
| ACI-7079-2504A6-Ab1 | 2504A6C8 | 51-58 (SEQ ID NO: 136) | 51-54, 57-58 |
| ACI-7079-2503C6-Ab1 | 2503C6H9 | 82-96 (SEQ ID NO: 130) | 92-94, 96 |
| ACI-7079-2511B3-Ab3 | 2511B3B12 | 82-96 (SEQ ID NO: 130) | 92-94, 96 |
| ACI-7079-2501B11-Ab3 | 2501B11C7 | 91-105 (SEQ ID NO: 131) | 98, 102 |
| ACI-7079-2606A6-Ab2 | 2606A6D5 | 91-105 (SEQ ID NO: 131) | 96, 98, 100, 102 |
| ACI-7079-2501G2-Ab2 | 2501G2E5 | 118-132 (SEQ ID NO: 134) | 127-128 |
| ACI-7079-2506E2-Ab2 | 2506E2G4 | 118-132 (SEQ ID NO: 134) | 118-132 |
| ACI-7079-2507B3-Ab1 | 2507B3G8 | 127-140 (SEQ ID NO: 135) | 129, 135 |
| ACI-7079-2602G4-Ab4 | 2602G4H1 | 127-140 (SEQ ID NO: 135) | 129, 135 |
| ACI-7079-2603F3-Ab1 | 2603F3H3 | 127-140 (SEQ ID No: 135) | 129, 135-136 |
| ACI-7079-2605B3-Ab2 | 2605B3D1 | 127-140 (SEQ ID NO: 135) | 129, 135-136 |
| ACI-7079-2601B6-Ab1 | 2601B6D2 | Non-linear epitope | Non-linear epitope |
| ACI-7087-4119E10-Ab2 | 4119E10D12 | 28-42 (SEQ ID NO: 124)/ 37-51 (SEQ ID NO: 125) | 33-37 |
| ACI-7087-4125E6-Ab1 | 4125E6D5 | Non-linear epitope | Non-linear epitope |
| ACI-7088-4301D5-Ab2 | 4301D5B10 | 28-42 (SEQ ID NO: 124)/ 37-51 (SEQ ID NO: 125) | 37-42 |
| ACI-7088-4301E12-Ab2 | 4301E12B9 | 82-96 (SEQ ID NO: 130) | 92-96 |
| ACI-7088-4301H3-Ab2 | 4301H3A5 | 91-105 (SEQ ID NO: 131) | 101 |
| ACI-7088-4303A1-Ab1 | 4303A1E7 | 1-15 (SEQ ID NO: 121) | 7-10 |
| ACI-7088-4303A3-Ab1 | 4303A3E4 | 37-51 (SEQ ID NO: 125) | n.d. |
| ACI-7088-4303B6-Ab1 | 4303B6C11 | 1-15 (SEQ ID NO: 121) | 7-10 |
| ACI-7088-4303H6-Ab1 | 4303H6D7 | 91-105 (SEQ ID NO: 131) | 99 |
| ACI-7088-4305H7-Ab1 | 4305H7A4 | 1-15 (SEQ ID NO: 121)/ 91-105 (SEQ ID NO: 131) | 7-10/101 |

TABLE 4-continued

Antibody binding epitopes

| Antibody Code | Hybridoma Code | Epitope (aa) | Critical residues (aa) - Alanine scanning library |
|---|---|---|---|
| ACI-7088-4317A4-Ab1 | 4317A4D2 | 1-15 (SEQ ID NO: 121) | 7-10 |
| ACI-7089-4409F1-Ab1 | 4409F1A8 | 82-96 (SEQ ID NO: 130) | 92-96 |
| ACI-7089-4415G5-Ab1 | 4415G5A11 | Non-linear epitope | Non-linear epitope |
| ACI-7089-4417G6-Ab1 | 4417G6B12 | 37-51 (SEQ ID NO: 125) | Not determined |
| ACI-7089-4418C5-Ab1 | 4418C5G1 | 82-96 (SEQ ID NO: 130) | 92-96 |
| ACI-7089-4418F6-Ab1 | 4418F6G7 | 82-96 (SEQ ID NO: 130) | 92-96 |
| ACI-8033-5A12-Ab1 | 917.5A12A11C9 | 100-114 (SEQ ID NO: 132)/ 109-123 (SEQ ID NO: 133) | 105-120 |
| ACI-8033-25A3-Ab1 | 917.25A3E9F6 | 81-120 (SEQ ID NO: 137) | 105-120 |
| ACI-8033-1G10-Ab1 | 917.1G10A10F6 | 109-123 (SEQ ID NO: 133) | 114-115 |
| ACI-8033-19A2-Ab1 | 917.19A2E9E5 | 109-123 (SEQ ID NO: 133) | 105-120 |
| ACI-8033-8C10-Ab1 | 917.8C10C6G3 | 82-96 (SEQ ID NO: 130) | 93-94 |
| ACI-8033-7A2-Ab1 | 917.7A2B6A9 | 109-123 (SEQ ID NO: 133) | 105-120 |
| ACI-8033-1A12-Ab1 | 917.1A12C1B4 | 109-123 (SEQ ID NO: 133) | 112-114 |
| ACI-8033-4F3-Ab1 | 917.4F3F4G6 | 91-105 (SEQ ID NO: 131) | 99 |
| ACI-8033-17F5-Ab1 | 917.17F5F5G9 | 91-105 (SEQ ID NO: 131) | 92-105 |
| ACI-8033-18C11-Ab1 | 917.18C11A11F10 | 100-114 (SEQ ID NO: 132) | 100-105/108-113 |
| ACI-8033-18D12-Ab1 | 917.18D12F10D6 | 100-114 (SEQ ID NO: 132) | 100-105/108-113 |
| ACI-8033-1F8-Ab1 | 917.1F8D8E4 | 82-96 (SEQ ID NO: 130) | 92-96 |
| ACI-8033-22E5-Ab1 | 917.22E5C5F7 | 109-123 (SEQ ID NO: 133) | 115 |
| ACI-8033-27D8-Ab1 | 917.27D8E1H10E10 | 81-120 (SEQ ID NO: 137) | 105-120 |
| ACI-8033-21C8-Ab1 | 917.21C8E4C8 | 100-114 (SEQ ID NO: 132) | 100-105/108-113 |

Inhibition or Delay of Seeded Alpha-Synuclein Aggregation

Monoclonal anti-alpha-synuclein antibodies were evaluated for their ability to inhibit the aggregation of alpha-synuclein in vitro. The presence of alpha-synuclein pre-formed aggregates (seeds) increases the de novo aggregation propensity of monomeric a-synuclein. Alpha-synuclein antibodies were incubated with alpha-synuclein seeds prior to adding the monomeric alpha-synuclein for the aggregation assay. Kinetics of alpha-synuclein aggregation were monitored by thioflavin T (ThT) fluorescence. The ability of alpha-synuclein antibodies to inhibit the seeded aggregation was quantified by a percent change in the aggregation half-time (time to reach half-maximum ThT fluorescence signal).

Alpha-synuclein recombinant protein (rPeptide, S-1001-4) at concentration of 5 mg/mL was re-suspended and dialyzed against DPBS (Slide-A-Lyzer Mini Dialysis 10K MWCO, ThermoScientific, 88404) four times of 60 minutes each at 4° C. Higher molecular weight species were then removed by centrifugal filtration (Microcon DNA Fast Flow Centrifugal Filter Unit with Ultracel membrane, Sigma, MRCFOR100). Sonicated alpha-synuclein fibrils were diluted with PBS to a final concentration of 1.0 mg/mL. Aggregations were assembled in low-binding 96-well plates (ThermoScientific, 278752), in triplicate for each condition. Alpha-synuclein seeds were used at 1% the final concentration of monomeric alpha-synuclein (14 μM).

Alpha-synuclein seeds (34.5 pmoles) were incubated with alpha-synuclein antibodies (787 pmoles, ~22.8 equivalents) for 1 hour at at 25° C. As a reference control, alpha-synuclein seeds were incubated without the addition of alpha-synuclein antibodies. The Syn303 antibody (BioLegend, 824301) was used as a reference standard (Tran et al., Cell Rep. 2014, 7 (6): 2054-65). To control for any non-alpha-synuclein specific effect from the antibodies, the mouse isotype control (IgG2a) was produced recombinantly or purchased (ThermoFisher, 02-6200) and was used as a negative control.

Monomeric aSyn and ThT (3 mM stock solution, Sigma, D8537) were added to reach a final concentration of 14 μM and 46 μM respectively. Each aggregation was then aliquoted into 3 separate wells (65 μL/well) of the 96-well plates. Kinetic measurements were performed using an M200 Infinite Pro Microplate Reader (Tecan, Switzerland).

ThT fluorescent measurements were obtained in triplicate for each aggregation condition (technical repeats) and run twice on independent days (for a total of N=6). A baseline correction was performed by subtraction of the initial ThT value (t=0) and data was then normalized as a percent maximum ThT signal (see Equation 1). Aggregation half-times (½) were calculated from non-linear regressions using either a sigmoidal dose-response (see Equation 2) or a one-phase association (see Equation 3) (GraphPad Prism 7) and represent the time taken to reach half the maximum ThT signal.

$$\%ThT(x) = \frac{(ThT(x)) - (ThT(x_0))}{(ThT(x_{max})) - (ThT(x_0))} * 100 \quad \text{Equation 1}$$

Where % ThT(x) is the percent ThT signal at time t=x, $ThT(x_0)$ is the ThT signal at t=0 and ThT $(X_{max})$ is the maximum ThT signal.

$$\%ThT(x) = \text{Bottom} + \frac{(\text{Top} - \text{Bottom})}{\left(1 + 10^{(LogEC50 - X) - HillSlope}\right)} \quad \text{Equation 2}$$

Where Bottom is a fit of the minimum ThT signal, Top is a fit of the maximum ThT signal, EC50 is the x value when the ThT signal is halfway between Bottom and Top, and the HillSlope is the steepness of the curve. Here, the aggregation half-time $(T_{1/2})$ is obtained directly from EC50.

$$\%\ ThT(x) = ThT(x_0) + ((\text{Plateau} - ThT(x_0)) * (1 - \exp(-K*x))) \quad \text{Equation 3:}$$

Where ThT $(x_0)$ is the initial ThT signal, Plateau is the fit of the maximum ThT signal, and K is the rate constant. Here, the aggregation half-time $(T_{1/2})$ is calculated from In (2)/K.

$$\%\ \text{Increase}\ \tau_{1/2} = \frac{\tau_{mAb} - \tau_{nomAb}}{\tau_{nomAb}} * 100 \quad \text{Equation 4}$$

Where $T_{no\ mab}$ is the aggregation half-time in the absence of antibody (mAb) and $T_{mab}$ is the aggregation half-time in the presence of the indicated antibody.

$$\text{Propagation of Error} = \%\tau_{mAb} * \sqrt{\left(\frac{SEM_{mAb}}{\tau_{mAb}}\right)^2 + \left(\frac{SEM_{nomAb}}{\tau_{nomAb}}\right)^2} \quad \text{Equation 5}$$

Where % $T_{mAb}$ is the percent increase in $T_{1/2}$ from Equation 4, $T_{no\ mab}$ is the aggregation half-time in the absence of mAb, $T_{mab}$ is the aggregation half-time in the presence of the indicated mAb, and SEM is the standard error (calculations resulting from fitting of Equations 2 and 3).

Aggregation half-times $(T_{1/2})$ were obtained using either a sigmoidal fit (Equation 2) or an exponential fit (Equation 3) dependent upon the kinetic profile and best fit. Varied time frames were used to obtain optimal fitting as ThT signals can decrease following completion of aggregation. Change in $T_{1/2}$ values, in the presence of the indicated antibodies, were normalized relative to the $T_{1/2}$ value in the absence of antibody. FIG. 3A, FIG. 7A, FIG. 16A, and FIG. 17A shows the comparison of changes in $T_{1/2}$ values as normalized to the aggregation in the absence of antibody. Significant increases in $T_{1/2}$ values were observed for all antibodies proving the good efficacy of antibodies in delaying the seeded and/or spontaneous aggregation of alpha-synuclein. Pre-incubation with either Syn303 or the IgG2a control showed no significant effect on the seeded aggregation (FIG. 3A).

The percent increase in $T_{1/2}$ values were calculated relative to the seeded aggregation in the absence of antibody (see Equation 4). FIG. 3B, FIG. 7B, FIG. 16B, and FIG. 17B shows the calculated percent increase in $T_{1/2}$ values upon pre-incubation of alpha-synuclein seeds with the indicated antibodies proving the good efficacy of antibodies in delaying the seeded and/or spontaneous aggregation of alpha-synuclein. Relative to the IgG2a control, no significant change increase in $T_{1/2}$ was observed for pre-incubation with the commercially available Syn303 antibody (FIG. 3B). Pre-incubation of alpha-synuclein seeds with all antibodies of the present invention showed a significant percent increase in 11/2 values.

Affinity measurements on alpha-synuclein monomers and alpha-synuclein fibrils by SPR Affinity measurements were performed on an surface plasmon resonance (SPR) instrument (Biacore T200, GE Healthcare Life Sciences) using CM5 Series S sensor chips (GE Healthcare, BR-1005-30). Flow channels (Fc) 1-4 were activated with a fresh solution of EDC/NHS (Amine Coupling Kit, 1:1 ratio of both reagents, GE Healthcare, BR-1006-33). The goat anti-mouse antibody (GE Healthcare, BR-1008-38) was captured at a concentration of 30 μg/mL diluted in 10 mM sodium acetate (pH 5.0). Following, all unreacted activated ester groups were capped with 1 M ethanolamine (GE Healthcare, BR-1006-33). Any non-covalently bound antibodies were removed by three successive regenerations of 10 mM Glycine pH 1.7 (GE Healthcare, 28-9950-84). Immobilization levels were evaluated following ethanolamine capping (Bound) and finally following regeneration (Final). Non-covalent immobilization of alpha-synuclein antibodies was performed using a target immobilization method of 2000 response units (RU). Antibodies were diluted in 10 mM sodium acetate pH 5.5 (GE Healthcare, BR-1003-52) to a final concentration of 5 μg/mL.

Binding affinity of alpha-synuclein antibodies to monomeric or fibrillar alpha-synuclein species was performed using a single-cycle kinetics method. The instrument was primed with 1xHBS-P+buffer (10X stock from GE Healthcare, BR-1003-52 diluted in Milli-Q water). Injections of monomeric alpha-synuclein (aSyn) (Boston Biochem, SP-485), increasing in concentration from 0.62-50 nM prepared from serial 2-fold dilutions, were performed with contact times of 300 sec/injection at a flow rate of 30 μL/min. A dissociation phase of 900 sec followed the final 50 nM injection. Regeneration of the sensor to the goat anti-mouse antibody layer was achieved using 3 regenerations of 10 mM Glycine pH 1.7. Injections of alpha-synuclein fibrils of increasing concentration from 5.56-450 nM prepared from serial 2-fold dilutions, were performed with contact times of 300 sec/injection at a flow rate of 30 μL/min. A dissociation phase of 900 sec followed the final 450 nM injection. Regeneration of the sensor to the goat anti-mouse antibody layer was achieved using 3 regenerations of 10 mM Glycine pH 1.7. Results obtained from single-cycle kinetics were evaluated by Biacore T200 evaluation software with 1:1 binding homogenous Langmuir model (with a global Rmax) with Cycle 5 as a blank subtraction. The following kinetic parameters were obtained: on-rate (ka), off-rate (kd), affinity constant (KD, ratio of kd by ka), maximum response (Rmax), and goodness of fit (Chi2).

Non-covalent capture of the alpha-synuclein antibodies was performed in three separate runs. Capture levels ranged from ~1800 to ~2100 RU based on the target immobilization level of 2000 R U. Sensograms were obtained for responses to monomeric and fibrillar alpha-synuclein, representative examples for two antibodies are shown in FIG. 4. Kinetic constants were determined from 1:1 homogenous binding models for most of the cases. For ACI-7067-1101C8-Ab2 versus monomeric aSyn, a heterogeneous ligand model was used to obtain ka and kd values and steady-state model was used to determine KD and Rmax. The kinetic fitting parameters from single-cycle kinetics affinity measurements by SPR are shown in Table 5. ACI-7067-1101C8-Ab2, ACI-7079-2503C6-Ab1, ACI-7079-2603F3-Ab1, ACI-7088-4303B6-Ab1, ACI-8033-4F3-Ab1 and ACI-7067-1113D10-Ab1 demonstrate a binding preference to fibrillar alpha-synuclein and display significantly slower dissociation rates (kd) from fibrillar alpha-synuclein compared to monomeric alpha-synuclein (FIG. 4).

TABLE 5

Affinity measurements obtained by SPR

| Antibody | Hybridoma | Alpha-synuclein monomers | | | Alpha-synuclein fibrils | | |
|---|---|---|---|---|---|---|---|
| Code | Code | ka (1/Ms) | kd (1/s) | KD (nM) | ka (1/Ms) | kd (1/s) | KD (nM) |
| ACI-7067-1101C8-Ab2 | 1101C8F7 | 5.55E+04 | 2.65E−02 | 43.7 | 1.76E+05 | 2.83E−04 | 2.9 |
| ACI-7067-1102G3-Ab1 | 1102G3F2 | 1.29E+05 | 1.03E−03 | 8 | 4.60E+04 | 1.35E−03 | 30.6 |
| ACI-7067-1106A8-Ab2 | 1106A8H3 | 2.18E+05 | 5.00E−03 | 23.2 | 2.84E+05 | 7.21E−03 | 25 |
| ACI-7067-1107G5-Ab2 | 1107G5B6 | 1.58E+05 | 1.14E−03 | 7.2 | 3.45E+05 | 2.18E−03 | 16.1 |
| ACI-7067-1108H1-Ab1 | 1108H1E1 | 1.31E+05 | 5.65E−04 | 4.4 | 2.71E+05 | 1.18E−03 | 14.3 |
| ACI-7067-1111B12-Ab2 | 1111B12H10 | 1.72E+05 | 1.40E−03 | 8.1 | 2.63E+04 | 1.01E−03 | 39.2 |
| ACI-7067-1112H8-Ab2 | 1112H8C12 | 2.50E+05 | 1.58E−03 | 6.3 | 2.85E+05 | 2.45E−03 | 18.7 |
| ACI-7067-1108B11-Ab2 | 1108B11D3 | 1.91E+05 | 1.54E−03 | 8.1 | 2.51E+05 | 2.05E−03 | 18.6 |
| ACI-7067-1113D10-Ab1 | 1113D10E3D5 | 1.03E+04 | 2.26E−02 | 14 | 6.94E+03 | 4.16E−07 | 0.06 |
| ACI-7067-1116F2-Ab1 | 1116F2A2 | 4.70E+04 | 2.32E−04 | 4.9 | 8.30E+03 | 4.58E−04 | 55.1 |
| ACI-7067-1206E5-Ab1 | 1206E5D2 | 1.65E+05 | 6.36E−05 | 0.4 | 5.73E+04 | 4.05E−04 | 8.3 |
| ACI-7079-2501B11-Ab3 | 2501B11C7 | 1.41E+05 | 3.35E−04 | 2.4 | 1.09E+04 | 3.47E−04 | 31.8 |
| ACI-7079-2501D10-Ab1 | 2501D10C3 | 2.64E+05 | 4.30E−04 | 1.6 | 1.73E+04 | 4.27E−04 | 24.7 |
| ACI-7079-2501G2-Ab2 | 2501G2E5 | 2.91E+05 | 8.40E−04 | 2.9 | 1.90E+04 | 5.28E−04 | 27.8 |
| ACI-7079-2503C6-Ab1 | 2503C6H9 | 4.05E+04 | 1.20E−04 | 3.0 | 9.45E+03 | 3.28E−07 | 0.004 |
| ACI-7079-2504A6-Ab1 | 2504A6C8 | 1.63E+05 | 2.36E−04 | 1.4 | 1.66E+04 | 1.92E−04 | 11.5 |
| ACI-7079-2506E2-Ab2 | 2506E2G4 | 8.09E+04 | 6.15E−04 | 7.6 | 5.19E+03 | 4.76E−04 | 91.9 |
| ACI-7079-2506F3-Ab1 | 2506F3E12 | 2.10E+05 | 5.10E−04 | 2.4 | 1.83E+04 | 1.61E−04 | 8.8 |
| ACI-7079-2507B3-Ab1 | 2507B3G8 | 2.45E+05 | 6.42E−04 | 2.6 | 1.91E+04 | 6.68E−04 | 34.9 |
| ACI-7079-2511B3-Ab3 | 2511B3B12 | 9.28E+04 | 5.83E−04 | 6.3 | 1.06E+04 | 3.12E−04 | 29.5 |

TABLE 5-continued

| Antibody Code | Hybridoma Code | Alpha-synuclein monomers ka (1/Ms) | Alpha-synuclein monomers kd (1/s) | Alpha-synuclein monomers KD (nM) | Alpha-synuclein fibrils ka (1/Ms) | Alpha-synuclein fibrils kd (1/s) | Alpha-synuclein fibrils KD (nM) |
|---|---|---|---|---|---|---|---|
| Affinity measurements obtained by SPR | | | | | | | |
| ACI-7079-2601B6-Ab1 | 2601B6D2 | 2.90E+05 | 2.38E−02 | 82.1 | 1.74E+04 | 3.82E−04 | 22.0 |
| ACI-7079-2602G4-Ab4 | 2602G4H1 | 2.23E+05 | 8.67E−04 | 3.9 | 1.24E+04 | 2.34E−04 | 18.9 |
| ACI-7079-2603C1-Ab3 | 2603C1H6 | 5.58E+08 | 6.06E+00 | 10.9 | 1.28E+09 | 5.17E+01 | 40.3 |
| ACI-7079-2603F3-Ab1 | 2603F3H3 | 5.08E+04 | 1.49E−02 | 292.8 | 7.31E+03 | 1.60E−08 | 0.002 |
| ACI-7079-2605B3-Ab2 | 2605B3D1 | 2.83E+05 | 1.09E−03 | 3.9 | 1.68E+04 | 2.94E−04 | 17.4 |
| ACI-7079-2606A6-Ab2 | 2606A6D5 | 8.60E+05 | 4.12E−03 | 4.8 | 1.54E+04 | 8.62E−04 | 56.2 |
| ACI-7087-4119E10-Ab2 | 4119E10D12 | 1.80E+04 | 1.88E−02 | 1042.5 | 2.80E+05 | 4.53E−03 | 16.2 |
| ACI-7087-4125E6-Ab1 | 4125E6D5 | 5.91E+04 | 2.61E−02 | 442.1 | 1.12E+04 | 5.67E−04 | 50.7 |
| ACI-7088-4301D5-Ab2 | 4301D5B10 | 5.69E+04 | 3.53E−02 | 619.8 | 1.08E+04 | 3.85E−04 | 35.8 |
| ACI-7088-4301E12-Ab2 | 4301E12B9 | 1.98E+04 | 1.18E−04 | 6.0 | 4.25E+03 | 1.66E−04 | 39.0 |
| ACI-7088-4301H3-Ab2 | 4301H3A5 | 2.76E+04 | 3.29E−03 | 119.0 | 1.04E+04 | 8.98E−04 | 86.5 |
| ACI-7088-4303A1-Ab1 | 4303A1E7 | 1.70E+06 | 6.32E−02 | 37.1 | 1.81E+04 | 2.44E−04 | 13.5 |
| ACI-7088-4303A3-Ab1 | 4303A3E4 | 1.04E+06 | 1.07E−03 | 1.0 | 6.47E+04 | 6.06E−04 | 9.4 |
| ACI-7088-4303B6-Ab1 | 4303B6C11 | 1.35E+06 | 1.06E−01 | 78.5 | 1.37E+04 | 1.30E−04 | 9.5 |
| ACI-7088-4303H6-Ab1 | 4303H6D7 | 3.44E+04 | 6.70E−03 | 194.8 | 1.46E+04 | 6.36E−04 | 43.7 |
| ACI-7088-4305H7-Ab1 | 4305H7A4 | 2.73E+07 | 9.24E−02 | 3.4 | 2.42E+04 | 2.03E−04 | 8.4 |
| ACI-7088-4317A4-Ab1 | 4317A4D2 | 3.28E+03 | 1.20E−02 | 3655.6 | 3.37E+05 | 9.98E−04 | 3.0 |
| ACI-7089-4409F1-Ab1 | 4409F1A8 | 1.54E+05 | 9.92E−04 | 6.4 | 6.67E+05 | 5.87E−03 | 8.8 |
| ACI-7089-4415G5-Ab1 | 4415G5A11 | 6.00E+04 | 1.41E−04 | 2.4 | 2.42E+05 | 3.10E−04 | 1.3 |
| ACI-7089-4417G6-Ab1 | 4417G6B12 | 2.47E+08 | 5.58E+00 | 22.6 | 1.79E+05 | 8.74E−03 | 48.7 |
| ACI-7089-4418C5-Ab1 | 4418C5G1 | 4.50E+04 | 1.41E−04 | 3.1 | 2.07E+05 | 9.40E−06 | 0.05 |
| ACI-7089-4418F6-Ab1 | 4418F6G7 | 8.18E+04 | 9.25E−06 | 0.1 | 2.72E+05 | 1.14E−05 | 0.04 |
| ACI-8033-5A12-Ab1 | 917.5A12A11C9 | Not determined | Not determined | Not determined | 3.06E+04 | 4.37E−06 | 0.1 |
| ACI-8033-25A3-Ab1 | 917.25A3E9F6 | Not determined | Not determined | Not determined | Not determined | Not determined | Not determined |
| ACI-8033-1G10-Ab1 | 917.1G10A10F6 | Not determined | Not determined | Not determined | 1.77E+04 | 6.54E−05 | 3.7 |
| ACI-8033-19A2-Ab1 | 917.19A2E9E5 | 1.33E+07 | 8.28E−02 | 6.2 | 1.77E+04 | 1.19E−04 | 6.7 |

TABLE 5-continued

| Affinity measurements obtained by SPR | | | | | | | |
|---|---|---|---|---|---|---|---|
| Antibody | Hybridoma | Alpha-synuclein monomers | | | Alpha-synuclein fibrils | | |
| Code | Code | ka (1/Ms) | kd (1/s) | KD (nM) | ka (1/Ms) | kd (1/s) | KD (nM) |
| ACI-8033-8C10-Ab1 | 917.8C10C6G3 | 4.31E+04 | 1.14E−04 | 2.6 | 4.96E+03 | 5.59E−05 | 11.3 |
| ACI-8033-7A2-Ab1 | 917.7A2B6A9 | Not determined | Not determined | Not determined | 8.81E+03 | 7.83E−05 | 8.9 |
| ACI-8033-1A12-Ab1 | 917.1A12C1B4 | 1.02E+06 | 3.27E−02 | 31.9 | 6.66E+03 | 6.53E−05 | 9.8 |
| ACI-8033-4F3-Ab1 | 917.4F3F4G6 | 9.70E+04 | 1.60E−04 | 1.7 | 4.50E+03 | 2.24E−07 | 0.05 |
| ACI-8033-17F5-Ab1 | 917.17F5F5G9 | 9.66E+04 | 2.32E−04 | 2.4 | 1.37E+04 | 1.20E−04 | 8.7 |
| ACI-8033-18C11-Ab1 | 917.18C11A11F10 | 1.43E+05 | 2.63E−04 | 1.8 | 8.27E+03 | 2.51E−04 | 30.4 |
| ACI-8033-18D12-Ab1 | 917.18D12F10D6 | 8.25E+07 | 2.60E−01 | 3.2 | 3.50E+02 | 2.33E−03 | 570.9 |
| ACI-8033-1F8-Ab1 | 917.1F8D8E4 | 3.04E+04 | 7.38E−04 | 24.3 | 9.83E+02 | 9.96E−04 | 1013.0 |
| ACI-8033-22E5-Ab1 | 917.22E5C5F7 | Not determined | Not determined | Not determined | 1.80E+04 | 3.27E−05 | 1.8 |
| ACI-8033-27D8-Ab1 | 917.27D8E1H10E10 | Not determined | Not determined | Not determined | Not determined | Not determined | Not determined |
| ACI-8033-21C8-Ab1 | 917.21C8E4C8 | 3.01E+05 | 4.82E−04 | 1.6 | 8.81E+03 | 1.56E−04 | 17.7 |

Target engagement on human alpha-synuclein aggregates

Target engagement was evaluated in immunohistochemistry experiments on tissues from PD and Multiple System Atrophy (MSA) donor brains. Human brain tissues were obtained from the Netherlands Brain Bank. All tissues have been collected from donors for or from whom a written informed consent for a brain autopsy and the use of the material and clinical information for research purposes had been obtained by the Netherlands Brain Bank. Immunohistochemistry was performed on 10 μm thick frozen sections using fluorescent secondary antibody detection. An antibody recognizing alpha-synuclein phosphorylated at Ser129, [EP1536Y] (pSyn) (Abcam ab51253) was used as control for detecting pathological aggregated and phosphorylated alpha-synuclein. Antibodies ACI-7067-1101C8-Ab2, ACI-7067-1113D10-Ab1 and ACI-7067-1108B11-Ab2 bind to pathological alpha-synuclein aggregates in Lewy bodies and Lewy neurites in PD cases (FIG. 5A) and in glial cytoplasmic inclusions in MSA cases (FIG. 5B). Similar results were obtained with other antibodies listed in Table 5 (data not shown).

Antibody variable region gene sequencing

Clonal hybridoma cell lysates were used for variable region gene sequencing. Mouse hybridomas were harvested and lysed using a lysis buffer containing guanidinium salts that deactivates RNases. Genomic DNA was then eliminated by RNase-free DNase, and RNA was purified with a silica-based affinity column using multiple washes and eluted from the column using RNase-free water. Once the RNA was extracted, its purity and concentration was measured spectrophotometrically. The integrity of the RNA was assessed on a denaturing agarose gel and RNA was reverse transcribed into cDNA using reverse transcriptase (RT). Before adding the reaction mixture, the RNA was heated to 70° C. for 10 min in order to disrupt RNA secondary structures. The RT products were directly used for PCR amplification. For high-fidelity PCR amplification of the cDNA, each of the variable region primers corresponding to the different gene families encoding for antibodies were individually mixed with the constant primer, for variable heavy chain domain (VH) and variable light chain domain (VL) separately. In first intention, a degenerate primer pool was used (12 for VH and 12 for VL) and, depending on the results, a second pool was used to obtain PCR products. After the PCR reaction, the products were analyzed by gel electrophoresis on 2% agarose gels stained with ethidium bromide. The PCR products for VL and VH were individually purified on an agarose gel using tris-acetate-EDTA (TAE). The purified fragments excised from the gel were then sequenced using the dye-terminator sequencing method. The same primers as those used for PCR were used for the sequencing reaction. Sequencing was carried out in both directions to provide overlap at both ends. Sequencing data were analyzed on the Ig Blast/Kabat database. Nucleotide sequences for VH and VL are shown in Table 6. Protein sequences for VH and VL, and their complementarity-determining regions (CDRs) are shown in Table 7.

TABLE 6

| Nucleotide sequence of the heavy chain and light chain variable domains (VH and VL) | | | |
|---|---|---|---|
| Antibody Code | Hybridoma Code | VH | VL |
| ACI-7067-1101C8-Ab2 | 1101C8F7 | GAGGTGCAGCTTGTTGAGTCTGGTGGAGGATT<br>GGTGCAGCCTAAAGGGTCATTGAAACTCTCAT<br>GTGCAGCCTCTGGATTCAGCTTCAATATCTAC<br>GCCATGAACTGGGTCCGCCAGGCTCCAGGAA<br>AGGGTTTGGAATGGGTTGCTCGCATAAGAAGT | GATGTTTTGATGACCCAAACTCCACTCTCCCTGC<br>CTGTCAGTCTTGGAGATCAAGCCTCCATCTCTTG<br>CAGATCTAGTCAGAGCATTGTACATAGTAATGGAA<br>ACACCTATTTAGAATGGTACTTGCAGAAACCAGG<br>CCAGTCTCCAAAGCTCCTGATCTACAAAGTTTCCA |

TABLE 6-continued

Nucleotide sequence of the heavy chain and light chain variable domains (VH and VL)

| Antibody Code | Hybridoma Code | VH | VL |
|---|---|---|---|
| | | AAAAGTAATAATTATGCAACATATTATGCCGATTCAGTGAAAGACAGATTCACCATCTCCAGAGCTGATTCAGAAAGCATGCTCTATCTGCAAATGAACAACTTGAAAACTGAGGACACAGCCATGTATTACTGTGTAAGGGTGGGCCTACGGTTCTATGCTATGGACTACTGGGGTCAAGGCACCTCAGTCACCGTCTCCTCA (SEQ ID NO: 18) | ACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTACTGCTTTCAAGGTTCACAAGGTCCGCTCACGTTCGGTGCTGGGACCAAGCTGGAGCTGAAA (SEQ ID NO: 19) |
| ACI-7067-1102G3-Ab1 | 1102G3F2 | GAAGTGAAGCTTGAGGAGTCTGGAGGAGGCTTGGTGCAACCTGGAGGATCCATGAAACTCTCTTGTGCTGCCTCTGGATTCACTTTTAGTGACGCCTGGATGAACTGGGTCCGCCAGTCTCCAGAGAAGGGGCTTGAGTGGGTTGCTGAAATTAGAAACAAAGCTCATAATCATGCAACATACTATGCTGAGTCTGTGAAAGGGAGGTTCACCATCTCAGGAGATGATTCCAAAAGTAGTGTCTACCTGCAAATGAACAACTTAAGAGCTGAAGACACTGGCATTTATTACTGTACCATTTACTCTTATTGGGGCCAAGGGACTCTGGTCACTGTCTCTGCA (SEQ ID NO: 28) | AGTATTGTGATGACCCAGACTCCCAAATTCCTGCTTGTATCAGCAGGAGACAGGGTTACCATAACCTGCAAGGCCAGTCAGAGTGTGACTAAAGATGTAGCTTGGTACCAACAGAAGCCAGGGCAGTCTCCTAAACTGCTGATATACTCTACATCCAATCGCTACAGTGGAGTCCCTGATCGCTTCACTGGCAGTGGATATGGGACGGATTTCACTTTCACCATCAATACTGTGCAGACTGAAGACCTGGCAGTTTATTTCTGTCAGCAGGATTACAGGATTCCGTACACGTTCGGAGGGGGGACCAAGCTGGAAATAAAA (SEQ ID NO: 29) |
| ACI-7067-1106A8-Ab2 | 1106A8H3 | GAGGTGCAGCTTGTTGAGTCTGGTGGAGGATTGGTGCAGCCTAAAGGATCATTGAAACTCTCATGTGCCGCCTCTGGTTTCACCTTCAATACCTATGCCATGCACTGGGTCCGCCAGGCTCCAGGAAAGGGTTTGGAATGGGTTGCTCGCATAAGAAGTAAAGGTAGTAATTATGCAACAAATTATGCCGATTCAGTGAAAGACAGATTCACCATCTCCAGAGATGATTCGCAAAGCATGCTCTATCTGCAAATGAACAACCTGAAAACTGAGGACACAGCCATGTATTACTGTGTGAGAGGACACGGTAGTAGCTACTTTTCTTACTGGGGCCAAGGGACTCTGGTCACTGTCTCTGCA (SEQ ID NO: 38) | CAAATTGTTCTCACCCAGTCTCCAGCAATCATGTCTGCATCTCCAGGGGAGAAGGTCACCATGACCTGCAGTGCCAGCTCAAGTGTAAGTTACATGCACTGGTACCAGCAGAAGTCAGGCACCTCCCCCAAAAGATGGATTTATGACACATCCAATCTGGCTTCTGGAGTCCCTGCTCGCTTCAGTGGCAGTGGGTCTGGGACCTCTTACTCTCTCACAATCAGCAGCATGGAGGCTGAAGATGCTGCCACTTATTACTGCCAGCAGTGGAATAGTCACCCACCCACGTTCGGTGCTGGGACCAAGCTGGAACTGAAA (SEQ ID NO: 39) |
| ACI-7067-1107G5-Ab2 | 1107G5B6 | CAGGTCCAACTGCAGCAGCCTGGGACTGAACTGGTGAAGCCTGGGGCTTCAGTGAAGCTGTCCTGCAAGGCTTCTGGCTACACCTTCACCAAATACTGGATGCACTGGGTGAAGCAGAGGCCTGGACAAGGCCTTGAGTGGATTGGAAATATTAATCCTAACAATGGTGATACTAACTACAATGAGAAGTTCAAGAGCAAGGCCACACTGACTGTAGACAAATCCTCCAGCACAGCCTACATGCAGCTCAGCAGTCTGACATCTGAGGACTCTGCGGTCTATTATTGTGCAATTGCTATGGACTACTGGGGTCAAGGAACCTCAGTCACCGTCTCCTCA (SEQ ID NO: 48) | GACATCCAGATGACCCAGTCTCCATCCTCCTTATCTGCCTTTCTGGGAGAAAGAGTCAGTCTCACTTGTCGGGCAAGTCAGGACATTGGTAATAACTTAAACTGGTTTCAGCAGGAACCAGATGGAACTATTAAACGTCTGATCTACGCCACATCCAGTTTAGATTCTGGTGTCCCCAAAAGGTTCAGTGGCAGTAGGTCTGGGTCAGAATATTCTCTCACCATCAGCAGCCTTGAGTCTGAAGATTTTGTAGACTATTACTGTCTACAATTTGGTAGTTCTCCGCTCACGTTCGGTGCTGGGACCAAGCTGGAGCTGAAA (SEQ ID NO: 49) |
| ACI-7067-1108H1-Ab1 | 1108HIE1 | GAGGTGAAGCTGGTGGAGTCTGGAGGAGGCTTGGTGCAACCTGGAGGATCCATGAAACTCTCTTGTACTGCCTCTGGATTCACTTTTAGTGACGCCTGGATGAACTGGGTCCGCCAGTCTCCAGAGAAGGGGCTTGAGTGGGTTGCTGAAATTAGAAACAAAGCTCATAATCATGCAACAAACTATGCTGAGTCTGTGAAGGGGAGGTTCACCATCTCAGGAGATGATTCCAAAAGTAGTGTCTACCTGCAAATGAACAACTTAAGAGCTGAAGACACTGGCATTTATTACTGTACCATTTACTCTTTTTGGGGCCAAGGGACTCTGGTCACTGTCTCTGCA (SEQ ID NO: 58) | AGTATTGTGATGACCCAGACTCCCAAATTCCTGCTTGTATCAGCAGGAGACAGGGTTACCATAACCTGCAAGGCCAGTCAGAGTGTGACTAATTATGTAGCTTGGTACCATCAGAAGCCAGGGCAGTCTCCTAAACTGCTGATATACTCTGCATCCAATCGCTACAGTGGAGTCCCTGATCGCTTCACTGGCAGTGGATATGGGACGGATTTCACTTTCACCATCAATACTGTGCAGACTGAAGACCTGGCAGTTTATTTCTGTCAGCAGGATTACAGGATTCCGTACACGTTCGGAGGGGGGACTAAGCTGGAAATAAAA (SEQ ID NO: 59) |
| ACI-7067-1111B12-Ab2 | 1111B12H10 | CAGGTCCAACTGCTGCAGCCTGGGACTGCACTGGTGATGCCTGGGGCTTCAGTGAAGCTGTCCTGCAAGGCTTCTGGCTACACCTTCACCACCTACTGGATGCACTGGGTGAAGCAGAGGCCTGGACAAGGCCTTGAGTGGATTGGAAATATTAATCCTATCAATGGTGGTAGTAACTACAATGAGAAGTTCAAGAGCAAGGCCTCACTGACTGTAGACAAGTCCTCCAGCACAGCCTACATGCAGCTCAGCAGCCTGACATCTGAGGACTCTGCGGTCTATTATTGTGTCATTGCTATGGACTACTGGGGTCAAGGAACCTCAGTCACCGTCTCCTCA (SEQ ID NO: 68) | GACATCCAGATGACCCAGTCTCCATCCTCCTTATCTGCCTCTCTGGGAGAAAGAGTCAGTCTCACATGTCGGGCAAGTCAGGACATTGGTATTAGCTTAAACTGGTTTCAGCAGGAACCAGATGGAACTATTAAACGCCTGATCTACGCCACATCCAGTTTAGATTCTGGTGTCCCCAAAAGGTTCAGTGGCAATAGGTCTGGGTCAGATTATTCTCTCACCATCAGTAGCCTTGAGTCTGAAGATTTTGCAGACTATTACTGTCTACAATTTGCTAGTTCTCCGCTCACGTTCGGTGCTGGGACCAAGCTGGAGCTGAAA (SEQ ID NO: 69) |
| ACI-7067-1112H8-Ab2 | 1112H8C12 | GAAGTGAAGCTTGAGGAGTCTGGAGGAGGCTTGGTGCAACCTGGAGGATCCATGAAACTCTCTTGTGCTGCCTCTGGATTCACTTTTACTGACGCCTGGATGAACTGGGTCCGCCAGTCTCCAGAAAAGGGGCTTGAGTGGATTGCTGAAATTAGAAAC | AGTATTGTGATGACCCAGACTCCCAAATTCCTGCTTATGTCACCAGGAGACAGGGTTACCATGACCTGCACGGCCAGTCAGAGTGTGAGTAATTATGTGGCTTGGTACCAACAGAAGCCAGGGCAGTCTCCTAAACTGCTGATATACTCTGCATCCAATCGCTTCACTGGA |

TABLE 6-continued

| Nucleotide sequence of the heavy chain and light chain variable domains (VH and VL) | | | |
|---|---|---|---|
| Antibody Code | Hybridoma Code | VH | VL |
| | | AAAGCTCATAATTATGCAACATACTATGCTGAG<br>TCTGTGAAAGGGAGGTTCGACATCTCAGGAGA<br>TGATTCCAAAAGTAGTGTCTACCTGCAAATGAA<br>CAACTTGAGAGTTGAAGACACTGGCATTTATTA<br>CTGTACCATTTACTCTTACTGGGGCCCAGGGA<br>CTCTGGTCACTGTCTCTGCA<br>(SEQ ID NO: 78) | GTCCCTGATCGCTTCACTGGCAGTGGATATGGGA<br>CGGATTTCACTTTCACCATCAACACTGTGCAGACT<br>GAAGACATGGCAGTTTATTTCTGTCAGCAGGATTA<br>CACCTCTCCGTACACGTTCGGGGGGGGGACCAA<br>GCTGGAAATAAAA (SEQ ID NO: 79) |
| ACI-7067-<br>1108B11-<br>Ab2 | 1108B11D3 | GAGGTGCAGCTTGTTGAGTCTGGTGGAGGATT<br>GGTGCAGCCTAAAGGATCATTGAAACTCTCAT<br>GTGCCGCCTCTGGTTTCACCTTCAATACCTAT<br>GCCATGCACTGGGTCCGCCAGGCTCCAGGAA<br>AGGGTTTGGAATGGGTTGCTCGCATAAGAAGT<br>AAAGGTAGTAATTATGCAACAAATTATGCCGAT<br>TCAGTGAAAGACAGATTCACCATCTCCAGAGA<br>TGATTCGCAAAGCATGCTCTATCTGCAAATGAA<br>CAACCTGAAAACTGAGGACACAGCCATGTATT<br>ACTGTGTGAGAGGACACGGTAGTAGCTACTTT<br>TCTTACTGGGGCCAAGGGACTCTGGTCACTGT<br>CTCTGCA (SEQ ID NO: 38) | CAAATTGTTCTCACCCAGTCTCCAGCAATCATGTC<br>TGCATCTCCAGGGGAGAGGATCACCATGACCTGC<br>AGTGCCAACTCAAGTGTTACTTACATGCACTGGTA<br>CCAGCAGAAGTCAGGCACCTCCCCCAAAAGATG<br>GATTTATGACACATCCAATCTGGCTTCTGGAGTCC<br>CTGCTCGCTTCAGTGGCAGTGGGTCTGGGACCT<br>CTTACTCTCTCACAATCAGCAGCATGGAGGCTGA<br>AGATGCTGCCACTTATTACTGCCAGCAGTGGAAA<br>AGTCACCCACCCACGTTCGGTGCTGGGACCAAG<br>CTGGAACTGAAA (SEQ ID NO: 89) |
| ACI-7067-<br>1113D10-<br>Ab1 | 1113D10E3D5 | GAGGTGCAGCTTGTTGAGTCTGGTGGAGGATT<br>GGTGCAGCCTAAAGGATCATTGAAACTCTCAT<br>GTGCCGCCTCTGGTTTCACCTTCAATACCTAT<br>GCCCTGCACTGGGTCCGCCAGGCTCCAGGAA<br>AGGGTTTGGAATGGGTTGCTCGCATAAGAAGT<br>AAAAGTAGTAATTATGCAACATATTATGCCGAT<br>TCAGTGAAAGACAGATTCACCATCTCCAGAGA<br>TGATTCACAAAGCATGCTCTATCTGCAAATGAA<br>CAACCTGAAAACTGAGGACACAGGCATGTATT<br>ACTGTGTAAGAGGGGGGTGTTTCTCCCTTTGAC<br>TACTGGGGCCAAGGCACCACTCTCACAGTCTC<br>CTCA (SEQ ID NO: 98) | CAAATTGTTCTCACCCAGTCTCCAGCAATCATGTC<br>TGCATCTCCAGGGGAGAAGGTCACCATGACCTGC<br>AGTGCCAGCTCAAGTGTAAGTTACATGCACTGGT<br>ACCAGCAGAAGTCAGGCACCTCCCCCAAAAGATG<br>GATTTATGACACATCCAAACTGGCTTCTGGAGTC<br>CCTGCTCGCTTCAGTGGCAGTGGGTCTGGGACC<br>TCTTACTCTCTCACAATCAGCAGCATGGAGGCTG<br>AAGATTCTGCCACTTATTACTGCCAGCAGTGGAG<br>TAATAACCCACCGACGTTCGGTGGAGGCACCAAG<br>CTGGAAATCAAA (SEQ ID NO: 99) |
| ACI-7067-<br>1116F2-<br>Ab1 | 1116F2A2 | GATGTACAACTTCAGGAGTCAGGACCTGGCTT<br>CGTGAAACCTTCTCAGTCTCTGTCTCTCACCTG<br>CTCTGTCACTGGCTACTCAATAACCAGAGGTTT<br>TTACTGGAACTGGATCCGACAGTTTCCAGGAA<br>ACAAACTGGAATGGATGGGCTACATAAGTGAC<br>GATGGTAATAGTAACTACAATCCCTCTCTCAAA<br>AATCGAATCTCCATCACTCGTGACACATTTAAG<br>AATCAGGTTTTCCTGAGGTTGAACTCTGTGACT<br>ACTGAGGACACTGCCACATACTATTGTACAAG<br>AGGAGATCTACTTTGGGGCCAAGGCACCACTC<br>TCACAGTCTCCTCA (SEQ ID NO: 108) | GATGTTGTGATGACCCAGACTGCACTCACTTTGT<br>CGGTTACCATTGGACAACCAGCCTCCATCTCTTG<br>CAAGTCAAGTCAAAGCCTCTTAGATAGTGATGGA<br>GAGACATATTTGAATTGGTTGTTACAGAGGCCAG<br>GCCAGTCTCCAAAGCGCCTAATCTATCTGGTGTC<br>TAAACTGGACTCTGGAGTCCCTGACAGGTTCACT<br>GGTAGTGGATCAGGGACAGATTTCGCACTGAAAA<br>TCAGCAGAGTGGAGGCTGAGGACTTGGGAATTTA<br>TTATTGCTGGCAAGGTACACATTTTCCTCAGACGT<br>TCGGTGGAGGCACCAAGCTGGAAATCAAA (SEQ<br>ID NO: 109) |
| ACI-7067-<br>1206E5-<br>Ab1 | 1206E5D2 | CAGGTTCAGCTGCAGCAGTCTGGACCTGAGCT<br>GGTGAAGCCTGGGGCTTCAGTGAAGATGTCCT<br>GCAAGGCTTCTGGATACACATTCACTGACTAT<br>GTTATAAGCTGGGTGAAGCAGGGAACTGGACA<br>GGGCCTTGAGTGGATTGGAGAGATTTATCCTG<br>GAAATGATAGTACTTACTACAATGAGAAGTTCA<br>AGGGCAAGGCCACACTGACTGCAGACAAATCC<br>TCCAACACAGCCTACATGCAGCTCAGCAGCCT<br>GACATCTGAGGACTCTGCGGTCTATTTCTGTG<br>CAAGAGAGGGGGTCTCTAATGGTTACCTATAT<br>TTGTCTATGGACTACTGGGGTCAAGGAACCTC<br>AGTCACCGTCTCCTCA (SEQ ID NO: 118) | GATGTTTTGATGACCCAAACTCCACTCACTTTGTC<br>GGTTACCATTGGACAACCAGCCTCTATCTCTTGC<br>AAGTCAAGTCAGAGCCTCTTATATAGTAATGGAAA<br>AACCTATTTGAATTGGTTATTACAGAGGCCAGGC<br>CAGTCTCCAAAGCGCCTAATCTATCTGGTGTCTAA<br>ACTGGACTCTGGAGTCCCTGACAGGTTCACTGGC<br>AGTGGATCAGGAACAGATTTTACACTGAAAATCA<br>GCAGAGTGGAGGCTGAGGATTTGGGAGTTTATTA<br>CTGCGTGCAAGGTACACATTTTCCGTGGACGTTC<br>GGTGGAGGCACCAAGCTGGAAATCAAA (SEQ ID<br>NO: 119) |
| ACI-7079-<br>2501B11-<br>Ab3 | 2501B11C7 | CAGGTTCAGCTGCAGCAGTCTGGACCTGAGCT<br>GGTGAAGCCTGGGGCCTCAGTGAAGATTTCCT<br>GCAAGGCTTCTGGCTACGCATTCAGTAGTTTC<br>TGGATGAACTGGATGAAACAGAGGCCTGGAAA<br>GGGTCTTGAGTGGATTGGACGGATTTATCCTG<br>GAGATGGAGATGCTCACTACAATGGGGAGTTC<br>AAGGGCAGGGCCACACTGACTGCAGACAAAT<br>CCTCCAGCACAGCCTACATGCAACTCAGCAGC<br>CTGACATCTGAGGACTCTGCGGTCTACTTCTG<br>TGCAAGAAAGGGGGATTTCTACGGTAGTAACT<br>ACGACTATTGGGGCCAAGGCACCACTCTCACA<br>GTCTCCTCA<br>(SEQ ID NO: 288) | CAGGCTGTTGTGACTCAGGAATCTGCACTCACCA<br>CATCACCTGGTGAAACAGTCACACTCACTTGTCG<br>CTCAAGTACTGGGGCTGTTACAACTAGTAACTAT<br>GCCAACTGGGTCCAAGAAAAACCAGATCATTTATT<br>CACTGGTCTAATAGGTGGTACCAACAACCGAGCT<br>CCAGGTGTTCCTGCCAGATTCTCAGGCTCCCTGA<br>TTGGAGACAAGGCTGCCCTCACCATCACAGGGG<br>CACAGACTGAGGATGAGGCAATATATTTCTGTGC<br>TCTATGGTACAGCAACCATTTGGTGTTCGGTGGA<br>GGAACCAGACTGACTGTCCTA<br>(SEQ ID NO: 289) |

TABLE 6-continued

Nucleotide sequence of the heavy chain and light chain variable domains (VH and VL)

| Antibody Code | Hybridoma Code | VH | VL |
|---|---|---|---|
| ACI-7079-2501D10-Ab1 | 2501D10C3 | GAGGTGCAGCTTGTTGAGTCTGGTGGAGGATT GGTGCAGCCTAAAGGATCATTGAAAGTCTCAT GTGCCGCCTCTGGTTTCACCTTCAAGACCTAT GCCATGCACTGGGTCCGCCAGGCTCCGGGAA AGGGTTTGGAATGGGTTGCTCGCATAAGAAGT GAAAACAGTAATTTTGCAAAATATTATGCCGAT TCAGTGAAGGACAGATTCACCATCTCCAGAGA TGATTCACAAAGTATGCTCTATCTGCAAATGAA CAACCTGAAAACTGAGGACACAGCCATGTATT ATTGTGTAAGGGGATATAACGGCAGTAGCCTT GACTACTGGGGCCAAGGCACCACTCTCACAGT CTCCTCA (SEQ ID NO: 298) | CAAATTGTTCTCACCCAGTCTCCAGCAATCATGTC TGCATTTCCAGGGGAGAGGGTCACCATGACCTGC AGTGCCAGCTCAAGTGTAAATTACATGCACTGGT ACCAGCAGAAGTCCGGCACCTCCCCCAAAAGATG GATTTATGACACATCCAAACTGGCTTCTGGAGTC CCTGCTCGCTTCAGTGGCGGTGGGTCTGGGACC TCTTACTCTCTCACAATCAGCAACATGGAGGCTG AAGATGCTGCCACTTATTACTGCCAGCAGTGGAG AAGTAATCCACCCACTTTCGGAGGGGGGACCAAG CTGGAAATAAAA (SEQ ID NO: 199) |
| ACI-7079-2501G2-Ab2 | 2501G2E5 | GAGGTGCAGCTTGTTGAGTCTGGTGGAGGATT GGTGCAGCCTAAAGGGTCATTGAAACTCTCAT GTGCAGCCTCTGGATTCAACTTCAATACCTATG CCATGAACTGGGTCCGCCAGGCTCCAGGAAA GGGTTTGGAATGGGTTGCTCGCATAAGAACTA AAAGTAATAATTTTGCAACATATTATGCCCATT CAGTGAAAGACAGATTCACCATCTCCAGAGAT GATTCAGAAAGCATGCTCTATCTGCAAATGAAC AACTTGAAAACTGAGGACACAGCCATGTATTA CTGTGTGAGACAGGGACTAGCCTACTATGCTA TGGACTACTGGGGTCAAGGAACCTCAGTCACC GTCTCCTCA (SEQ ID NO: 148) | GATGTTTTGATGACCCAAACTCCACTCTCCCTGC CTGTCAGTCTTGGAGATCAAGTCTCCATCTCTTGC AGATCTAGTCAAACCATTGTACATAGTAATGGAAA CACCTATTTAGAATGGTACCTGCAGAAACCAGGC CAGTCTCCAAAGCTCCTGATCTACAAAGTTTCCAA CCGATTTTCTGGGGTCCCAGACAGGTTCAGTGGC AGTGGATCAGGGACAGATTTCACACTCAAGATCA GCAGAGTGGAGGCTGAGGATCTGGGAGTTTATTA CTGCTTTCAAGGTTCACAAGGTCCGCTCACGTTC GGTGCTGGGACCAAACTGGAGCTGAAA (SEQ ID NO: 149) |
| ACI-7079-2503C6-Ab1 | 2503C6H9 | GATGTACAGCTTCAGGAGTCAGGACCTGGCCT CGTGAAACCTTCTCAGTCTCTGTCTCTCACCTG CTCTGTCACTGGCTACTCCATCACCAGTGGTT ATTACTGGAACTGGATCCGACTATTTCCAGGA AACAAACTGGAATGGCTGGGCTACATAAACTA CGATGGTAGCAATAACTTCAACCCATCTCTCAA AAATCGAATCTCCATCACTCGTGACACATCTAA GAACCAGTTTTTCCTGAAATTGAATTCTGTGAC TTCTGAGGACACAGCCACATATTTCTGTTTAAG AGGGGACTGGGACTGGGGCCAAGGGACTCTG GTCACTGTCTCTGCA (SEQ ID NO: 158) | GATGTTGTGATGACCCAGACTCCACTCACTTTGT CGGTTACCATTGGACAACCAGCCTCCATCTCTTG CAAGTCAAGTCAGAGCCTCTTAGATAGTGATGGA GAGACATATTTGAATTGGTTGTTACAGAGGCCAG GCCAGTCTCCAAAGCGCCTAATCTGTCTGGTGTC TAAACTGGACTCTGGAGTCCCTGACAGGTTCACT GGCAGTGGATCAGGGACAGATTTCACACTGAAAA TCAGCAGAGTGGAGGCTGAGGATTTGGGAGTTTA TTATTGCTGGCAAGGTACACATTTTCCTCAGACGT TCGGTGGAGGCACCAGGCTGGAAATCAAA (SEQ ID NO: 159) |
| ACI-7079-2504A6-Ab1 | 2504A6C8 | CAGGTTCAGCTGCAGCAGTCTGGAGTTGAGCT GGCGAGGCCTGGGGCTTCAGTGAAACTGTCC TGCAAGGCTTCTGGCTACACCTTCACAAGCTA TGGTATAAGCTGGGTGAAGCAGAGAACTGGAC AGGGCCTTAAGTGGATTGGAGAGATTTATCCT GGAAGTGGTAATACTTACTACAATGAGAAGTTC AAGGGCAAGGCCACACTGACTGCAGACAAATC CTCCAGCACAGCGTACATGGAGCTCCGCAGC CTGACGTCTGAGGACTCTGCGGTCTATTTCTG TGCAACCGATTACGACGCCTACTGGGGCCAAG GCACCACTCTCACAGTCTCCTCA (SEQ ID NO: 168) | GATGTTGTGATGACCCAAACTCCACTCTCCCTGC CTGTCAGTCTTGGAGATCAAGCCTCCATCTCTTG CAGATCTAGTCAGAGCCTTGTACACAGTAATGGA AACACCTATTTACATTGGTACCTGCAGAAGCCAG GCCAGTCTCCAAAGCTCCTGATCTACAAAGTTTC CAACCGATTTTCTGGGGTCCCAGACAGGTTCAGT GGCAGTGGATCAGGGACAGATTTCACACTCAAGA TCAGCAGAGTGGAGGCTGAGGATCTGGGAGTTTA TTTCTGCTCTCAAAGTACACATGTTCCGCTCACGT TCGGTGCTGGGACCAAGCTGGAGCTGAAA (SEQ ID NO: 169) |
| ACI-7079-2506E2-Ab2 | 2506E2G4 | CAGGTTCAGTTGCAGCAGTCTGGACCTGAGCT GGTGAGGCCTGGGGCCTCAGTGAAGATTTCCT GCAAGGCTTCTGGCTACGCATTCAGTAACTCC TGGATGAACTGGGTGAAGCAGAGGCCTGGAA AGGGTCTTGAGTGGATTGGACGGATTTTTCCT GGAGATGGAGATACTTACTACGATGGGAAGTT CAAGGGCAAGGTCAAACTGACAACAGACAAAT TCTCCAACACAGCCTACATGCAACTCCGCAGC CTGACATCTGAGGACTCTGCGGTCTACTTCTG TGCAAGATGGGGGGGTACTAACGATGAGTGG TTTGCTCACTGGGGCCAAGGGACTCTGGTCAC TGTCTCTGTA (SEQ ID NO: 178) | GACATTGTGCTGACACAGTCTCCTGCTTCCTTAAC TGTATCTCTGGGGCAGAGGGCCACCATCTCATGC AGGGCCAGCCAAAGTGTCAGTACATCTAGGAATA GTTATATGCACTGGTACCAACAGAAACCAAGACA GCCACCCAAACTCCTCATCAAGTATGCATCCAAC CTAGAATCTGGGGTCCCTGCCAGGTTCAGTGGCA GTGGGTCTGGGGCAGACTTCACCCTCAACATCCA TCCTGTGGAGGAGGAGGATACTGCAACATATTAC TGTCAGCACAGTTGGGATATTCCGCTCACGTTCG GTACTGGGACCAAGCTGGAGCTGAGT (SEQ ID NO: 179) |
| ACI-7079-2506F3-Ab1 | 2506F3E12 | CAGGTCCAACTGCAGCAGCCTGGGGCTGAGC TTGTGAAGCCTGGGGCTTCAGTGAAGCTGTCC TGCAAGGCTTCTGGCTACACCTTCACCACCTA CTGGATGCAGTGGGTAAAACAGAGGCCTGGA CAGGGCCTTGAGTGGATCGGAGAGATTGATCC TTCTGATAGCTATATTAACTACAATCAAAAGTT | GATGTTTTGATGACCCAAACTCCACTCTCCCTGC CTGTCAGTCTTGGAGATCAAGCCTCCATCTCTTG CAGATCTAGTCAGAGCATTGTACATAGTAATGGAA ACACCTATTTAGAATGGTACCTGCAGAAACCAGG CCAGTCTCCAAAGCTCCTGATCTACAAAGTTTCCA ACCGATTTTCTGGGGTCCCAGACAGGTTCAGTGG |

TABLE 6-continued

| Nucleotide sequence of the heavy chain and light chain variable domains (VH and VL) | | | |
|---|---|---|---|
| Antibody Code | Hybridoma Code | VH | VL |
| | | CAAGGGCAAGGCCACATTGACTGTAGACACAT<br>CCTCCAGCACAGCCTTCATGCAGCTCAGCAGC<br>CTGACATCTGAGGACTCTGCGGTCTATTACTG<br>TGCAAGGGGGATGATGGACTACTGGGGTCAA<br>GGAACCTCAGTCACCGTCTCCTCA<br>(SEQ ID NO: 188) | CAGTGGATCAGGGACAGATTTCACACTCAAGATC<br>AGCAGAGTGGAGGCTGAGGATCTGGGAGTTTATT<br>ACTGCTTTAAAGGTTCACATGTTCCGTACACGTTC<br>GGAGGGGGGACCAAGCTGGAAATAAAA<br>(SEQ ID NO: 189) |
| ACI-7079-2507B3-Ab1 | 250763G8 | GAGGTGCAGCTTGTTGAGTCTGGTGGAGGATT<br>GGTGCAGCCTAAAGGATCATTGAAAGTCTCAT<br>GTGCCGCCTCTGGTTTCACCTTCAAGACCTAT<br>GCCATGCACTGGGTCCGCCAGGCTCCGGGAA<br>AGGGTTTGGAATGGGTTGCTCGCATAAGAAGT<br>GAAAACAGTAATTTTGCAAAATATTATGCCGAT<br>TCAGTGAAAGACAGATTCACCATCTCCAGAGA<br>TGATTCACAAAGTATGCTCTATCTGCAAATGCA<br>CACCCTGAAAACTGAGGACACAGCCATCTATT<br>ATTGTGTAAGGGGATATAACGGCAGTAGCCTT<br>GACTACTGGGGCCAAGGCACCACTCTCACAGT<br>CTCCTCA<br>(SEQ ID NO: 198) | CAAATTGTTCTCACCCAGTCTCCAGCAATCATGTC<br>TGCATTTCCAGGGGAGAGGGTCACCATGACCTGC<br>AGTGCCAGCTCAAGTGTAAATTACATGCACTGGT<br>ACCAGCAGAAGTCCGGCACCTCCCCCAAAAGATG<br>GATTTATGACACATCCAAACTGGCTTCTGGAGTC<br>CCTGCTCGCTTCAGTGGCGGTGGGTCTGGGACC<br>TCTTACTCTCTCACAATCAGCAACATGGAGGCTG<br>AAGATGCTGCCACTTATTACTGCCAGCAGTGGAG<br>AAGTAATCCACCCACTTTCGGAGGGGGGACCAAG<br>CTGGAAATAAAA<br>(SEQ ID NO: 199) |
| ACI-7079-2511B3-Ab3 | 2511B3B12 | GATGTACAGCTTCAGGAATCAGGACCTGGCCT<br>CGTGAAACCTTCTCAGTCTCTGTCTCTCACCTG<br>CTCTGTCACTGGCTTCTCCATCACCAGTTATTA<br>TTACTGGAACTGGATCCGGCAGITTCCAGGAA<br>ACAAACTGGAATGGATGGCCTACATAAGCTAC<br>GATGGTAGCAATAACTACAACCCATCTCTCAAA<br>AATCGAATCTCCATCACTCGTGACACATCTAAG<br>AACCAGTTTTTCCTGAAGTTGAATTCTGTGACT<br>ACTGAGGACACAGCCACATATTACTGTACAAG<br>AGGGGACTGGGACTGGGGCCAAGGGACTCTG<br>GTCACTGTCTCTGCA<br>(SEQ ID NO: 208) | GATGTTGTGATGACCCAGACTCCACTCACTTTGT<br>CGCTTACCATTGGACAACCAGCCTCCATCTCTTG<br>CAAGTCAAGTCAGAGCCTCTTAGATAGTGATGGA<br>GAGACATATTTGAATTGGTTGTTACAGAGGCCAG<br>GTCAGTCTCCAAAGCGCCTAATCTATCTGGTGTC<br>TAAACTGGAATCTGGAGTCCCTGACAGGTTCACT<br>GGCAGTGGATCAGGGACAGTTTTCACACTGAAAA<br>TCAGCAGAGTGGAGGCTGAGGATTTGGGAGTTTA<br>TTATTGCTGGCAAGGGACACATTTTCCTCAGACG<br>TTCGGTGGAGGCACCAAGCTGGAAATCAAA<br>(SEQ ID NO: 209) |
| ACI-7079-2601B6-Ab1 | 2601B6D2 | GAGATTCAACTGCAGCAGTCTGGGGCTGAGCT<br>TGTGAGGCCAGGGGCCTCAGTCAAGTTGTCCT<br>GCACAACTTCCGGCTTTAACATTAAAGACGACT<br>ATATTCACTGGGTGAAGCAGAGGCCTGAACAG<br>GGCCTGGAGTGGATTGGATGGATTGATCCTGA<br>GAATGGTGATACTGATTATGCCTCGAAGTTCC<br>AGGGCAAGGCCACTATAACAGCAGACACATCC<br>TCCAACACAGCCTACCTGCACCTCAGCAGCCT<br>GACATCAGAGGACGCTGCCGTCTATTTCTGTA<br>CTACAAGAGGATTTGGTTACTGGGGCCAAGGG<br>ACTCTGGTCACTGTCTCT<br>(SEQ ID NO: 218) | GACATTGTGATGACCCAGTCTCACAAATTCATGTC<br>CACATCAGTAGGAGACAGGGTCAGCATCACCTGC<br>AAGGCCAGTCAGGATGTGGGTAATGTTGTTGCCT<br>GGTATCAACAGAAACCAGGACAATCTCCTAAACT<br>ACTGATTTACTGGGCATCCTCCCGGCACACTGGA<br>GTCCCTGATCGCTTCACAGGCAGTGGATCTGGGA<br>CAGAATTCACTCTCACCATTAGCAATGTGCAGTCT<br>GAAGACTTGGCAGATTATTTCTGTCAGCAATATAG<br>CAGCTATCCGCTCACGTTCGGTGCTGGGACCAAG<br>CTGGAGCTGAAG<br>(SEQ ID NO: 219) |
| ACI-7079-2602G4-Ab4 | 2602G4H1 | GAGGTGCAGCTTGTTGAGTCTGGTGGAGGATT<br>GGTGCAGCCTAAAGGATCATTGAAACTCTCAT<br>GTGCCGCCTCTGGTTTCACCTTCAAGACCTAT<br>GCCATGCACTGGGTCCGCCAGGCTCCAGGAA<br>AGGGTTTGGAATGGGTTGCTCGCATAAGAAGT<br>AAAGGTAGTGATTATGCAACATATTATGCCGAT<br>TCAGTGAAGGACAGATTCACCATCTCCAGAGA<br>TGATTCACAAAGCATGCTCTATCTGCAAATGAA<br>CAACCTGAAAACTGAGGATACAGCCATGTATTT<br>CTGTGTGAGAGGGGGTGCTGACTCCTGGTTTG<br>CTTACTGGGGCCAAGGGACTCTGGTCACTGTC<br>TCTACA<br>(SEQ ID NO: 228) | CAAATTGTTCTCACCCAGTCTCCAGCAATCATGTC<br>TGCATCTCCAGGGGAGAGGATCACCATGACCTGC<br>ACTGCCAGCTCAAGTGTAAGTTACATGCACTGGT<br>ACCAGCAGAAGTCAGGCACCTCCCCCAAAAGATG<br>GATTTATGACACATCCAAACTGGCTTCTGGAGTC<br>CCTGCTCGCTTCAGTGGCAGTGGGTCTGGGGCC<br>TCTTATACTCTCACAATCAGCAGCATGGAGGCTG<br>AAGATGCTGCCACTTATTACTGCCAGCAGTGGAA<br>TCGTAACCCACCGACGTTCGGTGGAGGCACCCA<br>GCTGGCAATCAAA<br>(SEQ ID NO: 229) |
| ACI-7079-2603C1-Ab3 | 2603C1H6 | CAGGTCCAACTGCAGCAACCTGGGGCTGACC<br>TTGTGAAGCCTGGGGCTTCAGTGAAGCTGTCC<br>TGTAAGGCTTCTGGCTACACCTTCACCAGTTA<br>CTGGATGCAGTGGACAAAACAGAGGCCTGGA<br>CAGGGCCTTGAGTGGATCGGAGAGATTGATCC<br>TTCTGATAGCTATGCTAACTACAATCAAAAGTT<br>CAAGGGCAAGGCCACATTGACTGTTGACAAAT<br>ATTCCAGCACAGCCTACATGCAGCTCAACAGC<br>CTGACATCTGAGGACTCTGCGGTCTATTACTG<br>TGCCCTCTATGATGGTCCCTCTTACTGGGGCC<br>AAGGGACTCTGGTCACTGTCTCT<br>(SEQ ID NO: 238) | GAAAATGTTCTCACCCAGTCTCCAGCAATCATGTC<br>TGCATCTCCAGGGGAAAAGGTCACCATGACCTGC<br>AGTGCCGGCTCAAGTGTAAGTTACATGCACTGGT<br>TCCAACAGAAGTCAAGCACCTCCCCCAAACTCTG<br>GATTTATGACACATCCAAACTGCCTTCTGGAGTCC<br>CAGGTCGCTTCAGTGGCAGTGGGTCTGGAAACTC<br>TTACTCTCTCACGATCAGCAGCATGGAGGCTGAA<br>GATGTTGCCACTTATTACTGTTTTCAGGGGAGTG<br>GGTACCCGTACACGTTCGGAGGGGGGACCAAGC<br>TGGAAATAAAA<br>(SEQ ID NO: 239) |

TABLE 6-continued

Nucleotide sequence of the heavy chain and light chain variable domains (VH and VL)

| Antibody Code | Hybridoma Code | VH | VL |
|---|---|---|---|
| ACI-7079-2603F3-Ab1 | 2603F3H3 | GAGGTGCAGCTTGTTGAGTCTGGTGGAGGATT<br>GGTGCAGCCTAAAGGATCATTGAAACTCTCAT<br>GTGCCGCCTCTGGTTTCACCTTCAATACCTAT<br>GCCATGCACTGGGTCCGCCAGGCTCCAGGAA<br>AGGGTTTGGAATGGGTTGCTCGCATAAGAAGT<br>AAAGGTAGTAATTATGCAACATATTATGCCGAT<br>TCAGTGAAAGACAGATTCACCATCTCCAGAGA<br>TGATTCACAAAGCATGCTCTATCTGCAAATGAA<br>CAACCTGAAAACTGAGGACACAGCCATGTATT<br>ACTGTGTGAGAGGGGGTGGTGACTCCTGGTTT<br>GCTTACTGGGGCCAAGGGACTCTGGTCACTGT<br>CTCTGCA<br>(SEQ ID NO: 248) | CAAATTGTTCTCACCCAGTCTCCAGCAATCATGTC<br>TGCATCTCCAGGGGAGAGGGTCACCATGACCTG<br>CACTGCCAGCTCAAGTGTAAGTTACATGCACTGG<br>TACCAGCAGAAGTCAGGCACCTCCCCCAAAAGAT<br>GGATTTATGACACATCCAAACTGGCTTCTGGAGT<br>CCCTGCTCGCTTCAGTGGCAGTGGGTCTGGGGC<br>CTCTTATACTCTCACAATCAGCAGCATGGAGGCT<br>GAAGATGCTGCCACTTATTACTGCCAGCAGTGGA<br>ATAGTAACCCACCGACGTTCGGTGGAGGCACCCA<br>GCTGGCAATCAAA<br>(SEQ ID NO: 249) |
| ACI-7079-2605B3-Ab2 | 2605133D1 | GAGGTGCAGCTTGTTGAGTCTGGTGGAGGATT<br>GGTGCAGCCTAAAGGATCATTGAAACTCTCAT<br>GTGCCGCCTCTGGTTTCATCTTTAAAACCTATG<br>CCATGCATTGGGTCCGCCAGGCTCCAGGAAA<br>GGGTTTGGAATGGGTTGCTCGAATAAGAAGTA<br>AAGGTGGTAATTATGCAACATATTTTGCCGATT<br>CAGTGAAAGACAGATTCACCATCTCCAGAGAT<br>GATTCACAAAATATGCTCTATCTGCAAGTGAAC<br>AACCTGAAAATTGAGGACACAGCCATGTATTTC<br>TGTGTGAGAGGGGGTAATTACTCCTGGTTTGC<br>TTACTGGGGCCAAGGGACTCTGGTCACTGTCT<br>CTGCA<br>(SEQ ID NO: 258) | CAAATTGTTCTCACCCAGTCTCCAGCAATCATGTC<br>TGCTTCTCCAGGGGAGAAGGTCACCATGACCTGC<br>AGTGCCAGCTCAAGTGTAACTTACATGCATTGGT<br>ACCAGCAGAAGTCAGGCACCTCCCCCAAAAGATG<br>GATTTATGACACATCCCAACTGGCTTCTGGAGTC<br>CCTGCTCGCTTCAGTGGCAGTGGGTCTGGGACC<br>TCTCACTCTCTCACAATCAGCAGCATGGAGACTG<br>AAGATGCTGCCACTTATTACTGCCAACAATGGACT<br>AGAAACCCACCGACGTTCGGTGGAGGCACCAAG<br>CTGGCAATCAAA<br>(SEQ ID NO: 259) |
| ACI-7079-2606A6-Ab2 | 2606A6D5 | CAGGTTCAGCTGCAACAGTCTGGACCTGAGCT<br>GGTGAAGCCTGGGGCCTCAGTGAAGATTTCCT<br>GCAAGGCTTCTGGCTTCGCATTCAGTAGCTCC<br>TGGATGAACTGGGTGAAGCAGAGGCCTGGAA<br>AGGGTCTTGAGTGGGTTGGACGGATTTTTCCT<br>GGAGATGGAGATACTAACTACGATAGGAAGTT<br>CAAGGACAAGGCCACACTGACTGCAGACAAAT<br>CCTCCAGCACAGCCTACATGCAACTCAGCAGC<br>CTGACATCTGAGGACTCTGCGGTCTACTTCTG<br>TGCAAGATGGACGGGGGGTTACGACTGGTTT<br>GCTTACTGGGGCCAAGGGACTCTGGTCACTGT<br>CTCTGCA<br>(SEQ ID NO: 268) | GACATTGTGCTGACACAGTCTCCTGCTTCCTTAG<br>CTGTATCTCTGGGGCAGAGGGCCACCATCTCATG<br>CAGGGCCAGCCAAAGTGTCAGTACATCTAACTAT<br>AATTATCTTCACTGGTACCAACAGAAACCAGGACA<br>GCCACCCAAACTCCTCATCACGTATGCATCCAAC<br>CTAGAATCTGGGGTCCCTGCCAGGTTCAGTGGCA<br>GTGGGTCTGGGACAGACTTCACCCTCAACATCCA<br>TCCTGTGGAGGAGGGAGATACTGCAACATATTAC<br>TGTCAACACAGTTGGGAGATTCCGCTCACGTTCG<br>GTGCTGGGACCAAGCTGGAGCTGAAA<br>(SEQ ID NO: 269) |
| ACI-7079-2509E5-Ab2 | 2509E5E5 | GAGGTCCAGCTGCAACAGTCTGGACCTGAACT<br>GGTGAAGCCTGGGGCTTCGCTGAAGATGTCCT<br>GCAAGGCTTCTGGATACTCATTCACTGACTAC<br>AACATGCACTGGGTGAAACAGAGCCGTGGAAA<br>GAGCCTTGAGTGGATTGGATATATTAACCCTAA<br>CAATGGTGTTCCCACGTATAAGCAGAAGTTCA<br>AGGGCAGGGCCACCTTGACTGTAAACCAGTCC<br>TCCAGCACAGCCTACATGGAGATCCGCAGCCT<br>GACATCGGAAGATTCTGCAGTCTATTACTGTAC<br>AAGAGGGGGTGATCACCGGTTTGCTTACTGGG<br>GCCAAGGGACTCTGGTCACTGTCTCTGCA<br>(SEQ ID NO: 278) | GACATTGTGCTGACCCAATCTCCAGCTTCTTTGG<br>CTGTGTCTCTAGGGCAGAGGGCCACCATCTCCTG<br>CAGAGCCAGCGAAAGTGTTGATTATTATGGCTTTA<br>GTTTTGTGAACTGGTTCCAACAGAAACCAGGACA<br>GCCACCCAAACTCCTCATCTATAGTGCGTCCTAC<br>AAAGGATCCGGGGTCCCTGTCAGGTTCAGTGGC<br>AGTGGGTCTGGGACAGACTTCAGTCTCAGCATCC<br>ATCCTATGGAGGCGGATGATACTGCAATGTATTT<br>CTGTCAGCAAAATAAGGAGGTTCCGCTCACGTTC<br>GGTGCTGGGACCAAGCTGGAGCTGAAA<br>(SEQ ID NO: 279) |
| ACI-7087-4119E10-Ab2 | 4119E10D12 | CAGGTTCAACTGCAGCAGTCTGGGGCTGAGCT<br>GGTGAGGCCTGGGGCTTCAGTGACGCTGTCC<br>TGCAAGGCTTCGGGCTACACATTTTCTGACTAT<br>GAAATGAACTGGGTGAAGCAGACACCTGTGCA<br>TGGCCTGGAATGGATTGGAGCTATTGATCCTG<br>AAACTGGTGGTACTGCCTACAATCAGAAGTTC<br>AAGGGCAAGGCCATACTGACTTCAGACAAATC<br>CTCCAGCACAGCCTACATGGAGCTCCGCAGC<br>CTGACATCTGAGGACTCTGCCGTCTATTACTG<br>TACAAGATTCCTGTTAATCGACTTTGACTATTG<br>GGGCCAAGGCACCACTCTCACAGTCTCCTCA<br>SEQ ID NO: 308 | GATGTCTTGATGACCCAAACTCCACTCTCCCTGC<br>CTGTCAGTCTTGGAGATCAAGCCTCCATCTCTTG<br>CAGATCTAGTCAGAGCATTGTACATAGTAATGGAA<br>ACACCTATTTAGAATGGTACCTGAAGAAAGCAGG<br>CCAGTCTCCAAAGGTCCTGATCTACAAAGTTTCCA<br>ACCGATTTTCTGGGGTCCCAGACAGGTTCAGTGG<br>CAGTGGATCAGGGACAGATTTCACACTCAAAATC<br>AGCAGGGTGGAGGCTGAGGATCTGGGAGTTTATT<br>ACTGCTTTCAAGGTTCACATGTTCCGTACACATTC<br>GGAGGGGGGACCGAGCTGGAAATAAAA<br>SEQ ID NO: 309 |
| ACI-7087-4125E6-Ab1 | 4125E6D5 | CAGGTCCAACTGCAGCAGCCTGGGACTGAACT<br>GGTGAAGCCTGGGGCTTCAGTGAGGCTGTCC<br>TGCAAGGCTTCTGGCTACGCCTTCACCAGCTA<br>CTGGATGCACTGGGTGAAGCAGAGGCCTGGA<br>CAAGGCCTTGAGTGGATTGGAAATATTAATCCT<br>AGCAATGGTGGTACTAACTACAATGAGAAGTT | GACATCCAGATGACCCAGTCTCCATCCTCCTTAT<br>CTGCCTCTCTGGGAGAAAGAGTCACTCTCACTTG<br>TCGGGCAAGTCAGGACATTGGTAATTACTTAAACT<br>GGCTTCAGCAGGAACCAGATGGAACTATTAAACG<br>CCTGATCTACGCCACATCCAGTTTAGATTCTGGT<br>GTCCCCAAAAGGTTCAGTGGCAGTAGGTCTGGGT |

TABLE 6-continued

| Nucleotide sequence of the heavy chain and light chain variable domains (VH and VL) | | | |
|---|---|---|---|
| Antibody Code | Hybridoma Code | VH | VL |
| | | CAAGAACAAGGCCACACTGACTGTAGACAAAT CCTCCAGCACAGCCTATATGCAGCTCAGCGGC CTGACATCTGAGGACTCTGCGGTCTATTATTGT GCAACGGGCCTTCACTACTGGGGCCAAGGCA CCACTCTCACAGTCTCCTCA SEQ ID NO: 318 | CAGATTATTCTCTCACCATCAGCAGCCTTGAGTCT GAAGATTTTGTAGACTATTACTGTCTACAATTTGC TAGTTCTCCGCTCACGTTCGGTCCTGGGACCAAA CTGGAACTGAAA SEQ ID NO: 319 |
| ACI-7088-4301D5-Ab2 | 4301D5B10 | CAGGTCCAGCTGCAGCAGTCTGGACCTGAGC TGGTGAGGCCTGGGGCTTCAGTGAAGATATCC TGCAAGGCTTCTGGCTACAGGTTCACAAGCTA CTATATACACTGGGTGAAGCAGAGGCCTGGAC AGGGACTTGAGTGGATTGGATGGATTTATCCT GGAAGTGATAATACTAAGCACAATGACAAGTT CAAGGGCAAGGCCACACTGACGGCAGACACA TCCTCCAGCACTGCCTACATGCAGCTCAGCAG CCTAACATCTGAGGACTCTGCGGTCTATTTCT GTGCAAGAGACTACGACGTGGGGTTTGGTTAC TGGGGCCAAGGGACTCTGGTCACTGTCTCTGC A SEQ ID NO: 328 | GACATTGTGCTGACCCAATCTCCAGCTTCTTTGG CTGTGTCTCTAGGGCAGAGGGCCACCATCTCCTG CAGAGCCAGCGAAAGTGTTGATAATTATGGCATT AGTTTTATGAACTGGTTCCAACAGAAACCAGGAC AGCCACCCAAACTCCTCATCTATGCTGCATCCAA CCAAGGATCCGGGGTCCCTGCCAGGTTTAGTGG CATTGGGTCTGGGACAGACTTCAGCCTCAACATC CATCCTATGGAGGAGGATGATACTGCAATGTATTT CTGTCAGCAAAGTCAGGAGGTTCCGCTCACGTTC GGTGCTGGGACCAAGCTGGAGCTGAAA SEQ ID NO: 329 |
| ACI-7088-4301E12-Ab2 | 4301E12B9 | GATGTACAGCTTCAGGAGTCAGGACCTGGCCT CGTGAAACCTTCTCAGTCTCTGTCTCTCACCTG CTCTGTCACTGGCTACTCCATCACCAGTGGTT ATTACTGGAACTGGATCCGGCAGTTTCCAGGA AACAAACTGGAATGGATGGGCTACATAAGCGA CGATGGTAGTAAAAATTACAACCCATCTCTCAA AAATCGAATCTCCATCACTCGTGACACATCTAA GAACCAGCTTTTCATGAAGTTGAATTCTGTGAC TACTGAGGACACAGCCACATATTACTGTGCAA GAGGCGATTCCCGCCTGGGCCAAGGGACTCT GGTCACTGTCTCTGCA SEQ ID NO: 338 | GATGTTGTGTTGACCCAGACTCCACTCACTTTGTC GGTTACCATTGGACAACCAGCCTCCATCTCTTGC AGGTCAAGTCAGAACCTCTTAGATAGTGATGGAG AGACATATTTGAATTGGTTGTTACAGAGGCCAGG CCAGTCTCCAAAGCGCCTAATCTATCTGGTGTCT GAGCTGGACTCTGGAGTCCCTGACAGGTTCACTG GCAGTGGATCAGGGACAGATTTCACACTGAAAAT CAGCAGAGTGGAGGCTGAGGATTTGGGAGTTTAT TATTGCTGGCAAGGTACACATTTTCCTCAGACGTT CGGTGGAGGCACCAAGCTGGAAATCATT SEQ ID NO: 339 |
| ACI-7088-4301H3-Ab2 | 4301H3A5 | GAGGTCCAGCTGCAACAATCTGGACCTGAACT GGTGAAGCCTGGGGCTTCAGTGAAGATATCTT GTAAGGCTTCTGGATACACGTTCGCTGACTAC TTCATGAACTGGGTGAAGCAGAGCCATGGAAA GAGCCTTGAGTGGATTGGAGATATTAATCCTA ACAATGGTGGTACTACCTACAACCAGAAGTTC AAGGGCAAGGCCACATTGACTGTAGACAAGTC CTCCAACACAGCCTACATGGAGCTCCGCAGCC TGACATCTGAGGACTCTGCAGTCTACTACTGT GCAAGAGGTAGAAACTACGCTATGGACTACTG GGGTCAAGGAACCTCAGTCACCGTCTCCTCA SEQ ID NO: 348 | GACATTGTGATGTCACAGTCTCCATCCTCCCTGG CTGTGTCAGCAGGAGAGAAGGTCACTATGAGCTG CAAATCCAGTCAGAGTCTCCTCAACAGTAGAACC CGAAAGAATTATTTGGCTTGGTACCAGCAGAAAC CAGGGCAGTCTCCTAAATTGTTGATCTACTCGGC ATCCACTAGGGAATCTGGGGTCCCTGATCGCTTC ACAGGCAGTGGATTTGGGACAGATTTCACTCTCA CCATCAGCAGTGTGCAGGCTGAGGACCTGGCAG TTTATTACTGCAAGCAATCTTATGATCTGTGGACG TTCGGTGGAGGCACCAAGCTGGAAATCAAA SEQ ID NO: 349 |
| ACI-7088-4303A1-Ab1 | 4303A1E7 | GAGGTTCAGCTGCAGCAGTCTGGGGCTGAAC TTGTGAGGCCAGGGGCCTCAGTCAAGTTGTCC TGCACAGCTTCTGGCTTTAACATTAAAGACGAC TATATGCACTGGGTGAAACAGAGGCCTGAACA GGGCCTGGAGTGGATTGGATGGATTGATCCTG AGAATGGTGATTCTGAATATGCCTCGAAGTTC CAGGGCAAGGCCACTATGACAGCAGACACATC CTCCAACACAGCCTACCTGCAACTCAGCAGCC TGACATCTGAGGACACTGCCGTCTATTATTGTA AAACATGGGGGACAGCTCAGGCCCTCTTTCCT TACTGGGGCCAAGGGACTCTGGTCACTGTCTC TGCA SEQ ID NO: 358 | GACATTGTGATGACCCAGTCTCAAAAATTCATGTC CACATCAGTAGGAGACAGGGTCAGCATCACCTGC AAGGCCAGTCAGAATGTGGGTACTTCTGTAGGCT GGTATCAACAAAAAGCAGGACAATCTCCTAAACTA CTGATTCACTCGGCATCTAATCGGTACACTGGAG TCCCTGATCGCTTCACAGGCAGTGGATCTGGGAC AGATTTCACTCTCACCATCAACAATATGCAGTCTG AAGACCTGGCAGATTATTTCTGCCAGCAATATAGA AGTTATCCGCTCACGTTCGGTGCTGGGACCAAGC TGGAGCTGAAA SEQ ID NO: 359 |
| ACI-7088-4303A3-Ab1 | 4303A3E4 | CAGGTTCAACTGCAGCAGTCTGGGGCTGAGCT GGTGAGGCCTGGGGCTTCAGTGACGCTGTCC TGCAAGGCTTCGGGCTACACATTTACTGACTA TGAAATGCACTGGGTGAAACAGACACCTGTGC ATGGCCTGGAGTGGATTGGAGTTATTGATCCT GAAACTGGTGGTGCTGTCCAGAATCAGAAGTT CAAGGGCAAGGCCATACTGACTGCAGACAATT CCTCCAGCACAGCCTACATGGACCTCCGCAGC CTGACATCTGAGGACTCTGCCGTCTATAACTG TGCAATGGGTGCGGCATTACGGCTTGCTTACT GGGGCCAAGGGACTCTGGTCACTGTCTCTGC A SEQ ID NO: 368 | GATGTTTTGATGACCCAAACTCCACTCTCCCTGC CTGTCAGTCTTGGAGATCAAGCCTCCATCTCTTG CAGATCTAGTCAGAGCATTGTACATAGTAATGGAA ACTCCTATTTAGAATGGTACCTGCAGAAACCAGG CCAGTCTCCAAAGCTCCTGATCTACAAAGTTTCCA ACCGATTTTCTGGGGTCCCAGACAGGTTCAGTGG CAGTGGATCAGGGACAGATTTCACACTCAAGATC AACAGAGTGGAGGCTGAGGATCTGGGAGTTTATT ACTGCTTTCAAGGTTCACATGTTCCATTCACGTTC GGCTCGGGGACAAAGTTGGAAATAAAA SEQ ID NO: 369 |

TABLE 6-continued

Nucleotide sequence of the heavy chain and light chain variable domains (VH and VL)

| Antibody Code | Hybridoma Code | VH | VL |
|---|---|---|---|
| ACI-7088-4303B6-Ab2 | 4303B6C11 | GAGGTCCAGCTGCAACAATCTGGACCTGAGCTGGTGAAGCCTGGGGCTTCAGTGAAGATATCCTGTAAGGCTTCTGGATACACGTTCACTGACTACTACATGAACTGGGTGAAGCAGAGCCATGGAAAGAGCCTTGAGTGGATTGGAGATATTAATCCTAACAATGGTGGTACTACCTACAACCAGAAGTTCAAGGACAAGGCCACATTGACTGTGGACAGGTCCTCCAGCACAGCCTACATGGAACTCCGCAGCCTGACATCTGGGGACTCTGCAGTCTATTACTGTGCAAGATCGGGGTACTCCGGTAGTCGCCTCTACTATGCTATGGACTACTGGAGTCAAGGATCCTCAGTCACCGTCTCCTCA SEQ ID NO: 378 | GACATTGTGATGTCACAGTCTCCATCCTCCCTGGCTGTGTCAGCACGAGAGAAGGTCACTATGAGCTGCAAATCCAGTCAGAGTCTGCTCAACAGTAGAACCCGAAAGAACTACTTGGCTTGGTACCAGCAGAAACCAGGGCAGTCTCCTAAACTGCTGATCTTCTGGGCTTCCACTAGGGAATCTGGGGTCCCTGATCGCTTCACTGGCAGTGGATCTGGGACAGATTTCACTCTCACCATCAGCAGTGTGCAGGCTGAAGACCTGGCAGTTTATTACTGCAAACAATCTTATGATCTGTGGACGTTCGGTGGCGGCACCAAGCTGGAAATCAAA SEQ ID NO: 379 |
| ACI-7088-4303H6-Ab1 | 4303H6D7 | GAGGTTCAGCTGCAGCAGTCTGGGGCTGAGCTTGTGAGGCCAGGGGCCTCAGTCAAGTTGTCCTGCACAGCTTCTGGCTTTAACATTCAAGACGACTATATGCACTGGGTGAAGCAGAGGCCTGAACAGGGCCTGGAGTGGATTGGTTGGATTGATCCTGAGAATGGTGATACTGAATATGCCTCGAAATTCCAGGGCAAGGCCACTTTAACAGCAGACACATCCTCCAACACAGCCTACCTGCAGCTCAGCAGACTGACATCTGAGGACACTGCCGTCTATTACTGTACTACAGCGGGCTCAGGCGTCCAACTCTTTGACTACTGGGGCCAAGGCACCACTCTCACAGTCTCCTCA SEQ ID NO: 388 | GACATTTTGATGACCCAGTCTCAAAAATTCATGTCCACATCAGTAGGAGACAGGGTCAGCGTCACCTGCAAGGCCAGTCAGAATGTGGGTACTAATGTAGCCTGGTATCAACAGAAACCAGGGCAATCTCCTAAACCACTGATTTCCTCGGCATCCTCCCGGTACAGTGGCGTCCCTGATCGCTTCACAGGCAGTGGATCTGGGACAGATTTCACTCTCACCATCAGCAATGTGCAGTCTGAAGACTTGGCAGACTATTTCTGTCAGCAATATAACCGCTATCCTCTCACGTTCGGTGCTGGGACCAAGCTGGAGCTGAAA SEQ ID NO: 389 |
| ACI-7088-4305H7-Ab1 | 4305H7A4 | GAGGTTCAGCTGCAGCAGTCTGGGGCTGAACTTGTGAGGCCAGGGGCCTCAGTCAAGTTGTCCTGCACAGCTTCTGGCTTTAACATTAAAGACGACTATATGCACTGGGTGAAGCAGAGGCCTGAACAGGGCCTGGAGTGGATTGGATGGATTGATCCTGAGAATGGTGATACTGAATATGCCTCGAAGTTCCAGGGCAAGGCCACTATGATAGCAGACACATCCTCCAACACAGCCTACCTGCAACTCAGCAGCCTGACATCTGAGGACACTGCCGTCTATTATTGTAAAACATGGGGGACAACTCAGGCCCTCTTTCCTTACTGGGGCCAAGGGACTCTGGTCACTGTCTCTGCA SEQ ID NO: 398 | GACATTGTGATGACCCAGTCTCAAAAATTCATGTCCACATCAGTAGGAGACAGGGTCAGCATCACCTGCAAGGCCAGTCAGAATGTGGGTACTGCTGTAGGCTGGTATCAACAAAAAGCAGGACAATCTCCTAAACTACTGATTCACTCGGCATCCAATCGGTACACTGGAGTCCCTGATCGCTTCACAGGCAGTGGATCTGGGACAGATTTCACTCTCACCATCAACAATATGCAGTCTGAAGACCTGGCAGATTATTTCTGCCAGCAATATAGAAGTTATCCGCTCACGTTCGGTGCTGGGACCAAGCTGGAGCTGAAA SEQ ID NO: 399 |
| ACI-7088-4317A4-Ab1 | 4317A4D2 | GAGGTTCAGCTGCAGCAGTCTGGGGCTGAACTTGTGAGGCCAGGGGCCTCAGTCAAGTTGTCCTGCACAGCTTCTGGCTTTAACATTAAAGACGACTATATGCACTGGGTGAAGCAGAGGCCTGAACAGGGCCTGGAGTGGATTGGATGGATTGATCCTGAGAATGGTGATACTGAATATGCCTCGAAGTTCCAGGGCAAGGCCACTATGACAGCAGACACATCCTCCAACACAGCCTACCTGCAACTCAGCAGCCTGACATCTGAGGACACTGCCGTCTATTATTGTAAAACATGGGGGACAACTCAGGCCCTCTTTCCTTACTGGGGCCAAGGGACTCTGGTCACTGTCTCTGCA SEQ ID NO: 408 | GACATTGTGATGACCCAGTCTCAAAAGTTCATGTACACATCAGTGGGAGACAGGGTCAGCATCACCTGCAAGGCCAGTCAGAATGTGGGTAATGCTGTAGGCTGGTATCAACAAAAAGCAGGACAATCTCCTAAACTACTGATTCACTCGGCATCCAATCGGTACACTGGAGTCCCTGATCGCTTCACAGGCACTGGATCTGGGACAGATTTCACTCTCACCATCAACAATATGCAGTCTGAAGACCTGGCAGATTATTTCTGCCAGCAATATAGAAGTTATCCGCTCACGTTCGGTGCTGGGACCAAGCTGGAGCTGAAA SEQ ID NO: 409 |
| ACI-7089-4409F1-Ab1 | 4409F1A8 | GATGTACAGCTTCAGGAGTCAGGACCTGGCCTCGTGAAACCTTCTCAGTCTCTGTCTCTCACCTGCTCTGTCACTGGCTACTCCATCACCAGGGGTTATTACTGGAACTGGATCCGGCAGTTTCCAGGAAACAAACTGGAATGGATGGGCTACATAAGCTACGATGGTAGCAATAACTACAACCCATCTCTCAGAAATCGAATCTCCATCACTCGTGACACATCTAAGAACCAGTTTTTCCTGAAGTTGAAATCTGTGACTACTGAGGACACAGCCACATATTTCTGTGCAAGAGGGGATAGTAACTGGGGCCAAGGCACCACTCTCACAGTCTCCTCA SEQ ID NO: 418 | GATGTTGTGATGACCCAGACTCCACTCACTTTGTCGGTTACCATTGGACAACCAGCCTCCATCTCTTGCAAGTCAAGTCAGAGCCTCTTAGATAGTGATGGAGAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGTAGTGGATCAGGGACAGATTTCACACTGAAAATCAGCAGAGTGGAGGCTGAGGATTTGGGAGTTTATTATTGCTGGCAAGGTACACATTTTCCTCAGACGTTCGGTGGAGGCACCAAGTTGGAAATCAAA SEQ ID NO: 419 |
| ACI-7089-4415G5-Ab1 | 4415G5A11 | CAGGTTCAGCTGCAGCAGTCTGGAGCTGAGCTGGCGAGGCCTGGGGCTTCAGTGAAGGTGTCCTGCAAGGCTTCTGGCTACACCTTCACAAGCTCTGGTATAAGCTGGTTGAAGCACAGAACTGGACAGGGCCTTGAGTGGATTGGAGACATTTATCCTAGAAGTGGTAATACTTACTACAATGAGAAATTC | GATATTGTGATAACCCAGGATGACCTCTCCAATCCTGTCACTTCTGGAGAATCAGTTTCCATCTCCTGCAGGTCTAGTAAGAGTCTCCTATATAAGGATGGGAAGACATACTTGAATTGGTTTCTGCAGAGACCAGGACAATCTCCTCAGCTCCTGATCTATTTGATGTCCACCCGTGCATCAGGAGTCTCAGACCGGTTTAGTGG |

TABLE 6-continued

Nucleotide sequence of the heavy chain and light chain variable domains (VH and VL)

| Antibody Code | Hybridoma Code | VH | VL |
|---|---|---|---|
| | | AAGGACAAGGCCACACTGACTGCAGACAAATC<br>CTCCAGCACGGCGTACATGGAGCTCCGCAGC<br>CTGACATCTGAGGACTCTGCGGTCTATTTCTG<br>TGCAAGTGGTAACTACTGGGGCCAAGGCACCA<br>CTCTCACAGTCTCCTCA<br>SEQ ID NO: 428 | CAGTGGGTCAGGAACAGATTTCACCCTGGAAATC<br>AGTAGAGTGAAGGCTGAGGATGTGGGTGTGTATT<br>ACTGTCAACAACTTTTAGAGTATCCGCTCACGTTC<br>GGTGCTGGGACCAAGCTGGAGCTGAAA<br>SEQ ID NO: 429 |
| ACI-7089-4417G6-Ab1 | 4417G6B12 | CAGGTTCAACTGCAGCAGTCTGGGGCTGAGTT<br>GGTGAGGCCTGGGGCTTCAGTGACGCTGTCC<br>TGCAAGGCTTCGGGCTACACATTTACTGGCTA<br>TGAAATGCACTGGGTGAAGCAGACACCTGTGC<br>ATGGCCTGGAATGGATTGGAGCTATTGATCCT<br>GAAACCGGTGGAACTGCCTATATTCAGAAGTT<br>CAAGGGCAAGGCCACACTGACTGCAGACAAAT<br>CCTCCAGCACAGCCTACATGGAGCTCCGCAG<br>CCTGACATCTGAGGACTCTGCCGTCTATTACT<br>GTACAAGAGGCTGGGACTATTTTGACTACTGG<br>GGCCAAGGCACCACTCTCACAGTCTCCTCA<br>SEQ ID NO: 438 | GATGTTGTGATGACCCAAACTCCACTCTCCCTGC<br>CTGTCAGTCTTGGAGATCAAGCCTCCATCTCTTG<br>CAGATCTAGTCAGAGCCTTCTACACAGTAATGGA<br>TTCACCTATTTACATTGGTACCTGCAGAAGCCAG<br>GCCAGTCTCCAAAGCTCCTGATCTACAGAGTTTC<br>CAATCGATTTTCTGGGGTCCCAGACAGGTTCAGT<br>GGCAGTGGATCAGGGACAGATTTCACACTCAAGA<br>TCAGCAGAGTGGAGGCTGAGGATCTGGGAGTTTA<br>TTTCTGCTCTCAAAGTACACATGTTCCGTACACGT<br>TCGGAGGGGGGACCAAGCTGGAAATAAAA<br>SEQ ID NO: 439 |
| ACI-7089-4418C5-Ab1 | 4418C5G1 | GATGGACAACTTCAGGAGTCAGGACCTGGCCT<br>CGTGAAACCTTCTCAGTCTCTGTCTCTCACCTG<br>CTCTGTCACTGGCTACTCCATCACCAGTGGAT<br>ATTACTGGAACTGGATCCGGCAGTTTCCAGGA<br>AACAAACTGGAATGGATGGGCTACATAAACTA<br>CGATGGTAGCAATAACTACAACCCATCTCTCAA<br>AAATCGAATCTCCATCACTCGTGACACATCTAA<br>GAATCAGTTTTTCCTGAAGTTCAATTTTGTGAC<br>TACTGAGGACACAGCCACATATTACTGTGTGA<br>GGGGGGACGTCTACTGGGGCCAAGGCACCAC<br>TCTCACAGTCTCCTCA<br>SEQ ID NO: 448 | GATGTTGTGATGACCCAGACTCCACTCACTTTGT<br>CGGTTACCATTGGACAACCAGCCTCCATCTCTTG<br>CAAGTCAAGTCAGAGCCTCTTAGATAGTGATGGA<br>GAGACATATTTGAATTGGTTATTACAGAGGCCAG<br>GCCAGTCTCCAAAGCGCCTAATCTATCTGGTGTC<br>TAAACTGGACTCTGGAGTCCCTGACAGGTTCACT<br>GGCAGTGGATCAGGGACAGATTTCACACTGAAAA<br>TCAGCAGAGTGGAGGCTGAGGATTTGGGAGTTTA<br>TTATTGCTGGCAAGGTACACATTTTCCTCAGACGT<br>TCGGTGGAGGCACCAAGCTGGAAATCAAA<br>SEQ ID NO: 449 |
| ACI-7089-4418F6-Ab1 | 4418F6G7 | CAGGTTCAGCTGCAGCAGTCTGGAGCTGAGCT<br>GGCGAGGCCTGGGGCTTCAGTGAAGGTGTCC<br>TGCAAGGCTTCTGGCTACACCTTCACAAGTTC<br>TGGTATAAGCTGGTTGAAGCACAGAACTGGAC<br>AGGGCCTTGAGTGGATTGGAGACATTTATCCT<br>AGAAGTGGTAATACTTACTACAATGAGAAATTC<br>AAGGACAAGGCCACACTGACTGCAGACAAATC<br>CTCCAGCACGGCGTACATGGAGCTCCGCAGC<br>CTGACATCTGAGGACTCTGCGGTCTATTTCTG<br>TTCAAGTGGTAACTACTGGGGCCAAGGCACCA<br>CTCTCACAGTCTCCTCA<br>SEQ ID NO: 458 | GATATTGTGATAACCCAGGATGACCTCTCCAATC<br>CTGTCACTTCTGGAGAATCAGTTTCCATCTCCTGT<br>AGGTCTAGTAAGAGTCTCCTATATAAGGATGGGA<br>AGACATACTTGAATTGGTTTCTGCAGAGACCAGG<br>ACAATCTCCTCAGCTCCTGATCTATTTGATGTCCA<br>CCCGTGCATCAGGAGTCTCAGACCGGTTTAGTGG<br>CAGTGGGTCAGGAACAGATTTCACCCTGGAAATC<br>AGTAGAGTGAAGGCTGAGGATGTGGGTGTGTATT<br>ACTGTCAACAACTTTTAGAGTATCCGCTCACGTTC<br>GGTGCTGGGACCAAGCTGGAGCTGAAA<br>SEQ ID NO: 459 |
| ACI-8033-5A12-Ab1 | 917.5A12A11C9 | CAGGTCCACCTGAAGCAGTCTGGGGCTGACC<br>TGGTGAGGCCTGGGGCTTCAGTGAAGCTGTC<br>CTGCAAGGCGTCTGGCTACACTTTCACTGACT<br>ACTATATAAACTGGGTGAAGCAGAGGCCTGGA<br>CAGGGACTTGAGTGGATTGCAAGGATTTATCC<br>TGGAAGTGGTAATACTTACTACAATGAGAAGTT<br>CAAGGGCAGGGCCACACTGAGTGCAGAAAAA<br>TCCTCCACCACTGCCTACATGCAGCTCAGCAG<br>CCTGACATCTGAGGACTCTGCTGTCTATTTCTG<br>TGTAGTGGGGTACTACGGTGCCTGGGGCCAA<br>GGCACCACTCTCACAGTCTCCTCA<br>SEQ ID NO: 468 | GATGTTGTGATGACCCAAACTCCACTCTCCCTGC<br>CTGTCAGTCTTGGAGATCAAGCCTCCATCTCTTGT<br>AGATCTAGTCAGAGCCTTGTACACAGTAATGGAA<br>AAACCCATTTACATTGGTACCTGCAGAAGCCAGG<br>CCAGTCTCCAAAGCTCCTGATCTATAAAGTTTCCA<br>ACCGATTTTCTGGGGTCCCAGACAGGTTCAGTGG<br>CAGTGGATCAGGGACAGATTTCACACTCAAGATC<br>AGCAGAGTGGAGGCTGAGGATCTGGGAGTTTATT<br>TCTGCTCTCAAAGTACACATGTTCCGTGGACGTT<br>CGGTGGAGGCACCAAGCTGGAAATCAAA<br>SEQ ID NO: 469 |
| ACI-8033-25A3-Ab1 | 917.25A3E9F6 | GAGGTGCAGCTTGTTGAGTCTGGTGGAGGATT<br>GGTGCAGCCTAAAGGGTCATTGAAACTCTCAT<br>GTGCAGCCTCTGGATTCAGCTTCAATACCTAC<br>GCCATGAACTGGGTCCGCCAGGCTCCAGGAA<br>AGGGTTTGGAATGGGTTGCTCGCATAAGAAGT<br>AAAAGTAATAATTTTGCAACATATTATGCCGAT<br>TCAGTGAAAGACAGATTCACCATCTCCAGAGA<br>TGAATCAGAAAGCATGCTCTATCTGCAAATGAA<br>CAACTTGAAAACTGAGGACACAGCCATGTATT<br>ACTGTGTGAGGTCCTTTGACTACTGGGGCCAA<br>GGCACCACTCTCACAGTCTCCTCA<br>SEQ ID NO: 478 | GACATCAAGATGACCCAGTCTCCATCTTCCATGTA<br>TGCATCTCTAGGAGAGAGAGTCACTATCACTTGC<br>AAGGCGAGTCAGGACATTAATAGCTATTTAAGCT<br>GGTTCCAGCAGAAACCAGGGAAATCTCCTAAGAC<br>CCTAATCTATCGTGCAAAAAGATTGGTAGATGGG<br>GTCCCATCAAGGTTCAGTGGCAGTGGATCTGGGC<br>AAGATTATTCTCTCACCATCAGCAGCCTGGAGTAT<br>GAAGATATGGGAATTTATTATTGTCTACAGTATGA<br>TGAGTTTCCATTCACGTTCGGCTCGGGGACAAAG<br>TTGGAAATAAAA<br>SEQ ID NO: 479 |
| ACI-8033-1G10-Ab1 | 917.1G10A10F6 | GATGTGCAGCTTCAGGAGTCAGGACCTGGCCT<br>GGTGAAACCTTCTCAGACAGTGTTCCTCACCT<br>GCACTGTCACTGGCATTTCCATCACCACTGGA | GATGTTGTGATGACCCAAACTCCACTCTCCCTGC<br>CTGTCAGTCTTGGAGATCAAGCCTCCATCTCTTG<br>CAGATCTAGTCAGAGCCTTGTACACAGTAATGGA |

TABLE 6-continued

| Nucleotide sequence of the heavy chain and light chain variable domains (VH and VL) | | | |
|---|---|---|---|
| Antibody Code | Hybridoma Code | VH | VL |
| | | AATTACAGGTGGAGCTGGATCCGGCAGTTTCC AGGAAACAAACTGGAGTGGATAGGGTACATAT ACTACAGTGGTACCATTACCTACAATCCATCTC TCACAAGTCGAACCACCATCACTAGAGACACT CCCAAGAACCAGTTCTTCCTGGAAATGAACTC TTTGACTGCTGAGGACACAGCCACATACTACT GTGCACGGATTTACTACGGTAATGCTATGGAC TACTGGGGTCAAGGAACCTCAGTCACCGTCTC CTCA SEQ ID NO: 488 | AACACCTATTTACATTGGTACCTGCAGAAGCCAG GCCAGTCTCCAAAGCTCCTGATCTACAAAGTTTC CAACCGATTTTCTGGGGTCCCAGACAGGTTCAGT GGCAGTGGATCAGGGACAGATTTCACACTCAAGA TCAGCAGAGTGGAGGCTGAGGATCTGGGAGTTTA TTTCTGCTCTCAAAGTACACATGTTCCTCACACGT TCGGAGGGGGGACCAAGCTGGAAATAAAA SEQ ID NO: 489 |
| ACI-8033-19A2-Ab1 | 917.19A2E9E5 | GAGGTGCAACTTGTTGAGTCTGGTGGAGGATT GGTGCAGCCTAAAGGGTCATTGAAACTCTCAT GTGCAGCCTCTGGATTCAGCTTCAATACCTAC GCCATGAACTGGGTCCGCCAGGCTCCAGGAA AGGGTTTGGAATGGGTTGCTCGCATAAGAAGT AAAAGTAATAATTATGCAACATATTATGTCGATT CAGTGAAAGACAGATTCACCATCTCCAGAGAT GATTCAGAAAGCATGCTCTATCTGCAAATGAAC AACTTGAAAACTGAGGACACAGCCCTGTATTA CTGTGTGAGCGAATCCGCTTACTGGGGCCAAG GGACTCTGGTCACTGTCTCTGCA SEQ ID NO: 498 | GATGTTGTGATGACCCAAACTCCACTCTCCCTGC CTGTCAGTCTTGGAGATCAAGCCTCCATCTCTTG CAGATCTAGTCAGAGCCTTGTACACAGTAATGGA AACACCTATTTATATTGGTACCTGCAGAAGCCAG GCCAGTCTCCAAAGCTCCTGATCTACAAAGTTTC CAACCGACTTTCTGGGGTCCCAGACAGGTTCAGT GGCAGTGGATCAGGGACAGATTTCACACTCAAGA TCAGCAGAGTGGAGGCTGAGGATCTGGGAGTTTA TTTCTGCTCTCAAAGTACACATGTTCCATTCACGT TCGGCTCGGGGACAAAGTTGGAAATAAAA SEQ ID NO: 499 |
| ACI-8033-8010-Ab1 | 917.8010C6G3 | GATGTACAGCTTCAGGAGTCAGGACCTGGCCT CGTGAAACCTTCTCAGTCTCTGTCTCTCACCTG CTCTGTCACTGGCCAATCCATCACCAGTGGTT ATTACTGGAACTGGATCCGGCAATTTCCAGGA AACAAACTGGAATGGATGGGCTACATAAGCAA CGATGGTAGCAGTAAAACCAACCCATCTCTCA CAAATCGAATCTCCGTCACTCGTGACACATCTA AGAACCAGGTTTTCCTGAAGTTGAAATCTGTGA CTACTGAGGACACAGCCACATATTACTGTGTA AGAGGGGACCAGCACTGGGGCCAAGGCACCG CTCTCACAGTCTCCTCA SEQ ID NO: 508 | GATGTTGTGTTGACCCAGACTCCACTCACTTTGTC AGTTACCATTGGGCAACCAGCCTCCATCTCTTGC AAGTCAAGTCAGAGCCTCTTAGATAGTGATGGAG AGACATATTTGAATTGGTTGTTACAGAGGCCAGG CCAGTCTCCAAAGCGCCTAATCTATCTGGTGTCT GAACTGGACTCTGGAGTCTCTGACAGGTTCACTG GCAGTGGTTCAGGGACAGATTTCACACTGAAAAT CAGCAGACTGGAGGCTGAGGATTTGGGAGTTTAT TATTGCTGGCAAGGTACACATTTTCCTCAGACGTT CGGTGGAGGCACCAAGCTGGAAATCAAA SEQ ID NO: 509 |
| ACI-8033-7A2-Ab1 | 917.7A2B6A9 | CAGGTCCAACTACAGCAGCCTGGGACTGAACT GGTGAAGCCTGGGGCTTCAGTGAACCTGCCC TGCAAGGCTTCTGGCTACACCTTCACCAGCTA CTGGATGCACTGGGTGAAGCAGAGGCCTGGT CAAGGCCTTGATTGGATTGGAAATGTTAATCCT AACAATAGTGATAGTAATTACAATGAGAAGTTC AAGAGGAAGGCCACACTGACTGTAGACAAATC CTCCAGCACAGCCTACATGCACCTCAGCAGCC TGACATCTGAGGACTCTGCGGTCTATTATTGT GCAAGATCTCCTTACTACGGTGGCCGTTACCT TGACTACTGGGGCCAAGGCACCACTCTCACAG TCTCCTCA SEQ ID NO: 518 | GACATTGTGATGTCACAGTCTCCATCCTCCCTAG CTGTGTCAGTTGGAGAGAAGGTTACTATGACCTG CAAGTCCAGTCAGAGCCTTTTATATAGAAGCAATC AAAAGAACTACTTGGCCTGGTACCAGCAGAAACC AGGACAGTCTCCTAAACTGTTGATTTACTGGGCAT TCACTAGGGAATCTGGGGTCCCTGATCGCTTCAC AGGCAGTGGATCTGGGACAGATTTCACTCTCACC ATCAGCAGTGTGAAGGCTGAAGACCTGGCAGTTT ATTACTGTCAGCAATATTATAGCTATCCTCTCACG TTCGGTGCTGGGACCAAGCTGGAGCTGAAA SEQ ID NO: 519 |
| ACI-8033-1A12-Ab1 | 917.1A12C1B4 | CAGGTCCACCTGAAGCAGTCTGGGGCTGACC TGGTGAGGCCTGGGGCTTCAGTGAAGCTGTC CTGCAAGGCGTCTGGCTACAGTTTCACTGACT TTTATATAAATTGGGTGAAGCAGACGCCTGGA CAGGGACTTGAGTGGATTGCGAGGATTTATCC TGGAAATAATAATACTTTCTACAATGAGAAATT CAAGGGCAAGGCCACACTGAGTGCAGAAAAAT CCTCCACCACTGCCTACATGCAGCTCAGCAGC CTGACATCTGAGGACTCTGCTGTCTATTTCTGT GTAGTGGGGTACTACGGTGCCTGGGGCCAAG GCACCACTCTCACAGTCTCCTCA SEQ ID NO: 528 | GATGTTGTGATGACCCAAACTCCACTCTCCCTGC CTGTCAGTCTTGGAGATCAAGCCTCCATCTCTTG CAGATCTAGTCAGAGCCTTGTACACAGTAATGGA AACACCCATTTGCATTGGTACCTGCAGAAGCCAG GCCAGTCTCCAAAGCTCCTGATCTATAAAGTTTCC AACCGATTTTCTGGGGTCCCAGACAGGTTCAGTG GCAGTGGATCAGGGACAGATTTCACACTCAAGAT CAGCAGAGTGGAGGCTGAGGATCTAGGATTTTAT TTCTGCTCTCAAAGTACACATGTTCCGTGGACGTT CGGTGGAGGCACCAAGCTGGAAATCAAA SEQ ID NO: 529 |
| ACI-8033-4F3-Ab1 | 917.4F3F4G6 | GAGGTCCAGCTGCAACAATCTGGACCTGAGCT GGTGAAGCCTGGGGCTTCAGTGAAGATATCCT GTAAGGCTTCTGGATACACGTTCACTGACTAC TACATGAACTGGGTGAAGCAGAGCCATGGAAA GAGCCTTGAATGGATTGGAGATATTAATCCTAA CACTGGTACTAATAGCTACAACCAGAAGTTCAA GGGCAGGGCCTCACTGACTGTAGACAAGTTCT CCAGCGCAGCCTACATGGAGCTCCGCAGCCT | GACATTGTGATGTCACAGTCTCCATCCTCCCTGG CTGTGTCAGCAGGAGAGAAGGTCACTATGAGCTG CAAATCCAGTCAGAGTCTGCTCAACAGTAGAACC CGAAAGAACTACTTGGCTTGGTACCAGCAGAAAC CAGGGCAGTCTCCTAAACTGCTGATCTACTGGGC ATCCACTAGGGAATCTGGGGTCCCTGATCGCTTC ACAGGCAGTGGATCTGGGACAGATTTCACTCTCA CCATCAGCAGTGTGCAGGCTGAAGACCTGGCAG |

TABLE 6-continued

Nucleotide sequence of the heavy chain and light chain variable domains (VH and VL)

| Antibody Code | Hybridoma Code | VH | VL |
|---|---|---|---|
| | | GACATCTGAGGACTCTGCAGTCTATTACTGTG CAAGAACCGGCTATGGCGACCCTATTTCCTCA TATTACTATGCTCTGGACTACTGGGGTCAAGG AACCTCAGTCACCGTCTCCTCA SEQ ID NO: 538 | TTTATTACTGCAAGCAATCTTATAATCTGTGGACG TTCGGTGGAGGCACCAAGCTGGAAATCAAA SEQ ID NO: 539 |
| ACI-8033-17F5-Ab1 | 917.17F5F5G9 | GAGGTCCAACTGCAACAATCTGGACCTGAGCT GGTGAAGCCTGGGGCTTCAGTGAAGATATCCT GTAAGGCTTCTGGATACACGTTCACTGACTAC TTCATGAACTGGGTGAAGCAGAGCCATGGAAA GAGCCTTGAGTGGATTGGAGATATTAATCCTA ACATTGATGTTACTAACTACAACCAGAAGTTCA AGGGCAAGGCCACATTGACTGTAGACAAGTCC TCCAGCACAGCCTACATGGAGCTCCGCAGCCT GACATCTGAGGACTCTGCAGTCTATTACTGTG CAAGAGGGCGGGACTATGCTATGGACTTCTGG GGTCAAGGAACCTCAGTCACCGTCTCCTCA SEQ ID NO: 548 | GACATTGTGATGTCACAGTCTCCATCCTCCCTGG CTGTGTCAGCAGGAGAGAAGGTCACTATGAGCTG CAAATCCAGTCAGAGTCTGCTCAACAGTAGAACC CGAAAGAACTACTTGGCTTGGTACCAGCAGAAAC CAGGGCAGTCTCCTAAACTGCTGATCTACTGGGC ATCCACTAGGGAATCTGGGGTCCCTGATCGCTTC ACAGGCAGTGGATCTGGGACAGATTTCACCCTCA CCATCAGCAGTGTGCAGGCTGAAGACCTGGCAG TTTATTACTGCAAGCAATCTTATGATCTGTGGACG TTCGGTGGAGGCACCAAGCTGGAAATCAAA SEQ ID NO: 549 |
| ACI-8033-18C11-Ab1 | 917.18C11A11F10 | CAGGTCCAACTCCAGCAGCCTGGGGCTGAGC TTGTGAAGCCTGGGGCTTCAGTGAAGATGTCC TGCAAGGCTGCTGGCTACACCTTCAGCAGCTA CTGGATAACCTGGGTGAGGCAGAGGCCTGGA CAAGGCCTTGACTGGATTGGAGATATTTATCCT GGTGGAGGTGTTACTAACTACAATGAGAAGTT CAAGACCAAGGCCACACTGACTGTAGACACAT CCTCCAGCACAGCCTACATGCAGCTCAGCAGC CTGACATCTGAGGACTCTGCGGTCTATTACTG TGCGACAGCTCAGACTACGTTTGCTTACTGGG GCCAAGGGACTCTGGTCACTGTCTCTGCA SEQ ID NO: 558 | GATGTTTTGATGACCCAAACTCCACTGTCCCTGC CTGTCAGTCTTGGAGATCAAGCCTCCATCTCTTG CAGATCTAGTCAGAACATTGTACATAATAATGGAA ACACCTATTTAGAATGGTACCTGCAGAAACCAGG CCAGTCTCCAAAGCTCCTGATCTACAAAGTTTCCA ACCGATTTTCTGGGGTCCCAGACAGGTTCAGTGG CAGTGGATCAGGGACAGATTTCACACTCAAGATC AGCAGAGTGGAGGCTGAGGATCTGGGAGTTTATT ACTGCTTTCAAGGTTCACATGTTCCTCGGACGTTC GGTGGAGGCACCAAGCTGGAAATCAAA SEQ ID NO: 559 |
| ACI-8033-18D12-Ab1 | 917.18D12F10D6 | CAGGTCCAACTCCAGCAGCCTGGGGCTGAGC TTGTGAAGCCTGGGGCTTCAGTGAAGATGTCC TGCAAGGCTTCTGGCTACACCTTCACCAGCTA CTGGATAACCTGGGTGAGGCAGAGGCCTGGA CAAGGCCTTGACTGGATTGGAGATATTTATCCT GGTGGAGGTGTTACTAACTACAATGAGAAGTT CAAGACCAAGGCCACACTGACTGTAGACACAT CCTCCAGCACAGCCTACATGCACCTCAGCAGC CTGACATCTGAGGACTCTGCGGTCTATTTCTG TGCGACAGCTCAGACTACGTTTGCTCACTGGG GCCAAGGGACTCTGGTCACTGTCTCTGCA SEQ ID NO: 568 | GATGTTTTGATGACCCAAACTCCACTCTCCCTGC CCGTCAGTCTTGGAGATCAAGCCTCCATCTCTTG CAGATCTAGTCAGAATATTGCACATAATAATGGAA ACACCTATTTAGAATGGTACCTGCAGAAACCAGG CCAGTCTCCAAAGCTCCTGATCTACAAAGTTTCCA ACCGATTTTCTGGGGTCCCAGACAGGTTCAGTGG CAGTGGATCAGGGACAGATTTCACACTCAAGATC AGCAGAGTGGAGGCTGAGGATCTGGGAGTTTATT ACTGCTTTCAAGGTTCACATGTTCCTCGGACGTTC GGTGGAGGCACCAAGCTGGAAATCAAA SEQ ID NO: 569 |
| ACI-8033-1F8-Ab1 | 917.1F8D8E4 | GATGTACAGCTTCAGGAGTCAGGACCTGGCCT CGTGAAACCTTCTCAGTCTCTGTCTCTCACCTG CTCTGTCACTGGCTACTCCATCACCAGTGGGT TTTACTGGAACTGGATCCGGCAATTTCCAGGA AATAAACTGGAATGGATGGGCTACATAAGCTA CGATGGTAGCAATAACTACAACCCATCTCTCAA AAATCGAATCTCCATTATTCGTGACACATCTAA GAACCAGTTTTTCCTGAAGTTGAAATCTGTGAC TTCTGAGGACACAGCCACATATTATTGTGTAAG AGGGGACGTCGACTGGGGCCAAGGCACCACT CTCACTGTCTCCTCA SEQ ID NO: 578 | GATGTTGTGATGACCCAGACTCCACTCACTTTGT CGGTCACCATTGGACAACCAGCCTCCATCTCTTG CAAGTCAAGTCAGAGCCTCTTAGATAGTGATGGA GAGACATATTTGAATTGGTTGTTTCAGAGGCCAG GCCAGTCTCCAAAGCGCCTAATCTATCTGGTGTC TAAACTGGACTCTGGAGTCCCTGACAGGTTCACT GGCAGTGGATCAGGGACAGATTTCACACTGAAAA TCAGCAGAGTGGAGCCTGAGGATTTGGGAGTTTA TTATTGCTGGCAAGGTACACATTTTCCTCAGACGC TCGGTGGAGGCACCAAGCTGGAAATCAAA SEQ ID NO: 579 |
| ACI-8033-22E5-Ab1 | 917.22E5C5F7 | GAGGTGCAACTAGTGGAGTCTGGGGGAGACT TAGTGAAGCCTGGAGGGTCCCTGAAACTCTCC TGTGCAGCCTCTGGATTCACTTTCAGTAGCTAT GGCATGTCTTGGGTTCGCCAGACTCCAGACAA GAGGCTGGAGTGGGTCGCAACCATTAGTAATG GTGGTAGTTACACCTACTATCCAGACAGTGTG AAGGGGCGATTCACCATCTCCAGAGACAATGC CAAGAACACCCTGTACCTGCAAATGAGCAGTC TGAAGTCTGAGGACACAGCCATGTATTACTGT GCAAGACAATTACGACGGGACGGTTGGTACTT CGATGTCTGGGGCACAGGGACCACGGTCACC GTCTCCTCA SEQ ID NO: 588 | GAAATTGTGCTCACCCAGTCTCCAGCACTCATGG CTGCATCTCCAGGGGAGAAGGTCACCATCACCTG CAGTGTCAGCTCAAGTATAAGTTCCAGCAAGTTG CACTGGTACCAGCAGAAGTCAGAAACCTCCCCCA AACTCTGGATTTATGGCACATCCAACCTGGCTTCT GGAGTCCCTGTTCGCTTCAGTGGCAGTGGATCTG GGACCTCTTATTCTCTCACAATCAGCAGCATGGA GGCTGAAGATGCTGCCACTTATTACTGTCAACAG TGGAGTAGTTACCCACTCACGTTCGGTGCTGGGA CCAAGCTGGAGCTGAAA SEQ ID NO: 589 |
| ACI-8033-27D8-Ab1 | 917.27D8E1H10E10 | GAGGTGCAGCTTGTTGAGTCTGGTGGAGGATT GGTGCAGCCTAAAGGGTCATTGAAACTCTCAT GTGCAGCCTCTGGATTCACCTTCAATACCTAC | GACATCAAGATGACCCAGTCTCCATCTTCCATGTA TGCATCTCTAGGAGAGAGAGTCACTATCACTTGC AAGGCGAGTCAGGACATTAATAGCTATTTAAGCT |

TABLE 6-continued

| Nucleotide sequence of the heavy chain and light chain variable domains (VH and VL) | | | |
|---|---|---|---|
| Antibody Code | Hybridoma Code | VH | VL |
| | | GCCATGAACTGGGTCCGCCAGGCTCCAGGAA<br>AGGGTTTGGAATGGGTTGCTCGCATAAGAAGT<br>AAAAGTAATAATTTTGCAACATATTATGCCGAT<br>TCAGTGAAAGACAGATTCACCATCTCCAGAGA<br>TGAATCAGAAAGCATGCTCTATCTGCAAATGAA<br>CAACTTGAAAGCTGAGGACACAGCCATGTATT<br>ACTGTGTGAGGTCCTTTGACTACTGGGGCCAA<br>GGCACCACTCTCACAGTCTCCTCA<br>SEQ ID NO: 598 | GGTTCCAGCAGAAACCAGGGAAATCTCCTAAGAC<br>CCTAATCTATCGTGCAAAAAGATTGGTAGATGGG<br>GTCCCATCAAGGTTCAGTGGCAGTGGATCTGGGC<br>AAGATTATTCTCTCACCATCAGCAGCCTGGAGTAT<br>GAAGATATGGGAATTTATTATTGTCTACAGTATGA<br>TGAGTTTCCATTCACGTTCGGCTCGGGGACAAAG<br>TTGGAAATAAAA<br>SEQ ID NO: 479 |
| ACI-8033-2108-Ab1 | 917.21C8E4C8 | CAGGTCCAACTCCAGCAGCCTGGGGCTGAGC<br>TTGTGAAGCCTGGGGCTTCAGTGAAGATGTCC<br>TGCAAGGCTTCTGGCTACACCTTCACCAGCTA<br>CTGGATAACCTGGGTGAGGCAGAGGCCTGGA<br>CAAGGCCTTGACTGGATTGGAGATATTTATCCT<br>GGTGGAGGTGTTACTAACTACAATGAGAAGTT<br>CAAGACCAAGGCCACACTGACTGTAGACACAT<br>CCTCCAGCACAGCCTACATGCACCTCAGCAGC<br>CTGACATCTGAGGACTCTGCGGTCTATTTCTG<br>TGCGACAGCTCAGACTACGTTTGCTTACTGGG<br>GCCAAGGGACTCTGGTCACTGTCTCTGCA<br>SEQ ID NO: 608 | GATGTTTTGATGACCCAAACTCCACTCTCCCTGC<br>CTGTCAGTCTTGGAGATCAAGCCTCCATCTCTTG<br>CAGATCTAGTCAGAACATTGTACATAATAATGGAA<br>ACACCTATTTAGAATGGTACCTGCAGAAACCAGG<br>CCAGTCTCCAAAGCTCCTGATCTACAAAGTTTCCA<br>ACCGATTTTCTGGGGTCCCAGACAGGTTCAGTGG<br>CAGTGGATCAGGGACAGATTTCACACTCAAGATC<br>AGCAGAGTGGAGGCTGAGGATCTGGGAGTTTATT<br>ACTGCTTTCAAGGTTCACATGTTCCTCGGACGTTC<br>GGTGGAGGCACCAAGCTGGAAATCAAA<br>SEQ ID NO: 609 |

TABLE 7

| Amino acid sequence of the heavy chain and light chain variable domains (VH and VL) and their CDRs | | | | | | | | | |
|---|---|---|---|---|---|---|---|---|---|
| Antibody Code | Hybridoma Code | VH | VH CDR1 | VH CDR2 | VH CDR3 | VL | VL CDR1 | VL CDR2 | VL CDR3 |
| ACI-7067-1101C8-Ab2 | 1101C8F7 | EVQLVESGGGL<br>VQPKGSLKLSC<br>AASGFSFNIYAM<br>NWVRQAPGKGL<br>EWVARIRSKSN<br>NYATYYADSVK<br>DRFTISRADSES<br>MLYLQMNNLKT<br>EDTAMYYCVRV<br>GLRFYAMDYWG<br>QGTSVTVSS<br>(SEQ ID NO: 10) | IYAMN<br>(SEQ ID NO: 11) | RIRSKS<br>NNYATY<br>YADSVK<br>D<br>(SEQ ID NO: 12) | VGLRFY<br>AMDY<br>(SEQ ID NO: 13) | DVLMTQTPLSL<br>PVSLGDQASIS<br>CRSSQSIVHSN<br>GNTYLEWYLQK<br>PGQSPKLLIYKV<br>SNRFSGVPDRF<br>SGSGSGTDFTL<br>KISRVEAEDLG<br>VYYCFQGSQG<br>PLTFGAGTKLE<br>LK<br>(SEQ ID NO: 14) | RSSQSIV<br>HSNGNT<br>YLE<br>(SEQ ID NO: 15) | KVSNRF<br>S<br>(SEQ ID NO: 16) | FQGSQ<br>GPLT<br>(SEQ ID NO: 17) |
| ACI-7067-1102G3-Ab1 | 1102G3F2 | EVKLEESGGGL<br>VQPGGSMKLSC<br>AASGFTFSDAW<br>MNWVRQSPEK<br>GLEWVAEIRNKA<br>HNHATYYAESV<br>KGRFTISGDDSK<br>SSVYLQMNNLR<br>AEDTGIYYCTIYS<br>YWGQGTLVTVS<br>A<br>(SEQ ID NO: 20) | DAWM<br>(SEQ ID NO: 21) | EIRNKA<br>HNHATY<br>YAESVK<br>G<br>(SEQ ID NO: 22) | YSY | SIVMTQTPKFLL<br>VSAGDRVTITC<br>KASQSVTKDVA<br>WYQQKPGQSP<br>KLLIYSTSNRYS<br>GVPDRFTGSGY<br>GTDFTFTINTVQ<br>TEDLAVYFCQQ<br>DYRIPYTFGGG<br>TKLEIK<br>(SEQ ID NO: 24) | KASQSV<br>TKDVA<br>(SEQ ID NO: 25) | STSNRY<br>S<br>(SEQ ID NO: 26) | QQDYRI<br>PYT<br>(SEQ ID NO: 27) |
| ACI-7067-1106A8-Ab2 | 1106A8H3 | EVQLVESGGGL<br>VQPKGSLKLSC<br>AASGFTFNTYA<br>MHWVRQAPGK<br>GLEWVARIRSK<br>GSNYATNYADS<br>VKDRFTISRDDS<br>QSMLYLQMNNL<br>KTEDTAMYYCV<br>RGHGSSYFSYW<br>GQGTLVTVSA<br>(SEQ ID NO: 30) | TYAMH<br>(SEQ ID NO: 31) | RIRSKG<br>SNYATN<br>YADSVK<br>D<br>(SEQ ID NO: 32) | GHGSS<br>YFSY<br>(SEQ ID NO: 33) | QIVLTQSPAIMS<br>ASPGEKVTMTC<br>SASSSVSYMH<br>WYQQKSGTSP<br>KRWIYDTSNLA<br>SGVPARFSGSG<br>SGTSYSLTISSM<br>EAEDAATYYCQ<br>QWNSHPPTFG<br>AGTKLELK<br>(SEQ ID NO: 34) | SASSSV<br>SY<br>(SEQ ID NO: 35) | DTSNLA<br>S<br>(SEQ ID NO: 36) | QQWNS<br>HPPT<br>(SEQ ID NO: 37) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| ACI-7067-1107G5-Ab2 | 1107G5B6 | QVQLQQPGTELVKPGASVKLSCKASGYTFTKYWMHWVKQRPGQGLEWIGNINPNNGDTNYNEKFKSKATLTVDKSSSTAYMQLSSLTSEDSAVYYCAIAMDYWGQGTSVTVSS (SEQ ID NO: 40) | KYWMH (SEQ ID NO: 41) | NINPNNGDTNYNEKFKS (SEQ ID NO: 42) | AMDY (SEQ ID NO: 43) | DIQMTQSPSSLSAFLGERVSLTCRASQDIGNNLNWFQQEPDGTIKRLIYATSSLDSGVPKRFSGSRSGSEYSLTISSLESEDFVDYYCLQFGSSPLTFGAGTKLELK (SEQ ID NO: 44) | RASQDIGNNLN (SEQ ID NO: 45) | ATSSLDS (SEQ ID NO: 46) | LQFGSSPLT (SEQ ID NO: 47) |
| ACI-7067-1108H1-Ab1 | 1108H1E1 | EVKLVESGGGLVQPGGSMKLSCTASGFTFSDAWMNWVRQSPEKGLEWVAEIRNKAHNHATNYAESVKGRFTISGDDSKSSVYLQMNNLRAEDTGIYYCTIYSFWGQGTLVTVSA (SEQ ID NO: 50) | DAWM (SEQ ID NO: 21) | EIRNKAHNHATNYAESVKG (SEQ ID NO: 52) | YSF | SIVMTQTPKFLLVSAGDRVTITCKASQSVTNYVAWYHQKPGQSPKLLIYSASNRYSGVPDRFTGSGYGTDFTFTINTVQTEDLAVYFCQQDYRIPYTFGGGTKLEIK (SEQ ID NO: 54) | KASQSVTNYVA (SEQ ID NO: 55) | SASNRYS (SEQ ID NO: 56) | QQDYRIPYT (SEQ ID NO: 27) |
| ACI-7067-1111B12-Ab2 | 1111B12H10 | QVQLLQPGTALVMPGASVKLSCKASGYTFTTYWMHWVKQRPGQGLEWIGNINPINGGSNYNEKFKSKASLTVDKSSSTAYMQLSSLTSEDSAVYYCVIAMDYWGQGTSVTVSS (SEQ ID NO: 60) | TYWMH (SEQ ID NO: 61) | NINPINGGSNYNEKFKS (SEQ ID NO: 62) | AMDY (SEQ ID NO: 43) | DIQMTQSPSSLSASLGERVSLTCRASQDIGISLNWFQQEPDGTIKRLIYATSSLDSGVPKRFSGNRSGSDYSLTISSLESEDFADYYCLQFASSPLTFGAGTKLELK (SEQ ID NO: 64) | RASQDIGISLN (SEQ ID NO: 65) | ATSSLDS (SEQ ID NO: 46) | LQFASSPLT (SEQ ID NO: 67) |
| ACI-7067-1112H8-Ab2 | 1112H8C12 | EVKLEESGGGLVQPGGSMKLSCAASGFTFTDAWMNWVRQSPEKGLEWIAEIRNKAHNYATYYAESVKGRFDISGDDSKSSVYLQMNNLRVEDTGIYYCTIYSYWGPGTLVTVSA (SEQ ID NO: 70) | DAWM (SEQ ID NO: 21) | EIRNKAHNYATYYAESVKG (SEQ ID NO: 72) | YSY | SIVMTQTPKFLLMSPGDRVTMTCTASQSVSNYVAWYQQKPGQSPKLLIYSASNRFTGVPDRFTGSGYGTDFTFTINTVQTEDMAVYFCQQDYTSPYTFGGGTKLEIK (SEQ ID NO: 74) | TASQSVSNYVA (SEQ ID NO: 75) | SASNRFT (SEQ ID NO: 76) | QQDYTSPYT (SEQ ID NO: 77) |
| ACI-7067-1108B11-Ab2 | 1108B11D3 | EVQLVESGGGLVQPKGSLKLSCAASGFTFNTYAMHWVRQAPGKGLEWVARIRSKGSNYATNYADSVKDRFTISRDDSQSMLYLQMNNLKTEDTAMYYCVRGHGSSYFSYWGQGTLVTVSA (SEQ ID NO: 30) | TYAMH (SEQ ID NO: 31) | RIRSKGSNYATNYADSVKD (SEQ ID NO: 32) | GHGSSYFSY (SEQ ID NO: 33) | QIVLTQSPAIMSASPGERITMTCSANSSVTYMHWYQQKSGTSPKRWIYDTSNLASGVPARFSGSGSGTSYSLTISSMEAEDAATYYCQQWKSHPPTFGAGTKLELK (SEQ ID NO: 84) | SANSSVTYMH (SEQ ID NO: 85) | DTSNLAS (SEQ ID NO: 36) | QQWKSHPPT (SEQ ID NO: 87) |
| ACI-7067-1113D10-Ab1 | 1113D10E3D5 | EVQLVESGGGLVQPKGSLKLSCAASGFTFNTYALHWVRQAPGKGLEWVARIRSKSSNYATYYADSVKDRFTISRDDSQS | TYALH (SEQ ID NO: 91) | RIRSKSSNYATYYADSVKD (SEQ ID NO: 92) | GGVSPFDY (SEQ ID NO: 93) | QIVLTQSPAIMSASPGEKVTMTCSASSSVSYMHWYQQKSGTSPKRWIYDTSKLASGVPARFSGSGSGTSYSLTISSM | SASSSVSYMH (SEQ ID NO: 95) | DTSKLAS (SEQ ID NO: 96) | QQWSNNPPT (SEQ ID NO: 97) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | MLYLQMNNLKT EDTGMYYCVRG GVSPFDYWGQ GTTLTVSS (SEQ ID NO: 90) | | | | EAEDSATYYCQ QWSNNPPTFG GGTKLEIK (SEQ ID NO: 94) | | | |
| ACI-7067-1116F2-Ab1 | 1116F2A2 | DVQLQESGPGF VKPSQSLSLTCS VTGYSITRGFYW NWIRQFPGNKL EWMGYISDDGN SNYNPSLKNRISI TRDTFKNQVFLR LNSVTTEDTATY YCTRGDLLWGQ GTTLTVSS (SEQ ID NO: 100) | RGFYW N (SEQ ID NO: 101) | YISDDG NSNYNP SLKN (SEQ ID NO: 102) | GDLL (SEQ ID NO: 103) | DVVMTQTALTL SVTIGQPASISC KSSQSLLDSDG ETYLNWLLQRP GQSPKRLIYLVS KLDSGVPDRFT GSGSGTDFALK ISRVEAEDLGIY YCWQGTHFPQ TFGGGTKLEIK (SEQ ID NO: 104) | KSSQSLL DSDGET YLN (SEQ ID NO: 105) | LVSKLD S (SEQ ID NO: 106) | WQGTH FPQT (SEQ ID NO: 107) |
| ACI-7067-1206E5-Ab1 | 1206E5D2 | QVQLQQSGPEL VKPGASVKMSC KASGYTFTDYVI SWVKQGTGQGL EWIGEIYPGNDS TYYNEKFKGKAT LTADKSSNTAY MQLSSLTSEDS AVYFCAREGVS NGYLYLSMDYW GQGTSVTVSS (SEQ ID NO: 110) | DYVIS (SEQ ID NO: 111) | EIYPGN DSTYYN EKFKG (SEQ ID NO: 112) | EGVSN GYLYLS MDY (SEQ ID NO: 113) | DVLMTQTPLTL SVTIGQPASISC KSSQSLLYSNG KTYLNWLLQRP GQSPKRLIYLVS KLDSGVPDRFT GSGSGTDFTLK ISRVEAEDLGV YYCVQGTHFP WTFGGGTKLEI K (SEQ ID NO: 114) | KSSQSLL YSNGKT YLN (SEQ ID NO: 115) | LVSKLD S (SEQ ID NO: 106) | VQGTH FPWT (SEQ ID NO: 117) |
| ACI-7079-2501B11-Ab3 | 2501611C7 | QVQLQQSGPEL VKPGASVKISCK ASGYAFSSFWM NWMKQRPGKG LEWIGRIYPGDG DAHYNGEFKGR ATLTADKSSSTA YMQLSSLTSED SAVYFCARKGD FYGSNYDYWGQ GTTLTVSS (SEQ ID NO: 280) | SFWM (SEQ ID NO: 281) | RIYPGD GDAHY NGEFK G (SEQ ID NO: 282) | KGDFY GSNYD Y (SEQ ID NO: 283) | QAVVTQESALT TSPGETVTLTC RSSTGAVTTSN YANWVQEKPD HLFTGLIGGTN NRAPGVPARFS GSLIGDKAALTI TGAQTEDEAIY FCALWYSNHLV FGGGTRLTVL (SEQ ID NO: 284) | RSSTGA VTTSNY AN (SEQ ID NO: 285) | GTNNR AP (SEQ ID NO: 286) | ALWYS NHLV (SEQ ID NO: 287) |
| ACI-7079-2501D10-Ab1 | 2501D10C3 | EVQLVESGGGL VQPKGSLKVSC AASGFTFKTYA MHWVRQAPGK GLEWVARIRSE NSNFAKYYADS VKDRFTISRDDS QSMLYLQMNNL KTEDTAMYYCV RGYNGSSLDYW GQGTTLTVSS (SEQ ID NO: 290) | TYAMH (SEQ ID NO: 31) | RIRSEN SNFAKY YADSVK D (SEQ ID NO: 192) | GYNGS SLDY (SEQ ID NO: 193) | QIVLTQSPAIMS AFPGERVTMTC SASSSVNYMH WYQQKSGTSP KRWIYDTSKLA SGVPARFSGG GSGTSYSLTISN MEAEDAATYYC QQWRSNPPTF GGGTKLEIK (SEQ ID NO: 194) | SASSSV NYMH (SEQ ID NO: 195) | DTSKLA S (SEQ ID NO: 96) | QQWRS NPPT (SEQ ID NO: 197) |
| ACI-7079-2501G2-Ab2 | 2501G2E5 | EVQLVESGGGL VQPKGSLKLSC AASGFNFNTYA MNWVRQAPGK GLEWVARIRTKS NNFATYYAHSV KDRFTISRDDSE SMLYLQMNNLK TEDTAMYYCVR QGLAYYAMDYW GQGTSVTVSS (SEQ ID NO: 140) | TYAMN (SEQ ID NO: 141) | RIRTKS NNFATY YAHSVK D (SEQ ID NO: 142) | QGLAYY AMDY (SEQ ID NO: 143) | DVLMTQTPLSL PVSLGDQVSIS CRSSQTIVHSN GNTYLEWYLQK PGQSPKLLIYKV SNRFSGVPDRF SGSGSGTDFTL KISRVEAEDLG VYYCFQGSQG PLTFGAGTKLE LK (SEQ ID NO: 144) | RSSQTIV HSNGNT YLE (SEQ ID NO: 145) | KVSNRF S (SEQ ID NO: 16) | FQGSQ GPLT (SEQ ID NO: 17) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| ACI-7079-250306-Ab1 | 250306H9 | DVQLQESGPGLVKPSQSLSLTCSVTGYSITSGYYWNWIRLFPGNKLEWLGYINYDGSNNFNPSLKNRISITRDTSKNQFFLKLNSVTSEDTATYFCLRGDWDWGQGTLVTVSA (SEQ ID NO: 150) | SGYYWN (SEQ ID NO: 151) | YINYDGSNNFNPSLKN (SEQ ID NO: 152) | GDWD (SEQ ID NO: 153) | DVVMTQTPLTLSVTIGQPASISCKSSQSLLDSDGETYLNWLLQRPGQSPKRLICLVSKLDSGVPDRFTGSGSGTDFTLKISRVEAEDLGVYYCWQGTHFPQTFGGGTRLEIK (SEQ ID NO: 154) | KSSQSLLDSDGETYLN (SEQ ID NO: 105) | LVSKLDS (SEQ ID NO: 106) | WQGTHFPQT (SEQ ID NO: 107) |
| ACI-7079-2504A6-Ab1 | 2504A6C8 | QVQLQQSGVELARPGASVKLSCKASGYTFTSYGISWVKQRTGQGLKWIGEIYPGSGNTYYNEKFKGKATLTADKSSSTAYMELRSLTSEDSAVYFCATDYDAYWGQGTTLTVSS (SEQ ID NO: 160) | SYGIS (SEQ ID NO: 161) | EIYPGSGNTYYNEKFKG (SEQ ID NO: 162) | DYDAY (SEQ ID NO: 163) | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPLTFGAGTKLELK (SEQ ID NO: 164) | RSSQSLVHSNGNTYLH (SEQ ID NO: 165) | KVSNRFS (SEQ ID NO: 16) | SQSTHVPLT (SEQ ID NO: 167) |
| ACI-7079-2506E2-Ab2 | 2506E2G4 | QVQLQQSGPELVRPGASVKISCKASGYAFSNSWMNWVKQRPGKGLEWIGRIFPGDGDTYYDGKFKGKVKLTTDKFSNTAYMQLRSLTSEDSAVYFCARWGGTNDEWFAHWGQGTLVTVSV (SEQ ID NO: 170) | NSWMN (SEQ ID NO: 171) | RIFPGDGDTYYDGKFKG (SEQ ID NO: 172) | WGGTNDEWFAH (SEQ ID NO: 173) | DIVLTQSPASLTVSLGQRATISCRASQSVSTSRNSYMHWYQQKPRQPPKLLIKYASNLESGVPARFSGSGSGADFTLNIHPVEEEDTATYYCQHSWDIPLTFGTGTKLELS (SEQ ID NO: 174) | RASQSVSTSRNSYMH (SEQ ID NO: 175) | YASNLES (SEQ ID NO: 176) | QHSWDIPLT (SEQ ID NO: 177) |
| ACI-7079-2506F3-Ab1 | 2506F3E12 | QVQLQQPGAELVKPGASVKLSCKASGYTFTTYWMQWVKQRPGQGLEWIGEIDPSDSYINYNQKFKGKATLTVDTSSSTAFMQLSSLTSEDSAVYYCARGMMDYWGQGTSVTVSS (SEQ ID NO: 180) | TYWMQ (SEQ ID NO: 181) | EIDPSDSYINYNQKFKG (SEQ ID NO:182) | GMMDY (SEQ ID NO: 183) | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFKGSHVPYTFGGGTKLEIK (SEQ ID NO: 184) | RSSQSIVHSNGNTYLE (SEQ ID NO: 15) | KVSNRFS (SEQ ID NO: 16) | FKGSHVPYT (SEQ ID NO: 187) |
| ACI-7079-2507B3-Ab1 | 2507B3G8 | EVQLVESGGGLVQPKGSLKVSCAASGFTFKTYAMHWVRQAPGKGLEWVARIRSENSNFAKYYADSVKDRFTISRDDSQSMLYLQMHTLKTEDTAIYYCVRGYNGSSLDYWGQGTTLTVSS (SEQ ID NO: 190) | TYAMH (SEQ ID NO: 31) | RIRSENSNFAKYYADSVKD (SEQ ID NO: 192) | GYNGSSLDY (SEQ ID NO: 193) | QIVLTQSPAIMSAFPGERVTMTCSASSSVNYMHWYQQKSGTSPKRWIYDTSKLASGVPARFSGGGSGTSYSLTISNMEAEDAATYYCQQWRSNPPTFGGGTKLEIK (SEQ ID NO: 194) | SASSSVNYMH (SEQ ID NO: 195) | DTSKLAS (SEQ ID NO: 96) | QQWRSNPPT (SEQ ID NO: 197) |
| ACI-7079-2511B3-Ab3 | 2511B3B12 | DVQLQESGPGLVKPSQSLSLTCSVTGFSITSYYYWNWIRQFPGNKLEWMAYISYDGSNNYNPSLKNRISITRDTSKNQFFLKLNSVTTEDTAT | SYYYWN (SEQ ID NO: 201) | YISYDGSNNYNPSLKN (SEQ ID NO: 202) | GDWD (SEQ ID NO: 153) | DVVMTQTPLTLSLTIGQPASISCKSSQSLLDSDGETYLNWLLQRPGQSPKRLIYLVSKLESGVPDRFTGSGSGTVFTLKISRVEAEDLGVY | KSSQSLLDSDGETYLN (SEQ ID NO: 105) | LVSKLES (SEQ ID NO: 206) | WQGTHFPQT (SEQ ID NO: 107) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | YYCTRGDWDWGQGTLVTVSA (SEQ ID NO: 200) | | | | YCWQGTHFPQTFGGGTKLEIK (SEQ ID NO: 204) | | | |
| ACI-7079-2601B6-Ab1 | 2601B6D2 | EIQLQQSGAELVRPGASVKLSCTTSGFNIKDDYIHWVKQRPEQGLEWIGWIDPENGDTDYASKFQGKATITADTSSNTAYLHLSSLTSEDAAVYFCTTRGFGYWGQGTLVTVS (SEQ ID NO: 210) | DDYIH (SEQ ID NO: 211) | WIDPENGDTDYASKFQG (SEQ ID NO: 212) | RGFGY (SEQ ID NO: 213) | DIVMTQSHKFMSTSVGDRVSITCKASQDVGNVVAWYQQKPGQSPKLLIYWASSRHTGVPDRFTGSGSGTEFTLTISNVQSEDLADYFCQQYSSYPLTFGAGTKLELK (SEQ ID NO: 214) | KASQDVGNVVA (SEQ ID NO: 215) | WASSRHT (SEQ ID NO: 216) | QQYSSYPLT (SEQ ID NO: 217) |
| ACI-7079-2602G4-Ab4 | 2602G4H1 | EVQLVESGGGLVQPKGSLKLSCAASGFTFKTYAMHWVRQAPGKGLEWVARIRSKGSDYATYYADSVKDRFTISRDDSQSMLYLQMNNLKTEDTAMYFCVRGGADSWFAYWGQGTLVTVST (SEQ ID NO: 220) | TYAMH (SEQ ID NO: 31) | RIRSKGSDYATYYADSVKD (SEQ ID NO: 222) | GGADSWFAY (SEQ ID NO: 223) | QIVLTQSPAIMSASPGERITMTCTASSSVSYMHWYQQKSGTSPKRWIYDTSKLASGVPARFSGSGSGASYTLTISSMEAEDAATYYCQQWNRNPPTFGGGTQLAIK (SEQ ID NO: 224) | TASSSVSYMH (SEQ ID NO: 225) | DTSKLAS (SEQ ID NO: 96) | QQWNRNPPT (SEQ ID NO: 227) |
| ACI-7079-2603C1-Ab3 | 2603C1H6 | QVQLQQPGADLVKPGASVKLSCKASGYTFTSYWMQWTKQRPGQGLEWIGEIDPSDSYANYNQKFKGKATLTVDKYSSTAYMQLNSLTSEDSAVYYCALYDGPSYWGQGTLVTVS (SEQ ID NO: 230) | SYWMQ (SEQ ID NO: 231) | EIDPSDSYANYNQKFKG (SEQ ID NO: 232) | YDGPSY (SEQ ID NO: 233) | ENVLTQSPAIMSASPGEKVTMTCSAGSSVSYMHWFQQKSSTSPKLWIYDTSKLPSGVPGRFSGSGSGNSYSLTISSMEAEDVATYYCFQGSGYPYTFGGGTKLEIK (SEQ ID NO: 234) | SAGSSVSYMH (SEQ ID NO: 235) | DTSKLPS (SEQ ID NO: 236) | FQGSGYPYT (SEQ ID NO: 237) |
| ACI-7079-2603F3-Ab1 | 2603F3H3 | EVQLVESGGGLVQPKGSLKLSCAASGFTFNTYAMHWVRQAPGKGLEWVARIRSKGSNYATYYADSVKDRFTISRDDSQSMLYLQMNNLKTEDTAMYYCVRGGGDSWFAYWGQGTLVTVSA (SEQ ID NO: 240) | TYAMH (SEQ ID NO: 31) | RIRSKGSNYATYYADSVKD (SEQ ID NO: 242) | GGGDSWFAY (SEQ ID NO: 243) | QIVLTQSPAIMSASPGERVTMTCTASSSVSYMHWYQQKSGTSPKRWIYDTSKLASGVPARFSGSGSGASYTLTISSMEAEDAATYYCQQWNSNPPTFGGGTQLAIK (SEQ ID NO: 244) | TASSSVSYMH (SEQ ID NO: 225) | DTSKLAS (SEQ ID NO: 96) | QQWNSNPPT (SEQ ID NO: 247) |
| ACI-7079-2605B3-Ab2 | 2605B3D1 | EVQLVESGGGLVQPKGSLKLSCAASGFIFKTYAMHWVRQAPGKGLEWVARIRSKGGNYATYFADSVKDRFTISRDDSQNMLYLQVNNLKIEDTAMYFCVRGGNYSWFAYWGQGTLVTVSA (SEQ ID NO: 250) | TYAMH (SEQ ID NO: 31) | RIRSKGGNYATYFADSVKD (SEQ ID NO: 252) | GGNYSWFAY (SEQ ID NO: 253) | QIVLTQSPAIMSASPGEKVTMTCSASSSVTYMHWYQQKSGTSPKRWIYDTSQLASGVPARFSGSGSGTSHSLTISSMETEDAATYYCQQWTRNPPTFGGGTKLAIK (SEQ ID NO: 254) | SASSSVTYMH (SEQ ID NO: 255) | DTSQLAS (SEQ ID NO: 256) | QQWTRNPP (SEQ ID NO: 257) |
| ACI-7079-2606A6-Ab2 | 2606A6D5 | QVQLQQSGPELVKPGASVKISCKASGFAFSSSWMNWVKQRPGKGLEWVGRIFPGDG | SSWMN (SEQ ID NO: 261) | RIFPGDGDTNYDRKFKD (SEQ ID NO: 262) | WTGGYDWFAY (SEQ ID NO: 263) | DIVLTQSPASLAVSLGQRATISCRASQSVSTSNYNYLHWYQQKPGQPPKLLITYAS | RASQSVSTSNYNYLH (SEQ ID NO: 265) | YASNLES (SEQ ID NO: 176) | QHSWEIPLT (SEQ ID NO: 267) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | DTNYDRKFKDKATLTADKSSSTAYMQLSSLTSEDSAVYFCARWTGGYDWFAYWGQGTLVTVSA (SEQ ID NO: 260) | | | | NLESGVPARFSGSGSGTDFTLNIHPVEEGDTATYYCQHSWEIPLTFGAGTKLELK (SEQ ID NO: 264) | | | |
| ACI-7079-2509E5-Ab2 | 2509E5E5 | EVQLQQSGPELVKPGASLKMSCKASGYSFTDYNMHWVKQSRGKSLEWIGYINPNNGVPTYKQKFKGRATLTVNQSSSTAYMEIRSLTSEDSAVYYCTRGGDHRFAYWGQGTLVTVSA (SEQ ID NO: 270) | DYNMH (SEQ ID NO: 271) | YINPNNGVPTYKQKFKG (SEQ ID NO: 272) | GGDHRFAY (SEQ ID NO: 273) | DIVLTQSPASLAVSLGQRATISCRASESVDYYGFSFVNWFQQKPGQPPKLLIYSASYKGSGVPVRFSGSGSGTDFSLSIHPMEADDTAMYFCQQNKEVPLTFGAGTKLELK (SEQ ID NO: 274) | RASESVDYYGFSFVN (SEQ ID NO: 275) | SASYKGS (SEQ ID NO: 276) | QQNKEVPLT (SEQ ID NO: 277) |
| ACI-7087-4119E10-Ab2 | 4119E10D12 | QVQLQQSGAELVRPGASVTLSCKASGYTFSDYEMNWVKQTPVHGLEWIGAIDPETGGTAYNQKFKGKAILTSDKSSSTAYMELRSLTSEDSAVYYCTRFLLIDFDYWGQGTTLTVSS (SEQ ID NO: 300) | DYEMN (SEQ ID NO: 301) | AIDPETGGTAYNQKFKG (SEQ ID NO: 302) | FLLIDFDY (SEQ ID NO: 303) | DVLMTQTPLSLPVSLGDQASISCRSSQSIVHSNGNTYLEWYLKKAGQSPKVLIYKVSNRFSGVPDRFSGSGSGTDFTLKISRVEAEDLGVYYCFQGSHVPYTFGGGTELEIK (SEQ ID NO: 304) | RSSQSIVHSNGNTYLE (SEQ ID NO: 15) | KVSNRFS (SEQ ID NO: 16) | FQGSHVPYT (SEQ ID NO: 307) |
| ACI-7087-4125E6-Ab1 | 4125E6D5 | QVQLQQPGTELVKPGASVRLSCKASGYAFTSYWMHWVKQRPGQGLEWIGNINPSNGGTNYNEKFKNKATLTVDKSSSTAYMQLSGLTSEDSAVYYCATGLHYWGQGTTLTVSS (SEQ ID NO: 310) | SYWMH (SEQ ID NO: 311) | NINPSNGGTNYNEKFKN (SEQ ID NO: 312) | GLHY (SEQ ID NO: 313) | DIQMTQSPSSLSASLGERVTLTCRASQDIGNYLNWLQQEPDGTIKRLIYATSSLDSGVPKRFSGSRSGSDYSLTISSLESEDFVDYYCLQFASSPLTFGPGTKLELK (SEQ ID NO: 314) | RASQDIGNYLN (SEQ ID NO: 315) | ATSSLDS (SEQ ID NO: 46) | LQFASSPLT (SEQ ID NO: 67) |
| ACI-7088-4301D5-Ab2 | 4301D5B10 | QVQLQQSGPELVRPGASVKISCKASGYRFTSYYIHWVKQRPGQGLEWIGWIYPGSDNTKHNDKFKGKATLTADTSSSTAYMQLSSLTSEDSAVYFCARDYDVGFGYWGQGTLVTVSS (SEQ ID NO: 320) | SYYIH (SEQ ID NO: 321) | WIYPGSDNTKHNDKFKG (SEQ ID NO: 322) | DYDVGFGY (SEQ ID NO: 323) | DIVLTQSPASLAVSLGQRATISCRASESVDNYGISFMNWFQQKPGQPPKLLIYAASNQGSGVPARFSGIGSGTDFSLNIHPMEEDDTAMYFCQQSQEVPLTFGAGTKLELK (SEQ ID NO: 324) | RASESVDNYGISFMN (SEQ ID NO: 325) | AASNQGS (SEQ ID NO: 326) | QQSQEVPLT (SEQ ID NO: 327) |
| ACI-7088-4301E12-Ab2 | 4301E12B9 | DVQLQESGPGLVKPSQSLSLTCSVTGYSITSGYYWNWIRQFPGNKLEWMGYISDDGSKNYNPSLKNRISITRDTSKNQLFMKLNSVTTEDTATYYCARGDSRLGQGTLVTVSA (SEQ ID NO: 330) | SGYYWN (SEQ ID NO: 151) | YISDDGSKNYNPSLKN (SEQ ID NO: 332) | GDSR (SEQ ID NO: 333) | DVVLTQTPLTLSVTIGQPASISCRSSQNLLDSDGETYLNWLLQRPGQSPKRLIYLVSELDSGVPDRFTGSGSGTDFTLKISRVEAEDLGVYYCWQGTHFPQTFGGGTKLEII (SEQ ID NO: 334) | RSSQNLLDSDGETYLN (SEQ ID NO: 335) | LVSELDS (SEQ ID NO: 336) | WQGTHFPQT (SEQ ID NO: 107) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| ACI-7088-4301H3-Ab2 | 4301H3A5 | EVQLQQSGPELVKPGASVKISCKASGYTFADYFMNWVKQSHGKSLEWIGDINPNNGGTTYNQKFKGKATLTVDKSSNTAYMELRSLTSEDSAVYYCARGRNYAMDYWGQGTSVTVSS (SEQ ID NO: 340) | DYFMN (SEQ ID NO: 341) | DINPNNGGTTYNQKFKG (SEQ ID NO: 342) | GRNYAMDY (SEQ ID NO: 343) | DIVMSQSPSSLAVSAGEKVTMSCKSSQSLLNSRTRKNYLAWYQQKPGQSPKLLIYSASTRESGVPDRFTGSGFGTDFTLTISSVQAEDLAVYYCKQSYDLWTFGGGTKLEIK (SEQ ID NO: 344) | KSSQSLLNSRTRKNYLA (SEQ ID NO: 345) | SASTRES (SEQ ID NO: 346) | KQSYDLWT (SEQ ID NO: 347) |
| ACI-7088-4303A1-Ab1 | 4303A1E7 | EVQLQQSGAELVRPGASVKLSCTASGFNIKDDYMHWVKQRPEQGLEWIGWIDPENGDSEYASKFQGKATMTADTSSNTAYLQLSSLTSEDTAVYYCKTWGTAQALFPYWGQGTLVTVSA (SEQ ID NO: 350) | DDYMH (SEQ ID NO: 351) | WIDPENGDSEYASKFQG (SEQ ID NO: 352) | WGTAQALFPY (SEQ ID NO: 353) | DIVMTQSQKFMSTSVGDRVSITCKASQNVGTSVGWYQQKAGQSPKLLIHSASNRYTGVPDRFTGSGSGTDFTLTINNMQSEDLADYFCQQYRSYPLTFGAGTKLELK (SEQ ID NO: 354) | KASQNVGTSVG (SEQ ID NO: 355) | SASNRYT (SEQ ID NO: 356) | QQYRSYPLT (SEQ ID NO: 357) |
| ACI-7088-4303A3-Ab1 | 4303A3E4 | QVQLQQSGAELVRPGASVTLSCKASGYTFTDYEMHWVKQTPVHGLEWIGVIDPETGGAVQNQKFKGKAILTADNSSSTAYMDLRSLTSEDSAVYNCAMGAALRLAYWGQGTLVTVSS (SEQ ID NO: 360) | DYEMH (SEQ ID NO: 361) | VIDPETGGAVQNQKFKG (SEQ ID NO: 362) | GAALRLAY (SEQ ID NO: 363) | DVLMTQTPLSLPVSLGDQASISCRSSQSIVHSNGNSYLEWYLQKPGQSPKLLIYKVSNRFSGVPDRFSGSGSGTDFTLKINRVEAEDLGVYYCFQGSHVPFTFGSGTKLEIK (SEQ ID NO: 364) | RSSQSIVHSNGNSYLE (SEQ ID No: 365) | KVSNRFS (SEQ ID No: 16) | FQGSHVPFT (SEQ ID NO: 367) |
| ACI-7088-4303B6-Ab2 | 4303B6C11 | EVQLQQSGPELVKPGASVKISCKASGYTFTDYYMNWVKQSHGKSLEWIGDINPNNGGTTYNQKFKDKATLTVDRSSSTAYMELRSLTSGDSAVYYCARSGYSGSRLYYAMDYWSQGSSVTVSS (SEQ ID NO: 370) | DYYMN (SEQ ID NO: 371) | DINPNNGGTTYNQKFKD (SEQ ID NO: 372) | SGYSGSRLYYAMDY (SEQ ID NO: 373) | DIVMSQSPSSLAVSAREKVTMSCKSSQSLLNSRTRKNYLAWYQQKPGQSPKLLIFWASTRESGVPDRFTGSGSGTDFTLTISSVQAEDLAVYYCKQSYDLWTFGGGTKLEIK (SEQ ID NO: 374) | KSSQSLLNSRTRKNYLA (SEQ ID NO: 345) | WASTRES (SEQ ID NO: 376) | KQSYDLWT (SEQ ID NO: 347) |
| ACI-7088-4303B6-Ab1 | 4303H6D7 | EVQLQQSGAELVRPGASVKLSCTASGFNIQDDYMHWVKQRPEQGLEWIGWIDPENGDTEYASKFQGKATLTADTSSNTAYLQLSRLTSEDTAVYYCTTAGSGVQLFDYWGQGTTLTVSA (SEQ ID NO: 380) | DDYMH (SEQ ID NO: 351) | WIDPENGDTEYASKFQG (SEQ ID NO: 382) | AGSGVQLFDY (SEQ ID NO: 383) | DILMTQSQKFMSTSVGDRVSVTCKASQNVGTNVAWYQQKPGQSPKPLISSASSRYSGVPDRFTGSGSGTDFTLTISNVQSEDLADYFCQQYNRYPLTFGAGTKLELK (SEQ ID NO: 384) | KASQNVGTNVA (SEQ ID NO: 385) | SASSRYS (SEQ ID NO: 386) | QQYNRYPLT (SEQ ID NO: 387) |
| ACI-7088-4305H7-Ab1 | 4305H7A4 | EVQLQQSGAELVRPGASVKLSCTASGFNIKDDYMHWVKQRPEQGL | DDYMH (SEQ ID NO: 351) | WIDPENGDTEYASKFQG (SEQ ID | WGTTQALFPY (SEQ ID NO: 393) | DIVMTQSQKFMSTSVGDRVSITCKASQNVGTAVGWYQQKAGQS | KASQNVGTAVG (SEQ ID NO: 395) | SASNRYT (SEQ ID NO: 356) | QQYRSYPLT (SEQ ID NO: 357) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | EWIGWIDPENG DTEYASKFQGK ATMIADTSSNTA YLQLSSLTSEDT AVYYCKTWGTT QALFPYWGQGT LVTVSS (SEQ ID NO: 390) | | NO: 382) | | PKLLIHSASNRY TGVPDRFTGSG SGTDFTLTINN MQSEDLADYFC QQYRSYPLTFG AGTKLELK (SEQ ID NO: 394) | | | |
| ACI-7088-4317A4-Ab1 | 4317A4D2 | EVQLQQSGAEL VRPGASVKLSC TASGFNIKDDYM HWVKQRPEQGL EWIGWIDPENG DTEYASKFQGK ATMTADTSSNT AYLQLSSLTSED TAVYYCKTWGT TQALFPYWGQG TLVTVSA (SEQ ID NO: 400) | DDYMH (SEQ ID NO: 351) | WIDPEN GDTEYA SKFQG (SEQ ID NO: 382) | WGTTQ ALFPY (SEQ ID NO: 393) | DIVMTQSQKFM YTSVGDRVSIT CKASQNVGNA VGWYQQKAGQ SPKLLIHSASNR YTGVPDRFTGT GSGTDFTLTINN MQSEDLADYFC QQYRSYPLTFG AGTKLELK (SEQ ID NO: 404) | KASQNV GNAVG (SEQ ID NO: 405) | SASNRY T (SEQ ID NO: 356) | QQYRS YPLT (SEQ ID NO: 357) |
| ACI-7089-4409F1-Ab1 | 4409F1A8 | DVQLQESGPGL VKPSQSLSLTCS VTGYSITRGYY WNWIRQFPGNK LEWMGYISYDG SNNYNPSLRNRI SITRDTSKNQFF LKLKSVTTEDTA TYFCARGDSNW GQGTTLTVSA (SEQ ID NO: 410) | RGYYW N (SEQ ID NO: 411) | YISYDG SNNYNP SLRN (SEQ ID NO: 412) | GDSN (SEQ ID NO: 413) | DVVMTQTPLTL SVTIGQPASISC KSSQSLLDSDG ETYLNWLLQRP GQSPKRLIYLVS KLDSGVPDRFT GSGSGTDFTLK ISRVEAEDLGV YYCWQGTHFP QTFGGGTKLEI K (SEQ ID NO: 414) | KSSQSLL DSDGET YLN (SEQ ID NO: 105) | LVSKLD S (SEQ ID NO: 106) | WQGTH FPQT (SEQ ID NO: 107) |
| ACI-7089-4415G5-Ab1 | 4415G5A11 | QVQLQQSGAEL ARPGASVKVSC KASGYTFTSSGI SWLKHRTGQGL EWIGDIYPRSGN TYYNEKFKDKAT LTADKSSSTAYM ELRSLTSEDSAV YFCASGNYWGQ GTTLTVSA (SEQ ID NO: 420) | SSGIS (SEQ ID NO: 421) | DIYPRS GNTYYN EKFKD (SEQ ID NO: 422) | GNY | DIVITQDDLSNP VTSGESVSISC RSSKSLLYKDG KTYLNWFLQRP GQSPQLLIYLM STRASGVSDRF SGSGSGTDFTL EISRVKAEDVG VYYCQQLLEYP LTFGAGTKLEL K (SEQ ID NO: 424) | RSSKSLL YKDGKT YLN (SEQ ID NO: 425) | LMSTRA S (SEQ ID NO: 426) | QQLLEY PLT (SEQ ID NO: 427) |
| ACI-7089-4417G6-Ab1 | 4417G6B12 | QVQLQQSGAEL VRPGASVTLSC KASGYTFTGYE MHKQTPVHGLE WIGAIDPETGGT AYIQKFKGKATL TADKSSSTAYM ELRSLTSEDSAV YYCTRGWDYFD YWGQGTTLTVS A (SEQ ID NO:430) | GYEMH (SEQ ID NO: 431) | AIDPET GGTAYI QKFKG (SEQ ID NO: 432) | GWDYF DY (SEQ ID NO: 433) | DVVMTQTPLSL PVSLGDQASIS CRSSQSLLHSN GFTYLHWYLQK PGQSPKLLIYRV SNRFSGVPDRF SGSGSGTDFTL KISRVEAEDLG VYFCSQSTHVP YTFGGGTKLEIK (SEQ ID NO: 434) | RSSQSL LHSNGF TYLH (SEQ ID NO: 435) | RVSNRF S (SEQ ID NO: 436) | SQSTH VPYT (SEQ ID NO:437) |
| ACI-7089-4418C5-Ab1 | 4418C5G1 | DGQLQESGPGL VKPSQSLSLTCS VTGYSITSGYYW NWIRQFPGNKL EWMGYINYDGS NNYNPSLKNRIS ITRDTSKNQFFL KFNFVTTEDTAT | SGYYW N (SEQ ID NO: 151) | YINYDG SNNYNP SLKN (SEQ ID NO: 442) | GDVY (SEQ ID NO: 443) | DVVMTQTPLTL SVTIGQPASISC KSSQSLLDSDG ETYLNWLLQRP GQSPKRLIYLVS KLDSGVPDRFT GSGSGTDFTLK ISRVEAEDLGV | KSSQSLL DSDGET YLN (SEQ ID NO: 105) | LVSKLD S (SEQ ID NO: 106) | WQGTH FPQT (SEQ ID NO: 107) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | YYCVRGDVYWGQGTTLTVSS (SEQ ID NO: 440) | | | | YYCWQGTHFPQTFGGGTKLEIK (SEQ ID NO: 414) | | | |
| ACI-7089-4418F6-Ab1 | 4418F6G7 | QVQLQQSGAELARPGASVKVSCKASGYTFTSSGISWLKHRTGQGLEWIGDIYPRSGNTYYNEKFKDKATLTADKSSSTAYMELRSLTSEDSAVYFCSSGNYWGQGTTLTVSS (SEQ ID NO: 450) | SSGIS (SEQ ID NO: 421) | DIYPRSGNTYYNEKFKD (SEQ ID NO: 422) | GNY | DIVITQDDLSNPVTSGESVSISCRSSKSLLYKDGKTYLNWFLQRPGQSPQLLIYLMSTRASGVSDRFSGSGSGTDFTLEISRVKAEDVGVYYCQQLLEYPLTFGAGTKLELK (SEQ ID NO: 424) | RSSKSLLYKDGKTYLN (SEQ ID NO: 425) | LMSTRAS (SEQ ID NO: 426) | QQLLEYPLT (SEQ ID NO: 427) |
| ACI-8033-5A12-Ab1 | 917.5A12 A11C9 | QVHLKQSGADLVRPGASVKLSCKASGYTFTDYYINWVKQRPGQGLEWIARIYPGSGNTYYNEKFKGRATLSAEKSSTTAYMQLSSLTSEDSAVYFCVVGYYGAWGQGTTLTVSS (SEQ ID NO: 460) | DYYIN (SEQ ID NO: 461) | RIYPGSGNTYYNEKFKG (SEQ ID NO: 462) | GYYGA (SEQ ID NO: 463) | DVVMTQTPLSLPVSLGDQASISCRSSQSLVHSNGKTHLHWYLQKPGQSPKLLIYKVSNRFSGVPDRFSGSGSGTDFTLKISRVEAEDLGVYFCSQSTHVPWTFGGGTKLEIK (SEQ ID NO. 464) | RSSQSLVHSNGKTHLH (SEQ ID NO: 465) | KVSNRFS (SEQ ID NO: 16) | SQSTHVPWT (SEQ ID NO: 467) |
| ACI-8033-25A3-Ab1 | 917.25A3 E9F6 | EVQLVESGGGLVQPKGSLKLSCAASGFSFNTYAMNWVRQAPGKGLEWVARIRSKSNNFATYYADSVKDRFTISRDESESMLYLQMNNLKTEDTAMYYCVRSFDYWGQGTTLTVSS (SEQ ID NO: 470) | TYAMN (SEQ ID NO: 141) | RIRSKSNNFATYYADSVKD (SEQ ID NO: 472) | SFDY (SEQ ID NO: 473) | DIKMTQSPSSMYASLGERVTITCKASQDINSYLSWFQQKPGKSPKTLIYRAKRLVDGVPSRFSGSGSGQDYSLTISSLEYEDMGIYYCLQYDEFPFTFGSGTKLEIK (SEQ ID NO: 474) | KASQDINSYLS (SEQ ID NO: 475) | RAKRLVD (SEQ ID NO: 476) | LQYDEFPFT (SEQ ID NO: 477) |
| ACI-8033-1G10-Ab1 | 917.1G10 A10F6 | DVQLQESGPGLVKPSQTVFLTCTVTGISITTGNYRWSWIRQFPGNKLEWIGYIYYSGTITYNPSLTSRTTITRDTPKNQFFLEMNSLTAEDTATYYCARIYYGNAMDYWGQGTSVTVSS (SEQ ID NO: 480) | TGNYRWS (SEQ ID NO: 481) | YIYYSGTITYNPSLTS (SEQ ID NO: 482) | IYYGNAMDY (SEQ ID NO: 483) | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPHTFGGGTKLEIK (SEQ ID NO: 484) | RSSQSLVHSNGNTYLH (SEQ ID NO: 165) | KVSNRFS (SEQ ID NO: 16) | SQSTHVPHT (SEQ ID NO: 487) |
| ACI-8033-19A2-Ab1 | 917.19A2 E9E5 | EVQLVESGGGLVQPKGSLKLSCAASGFSFNTYAMNWVRQAPGKGLEWVARIRSKSNNYATYYVDSVKDRFTISRDDSESMLYLQMNNLKTEDTALYYCVSESAYWGQGTLVTVSA (SEQ ID NO: 490) | TYAMN (SEQ ID NO: 141) | RIRSKSNNYATYYVDSVKD (SEQ ID NO: 492) | ESAY (SEQ ID NO: 493) | DVVMTQTPLSLPVSLGDQASISCRSSQSLVHSNGNTYLYWYLQKPGQSPKLLIYKVSNRLSGVPDRFSGSGSGTDFTLKISRVEAEDLGVYFCSQSTHVPFTFGSGTKLEIK (SEQ ID NO: 494) | RSSQSLVHSNGNTYLY (SEQ ID NO: 495) | KVSNRLS (SEQ ID NO: 496) | SQSTHVPFT (SEQ ID NO: 497) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| ACI-8033-8C10-Ab1 | 917.8C10 C6G3 | DVQLQESGPGLVKPSQSLSLTCSVTGQSITSGYYWNWIRQFPGNKLEWMGYISNDGSSKTNPSLTNRISVTRDTSKNQVFLKLKSVTTEDTATYYCVRGDQHWGQGTALTVSS (SEQ ID NO: 500) | SGYYWN (SEQ ID NO: 151) | YISNDGSSKTNPSLTN (SEQ ID NO: 502) | GDQH (SEQ ID NO: 503) | DVVLTQTPLTLSVTIGQPASISCKSSQSLLDSDGETYLNWLLQRPGQSPKRLIYLVSELDSGVSDRFTGSGSGTDFTLKISRLEAEDLGVYYCWQGTHFPQTFGGGTKLEIK (SEQ ID NO: 504) | KSSQSLLDSDGETYLN (SEQ ID NO: 105) | LVSELDS (SEQ ID NO: 336) | WQGTHFPQT (SEQ ID NO: 107) |
| ACI-8033-7A2-Ab1 | 917.7A2B 6A9 | QVQLQQPGTELVKPGASVNLPCKASGYTFTSYWMHWVKQRPGQGLDWIGNVNPNNSDSNYNEKFKRKATLTVDKSSSTAYMHLSSLTSEDSAVYYCARSPYYGGRYLDYWGQGTTLTVSS (SEQ ID NO: 510) | SYWMH (SEQ ID NO: 311) | NVNPNNSDSNYNEKFKR (SEQ ID NO: 512) | SPYYGGRYLDY (SEQ ID NO: 513) | DIVMSQSPSSLAVSVGEKVTMTCKSSQSLLYRSNQKNYLAWYQQKPGQSPKLLIYWAFTRESGVPDRFTGSGSGTDFTLTISSVKAEDLAVYYCQQYYSYPLTFGAGTKLELK (SEQ ID NO: 514) | KSSQSLLYRSNQKNYLA (SEQ ID NO: 515) | WAFTRES (SEQ ID NO: 516) | QQYYSYPLT (SEQ ID NO: 517) |
| ACI-8033-1A12-Ab1 | 917.1A12 C1B4 | QVHLKQSGADLVRPGASVKLSCKASGYSFTDFYINWVKQTPGQGLEWIARIYPGNNNTFYNEKFKGKATLSAEKSSTTAYMQLSSLTSEDSAVYFCVVGYYGAWGQGTTLTVSS (SEQ ID NO: 520) | DFYIN (SEQ ID NO: 521) | RIYPGNNNTFYNEKFKG (SEQ ID NO: 522) | GYYGA (SEQ ID NO: 463) | DVVMTQTPLSLPVSLGDQASISCRSSQSLVHSNGNTHLHWYLQKPGQSPKLLIYKVSNRFSGVPDRFSGSGSGTDFTLKISRVEAEDLGFYFCSQSTHVPWTFGGGTKLEIK (SEQ ID NO: 524) | RSSQSLVHSNGNTHLH (SEQ ID NO: 525) | KVSNRFS (SEQ ID NO: 16) | SQSTHVPWT (SEQ ID NO: 467) |
| ACI-8033-4F3-Ab1 | 917.4F3F 4G6 | EVQLQQSGPELVKPGASVKISCKASGYTFTDYYMNWVKQSHGKSLEWIGDINPNTGTNSYNQKFKGRASLTVDKFSSAAYMELRSLTSEDSAVYYCARTGYGDPISSYYYALDYWGQGTSVTVSS (SEQ ID NO: 530) | DYYMN (SEQ ID NO: 371) | DINPNTGTNSYNQKFKG (SEQ ID NO: 532) | TGYGDPISSYYYALDY (SEQ ID NO: 533) | DIVMSQSPSSLAVSAGEKVTMSCKSSQSLLNSRTRKNYLAWYQQKPGQSPKLLIYWASTRESGVPDRFTGSGSGTDFTLTISSVQAEDLAVYYCKQSYNLWTFGGGTKLEIK (SEQ ID NO: 534) | KSSQSLLNSRTRKNYLA (SEQ ID NO: 345) | WASTRES (SEQ ID NO: 376) | KQSYNLWT (SEQ ID NO: 537) |
| ACI-8033-17F5-Ab1 | 917.17F5 F5G9 | EVQLQQSGPELVKPGASVKISCKASGYTFTDYFMNWVKQSHGKSLEWIGDINPNIDVTNYNQKFKGKATLTVDKSSSTAYMELRSLTSEDSAVYYCARGRDYAMDFWGQGTSVTVSS (SEQ ID NO: 540) | DYFMN (SEQ ID NO: 341) | DINPNIDVTNYNQKFKG (SEQ ID NO: 542) | GRDYAMDF (SEQ ID NO: 543) | DIVMSQSPSSLAVSAGEKVTMSCKSSQSLLNSRTRKNYLAWYQQKPGQSPKLLIYWASTRESGVPDRFTGSGSGTDFTLTISSVQAEDLAVYYCKQSYDLWTFGGGTKLEIK (SEQ ID NO: 544) | KSSQSLLNSRTRKNYLA (SEQ ID NO: 345) | WASTRES (SEQ ID NO: 376) | KQSYDLWT (SEQ ID NO: 347) |
| ACI-8033-18C11-Ab1 | 917.18C1 1A11F10 | QVQLQQPGAELVKPGASVKMSCKAAGYTFSSYWITWVRQRPGQGLDWIGDIYPGGG | SYWIT (SEQ ID NO: 551) | DIYPGGGVTNYNEKFKT (SEQ ID NO: 552) | AQTTFAY (SEQ ID NO: 553) | DVLMTQTPLSLPVSLGDQASISCRSSQNIVHNNGNTYLEWYLQKPGQSPKLLIYKV | RSSQNIVHNNGNTYLE (SEQ ID NO: 555) | KVSNRFS (SEQ ID NO: 16) | FQGSHVPRT (SEQ ID NO: 557) |

TABLE 7-continued

Amino acid sequence of the heavy chain and light chain variable domains (VH and VL) and their CDRs

| Antibody Code | Hybridoma Code | VH | VH CDR1 | VH CDR2 | VH CDR3 | VL | VL CDR1 | VL CDR2 | VL CDR3 |
|---|---|---|---|---|---|---|---|---|---|
| | | VTNYNEKFKTKA TLTVDTSSSTAY MQLSSLTSEDS AVYYCATAQTTF AYWGQGTLVTV SA (SEQ ID NO: 550) | | | | SNRFSGVPDRF SGSGSGTDFTL KISRVEAEDLG VYYCFQGSHVP RTFGGGTKLEI K (SEQ ID NO: 554) | | | |
| ACI-8033-18D12-Ab1 | 917.18D1 2F10D6 | QVQLQQPGAEL VKPGASVKMSC KASGYTFTSYWI TWVRQRPGQGL DWIGDIYPGGG VTNYNEKFKTKA TLTVDTSSSTAY MHLSSLTSEDSA VYFCATAQTTFA HWGQGTLVTVS A (SEQ ID NO: 560) | SYWIT (SEQ ID NO: 551) | DIYPGG GVTNYN EKFKT (SEQ ID NO: 552) | AQTTFA H (SEQ ID NO: 563) | DVLMTQTPLSL PVSLGDQASIS CRSSQNIAHNN GNTYLEWYLQK PGQSPKLLIYKV SNRFSGVPDRF SGSGSGTDFTL KISRVEAEDLG VYYCFQGSHVP RTFGGGTKLEI K (SEQ ID NO: 564) | RSSQNIA HNNGNT YLE (SEQ ID NO: 565) | KVSNRF S (SEQ ID NO: 16) | FQGSH VPRT (SEQ ID NO: 557) |
| ACI-8033-1F8-Ab1 | 917.1F8D 8E4 | DVQLQESGPGL VKPSQSLSLTCS VTGYSITSGFYW NWIRQFPGNKL EWMGYISYDGS NNYNPSLKNRIS IIRDTSKNQFFLK LKSVTSEDTATY YCVRGDVDWG QGTTLTVSS (SEQ ID NO: 570) | SGFYW N (SEQ ID NO: 571) | YISYDG SNNYNP SLKN (SEQ ID NO: 202) | GDVD (SEQ ID NO: 573) | DVVMTQTPLTL SVTIGQPASISC KSSQSLLDSDG ETYLNWLFQRP GQSPKRLIYLVS KLDSGVPDRFT GSGSGTDFTLK ISRVEPEDLGV YYCWQGTHFP QTLGGGTKLEI K (SEQ ID NO: 574) | KSSQSLL DSDGET YLN (SEQ ID NO: 105) | LVSKLD S (SEQ ID NO: 106) | WQGTH FPQT (SEQ ID NO: 107) |
| ACI-8033-22E5-Ab1 | 917.22E5 C5F7 | EVQLVESGGDL VKPGGSLKLSC AASGFTFSSYG MSWVRQTPDKR LEWVATISNGGS YTYYPDSVKGR FTISRDNAKNTL YLQMSSLKSED TAMYYCARQLR RDGWYFDVWG TGTTVTVSS (SEQ ID NO: 580) | SYGMS (SEQ ID NO: 581) | TISNGG SYTYYP DSVKG (SEQ ID NO: 582) | QLRRD GWYFD V (SEQ ID NO: 583) | EIVLTQSPALMA ASPGEKVTITCS VSSSISSSKLH WYQQKSETSP KLWIYGTSNLA SGVPVRFSGSG SGTSYSLTISSM EAEDAATYYCQ QWSSYPLTFGA GTKLELK (SEQ ID NO: 584) | SVSSSIS SSKLH (SEQ ID NO: 585) | GTSNLA S (SEQ ID NO: 586) | QQWSS YPLT (SEQ ID NO: 587) |
| ACI-8033-27D8-Ab1 | 917.27D8 E1H10E10 | EVQLVESGGGL VQPKGSLKLSC AASGFTFNTYA MNWVRQAPGK GLEWVARIRSKS NNFATYYADSV KDRFTISRDESE SMLYLQMNNLK AEDTAMYYCVR SFDYWGQGTTL TVSS (SEQ ID NO: 590) | TYAMN (SEQ ID NO: 141) | RIRSKS NNFATY YADSVK D (SEQ ID NO: 472) | SFDY (SEQ ID NO: 473) | DIKMTQSPSSM YASLGERVTITC KASQDINSYLS WFQQKPGKSP KTLIYRAKRLVD GVPSRFSGSGS GQDYSLTISSLE YEDMGIYYCLQ YDEFPFTFGSG TKLEIK (SEQ ID NO: 474) | KASQDIN SYLS (SEQ ID NO: 475) | RAKRLV D (SEQ ID NO: 476) | LQYDEF PFT (SEQ ID NO: 477) |
| ACI-8033-2108-Ab1 | 917.21C8 E4C8 | QVQLQQPGAEL VKPGASVKMSC KASGYTFTSYWI TWVRQRPGQGL DWIGDIYPGGG VTNYNEKFKTKA TLTVDTSSSTAY MHLSSLTSEDSA VYFCATAQTTFA YWGQGTLVTVS | SYWIT (SEQ ID NO: 551) | DIYPGG GVTNYN EKFKT (SEQ ID NO: 552) | AQTTFA Y (SEQ ID NO: 553) | DVLMTQTPLSL PVSLGDQASIS CRSSQNIVHNN GNTYLEWYLQK PGQSPKLLIYKV SNRFSGVPDRF SGSGSGTDFTL KISRVEAEDLG VYYCFQGSHVP RTFGGGTKLEI | RSSQNIV HNNGNT YLE (SEQ ID No: 555) | KVSNRF S (SEQ ID NO: 16) | FQGSH VPRT (SEQ ID NO: 557) |

TABLE 7-continued

| Amino acid sequence of the heavy chain and light chain variable domains (VH and VL) and their CDRs | | | | | | | | | |
|---|---|---|---|---|---|---|---|---|---|
| Antibody Code | Hybridoma Code | VH | VH CDR1 | VH CDR2 | VH CDR3 | VL | VL CDR1 | VL CDR2 | VL CDR3 |
| | | A (SEQ ID NO: 600) | | | | K (SEQ ID NO: 554) | | | |

Figure 8:
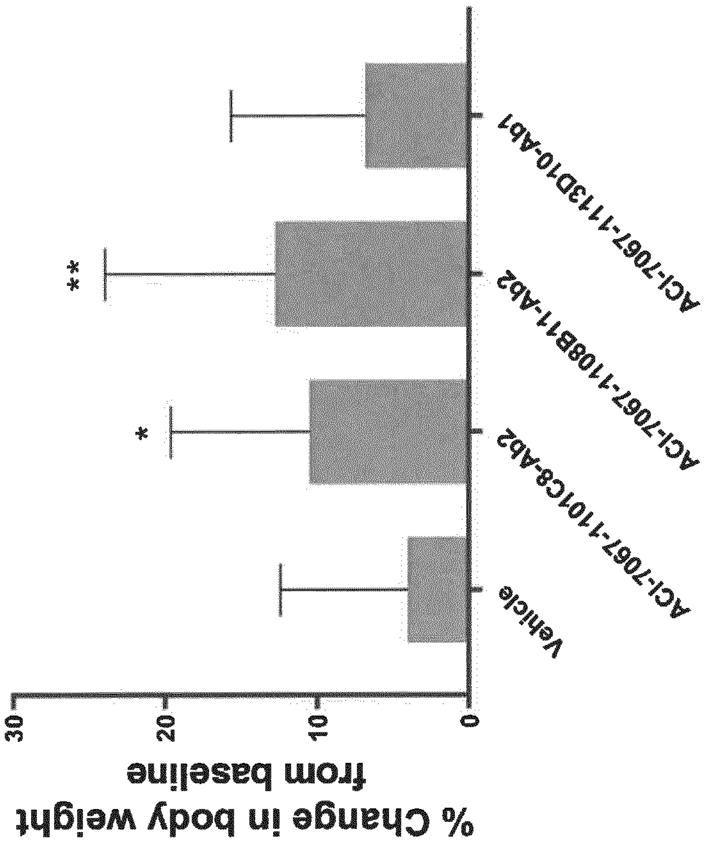
Figure 9:
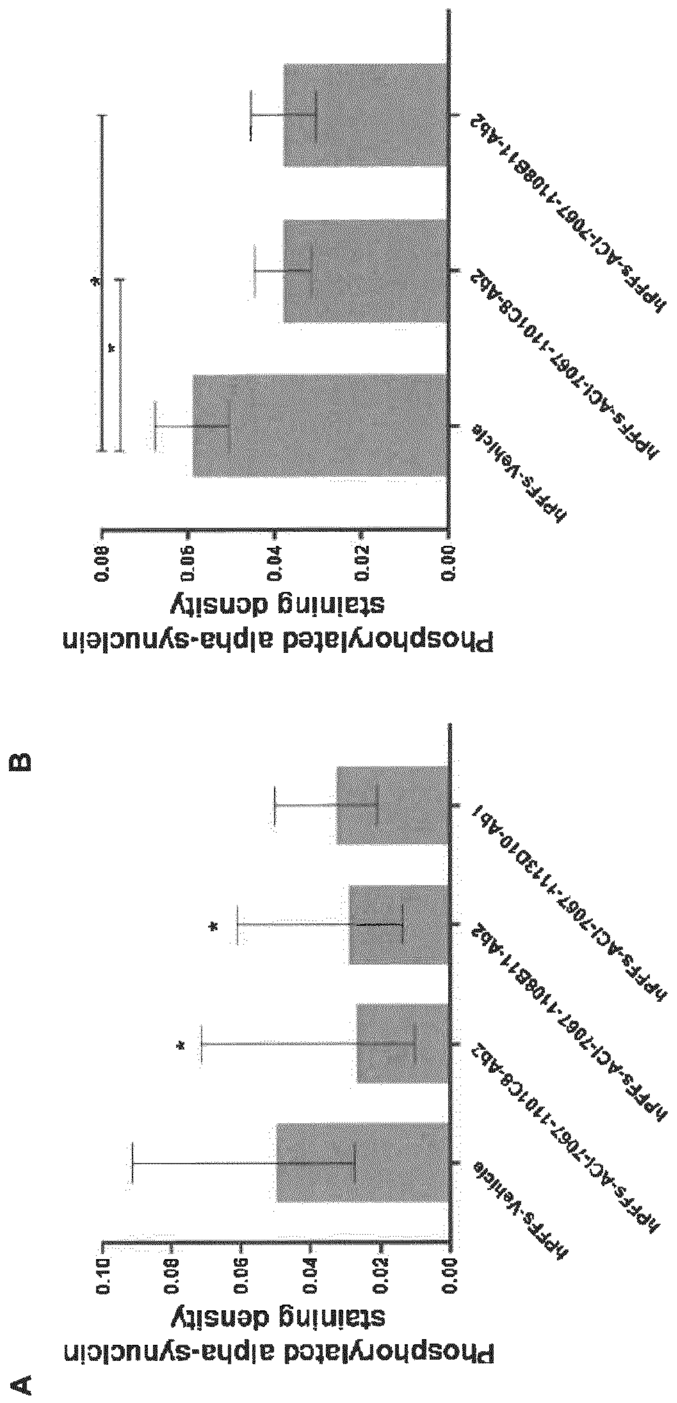
Figure 10:
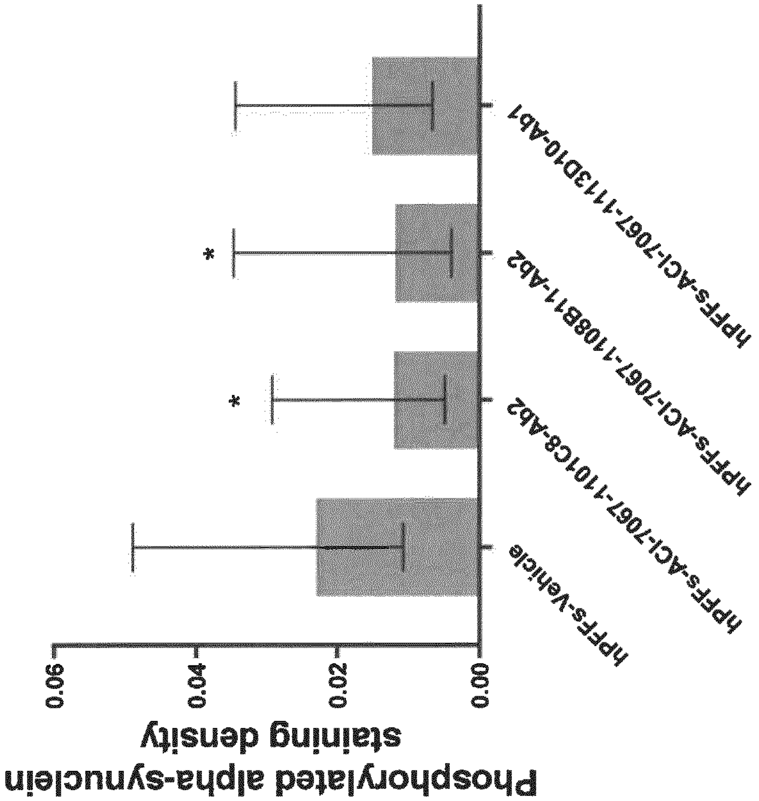
Figure 11:
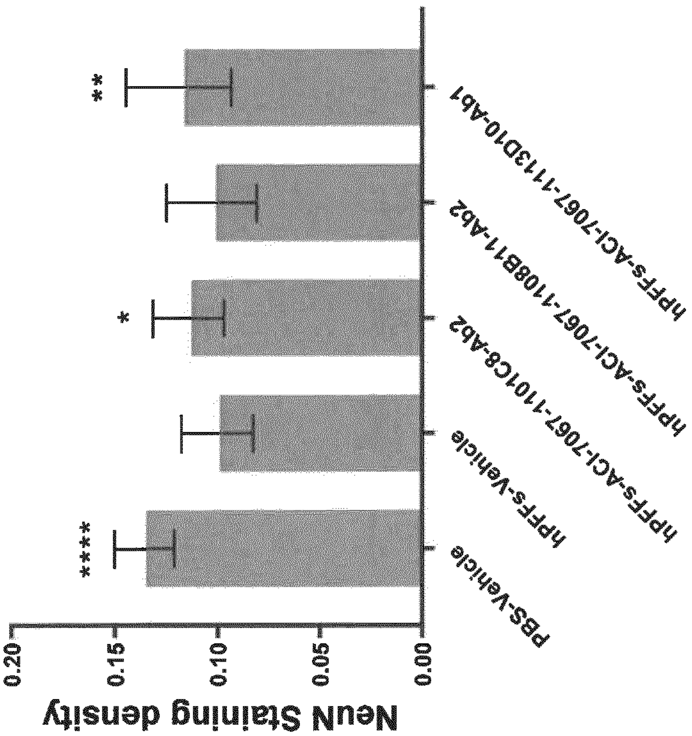

Efficacy of alpha-synuclein antibodies in an in vivo mouse model of Parkinson's disease Animal studies were performed in accordance with all local Animal Care guidelines. Male, hemizygous transgenic-M83 mice were inoculated with human alpha-synuclein pre-formed fibrils (hPFFs) or phosphate buffered saline (PBS) as negative control via stereotactic injection into the anterior olfactory nucleus as described in Luk et al., 2012. Vehicle control (formulation buffer comprising of: 25 mM histidine, 150 mM NaCl, 0.02% poloxamer 188, pH 5.5) or antibodies (ACI-7067-1101C8-Ab2, ACI-7067-1108B11-Ab2, or ACI-7067-1113D10-Ab1) against alpha-synuclein were injected intraperitoneally (i.p.) at 30 mg/kg/week, for 17 weeks starting at the week of surgery (Week 0) to Week 16 following stereotaxic surgery. The health status of mice was monitored daily and body weight was recorded on a weekly basis. No adverse effects were observed post-dosing; animals showed no distress or discomfort and had normal activity level. ACI-7067-1101C8-Ab2 and ACI-7067-1108B11-Ab2 demonstrated a significant reduction in the rate of body weight loss as compared to the vehicle treated control group injected with human pre-formed fibrils, while for ACI-7067-1113D10-Ab1 a trend of reduction in the rate of body weight was observed (FIG. 8).

After 17 weeks post inoculation, mice were sacrificed by perfusion with 20 ml of phosphate buffered saline, followed by transcardiac infusion of 20 mL of 10% neutral-buffered formalin. Brains were immersion-fixed in 10% neutral-buffered formalin for 72 hours. Fixed brains for paraffin embedding were dehydrated through graded ethanol and xylene, and then infiltrated with paraffin wax. Processed brains were oriented and embedded in paraffin blocks followed by sectioning at 5 microns. For quantification of pathological alpha-synuclein, slides initially underwent a two-step epitope retrieval and were treated with mild PK digestion prior to staining with an antibody directed against phosphorylated alpha-synuclein [EP1536Y]. Neuronal density measurements were performed by staining for NeuN, a neuronal specific protein, by IHC with the antibody clone A60 (Millipore). Data for all IHC measurements were acquired by an Axio Scan.Z1 digital whole slide scanner (Carl Zeiss). Regions of interest, brain areas interconnected with the injection site, were manually delimited and quantification of IHC staining, percent area stained, was performed on each of the slides using an automated software algorithm. The IHC analysis and quantification was performed in a blinded manner with respect to the treatment groups. Disease spreading and propagation of pathology in the M83 mouse model was monitored by an increase in pathological phosphorylated alpha-synuclein IHC staining (normalized by neuronal density) and a decrease in NeuN IHC staining for the human pre-formed fibril injected groups. ACI-7067-1101C8-Ab2 and ACI-7067-1108B11-Ab2 significantly delayed the aggregation and seeding of pathological alpha-synuclein indicated by the significantly reduced levels of alpha-synuclein pathology in the piriform cortex and brainstem contralateral to the injection site (FIG. 9A, FIG. 9B, and FIG. 10), while a trend for delayed aggregation and seeding of pathological alpha-synuclein indicated by the reduced levels of alpha-synuclein pathology in the piriform cortex and brainstem contralateral to the injection site was observed for ACI-7067-1113D10-Ab1. Summarizing, ACI-7067-1101C8-Ab2 and ACI-7067-1108B11-Ab2 significantly decrease pathological alpha-synuclein spreading in vivo as measured by a reduction of pathological alpha-synuclein. Furthermore ACI-7067-1101C8-Ab2 and ACI-7067-1113D10-Ab1 demonstrated a significant recovery in neuronal loss in the cortex ipsilateral to the injection site (FIG. 11) while a trend for recovery in neuronal loss in the cortex ipsilateral to the injection site was observed for ACI-7067-1108B11-Ab2.

Inhibiting a-Syn Propagation in Cells

Monoclonal anti-alpha-synuclein antibodies were evaluated for their ability to inhibit the uptake and seeding of alpha-synuclein aggregation in an in vitro cellular model that is susceptible to alpha-synuclein seeding and in mouse primary cortical neurons. The addition of alpha-synuclein seeds to the cellular model or primary neurons initiates the de novo aggregation of monomeric a-synuclein. The formation of de novo a-syn aggregates or de novo pathological alpha-synuclein (phosphorylated alpha-synuclein) was assessed in the presence or absence of alpha-synuclein antibodies relative to an isotype control antibody. The ability of alpha-synuclein antibodies to inhibit uptake or seeded aggregation was quantified as a percent change in the number of alpha-synuclein aggregates observed.

For the in vitro cellular model, alpha-synuclein antibodies (ACI-7067-1101C8-Ab2, ACI-7067-1108B11-Ab2, or ACI-7067-1113D10-Ab1) or an isotype control antibody were incubated with 0.4 µL/well Ab-DeliverIN™ Transfection Reagent (OZ Biosciences, AI21000) for 30 min at room temperature in low-binding 96-well plates (Eppendorf (Microplate 96/V-PP, Sigma, EP951040227). Antibodies/Ab-DeliverIN were then added to the cells, plated at a density of 8,000 cells/well 24 hours prior to treatment, and placed back in the incubator (at 37° C. with 5% $CO_2$) for 5 hours. Alpha-synuclein seeds (0.05 µg/well) were diluted in a reduced-serum medium (Opti-MEM™, Life Technologies, 31985070) and incubated with 0.2 µL/well Lipofectamine™ 2000 Transfection Reagent (Life Technologies, 11668019) for 30 min at 25° C. in a low-binding 96-well plate. Alpha-synuclein seeds/lipofectamine were then added to cells. As a reference control, cells were also transduced with lipofectamine without alpha-synuclein seeds. Cells were placed back in the incubator (at 37° C. with 5% $CO_2$). Cells were then supplemented at 24 hours post-transduction with 100 µL of DMEM/glutamax (Gibco, 31966-021), supplemented with 5% Fetal Bovine Serum (qualified and heat inactivated; Gibco, 10500-064) and 1% Penicillin-Streptomycin (10,000 U/mL; Gibco, 15140-122). At 96 hours, post initial transduction, cells were fixed with an equal volume of cold 2% Triton X-100, 8% PFA in PBS, and Hoechst 33342

(1:10,000). Media was removed and washed three times with PBS, fixed cells were left in PBS, kept protected from light, and high-content imaging analysis was performed to detect and quantify the formation of de novo alpha-synuclein aggregates. Use of an intrinsically fluorescent reporter protein allowed for the detection of de novo alpha-synuclein aggregates. The percent aggregates formed were then calculated relative to conditions in the absence of antibodies. $IC_{50}$ values were obtained from fitting using Equation 6 (GraphPad Prism 7).

$$Y = \frac{\text{Bottom} + (\text{Top} - \text{Bottom})}{1 + 10^{(\log IC_{50} - X) * \text{Hill Slope}}} \quad \text{Equation 6}$$

ACI-7067-1101C8-Ab2, ACI-7067-1108B11-Ab2, and ACI-7067-1113D10-Ab1 reduced the seeding capacity of alpha-synuclein aggregates in a dose-dependent fashion (FIG. 12).

For the mouse primary cortical neurons, cells were cultured in 384-well plates. At 6 days in vitro (DIV), alpha-synuclein antibodies (ACI-7067-1101C8-Ab2, ACI-7067-1108B11-Ab2, or ACI-7067-1113D10-Ab1) or an isotype control antibody were added to cells plated at a density of 40,000 cells/well and incubated for 30 min. Alpha-synuclein seeds (8 μg) were then added to the cells. At 13 DIV (7 days after alpha-synuclein seed addition) the cells were fixated with PFA and stained with an antibody directed against phosphorylated alpha-synuclein (EP1536Y) and Hoechst stain. High-content image analysis was performed to detect and quantify the formation of de novo alpha-synuclein aggregates/cell. The percent aggregates formed were then calculated relative to conditions in the absence of antibodies. Data was combined from three independent experiments and $IC_{50}$ values were obtained from fitting using Equation 7 (GraphPad Prism 7).

$$Y = \frac{100}{1 + \left(\frac{IC_{50}}{X}\right)^{\text{Hill Slope}}} \quad \text{Equation 7}$$

ACI-7067-1101C8-Ab2, ACI-7067-1108B11-Ab2, and ACI-7067-1113D10-Ab1 reduced the uptake and seeding capacity of alpha-synuclein aggregates in a dose-dependent fashion (FIG. 13).

Humanization of Anti-Human a Synuclein Mouse Monoclonal Antibody

Design of the Humanized Variable Regions

Homology matching was used to choose human acceptor frameworks on which to graft ACI-7067-1101C8-Ab2 CDRs. Databases of human and mouse germline variable genes such as the IMGT database (Ehren mann, F et al, (2010) Nucl. Acids Res., 38 (S1): D301-D307) or IgBlast (Ye J. et al, (2013), Nucleic Acids Res. 2013 July; 41 (Web Server issue): W34-W40) or the VBASE2 (Retter I et al, (2005) Nucleic Acids Res. 33, Database issue D671-D674) may be used to identify the closest human variable domain subfamilies to the murine heavy and light chain V regions (SEQ ID NO: 10 and SEQ ID NO: 14, respectively). Selection of heavy and light chain variable sequences (VH and VL) within these subfamilies to be used as acceptor may be based upon sequence homology and/or a match of canonical structure of the CDR1 and CDR2 loop regions to help preserve the correct conformation of the six CDRs after grafting.

For example, use of the IMGT database indicates the best sequence homology between ACI-7067-1101C8-Ab2 heavy chain variable domain framework and the members of the human heavy chain variable domain subfamily 3. Highest homologies and identities of both CDRs and framework sequences were observed for germline sequences: IGHV3-73*01, IGHV3-73 *02, IGHV3-72*01, IGHV3-49*01, all of which had sequence identity above 75% for the whole sequence up to CDR3. IGHV3-73*01 and IGHV3-73 *02 showed 79% sequence identity while IGHV3-72*01 and IGHV3-49*01 showed a sequence identity of 76% and 75% respectively. IGHV3-73*01 was selected as the VH framework due to its high sequence homology and known stability.

Using the same approach, ACI-7067-1101C8-Ab2 light chain variable domain sequence showed the best sequence homology to the members of the human light chain variable domain kappa subfamily 2. Highest homologies and identities of both CDRs and framework sequences were observed for germline sequences: IGKV2-30*02, IGKV2-30*01, IGKV2D-29*02, IGKV2-24*01 all of which had sequence identity above 79% for the whole sequence up to CDR3. IGKV2-30*02 showed the highest sequence identity with 81%, while IGKV2-30*01, IGKV2D-29*02 had sequence identity of 80%. IGKV2-30*02 was selected as the VL framework due to its high sequence homology.

Potential deamidation and isomerization sites were identified within ACI-7067-1101C8-Ab2 CDR sequences at positions N53 and D61 in the variable heavy chain and position N28 in the variable light chain (according to Kabat numbering system). By 3D homology modelling, these PTM sites were confirmed to be solvent accessible. Point mutations N54A and D61A were introduced in the VH region whereas G29A was introduce in the VL region to remove the deamidation site in CDR L1. When combined all mutations retained the binding of ACI-7067-1101C8-Ab2 to its target; this set of mutations was included in the first humanized variant of ACI-7067-1101C8-Ab2.

As starting point for the humanization process, murine CDRs were grafted on human acceptor frameworks for both VH and VL regions. The resulting human-mouse hybrid heavy chain variable sequence had human IGHV3-73*01 framework regions, ACI-7067-1101C8-Ab2 mouse CDRs, and the best matching JH segment identified from the IMGT searches mentioned above.

Similarly, the human-mouse hybrid light chain variable domain had human IGKV2-30*02 framework regions, ACI-7067-1101C8-Ab2 mouse CDRs, and the best matching J K segment.

To accommodate CDRs on to the human acceptor framework key positions were modified by substituting human residues to mouse residues. This process is called back-mutation and is the most unpredictable procedure in the humanization of monoclonal antibodies. It requires the identification and selection of critical framework residues from the mouse antibody that need to be retained in order to preserve affinity while at the same time minimizing potential immunogenicity in the humanized antibody.

To identify residues that may impact most greatly the CDR conformation and/or VH/VL orientation, a 3D model for the human-mouse hybrid VH-VL pair was generated by homology modelling using the Abodybuilder server (Dunbar, J. et al (2016). Nucleic Acids Res. 44. W474-W478) and PBD: 1NBV as a template for the framework structure and VH/VL orientation. Model analysis allowed the selection of a subset of positions based on their putative influence on CDR loop conformation and/or heavy chain-light chain variable domain packing. This subset of positions consisted of positions 28, 49, 78, 93 and 100b in the variable heavy chain and positions 27B and 36 in the variable light chain.

From this first design, new sets of variable heavy and light chains were generated by introducing backmutation from human to mouse residues at the positions described above. Table 8 and 11 show the combination of backmutations in each different variable domain according to Kabat numbering system.

TABLE 8

Backmutations and sequence identity to the acceptor human framework of hACI-7067-1101C8-Ab2 heavy chain variable region.

| Chain | Backmutation | Seq identity to IGHV3-73*01 |
|---|---|---|
| hACI-7067-1101C8-Ab2__H1 | S28T/G49A/A78L/T93V | 86% |
| hACI-7067-1101C8-Ab2__H2 | S28T/A78L/T93V | 87% |
| hACI-7067-1101C8-Ab2__H3 | S28T/T93V | 88% |
| hACI-7067-1101C8-Ab2__H4 | S28T/G49A | 88% |
| hACI-7067-1101C8-Ab2__H5 | G49A/T93V | 88% |
| hACI-7067-1101C8-Ab2__H6 | S28T/G49A/A78L/T93V/M100bS | 85% |
| hACI-7067-1101C8-Ab2__H7 | S28T/G49A/A78L/T93V/M100bT | 85% |
| hACI-7067-1101C8-Ab2__H8 | S28T/A78L/M100bL | 89% |
| hACI-7067-1101C8-Ab2__H9 | A78L | 90% |
| hACI-7067-1101C8-Ab2__H10 | A78L/M100bL | 90% |
| hACI-7067-1101C8-Ab2__H11 | — | 91% |
| hACI-7067-1101C8-Ab2__H12 | —/M100bL | 91% |

TABLE 9

DNA of the humanized heavy chain variable domains (VH)

| Antibody chain code | Heavy chain |
|---|---|
| hACI-7067-1101C8-Ab2_H1 | GAGGTGCAGCTGGTGGAGAGCGGAGGAGGACTGGTCCAGCCCGGCGGATCTCTGAAACTGAGCTGCGC CGCCAGCGGCTTCAGCTTCAACATCTACGCCATGAACTGGGTGAGGCAAGCCCCCGGCAAAGGACTGGA GTGGGTGGCTAGAATCAGAAGCAAGAGCAACGCCTACGCCACCTACTACGCCGCCTCCGTGAAGGGAAG ATTCACCATCTCTAGAGACGACAGCAAGAACACACTGTATCTGCAGATGAACAATCTGAAGACCGAGGAC ACCGCCGTGTACTACTGCGTGAGAGTGGGACTGAGGTTCTACGCCATGGACTACTGGGGCCAAGGCACA CTGGTGACAGTGAGCTCC (SEQ ID NO: 618) |
| hACI-7067-1101C8-Ab2_H2 | GAGGTGCAGCTGGTGGAGAGCGGAGGAGGACTGGTCCAGCCCGGCGGATCTCTGAAACTGAGCTGCGC CGCCAGCGGCTTCAGCTTCAACATCTACGCCATGAACTGGGTGAGGCAAGCCCCCGGCAAAGGACTGGA GTGGGTGGGAAGAATCAGAAGCAAGAGCAACGCCTACGCCACCTACTACGCCGCCTCCGTGAAGGGAAG ATTCACCATCTCTAGAGACGACAGCAAGAACACACTGTATCTGCAGATGAACAATCTGAAGACCGAGGAC ACCGCCGTGTACTACTGCGTGAGAGTGGGACTGAGGTTCTACGCCATGGACTACTGGGGCCAAGGCACA CTGGTGACAGTGAGCTCC (SEQ ID NO: 628) |
| hACI-7067-1101C8-Ab2_H3 | GAGGTGCAGCTGGTGGAGAGCGGAGGAGGACTGGTCCAGCCCGGCGGATCTCTGAAACTGAGCTGCGC CGCCAGCGGCTTCAGCTTCAACATCTACGCCATGAACTGGGTGAGGCAAGCCCCCGGCAAAGGACTGGA GTGGGTGGGAAGAATCAGAAGCAAGAGCAACGCCTACGCCACCTACTACGCCGCCTCCGTGAAGGGAAG ATTCACCATCTCTAGAGACGACAGCAAGAACACAGCTTATCTGCAGATGAACAATCTGAAGACCGAGGAC ACCGCCGTGTACTACTGCGTGAGAGTGGGACTGAGGTTCTACGCCATGGACTACTGGGGCCAAGGCACA CTGGTGACAGTGAGCTCC (SEQ ID NO: 638) |
| hACI-7067-1101C8-Ab2_H4 | GAGGTGCAGCTGGTGGAGAGCGGAGGAGGACTGGTCCAGCCCGGCGGATCTCTGAAACTGAGCTGCGC CGCCAGCGGCTTCACCTTCAACATCTACGCCATGAACTGGGTGAGGCAAGCCCCCGGCAAAGGACTGGA GTGGGTGGGAAGAATCAGAAGCAAGAGCAACGCCTACGCCACCTACTACGCCGCCTCCGTGAAGGGAAG ATTCACCATCTCTAGAGACGACAGCAAGAACACACTGTATCTGCAGATGAACAATCTGAAGACCGAGGAC ACCGCCGTGTACTACTGCGTGAGAGTGGGACTGAGGTTCTACGCCATGGACTACTGGGGCCAAGGCACA CTGGTGACAGTGAGCTCC (SEQ ID NO: 648) |
| hACI-7067-1101C8-Ab2_H5 | GAGGTGCAGCTGGTGGAGAGCGGAGGAGGACTGGTCCAGCCCGGCGGATCTCTGAAACTGAGCTGCGC CGCCAGCGGCTTCAGCTTCAACATCTACGCCATGAACTGGGTGAGGCAAGCCCCCGGCAAAGGACTGGA GTGGGTGGGAAGAATCAGAAGCAAGAGCAACGCCTACGCCACCTACTACGCCGCCTCCGTGAAGGGAAG ATTCACCATCTCTAGAGACGACAGCAAGAACACACTGTATCTGCAGATGAACAATCTGAAGACCGAGGAC ACCGCCGTGTACTACTGCACCAGAGTGGGACTGAGGTTCTACGCCATGGACTACTGGGGCCAAGGCACA CTGGTGACAGTGAGCTCC (SEQ ID NO: 658) |
| hACI-7067-1101C8-Ab2_H6 | GAGGTGCAGCTGGTGGAAAGCGGCGGCGGACTGGTGCAACCCGGCGGATCTCTGAAGCTGAGCTGTGC CGCCAGCGGCTTCAGCTTCAACATCTACGCCATGAACTGGGTGAGACAAGCCCCCGGCAAAGGACTGGA ATGGGTGGCCAGAATTAGAAGCAAGTCCAACGCCTACGCCACCTACTACGCCGCCAGCGTGAAGGGCAG ATTCACCATCTCTAGAGACGACAGCAAGAACACACTGTATCTGCAGATGAACAATCTGAAGACCGAGGAC ACCGCCGTGTACTACTGCGTGAGGGTGGGACTGAGATTCTACGCCAGCGACTACTGGGGCCAAGGCACA CTGGTGACCGTGTCCAGC (SEQ ID NO: 668) |
| hACI-7067-1101C8-Ab2_H7 | GAGGTGCAGCTGGTGGAAAGCGGCGGCGGACTGGTGCAACCCGGCGGATCTCTGAAGCTGAGCTGTGC CGCCAGCGGCTTCAGCTTCAACATCTACGCCATGAACTGGGTGAGACAAGCCCCCGGCAAAGGACTGGA ATGGGTGGCCAGAATTAGAAGCAAGTCCAACGCCTACGCCACCTACTACGCCGCCAGCGTGAAGGGCAG ATTCACCATCTCTAGAGACGACAGCAAGAACACACTGTATCTGCAGATGAACAATCTGAAGACCGAGGAC ACCGCCGTGTACTACTGCGTGAGGGTGGGACTGAGATTCTACGCCACCGACTACTGGGGCCAAGGCACA CTGGTGACCGTGTCCAGC (SEQ ID NO: 678) |
| hACI-7067-1101C8-Ab2_H8 | GAGGTGCAGCTGGTGGAAAGCGGCGGAGGACTGGTGCAACCCGGCGGATCTCTGAAGCTGAGCTGTGC CGCCTCCGGCTTCAGCTTCAACATCTACGCCATGAACTGGGTGAGGCAAGCCCCCGGCAAGGGACTGGA GTGGGTGGGCAGAATCAGAAGCAAGAGCAACGCCTACGCCACCTACTACGCCGCCAGCGTGAAGGGAAG |

TABLE 9-continued

| DNA of the humanized heavy chain variable domains (VH) | |
|---|---|
| **Antibody chain code** | **Heavy chain** |
| | ATTCACCATCTCTAGAGACGACAGCAAGAACACACTGTATCTGCAGATGAACAATCTGAAGACCGAGGAC ACCGCCGTGTACTACTGCACAAGAGTGGGACTGAGATTCTACGCTCTGGACTACTGGGGCCAAGGCACA CTGGTGACCGTGAGCAGC (SEQ ID NO: 688) |
| hACI-7067-1101C8-Ab2_H9 | GAGGTGCAGCTGGTGGAAAGCGGCGGAGGACTGGTGCAACCCGGCGGATCTCTGAAGCTGAGCTGTGC CGCCTCCGGCTTCACCTTCAACATCTACGCCATGAACTGGGTGAGGCAAGCCCCCGGCAAGGGACTGGA GTGGGTGGGCAGAATCAGAAGCAAGAGCAACGCCTACGCCACCTACTACGCCGCCAGCGTGAAGGGAAG ATTCACCATCTCTAGAGACGACAGCAAGAACACACTGTATCTGCAGATGAACAATCTGAAGACCGAGGAC ACCGCCGTGTACTACTGCACAAGAGTGGGACTGAGATTCTACGCTATGGACTACTGGGGCCAAGGCACAC TGGTGACCGTGAGCAGC (SEQ ID NO: 698) |
| hACI-7067-1101C8-Ab2_H10 | GAGGTGCAGCTGGTGGAAAGCGGCGGAGGACTGGTGCAACCCGGCGGATCTCTGAAGCTGAGCTGTGC CGCCTCCGGCTTCACCTTCAACATCTACGCCATGAACTGGGTGAGGCAAGCCCCCGGCAAGGGACTGGA GTGGGTGGGCAGAATCAGAAGCAAGAGCAACGCCTACGCCACCTACTACGCCGCCAGCGTGAAGGGAAG ATTCACCATCTCTAGAGACGACAGCAAGAACACACTGTATCTGCAGATGAACAATCTGAAGACCGAGGAC ACCGCCGTGTACTACTGCACAAGAGTGGGACTGAGATTCTACGCTCTGGACTACTGGGGCCAAGGCACA CTGGTGACCGTGAGCAGC (SEQ ID NO: 708) |
| hACI-7067-1101C8-Ab2_H11 | GAGGTGCAGCTGGTGGAGAGCGGAGGCGGACTGGTGCAACCCGGCGGATCTCTGAAACTGAGCTGTGC CGCCAGCGGCTTCACCTTCAACATCTACGCCATGAACTGGGTGAGACAAGCCCCCGGCAAGGGACTGGA GTGGGTGGGCAGAATTAGAAGCAAGAGCAACGCCTACGCCACCTACTACGCCGCCAGCGTCAAGGGAAG ATTCACCATCTCTAGAGACGACAGCAAGAACACCGCCTATCTGCAGATGAACAATCTGAAGACCGAGGAC ACCGCCGTGTACTACTGCACCAGAGTGGGACTGAGGTTCTACGCCATGGACTACTGGGGCCAAGGCACA CTGGTGACCGTGAGCTCC (SEQ ID NO: 718) |
| hACI-7067-1101C8-Ab2_H12 | GAGGTGCAGCTGGTGGAAAGCGGCGGAGGACTGGTGCAACCCGGCGGATCTCTGAAGCTGAGCTGTGC CGCCTCCGGCTTCACCTTCAACATCTACGCCATGAACTGGGTGAGGCAAGCCCCCGGCAAGGGACTGGA GTGGGTGGGCAGAATCAGAAGCAAGAGCAACGCCTACGCCACCTACTACGCCGCCAGCGTGAAGGGAAG ATTCACCATCTCTAGAGACGACAGCAAGAACACAGCTTATCTGCAGATGAACAATCTGAAGACCGAGGAC ACCGCCGTGTACTACTGCACAAGAGTGGGACTGAGATTCTACGCTCTGGACTACTGGGGCCAAGGCACA CTGGTGACCGTGAGCAGC (SEQ ID NO: 728) |

TABLE 10

| Amino acid sequence of the heavy chains (VH) and their CDRs | | | | |
|---|---|---|---|---|
| **Antibody chain code** | **Heavy chain** | **CDR H1** | **CDR H2** | **CDR H3** |
| hACI-7067-1101C8-Ab2_H1 | EVQLVESGGGLVQPGGSLKLSCAASGFSFNIYAMNWVR QAPGKGLEWVARIRSKSNAYATYYAASVKGRFTISRDDS KNTLYLQMNNLKTEDTAVYYCVRVGLRFYAMDYWGQGT LVTVSS (SEQ ID NO: 610) | IYAMN (SEQ ID NO: 11) | RIRSKSNAYAT YYAASVKG (SEQ ID NO: 612) | VGLRFYAMDY (SEQ ID NO: 13) |
| hACI-7067-1101C8-Ab2_H2 | EVQLVESGGGLVQPGGSLKLSCAASGFSFNIYAMNWVR QAPGKGLEWVGRIRSKSNAYATYYAASVKGRFTISRDDS KNTLYLQMNNLKTEDTAVYYCVRVGLRFYAMDYWGQGT LVTVSS (SEQ ID NO: 620) | IYAMN (SEQ ID NO: 11) | RIRSKSNAYAT YYAASVKG (SEQ ID NO: 612) | VGLRFYAMDY (SEQ ID NO: 13) |
| hACI-7067-1101C8-Ab2_H3 | EVQLVESGGGLVQPGGSLKLSCAASGFSFNIYAMNWVR QAPGKGLEWVGRIRSKSNAYATYYAASVKGRFTISRDDS KNTAYLQMNNLKTEDTAVYYCVRVGLRFYAMDYWGQGT LVTVSS (SEQ ID NO: 630) | IYAMN (SEQ ID NO: 11) | RIRSKSNAYAT YYAASVKG (SEQ ID NO: 612) | VGLRFYAMDY (SEQ ID NO: 13) |
| hACI-7067-1101C8-Ab2_H4 | EVQLVESGGGLVQPGGSLKLSCAASGFTFNIYAMNWVR QAPGKGLEWVGRIRSKSNAYATYYAASVKGRFTISRDDS KNTLYLQMNNLKTEDTAVYYCVRVGLRFYAMDYWGQGT LVTVSS (SEQ ID NO: 640) | IYAMN (SEQ ID NO: 11) | RIRSKSNAYAT YYAASVKG (SEQ ID NO: 612) | VGLRFYAMDY (SEQ ID NO: 13) |
| hACI-7067-1101C8-Ab2_H5 | EVQLVESGGGLVQPGGSLKLSCAASGFSFNIYAMNWVR QAPGKGLEWVGRIRSKSNAYATYYAASVKGRFTISRDDS KNTLYLQMNNLKTEDTAVYYCTRVGLRFYAMDYWGQGT LVTVSS (SEQ ID NO: 650) | IYAMN (SEQ ID NO: 11) | RIRSKSNAYAT YYAASVKG (SEQ ID NO: 612) | VGLRFYAMDY (SEQ ID NO: 13) |
| hACI-7067-1101C8-Ab2_H6 | EVQLVESGGGLVQPGGSLKLSCAASGFSFNIYAMNWVR QAPGKGLEWVARIRSKSNAYATYYAASVKGRFTISRDDS KNTLYLQMNNLKTEDTAVYYCVRVGLRFYASDYWGQGT LVTVSS (SEQ ID NO: 660) | IYAMN (SEQ ID NO: 11) | RIRSKSNAYAT YYAASVKG (SEQ ID NO: 612) | VGLRFYASDY (SEQ ID NO: 663) |

TABLE 10-continued

| Amino acid sequence of the heavy chains (VH) and their CDRs | | | | |
|---|---|---|---|---|
| Antibody chain code | Heavy chain | CDR H1 | CDR H2 | CDR H3 |
| hACI-7067-1101C8-Ab2_H7 | EVQLVESGGGLVQPGGSLKLSCAASGFSFNIYAMNWVRQAPGKGLEWVARIRSKSNAYATYYAASVKGRFTISRDDSKNTLYLQMNNLKTEDTAVYYCVRVGLRFYATDYWGQGTLVTVSS (SEQ ID NO: 670) | IYAMN (SEQ ID NO: 11) | RIRSKSNAYATYYAASVKG (SEQ ID NO: 612) | VGLRFYATDY (SEQ ID NO: 673) |
| hACI-7067-1101C8-Ab2_H8 | EVQLVESGGGLVQPGGSLKLSCAASGFSFNIYAMNWVRQAPGKGLEWVGRIRSKSNAYATYYAASVKGRFTISRDDSKNTLYLQMNNLKTEDTAVYYCTRVGLRFYALDYWGQGTLVTVSS (SEQ ID NO: 680) | IYAMN (SEQ ID NO: 11) | RIRSKSNAYATYYAASVKG (SEQ ID NO: 612) | VGLRFYALDY (SEQ ID NO: 683) |
| hACI-7067-1101C8-Ab2_H9 | EVQLVESGGGLVQPGGSLKLSCAASGFTFNIYAMNWVRQAPGKGLEWVGRIRSKSNAYATYYAASVKGRFTISRDDSKNTLYLQMNNLKTEDTAVYYCTRVGLRFYAMDYWGQGTLVTVSS (SEQ ID NO: 690) | IYAMN (SEQ ID NO: 11) | RIRSKSNAYATYYAASVKG (SEQ ID NO: 612) | VGLRFYAMDY (SEQ ID NO: 13) |
| hACI-7067-1101C8-Ab2_H10 | EVQLVESGGGLVQPGGSLKLSCAASGFTFNIYAMNWVRQAPGKGLEWVGRIRSKSNAYATYYAASVKGRFTISRDDSKNTLYLQMNNLKTEDTAVYYCTRVGLRFYALDYWGQGTLVTVSS (SEQ ID NO: 700) | IYAMN (SEQ ID NO: 11) | RIRSKSNAYATYYAASVKG (SEQ ID NO: 612) | VGLRFYALDY (SEQ ID NO: 683) |
| hACI-7067-1101C8-Ab2_H11 | EVQLVESGGGLVQPGGSLKLSCAASGFTFNIYAMNWVRQAPGKGLEWVGRIRSKSNAYATYYAASVKGRFTISRDDSKNTAYLQMNNLKTEDTAVYYCTRVGLRFYAMDYWGQGTLVTVSS (SEQ ID NO: 710) | IYAMN (SEQ ID NO: 11) | RIRSKSNAYATYYAASVKG (SEQ ID NO: 612) | VGLRFYAMDY (SEQ ID NO: 13) |
| hACI-7067-1101C8-Ab2_H12 | EVQLVESGGGLVQPGGSLKLSCAASGFTFNIYAMNWVRQAPGKGLEWVGRIRSKSNAYATYYAASVKGRFTISRDDSKNTAYLQMNNLKTEDTAVYYCTRVGLRFYALDYWGQGTLVTVSS (SEQ ID NO: 720) | IYAMN (SEQ ID NO: 11) | RIRSKSNAYATYYAASVKG (SEQ ID NO: 612) | VGLRFYALDY (SEQ ID NO: 683) |

TABLE 11

| Backmutations and sequence identity to the acceptor human framework of hACI-7067-1101C8-Ab2 light chain variable region. | | |
|---|---|---|
| Chain | Backmutation | Seq identity to IGKV2-30*02 |
| hACI-7067-1101C8-Ab2__L1 | L27BI/F36Y/R46L | 88% |
| hACI-7067-1101C8-Ab2__L2 | F36Y/R46L | 89% |
| hACI-7067-1101C8-Ab2__L3 | L27BI/R46L | 89% |
| hACI-7067-1101C8-Ab2__L4 | R46L | 91% |

TABLE 12

| DNA of the humanized light chain variable domains (VL) | |
|---|---|
| Antibody chain code | Light chain |
| hACI-7067-1101C8-Ab2_L1 | GACGTGGTGATGACCCAGAGCCCTCTGTCTCTGCCCGTGACACTGGGACAACCCGCCTCCATCAGCTGCAGATCCAGCCAGTCCATCGTGCACAGCAACGCCAACACCTATCTGGAGTGGTACCAGCAGAGACCCGGCCAGAGCCCTAGGCTGCTGATCTACAAGGTGTCCAATAGATTCAGCGGCGTGCCCGACAGATTCAGCGGAAGCGGCAGCGGCACAGACTTCACACTGAAGATCAGCAGAGTGGAGGCCGAGGACCTCGGCGTGTACTATTGCTTTCAAGGCAGCCAAGGCCCTCTGACCTTTGGACAAGGCACCAAGCTGGAGATCAAG (SEQ ID NO: 619) |
| hACI-7067-1101C8-Ab2_L2 | GACGTGGTGATGACCCAGAGCCCTCTGTCTCTGCCCGTGACACTGGGACAACCCGCCTCCATCAGCTGCAGATCCAGCCAGTCCCTGGTGCACAGCAACGCCAACACCTATCTGGAGTGGTACCAGCAGAGACCCGGCCAGAGCCCTAGGCTGCTGATCTACAAGGTGTCCAATAGATTCAGCGGCGTGCCCGACAGATTCAGCGGAAGCGGCAGCGGCACAGACTTCACACTGAAGATCAGCAGAGTGGAGGCCGAGGACCTCGGCGTGTACTATTGCTTTCAAGGCAGCCAAGGCCCTCTGACCTTTGGACAAGGCACCAAGCTGGAGATCAAG (SEQ ID NO: 629) |
| hACI-7067-1101C8-Ab2_L3 | GACGTGGTGATGACCCAGAGCCCTCTGTCTCTGCCCGTGACACTGGGACAACCCGCCTCCATCAGCTGCAGATCCAGCCAGTCCATCGTGCACAGCAACGCCAACACCTATCTGGAGTGGTTCCAGCAGAGACCCGGCCAGAGCCCTAGGCTGCTGATCTACAAGGTGTCCAATAGATTCAGCGGCGTGCCCGACAGATTCAGCGGAAGCGGCAGCGGCACAGACTTCACACTGAAGATCAGCAGAGTGGAGGCCGAGGACCTCGGCGTGTACTATTGCTTTCAAGGCAGCCAAGGCCCTCTGACCTTTGGACAAGGCACCAAGCTGGAGATCAAG (SEQ ID NO: 639) |

TABLE 12-continued

| DNA of the humanized light chain variable domains (VL) | |
|---|---|
| Antibody chain code | Light chain |
| hACI-7067-1101C8-Ab2_L4 | GATGTGGTGATGACCCAGAGCCCTCTGTCTCTGCCCGTGACACTGGGCCAGCCCGCCAGCATCAGCTGCAGATCCAGCCAGTCTCTGGTGCACAGCAACGCCAACACCTATCTGGAGTGGTTCCAGCAGAGACCCGGCCAGTCCCCTAGGCTGCTGATCTACAAGGTCTCCAATAGATTCAGCGGCGTGCCCGACAGATTTAGCGGCAGCGGAAGCGGCACCGACTTTACACTGAAGATCAGCAGAGTGGAGGCTGAGGATCTGGGCGTGTACTACTGCTTTCAAGGCAGCCAAGGCCCTCTGACCTTTGGCCAAGGCACCAAGCTGGAGATCAAG (SEQ ID NO: 649) |

TABLE 13

| Amino acid sequence of the light chains (VL) and their CDRs | | | | |
|---|---|---|---|---|
| Antibody chain code | Light chain | CDR L1 | CDR L2 | CDR L3 |
| hACI-7067-1101C8-Ab2_L1 | DVVMTQSPLSLPVTLGQPASISCRSSQSIVHSNANTYLEWYQQRPGQSPRLLIYKVSNRFSGVPDRFSGSGSGTDFTLKISRVEAEDLGVYYCFQGSQGPLTFGQGTKLEIK (SEQ ID NO: 614) | RSSQSIVHSNANTYLE (SEQ ID NO: 615) | KVSNRFS (SEQ ID NO: 16) | FQGSQGPLT (SEQ ID NO: 17) |
| hACI-7067-1101C8-Ab2_L2 | DVVMTQSPLSLPVTLGQPASISCRSSQSLVHSNANTYLEWYQQRPGQSPRLLIYKVSNRFSGVPDRFSGSGSGTDFTLKISRVEAEDLGVYYCFQGSQGPLTFGQGTKLEIK (SEQ ID NO: 624) | RSSQSLVHSNANTYLE (SEQ ID NO: 625) | KVSNRFS (SEQ ID NO: 16) | FQGSQGPLT (SEQ ID NO: 17) |
| hACI-7067-1101C8-Ab2_L3 | DVVMTQSPLSLPVTLGQPASISCRSSQSIVHSNANTYLEWFQQRPGQSPRLLIYKVSNRFSGVPDRFSGSGSGTDFTLKISRVEAEDLGVYYCFQGSQGPLTFGQGTKLEIK (SEQ ID NO: 634) | RSSQSIVHSNANTYLE (SEQ ID NO: 615) | KVSNRFS (SEQ ID NO: 16) | FQGSQGPLT (SEQ ID NO: 17) |
| hACI-7067-1101C8-Ab2_L4 | DVVMTQSPLSLPVTLGQPASISCRSSQSLVHSNANTYLEWFQQRPGQSPRLLIYKVSNRFSGVPDRFSGSGSGTDFTLKISRVEAEDLGVYYCFQGSQGPLTFGQGTKLEIK (SEQ ID NO: 644) | RSSQSLVHSNANTYLE (SEQ ID NO: 625) | KVSNRFS (SEQ ID NO: 16) | FQGSQGPLT (SEQ ID NO: 17) |

Production of humanized antibody variants

DNA coding sequence for both heavy and light variable domains were synthesized and cloned using standard molecular biology techniques into plasmid allowing the expression in mammalian cells. Heavy chain variable domains were fused to the human Immunoglobulin IgG1 constant domain and light chain variable domains were cloned into plasmid containing the constant Kappa light chain domain. The chimeric antibody and the humanized variants were transiently expressed in Expi293F cells by cotransfecting heavy and light chain plasmid using the ExpiFectamine™ 293 transfection kit (ThermoFischer scientific, A14524). Post transfection, cells were maintained at 37° C. under 150 rpm agitation and 8% $CO_2$ level. Six days after transfection, supernatants were harvested and purified onto Protein A column pre-packed with 1 mL MabSelect Sure resin (GE Healthcare Life Sciences, 17543803). The column was equilibrated with 0.1 M Tris, pH7.0 before being loaded with the cell culture fluid. Following loading, the column was washed with 0.1 M Tris, pH7.0 followed by elution using 0.1 M citrate, pH3.5. The elution was then neutralized by adding 0.1 M Tris, pH9.0. The samples were then dialyzed in PBS buffer, Characterization of ACI-7067-1101C8-Ab2 humanized variants by Surface Plasmon resonance (SPR)

All variants were screened by SPR for binding against both a-synuclein aggregates and monomers. Single concentration measurments were performed on an SPR instrument (Biacore 8K, GE Healthcare Life Sciences) using CM5 Series S sensor chips (GE Healthcare Life Sciences, 29-1496-03). Flow channels (Fc) 1-8 were activated with a fresh solution of EDC/NHS (Amine Coupling Kit, 1:1 ratio of both reagents, GE Healthcare Life Sciences, BR100050). 30 μg/mL of an F (ab)'2 Goat anti-human IgG Fc (Jackson ImmunoResearch Europe Ltd, 109-006-098) diluted in 10 mM NaAc (pH 4.5) was then injected to channel 1-8 for 420 s at a flow rate of 10 μL/min. The chip was deactivated by 1 M ethanolamine-HCl (GE Healthcare Life Sciences, BR100050) at a flow rate of 10 μL/min for 420 s.

A human IgG1 isotype control diluted in running buffer 1xHBS-EP+ (GE Healthcare Life Sciences, BR100669) was captured onto Fc1 via anti-human Fc lgG at a flow rate of 10 μL/min. ACI-7067-1101C8-Ab2 humanized variants diluted in running buffer 1xHBS-EP+were captured onto Fc2 via anti-human Fc IgG at a flow rate of 10 μL/min. 100 nM of analyte a-syn monomers (Boston Biochem, SP-485) and running buffer were injected orderly to Fc1-Fc2 at a flow rate of 30 μL/min for an association phase of 400 s, followed by 600 s of dissociation. 450 nM of analyte a-syn aggregates and running buffer were injected orderly to Fc1-Fc2 at a flow rate of 30 μL/min for an association phase of 400 s, followed by 3600 s of dissociation. 10 mM glycine pH 1.5 as regeneration buffer was injected following every dissociation phase.

The data for reference channel Fc1 and buffer channel were subtracted to generate the sensorgrams. The experimental data was fitted by 1:1 binding model or heterogeneous ligand model. The relative koff of the chimeric antibodies was determined for each humanized variant. Results are shown in Table 14.

TABLE 14

Relative koff of ACI-7067-1101C8-Ab2 humanized variants against the aggregated and monomeric forms of a-synuclein.

| Antibody code | Relative koff against a-syn monomer | Relative koff against a-syn aggregates |
|---|---|---|
| cACI-7067-1101C8-Ab2 | 1.0 | 1.0 |
| hACI-7067-1101C8-Ab2_H1L1 | 1.3 | 850.8 |
| hACI-7067-1101C8-Ab2_H1L2 | 0.6 | 130.9 |
| hACI-7067-1101C8-Ab2_H1L3 | 0.2 | 0.3 |
| hACI-7067-1101C8-Ab2_H1L4 | 0.1 | 0.3 |
| hACI-7067-1101C8-Ab2_H2L1 | 2.0 | 0.5 |
| hACI-7067-1101C8-Ab2_H2L2 | 1.1 | 1.9 |
| hACI-7067-1101C8-Ab2_H2L3 | 0.2 | 0.3 |
| hACI-7067-1101C8-Ab2_H2L4 | 0.1 | 0.2 |
| hACI-7067-1101C8-Ab2_H3L1 | 1.0 | 212.6 |
| hACI-7067-1101C8-Ab2_H3L2 | 0.6 | 1228.6 |
| hACI-7067-1101C8-Ab2_H3L3 | 0.1 | 0.2 |
| hACI-7067-1101C8-Ab2_H3L4 | 0.1 | 0.3 |
| hACI-7067-1101C8-Ab2_H4L1 | 1.9 | 0.5 |
| hACI-7067-1101C8-Ab2_H4L2 | 1.1 | 1.6 |
| hACI-7067-1101C8-Ab2_H4L3 | 0.2 | 0.3 |
| hACI-7067-1101C8-Ab2_H4L4 | 0.1 | 0.3 |
| hACI-7067-1101C8-Ab2_H5L1 | 1.1 | 1.5 |
| hACI-7067-1101C8-Ab2_H5L2 | 0.8 | 1.4 |
| hACI-7067-1101C8-Ab2_H5L3 | 0.2 | 0.2 |
| hACI-7067-1101C8-Ab2_H5L4 | 0.1 | 0.2 |
| hACI-7067-1101C8-Ab2_H6L1 | 0.3 | 1.0 |
| hACI-7067-1101C8-Ab2_H7L1 | N/A | 1418.8 |
| hACI-7067-1101C8-Ab2_H8L1 | 0.2 | 1.1 |
| hACI-7067-1101C8-Ab2_H9L1 | 1.3 | 5.5 |
| hACI-7067-1101C8-Ab2_H9L2 | 0.8 | 2.3 |
| hACI-7067-1101C8-Ab2_H10L1 | 0.2 | 1.7 |
| hACI-7067-1101C8-Ab2_H10L2 | 0.2 | 0.8 |
| hACI-7067-1101C8-Ab2_H11L1 | 0.8 | 62.0 |
| hACI-7067-1101C8-Ab2_H11L2 | 0.8 | 5.4 |
| hACI-7067-1101C8-Ab2_H12L1 | 0.2 | 1.0 |
| hACI-7067-1101C8-Ab2_H12L2 | 0.1 | 0.3 |

Ten variants were selected for full kinetics measurement by SPR based on their affinity to alpha-synuclein, expression level and/or sequence identity to the human acceptor framework.

Affinity measurements were performed on an surface plasmon resonance (SPR) instrument (Biacore 8K, GE Healthcare Life Sciences) using CM5 Series S sensor chips (GE Healthcare, BR-1005-30). Flow channels (Fc) 1-8 were activated with a fresh solution of EDC/NHS (Amine Coupling Kit, 1:1 ratio of both reagents, GE Healthcare Life Sciences, BR-1006-33). The anti-human antibody (GE Healthcare Life Sciences, BR-1008-39) was captured at a concentration of 30 μg/mL diluted in 10 mM sodium acetate (pH 5.0). Following, all unreacted activated ester groups were capped with 1 M ethanolamine (GE Healthcare Life Sciences, BR-1006-33). Any non-covalently bound antibodies were removed by three successive regenerations of 10 mM Glycine pH 1.7 (GE Healthcare Life Sciences, 28-9950-84). Immobilization levels were evaluated following ethanolamine capping (Bound) and finally following regeneration (Final).

Non-covalent immobilization of alpha-synuclein antibodies was performed using a target immobilization method of 200 response units (RU). Antibodies were diluted in 10 mM sodium acetate pH 5.5 (GE Healthcare, BR-1003-52) to a final concentration of 2 μg/mL. Binding affinity of alpha-synuclein antibodies to monomeric or fibrillar alpha-synuclein species was performed using a single-cycle kinetics method. The instrument was primed with 1xHBS-P+buffer (10X stock from GE Healthcare, BR-1003-52 diluted in Milli-Q water). Injections of monomeric alpha-synuclein (aSyn) (Boston Biochem, SP-485), increasing in concentration from 0.62-50 nM prepared from serial 2-fold dilutions, were performed with contact times of 300 sec/injection at a flow rate of 30 μL/min. A dissociation phase of 900 sec followed the final 50 nM injection. Regeneration of the sensor to the goat anti-human antibody layer was achieved using 3 regenerations of 10 mM Glycine pH 1.7. Injections of alpha-synuclein fibrils of increasing in concentration from 5.56-450 nM prepared from serial 2-fold dilutions, were performed with contact times of 300 sec/injection at a flow rate of 30 μL/min. A dissociation phase of 900 sec followed the final 450 nM injection. Regeneration of the sensor to the goat anti-human antibody layer was achieved using 3 regenerations of 10 mM Glycine pH 1.7. Results obtained from single-cycle kinetics were evaluated by Biacore K8 evaluation software with 1:1 binding homogenous Langmuir model (with a global Rmax) with Cycle 5 as a blank subtraction. The following kinetic parameters were obtained: on-rate (ka), off-rate (kd), affinity constant (KD, ratio of kd by ka), maximum response (Rmax), and goodness of fit (Chi2).

Kinetic constants were determined from 1:1 homogenous binding models for binding versus the aggregated form, while a steady state fit was used to determine KD values versus the monomeric form of alpha-synuclein. Kinetic constants are shown in Table 15.

TABLE 15

Affinity measurement performed on the selected humanized variants of ACI-7067-1101C8-Ab2

| Antibody Code | Alpha-synuclein monomers KD (nM) | Alpha-synuclein fibrils ka (1/Ms) | Alpha-synuclein fibrils kd (1/s) | Alpha-synuclein fibrils KD (nM) |
|---|---|---|---|---|
| cACI-7067-1101C8-Ab2 | 54.5 | 1.61E+04 | 5.84E−05 | 12.2 |
| hACI-7067-1101C8-Ab2_H5L1 | 20.13 | 2.20E+04 | 2.18E−05 | 1.0 |
| hACI-7067-1101C8-Ab2_H8L1 | 40.0 | 1.76E+04 | 3.60E−05 | 2.0 |
| hACI-7067-1101C8-Ab2_H9L1 | 18.2 | 2.39E+04 | 2.25E−05 | 0.9 |
| hACI-7067-1101C8-Ab2_H9L2 | 66.9 | 1.94E+04 | 1.83E−05 | 3.9 |
| hACI-7067-1101C8-Ab2_H10L1 | 48.2 | 1.15E+04 | 1.08E−04 | 0.9 |
| hACI-7067-1101C8-Ab2_H10L2 | 35.1 | 1.06E+04 | 9.27E−05 | 18.0 |
| hACI-7067-1101C8-Ab2_H11L1 | 48.0 | 1.03E+04 | 9.25E−05 | 32.5 |
| hACI-7067-1101C8-Ab2_H11L2 | 80.1 | 1.13E+04 | 6.98E−05 | 26.0 |
| hACI-7067-1101C8-Ab2_H12L1 | 64.4 | 1.06E+04 | 9.44E−05 | 19.4 |
| hACI-7067-1101C8-Ab2_H12L2 | 28.7 | 1.04E+04 | 1.42E−04 | 13.7 |

Overall all humanized variants retained affinity to alpha-synuclein with binding preference to fibrillar alpha-synuclein. hACI-7067-1101C8-Ab2_H5L1, hACI-7067-1101C8-Ab2_H8L1, hACI-7067-1101C8-Ab2_H9L1, hACI-7067-1101C8-Ab2_H9L2 and hACI-7067-1101C8-Ab2_H10L1 demonstrated an improved affinity against the aggregated form of alpha synuclein compared to the chimeric antibody cACI-7067-1101C8-Ab2.

Inhibition or delay of seeded alpha-synuclein aggregation of ACI-7067-1101C8-Ab2 humanized variants Antibodies were tested for their ability to inhibit or delay alpha synuclein seeded aggregation in the seeded alpha-synuclein aggregation assay previously described. Antibodies were compared to the chimeric antibodies to identify the best performing humanized variants. FIG. 18A shows the comparison of changes in T12 values as normalized to the aggregation in the absence of antibody. FIG. 18B shows the calculated percent increase in $T_{1/2}$ values upon pre-incubation of alpha-synuclein seeds, demonstrating the efficacy of the tested antibodies in delaying the seeded and/or spontaneous aggregation of alpha-synuclein. All humanized variants showed good efficacy in delaying the seeded aggregation compared to the no mAb control. Among all tested humanized variants, hACI-7067-1101C8-Ab2_H5L1, hACI-7067-1101C8-Ab2_H8L1, hACI-7067-1101C8-Ab2_H9L1, hACI-7067-1101C8-Ab2_H9L2, hACI-7067-1101C8-Ab2_H10L1, hACI-7067-1101C8-Ab2_H10L2 showed equal or improved efficacy in delaying alpha synuclein aggregation as compared to the chimeric antibody cACI-7067-1101C8-Ab2.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes in connection with the invention.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate.

The invention claimed is:

1. An alpha-synuclein binding molecule, which is a monoclonal antibody or an antigen-binding fragment thereof and which comprises:

a) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33;

VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or b) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 85; VL-CDR2 comprising the amino acid sequence of SEQ ID NO: 36; and VL-CDR3 comprising the amino acid sequence of SEQ ID NO: 87; or c) VH-CDR1 comprising the amino acid sequence of SEQ ID NO: 91; VH-CDR2 comprising the amino acid sequence of SEQ ID NO: 92; and VH-CDR3 comprising the amino acid sequence of SEQ ID NO: 93; VL-CDR1 comprising the amino acid sequence of SEQ ID NO: 95; VL-CDR2 comprising the amino acid sequence of SEQ ID NO: 96; and VL-CDR3 comprising the amino acid sequence of SEQ ID NO: 97; or d) VH-CDR1 comprising the amino acid sequence of SEQ ID NO: 31; VH-CDR2 comprising the amino acid sequence of SEQ ID NO: 192; and VH-CDR3 comprising the amino acid sequence of SEQ ID NO: 193; VL-CDR1 comprising the amino acid sequence of SEQ ID NO: 195; VL-CDR2 comprising the amino acid sequence of SEQ ID NO: 96; and VL-CDR3 comprising the amino acid sequence of SEQ ID NO: 197; or e) VH-CDR1 comprising the amino acid sequence of SEQ ID NO: 31; VH-CDR2 comprising the amino acid sequence of SEQ ID NO: 222; and VH-CDR3 comprising the amino acid sequence of SEQ ID NO: 223; VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 227; or f) VH-CDR1 comprising the amino acid sequence of SEQ ID NO: 31; VH-CDR2 comprising the amino acid sequence of SEQ ID NO: 242; and VH-CDR3 comprising the amino acid sequence of SEQ ID NO: 243; VL-CDR1 comprising the amino acid sequence of SEQ ID NO: 225; VL-CDR2 comprising the amino acid sequence of SEQ ID NO: 96; and VL-CDR3 comprising the amino acid sequence of SEQ ID NO: 247; or g) VH-CDR1 comprising the amino acid sequence of SEQ ID NO: 31; VH-CDR2 comprising the amino acid sequence of SEQ ID NO: 252; and VH-CDR3 comprising the amino acid sequence of SEQ ID NO: 253; VL-CDR1 comprising the amino acid sequence of SEQ ID NO: 255; VL-CDR2 comprising the amino acid sequence of SEQ ID NO: 256; and VL-CDR3 comprising the amino acid sequence of SEQ ID NO: 257.

2. The alpha-synuclein binding molecule of claim 1, comprising a. a Heavy Chain Variable Region (VH) comprising the sequence of SEQ ID NO: 30 or a heavy chain variable region (VH) having at least 94%, 95%, 96%, 97%, 98%, or 99% sequence identity to the amino acid sequence of SEQ ID NO: 30; and a Light Chain Variable Region (VL) comprising the sequence of SEQ ID NO: 34 or a light chain variable region (VL) having at least 98%, or 99% sequence identity to the amino acid sequence of SEQ ID NO: 34; or b. a Heavy Chain Variable Region (VH) comprising the sequence of SEQ ID NO: 30 or a heavy chain variable region (VH) having at least 94%, 95%, 96%, 97%, 98%, or 99% sequence identity to the amino acid sequence of SEQ ID NO: 30; and a Light Chain Variable Region (VL) comprising the sequence of SEQ ID NO: 84 or a light chain variable region (VL) having at least 94%, 95%, 96%, 97%, 98%, or 99% sequence identity to the amino acid sequence of SEQ ID NO: 84; or c. a Heavy Chain Variable Region (VH) comprising the sequence of SEQ ID NO: 90 or a heavy chain variable region (VH) having at least 94%, 95%, 96%, 97%, 98%, or 99% sequence identity to the amino acid sequence of SEQ ID NO: 90; and a Light Chain Variable Region (VL) comprising the sequence of SEQ ID NO: 94 or a light chain variable region (VL) having at least 99%, sequence identity to the amino acid sequence of SEQ ID NO: 94; or d. a Heavy Chain Variable Region (VH) comprising the sequence of SEQ ID NO: 190 or a heavy chain variable region (VH) having at least 88%, 89%, 90%, 91%, 92%, 93%, 94%, 95%, 96%, 97%, 98% or 99% sequence identity to the amino acid sequence of SEQ ID NO: 190; and a Light Chain Variable Region (VL) comprising the sequence of SEQ ID NO: 194 or a light chain variable region (VL) having at least 95%, 96%, 97%, 98% or 99% sequence identity to the amino acid sequence of SEQ ID NO: 194; or e. a Heavy Chain Variable Region (VH) comprising the sequence of SEQ ID NO: 220 or a heavy chain variable region (VH) having at least 97%, 98% or 99% sequence identity to the amino acid sequence of SEQ ID NO: 220; and a Light Chain Variable Region (VL) comprising the sequence of SEQ ID NO: 224 or a light chain variable region (VL) having at least 92%, 93%, 94%, 95%, 96%, 97%, 98% or 99% sequence identity to the amino acid sequence of SEQ ID NO: 224; or f. a Heavy Chain Variable Region (VH) comprising the sequence of SEQ ID NO: 240 or a heavy chain variable region (VH) having at least 96%, 97%, 98% or 99% sequence identity to the amino acid sequence of SEQ ID NO: 240; and a Light Chain Variable Region (VL) comprising the sequence of SEQ ID NO: 244 or a light chain variable region (VL) having at least 94%, 95%, 96%, 97%, 98% or 99% sequence identity to the amino acid sequence of SEQ ID NO: 244; or g. a Heavy Chain Variable Region (VH) comprising the sequence of SEQ ID NO: 250 or a heavy chain variable region (VH) having at least 90%, 91%, 92%, 93%, 94%, 95%, 96%, 97%, 98% or 99% sequence identity to the amino acid sequence of SEQ ID NO: 250; and a Light Chain Variable Region (VL) comprising the sequence of SEQ ID NO: 254 or a light chain variable region (VL) having at least 94%, 95%, 96%, 97%, 98% or 99% sequence identity to the amino acid sequence of SEQ ID NO: 254.

3. The alpha-synuclein binding molecule of claim 1, comprising a. a Heavy Chain Variable Region (VH) comprising the sequence of SEQ ID NO: 30 and a Light Chain Variable Region (VL) comprising the sequence of SEQ ID NO: 34; or b. a Heavy Chain Variable Region (VH) comprising the sequence of SEQ ID NO: 30 and a Light Chain Variable Region (VL) comprising the sequence of SEQ ID NO: 84; or c. a Heavy Chain Variable Region (VH) comprising the sequence of SEQ ID NO: 90 and a Light Chain Variable Region (VL) comprising the sequence of SEQ ID NO: 94; or d. a Heavy Chain Variable Region (VH) comprising the sequence of SEQ ID NO: 190 and a Light Chain Variable Region (VL) comprising the sequence of SEQ ID NO: 194; or e. a Heavy Chain Variable Region (VH) comprising the sequence of SEQ ID NO: 220 and a Light Chain Variable Region (VL) comprising the sequence of SEQ ID NO: 224; or f. a Heavy Chain Variable Region (VH) comprising the sequence of SEQ ID NO: 240 and a Light Chain Variable Region (VL) comprising the sequence of SEQ ID NO: 244; or g. a Heavy Chain Variable Region (VH) comprising the sequence of SEQ ID NO: 250 and a Light Chain Variable Region (VL) comprising the sequence of SEQ ID NO: 254.

4. The alpha-synuclein binding molecule of claim 1, which is a murine, chimeric, or humanized er a human antibody or an antigen-binding fragment thereof.

5. The alpha-synuclein binding molecule of claim 1, which is an IgA, IgD, IgE, IgM, IgG1, IgG2, IgG2a, IgG2b, IgG3 or IgG4 antibody or antigen-binding fragment thereof.

6. The alpha-synuclein binding molecule of claim 1, wherein the binding molecule is an IgG4 isotype including the S228P mutation.

7. A method for treating diseases, disorders and abnormalities associated with alpha-synuclein, the method comprising administering an effective amount of the alpha-synuclein binding molecule of claim 1 to a subject in need thereof.

8. The method according to claim 7, wherein the disease, disorder or abnormality is associated with aggregated alpha-synuclein in the form of Lewy bodies, Lewy neurites or glial cytoplasmic inclusions.

9. The method according to claim 7, wherein the disease, disorder or abnormality is a synucleinopathy, or is Parkinson's disease (PD), Lewy Body dementia (LBD), Parkinson's disease dementia (PDD), Diffuse Lewy Body Disease (DLBD), sporadic Alzheimer's disease, familial Alzheimer's disease with APP mutations, familial Alzheimer's disease with PS-1, PS-2 or other mutations, familial British dementia, Lewy body variant of Alzheimer's disease, multiple system atrophy (MSA), inclusion-body myositis, traumatic brain injury, chronic traumatic encephalopathy, dementia pugilistica, a tauopathy, Down syndrome, Creutzfeldt-Jakob disease, Huntington's disease, motor neuron disease, amyotrophic lateral sclerosis, neuroaxonal dystrophy, neurodegeneration with brain iron accumulation type 1 (Hallervorden-Spatz syndrome), prion disease, Gerstmann-Straussler-Scheinker disease, ataxia telangiectatica, Meige's syndrome, subacute sclerosing panencephalitis, Gaucher disease, Krabbe disease as well as other lysosomal storage disorders, or rapid eye movement (REM) sleep behavior disorder.

10. The method according to claim 9 for improving the motor capabilities or motor deficits, cognitive capabilities or cognitive deficits, behavioral impairments or REM sleep disorders of a subject suffering from a synucleinopathy.

11. The method of claim 10, wherein the synucleinopathy is multiple system atrophy (MSA), Parkinson's disease, Lewy Body dementia (LBD), Parkinson's disease dementia (PDD) or Diffuse Lewy Body Disease.

12. An immunodiagnostic method, the method comprising: contacting the alpha-synuclein binding molecule of claim 1 with a sample obtained from a subject to diagnose a disease, disorder or abnormality associated with alpha-synuclein in the subject.

13. A method for evaluating an alpha-synuclein binding molecule for the capability of inhibiting or delaying seeded or spontaneous alpha-synuclein aggregation, comprising the steps of:

a. bringing an alpha-synuclein binding molecule of claim 1 in contact with alpha-synuclein aggregates (seeds);

b. allowing the alpha-synuclein binding molecule to bind to alpha-synuclein aggregates, to form an immunological complex;

c. adding alpha-synuclein monomeric protein and a detectable dye, to the immunological complex; and d. determining the time to reach half-maximum signal of the detectable dye, relative to the seeded aggregation in the absence of binding molecule.

14. The method according to claim 13, wherein an increase in time to reach half-maximum signal of the detectable dye in the presence of binding molecule relative to the seeded aggregation in the absence of binding molecule indicates that the alpha-synuclein binding molecule is capable of inhibiting or delaying the seeded or spontaneous alpha-synuclein aggregation.

15. The method according to claim 13, wherein the detectable dye is thioflavin T.

16. A pharmaceutical composition comprising the alpha-synuclein binding molecule of claim 1 and a pharmaceutically acceptable carrier or excipient.

17. A nucleic acid encoding the alpha-synuclein binding molecule of claim 1.

18. A recombinant vector comprising the nucleic acid of claim 17.

19. A host cell comprising the nucleic acid of claim 17.

20. An isolated host cell that expresses the alpha-synuclein binding molecule of claim 1.

21. A method for producing an isolated alpha-synuclein binding molecule comprising the steps of: a) culturing the host cell of claim 19 under conditions suitable for producing the alpha-synuclein binding molecule, and b) isolating the alpha-synuclein binding molecule.

* * * * *